US009175088B2

(12) United States Patent
Sahin et al.

(10) Patent No.: US 9,175,088 B2
(45) Date of Patent: Nov. 3, 2015

(54) IDENTIFICATION OF TUMOR-ASSOCIATED MARKERS FOR DIAGNOSING OR MONITORING OVARIAN CANCER

(75) Inventors: Ugur Sahin, Mainz (DE); Özlem Türeci, Mainz (DE); Michael Koslowski, Mainz (DE)

(73) Assignee: BIONTECH AG, Mainz (DE)

( * ) Notice: Subject to any disclaimer, the term of this patent is extended or adjusted under 35 U.S.C. 154(b) by 557 days.

(21) Appl. No.: 12/765,251

(22) Filed: Apr. 22, 2010

(65) Prior Publication Data

US 2011/0104147 A1 May 5, 2011

Related U.S. Application Data

(63) Continuation of application No. PCT/EP2008/008924, filed on Oct. 22, 2008.

(30) Foreign Application Priority Data

Oct. 23, 2007 (EP) ..................................... 07020730

(51) Int. Cl.

| | |
|---|---|
| ***C12Q 1/68*** | (2006.01) |
| ***C12P 19/34*** | (2006.01) |
| ***C07H 21/02*** | (2006.01) |
| ***C07H 21/04*** | (2006.01) |
| ***C07K 16/30*** | (2006.01) |
| ***C07K 14/47*** | (2006.01) |

(52) U.S. Cl.

CPC ............. *C07K 16/30* (2013.01); *C07K 14/4748* (2013.01); *C12Q 1/6886* (2013.01); *C12Q 2600/158* (2013.01)

(58) Field of Classification Search

None

See application file for complete search history.

(56) References Cited

U.S. PATENT DOCUMENTS

| | | | | |
|---|---|---|---|---|
| 5,990,299 | A * | 11/1999 | Ruzdijic et al. | 536/24.5 |
| 7,371,840 | B2 * | 5/2008 | Press et al. | 536/23.5 |
| 2002/0086356 | A1 | 7/2002 | Tuschl | |
| 2003/0099974 | A1 | 5/2003 | Lillie et al. | |
| 2003/0148410 | A1 * | 8/2003 | Berger et al. | 435/7.23 |
| 2004/0005563 | A1 | 1/2004 | Mack et al. | |
| 2007/0037204 | A1 | 2/2007 | Aburatani et al. | |
| 2007/0099251 | A1 * | 5/2007 | Zhang et al. | 435/7.23 |
| 2008/0153104 | A1 * | 6/2008 | Aburatani et al. | 435/7.1 |
| 2009/0214550 | A1 | 8/2009 | Sahin et al. | |

FOREIGN PATENT DOCUMENTS

| | | | |
|---|---|---|---|
| JP | 2005/500833 | A | 1/2005 |
| JP | 2007506417 | A | 3/2007 |
| JP | 2007/526759 | A | 9/2007 |
| WO | 92/04381 | A1 | 3/1992 |
| WO | 96/33265 | A1 | 10/1996 |
| WO | 96/33739 | A1 | 10/1996 |
| WO | 0194641 | A2 | 12/2001 |
| WO | 02/102235 | A2 | 12/2002 |
| WO | 03/065006 | A1 | 8/2003 |
| WO | 2005113587 | A2 | 12/2005 |
| WO | 2006083986 | A2 | 8/2006 |
| WO | 2006100089 | A2 | 9/2006 |
| WO | 2007031222 | A2 | 3/2007 |

OTHER PUBLICATIONS

Schmidt et al. Blood. 1998. 91: 22-29.*
Garber et al. PNAS. 2001. 98: 13784-13789.*
Bhattacharjee et al. PNAS. 2001. 98:13790-13794.*
Ito et al. AntiCancer Research. 2002. 22(4):2385-2389.*
Dermer, G.B. Bio/Technology (1994) 12: 320.*
Liu et al. Clinical Immunology. 2004. 112: 225-230.*
Coleman, R. Drug Discovery Today. 2003. 8: 233-235.*
Saetre et al. Molecular Brain Research. 2004. 126: 198-206.*
Hanke et al. Clinical Chemistry. 2007. 53: 2070-2077.*
Palmer et al. BMC Genomics. 2006. 7:115.*
Min et al. BMC Genomics. 2010. 11:96.*
Mitsuhashi et al al. Journal of Laboratory Analysis. 1996. 10: 285-293.*
Lu et al. Clinical Cancer Research. 2004. 10: 3291-3300.*
Database Geneseq [Online] Dec. 2, 2004, Lilli I J. et al.: "Novel isolated polypeptide associated with breast cancer", XP002518625, retrieved from EBI, Database accession No. ACN90758.
Koslowski M et al: "Frequent nonrandom activation of germ-line genes in human cancer" Cancer Research, American Association for Cancer Research, Baltimore, MD, US, vol. 64, No. 17, Sep. 1, 2004, pp. 5988-5993, XP002309835, ISSN: 0008-5472.
Tuereci Ozlem et al: "Computational dissection of tissue contamination for identification of colon cancer-specific expression profiles." The FASEB Journal: Official Publication of the Federation of American Societies for Experimental Biology Mar. 2003, vol. 17, No. 3, Mar. 2003, pp. 376-385, XP002471061, ISSN: 1530-6860.
Prokopenko P. G et al: "Antigenic structure of ovarian cancer metastases." Bulletin of Experimental Biology and Medicine Jun. 2001, vol. 131, No. 6, Jun. 2001, pp. 561-563, XP002471062, ISSN: 0007-4888.
International Search Report for PCT/EP2008/008924, published Sep. 24, 2009, 6 pages.
International Preliminary Report on Patentability and Written Opinion of the International Searching Authority for PCT/EP2008/008924, 10 pages.
Harandi, "Immunoplacental therapy, a potential multi-epitope cancer vaccine", Medical Hypotheses 2006, vol. 66, 1182-1187.
Klamp et al., "Expression profiling of autoimmun regulator AIRE mRNA in a comprehensive set of human normal and neoplasitc tissues," Immunology Letters 2006, vol. 106, 172-179.
Koslowski et al., "A Placenta-specific gene ectopically activated in many human cancers is essentially involved in malignant cell processes," Cancer Research 2007, vol. 67, No. 19, 9528-9534, XP002471063.

(Continued)

*Primary Examiner* — Carla Myers

(74) *Attorney, Agent, or Firm* — McAndrews Held & Malloy, Ltd.

(57) ABSTRACT

The present technology relates to genetic products the expression of which is associated with cancer diseases. The present technology also relates to the therapy and diagnosis of diseases in which the genetic products are expressed or aberrantly expressed, in particular cancer diseases.

14 Claims, 28 Drawing Sheets

(56) References Cited

OTHER PUBLICATIONS

Human colon cancer antigen encoding cDNA Seq ID No: 1454, http://www.ebu.ac.uk/cgi-bin/epo/epofetch?AAH34372, dated Feb. 29, 2008, 2 pages, XP-002471064.
Shi et al., J. Histochem. Cytochem. 39: 741-748, 1991.
Shin et al., Lab. Invest. 64: 693-702, 1991.
Simpson AJ et al., Nat Rev Cancer 5: 615-25, 2005.
So et al., Mol. Cells 7: 178-186, 1997.
Spiller et al., J. Immunol. Methods 224: 51-60, 1999.
Stanislawski et al., Nat Immunol. 2: 962-70, 2001.
Stockton et al. 2001. Mol. Biol. Cell. 12: 1937-56.
Tuschl T. et al., "The siRNA User Guide", revised Oct. 11, 2002.
Zambrowicz BP & Sands AT. 2003. Nat. Rev. Drug Discov. Jan. 2003; 2(1): 38-51.
Ito Hirotaka et al: "Identification of ROBO1 as a novel heptacellular carcinoma antigen and a potential therapeutic and diagnostic target", Clinical Cancer Research: An Official Journal of the American Association for Cancer Research, vol. 12, No. 11 Pt 1, Jun. 1, 2006, pp. 3257-3264.
Database Geneseq [Online], May 5, 2005, Aburatani H et al: "Human TEG6 associated DNA Seq", Database accession No. ADX83391.
Xie M-H et al: "FGF-19, A Novel Fibroblast Growth Factor With Unique Specificity for FGFR4", Cytokine, Academic Press Ltd, Phiadelphia, PA, US, vol. 11, No. 10, Oct. 1, 1999, pp. 729-735.
Goddard A et al: "Human Pro Protein #33", 1-7 Genbank, Jan. 1, 2004.
Database UniProt [Online], May 20, 2004, Isogai T. et al.: "New polynucleotides and polypeptides useful in gene therapy, ...", retrieved from EBI, Database accession No. ADM02094.
Abate-Shen & Shen. 2002. Trends in Genetics S1-5.
Acevedo HF et al., Cancer 76: 1467-75, 1995.
Adams GP, Weiner LM, Nat Biotechnol 23: 1147-57, 2005.
Altman et al., Science 274: 94-96, 1996.
Anderson et al., J. Immunol. 143: 1899-1904, 1989.
Azorsa et al., J. Immunol. Methods 229: 35-48, 1999.
Balling R, 2001. Ann. Rev. Genomics Hum. Genet. 2: 463-92.
Beard J, Lancet 1: 1758-63, 1902.
Chomczynski & Sacchi, Anal. Biochem. 162: 156-159, 1987.
Cinamon G., Alon R. J. Immunol. Methods. Feb. 2003; 273(1-2): 53-62.
Clark, W.R. (1986), The Experimental Foundations of Modern Immunology, Wiley & Sons, Inc., New York.
Czauderna et al. 2003. Nucl. Acid Res. 31: 670.82.
de Wildt et al., J. Immunol. Methods 207: 61-67, 1997.
Dirnhofer S et al., Hum Pathol 29: 377-82, 1998.
Dunbar et al., Curr. Biol. 8: 413-416, 1998.
Durand & Seta, 2000; Clin. Chem. 46: 795-805.
Gardsvoll, J. Immunol. Methods 234: 107-116, 2000.
Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner).
Greenberg, J. Immunol. 136(5): 1917, 1986.
Gurchot C, Oncology 31: 310-3, 1975.
Hakomori, 1996; Cancer Res. 56: 5309-18.
Hannon, GJ. 2002. RNA interference. Nature 418: 244.51.
Iles RK, Chard T, J Urol 145: 453-8, 1991.
Jegstrup I. et al. 2003. Lab Anim. Jan. 2003; 37(1): 1.9.
Jung et al., Mol. Cells 12: 41.49, 2001.
Kasinrerk et al., Hybrid Hybridomics 21: 287-293, 2002.
Kast et al., Cell 59: 603-614, 1989.
Kayyem et al., Eur. J. Biochem. 208: 1-8, 1992.
Kessels et al., Nat Immunol. 2: 957-61, 2001.
Koslowski, M. et al., Cancer Res. 62, 6750-6755 (2002).
Kreig et al., Nature 374: 546-9, 1995.
Laurence DJ, Neville AM, Br J Cancer 26: 335-55, 1972.
Lemoine et al., Methods Mol. Biol. 75: 441-7, 1997.
Lynch et al., Eur. J. Immunol. 21: 1403-1410, 1991.
Maloy et al., Proc Natl Acad Sci USA 98: 3299-303, 2001.
Matsusue et al. 2003. J. Clin. Invest. 111: 737-47.
Niwa H. 2001. Cell Struct. Funct. Jun. 2001; 26(3): 137-48.
Ossendorp et al., Immunol Lett. 74: 75-9, 2000.
Ossendorp et al., J. Exp. Med. 187: 693-702, 1998.
Pardoll, Nat. Med. 4: 525-31, 1998.
Peters T. et al. 2003. Hum. Mol. Genet 12: 2109-20.
Riddel et al., Science 257: 238, 1992.
Roitt, I. (1991), Essential Immunology, 7th Edition, Blackwell Scientific Publications, Oxford.
Sambrook, J. et al., "Molecular Cloning: A Laboratory Manual", Editors, 2nd Edition, Cold Spring Harbor Laboratory press, Cold Spring Harbor, New York, 1989.
Science 268: 1432-1434, 1995.

* cited by examiner

IDENTIFICATION OF TUMOR-ASSOCIATED MARKERS FOR DIAGNOSING OR MONITORING OVARIAN CANCER

RELATED APPLICATIONS

The present application is a continuation of International Patent Application No. PCT/EP08/08924, which was filed Oct. 22, 2008, claiming the benefit of priority to European Patent Application No. 07020730.3, which was filed on Oct. 23, 2007. The entire text of the aforementioned applications is incorporated herein by reference in its entirety.

FEDERALLY SPONSORED RESEARCH OR DEVELOPMENT

[Not Applicable]

BACKGROUND OF THE INVENTION

The present technology relates to nucleic acids and encoded polypeptides which are expressed in cancers. The present technology also relates to agents which bind the polypeptides. The nucleic acids, polypeptides coded for by such nucleic acids and peptides derived therefrom, as well as related antibodies and cytolytic T lymphocytes, are useful, inter alia, in diagnostic and therapeutic contexts.

Despite interdisciplinary approaches and exhaustive use of classical therapeutic procedures, cancers are still among the leading causes of death.

More recent therapeutic concepts in cancer therapy aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced.

Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens.

The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998).

Antibody based cancer therapies have been successfully introduced into the clinic and have emerged as the most promising therapeutics in oncology over the last decade. Eight antibodies have been approved for treatment of neoplastic diseases, most of them, however in lymphoma and leukemia (Adams G P, Weiner L M, Nat Biotechnol 23:1147-57, 2005).

One of the challenges to be mastered for the advent of the next generation of upgraded antibody-based cancer therapeutics is the selection of appropriate target molecules, which is the key for a favorable toxicity/efficacy profile.

The search for genes tightly silenced in the vast majority of healthy tissues moves into the focus of attention the intriguing observation that genes of the gametogenic and/or trophoblastic lineage are frequently ectopically activated and robustly expressed in human cancer. Based on phenotypical similarities between germ cells, pregnancy trophoblast and cancer cells, John Beard proposed as much as 100 years ago a "trophoblastic theory of cancer" (Beard J, Lancet 1:1758-63, 1902; Gurchot C, Oncology 31:310-3, 1975). The discovery of the sporadic production of chorionic gonadotropin, alpha-fetoprotein, CEA and other trophoblastic hormones by cancer cells provided the first molecules shared between neoplastic and trophoblastic cells (Acevedo H F et al., Cancer 76:1467-75, 1995; Dirnhofer S et al., Hum Pathol 29:377-82, 1998; Gurchot C, Oncology 31:310-3, 1975; Iles R K, Chard T, J Urol 145:453-8, 1991; Laurence D J, Neville A M, Br J Cancer 26:335-55, 1972). The concept was reignited by the inauguration of the steadily growing so-called cancer/germline (CG) class of genes, which represents more than 100 members, each expressed in a variety of tumor types. The observation that entire trophoblastic and gametogenic programs escape transcriptional silencing and are ectopically activated in cancer cells (Koslowski M et al., Cancer Res 64:5988-93, 2004; Simpson A J et al., Nat Rev Cancer 5:615-25, 2005) indicates that within this class of genes with exquisitely selective tissue distribution, appropriate targets for mAB therapy may be found.

It was the object of the present technology to provide target structures for a diagnosis and therapy of cancers. This object is achieved by the subject matter of the claims.

BRIEF SUMMARY OF THE INVENTION

According to the present technology, placenta-specific genes are identified which are selectively or aberrantly expressed in tumor cells and thus, provide target structures for therapeutic and diagnostic approaches.

The nucleic acids identified according to the present technology to be selectively or aberrantly expressed in tumor cells are selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). These nucleic acids are also termed "tumor-associated nucleic acids" herein.

In another aspect, the present technology relates to antigens encoded by the tumor-associated nucleic acids identified according to the present technology. Accordingly, the tumor-associated antigens identified according to the present technology have an amino acid sequence encoded by a nucleic acid which is selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624 of the sequence listing, a part or derivative thereof, (b) a nucleic acid which hybridizes with the nucleic acid of (a)

under stringent conditions, (c) a nucleic acid which is degenerate with respect to the nucleic acid of (a) or (b), and (d) a nucleic acid which is complementary to the nucleic acid of (a), (b) or (c). In a preferred embodiment, the tumor-associated antigens identified according to the present technology comprise an amino acid sequence selected from the group consisting of SEQ ID NOs: 542, 546, 550, 554, 567, 571, 584, 588, 592, 596, 603, 607, 614, 621, and 625 of the sequence listing, a part or derivative thereof.

If, according to the present technology, reference is made to nucleic acids comprising certain nucleic acid sequences or tumor-associated antigens comprising certain amino acid sequences this also includes embodiments wherein the nucleic acids or tumor-associated antigens consist of these certain nucleic acid sequences or amino acid sequences, respectively.

The present technology generally relates to the use of tumor-associated nucleic acids and tumor-associated antigens identified according to the present technology or of parts or derivatives thereof, of nucleic acids directed against said tumor-associated nucleic acids, of antibodies or T cells directed against the tumor-associated antigens identified according to the present technology or parts or derivatives thereof and/or of host cells expressing the tumor-associated antigens identified according to the present technology or parts or derivatives thereof for therapy, prophylaxis, diagnosis and/or monitoring of neoplastic diseases.

This may also involve the use of a combination of two or more of these nucleic acids, antigens, antibodies, T cells and/or host cells.

In those embodiments of the present technology relating to the use of antibodies directed against the tumor-associated antigens identified according to the present technology or parts or derivatives thereof also T cell receptors directed against the tumor-associated antigens identified according to the present technology or parts or derivatives thereof, optionally in a complex with MHC molecules, may be used.

Especially suitable for therapy, prophylaxis, diagnosis and/or monitoring is a part of the tumor-associated antigens identified according to the present technology which corresponds to the non-transmembrane portion, in particular the extracellular portion of the tumor-associated antigens or is comprised thereof. Therefore, according to the present technology, a part of the tumor-associated antigens identified according to the present technology which corresponds to the non-transmembrane portion, in particular the extracellular portion of the tumor-associated antigens or is comprised thereof, or a corresponding part of the nucleic acids coding for the tumor-associated antigens identified according to the present technology is preferred for therapy, prophylaxis, diagnosis and/or monitoring. Similarly the use of antibodies is preferred which are directed against a part of the tumor-associated antigens identified according to the present technology which corresponds to the non-transmembrane portion, in particular the extracellular portion of the tumor-associated antigens or is comprised thereof.

Preferred diseases for a therapy, prophylaxis, diagnosis and/or monitoring are those in which one or more of the tumor-associated nucleic acids identified according to the present technology are selectively expressed or abnormally expressed. Particularly preferred diseases for a therapy, prophylaxis, diagnosis and/or monitoring are those in which one or more of the tumor-associated nucleic acids identified according to the present technology and/or one or more of the tumor-associated antigens encoded thereby are selectively expressed or abnormally expressed.

In one aspect, the present technology relates to a pharmaceutical composition comprising an agent which recognizes a tumor-associated antigen identified according to the present technology or a nucleic acid coding for the tumor-associated antigen and which is preferably selective for cells which have expression or abnormal expression of a tumor-associated antigen identified according to the present technology.

In a further aspect, the present technology relates to a pharmaceutical composition comprising an agent which (I) inhibits expression or activity of a tumor-associated antigen identified according to the present technology, and/or (II) has tumor-inhibiting or tumor-destroying activity and is selective for cells expressing or abnormally expressing a tumor-associated antigen identified according to the present technology, and/or (III) when administered, selectively increases the amount of complexes between an MHC molecule and a tumor-associated antigen identified according to the present technology or a part thereof, such as a peptide epitope. In particular embodiments, said agent may cause induction of cell death, reduction in cell growth, damage to the cell membrane or secretion of cytokines and preferably have a tumor-inhibiting activity.

In one embodiment, the agent is an antisense nucleic acid which hybridizes selectively with the nucleic acid coding for the tumor-associated antigen. In a further embodiment, the agent is a siRNA preferably comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a nucleic acid coding for the tumor-associated antigen, preferably mRNA coding for the tumor-associated antigen. In a further embodiment, the agent is an antibody which binds selectively to the tumor-associated antigen, in particular a complement-activated or toxin conjugated antibody which binds selectively to the tumor-associated antigen. In a preferred embodiment, the antibody which binds selectively to the tumor-associated antigen is coupled to a therapeutically useful substance and/or recruits natural or artificial effector mechanisms to said cell expressing or abnormally expressing said tumor-associated antigen. In a further embodiment, the agent is a cytotoxic T lymphocyte which recognizes the tumor-associated antigen or a part thereof bound by an MHC molecule on a cell and lyses the cells labeled in this way. In a further embodiment, the agent is a T helper lymphocyte which recognizes the tumor-associated antigen or a part thereof bound by an MHC molecule on a cell and enhances effector functions of other cells specifically recognizing said tumor-associated antigen or a part thereof.

In a further embodiment, the agent comprises two or more agents which each recognize different tumor-associated antigens or different nucleic acids coding for tumor-associated antigens and/or inhibit expression or activity of different tumor-associated antigens, and/or have tumor-inhibiting or tumor-destroying activity and are selective for cells expressing or abnormally expressing different tumor-associated antigens, and/or when administered, selectively increase the amount of complexes between MHC molecules and different tumor-associated antigens or parts thereof, wherein at least one of said different tumor-associated antigens is a tumor-associated antigen identified according to the present technology.

Preferably, a tumor-associated antigen selectively limited to tumors serves as a label for recruiting effector mechanisms to this specific location. In this aspect, the present technology includes embodiments wherein the agent itself does not have an ability to inhibit activity of a tumor-associated antigen or a tumor-inhibiting or tumor-destroying activity but mediates such effect, in particular by recruiting effector mechanisms, in particular those having cell damaging potential, to a specific location, in particular a tumor or tumor cells.

Preferably, said cells expressing or abnormally expressing a tumor-associated antigen identified according to the present technology are non-placenta cells.

The activity of a tumor-associated antigen identified according to the present technology can be any activity of a protein or a peptide. In one embodiment this activity is an enzymatic activity.

According to the present technology the phrase "inhibit expression or activity" includes a complete or essentially complete inhibition of expression or activity and a reduction in expression or activity.

The agent which, when administered, selectively increases the amount of complexes between an MHC molecule and a tumor-associated antigen identified according to the present technology or a part thereof comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule.

The present technology furthermore relates to a pharmaceutical composition which comprises one or more components selected from the group consisting of (i) a tumor-associated antigen identified according to the present technology or a part thereof, (ii) a nucleic acid which codes for a tumor-associated antigen identified according to the present technology or a part thereof, (iii) an antibody which binds to a tumor-associated antigen identified according to the present technology or to a part thereof, (iv) an antisense nucleic acid which hybridizes specifically with a tumor-associated nucleic acid identified according to the present technology/a nucleic acid coding for a tumor-associated antigen identified according to the present technology, (v) an siRNA directed against a tumor-associated nucleic acid identified according to the present technology/a nucleic acid coding for a tumor-associated antigen identified according to the present technology, (vi) a host cell which expresses a tumor-associated antigen identified according to the present technology or a part thereof, and (vii) isolated complexes between a tumor-associated antigen identified according to the present technology or a part thereof and an MHC molecule.

In one embodiment, a nucleic acid coding for a tumor-associated antigen identified according to the present technology or a part thereof is present in the pharmaceutical composition in an expression vector and functionally linked to a promoter. In a further embodiment, a nucleic acid coding for a tumor-associated antigen identified according to the present technology or a part thereof is present in the pharmaceutical composition in a virus as further described below.

A host cell present in a pharmaceutical composition of the present technology may secrete the tumor-associated antigen or the part thereof, may express it on the surface and preferably may additionally express an MHC molecule which binds to said tumor-associated antigen or said part thereof. In one embodiment, the host cell expresses the MHC molecule endogenously. In a further embodiment, the host cell expresses the MHC molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

In a further embodiment, an antibody present in a pharmaceutical composition of the present technology is a monoclonal antibody. In further embodiments, the antibody is a chimeric or humanized antibody, a fragment of an antibody or a synthetic antibody. The antibody may be coupled to a therapeutically or diagnostically useful agent also termed therapeutic or diagnostic agent herein.

An antisense nucleic acid present in a pharmaceutical composition of the present technology may comprise a sequence of 6-50, in particular 10-30, 15-30 and 20-30, contiguous nucleotides of the nucleic acid coding for the tumor-associated antigen identified according to the present technology.

In further embodiments, a tumor-associated antigen or a part thereof, provided by a pharmaceutical composition of the present technology either directly or via expression of a nucleic acid, binds to MHC molecules on the surface of cells, said binding preferably causing a cytolytic response and/or inducing cytokine release.

A pharmaceutical composition of the present technology may comprise a pharmaceutically compatible carrier and/or an adjuvant.

A pharmaceutical composition of the present technology is preferably used for the treatment or prevention of a disease characterized by selective expression or abnormal expression of a tumor-associated nucleic acid and/or tumor-associated antigen. In a preferred embodiment, the disease is a neoplastic disease, preferably cancer.

In a preferred embodiment, the pharmaceutical composition of the present technology is in the form of a vaccine which may be used therapeutically or prophylactically. Such vaccine preferably comprises a tumor-associated antigen identified according to the present technology or a part thereof, and/or a nucleic acid which codes for a tumor-associated antigen identified according to the present technology or a part thereof. In particular embodiments, the nucleic acid is present in a virus or host cell.

The present technology furthermore relates to methods of treating, preventing, diagnosing or monitoring, i.e. determining the regression, progression, course and/or onset of, a disease characterized by expression or abnormal expression of one of more tumor-associated nucleic acids identified according to the present technology, preferably also resulting in expression or abnormal expression of one of more tumor-associated antigens identified according to the present technology, preferably a neoplastic disease, in particular cancer. In one embodiment, the treatment or prevention comprises administering a pharmaceutical composition of the present technology.

The methods of diagnosing and/or methods of monitoring according to the present technology generally concern the detection of and/or determination of the quantity of one or more parameters selected from the group consisting of (i) a tumor-associated nucleic acid identified according to the present technology, or a part thereof, (ii) a tumor-associated antigen identified according to the present technology, or a part thereof, (iii) an antibody against a tumor-associated antigen identified according to the present technology or a part thereof, and (iv) T lymphocytes, preferably cytotoxic or T helper lymphocytes, which are specific for a tumor-associated antigen identified according to the present technology or a part thereof and/or a complex between the tumor-associated antigen or a part thereof and an MHC molecule, in a biological sample isolated from a patient, preferably from a patient having said disease, being suspected of having or falling ill with said disease or having a potential for said disease. Means for accomplishing said detection and/or determination of the quantity are described herein and will be apparent to the skilled person.

Preferably, the presence of said nucleic acid or said part thereof, said tumor-associated antigen or said part thereof, said antibody and/or said T lymphocytes and/or a quantity of said nucleic acid or said part thereof, said tumor-associated antigen or said part thereof, said antibody and/or said T lymphocytes which is increased compared to a patient without said disease is indicative for the presence of said disease or a potential for a development of said disease.

The methods of diagnosing and/or monitoring of the present technology also include embodiments wherein by detection or determination of the quantity of said nucleic acid or said part thereof, said tumor-associated antigen or said part thereof, said antibody and/or said T lymphocytes it is possible to assess and/or prognose the metastatic behavior of said disease, wherein, preferably, the presence of said nucleic acid or said part thereof, said tumor-associated antigen or said part thereof, said antibody and/or said T lymphocytes and/or a quantity of said nucleic acid or said part thereof, said tumor-associated antigen or said part thereof, said antibody and/or said T lymphocytes which is increased compared to a patient without said disease or without a metastasis of said disease is indicative for a metastatic behavior of said disease or a potential for a metastatic behavior of said disease.

In particular embodiments, said detection or determination of the quantity comprises (i) contacting a biological sample with an agent which binds specifically to said tumor-associated nucleic acid or said part thereof, to said tumor-associated antigen or said part thereof, to said antibody or to said T lymphocytes, and (ii) detecting the formation of or determining the amount of a complex between the agent and the nucleic acid or the part thereof, the tumor-associated antigen or the part thereof, the antibody, or the T lymphocytes.

In one embodiment, the disease is characterized by expression or abnormal expression of two or more different tumor-associated nucleic acids preferably also resulting in expression or abnormal expression of two or more different tumor-associated antigens and a detection or determination of the quantity comprises a detection or determination of the quantity of two or more different tumor-associated nucleic acids or of parts thereof, of two or more different tumor-associated antigens or of parts thereof, of two or more antibodies binding to said two or more different tumor-associated antigens or to parts thereof and/or of two or more T lymphocytes specific for said two or more different tumor-associated antigens or parts thereof, or complexes thereof with MHC molecules. In a further embodiment, the biological sample isolated from the patient is compared to a comparable normal biological sample.

The methods of monitoring according to the present technology preferably comprise a detection of and/or determination of the quantity of one or more of the parameters mentioned above in a first sample at a first point in time and in a further sample at a second point in time, wherein the course of the disease is determined by comparing the two samples.

Preferably, a level of said nucleic acid or said part thereof, said tumor-associated antigen or said part thereof, said antibody and/or said T lymphocytes which is increased in a sample compared to a sample taken earlier from a patient indicates that the patient has developed or is about to develop cancer and/or a metastasis of cancer and/or a relapse of cancer. Preferably, a level of said nucleic acid or said part thereof, said tumor-associated antigen or said part thereof, said antibody and/or said T lymphocytes which is decreased in a sample compared to a sample taken earlier from a patient indicates regression of cancer and/or a metastasis of cancer in said patient and thus, preferably indicates a successful cancer therapy.

According to the present technology, detection of a nucleic acid or of a part thereof or determining the quantity of a nucleic acid or of a part thereof may be carried out using a oligo- or polynucleotide probe which hybridizes specifically to said nucleic acid or said part thereof or may be carried out by selective amplification of said nucleic acid or said part thereof, e.g. by means of PCR amplification. In one embodiment, the oligo- or polynucleotide probe comprises a sequence of 6-50, in particular 10-30, 15-30 and 20-30, contiguous nucleotides of said nucleic acid.

In particular embodiments, the tumor-associated antigen or the part thereof which is to be detected or the quantity of which is to be determined in the methods of the present technology is present intracellularly, on the cell surface or in a complex with an MHC molecule.

According to the present technology, detection of a tumor-associated antigen or of a part thereof or determining the quantity of a tumor-associated antigen or of a part thereof may be carried out using an antibody binding specifically to said tumor-associated antigen or said part thereof.

According to the present technology, detection of an antibody or determining the quantity of an antibody may be carried out using a protein or peptide binding specifically to said antibody.

According to the present technology, detection of or determining the quantity of T lymphocytes which are specific for a tumor-associated antigen or a part thereof and/or a complex thereof with an MHC molecule may be carried out using a cell presenting the complex between said tumor-associated antigen or said part thereof and an MHC molecule. T lymphocytes may additionally be detected by detecting their proliferation, their cytokine production, and their cytotoxic activity triggered by specific stimulation with a complex of an MHC molecule and a tumor-associated antigen or a part thereof. T lymphocytes may also be detected with aid of a recombinant MHC molecule or a complex of two or more MHC molecules loaded with immunogenic fragments of one or more tumor-associated antigens.

An agent which is used for detection or determining the quantity in the methods of the present technology such as a oligo- or polynucleotide probe, an antibody, a protein or peptide or a cell is preferably labeled in a detectable manner, in particular by a detectable marker such as a radioactive marker or an enzymic marker.

In a particular aspect, the present technology relates to a method of treating, preventing, diagnosing or monitoring a disease characterized by expression or abnormal expression of a tumor-associated antigen identified according to the present technology, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of an antibody.

In certain embodiments, the methods of the present technology of diagnosing or monitoring a disease are performed with a biological sample containing or suspected of containing disseminating tumor cells or metastatic tumor cells. Such biological samples include, for example, blood, serum, bone marrow, sputum, bronchial aspirate, and/or bronchial lavage. Preferably, the methods of the present technology of diagnosing or monitoring a disease are performed with a biological sample not containing placental cells and, in particular, being a non-placenta biological sample isolated from a subject.

In one particular aspect, the present technology relates to a method of treating a patient having a disease characterized by expression or abnormal expression of a tumor-associated antigen identified according to the present technology, which method comprises (i) providing a sample containing immunoreactive cells, either obtained from said patient or from another individual of the same species, in particular a healthy individual, or an individual of a different species, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. In one embodiment, the method includes cloning of the T cell receptor of cytolytic T cells obtained and transferring the nucleic acid coding for the T cell receptor to T cells, either obtained from said patient or from another individual of the same species, in particular a healthy individual, or an individual of a different species, which T cells thus receive the desired specificity and, as under (iii), may be introduced into the patient.

In one embodiment, the host cell endogenously expresses an MHC molecule. In a further embodiment, the host cell recombinantly expresses an MHC molecule and/or the tumor-associated antigen or the part thereof. Preferably, the host cell presents the tumor-associated antigen or the part thereof by MHC molecules on its surface. The host cell is preferably nonproliferative. In a preferred embodiment, the host cell is an antigen-presenting cell, in particular a dendritic cell, a monocyte or a macrophage.

The present technology also relates to a method of treating a disease characterized by expression or abnormal expression of a tumor-associated antigen identified according to the present technology, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

The present technology furthermore relates to a nucleic acid selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In a further aspect, the present technology relates to a recombinant nucleic acid molecule, in particular DNA or RNA molecule, which comprises a nucleic acid of the present technology.

The present technology also relates to host cells which contain a nucleic acid or recombinant nucleic acid molecule of the present technology.

The host cell may also comprise a nucleic acid coding for a MHC molecule. In one embodiment, the host cell endogenously expresses the MHC molecule. In a further embodiment, the host cell recombinantly expresses the MHC molecule and/or the nucleic acid or recombinant nucleic acid molecule of the present technology or a part thereof. Preferably, the host cell is nonproliferative. In a preferred embodiment, the host cell is an antigen-presenting cell, in particular a dendritic cell, a monocyte or a macrophage.

In a further embodiment, the present technology relates to oligonucleotides which hybridize with a nucleic acid identified according to the present technology and which may be used as genetic probes or as "antisense" molecules. Nucleic acid molecules in the form of oligonucleotide primers or competent probes, which hybridize with a nucleic acid identified according to the present technology or parts thereof, may be used for detecting said nucleic acid and/or finding nucleic acids which are homologous to said nucleic acid identified according to the present technology, e.g. by PCR amplification, Southern and Northern hybridization. Hybridization may be carried out under low stringency, more preferably under medium stringency and most preferably under high stringency conditions.

In a further aspect, the present technology relates to a protein or peptide which is encoded by a nucleic acid selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the protein or peptide comprises an amino acid sequence selected from the group consisting of SEQ ID NOs: 542, 546, 550, 554, 567, 571, 584, 588, 592, 596, 603, 607, 614, 621, and 625 of the sequence listing, a part or derivative thereof.

In a further aspect, the present technology relates to an immunogenic fragment of a tumor-associated antigen identified according to the present technology. Said fragment preferably binds to a MHC molecule or an antibody, preferably to a human HLA receptor or a human antibody. According to the present technology, a part or fragment preferably comprises a sequence of at least 5, at least 6, in particular at least 8, at least 10, at least 12, at least 15, at least 20, at least 30 or at least 50, amino acids.

In a further aspect, the present technology relates to an agent which binds to a tumor-associated antigen identified according to the present technology or to a part thereof. In a preferred embodiment, the agent is a protein or peptide, in particular an antibody, a T cell receptor or an MHC molecule. In further embodiments, the antibody is a monoclonal, chimeric, or humanized antibody, an antibody produced by combinatory techniques, or a fragment of an antibody. In one preferred embodiment, the present technology relates to an antibody which binds selectively to a complex of (i) a tumor-associated antigen identified according to the present technology or a part thereof and (ii) an MHC molecule to which said tumor-associated antigen identified according to the present technology or said part thereof binds, with said antibody not binding to (i) or (ii) alone.

According to the present technology, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

Such specific antibodies may, for example, be obtained by immunization using the aforementioned peptides.

The present technology furthermore relates to a conjugate between an agent of the present technology which binds to a tumor-associated antigen identified according to the present technology or to a part thereof or an antibody of the present technology and a therapeutic or diagnostic agent. In one embodiment, the therapeutic or diagnostic agent is a toxin.

In a further aspect, the present technology relates to a kit for detecting a disease characterized by expression or abnormal expression of one of more tumor-associated nucleic acids identified according to the present technology, preferably also resulting in expression or abnormal expression of one of more tumor-associated antigens identified according to the present technology, preferably a neoplastic disease, in particular cancer, which kit comprises agents for detection or determining the quantity (i) of the tumor-associated nucleic acid or of a part thereof, (ii) of the tumor-associated antigen or of a part thereof, (iii) of antibodies which bind to the tumor-associated antigen or to a part thereof, and/or (iv) of T cells which are specific for the tumor-associated antigen or a part thereof or a complex thereof with an MHC molecule. Such agents are described herein above.

In one embodiment, the present technology relates to a pharmaceutical composition which comprises an agent that (I) inhibits expression or activity of a tumor-associated antigen and/or (II) has tumor-inhibiting activity, and is selective for cells expressing or abnormally expressing a tumor-associated antigen and/or (III) when administered, selectively increases the amount of complexes between an MHC molecule and a tumor-associated antigen or a part thereof, the tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In another embodiment, the present technology relates to a pharmaceutical composition which comprises one or more components selected from the group consisting of: (i) a tumor-associated antigen or a part thereof, (ii) a nucleic acid which codes for a tumor-associated antigen or a part thereof, (iii) an antibody which binds to a tumor-associated antigen or a part thereof, (iv) an antisense nucleic acid which hybridizes specifically with a nucleic acid coding for a tumor-associated antigen, (v) an siRNA directed against a nucleic acid coding for a tumor-associated antigen, (vi) a host cell which expresses a tumor-associated antigen or a part thereof, and (vii) isolated complexes between a tumor-associated antigen or a part thereof and an MHC molecule, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a method of diagnosing or monitoring a cancer disease which comprises detecting or determining the quantity (i) of a tumor-associated nucleic acid or of a part thereof, and/or (ii) of a tumor-associated antigen or of a part thereof, and/or (iii) of an antibody to the tumor-associated antigen or a part thereof and/or (iv) of T lymphocytes which are specific to the tumor-associated antigen or to a part thereof in a biological sample isolated from a patient, said tumor-associated nucleic acid being selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and said tumor-associated antigen having a sequence encoded by a nucleic acid which is selected from said group of nucleic acids.

In a further embodiment, the present technology relates to a method of treating or preventing a disease characterized by expression or abnormal expression of a tumor-associated antigen which comprises administration of a pharmaceutical composition of the present technology, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a method of treating, preventing, diagnosing or monitoring a disease characterized by expression or abnormal expression of a tumor-associated antigen which comprises administering an antibody that binds to said tumor-associated antigen or to a part thereof and is coupled to a therapeutic or diagnostic agent, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

Another embodiment of the present technology relates to a method of treating a patient having a disease characterized by expression or abnormal expression of a tumor-associated antigen which comprises: (i) providing a sample containing immunoreactive cells, (ii) contacting said sample with a host cell expressing said tumor-associated antigen or a part thereof, under conditions which favor production of cytolytic or cytokine-releasing T cells against said tumor-associated antigen or said part thereof, and (iii) introducing the cytolytic or cytokine-releasing T cells into the patient in an amount suitable for lysing cells expressing the tumor-associated antigen or a part thereof, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

An additional embodiment of the present technology relates to a method of inhibiting the development of cancer in a patient which comprises administering an effective amount of a pharmaceutical composition of the present technology.

In yet another embodiment, the present technology relates to an agent, which binds specifically to a protein or polypeptide or to a part thereof, said protein or polypeptide being encoded by a nucleic acid selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In an additional embodiment, the present technology relates to an antibody, which binds selectively to a complex of: (i) a protein or polypeptide or a part thereof and (ii) an MHC molecule to which said protein or polypeptide or said part thereof binds, with said antibody not binding to (i) or (ii) alone and said protein or polypeptide being encoded by a nucleic acid selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a kit for detecting cancer, which comprises agents for detecting or determining the quantity of (i) of a tumor-associated nucleic acid or of a part thereof, and/or (ii) of a tumor-associated antigen or of a part thereof, and/or (iii) of antibodies which bind to the tumor-associated antigen or to a part thereof, and/or (iv) of T cells which are specific for a complex between the tumor-associated antigen or a part thereof and an MHC molecule, said tumor-associated nucleic acid being selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and said tumor-associated antigen having a sequence encoded by a nucleic acid which is selected from said group of nucleic acids.

DETAILED DESCRIPTION OF THE INVENTION

Figure 1:
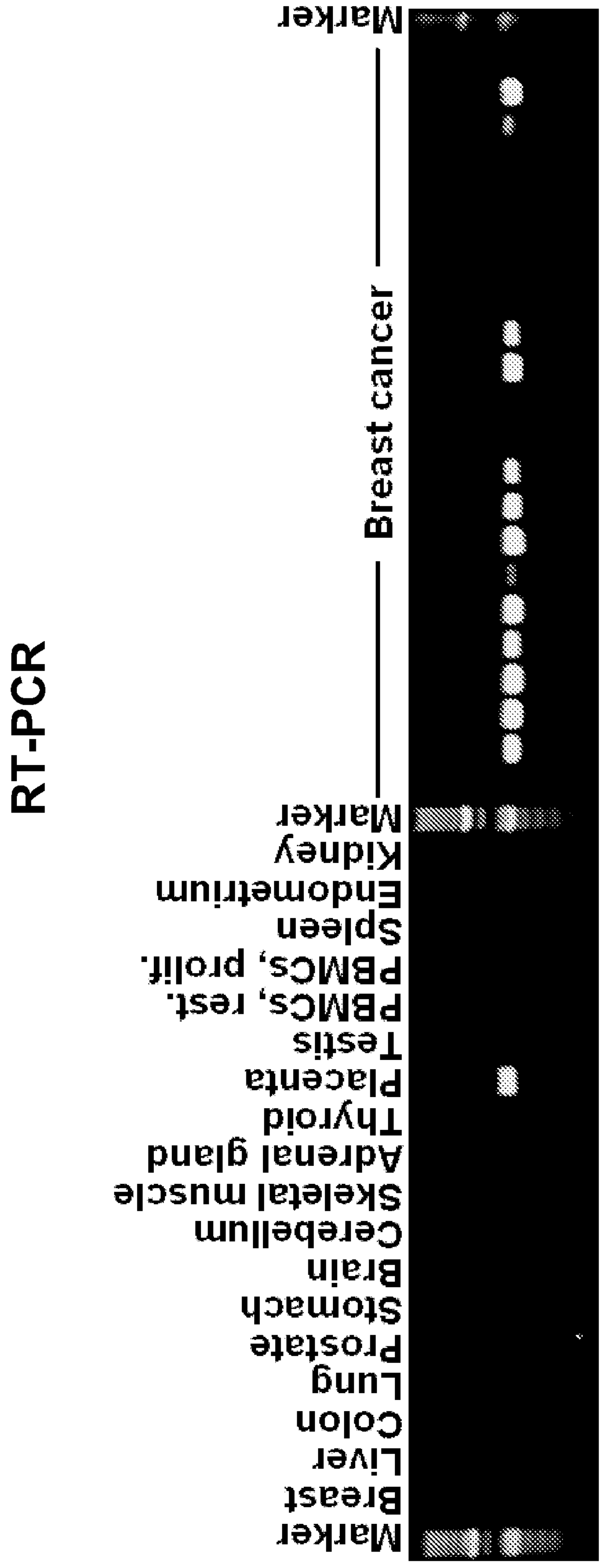
FIG. 1. Expression of a tumor-associated nucleic acid identified according to the present technology in normal tissues and cancer tissue. Significant expression of the nucleic acid sequence according to SEQ ID NO:540 was found only in placenta tissue and mamma carcinomas.

A reference herein to a range of numerical values is to be understood so as to specify and mention each of the individual numerical values comprised by said range. For example, a reference to SEQ ID NOs: 1-540 is to be understood so as to refer to each and every of the following individual SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, and 540.

According to the present technology, a "reference" such as a reference sample or reference organism may be used to correlate and compare the results obtained in the methods of the present technology from a test sample or test organism, i.e. a patient. Typically the reference organism is a healthy organism, in particular an organism which does not suffer from cancer.

A "reference value" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the present technology, a nucleic acid is preferably deoxyribonucleic acid (DNA) or ribonucleic acid (RNA). Nucleic acids comprise according to the present technology genomic DNA, cDNA, mRNA, recombinantly produced and chemically synthesized molecules. According to the present technology, a nucleic acid may be present as a single-stranded or double-stranded and linear or covalently circularly closed molecule.

The terms "tumor-associated nucleic acid identified according to the present technology" and "nucleic acid encoding a tumor-associated antigen identified according to the present technology" have similar meanings. However, the different terms are used herein to account for the fact that in some embodiments only the expression of nucleic acid, in particular mRNA, is of relevance while the expression of protein is not a critical factor.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

If reference is made herein to the detection of or the determination of the quantity of a nucleic acid, the nucleic acid which is actually to be detected or the quantity of which is actually to be determined is preferably mRNA. However, it should be understood that this may also include embodiments wherein mRNA is detected or the quantity of mRNA is determined indirectly. For example, mRNA may be transformed into cDNA and the cDNA detected or its quantity determined. mRNA is given herein as the cDNA equivalent. One skilled in the art would understand that the cDNA sequence is equivalent to the mRNA sequence, and can be used for the same purpose herein, e.g., the generation of probes hybridizing to the nucleic acid to be detected. Thus, if reference is made herein to the sequences shown in the sequence listing this is also to include the RNA equivalents of said sequences.

The nucleic acids described according to the present technology have preferably been isolated. The term "isolated nucleic acid" means according to the present technology that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A degenerate nucleic acid according to the present technology is a nucleic acid that differs from a reference nucleic acid in codon sequence due to the degeneracy of the genetic code.

"Derivative" of a nucleic acid means according to the present technology that single or multiple such as at least 2, at least 4, or at least 6 and preferably up to 3, up to 4, up to 5, up to 6, up to 10, up to 15, or up to 20 nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

Preferably the degree of identity between a specific nucleic acid sequence described herein and a nucleic acid sequence which is a derivative of said specific nucleic acid sequence, which hybridizes with said specific nucleic acid sequence and/or which is degenerate with respect to said specific nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence, such as the nucleic acid sequences given in the sequence listing.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the present technology is at least 70%, preferably at least 75%, preferably at least 80%, more preferably at least 85%, even more preferably at least 90% or most preferably at least 95%, 96%, 97%, 98% or 99%.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

In one embodiment, a nucleic acid sequence which is a derivative of a specific nucleic acid sequence, which is degenerate with respect to a specific nucleic acid sequence or which is a part of a specific nucleic acid sequence has a relevant function and/or activity of the specific nucleic acid sequence, i.e. it may encode a protein or peptide having the same activity or immunological properties as the protein or peptide encoded by the specific nucleic acid sequence and, in one embodiment, encodes the same protein or peptide.

Nucleic acids coding for tumor-associated antigens may, according to the present technology, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the present technology promoters, enhancers and other control elements which regulate expression of a gene. In particular embodiments of the present technology, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the present technology, a nucleic acid may furthermore be present in combination with another nucleic acid which codes for a peptide controlling secretion of the protein or peptide encoded by said nucleic acid from a host cell. According to the present technology, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the present technology a vector, where appropriate with a promoter, which controls expression of a nucleic acid, for example a nucleic acid coding for a tumor-associated antigen identified according to the present technology. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor-associated antigen identified according to the present technology may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the present technology, the term "host cell" relates to any cell which can be transformed or transfected with an exogenous nucleic acid. The term "host cells" comprises according to the present technology prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the present technology, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the present technology in which a MHC molecule presents a tumor-associated antigen or a part thereof, an expression vector may also comprise a nucleic acid sequence coding for said MHC molecule. The nucleic acid sequence coding for the MHC molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the MHC molecule, both nucleic acids coding therefor may be transfected into the cell either on the same expression vector or on different expression vectors. If the cell already expresses the MHC molecule, only the nucleic acid sequence coding for the tumor-associated antigen or the part thereof can be transfected into the cell.

The present technology also comprises kits for detection and/or determination of the quantity of nucleic acids. Such kits comprise, for example, a pair of amplification primers which hybridize to the nucleic acid which is to be detected or the amount of which is to be determined. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid, and the other primer will hybridize to the complementary strand in an arrangement which allows amplification of the nucleic acid.

"Antisense molecules" or "antisense nucleic acids" may be used for regulating, in particular reducing, expression of a nucleic acid. The term "antisense molecule" or "antisense nucleic acid" refers according to the present technology to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the present technology, an "antisense molecule" also comprises a construct which contains a nucleic acid or a part thereof in reverse orientation with respect to its natural promoter. An antisense transcript of a nucleic acid or of a part thereof may form a duplex with naturally occurring mRNA and thus prevent accumulation of or translation of the mRNA. Another possibility is the use of ribozymes for inactivating a nucleic acid.

Antisense oligonucleotides preferred according to the present technology have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the present technology consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the present technology is a "modified" oligonucleotide. Here, the oligonucleotide may be modified in very different ways, without impairing its ability to bind its target, in order to increase, for example, its stability or therapeutic efficacy. According to the present technology, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

It is to be understood that all embodiments described above with respect to oligonucleotides may also apply to polynucleotides.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the present technology can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e. g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the present technology can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the present technology can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Such embodiments are included according to the present technology when reference is made herein to the administration of siRNA or the incorporation of siRNA into pharmaceutical compositions. Suitable promoters for expressing siRNA of the present technology from a plasmid include, for example, the U6 or H1 RNA pol III promoter sequences and the cytomegalovirus promoter.

Selection of other suitable promoters is within the skill in the art. The recombinant plasmids of the present technology can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. siRNA can be expressed from a recombinant viral vector either as two separate, complementary RNA molecules, or as a single RNA molecule with two complementary regions.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the present technology have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay or as therapeutics. Proteins and peptides described according to the present technology may be isolated from biological samples such as tissue or cell homogenates and may also be expressed recombinantly in a multiplicity of pro- or eukaryotic expression systems.

For the purposes of the present technology, "derivatives" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

"Conservative substitutions" may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Preferably the degree of similarity, preferably identity between a specific amino acid sequence described herein and an amino acid sequence which is a derivative of said specific amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

In one embodiment, a protein or peptide which is a derivative of a specific protein or peptide or which is a part of a specific protein or peptide has a relevant function and/or activity of the specific protein or peptide, i.e. it may have the same activity or immunological properties as the specific protein or peptide.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the present technology, "derivatives" of proteins and peptides also comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides.

According to the present technology, a part or fragment of a tumor-associated antigen preferably has a functional property of the protein or peptide from which it has been derived. Such functional properties comprise the interaction with antibodies, the interaction with other peptides or proteins, the selective binding of nucleic acids and an enzymatic activity. A particular property is the ability to form a complex with MHC molecules and, where appropriate, generate an immune response, preferably by stimulating cytotoxic or T helper cells. A part or fragment of a tumor-associated antigen preferably comprises a sequence of at least 6, in particular at least 8, at least 10, at least 12, at least 15, at least 20, at least 30 or at least 50, consecutive amino acids of the tumor-associated antigen. A part or fragment of a tumor-associated antigen preferably comprises a sequence of up to 8, in particular up to 10, up to 12, up to 15, up to 20, up to 30 or up to 55, consecutive amino acids of the tumor-associated antigen. A part or fragment of a tumor-associated antigen is preferably a part of the tumor-associated antigen which corresponds to the non-transmembrane portion, in particular the extracellular portion of the antigen, or is comprised thereof.

Preferred parts or fragments of a tumor-associated antigen are in particular suitable for the stimulation of cytotoxic T-lymphocytes in vivo but also for the production of expanded and stimulated T-lymphocytes for the therapeutic adoptive transfer ex vivo.

A part or a fragment of a nucleic acid coding for a tumor-associated antigen relates according to the present technology to the part of the nucleic acid, which codes at least for the tumor-associated antigen and/or for a part or a fragment of said tumor-associated antigen, as defined above. A part or fragment of a nucleic acid coding for a tumor-associated antigen is preferably that part of the nucleic acid corresponding to the open reading frame.

According to the present technology, particular embodiments ought to involve providing "dominant negative" proteins or peptides derived from tumor-associated antigens. A dominant negative protein or peptide is an inactive protein or peptide variant which, by way of interacting with the cellular machinery, displaces an active protein or peptide from its interaction with the cellular machinery or which competes with the active protein or peptide, thereby reducing the effect of said active protein.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the present technology, the term "antibody" also includes $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

The present technology also comprises proteins and peptides which bind specifically to tumor-associated antigens. Binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Antibodies may also be coupled to specific diagnostic substances for displaying cells and tissues expressing tumor-associated antigens. They may also be coupled to therapeutically useful substances.

Diagnostic substances or agents include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the present technology, the terms "therapeutically useful substance", "therapeutic substance" or "therapeutic agent" means any molecule which may exert a therapeutic effect. According to the present technology, a therapeutically useful substance is preferably selectively guided to a cell which expresses one or more tumor-associated antigens and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the present technology an MHC molecule is an HLA molecule.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

The term "patient" means according to the present technology a human being, a nonhuman primate or another animal, in particular a mammal such as a cow, horse, pig, sheep, goat, dog, cat or a rodent such as a mouse and rat. In a particularly preferred embodiment, the patient is a human being.

According to the present technology the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the present technology, the term "disease" refers to any pathological state in which tumor-associated nucleic acids and/or tumor-associated antigens are expressed or abnormally expressed. "Abnormal expression" means according to the present technology that expression is altered, preferably increased, compared to the state in a healthy individual. An increase in expression refers to an increase by at least 10%, in particular at least 20%, at least 50% or at least 100%. In one embodiment, expression is only found in tissue of a diseased individual, while expression in a healthy individual is repressed or is repressed in a healthy individual except for placenta. One example of such a disease is cancer, wherein the term "cancer" according to the present technology comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the matastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the present technology also comprises cancer metastases.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the present technology relates to "distant metastasis" which relates to a metastasis which is remote from the primary tumor and the regional lymph node system.

According to the present technology, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the present technology, the term "biological sample" also includes fractions of biological samples. Preferably, the term "biological sample" according to the present technology does not include samples derived from placental tissue.

According to the present technology, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

The terms "T cell" and "T lymphocyte" are used interchangeably herein and include T helper cells and cytotoxic T cells which comprise cytolytic T cells.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for obtaining specific clones of cytotoxic T lymphocytes (Altman et al., *Science* 274:94-96, 1996; Dunbar et al., *Curr. Biol.* 8:413-416, 1998).

The present technology also includes therapeutic methods referred to as adoptive transfer (Greenberg, *J. Immunol.* 136 (5):1917, 1986; Riddel et al., *Science* 257:238, 1992; Lynch et al., *Eur. J. Immunol.* 21:1403-1410, 1991; Kast et al., *Cell* 59:603-614, 1989), wherein cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al., Nat Immunol. 2:962-70, 2001; Kessels et al., Nat Immunol. 2:957-61, 2001).

Adoptive transfer is not the only form of therapy which can be applied according to the present technology. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001).

The pharmaceutical compositions and methods of treatment described according to the present technology may also be used for immunization or vaccination to therapeutically treat or prevent a disease described herein. According to the present technology, the terms “immunization” or “vaccination” preferably relate to an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization or a vaccination, preferably one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and/or stimulating particular lymphocytes. Adjuvants are known and comprise in a non-limiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund’s adjuvant, complete Freund’s adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 μg to about 100 μg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

The present technology also provides for administration of nucleic acids, proteins or peptides. Proteins and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The present technology also provides for administering nucleic acids in vivo by using vectors such as viruses and target-controlled liposomes. If according to the present technology reference is made to the administration or incorporation into pharmaceutical compositions of nucleic acids this includes embodiments wherein the nucleic acid is present in such vectors.

In a preferred embodiment, a virus or viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the present technology may be administered in pharmaceutically compatible preparations. Such preparations may usually contain pharmaceutically compatible concentrations of salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds.

The therapeutically active compounds of the present technology may be administered via any conventional route, including by injection or infusion. The administration may be carried out, for example, orally, intravenously, intraperitoneally, intramuscularly, subcutaneously or transdermally. Preferably, antibodies are therapeutically administered by way of a lung aerosol. Antisense nucleic acids are preferably administered by slow intravenous administration.

The compositions of the present technology are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. According to the present technology, a diagnosis or treatment of cancer may also include the diagnosis or treatment of cancer metastases which have already formed or will form. According to the present technology, the term "treatment" comprises therapeutic and prophylactic treatment, i.e. prevention.

An effective amount of a composition of the present technology will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the present technology are preferably sterile and contain an effective amount of the therapeutically active substance to generate the desired reaction or the desired effect.

The doses administered of the compositions of the present technology may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 μg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the present technology are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the present technology. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the present technology may comprise a pharmaceutically compatible carrier. According to the present technology, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the present technology are usually such that no interaction occurs which substantially impairs the desired pharmaceutical efficacy.

The pharmaceutical compositions of the present technology may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the present technology may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present technology is described in detail by the figures and examples below, which are used only for illustration purposes and are not meant to be limiting. Owing to the description and the examples, further embodiments which are likewise included in the present technology are accessible to the skilled worker.

EXAMPLES

The techniques and methods mentioned herein are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1

Screening for Placenta-Specific Genes Aberrantly Activated in Tumors

Tissues and Cell Lines

Tissues were obtained as human surplus materials during routine diagnostic or therapeutic procedures and were stored at −80° C. until use. Cell lines were purchased from the American Type Culture Collection (ATCC) and the German Resource Collection of Microorganisms and Cell Culture (DSMZ).

RNA Isolation and Microarray Hybridization

Total RNA was isolated using the RNeasy Mini Kit protocol (Qiagen). Quantification of isolated RNA was performed using UV-spectroscopy and the quality was determined both by $A_{260}/A_{280}$ ratio and Agilent bioanalyzer (Agilent Technologies). Five micrograms total RNA were used for cDNA synthesis with 5 pmol $\mu l^{-1}$ T7-oligo$(dT)_{24}$ primer and was performed at 43° C. for 90 minutes with the "Superscript First-Strand Synthesis-System" for RT-PCR (Invitrogen). Second-strand synthesis was performed with complete cDNA. The cDNA solution was incubated at 16° C. for 2 hours followed by an incubation step for 20 min with 6 U T4-DNA polymerase at 16° C. and the reaction was stopped using 10 μl of 0.5 M EDTA. After purification of the double stranded cDNA using the GeneChip Sample Cleanup Module (Affymetrix) labeled cRNA was generated from the cDNA sample by an in vitro transcription reaction that was supplemented with biotin-11-CTP and biotin-16-UTP (Enzo Diagnostics) according to the manufacturer's instructions. The cRNA was quantified by $A_{260}$, and the quality was determined using the labchip bioanalyzer (Agilent). Only cRNA specimens with a high quality were selected for further analyses. Fragmented cRNA (15 μg) was used to prepare 300 μl hybridization cocktail (100 mM MES, 1 M NaCl, 20 mM EDTA, 0.01% Tween-20) containing 0.1 mg $ml^{-1}$ of herring sperm DNA, and 0.5 mg $ml^{-1}$ acetylated bovine serum albumin. Control cRNA was used in order to compare hybridization efficiencies between arrays and to standardize the quantification of measured transcript levels and was included as component of the 'Eukaryotic Hybridization Control kit' (Affymetrix, Santa Clara, Calif., USA). The cocktails were heated to 95° C. for 5 minutes, equilibrated at 45° C. for 5 minutes, and clarified by centrifugation. The cocktail was hybridized to HG U133 Plus 2.0 arrays (Affymetrix) at 45° C. for 16 hours. The arrays were washed and stained with a streptavidin-conjugated fluor using the GeneChip fluidics station protocol EukGE-WS2 (Affymetrix) according to the manufacturer's instructions. Arrays were scanned with an argon-ion laser confocal scanner (Hewlett-Packard, Santa Clara, Calif.) with detection at 570 nm. Data were extracted using Microarray Suite version 5.0 (Affymetrix) and linearly scaled to achieve an average intensity of 2,500 per gene. Text files were exported to determine the intensity of each interrogating oligonucleotide perfect match probe cells or mismatch probe cells. In addition, the ratios of 5'- and 3'-ends of mRNA were analyzed of six randomly selected specimens (two of each group) using microarray test-chips (Test3 Array) containing 24 human housekeeping/maintenance genes (Affymetrix) and RNA degradation was not observed.

Bioinformatic Analysis

The GeneChip® Operating Software 1.4 (Affymetrix) and ArrayAssist software package 5.2 (Stratagene) were used for statistical analyses.

Results

Screening of samples from the 18 normal tissues shown below in table 1 and 30 tumor cell lines of different entities shown below in table 2 resulted in the sequences described herein which are expressed in placenta among the normal tissues investigated and in tumor cell lines.

TABLE 1

Tissues used for microarray expression analysis

| Tissue | Number |
|---|---|
| Placenta | 2 |
| Testis | 2 |
| Mammary gland | 2 |
| Thymus | 2 |
| Skin | 2 |
| Liver | 2 |
| Colon | 2 |
| Esophagus | 2 |
| Stomach | 2 |
| Lung | 2 |
| Kidney | 2 |
| Lymph node | 2 |
| Skeletal muscle | 2 |
| Myocard | 1 |
| Brain | 1 |
| Cerebellum | 1 |
| resting PBMCs | 2 |
| activ. PBMCs | 2 |

TABLE 2

Cell lines used for microarray expression analysis

| Cell line | Tissue |
|---|---|
| BT-549 | Breast cancer |
| MDA-MB-231 metastasizing | Breast cancer |
| MDA-MB-231 non-metastasizing | Breast cancer |
| MDA-MB-435S | Breast cancer |
| MDA-MB-468 | Breast cancer |
| SK-BR-3 | Breast cancer |
| Caov-3 | Ovarian cancer |
| FU-OV | Ovarian cancer |
| NIH-OVCAR-3 | Ovarian cancer |
| COLO-205 | Colorectal cancer |
| HCT-116 | Colorectal cancer |
| HCT-116 DKO | Colorectal cancer |
| HCT-15 | Colorectal cancer |
| HT-29 | Colorectal cancer |
| LOVO | Colorectal cancer |
| SW-480 | Colorectal cancer |
| CPC-N | Lung cancer |
| LOU-NH-91 | Lung cancer |
| SHP-77 | Lung cancer |
| SK-MES-1 | Lung cancer |
| NCI-H-187 | Lung cancer |
| NCI-H-209 | Lung cancer |
| NCI-H-522 | Lung cancer |
| DU-145 | Prostate cancer |
| Uncap | Prostate cancer |
| PC-3 | Prostate cancer |
| MEL-JUSO | Melanoma |
| Murkowski | Melanoma |
| SK-MEL-37 | Melanoma |
| HELA | Cervical cancer |

Example 2

Validation of the Identified Tumor-Associated Markers

1. Examination of RNA Expression

The identified tumor-associated markers are first validated with the aid of RNA which is obtained from various tissues or from tissue-specific cell lines. Since the differential expression pattern of healthy tissue in comparison with tumor tissue is of decisive importance for the subsequent therapeutic application, the target genes are preferably characterized with the aid of these tissue samples.

Total RNA is isolated from native tissue samples or from tumor cell lines by standard methods of molecular biology. Said isolation may be carried out, for example, with the aid of the RNeasy Maxi kit (Qiagen, Cat. No. 75162) according to the manufacturer's instructions. This isolation method is based on the use of chaotropic reagent guanidinium isothiocyanate. Alternatively, acidic phenol can be used for isolation (Chomczynski & Sacchi, Anal. Biochem. 162: 156-159, 1987). After the tissue has been worked up by means of guanidinium isothiocyanate, RNA is extracted with acidic phenol, subsequently precipitated with isopropanol and taken up in DEPC-treated water.

2-4 μg of the RNA isolated in this way are subsequently transcribed into cDNA, for example by means of Superscript II (Invitrogen) according to the manufacturer's protocol. cDNA synthesis is primed with the aid of random hexamers (e.g. Roche Diagnostics) according to standard protocols of the relevant manufacturer. For quality control, the cDNAs are amplified over 30 cycles, using primers specific for the p53 gene which is expressed only lowly. Only p53-positive cDNA samples will be used for the subsequent reaction steps.

The targets are analyzed in detail by carrying out an expression analysis by means of PCR or quantitative PCR (qPCR) on the basis of a cDNA archive which has been isolated from various normal and tumor tissues and from tumor cell lines. For this purpose, 0.5 μl of cDNA of the above reaction mixture is amplified by a DNA polymerase (e.g. 1 U of HotStarTaq DNA polymerase, Qiagen) according to the protocols of the particular manufacturer (total volume of the reaction mixture: 25-50 μl). Aside from said polymerase, the amplification mixture comprises 0.3 mM dNTPs, reaction buffer (final concentration 1×, depending on the manufacturer of the DNA polymerase) and in each case 0.3 mM gene-specific "sense" and "antisense" primers.

The specific primers of the target gene are, as far as possible, selected in such a way that they are located in two different exons so that genomic contaminations do not lead to false-positive results. In a non-quantitative end point PCR, the cDNA is typically incubated at 95° C. for 15 minutes in order to denature the DNA and to activate the Hot-Start enzyme. Subsequently the DNA is amplified over 35 cycles (1 min at 95° C., 1 min at the primer-specific hybridization temperature (approx. 55-65° C.), 1 min at 72° C. to elongate the amplicons). Subsequently, 10 μl of the PCR mixture are applied to agarose gels and fractionated in the electric field. The DNA is made visible in the gels by staining with ethidium bromide and the PCR result is documented by way of a photograph.

As an alternative to conventional PCR, expression of a target gene may also be analyzed by quantitative real time PCR. Meanwhile various analytical systems are available for this analysis, of which the best known ones are the ABI PRISM sequence detection system (TaqMan, Applied Biosystems), the iCycler (Biorad) and the Light cycler (Roche Diagnostics). As described above, a specific PCR mixture is subjected to a run in the real time instruments. By adding a DNA-intercalating dye (e.g. ethidium bromide, CybrGreen), the newly synthesized DNA is made visible by specific light excitation (according to the dye manufacturers' information). A multiplicity of points measured during amplification enables the entire process to be monitored and the nucleic acid concentration of the target gene to be determined quantitatively. The PCR mixture is normalized by measuring a housekeeping gene (e.g. 18S RNA, β-actin). Alternative strategies via fluorescently labeled DNA probes likewise allow quantitative determination of the target gene of a specific tissue sample (see TaqMan applications from Applied Biosystems).

As shown in FIG. 1, placenta was confirmed in RT-PCR analyses as the only healthy tissue expressing the nucleic acid sequence according to SEQ ID NO:540. No significant expression was found in any other normal tissue. However, high and significant levels of expression were found in breast cancer.

Figure 2:
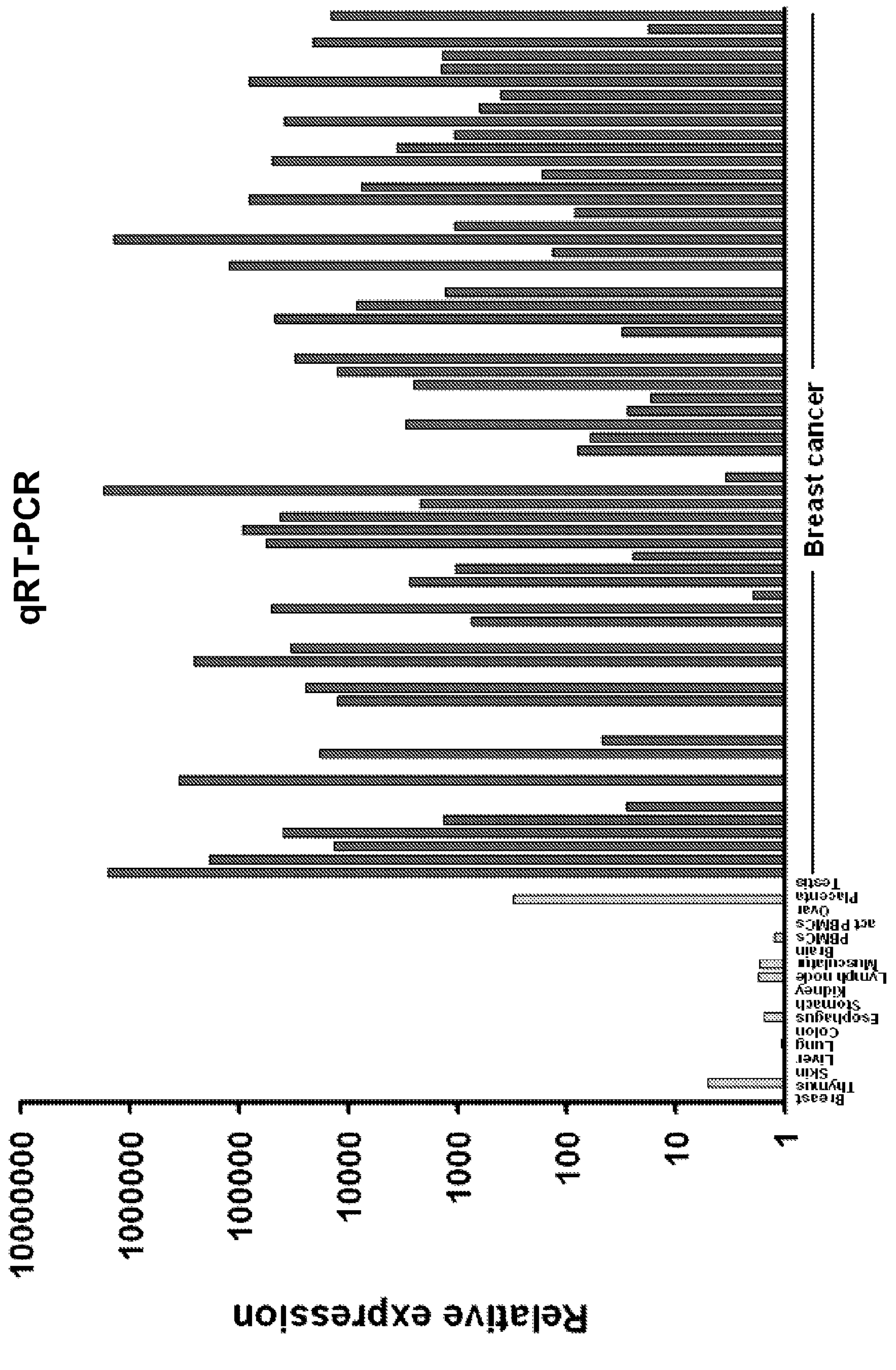
FIG. 2. Quantitative expression of a tumor-associated nucleic acid identified according to the present technology in normal tissues and cancer tissue. Quantitative RT-PCR showed selective expression of the nucleic acid sequence according to SEQ ID NO:540 in placenta tissue and mamma carcinomas.

Quantitative real-time RT-PCR analyses revealed that the nucleic acid sequence according to SEQ ID NO:540 was expressed in significant levels in the majority of breast cancer samples analyzed; cf. FIG. 2.

2. Cloning

The complete target gene which is required for further characterization of the tumor-associated marker is cloned according to common molecular-biological methods (e.g. in "Current Protocols in Molecular Biology", John Wiley & Sons Ltd., Wiley InterScience). In order to clone the target gene or to analyze its sequence, said gene is first amplified by a DNA polymerase having a proof reading function (e.g. pfu, Roche Diagnostics). The amplicon is then ligated by standard methods into a cloning vector. Positive clones are identified by sequence analysis and subsequently characterized with the aid of prediction programs and known algorithms.

3. Prediction of the Protein

Genes found according to the present technology (in particular those from the RefSeq XM domain) may require cloning of the full-length gene, determination of the open reading frame and deduction and analysis of the protein sequence.

In order to clone the full-length sequence, common protocols for the rapid amplification of cDNA ends and the screening of cDNA expression libraries with gene-specific probes may be used (Sambrook et al., *Molecular Cloning: A Laboratory Manual,* 2nd edition (1989), Cold Spring Harbor Laboratory Press, Cold Spring Harbor, N.Y.).

After assembling the fragments found in this way, potential open reading frames (ORF) can be predicted using common prediction programs. Since the position of the PolyA tail and of polyadenylation motifs predetermines the orientation of the potential gene product, only the 3 reading frames of that particular orientation remain out of a possible 6 reading frames. The former often yield only one sufficiently large open reading frame which may code for a protein, while the other reading frames have too many stop codons and would not code for any realistic protein. In the case of alternative open reading frames, identification of the authentic ORF is assisted by taking into account the Kozak criteria for optimal transcription initiation and by analyzing the deduced protein sequences which may arise. Said ORF is further verified by generating immune sera against proteins deduced from the potential ORFs and analyzing said immune sera for recognition of a real protein in tissues and cell lines.

4. Production of Antibodies

The tumor-associated antigens identified according to the present technology are characterized, for example, by using antibodies. The present technology further comprises the diagnostic or therapeutic use of antibodies. Antibodies may recognize proteins in the native and/or denatured state (Anderson et al., *J. Immunol.* 143: 1899-1904, 1989; Gardsvoll, *J. Immunol. Methods* 234: 107-116, 2000; Kayyem et al., *Eur. J. Biochem.* 208: 1-8, 1992; Spiller et al., *J. Immunol. Methods* 224: 51-60, 1999).

Antisera comprising specific antibodies which specifically bind to the target protein may be prepared by various standard methods; cf., for example, "Monoclonal Antibodies: A Practical Approach" by Phillip Shepherd, Christopher Dean ISBN 0-19-963722-9, "Antibodies: A Laboratory Manual" by Ed Harlow, David Lane ISBN: 0879693142 and "Using Antibodies: A Laboratory Manual: Portable Protocol NO" by Edward Harlow, David Lane, Ed Harlow ISBN: 0879695447. It is also possible here to generate affine and specific antibodies which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods.* 234: 107-116, 2000). This is especially important in the preparation of antibodies which are intended to be used therapeutically but also for many diagnostic applications. For this purpose, both the complete protein and extracellular partial sequences may be used for immunization.

Immunization and Production of Polyclonal Antibodies

Various immunization protocols are published. A species (e.g. rabbits, mice) is immunized by a first injection of the desired target protein. The immune response of the animal to the immunogen can be enhanced by a second or third immunization within a defined period of time (approx. 2-4 weeks after the previous immunization). Blood is taken from said animals and immune sera obtained, again after various defined time intervals (1st bleeding after 4 weeks, then every 2-3 weeks, up to 5 takings). The immune sera taken in this way comprise polyclonal antibodies which may be used to detect and characterize the target protein in Western blotting, by flow cytometry, immunofluorescence or immunohistochemistry.

The animals are usually immunized by any of four well-established methods, with other methods also in existence. The immunization may be carried out using peptides specific for the target protein, using the complete protein, or using extracellular partial sequences of a protein which can be identified experimentally or via prediction programs. Since the prediction programs do not always work perfectly, it is also possible to employ two domains separated from one another by a transmembrane domain. In this case, one of the two domains has to be extracellular, which may then be proved experimentally (see below). Immunization is offered commercially by different service providers.

(1) In the first case, peptides (length: 8-12 amino acids) are synthesized by in vitro methods (possibly carried out by a commercial service), and said peptides are used for immunization. Normally 3 immunizations are carried out (e.g. with a concentration of 5-100 μg/immunization).

(2) Alternatively, immunization may be carried out using recombinant proteins. For this purpose, the cloned DNA of the target gene is cloned into an expression vector and the target protein is synthesized, for example, cell-free in vitro, in bacteria (e.g. *E. coli*), in yeast (e.g. *S. pombe*), in insect cells or in mammalian cells, according to the conditions of the particular manufacturer (e.g. Roche Diagnostics, Invitrogen, Clontech, Qiagen). It is also possible to synthesize the target protein with the aid of viral expression systems (e.g. baculovirus, vacciniavirus, adenovirus). After it has been synthesized in one of said systems, the target protein is purified, normally by employing chromatographic methods. In this context, it is also possible to use for immunization proteins which have a molecular anchor as an aid for purification (e.g. His tag, Qiagen; FLAG tag, Roche Diagnostics; GST fusion proteins). A multiplicity of protocols can be found, for example, in "Current Protocols in Molecular Biology", John Wiley & Sons Ltd., Wiley InterScience. After the target protein has been purified, an immunization is carried out as described above.

(3) If a cell line is available which synthesizes the desired protein endogenously, it is also possible to use this cell line directly for preparing the specific antiserum. In this case, immunization is carried out by 1-3 injections with in each case approx. 1-5×$10^7$ cells.

(4) The immunization may also be carried out by injecting DNA (DNA immunization). For this purpose, the target gene is first cloned into an expression vector so that the target sequence is under the control of a strong eukaryotic promoter (e.g. CMV promoter). Subsequently, DNA (e.g. 1-10 μg per injection) is transferred as immunogen using a gene gun into capillary regions with a strong blood flow in an organism (e.g. mouse, rabbit). The transferred DNA is taken up by the animal's cells, the target gene is expressed, and the animal finally develops an immune response to the target protein (Jung et al., *Mol. Cells* 12: 41-49, 2001; Kasinrerk et al., *Hybrid Hybridomics* 21: 287-293, 2002).

Production of Monoclonal Antibodies

Monoclonal antibodies are traditionally produced with the aid of the hybridoma technology (technical details: see "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142, "Using Antibodies: A Laboratory Manual: Portable Protocol NO" by Edward Harlow, David Lane, Ed Harlow ISBN: 0879695447). A new method which is also used is the "SLAM" technology. Here, B cells are isolated from whole blood and the cells are made monoclonal. Subsequently the supernatant of the isolated B cell is analyzed for its antibody specificity. In contrast to the hybridoma technology, the variable region of the antibody gene is then amplified by single-cell PCR and cloned into a suitable vector. In this manner production of monoclonal antibodies is accelerated (de Wildt et al., J. Immunol. Methods 207:61-67, 1997).

5. Validation of the Targets by Protein-Chemical Methods Using Antibodies

The antibodies which can be produced as described above can be used to further analyze the target protein as follows:

Specificity of the Antibody

Assays based on cell culture with subsequent Western blotting are most suitable for demonstrating the fact that an antibody binds specifically only to the desired target protein (various variations are described, for example, in "Current Protocols in Protein Chemistry", John Wiley & Sons Ltd., Wiley InterScience). For the demonstration, cells are transfected with a cDNA for the target protein, which is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). As an alternative, it is also possible to use cell lines which express the target gene endogenously (detection via target gene-specific RT-PCR). As a control, in the ideal case, homologous genes are cotransfected in the experiment, in order to be able to demonstrate in the following Western blot the specificity of the analyzed antibody.

In the subsequent Western blotting, cells from cell culture or tissue samples which might contain the target protein are lysed in a 1% strength SDS solution, and the proteins are denatured in the process. The lysates are fractionated according to size by electrophoresis on 8-15% strength denaturing polyacrylamide gels (contain 1% SDS) (SDS polyacrylamide gel electrophoresis, SDS-PAGE). The proteins are then transferred by one of a plurality of blotting methods (e.g. semi-dry electroblot; Biorad) to a specific membrane (e.g. nitrocellulose, Schleicher & Schüll). The desired protein can be visualized on this membrane. For this purpose, the membrane is first incubated with the antibody which recognizes the target protein (dilution approx. 1:20-1:200, depending on the specificity of said antibody), for 60 minutes. After a washing step, the membrane is incubated with a second antibody which is coupled to a marker (e.g. enzymes such as peroxidase or alkaline phosphatase) and which recognizes the first antibody. It is then possible to make the target protein visible on the membrane in a color or chemi-luminescent reaction (e.g. ECL, Amersham Bioscience). An antibody with a high specificity for the target protein should in the ideal case only recognize the desired protein itself.

Localization of the Target Protein

Various methods are used to confirm the membrane localization, identified in the in silico approach, of the target protein. An important and well-established method using the antibodies described above is immunofluorescence (IF). For this purpose, cells of established cell lines which either synthesize the target protein (detection of the RNA by RT-PCR or of the protein by Western blotting) or else have been transfected with plasmid DNA are utilized. A wide variety of methods (e.g. electroporation, liposome-based transfection, calcium phosphate precipitation) are well established for transfection of cell lines with DNA (e.g. Lemoine et al., *Methods Mol. Biol.* 75: 441-7, 1997). The plasmid transfected into the cells, in immunofluorescence, may encode the unmodified protein or else couple different amino acid markers to the target protein. The principle markers are, for example, the fluorescent green fluorescent protein (GFP) in various differentially fluorescent forms, short peptide sequences of 6-12 amino acids for which high-affinity and specific antibodies are available, or the short amino acid sequence Cys-Cys-X-X-Cys-Cys (SEQ ID NO: 636)which can bind via its cysteines specific fluorescent substances (Invitrogen). Cells which synthesize the target protein are fixed, for example, with paraformaldehyde or methanol. The cells may then, if required, be permeabilized by incubation with detergents (e.g. 0.2% Triton X-100). The cells are then incubated with a primary antibody which is directed against the target protein or against one of the coupled markers. After a washing step, the mixture is incubated with a second antibody coupled to a fluorescent marker (e.g. fluorescein, Texas Red, Dako), which binds to the first antibody. The cells labeled in this way are then overlaid with glycerol and analyzed with the aid of a fluorescence microscope according to the manufacturer's information. Specific fluorescence emissions are achieved in this case by specific excitation depending on the substances employed. The analysis usually permits reliable localization of the target protein, the antibody quality and the target protein being confirmed in double stainings with, in addition to the target protein, also the coupled amino acid markers or other marker proteins whose localization has already been described in the literature being stained. GFP and its derivatives represent a special case, being excitable directly and themselves fluorescing. The membrane permeability which may be controlled through the use of detergents, in immunofluorescence, allows demonstration of whether an immunogenic epitope is located inside or outside the cell. The prediction of the selected proteins can thus be supported experimentally. An alternative possibility is to detect extracellular domains by means of flow cytometry. For this purpose, cells are fixed under non-permeabilizing conditions (e.g. with PBS/Na azide/2% FCS/5 mM EDTA) and analyzed in a flow cytometer in accordance with the manufacturer's instructions. Only extracellular epitopes can be recognized by the antibody to be analyzed in this method. A difference from immunofluorescence is that it is possible to distinguish between dead and living cells by using, for example, propidium iodide or trypan blue, and thus avoid false-positive results.

Another important detection is by immunohistochemistry (IHC) on specific tissue samples. The aim of this method is to identify the localization of a protein in a functionally intact tissue aggregate. IHC serves specifically for (1) being able to estimate the amount of target protein in tumor and normal tissues, (2) analyzing how many cells in tumor and healthy tissues synthesize the target gene, and (3) defining the cell type in a tissue (tumor, healthy cells) in which the target protein is detectable. Alternatively, the amounts of protein of a target gene may be quantified by tissue immunofluorescence using a digital camera and suitable software (e.g. Tillvision, Till-photonics, Germany). The technology has frequently been published, and details of staining and microscopy can therefore be found, for example, in "Diagnostic Immunohistochemistry" by David J., MD Dabbs ISBN: 0443065667 or in "Microscopy, Immunohistochemistry, and Antigen Retrieval Methods: For Light and Electron Microscopy" ISBN: 0306467704. It should be noted that, owing to the properties of antibodies, different protocols have to be used (an example is described below) in order to obtain a meaningful result.

Normally, histologically defined tumor tissues and, as reference, comparable healthy tissues are employed in IHC. It is also possible to use as positive and negative controls cell lines in which the presence of the target gene is known through RT-PCR analyses. A background control must always be included.

Formalin-fixed (another fixation method, for example with methanol, is also possible) and paraffin-embedded tissue pieces with a thickness of 4 μm are applied to a glass support and deparaffinated with xylene, for example. The samples are washed with TBS-T and blocked in serum. This is followed by incubation with the first antibody (dilution: 1:2 to 1:2000) for 1-18 hours, with affinity-purified antibodies normally being used. A washing step is followed by incubation with a second antibody which is coupled to an alkaline phosphatase (alternative: for example peroxidase) and directed against the first antibody, for approx. 30-60 minutes. This is followed by a color reaction using alkaline phosphatase (cf., for example, Shi et al., *J. Histochem. Cytochem.* 39: 741-748, 1991; Shin et al., *Lab. Invest.* 64: 693-702, 1991). To demonstrate antibody specificity, the reaction can be blocked by previous addition of the immunogen.

Analysis of Protein Modifications

Secondary protein modifications such as, for example, N- or O-glycosylations or myristilations may impair or even completely prevent the accessibility of immunogenic epitopes and thus call into question the efficacy of antibody therapies. Moreover, it has frequently been demonstrated that the type and amount of secondary modifications differ in normal and tumor tissues (e.g. Durand & Seta, 2000; Clin.

Chem. 46: 795-805; Hakomori, 1996; Cancer Res. 56: 5309-18). The analysis of these modifications is therefore essential to the therapeutic success of an antibody. Potential binding sites can be predicted by specific algorithms.

Analysis of protein modifications usually takes place by Western blotting (see above). Glycosylations which usually have a size of several kDa, especially lead to a larger total mass of the target protein, which can be fractionated in SDS-PAGE. To detect specific O- and N-glycosidic bonds, protein lysates are incubated prior to denaturation by SDS with O- or N-glycosylases (in accordance with their respective manufacturer's instructions, e.g. PNgase, endoglycosidase F, endoglycosidase H, Roche Diagnostics). This is followed by Western blotting as described above. Thus, if there is a reduction in the size of a target protein after incubation with a glycosidase, it is possible to detect a specific glycosylation and, in this way, also analyze the tumor specificity of a modification.

Functional Analysis of the Target Gene

The function of the target molecule may be crucial for its therapeutic usefulness, so that functional analyses are an important component in the characterization of therapeutically utilizable molecules. The functional analysis may take place either in cells in cell culture experiments or else in vivo with the aid of animal models. This involves either switching off the gene of the target molecule by mutation (knockout) or inserting the target sequence into the cell or the organism (knockin). Thus it is possible to analyze functional modifications in a cellular context firstly by way of the loss of function of the gene to be analyzed (loss of function). In the second case, modifications caused by addition of the analyzed gene can be analyzed (gain of function).

a. Functional Analysis in Cells

Transfection. In order to analyze the gain of function, the gene of the target molecule must be transferred into the cell. For this purpose, cells which allow synthesis of the target molecule are transfected with a DNA. Normally, the gene of the target molecule here is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). The gene may be synthesized either transiently, without genomic integration, or else stably, with genomic integration after selection with neomycin, for example.

RNA interference (siRNA). An inhibition of expression of the target gene, which may induce a complete loss of function of the target molecule in cells, may be generated by the RNA interference (siRNA) technology in cells (Hannon, G J. 2002. RNA interference. Nature 418: 244-51; Czauderna et al. 2003. Nucl. Acid Res. 31: 670-82). For this purpose, cells are transfected with short, double-stranded RNA molecules of approx. 20-25 nucleotides in length, which are specific for the target molecule. An enzymic process then results in degradation of the specific RNA of the target gene and thus in reduced expression of the target protein and consequently enables the target gene to be functionally analyzed.

Cell lines which have been modified by means of transfection or siRNA may subsequently be analyzed in different ways. The most common examples are listed below.

1. Proliferation and Cell Cycle Behavior

A multiplicity of methods for analyzing cell proliferation are established and are commercially supplied by various companies (e.g. Roche Diagnostics, Invitrogen; details of the assay methods are described in the numerous application protocols). The number of cells in cell culture experiments can be determined by simple counting or by colorimetric assays which measure the metabolic activity of the cells (e.g. wst-1, Roche Diagnostics). Metabolic assay methods measure the number of cells in an experiment indirectly via enzymic markers. Cell proliferation may be measured directly by analyzing the rate of DNA synthesis, for example by adding bromodeoxyuridine (BrdU), with the integrated BrdU being detected colorimetrically via specific antibodies.

2. Apoptosis and Cytotoxicity

A large number of assay systems for detecting cellular apoptosis and cytotoxicity are available. A decisive characteristic is the specific, enzyme-dependent fragmentation of genomic DNA, which is irreversible and in any case results in death of the cell. Methods for detecting these specific DNA fragments are commercially obtainable. An additional method available is the TUNEL assay which can detect DNA single-strand breaks also in tissue sections. Cytotoxicity is mainly detected via an altered cell permeability which serves as marker of the vitality state of cells. This involves on the one hand the analysis of markers which can typically be found intracellularly in the cell culture supernatant. On the other hand, it is also possible to analyze the absorbability of dye markers which are not absorbed by intact cells. The best-known examples of dye markers are Trypan blue and propidium iodide, a common intracellular marker is lactate dehydrogenase which can be detected enzymatically in the supernatant. Different assay systems of various commercial suppliers (e.g. Roche Diagnostics, Invitrogen) are available.

3. Migration Assay

The ability of cells to migrate is analyzed in a specific migration assay, preferably with the aid of a Boyden chamber (Corning Costar) (Cinamon G., Alon R. J. Immunol. Methods. 2003 February; 273(1-2):53-62; Stockton et al. 2001. Mol. Biol. Cell. 12: 1937-56). For this purpose, cells are cultured on a filter with a specific pore size. Cells which can migrate are capable of migrating through this filter into another culture vessel below. Subsequent microscopic analysis then permits determination of a possibly altered migration behavior induced by the gain of function or loss of function of the target molecule.

b. Functional Analysis in Animal Models

A possible alternative of cell culture experiments for the analysis of target gene function are complicated in vivo experiments in animal models. Compared to the cell-based methods, these models have the advantage of being able to detect faulty developments or diseases which are detectable only in the context of the whole organism. A multiplicity of models for human disorders are available by now (Abate-Shen & Shen. 2002. Trends in Genetics S1-5; Matsusue et al. 2003. J. Clin. Invest. 111:737-47). Various animal models such as, for example, yeast, nematodes or zebra fish have since been characterized intensively. However, models which are preferred over other species are mammalian animal models such as, for example, mice (*Mus musculus*) because they offer the best possibility of reproducing the biological processes in a human context. For mice, on the one hand transgenic methods which integrate new genes into the mouse genome have been established in recent years (gain of function; Jegstrup I. et al. 2003. Lab Anim. 2003 Jan.; 37(1):1-9). On the other hand, other methodical approaches switch off genes in the mouse genome and thus induce a loss of function of a desired gene (knockout models, loss of function; Zambrowicz B P & Sands A T. 2003. Nat. Rev. Drug Discov. 2003 January; 2(1):38-51; Niwa H. 2001. Cell Struct. Funct. 2001 June; 26(3):137-48); technical details have been published in large numbers.

After the mouse models have been generated, alterations induced by the transgene or by the loss of function of a gene can be analyzed in the context of the whole organism (Balling R, 2001. Ann. Rev. Genomics Hum. Genet. 2:463-92). Thus it is possible to carry out, for example, behavior tests as well as to biochemically study established blood parameters. Histological analyses, immunohistochemistry or electron microscopy enable alterations to be characterized at the cellular level. The specific expression pattern of a gene can be detected by in-situ hybridization (Peters T. et al. 2003. Hum. Mol. Genet 12:2109-20).

Example 3

Detailed Analysis of the Identified Tumor-Associated Markers

RNA-Isolation, RT-PCR and Real-Time RT-PCR

RNA extraction, first-strand cDNA synthesis, RT-PCR and real-time RT-PCR was performed as previously described (Koslowski, M. et al., Cancer Res. 62, 6750-6755 (2002), Koslowski, M. et al., Cancer Res. 64, 5988-5993 (2004)). Real-time quantitative expression analysis was performed in a 40 cycle RT-PCR. After normalization to HPRT (sense 5'-TGA CAC TGG CAA AAC AAT GCA-3'(SEQ ID NO: 628)); antisense 5'-GGT CCT TTT CAC CAG CAA GCT-3' (SEQ ID NO: 629), 62° C. annealing) gene-specific transcripts in tumor samples were quantified relative to normal tissues using ΔΔCT calculation.

siRNA Duplexes

The SEQ ID NO:540 siRNA duplexes (Qiagen, Hilden, Germany) were directed against target sequences 5'-NNC CAC AGA AGG UAC CAG UUA-3' (SEQ ID NO: 634) (siRNA#1; sense (5'-CCA CAG AAG GUA CCA GUU AUU-3' (SEQ ID NO: 630)), antisense (5'-UAA CUG GUA CCU UCU GUG GUU-3' (SEQ ID NO: 631)) and 5'-NNC AGC AAG ACU CCC UCU AAA-3' (SEQ ID NO: 635) (siRNA#2; sense (5'-CAG CAA GAC UCC CUC UAA AUU-3' (SEQ ID NO: 632)), antisense (5'-UUU AGA GGG AGU CUU GCU GUU-3' (SEQ ID NO: 633)) of the SEQ ID NO:540 mRNA sequence.

Cell Proliferation Analysis 24 h after transfection with siRNA duplexes $1\times10^4$ cells were cultured for 48 h in medium supplemented with 10% FCS. Proliferation was analyzed by measuring the incorporation of BrdU into newly synthesized DNA strands using the DELFIA cell proliferation Kit (Perkin Elmer, Boston, Mass.) according to the manufacturer's instructions on a Wallac Victor$^2$ multi-label counter (Perkin Elmer, Boston, Mass.).

Figure 3:
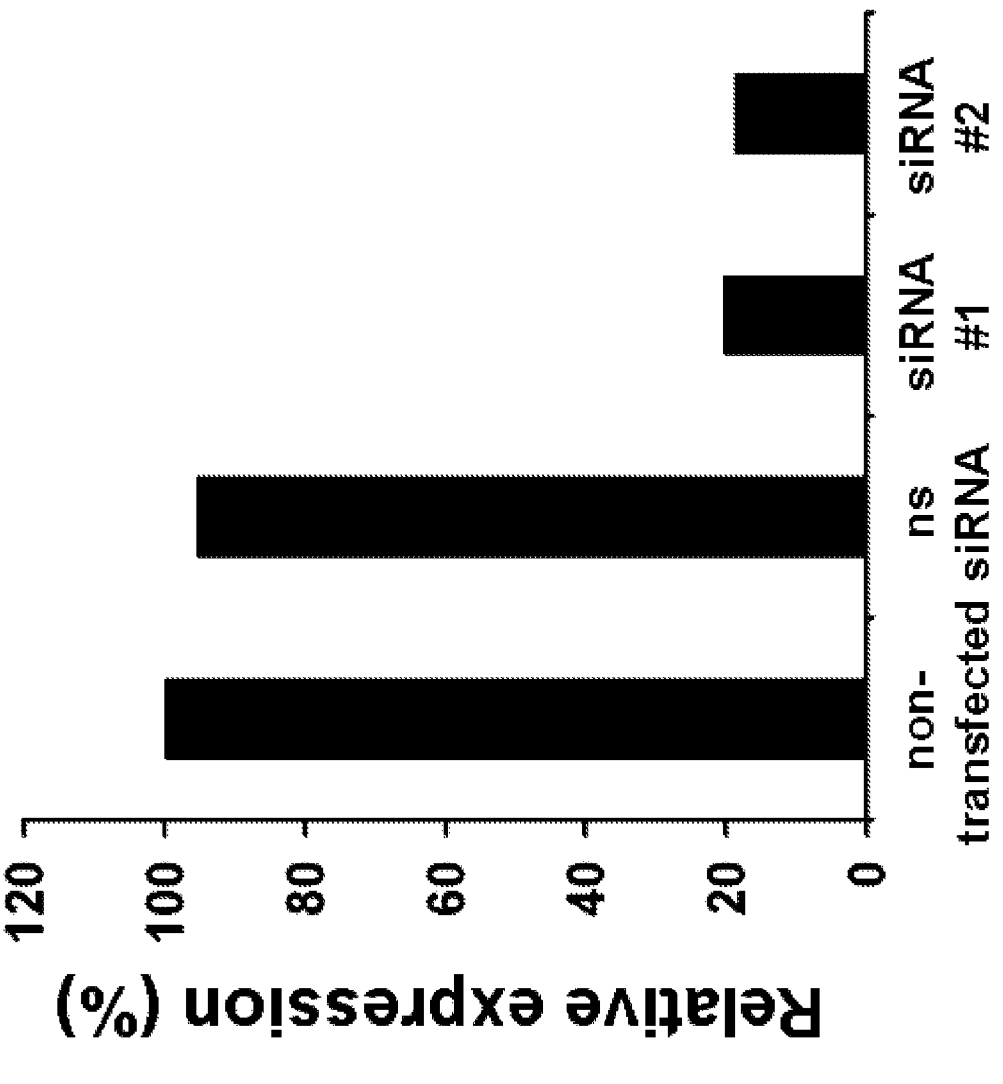
FIG. 3. Quantitative expression of SEQ ID NO:540 mRNA in MCF-7 breast cancer cells. Real-time RT-PCR 24 h after transfection with siRNA oligos showed that both SEQ ID NO:540-specific siRNAs (siRNA#1 (SEQ ID NO:630, 631), siRNA#2 (SEQ ID NO:632, 633)) induce robust silencing of SEQ ID NO:540 expression.

FIG. 3 shows the quantification of SEQ ID NO:540 mRNA expression in MCF-7 breast cancer cells by real-time RT-PCR 24 h after transfection with siRNA oligos. Compared to non-transfected cells and cells transfected with non-silencing (ns) siRNA both SEQ ID NO:540-specific siRNAs (siRNA#1 (SEQ ID NO:630, 631), siRNA#2 (SEQ ID NO:632, 633)) induce robust silencing of SEQ ID NO:540 expression.

Figure 4:
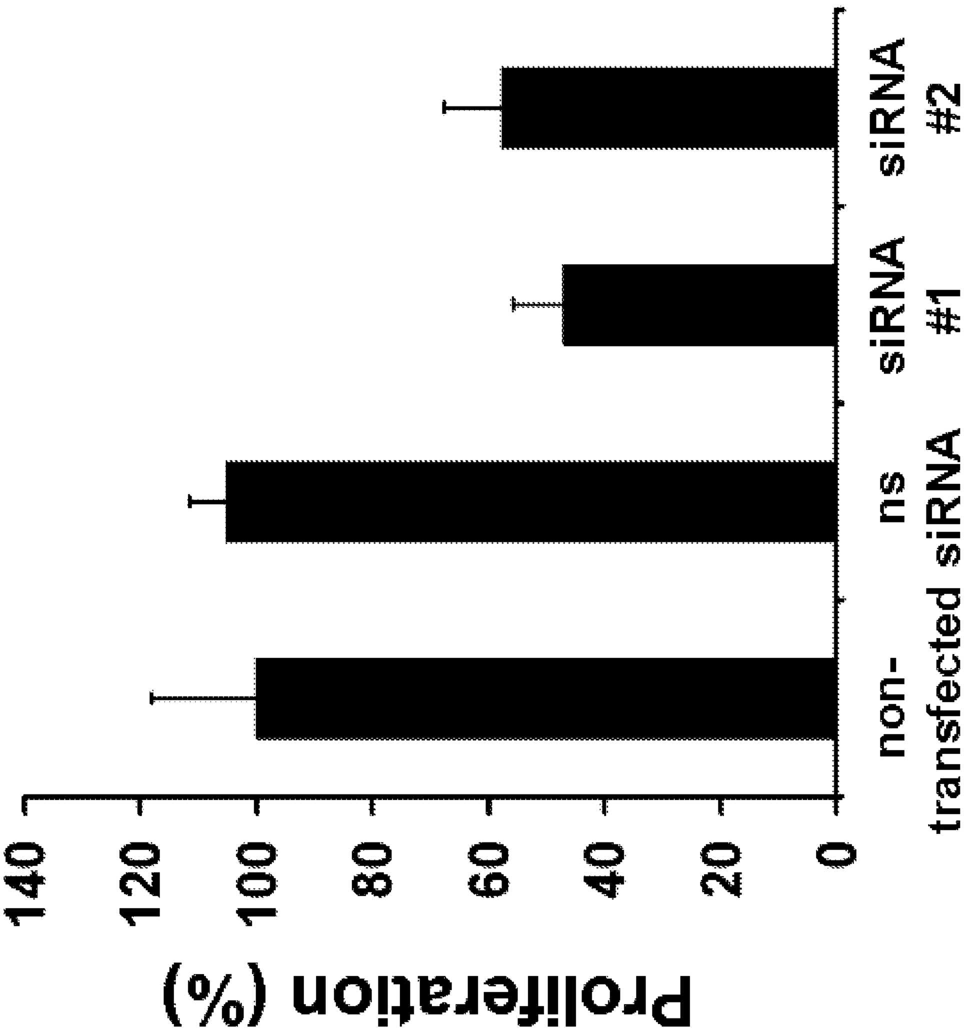
FIG. 4. Silencing of SEQ ID NO:540 expression by transfection with siRNA oligos results in impaired proliferation of MCF-7 breast cancer cells. Proliferation was quantified 96 h after transfection with siRNAs by measuring incorporation of BrdU in newly synthesized DNA strands. These results show that SEQ ID NO:540 is a positive factor for the proliferation of breast cancer cells.

FIG. 4 shows that silencing of SEQ ID NO:540 expression by transfection with siRNA oligos results in impaired proliferation of MCF-7 breast cancer cells. Proliferation was quantified 96 h after transfection with siRNAs by measuring incorporation of BrdU in newly synthesized DNA strands. These results show that SEQ ID NO:540 is a positive factor for the proliferation of breast cancer cells.

Figure 5:
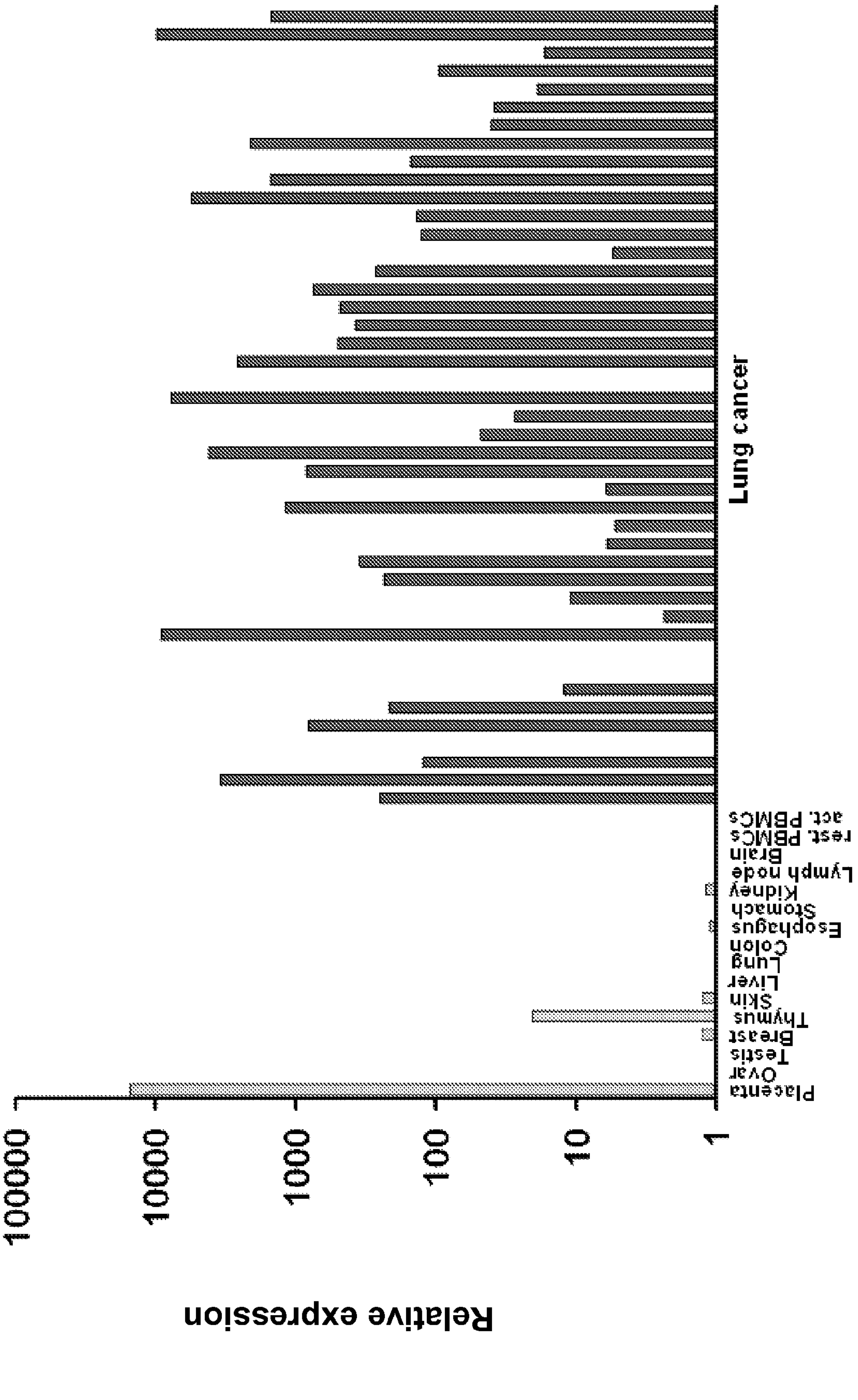
FIG. 5. Quantitative expression of SEQ ID NO:541 in normal tissues and cancer tissue. Real-time RT-PCR showed overexpression of the nucleic acid sequence according to SEQ ID NO:541 in lung cancer.

The nucleotide sequence according to SEQ ID NO:541 was deduced from SEQ ID NO:65 and codes for a 177 aa protein (SEQ ID NO:542) of unknown function. Expression of SEQ ID NO:541 in normal and cancerous tissues was quantified by real-time RT-PCR using sequence-specific oligos (SEQ ID NO:543, 544); see FIG. 5. In normal tissues SEQ ID NO:541 is highly expressed in placenta and shows only weak expression in thymus. SEQ ID NO:541 is overexpressed in lung cancer. Based on these expression results, SEQ ID NO:541 and its expression products qualify as molecular markers and/or target candidates for targeted therapies, in particular for this particular tumor type.

Figure 6:
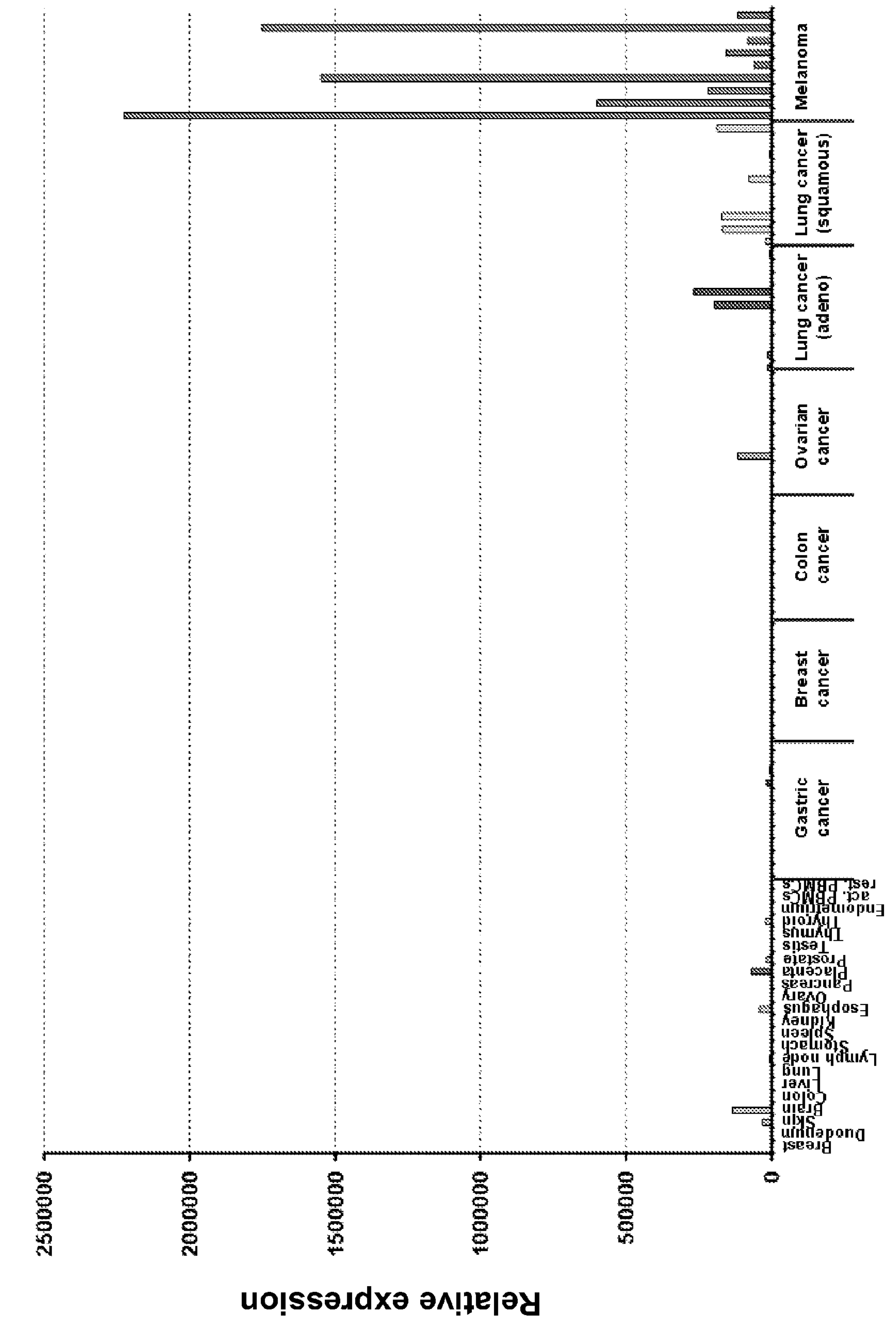
FIG. 6. Quantitative expression of SEQ ID NO:545 in normal tissues and cancer tissues. Real-time RT-PCR showed overexpression of the nucleic acid sequence according to SEQ ID NO:545 in malignant melanomas.

The nucleotide sequence according to SEQ ID NO:545 was deduced from SEQ ID NO:249 and codes for a member of the solute carrier (SLC) group of membrane proteins (SEQ ID NO:546). As is typical of integral membrane proteins, SLCs contain a number of hydrophobic transmembrane alpha helices connected to each other by hydrophilic intra- or extra-cellular loops. Depending on the SLC, these transporters are functional as either monomers or obligate homo- or hetero-oligomers. The protein encoded by SEQ ID NO:545 is a cell surface protein. Expression of SEQ ID NO:545 in normal and cancerous tissues was quantified by real-time RT-PCR using sequence-specific oligos (SEQ ID NO:547, 548); see FIG. 6. Compared to normal tissues, SEQ ID NO:545 is overexpressed in malignant melanomas. Based on these expression results, SEQ ID NO:545 and its expression products qualify as molecular markers and/or target candidates for targeted therapies, in particular for this particular tumor type.

Figure 7:
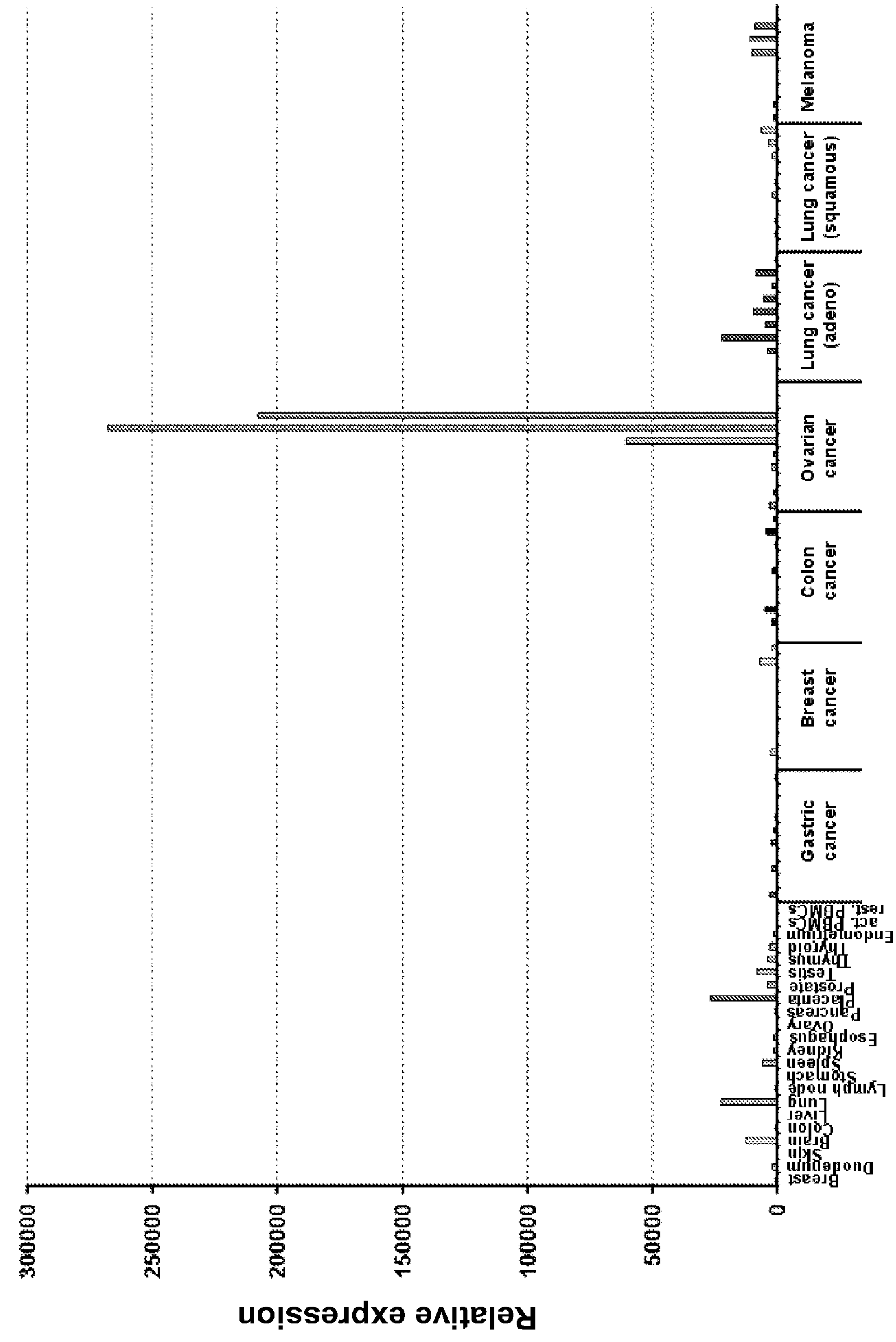
FIG. 7. Quantitative expression of SEQ ID NO:549 in normal tissues and cancer tissues. Real-time RT-PCR showed overexpression of the nucleic acid sequence according to SEQ ID NO:549 in ovarian cancer.

The nucleotide sequence according to SEQ ID NO:549 was deduced from SEQ ID NO:4 and codes for a 763 aa protein (SEQ ID NO:550) of unknown function. The protein harbors two potential transmembrane domains and a typical fibronectin type III domain. Fibronectin is a high-molecular-weight extracellular matrix glycoprotein that binds to membrane spanning receptor proteins (integrins). In addition to integrins, they also bind extracellular matrix components such as collagen, fibrin and heparan sulfate. The protein encoded by SEQ ID NO:549 might represent a hitherto unknown new fibronection-like protein. Expression of SEQ ID NO:549 in normal and cancerous tissues was quantified by real-time RT-PCR using sequence-specific oligos (SEQ ID NO:551, 552); see FIG. 7. Compared to normal tissues, SEQ ID NO:549 is overexpressed in ovarian cancer. Based on these expression results, SEQ ID NO:549 and its expression products qualify as molecular markers and/or target candidates for targeted therapies, in particular of this particular tumor type.

Figure 8:
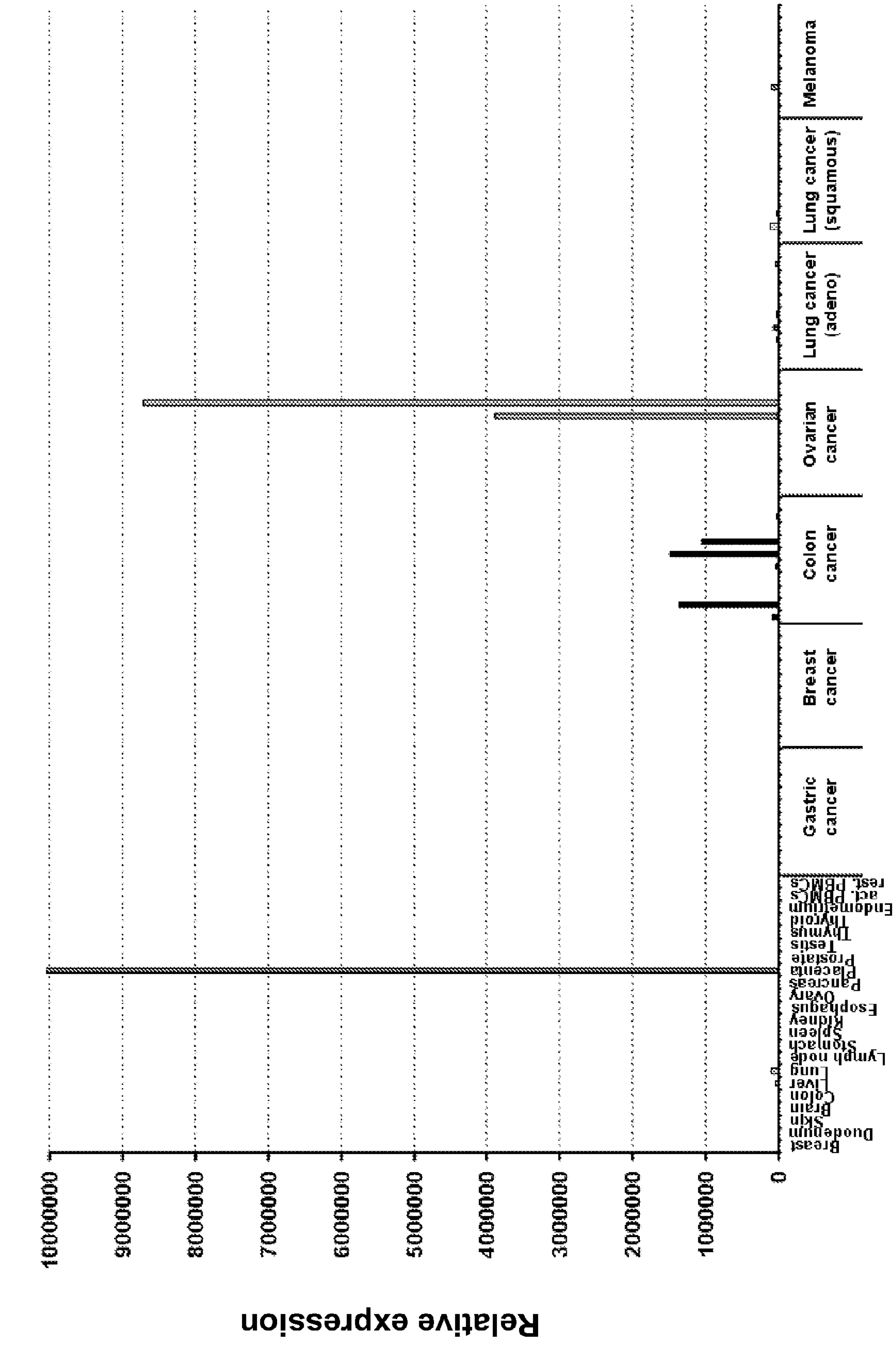
FIG. 8. Quantitative expression of SEQ ID NO:553 in normal tissues and cancer tissues. Real-time RT-PCR showed overexpression of the nucleic acid sequence according to SEQ ID NO:553 in colon cancer and ovarian cancer.

The nucleotide sequence according to SEQ ID NO:553 was deduced from SEQ ID NO:156 and codes for a 496 aa protein (SEQ ID NO:554) of unknown function. The protein harbors a potential transmembrane protein. Expression of SEQ ID NO:553 in normal and cancerous tissues was quantified by real-time RT-PCR using sequence-specific oligos (SEQ ID NO:555, 556); see FIG. 8. In normal tissues SEQ ID NO:553 is highly expressed in placenta. Compared to other normal tissues, SEQ ID NO:553 is overexpressed in colon cancer and ovarian cancer. Based on these expression results, SEQ ID NO:553 and its expression products qualify as molecular markers and/or target candidates for targeted therapies, in particular for these particular tumor types.

Figure 9:
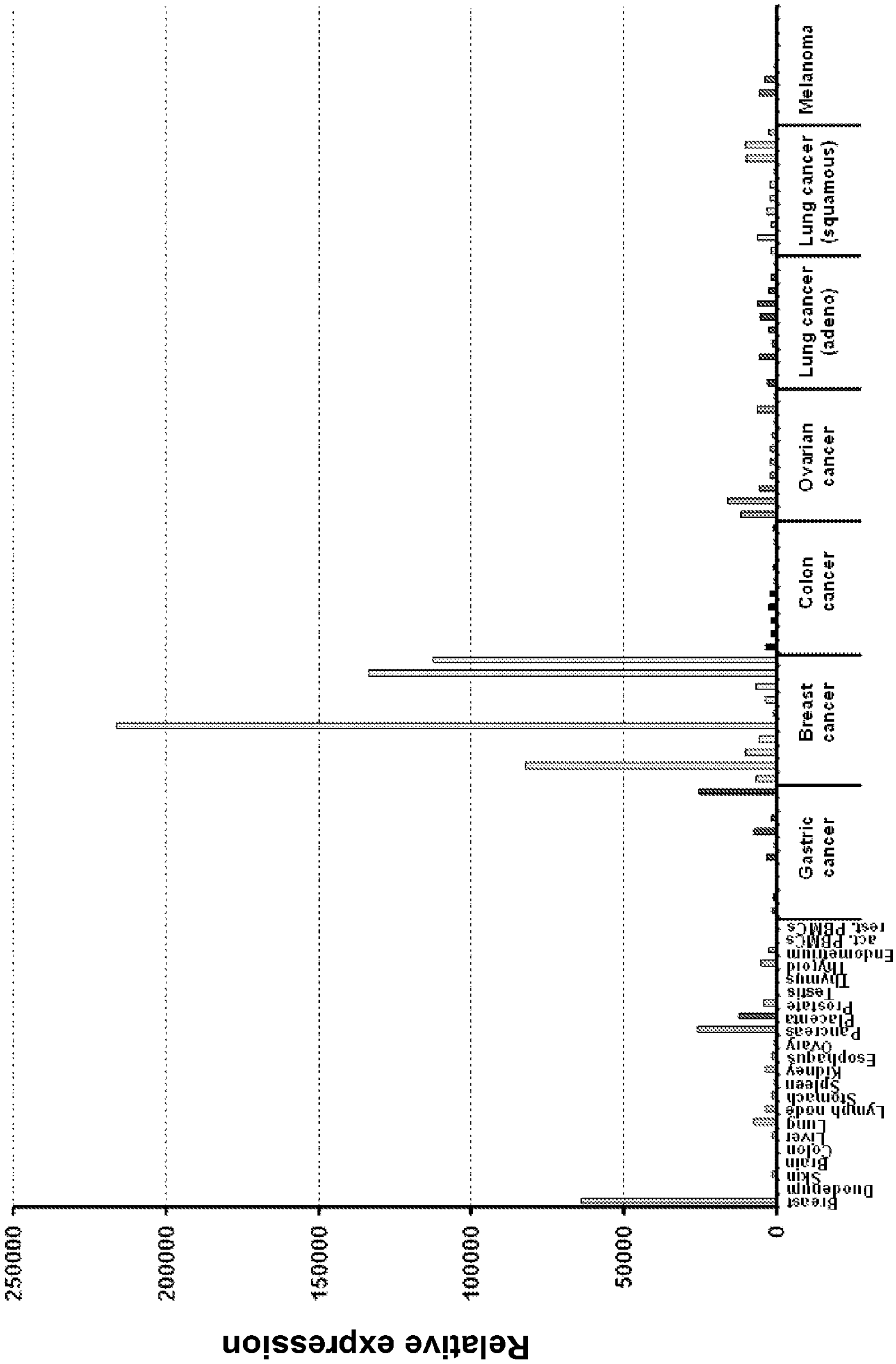
FIG. 9. Quantitative expression of SEQ ID NO:557 in normal tissues and cancer tissues. Real-time RT-PCR showed overexpression of the nucleic acid sequence according to SEQ ID NO:557 in breast cancer.

The nucleotide sequence according to SEQ ID NO:557 was deduced from SEQ ID NO:273. SEQ ID NO:557 represents a partial cDNA with no apparent open reading frame. Expression of SEQ ID NO:557 in normal and cancerous tissues was quantified by real-time RT-PCR using sequence-specific oligos (SEQ ID NO:558, 559); see FIG. 9. In normal tissues high expression of SEQ ID NO:557 is detectable in breast. Compared to normal tissues, SEQ ID NO:557 is overexpressed in breast cancer. Based on these expression results, SEQ ID NO:557 and its expression products qualify as molecular markers and/or target candidates for targeted therapies, in particular for this particular tumor type.

Figure 10:
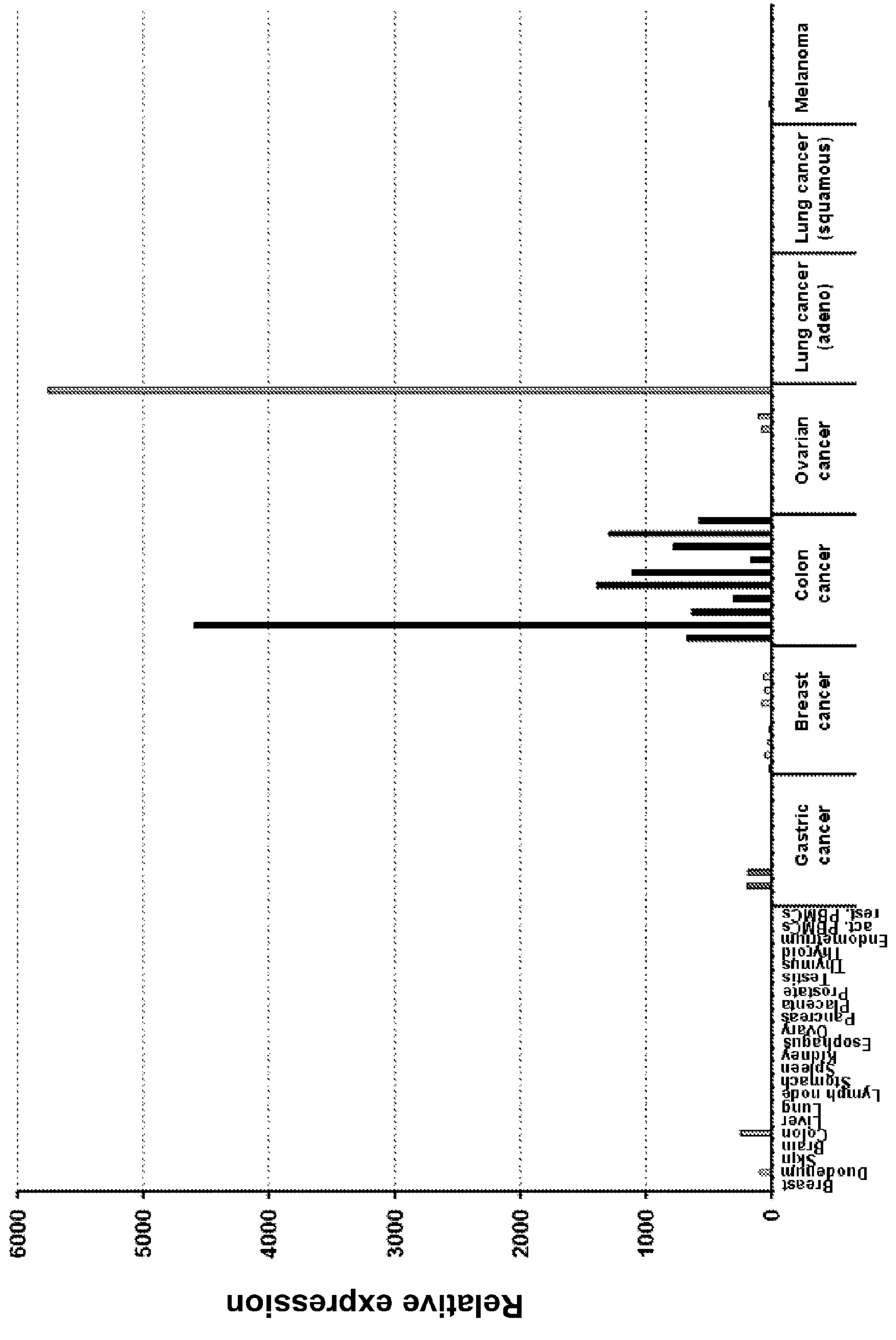
FIG. 10. Quantitative expression of SEQ ID NO:560 in normal tissues and cancer tissues. Real-time RT-PCR showed overexpression of the nucleic acid sequence according to SEQ ID NO:560 in colon cancer and ovarian cancer.

The nucleotide sequence according to SEQ ID NO:560 was deduced from SEQ ID NO:135. SEQ ID NO:560 has no apparent open reading frame. Expression of SEQ ID NO:560 in normal and cancerous tissues was quantified by real-time RT-PCR using sequence-specific oligos (SEQ ID NO:561, 562); see FIG. 10. In normal tissues expression of SEQ ID NO:560 is detectable in duodenum and colon. Compared to normal tissues, SEQ ID NO:560 is overexpressed in colon cancer and ovarian cancer. Based on these expression results, SEQ ID NO:560 and its expression products qualify as molecular markers and/or target candidates for targeted therapies, in particular for these particular tumor types.

Figure 11:
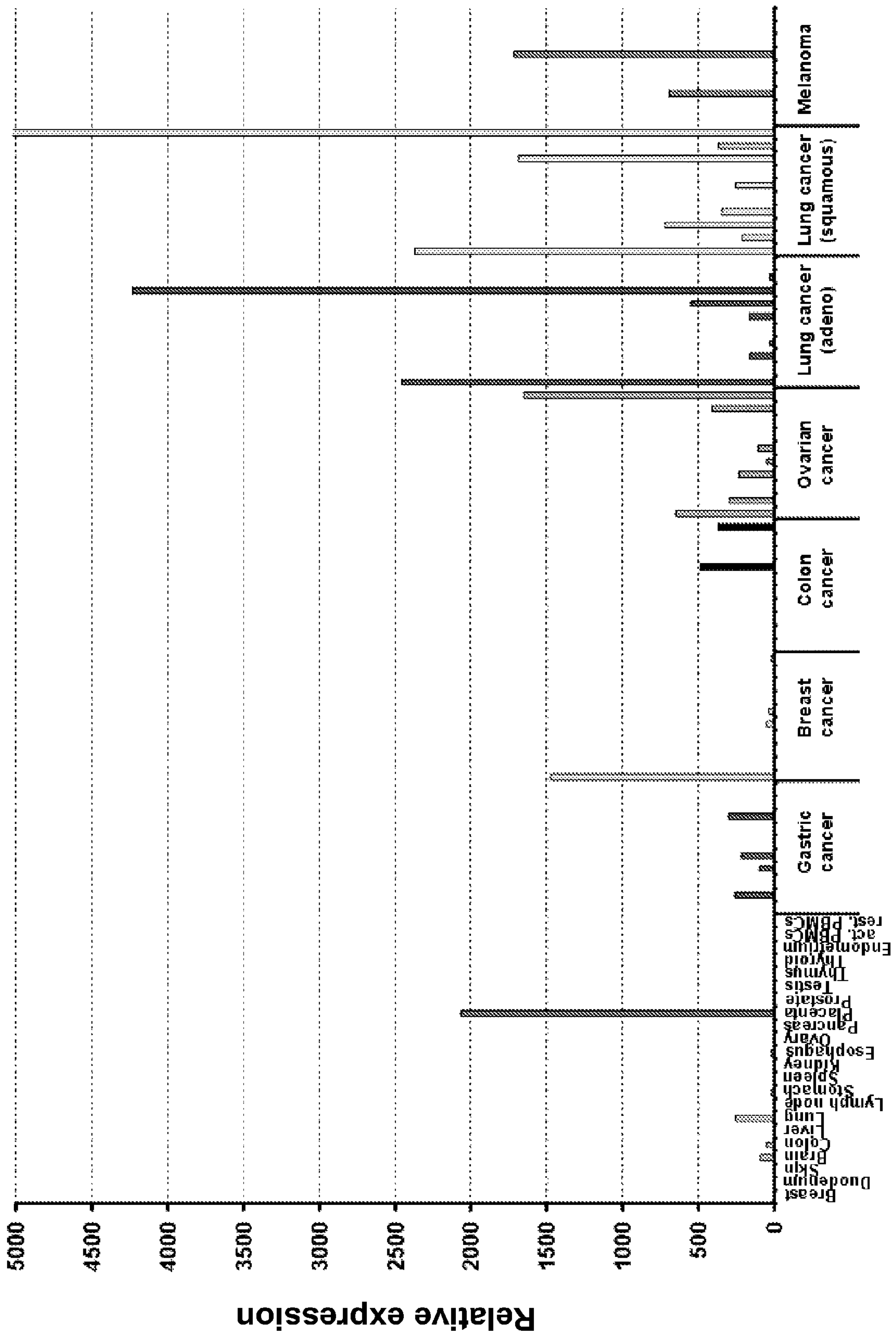
FIG. 11. Quantitative expression of SEQ ID NO:563 in normal tissues and cancer tissues. Real-time RT-PCR showed overexpression of the nucleic acid sequence according to SEQ ID NO:563 in breast cancer, colon cancer, ovarian cancer, lung cancer and melanoma.

The nucleotide sequence according to SEQ ID NO:563 was deduced from SEQ ID NO:177. SEQ ID NO:563 has no apparent open reading frame. Expression of SEQ ID NO:563 in normal and cancerous tissues was quantified by real-time RT-PCR using sequence-specific oligos (SEQ ID NO:564, 565); see FIG. 11. SEQ ID NO:563 is highly expressed in placenta. Compared to normal tissues, SEQ ID NO:563 is overexpressed in breast cancer, colon cancer, ovarian cancer, lung cancer and melanoma. Based on these expression results, SEQ ID NO:563 and its expression products qualify as molecular markers and/or target candidates for targeted therapies, in particular for these particular tumor types.

Figure 12:
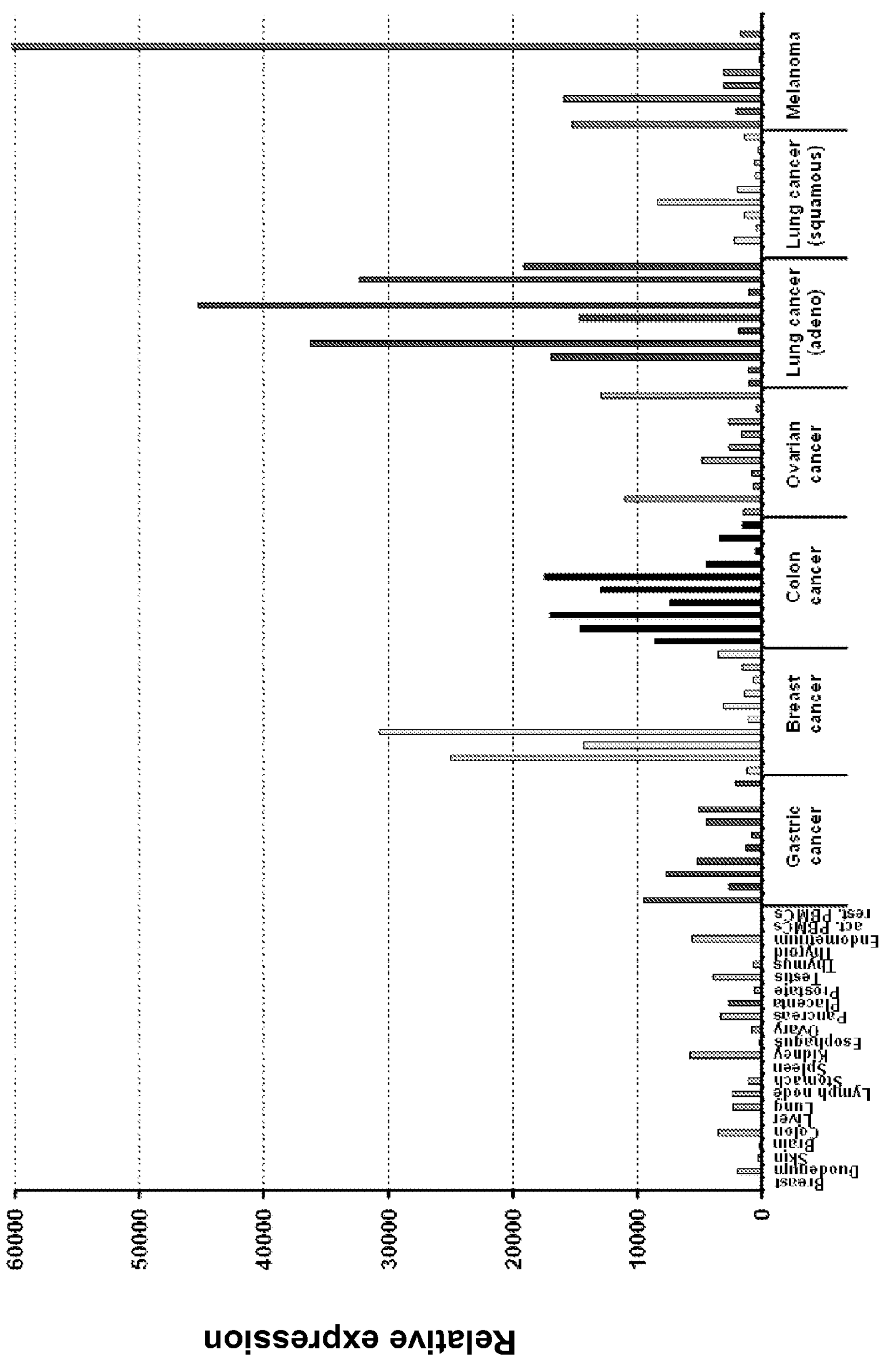
FIG. 12. Quantitative expression of SEQ ID NO:566 in normal tissues and cancer tissues. Real-time RT-PCR showed overexpression of the nucleic acid sequence according to SEQ ID NO:566 in gastric cancer, breast cancer, colon cancer, ovarian cancer, lung cancer and melanoma.

The nucleotide sequence according to SEQ ID NO:566 was deduced from SEQ ID NO:149 and codes for a 155 aa protein (SEQ ID NO:567) of unknown function. The protein sequence is partially homologous to members of the tumor necrosis factor receptor superfamily and harbors a potential transmembrane domain. The protein encoded by SEQ ID NO:566 might represent a new member of the tumor necrosis factor receptor superfamily. Expression of SEQ ID NO:566 in normal and cancerous tissues was quantified by real-time RT-PCR using sequence-specific oligos (SEQ ID NO:568, 569); see FIG. 12. Compared to normal tissues, SEQ ID NO:566 is overexpressed in gastric cancer, breast cancer, colon cancer, ovarian cancer, lung cancer and melanoma. Based on these expression results, SEQ ID NO:566 and its expression products qualify as molecular markers and/or target candidates for targeted therapies, in particular for these particular tumor types.

Figure 13:
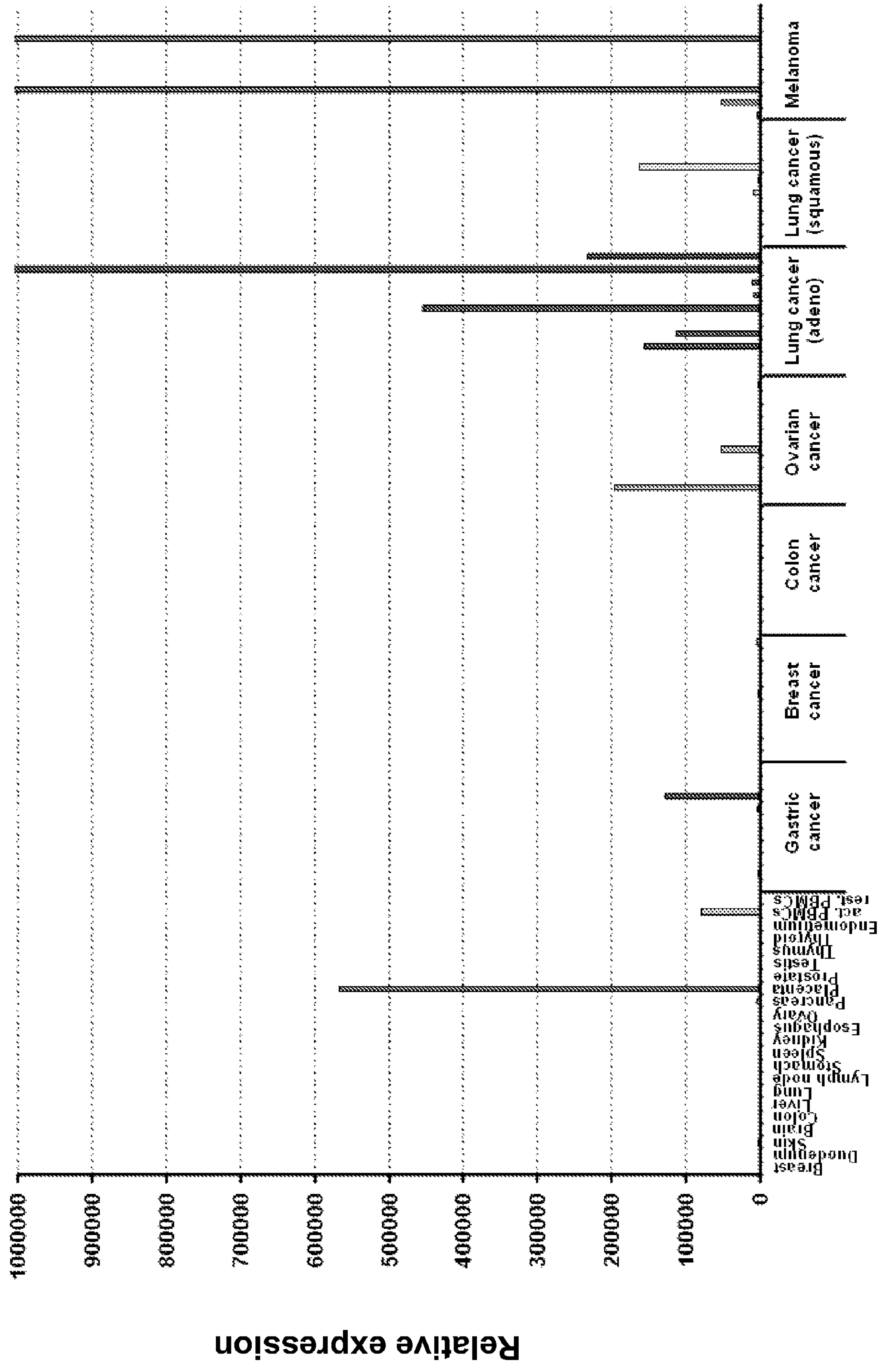
FIG. 13. Quantitative expression of SEQ ID NO:570 in normal tissues and cancer tissues. Real-time RT-PCR showed overexpression of the nucleic acid sequence according to SEQ ID NO:570 in ovarian cancer, lung cancer and melanoma.

The nucleotide sequence according to SEQ ID NO:570 was deduced from SEQ ID NO:53 and codes for a member of the kernel lipocain superfamily (SEQ ID NO:571). These secreted glycoproteins have distinct and essential roles in regulating an uterine environment suitable for pregnancy and in the timing and occurrence of the appropriate sequence of events in the fertilization process. Expression of SEQ ID NO:570 in normal and cancerous tissues was quantified by real-time RT-PCR using sequence-specific oligos (SEQ ID NO:572, 573); see FIG. 13. SEQ ID NO:570 is highly expressed in placenta. Compared to other normal tissues, SEQ ID NO:570 is overexpressed in ovarian cancer, lung cancer and melanoma. Based on these expression results, SEQ ID NO:570 and its expression products qualify as molecular markers and/or target candidates for targeted therapies, in particular for these particular tumor types.

Figure 14:
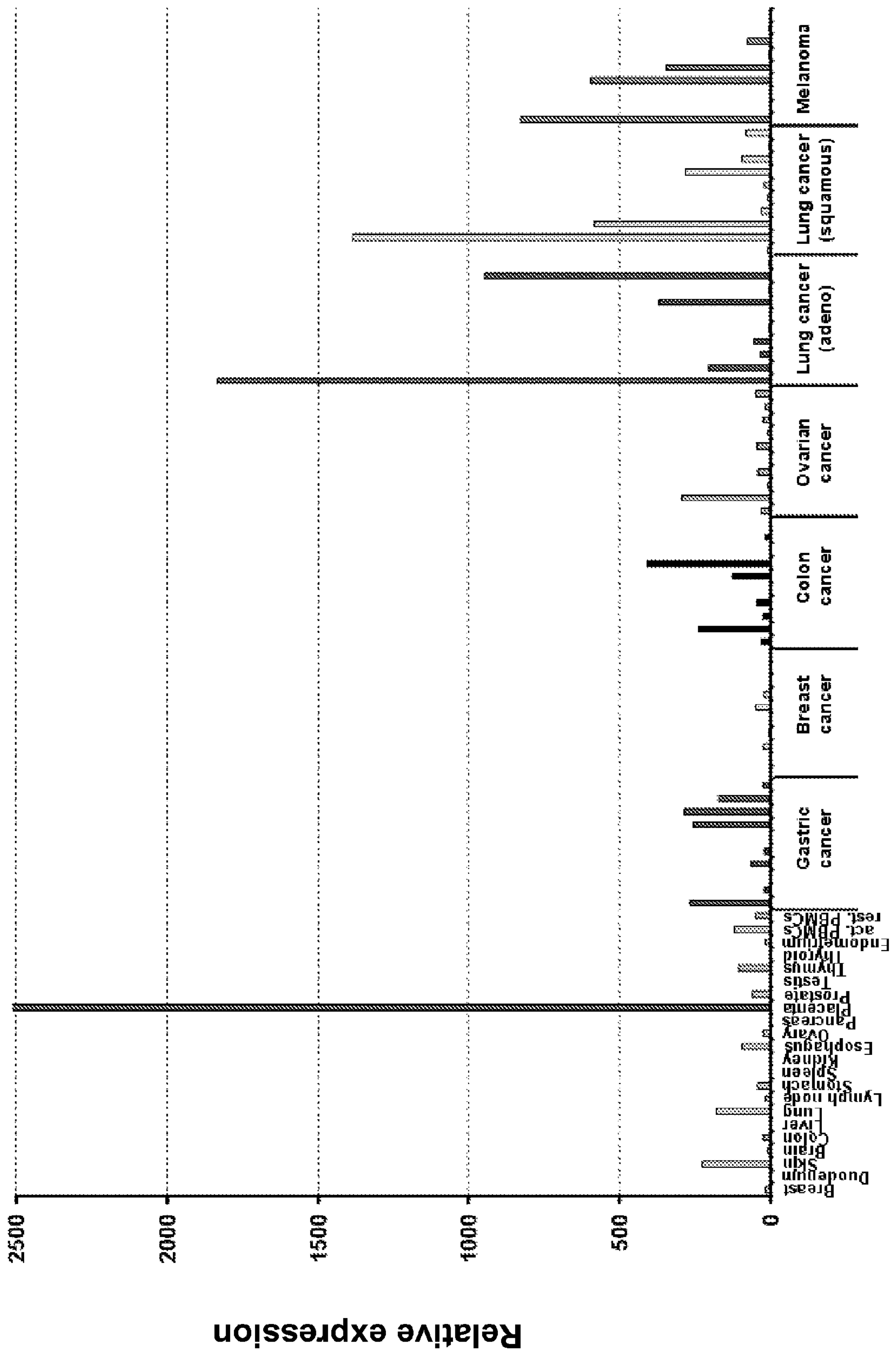
FIG. 14. Quantitative expression of SEQ ID NO:574 in normal tissues and cancer tissues. Real-time RT-PCR showed overexpression of the nucleic acid sequence according to SEQ ID NO:574 in lung cancer and melanoma.

The nucleotide sequence according to SEQ ID NO:574 has no apparent open reading frame. Expression of SEQ ID NO:574 in normal and cancerous tissues was quantified by real-time RT-PCR using sequence-specific oligos (SEQ ID NO:575, 576); see FIG. 14. SEQ ID NO:574 is highly expressed in placenta. Compared to other normal tissues, SEQ ID NO:574 is overexpressed in lung cancer and melanoma. Based on these expression results, SEQ ID NO:574 and its expression products qualify as molecular markers and/or target candidates for targeted therapies, in particular for these particular tumor types.

Figure 15:
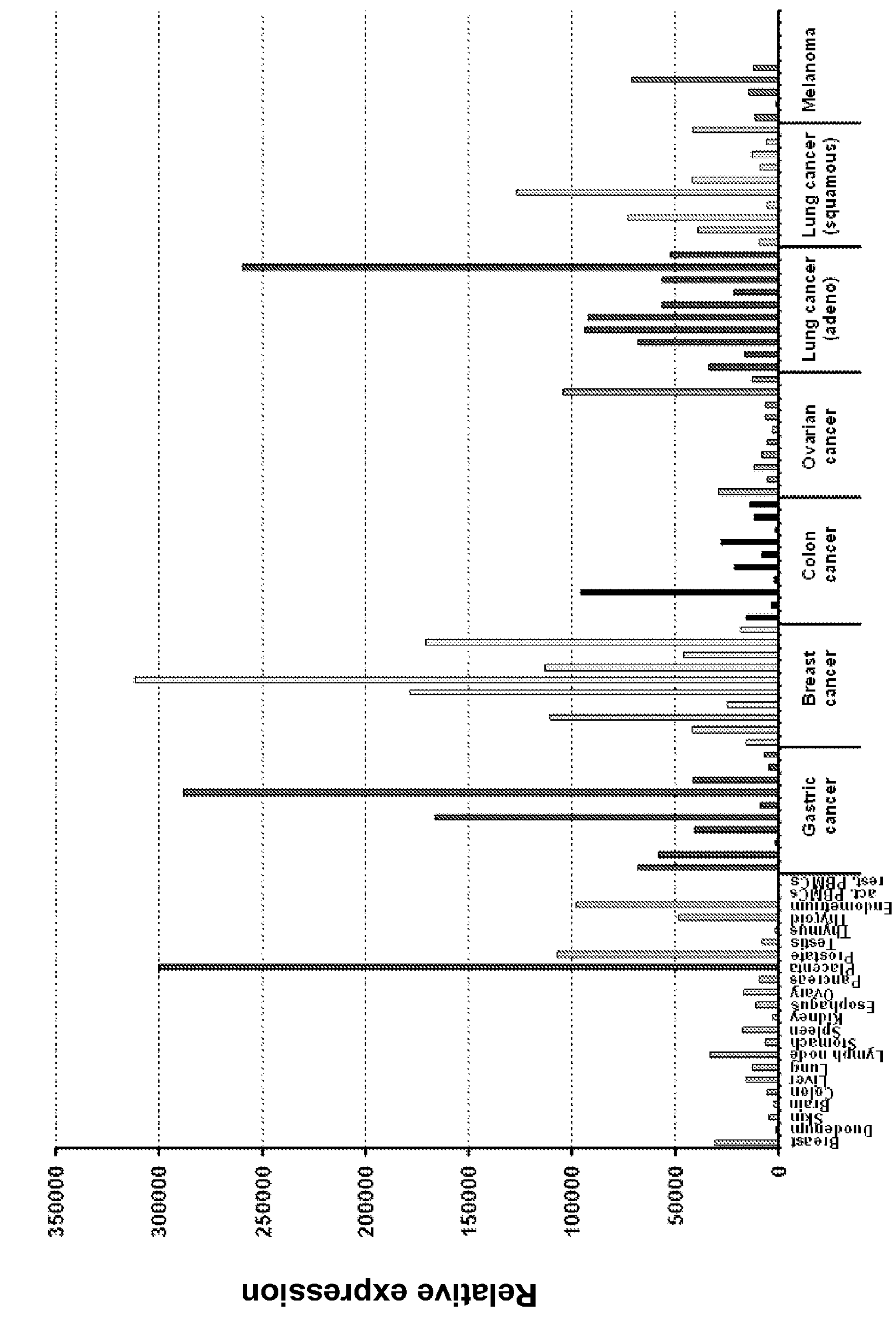
FIG. 15. Quantitative expression of SEQ ID NO:577 in normal tissues and cancer tissues. Real-time RT-PCR showed overexpression of the nucleic acid sequence according to SEQ ID NO:577 in gastric cancer, breast cancer and lung cancer.

The nucleotide sequence according to SEQ ID NO:577 was deduced from SEQ ID NO:20. SEQ ID NO:577 represents a partial cDNA with no apparent open reading frame. Expression of SEQ ID NO:577 in normal and cancerous tissues was quantified by real-time RT-PCR using sequence-specific oligos (SEQ ID NO:578, 579); see FIG. 15. SEQ ID NO:577 is highly expressed in placenta. Compared to other normal tissues, SEQ ID NO:577 is overexpressed in gastric cancer, breast cancer and lung cancer. Based on these expression results, SEQ ID NO:577 and its expression products qualify as molecular markers and/or target candidates for targeted therapies, in particular for these particular tumor types.

Figure 16:
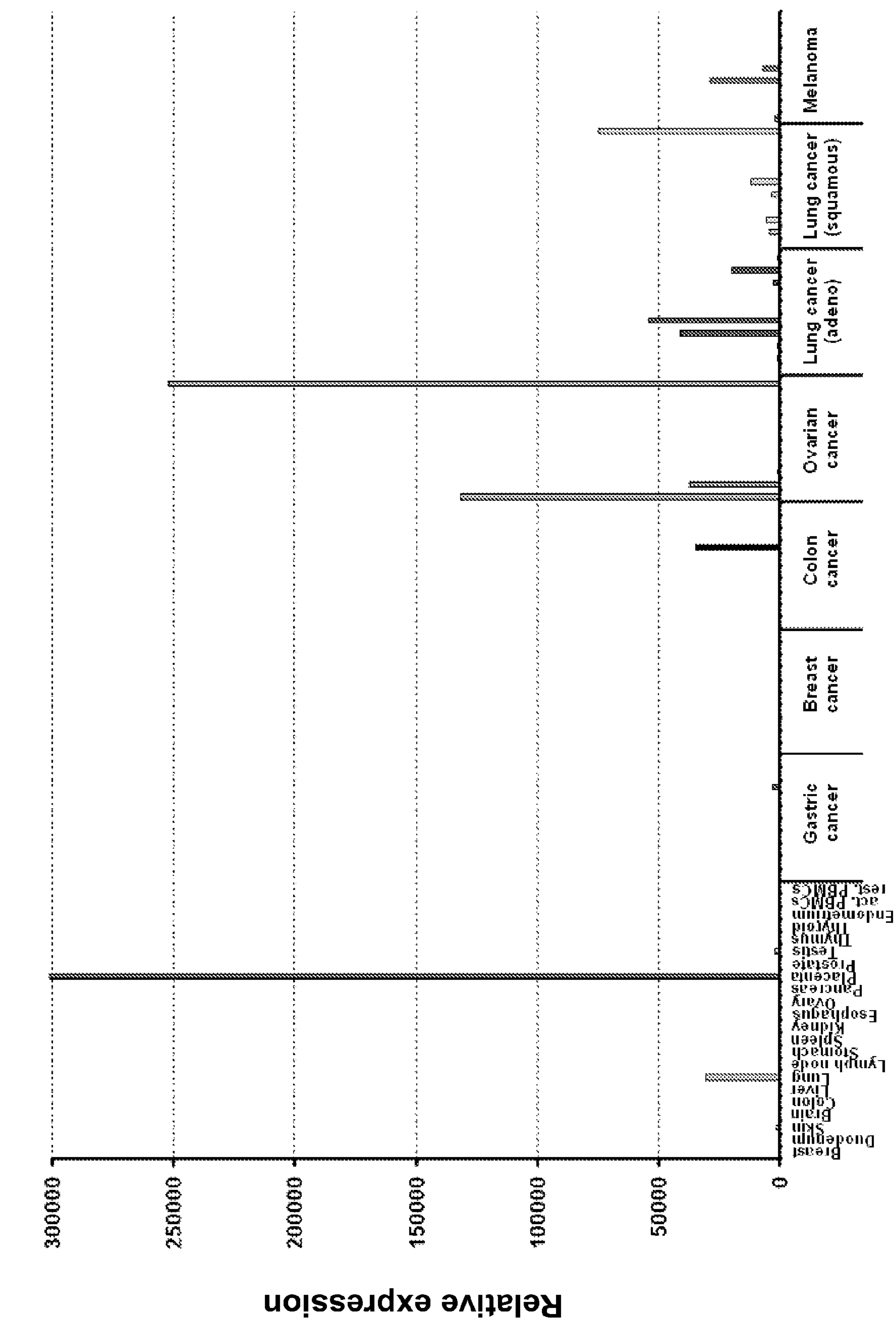
FIG. 16. Quantitative expression of SEQ ID NO:580 in normal tissues and cancer tissues. Real-time RT-PCR showed overexpression of the nucleic acid sequence according to SEQ ID NO:580 in ovarian cancer and lung cancer.

The nucleotide sequence according to SEQ ID NO:580 was deduced from SEQ ID NO:32. SEQ ID NO:580 represents a partial cDNA with no apparent open reading frame. Expression of SEQ ID NO:580 in normal and cancerous tissues was quantified by real-time RT-PCR using sequence-specific oligos (SEQ ID NO:581, 582); see FIG. 16. SEQ ID NO:580 is highly expressed in placenta. Compared to other normal tissues, SEQ ID NO:580 is overexpressed in ovarian cancer and lung cancer. Based on these expression results, SEQ ID NO:580 and its expression products qualify as molecular markers and/or target candidates for targeted therapies, in particular for these particular tumor types.

Figure 17:
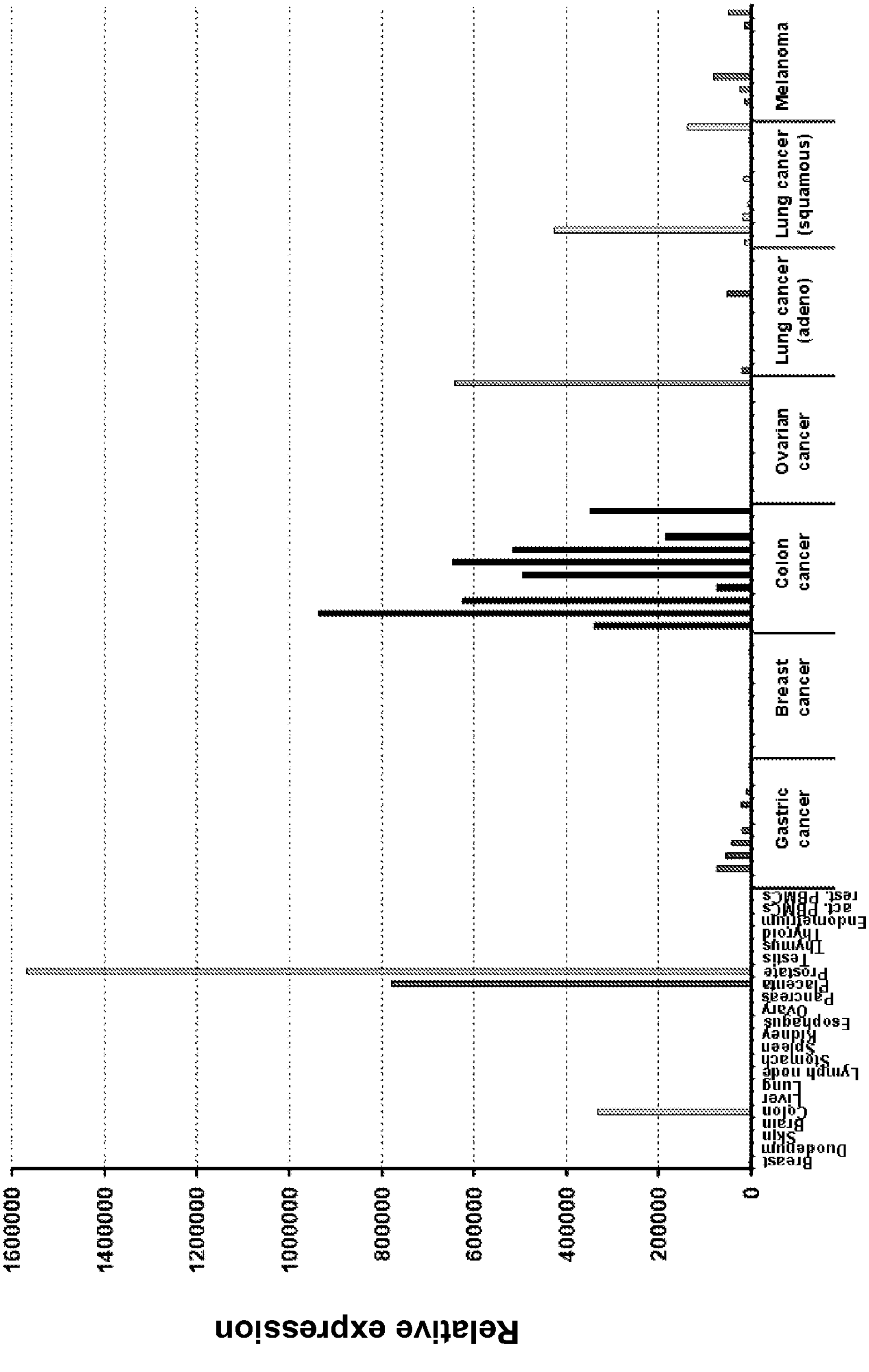
FIG. 17. Quantitative expression of SEQ ID NO:583 in normal tissues and cancer tissues. Real-time RT-PCR showed overexpression of the nucleic acid sequence according to SEQ ID NO:583 in colon cancer, ovarian cancer and lung cancer.

The nucleotide sequence according to SEQ ID NO:583 was deduced from SEQ ID NO:257 and codes for a member of the homeobox class of transcription factors (SEQ ID NO:584). Expression of these proteins is spatially and temporally regulated during embryonic development. Expression of SEQ ID NO:583 in normal and cancerous tissues was quantified by real-time RT-PCR using sequence-specific oligos (SEQ ID NO:585, 586); see FIG. 17. SEQ ID NO:583 is highly expressed in placenta and prostate. Compared to other normal tissues, SEQ ID NO:583 is overexpressed in colon cancer, ovarian cancer and lung cancer. Based on these expression results, SEQ ID NO:583 and its expression products qualify as molecular markers and/or target candidates for targeted therapies, in particular for these particular tumor types.

Figure 18:
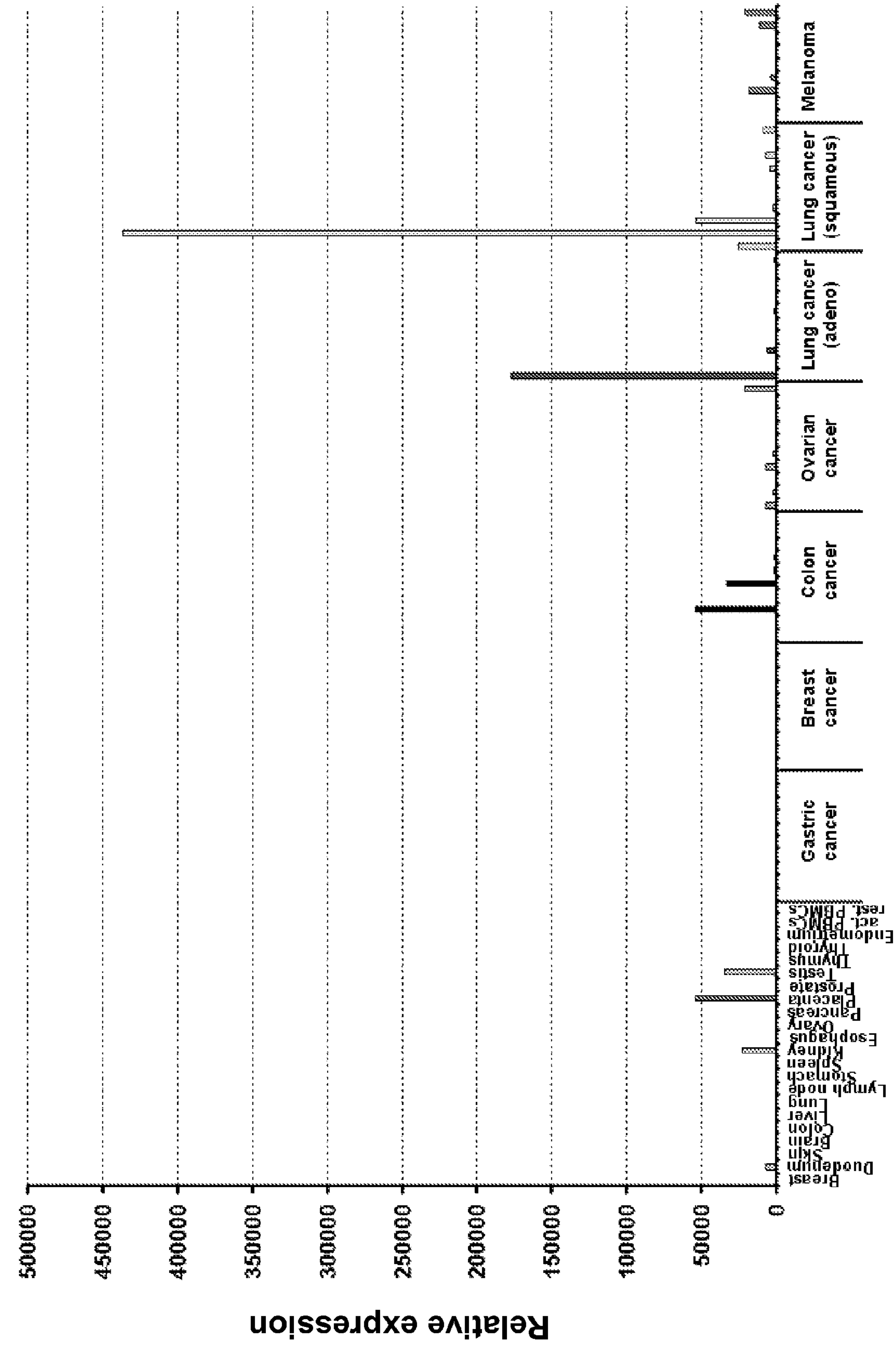
FIG. 18. Quantitative expression of SEQ ID NO:587 in normal tissues and cancer tissues. Real-time RT-PCR showed overexpression of the nucleic acid sequence according to SEQ ID NO:587 in lung cancer.

The nucleotide sequence according to SEQ ID NO:587 was deduced from SEQ ID NO:148 and codes for a member of the IGF-II mRNA-binding protein (IMP) family (SEQ ID NO:588). It functions by binding to the 5' UTR of the insulin-like growth factor 2 (IGF2) mRNA and regulating IGF2 translation. Expression of SEQ ID NO:587 in normal and cancerous tissues was quantified by real-time RT-PCR using sequence-specific oligos (SEQ ID NO:589, 590); see FIG. 18. Compared to normal tissues, SEQ ID NO:587 is overexpressed in lung cancer. Based on these expression results, SEQ ID NO:587 and its expression products qualify as molecular markers and/or target candidates for targeted therapies, in particular for this particular tumor type.

Figure 19:
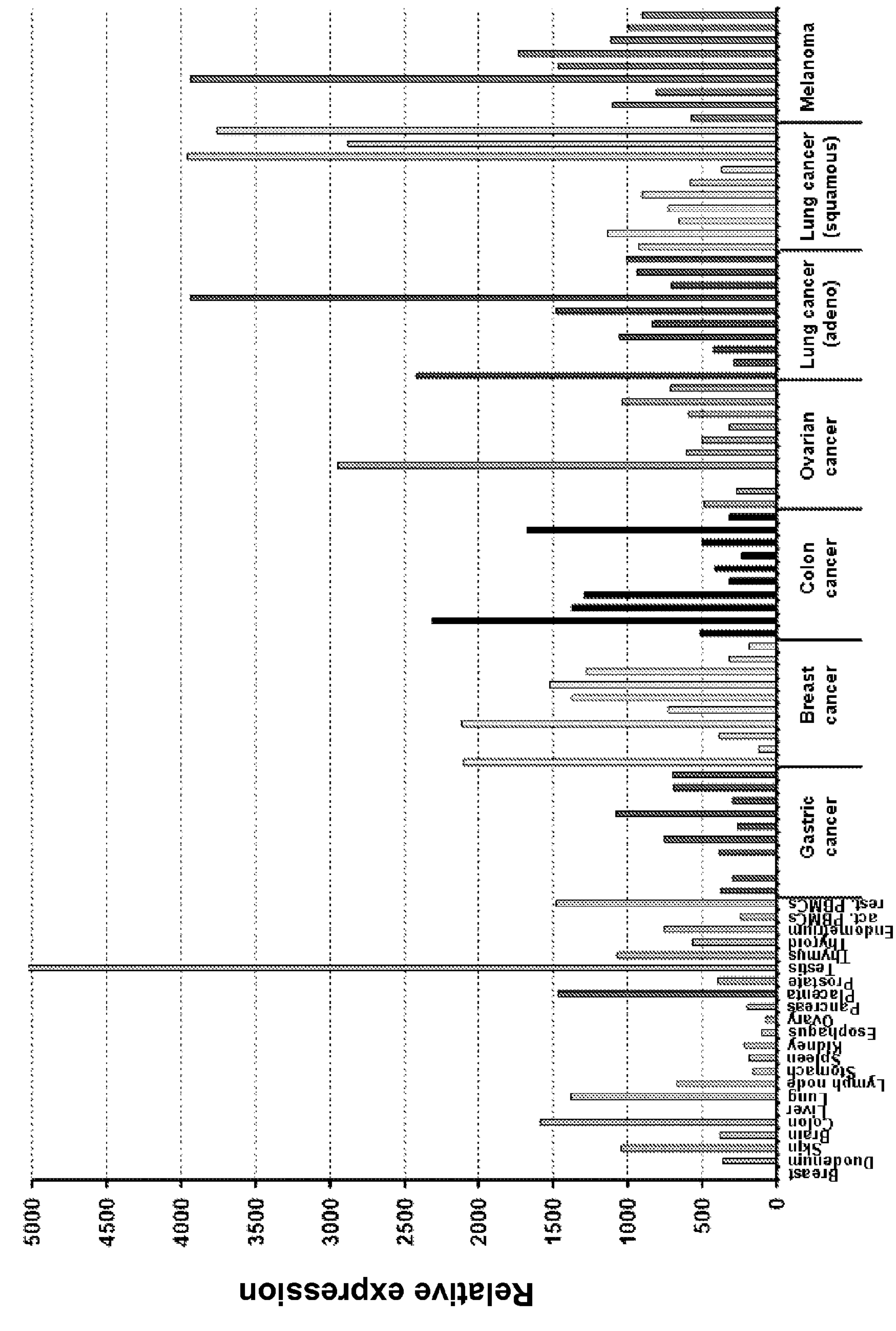
FIG. 19. Quantitative expression of SEQ ID NO:591 in normal tissues and cancer tissues. Real-time RT-PCR showed overexpression of the nucleic acid sequence according to SEQ ID NO:591 in breast cancer, colon cancer, ovarian cancer, lung cancer and melanoma.

The nucleotide sequence according to SEQ ID NO:591 was deduced from SEQ ID NO:194 and codes for a 372 aa protein (SEQ ID NO:592) of unknown function. Expression of SEQ ID NO:591 in normal and cancerous tissues was quantified by real-time RT-PCR using sequence-specific oligos (SEQ ID NO:593, 594); see FIG. 19. SEQ ID NO:591 is highly expressed in testis. Compared to other normal tissues, SEQ ID NO:591 is overexpressed in breast cancer, colon cancer, ovarian cancer, lung cancer and melanoma. Based on these expression results, SEQ ID NO:591 and its expression products qualify as molecular markers and/or target candidates for targeted therapies, in particular for these particular tumor types.

Figure 20:
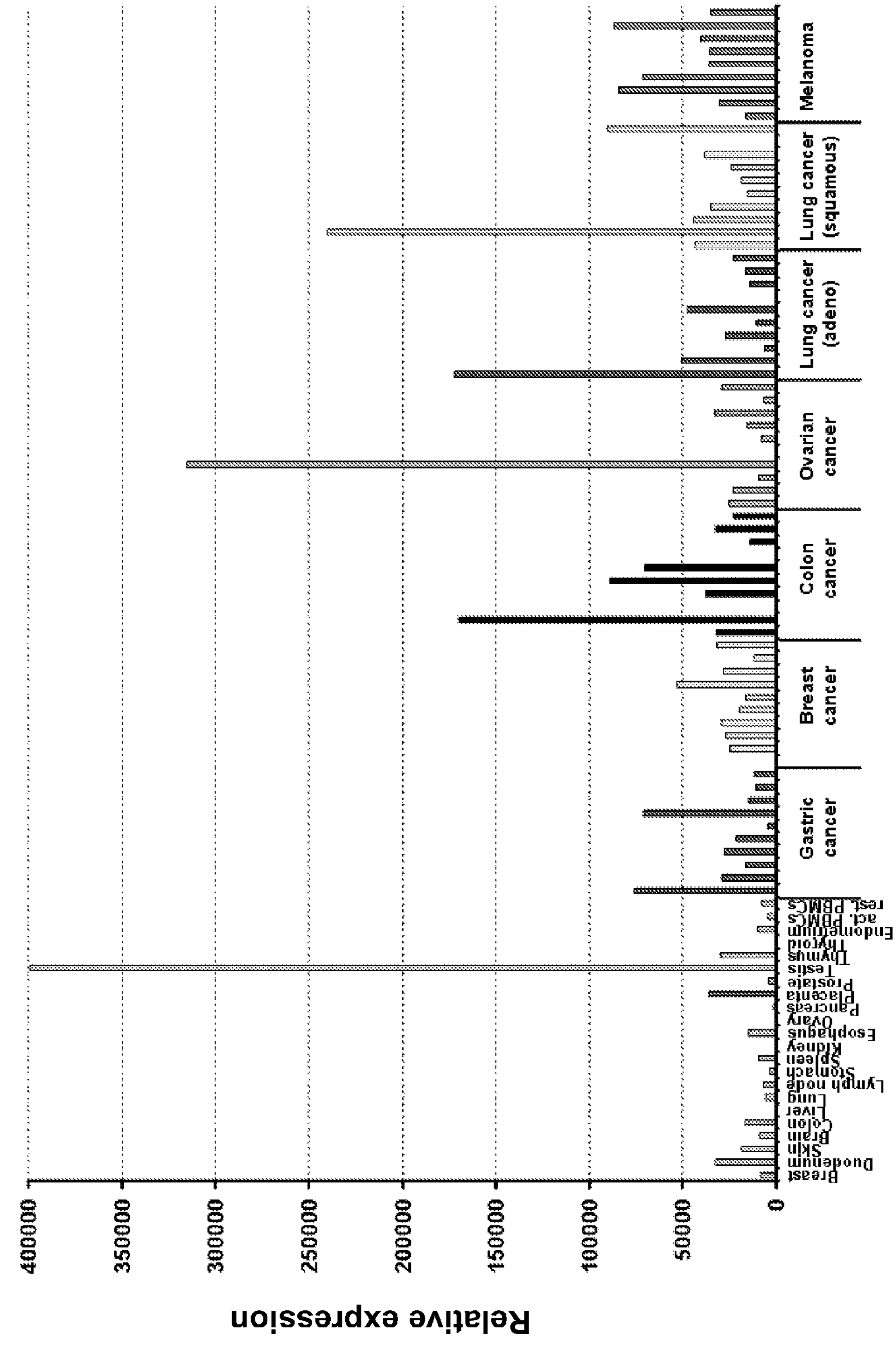
FIG. 20. Quantitative expression of SEQ ID NO:595 in normal tissues and cancer tissues. Real-time RT-PCR showed overexpression of the nucleic acid sequence according to SEQ ID NO:595 in gastric cancer, colon cancer, ovarian cancer, lung cancer and melanoma.

The nucleotide sequence according to SEQ ID NO:595 was deduced from SEQ ID NO:191 and codes for a 357 aa protein (SEQ ID NO:596) of unknown function. Expression of SEQ ID NO:595 in normal and cancerous tissues was quantified by real-time RT-PCR using sequence-specific oligos (SEQ ID NO:597, 598); see FIG. 20. SEQ ID NO:595 is highly expressed in testis. Compared to other normal tissues, SEQ ID NO:595 is overexpressed in gastric cancer, colon cancer, ovarian cancer, lung cancer and melanoma. Based on these expression results, SEQ ID NO:595 and its expression products qualify as molecular markers and/or target candidates for targeted therapies, in particular for these particular tumor types.

Figure 21:
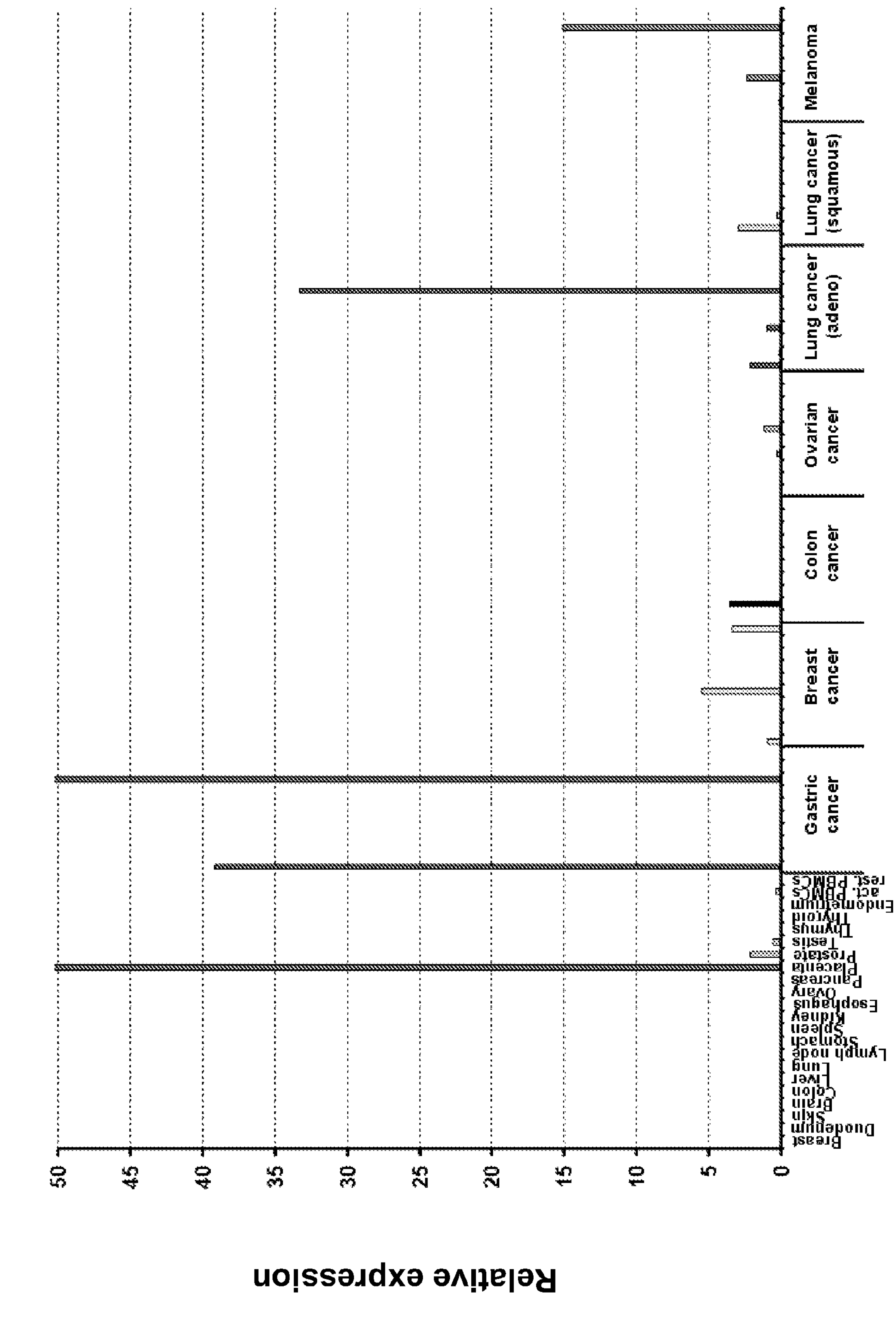
FIG. 21. Quantitative expression of SEQ ID NO:599 in normal tissues and cancer tissues. Real-time RT-PCR showed overexpression of the nucleic acid sequence according to SEQ ID NO:599 in gastric cancer, breast cancer, lung cancer and melanoma.

The nucleotide sequence according to SEQ ID NO:599 was deduced from SEQ ID NO:18 and has no apparent open reading frame. Expression of SEQ ID NO:599 in normal and cancerous tissues was quantified by real-time RT-PCR using sequence-specific oligos (SEQ ID NO:600, 601); see FIG. 21. SEQ ID NO:599 is highly expressed in placenta. Compared to other normal tissues, SEQ ID NO:599 is overexpressed in gastric cancer, breast cancer, lung cancer and melanoma. Based on these expression results, SEQ ID NO:599 and its expression products qualify as molecular markers and/or target candidates for targeted therapies, in particular for these particular tumor types.

Figure 22:
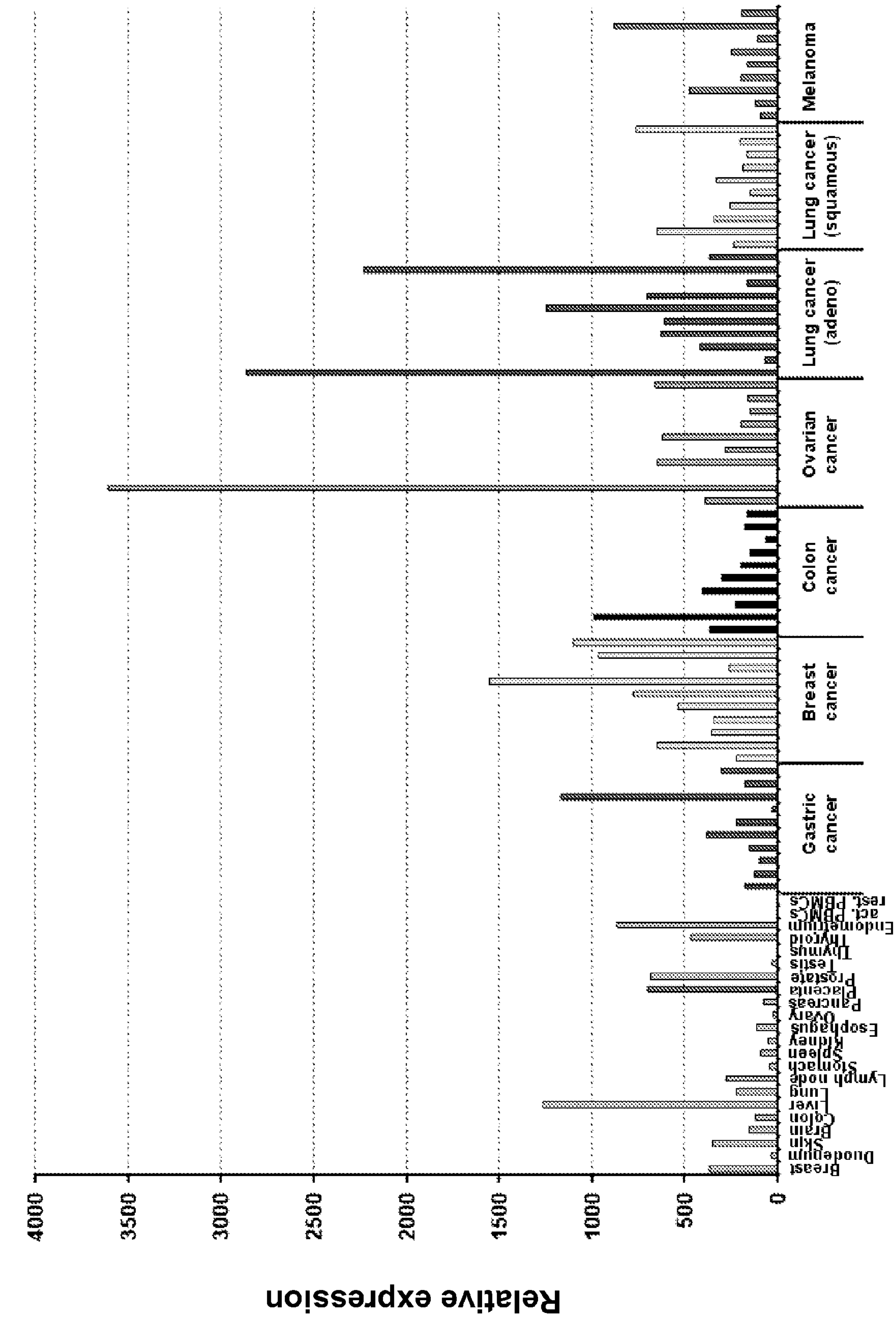
FIG. 22. Quantitative expression of SEQ ID NO:602 in normal tissues and cancer tissues. Real-time RT-PCR showed overexpression of the nucleic acid sequence according to SEQ ID NO:602 in ovarian cancer and lung cancer.

The nucleotide sequence according to SEQ ID NO:602 was deduced from SEQ ID NO:133 and codes for a member of the von Willebrand factor domain superfamily of extracellular matrix proteins (SEQ ID NO:603). Expression of SEQ ID NO:602 in normal and cancerous tissues was quantified by real-time RT-PCR using sequence-specific oligos (SEQ ID NO:604, 605); see FIG. 22. Compared to normal tissues, SEQ ID NO:602 is overexpressed in ovarian cancer and lung cancer. Based on these expression results, SEQ ID NO:602 and its expression products qualify as molecular markers and/or target candidates for targeted therapies, in particular for these particular tumor types.

Figure 23:
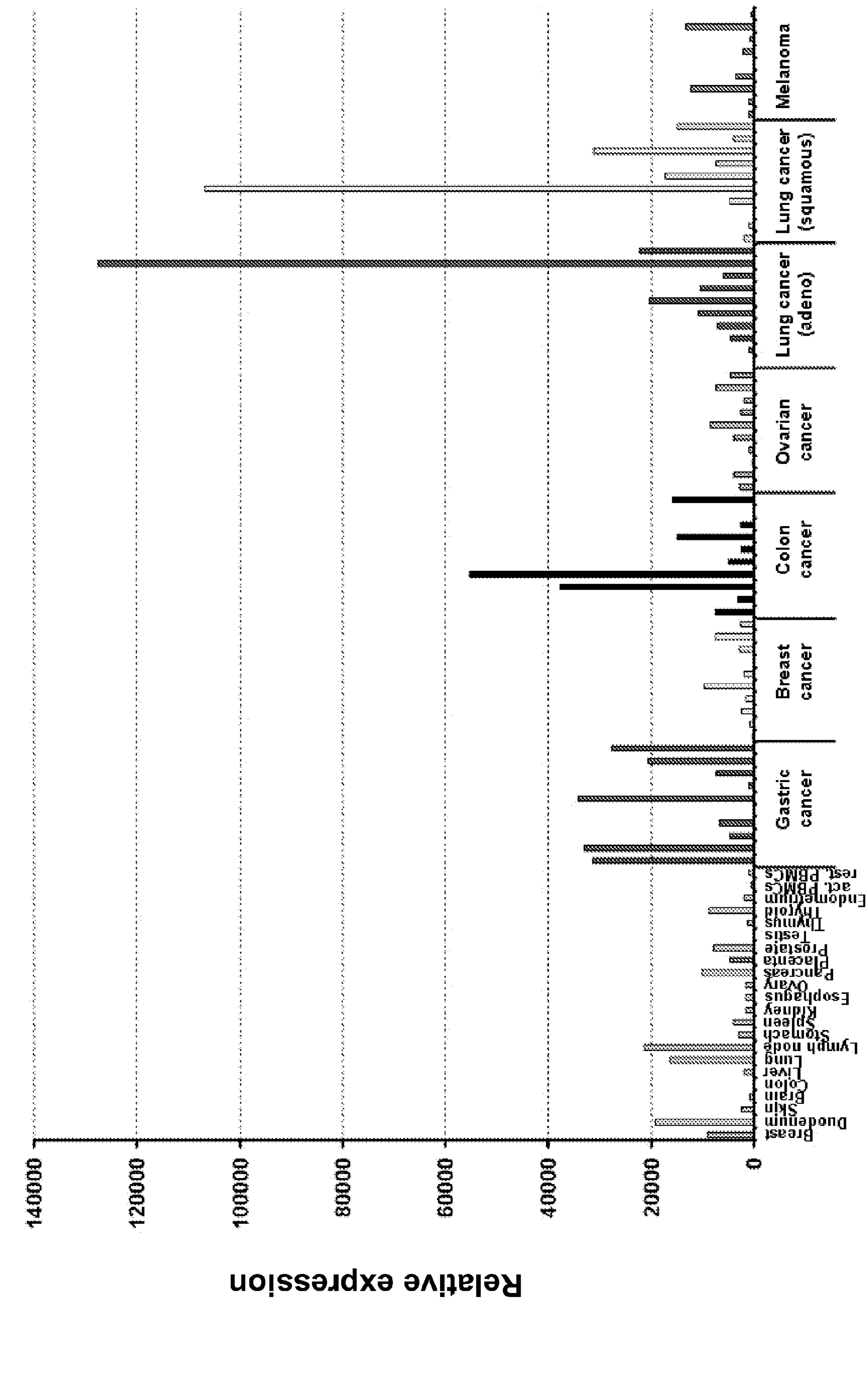
FIG. 23. Quantitative expression of SEQ ID NO:606 in normal tissues and cancer tissues. Real-time RT-PCR showed overexpression of the nucleic acid sequence according to SEQ ID NO:606 in gastric cancer, colon cancer and lung cancer.

The nucleotide sequence according to SEQ ID NO:606 was deduced from SEQ ID NO:128 and codes for a member of the Borg family of CDC42 effector proteins (SEQ ID NO:607). Borg family proteins contain a CRIB (Cdc42/Rac interactive-binding) domain. They bind to, and negatively regulate the function of CDC42. CDC42, a small Rho GTPase, regulates the formation of F-actin-containing structures through its interaction with the downstream effector proteins. Expression of SEQ ID NO:606 in normal and cancerous tissues was quantified by real-time RT-PCR using sequence-specific oligos (SEQ ID NO:608, 609); see FIG. 23. Compared to normal tissues, SEQ ID NO:606 is overexpressed in gastric cancer, colon cancer and lung cancer. Based on these expression results, SEQ ID NO:606 and its expression products qualify as molecular markers and/or target candidates for targeted therapies, in particular for these particular tumor types.

Figure 24:
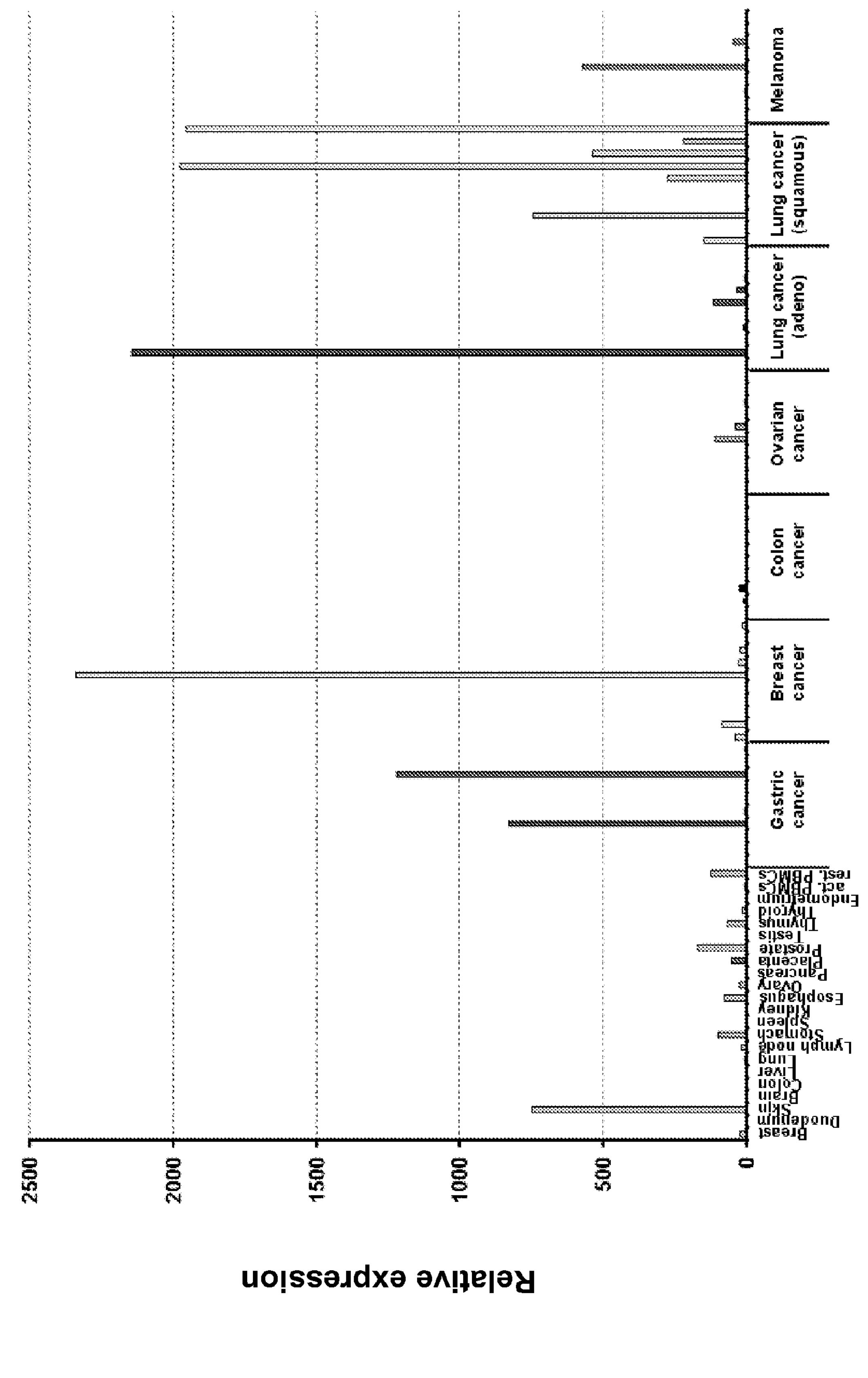
FIG. 24. Quantitative expression of SEQ ID NO:610 in normal tissues and cancer tissues. Real-time RT-PCR showed overexpression of the nucleic acid sequence according to SEQ ID NO:610 in gastric cancer, breast cancer and lung cancer.

The nucleotide sequence according to SEQ ID NO:610 was deduced from SEQ ID NO:118 and has no apparent open reading frame. Expression of SEQ ID NO:610 in normal and cancerous tissues was quantified by real-time RT-PCR using sequence-specific oligos (SEQ ID NO:611, 612); see FIG. 24. Compared to normal tissues, SEQ ID NO:610 is overexpressed in gastric cancer, breast cancer and lung cancer. Based on these expression results, SEQ ID NO:610 and its expression products qualify as molecular markers and/or target candidates for targeted therapies, in particular for these particular tumor types.

Figure 25:
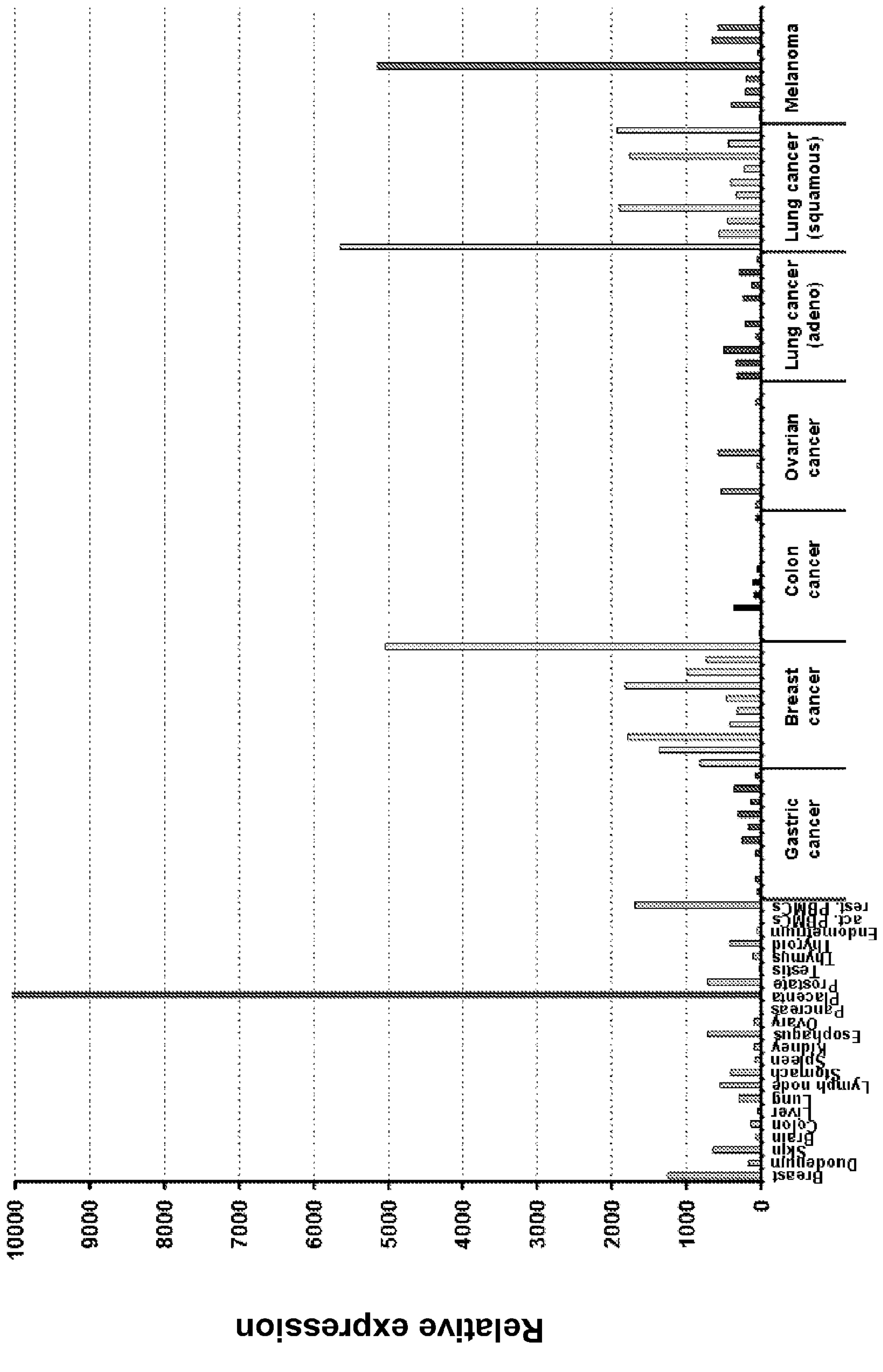
FIG. 25. Quantitative expression of SEQ ID NO:613 in normal tissues and cancer tissues. Real-time RT-PCR showed overexpression of the nucleic acid sequence according to SEQ ID NO:613 in breast cancer, lung cancer and melanoma.

The nucleotide sequence according to SEQ ID NO:613 was deduced from SEQ ID NO:116 and codes for a 76 aa protein (SEQ ID NO:614) of unknown function. Expression of SEQ ID NO:613 in normal and cancerous tissues was quantified by real-time RT-PCR using sequence-specific oligos (SEQ ID NO:615, 616); see FIG. 25. SEQ ID NO:613 is highly expressed in placenta. Compared to other normal tissues, SEQ ID NO:613 is overexpressed in breast cancer, lung cancer and melanoma. Based on these expression results, SEQ ID NO:613 and its expression products qualify as molecular markers and/or target candidates for targeted therapies, in particular for these particular tumor types.

Figure 26:
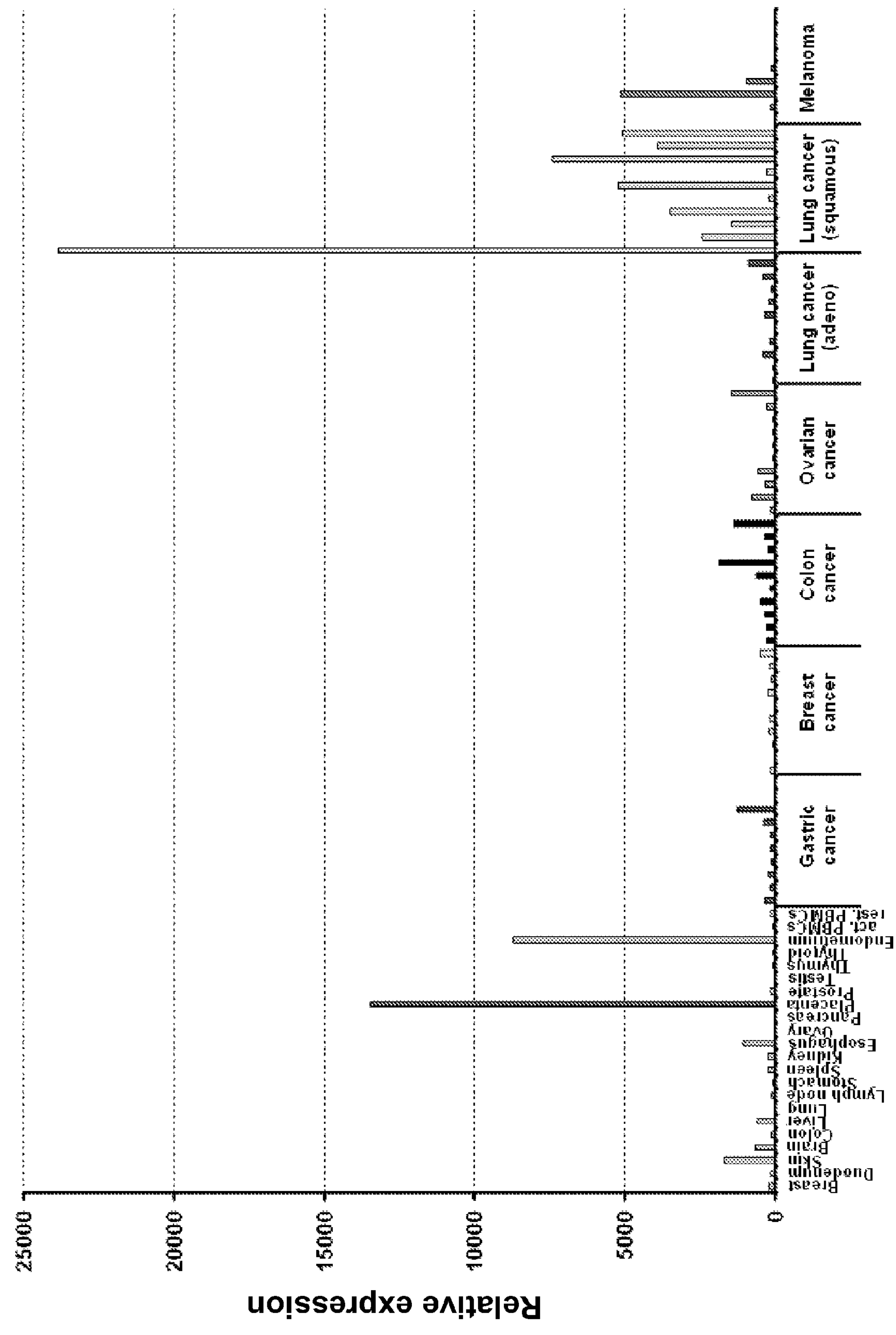
FIG. 26. Quantitative expression of SEQ ID NO:617 in normal tissues and cancer tissues. Real-time RT-PCR showed overexpression of the nucleic acid sequence according to SEQ ID NO:617 in lung cancer and melanoma.

The nucleotide sequence according to SEQ ID NO:617 was deduced from SEQ ID NO:267. SEQ ID NO:617 represents a partial cDNA with no apparent open reading frame. Expression of SEQ ID NO:617 in normal and cancerous tissues was quantified by real-time RT-PCR using sequence-specific oligos (SEQ ID NO:618, 619); see FIG. 26. SEQ ID NO:617 is highly expressed in placenta and endometrium. Compared to other normal tissues, SEQ ID NO:617 is overexpressed in lung cancer and melanoma. Based on these expression results, SEQ ID NO:617 and its expression products qualify as molecular markers and/or target candidates for targeted therapies, in particular for these particular tumor types.

Figure 27:
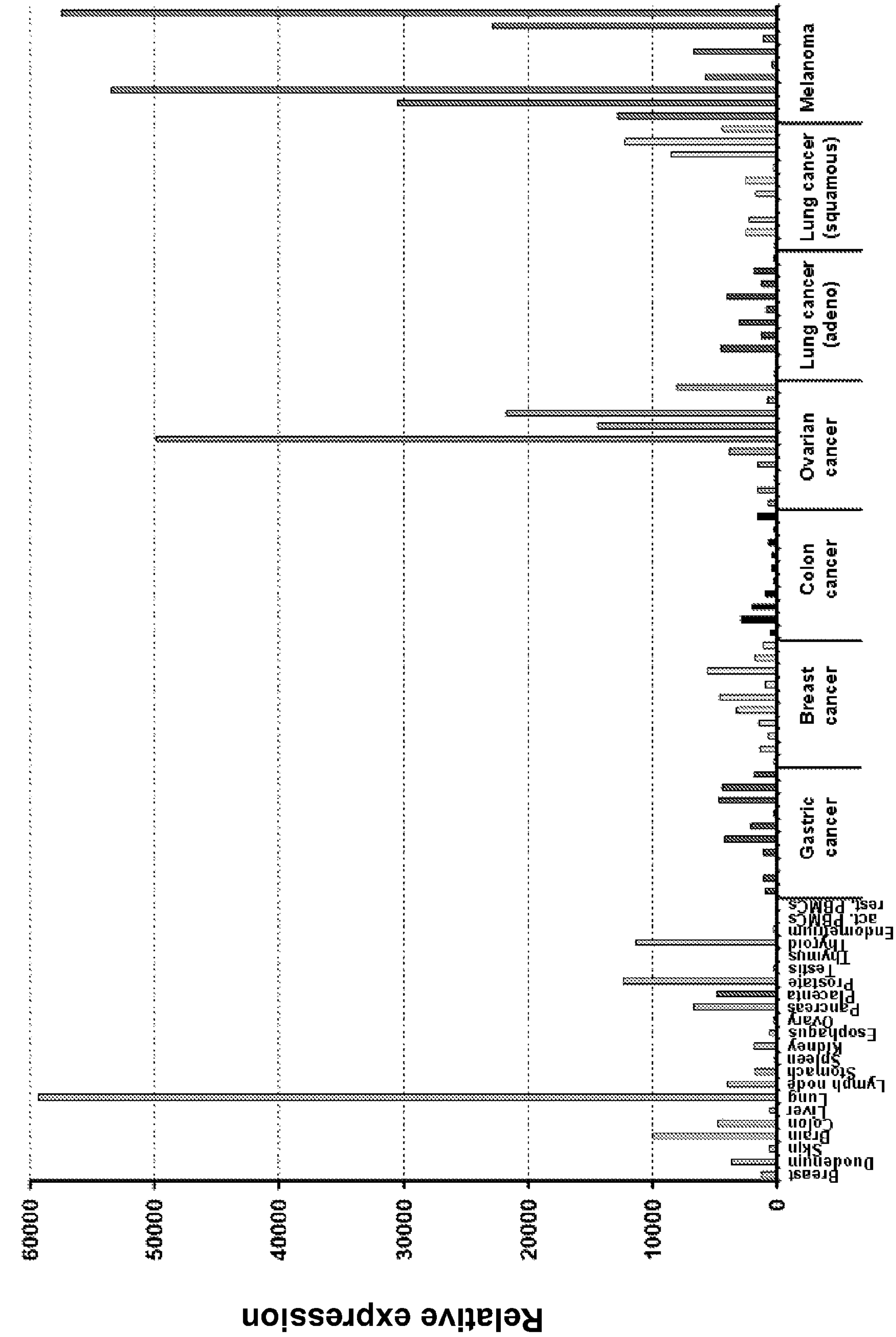
FIG. 27. Quantitative expression of SEQ ID NO:620 in normal tissues and cancer tissues. Real-time RT-PCR showed overexpression of the nucleic acid sequence according to SEQ ID NO:620 in ovarian cancer and melanoma.

The nucleotide sequence according to SEQ ID NO:620 was deduced from SEQ ID NO:182 and codes for a 829 aa protein (SEQ ID NO:621) harboring multiple putative transmembrane domains and a patched family domain. The transmembrane protein Patched is a receptor for the morphogene Sonic Hedgehog. This protein associates with the smoothened protein to transduce hedgehog signals. SEQ ID NO:620 might represent a novel member of the Patched family. Expression of SEQ ID NO:620 in normal and cancerous tissues was quantified by real-time RT-PCR using sequence-specific oligos (SEQ ID NO:622, 623); see FIG. 27. SEQ ID NO:620 is highly expressed in lung. Compared to other normal tissues, SEQ ID NO:620 is overexpressed in ovarian cancer and melanoma. Based on these expression results, SEQ ID NO:620 and its expression products qualify as molecular markers and/or target candidates for targeted therapies, in particular for these particular tumor types.

Figure 28:
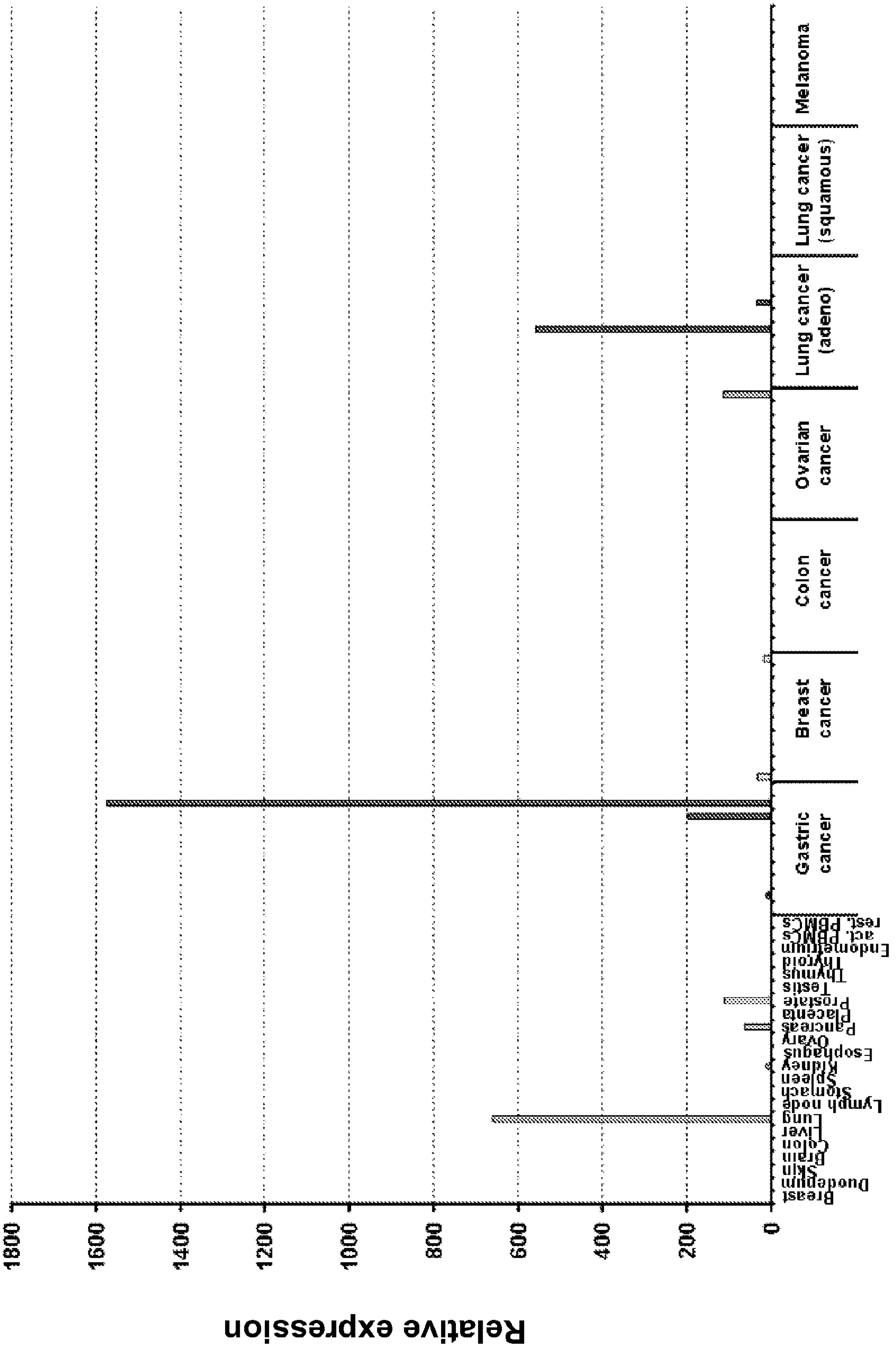
FIG. 28. Quantitative expression of SEQ ID NO:624 in normal tissues and cancer tissues. Real-time RT-PCR showed overexpression of the nucleic acid sequence according to SEQ ID NO:624 in gastric cancer and lung cancer.

The nucleotide sequence according to SEQ ID NO:624 was deduced from SEQ ID NO:184 and codes for a 323 aa protein (SEQ ID NO:625) similar to TWIK-related acid-sensitive $K^+$ channel, a member of the superfamily of potassium channel proteins that contain two pore-forming P domains. Expression of SEQ ID NO:624 in normal and cancerous tissues was quantified by real-time RT-PCR using sequence-specific oligos (SEQ ID NO:626, 627); see FIG. 28. SEQ ID NO:624 is highly expressed in lung. Compared to other normal tissues, SEQ ID NO:624 is overexpressed in gastric cancer and lung cancer. Based on these expression results, SEQ ID NO:624 and its expression products qualify as molecular markers and/or target candidates for targeted therapies, in particular for these particular tumor types.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A method of diagnosing or monitoring ovarian cancer, wherein the method comprises the steps of:

detecting the presence of or determining the quantity of a tumor-associated nucleic acid in a biological sample comprising ovarian tissue isolated from a human patient having or suspected of having ovarian cancer, and diagnosing or monitoring ovarian cancer based on the presence or quantity of the tumor-associated nucleic acid in the biological sample, wherein the tumor-associated nucleic acid is selected from the group consisting of (a) a nucleic acid that comprises a nucleic acid sequence consisting essentially of SEQ ID NO: 553, and (b) a nucleic acid that has at least 90% sequence identity with the nucleic acid of (a);

the detecting or determining comprises (i) contacting the biological sample with an agent that binds specifically to the tumor-associated nucleic acid, and (ii) detecting the formation of or determining the quantity of a complex between the agent and the tumor-associated nucleic acid wherein said agent is an oliqonucleotide or polynucleotide that hybridizes specifically to the tumor-associated nucleic acid or to the complementary nucleic acid sequence, and has a nucleic acid sequence comprising SEQ ID NO: 555 or 556; and the ovarian cancer that is characterized by expression of or abnormal expression of a tumor-associated antigen encoded by the tumor-associated nucleic acid.

2. The method of claim 1, wherein the monitoring of the ovarian cancer comprises determining regression, course or onset of the ovarian cancer in the patient.

3. The method of claim 1, wherein the method comprises a detection of the presence of or a determination of the quantity of the tumor-associated nucleic acid in a first sample at a first point in time and in a further sample at a second point in time and a comparison of the presence of or quantity of the tumor-associated nucleic acid in the two samples.

4. The method of claim 1, wherein the agent is labeled in a detectable manner.

5. The method of claim 1, wherein the ovarian tissue is from a tissue biopsy.

6. The method of claim 1, wherein the tumor-associated antigen comprises an amino acid sequence consisting essentially of SEQ ID NO: 554.

7. A method of diagnosing or monitoring ovarian cancer, wherein the method comprises the steps of:

detecting or determining the quantity of a tumor-associated nucleic acid in a biological sample comprising ovarian tissue isolated from a human patient having or suspected of having ovarian cancer, and diagnosing or monitoring ovarian cancer based on the presence or quantity of the tumor-associated nucleic acid in the biological sample, wherein the tumor-associated nucleic acid is selected from the group consisting of (a) a nucleic acid that comprises a nucleic acid sequence consisting essentially of SEQ ID NO: 553, and (b) a nucleic acid that has at least 90% sequence identity with the nucleic acid of (a);

the detecting or determining comprises (i) contacting the biological sample with an agent that binds specifically to the tumor-associated nucleic acid, and (ii) detecting the formation of or determining the quantity of a complex between the agent and the tumor-associated nucleic acid via real-time reverse-transcription polymerase chain reaction (RT-PCR);

the ovarian cancer is characterized by expression or abnormal expression of a tumor-associated antigen encoded by the tumor-associated nucleic acid; and the agent is an oligonucleotide or polynucleotide that hybridizes specifically to the tumor-associated nucleic acid or to the complementary nucleic acid sequence, and has a nucleic acid sequence comprising SEQ ID NO: 555 or 556.

8. The method of claim 7, wherein the monitoring of the ovarian cancer comprises determining regression, course or onset of the ovarian cancer in the patient.

9. The method of claim 7, wherein the method comprises a detection of the presence of or determination of the quantity of the tumor-associated nucleic acid in a first sample at a first point in time and in a further sample at a second point in time and a comparison of the presence of or quantity of the tumor-associated nucleic acid in the two samples.

10. The method of claim 7, wherein the agent is labeled in a detectable manner.

11. The method of claim 7, wherein the ovarian tissue is from a tissue biopsy.

12. The method of claim 7, wherein the tumor-associated antigen comprises an amino acid sequence consisting essentially of SEQ ID NO: 554.

13. The method of claim 7, wherein the agent is an oligonucleotide or polynucleotide that hybridizes specifically to the tumor-associated nucleic acid and has a nucleic acid sequence comprising SEQ ID NO: 555.

14. The method of claim 7, wherein the agent is an oligonucleotide or polynucleotide that hybridizes specifically to the tumor-associated nucleic acid and has a nucleic acid sequence comprising SEQ ID NO: 556.

* * * * *

SEQUENCE LISTING

<160> NUMBER OF SEQ ID NOS: 636

<210> SEQ ID NO 1
<211> LENGTH: 398
<212> TYPE: DNA
<213> ORGANISM: Homo sapiens
<220> FEATURE:
<221> NAME/KEY: misc_feature
<222> LOCATION: (272)..(272)
<223> OTHER INFORMATION: n is a, c, g, t or u
<220> FEATURE:
<221> NAME/KEY: misc_feature
<222> LOCATION: (274)..(274)
<223> OTHER INFORMATION: n is a, c, g, t or u
<220> FEATURE:
<221> NAME/KEY: misc_feature
<222> LOCATION: (284)..(284)
<223> OTHER INFORMATION: n is a, c, g, t or u

<400> SEQUENCE: 1
aacataggtg gaccgctgct gagtccaggc ttacttgcag agatctatgc tggccaggcc 60
ctgtgctagg cagcagagga catggaataa aatcaaataa ggtcactgtg tgcaggcacc 120
tcacggtgtg gtaaaggagc agccccatcc acaggttcta ttaattccag cctgtgagaa 180
ttggaaccac agggtgaatt ttggaggaca ggcacttaca ctaatctgga agcataatat 240
ataaagagta cctacaaatc aataaaaaaa ananaaaaaa aaanagcaaa gtatatgaac 300
agaaaattca atgaaaagga aatagaaatg gctcttaaat gaatgaaaac atactctcac 360
tcagagaaat gaaaatttaa cccatgtcaa gatacttg 398

<210> SEQ ID NO 2
<211> LENGTH: 99
<212> TYPE: DNA
<213> ORGANISM: Homo sapiens

<400> SEQUENCE: 2
atgcacagag catcacgtac aatggctcca tggacagccc agtgcccttg taccctaccg 60
attgcccccc ttcttatgag gcagtcatgg gactacgag 99

<210> SEQ ID NO 3
<211> LENGTH: 266
<212> TYPE: DNA
<213> ORGANISM: Homo sapiens

<400> SEQUENCE: 3
aggagaaaac ctctacttgt cctgcttcgc ggaatctaac ccaccggcag agtatttttg 60
gacaattaat gggaagtttc agcaatcagg acaaaagctc tctatccccc aaattactac 120
aaagcataga gggctctata cttgctctgt tcgtaactca gccactggca aggaaagctc 180
caaatccatg acagtcgaag tctctgctcc ttcaggaata ggacgtcttc ctctccttaa 240
tccaatatag cagccgtgaa gtcatt 266

<210> SEQ ID NO 4
<211> LENGTH: 492
<212> TYPE: DNA
<213> ORGANISM: Homo sapiens
<220> FEATURE:
<221> NAME/KEY: misc_feature
<222> LOCATION: (369)..(369)
<223> OTHER INFORMATION: n is a, c, g, t or u
<220> FEATURE:
<221> NAME/KEY: misc_feature
<222> LOCATION: (372)..(372)
<223> OTHER INFORMATION: n is a, c, g, t or u
<220> FEATURE:
<221> NAME/KEY: misc_feature
<222> LOCATION: (418)..(419)
<223> OTHER INFORMATION: n is a, c, g, t or u
<220> FEATURE:
<221> NAME/KEY: misc_feature
<222> LOCATION: (424)..(424)
<223> OTHER INFORMATION: n is a, c, g, t or u
<220> FEATURE:
<221> NAME/KEY: misc_feature
<222> LOCATION: (443)..(443)
<223> OTHER INFORMATION: n is a, c, g, t or u

<400> SEQUENCE: 4
aaaggagtca tcagcgtctc tttcctggat tatatctggg ttacctaaag ctctgtagct 60
ctgtggatca aatcaaagtt cttgttaccc aaaagttgcc caacattctc tgccacgtga 120
agatccgtga aaacaataat atttctagag aggaatggga atggatccaa aagctttctg 180
gctctgaatc tatggaaagt gtggatcata cttctgactg ccccatgcaa ttgttcttct 240
acgagctcca gatggcagtg aaagctctcc ttcagcagat caatatacct ctacaccagg 300
caaggaactt ccgcctctac acacaggagg tgttggaaat gggtcacaat gtgtcctttc 360
ttctcctgnt cnctgcctca gacgacgtct gtacagcccc aggacagaat aatccttnna 420
cccnacactc agggtttctt aanctccctc ttcagatgtt tgaacttggt atagtagctt 480
gtttcaccta ga 492

<210> SEQ ID NO 5
<211> LENGTH: 133
<212> TYPE: DNA
<213> ORGANISM: Homo sapiens

<400> SEQUENCE: 5
ttcaaaaact gctggtgagc ctatggaaga ggagccagcc ttgtgaagtg ccaagtcccc 60
ctctgatatt tcctgtgtgt gacatcattg tgtatccccc caccccagta ccctcagaca 120
tgtcttgtct gct 133

<210> SEQ ID NO 6
<211> LENGTH: 371
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, t or u

<400> SEQUENCE: 6
ggtttcggcc tctgcgaaag tgaaatgccc aagcctccgg ccaaagccca gaccagtaca 60
gtatgaattg tcctatgaga ctgaggggtt cggcttcatt cctacctgcc cgcaaagctc 120
gcccccagcc tcgaaaacaa agcgactggt ctgacgtggg gtccctgcgc ccctcctnta 180
gcgcgacagg acccccccag ggaagagcca gtacccgtgg gatgtcaccc cgtccccatc 240
taccggggtg gggggcctga aaggagaacg atttaaaata atcttcagaa agaaaaggga 300
ggagggagcg ggtgacacat cgttcacata aacccaattt ctggtttcga gtgaagtcaa 360
gatctccgcc c 371

<210> SEQ ID NO 7
<211> LENGTH: 215
<212> TYPE: DNA
<213> ORGANISM: Homo sapiens
<220> FEATURE:

<221> NAME/KEY: misc_feature
<222> LOCATION: (153)..(153)
<223> OTHER INFORMATION: n is a, c, g, t or u

<400> SEQUENCE: 7
ccatttaaca tgtatagtag gtcaacattg gtgcatccag aaaatgaagc atttaggaaa 60
tctgtttcag tgtcttttca atgtgtgtaa cttttacttg caaaccaatg gaaccaagaa 120
agtcatcatt tgcctaaaat gcagtcatca ccncaaatga ttcatttata ctatgtgagt 180
taattgcctt catctcatta atggccaagg aggga 215

<210> SEQ ID NO 8
<211> LENGTH: 322
<212> TYPE: DNA
<213> ORGANISM: Homo sapiens

<400> SEQUENCE: 8
actgttcagt actgcaaccc caggatacac aatggcatct ggctctgttt attcaccacc 60
tactcggcca ctacctagaa acaccctatc aagaagtgct tttaaattca agaagtcttc 120
aaagtactgt agctggaaat gcactgcact gtgtgccgta ggggtctcgg tgctcctggc 180
aatactcctg tcttatttta tagcaatgca tctctttggc ctcaactggc agctacagca 240
gactgaaaat gacacatttg agaatggaaa agtgaattct gataccatgc caacaaacac 300
tgtgtcatta ccttctggag ac 322

<210> SEQ ID NO 9
<211> LENGTH: 547
<212> TYPE: DNA
<213> ORGANISM: Homo sapiens

<400> SEQUENCE: 9
ttacccttca ttcacctatt acggttcagg agaaaacctc gacttgtcct gcttcacgga 60
atctaaccca ccggcagagt atttttggac aattaatggg aagtttcagc aatcaggaca 120
aaagctcttt atcccccaaa ttactagaaa tcatagcggg ctctatgttt gctctgttca 180
taactcagcc actggcaagg aaatctccaa atccatgaca gtcaaagtct ctggtccctg 240
ccatggagac ctgacagagt ttcagtcatg actgcaacaa ctgagacact gagaaaaaga 300
acaggctgat accttcatga aattcaagac aaagaagaaa aaaactcaat gttattggac 360
taaataatca aaaggataat gttttcataa ttttttattg gaaaatgtgc tgattctttg 420
aatgttttat tctccagatt tatgaacttt ttttcttcag caattggtaa agtatacttt 480
tgtaaacaaa aattgaaata tttgcttttg ctgtctatct gaatgcccca gaattgtgaa 540
actactc 547

<210> SEQ ID NO 10
<211> LENGTH: 396
<212> TYPE: DNA
<213> ORGANISM: Homo sapiens

<400> SEQUENCE: 10
gcaggggacg caccaaggat ggagatgttc caggggctgc tgctgttgct gctgctgagc 60
atgggcggga catgggcatc caaggagccg cttcggccac ggtgccgccc catcaatgcc 120
accctggctg tggagaagga gggctgcccc gtgtgcatca ccgtcaacac caccatctgt 180
gccggctact gccccaccat gacccgcgtg ctgcaggggg tcctgccggc cctgcctcag 240
gtggtgtgca actaccgcga tgtgcgcttc gagtccatcc ggctccctgg ctgcccgcgc 300

```
ggcgtgaacc ccgtggtctc ctacgccgtg gctctcagct gtcaatgtgc actctgccgc    360

cgcagcacca ctgactgcgg gggtcccaag gaccac                              396


<210> SEQ ID NO 11
<211> LENGTH: 311
<212> TYPE: DNA
<213> ORGANISM: Homo sapiens

<400> SEQUENCE: 11

aaatggtggt gtttgactgg tatatgacct tcctctggag gtgatcaacc agtaagggaa     60

aatcgctcca agtgagcatg cacacaacct cagtaaacac actgtgcatg tggcttctcc    120

caagtactag caggccactg cacatgtcac aactgagcaa cagcccaccc caatggaggg    180

atcaagggag gagaagaaaa accccggaac caaaagccag tttataaaaa tcctgagcca    240

aaggctgagg ggggcacttg atctctcaag ttccctactt ggccctcttc caagtgtgat    300

ttgcttcttt t                                                         311


<210> SEQ ID NO 12
<211> LENGTH: 246
<212> TYPE: DNA
<213> ORGANISM: Homo sapiens
<220> FEATURE:
<221> NAME/KEY: misc_feature
<222> LOCATION: (184)..(184)
<223> OTHER INFORMATION: n is a, c, g, t or u

<400> SEQUENCE: 12

gccttagccc ccgggattta gagcatcctc gcgaccaccc ggaggcttct gggggccact     60

ctgcggatga ggaagctgac gcctgggtgc agaaccccgg acccccggat tcagagccca    120

ggtccagccg cgcttccgca caaacttgcg ctcggagcaa gtcccctcct tcccagcact    180

catntgagac cagaggtgtc cccaccgtcc ccgctagcag cgctggttat attgtgggcc    240

aacctt                                                               246


<210> SEQ ID NO 13
<211> LENGTH: 516
<212> TYPE: DNA
<213> ORGANISM: Homo sapiens
<220> FEATURE:
<221> NAME/KEY: misc_feature
<222> LOCATION: (149)..(150)
<223> OTHER INFORMATION: n is a, c, g, t or u
<220> FEATURE:
<221> NAME/KEY: misc_feature
<222> LOCATION: (153)..(159)
<223> OTHER INFORMATION: n is a, c, g, t or u
<220> FEATURE:
<221> NAME/KEY: misc_feature
<222> LOCATION: (161)..(163)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (168)..(184)
<223> OTHER INFORMATION: n is a, c, g, t or u

<400> SEQUENCE: 13

ccttttgctt gagcagggtt cccaggaggg agaaagagaa gacaagagcc tgatgcccaa     60

ctttgtgtgt gtggggacgg gggagtcagg gccccccaag tcccacaata gccccaatgt    120
```

-continued

```
ttgcctatcc acctccccca agcccccttnn ccnnnnnnnc nnntnacnnn nnnnnnnnnn    180

nnnnctgctg ctgctgctgc tgctgcttaa aggctcatgc ttggagtggg gactggtcgg    240

tgcccagaaa gtctcttctg ccactgacgc ccccatcagg gattgggcct tctttccccc    300

ttcctttctg tgtctcctgc ctcatcggcc tgccatgacc tgcagccaag cccagccccg    360

tggggaaggg gagaaagtgg gggatggcta agaaagctgg gagataggga acagaagagg    420

gtagtgggtg ggctaggggg gctgccttat ttaaagtggt tgtttatgat tcttatacta    480

atttatacaa agatattaag gccctgttca ttaaga                              516
```

<210> SEQ ID NO 14
<211> LENGTH: 162
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, t or u

<400> SEQUENCE: 14

```
gagcctagag agtaaggaac gttatatagt tttccccaaa ggttcacttg aaagaacttt     60

tcattggttg tcatggtagt aatgtcctga tnttgaaatc tcccagaacc tagtagctct    120

taaacatgct ttcatcttgg ttcctttggt ctgacggaaa ct                        162
```

<210> SEQ ID NO 15
<211> LENGTH: 523
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, t or u

<400> SEQUENCE: 15

```
tttgcaaaag gtttccggga cactggaaat ggccgaagag aaaaaagana acagctcacc     60

ctgcagtcca tgagggtgtt tgatgaaaga cacaaaaagg agaatgggac ctctgatgag    120

tcctccagtg aacaagcagc tttcaactgc ttcgcccagg cttcttctcc agccgcctcc    180

actgtaggga catcgaacct caaagattta tgtcccagcg agggtgagag cgacgccgag    240

gccgagagca aagaggagca tggccccgag gcctgcgacg cggccaagat ctccaccacc    300

acgtcggagg agccctgccg tgacaagggc agccccgcgg tcaaggctca ccttttcgct    360

gctgagcggc cccgggacag cgggcggctg gacaaagcgt cgcccgactc acgccatagc    420

cccgccacca tctcgtccag cactcgcggc ctgggcgcgg aggagcgcag gagcccggtt    480

cgcgagggca cagcgccggc caaggtggaa gaggcgcgcg cgc                      523
```

<210> SEQ ID NO 16
<211> LENGTH: 424
<212> TYPE: DNA
<213> ORGANISM: Homo sapiens

<400> SEQUENCE: 16

```
actcggtcac actcagtaag tccttgcaga gtccatgggt ttcttcgaca agtggcttca     60

aggaagggaa ttcccaccct tgtcttccag caaggccaca cacatgaaac cagcagaaaa    120

gagtcttatt tgctggaaag acccccagca agggcatagt gagcccttac agtggttcca    180

gtcagaaaag gcaccacttg ggtgggcaca gccccatggg tgtccaactt ggtaagcaga    240

gcaaggctgg acttgagtcc ccgtcctcca caaaacacag agccacaagc cccagccctg    300
```

cagcagccct ccggaagcag cggggcactg gtttccttgt cccctgccat ctaccgagtg 360
gctcactctc aggtgggagt gctggtgatg gttaattagg actgcagaaa catgagcctc 420
ctta 424

<210> SEQ ID NO 17
<211> LENGTH: 524
<212> TYPE: DNA
<213> ORGANISM: Homo sapiens

<400> SEQUENCE: 17
ctatctttct ggtcacattg tcggtgtttc tgcatgttct ccattccgct cctgatgtgc 60
aggattgccc agaatgcacg ctacaggaaa acccattctt ctcccagccg ggtgccccaa 120
tacttcagtg catgggctgc tgcttctcta gagcatatcc cactccacta aggtccaaga 180
agacgatgtt ggtccaaaag aacgtcacct cagagtccac ttgctgtgta gctaaatcat 240
ataacagggt cacagtaatg gggggtttca aagtggagaa ccacacggcg tgccactgca 300
gtacttgtta ttatcacaaa tcttaaatgt tttaccaagt gctgtcttga tgactgctga 360
ttttctggaa tggaaaatta agttgtttag tgtttatggc tttgtgagat aaaactctcc 420
ttttccttac cataccactt tgacacgctt caaggatata ctgcagcttt actgccttcc 480
tccttatcct acagtacaat cagcagtcta gttcttttca tttg 524

<210> SEQ ID NO 18
<211> LENGTH: 538
<212> TYPE: DNA
<213> ORGANISM: Homo sapiens

<400> SEQUENCE: 18
gtagggcgaa ctctgctata cagtttatga tgtcagagtg aatactttct ttgagttgca 60
gtcagaaact gtagattttt aaaaatttaa aattcattat tctctgtcag tattccaaag 120
tgtatacaga aagctattgc actgttcagg agatggcgct taacattttg gaaattcaag 180
gtgatgaatg tccagataag actatctctc ctggtacaaa gtttgacaat gctgaacatt 240
tttaaaggtt ctttttgata tacaaagtgc accaatgagt gctttttaat tcttacaata 300
attctgggtg aggtaggtat ttttccaatt cccattttat gcttcggtag ccctttgtat 360
ttatacttca aaacacttgg ctctcttgta attatttaag aaattagttg tgattatttg 420
tttaatgtgc aggagttaca aaaggcaagc tttagaacaa gacagacctg gttatgattc 480
ctggctctga aagctgtaca ccctgtgacc ctagacaggt gttttaatgc ctcgctgc 538

<210> SEQ ID NO 19
<211> LENGTH: 324
<212> TYPE: DNA
<213> ORGANISM: Homo sapiens
<220> FEATURE:
<221> NAME/KEY: misc_feature
<222> LOCATION: (294)..(295)
<223> OTHER INFORMATION: n is a, c, g, t or u

<400> SEQUENCE: 19
tcttggtctt ctgctcatgg atgacgcacc agtcgtgcat gttcttggtg aagtcggcca 60
gcctgagcaa gcggaggacc tacgccggcc tggcattcca cgcctacggg aaggcaggca 120
agatgctggt ggagaccagc atgatcgggc tgatgctggg cacctgcatc gccttctacg 180
tcgtgatcgg cgacttgggg tccaacttct ttgcccggct gttcgggttt caggtgggcg 240

-continued gcaccttccg catgttcctg ctgttcgccg tgtcgctgtg catcgtgctc ccgnncagcc 300
tgcagcggaa catgatggcc tcca 324

<210> SEQ ID NO 20
<211> LENGTH: 414
<212> TYPE: DNA
<213> ORGANISM: Homo sapiens

<400> SEQUENCE: 20
agaaagcaga gcagcctcct ggaagaaggc cttgtcagct ttgtctgtgc ctcgcaaatc 60
agaggcaagg gagaggttgt taccagggga cactgagaat gtacatttga tctgccccag 120
ccacggaagt cagagtagga tgcacagtac aaaggagggg ggagtggagg cctgagaggg 180
aagtttctgg agttcagata ctctctgttg ggaacaggac atctcaacag tctcaggttc 240
gatcagtggg tcttttggca ctttgaacct tgaccacagg gaccaagaag tggcaatgag 300
gacacctgca ggaggggcta gcctgactcc cagaacttta agactttctc cccactgcct 360
tctgctgcag cccaagcagg gagtgtcccc ctcccagaag catatcccag atga 414

<210> SEQ ID NO 21
<211> LENGTH: 531
<212> TYPE: DNA
<213> ORGANISM: Homo sapiens

<400> SEQUENCE: 21
caaagtcatc tgaacttccg tttccccagg gcctccagct gccctcagac actgatgtct 60
gtccccaggt gctctctgcc cctcatgccc ctctcaccgg cccagtgccc cgactctcca 120
ggctttatca aggtgctaag gcccgggtgg gcagctcctc gtctcagagc cctcctccgg 180
cctggtgctg cctttacaaa cacctgcagg agaagggcca cggaagcccc aggctttaga 240
gccctcagca ggtctgggga gctagagcaa aggagggacc tcaggccttc cgtttcttct 300
tccagggtgg ggtggcctgg tgttccccta gccttccaaa cccaggtggc ctgcccttct 360
ccccagaggg aggcggcctc cgcccattgg tgctcatgca gactctgggg ctgaggtgcc 420
ccggggggtg atctctggtg ctcacagccg agggagccgt ggctccatgg ccagatgacg 480
gaaacagggt ctgaccaagt gccaggaaga cctgtgctat aaaccaccct g 531

<210> SEQ ID NO 22
<211> LENGTH: 522
<212> TYPE: DNA
<213> ORGANISM: Homo sapiens

<400> SEQUENCE: 22
atgtcctgcc atttggtcat aagacagttg catttactct gctaccattg cttcagttga 60
tatgaagaga gaaagctgtg ttgtgattta cactggatat ggaaatagag aggaacaaat 120
ctgtctgatc tactttcttc aacctctgta gtagctaata atataggaca gaatgctcca 180
aagaatgaaa atgaaagtca agattcaatg gatgaaagtg agaactcctc caggtcctgg 240
aaacaaacca tttagcatca ggtcagaagc tactccatgg aattctgaga ccacgaaagc 300
caggtcaggt ctcaaattca gtagcccacc acccacacca ccacccacac caccctgctt 360
cccctcatgc ttgctgcctc catttccttc tggaccacca ataattcccc caccacctcc 420
cacaggtcta gattttcttg atgatgttaa tgttttatga agtatgctaa tctcttggta 480
cattaagtgg ctatcatact ggctattata cagggctcaa gc 522

<210> SEQ ID NO 23
<211> LENGTH: 520
<212> TYPE: DNA
<213> ORGANISM: Homo sapiens
<220> FEATURE:
<221> NAME/KEY: misc_feature
<222> LOCATION: (98)..(98)
<223> OTHER INFORMATION: n is a, c, g, t or u
<220> FEATURE:
<221> NAME/KEY: misc_feature
<222> LOCATION: (142)..(142)
<223> OTHER INFORMATION: n is a, c, g, t or u

<400> SEQUENCE: 23
gaaaggcctg caattgtgtc ttcacgatgc ttttccaaga cagccaaggc aggtataatt 60
ttcctcagca agaaagagga acctcggagg tgtgcacngc ctggctggcc acccaggtat 120
tggcaaaagt gactgtcggg cntgctggcc cggcccccgc ccgccgtccc tggagcactc 180
acgatgcggt ccggcggcgg cgtgctccgg atgaagcact tgatctggcc cttctcgccg 240
tggagggcgt gctgggtctg ggtgctggag atgatggggg gtcctgttga gaaacagcgt 300
cccattaggc acccgggaag ggcacgtccc tgctggcgcc ctcttgggtg ggttcagaag 360
tgtattcatt aatccaagca ttcagcaaac atttgccgaa ggcctgtatg tgcaaggtaa 420
agtgcaaggt agaggactca gagataaatt aggcattcag tcataaacct ctcaagggat 480
catgagcgaa tgcttctaag tcagaacccc cagaagatac 520

<210> SEQ ID NO 24
<211> LENGTH: 488
<212> TYPE: DNA
<213> ORGANISM: Homo sapiens

<400> SEQUENCE: 24
agcagaacct cctagggttt ctccttccac tccttgccat gatcttcttc tactcccgta 60
ttggttgtgt cttggtgagg ctgaggcccg caggccaggg ccgggcttta aaaatagctg 120
cagccttggt ggtggccttc ttcgtgctat ggttcccata caatctcacc ttgtttctgc 180
atacgctgtt ggacctgcaa gtattcggga actgtgaggt cagccagcat ctagactacg 240
cactccaggt aacagagagc atcgccttcc ttcactgctg cttttccccc atcctgtatg 300
ccttctccag tcaccgcttc cgccagtacc tgaaggcttt cctggctgcc gtgcttggat 360
ggcacctggc acctggcact gcccaggcct cattatccag ctgttctgag agcagcatac 420
ttactgccct tgaggaaatg actggcatga atgaccttgg agagaggcag tctgagaact 480
accctaac 488

<210> SEQ ID NO 25
<211> LENGTH: 552
<212> TYPE: DNA
<213> ORGANISM: Homo sapiens

<400> SEQUENCE: 25
gaggagagac ctgcgtggga taatcaacag gggtctggag gacggggaga gctgggaata 60
tcagatctga ctgcgtgttc tcacttcgct tcctggaact tgctctcatt ttcctgggtg 120
catcaaacaa aacaaaaacc aaacacccag aggtctcatc tcccaggccc caggggagaa 180
agaggagtag catgaacgcc aaggaatgta cgttgagaat cactgctcca ggcctgcatt 240
actccttcag ctctggggca gaggaagccc agcccaagca cggggctggc agggcgtgag 300
gaactctcct gtggcctgct catcaccctt ccgacaggag cactgcatgt cagagcactt 360

```
taaaaacagg ccagcctgct tgggcgctcg gtctccaccc cagggtcata agtggggaga    420

gagcccttcc cagggcaccc aggcaggtgc agggaagtgc agagcttgtg gaaagcgtgt    480

gagtgaggga gacaggaacg gctctggggg tgggaagtgg ggctaggtct tgccaactcc    540

atcttcaata aa                                                        552


<210> SEQ ID NO 26
<211> LENGTH: 511
<212> TYPE: DNA
<213> ORGANISM: Homo sapiens

<400> SEQUENCE: 26

aagcctcaag gcacttctag gacctggctc ttctcaccaa gatgaactca ctggtttctt     60

ggcagctact gcttttcctc tgtgccaccc actttgggga gccattagaa aaggtggcct    120

ctgtggggaa ttctagaccc acaggccagc agctagaatc cctgggcctc ctggcccccg    180

gggagcagag cctgccgtgc accgagagga agccagctgc tactgccagg ctgagccgtc    240

gggggacctc gctgtccccg ccccccgaga gctccgggag ccgccagcag ccgggcctgt    300

ccgcccccca cagccgccag atccccgcac cccagggcgc ggtgctggtg cagcgggaga    360

aggacctgcc gaactacaac tggaactcct tcggcctgcg cttcggcaag cgggaggcgg    420

caccagggaa ccacggcaga agcgctgggc ggggctgggg cgcaggtgcg gggcagtgaa    480

cttcagaccc caaaggagtc agagcatgcg g                                   511


<210> SEQ ID NO 27
<211> LENGTH: 131
<212> TYPE: DNA
<213> ORGANISM: Homo sapiens

<400> SEQUENCE: 27

ctcctccagc aagacagatg cctagcccgt cctcaggaat ctgccgccag ggagaatggc     60

aaccctggcc agatagctgg aagcacaggg ttgctcttca acctgcctcc cggctcagtt    120

cactataaga a                                                         131


<210> SEQ ID NO 28
<211> LENGTH: 304
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u

<400> SEQUENCE: 28

tttcctctga gagaacagcg gtcttctgtc tgctgtggca nagcaagtca cttcttcttg     60

tagtgagaac tgaaaccaga accnatcatg tgccacttcc tggacacctc ctattaaata    120

ttaaagtcct ctcaccacag aagccggagt ttagtggtta ggggcacagg ttcttagata    180

tgaacatcag ttgcaaccta ccaactgcat gctcttggac aatttacatt tctgtgtatc    240

agctttcctt tttctttaga atgagatatt aatagtagca acccagaatt gtcatgaagc    300

ctaa                                                                 304


<210> SEQ ID NO 29
<211> LENGTH: 226
```

<212> TYPE: DNA
<213> ORGANISM: Homo sapiens

<400> SEQUENCE: 29
catggcaaag gcttgcccca aatctcaact tctcagacgt tccatacccc cacatgccaa 60
tttcagcacc caactgagat ccgaggagct cctgggaagc cctgggtgca ggacactggt 120
cgagagccaa aggtccctcc ccagacatct ggacactggg catagatttc tcaagaagga 180
agactcccct gcctccccag ggcctctgct ctcctgggag acaaag 226

<210> SEQ ID NO 30
<211> LENGTH: 567
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (226)..(226)
<223> OTHER INFORMATION: n is a, c, g, t or u
<220> FEATURE:
<221> NAME/KEY: misc_feature
<222> LOCATION: (255)..(256)
<223> OTHER INFORMATION: n is a, c, g, t or u
<220> FEATURE:
<221> NAME/KEY: misc_feature
<222> LOCATION: (261)..(261)
<223> OTHER INFORMATION: n is a, c, g, t or u
<220> FEATURE:
<221> NAME/KEY: misc_feature
<222> LOCATION: (284)..(284)
<223> OTHER INFORMATION: n is a, c, g, t or u
<220> FEATURE:
<221> NAME/KEY: misc_feature
<222> LOCATION: (313)..(313)
<223> OTHER INFORMATION: n is a, c, g, t or u
<220> FEATURE:
<221> NAME/KEY: misc_feature
<222> LOCATION: (328)..(328)
<223> OTHER INFORMATION: n is a, c, g, t or u
<220> FEATURE:
<221> NAME/KEY: misc_feature
<222> LOCATION: (333)..(334)
<223> OTHER INFORMATION: n is a, c, g, t or u
<220> FEATURE:
<221> NAME/KEY: misc_feature
<222> LOCATION: (356)..(356)
<223> OTHER INFORMATION: n is a, c, g, t or u
<220> FEATURE:
<221> NAME/KEY: misc_feature
<222> LOCATION: (411)..(411)
<223> OTHER INFORMATION: n is a, c, g, t or u
<220> FEATURE:
<221> NAME/KEY: misc_feature
<222> LOCATION: (471)..(471)
<223> OTHER INFORMATION: n is a, c, g, t or u
<220> FEATURE:
<221> NAME/KEY: misc_feature
<222> LOCATION: (473)..(473)
<223> OTHER INFORMATION: n is a, c, g, t or u
<220> FEATURE:
<221> NAME/KEY: misc_feature
<222> LOCATION: (492)..(492)
<223> OTHER INFORMATION: n is a, c, g, t or u
<220> FEATURE:
<221> NAME/KEY: misc_feature
<222> LOCATION: (497)..(500)
<223> OTHER INFORMATION: n is a, c, g, t or u
<220> FEATURE:

<221> NAME/KEY: misc_feature
<222> LOCATION: (503)..(503)
<223> OTHER INFORMATION: n is a, c, g, t or u
<220> FEATURE:
<221> NAME/KEY: misc_feature
<222> LOCATION: (510)..(511)
<223> OTHER INFORMATION: n is a, c, g, t or u
<220> FEATURE:
<221> NAME/KEY: misc_feature
<222> LOCATION: (513)..(513)
<223> OTHER INFORMATION: n is a, c, g, t or u

<400> SEQUENCE: 30

```
ggccaccaga ggattctcag ggctcctttg tcctggactg tggaactggg ggcagctggt     60

ccctggggtc tctgaagtca gtgtctccct cactgctcac tgccatggtg tctctgcctc    120

tgcttctctg tgtccctcat cttcctccca cttcattctg actggcaagc cctgtcctgc    180

acagcttctt ccccnacccc taggccttcc ccaganactc cctctnacta ggctggctgt    240

tctgttccct tcccnnctaa nactgtggcc tggcccacct cccnaggaaa taggaaaggt    300

gcagaaatca ccntggagtt gccactcntg ccnnggcttc atctcgagcc aatgtnccca    360

ggtcactaag agaatgagct tccactgtat tcccatccag ggctctttcc ntttgtgagg    420

ctgacctgtg gacaagacaa tgggacaggg ataggcagtt cctccatcca ntntcataat    480

tgccaggcaa gntcttnnnn ccncctgcan nancctcccc agtggatcag gggttagaga    540

tattcaaggg tagtttcagg agcacag                                        567
```

<210> SEQ ID NO 31
<211> LENGTH: 448
<212> TYPE: DNA
<213> ORGANISM: Homo sapiens
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (96)..(97)
<223> OTHER INFORMATION: n is a, c, g, t or u

<400> SEQUENCE: 31

```
taatgcggac gtaccgactg ccagatcttt acactcaccc ctccacctgc cccgaggagt     60

ccggtcacaa gggcccagcc antcacaaag acaccnnggt gtcccttcca ttttttttcca    120

cgaaggccca gaatccattt taggtttcca aacagacctt tcgtcccttc aaggtgtaac    180

caccgttttc cattccagcc attttattgg ccacaccgtt accttactta taggtatttc    240

cccagaagaa gactccagag aggaagctca tctgaggaaa gctgagaggg aagagaaacc    300

caaacatact gaagcaaaaa aaagcctatc cttcagaaaa aagcaacaaa aagatttctg    360

ttttatcttt cgaaactaaa actattggat ttgaagatta agtatcctaa acatcactga    420

ctagaaactg ttctctttgt cagcagtg                                       448
```

<210> SEQ ID NO 32
<211> LENGTH: 396
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, t or u

<400> SEQUENCE: 32

```
agtgtgcatg ttcactgggc atcttccctt cgaccccttt gcccacgtgg tgaccgctgg     60
```

ggagctgtga gagtgtgagg ggcacgttcc agccgtctgg actctttctc tcctactgag 120
acgcagccta taggtccgca ngccagtcct cccaggaact gaaatagtga aatatgagtt 180
ggcgaggaag atcaacatat aggcctaggc caagaagaag tttacagcct cctgagctga 240
ttggggctat gcttgaaccc actgatgaag agcctaaaga agagaaacca cccactaaaa 300
gtcggaatcc tacacctgat cagaagagag aagatgatca gggtgcagct gagattcaag 360
tgcctgacct ggaagccgat ctccaggagc tatgtc 396

<210> SEQ ID NO 33
<211> LENGTH: 484
<212> TYPE: DNA
<213> ORGANISM: Homo sapiens

<400> SEQUENCE: 33
cggtggcttg caacatgctc atgccagagc ccgctcaacg ctggctggtg ggcttcgtgt 60
tgtacacatt tctcatgggc ttcctgctgc ccgtgggggc tatctgcctg tgctacgtgc 120
tcatcattgc taagatgcgc atggtggccc tcaaggccgg ctggcagcag cgcaagcgct 180
cggagcgcaa gatcacctta atggtgatga tggtggtgat ggtgtttgtc atctgctgga 240
tgcctttcta cgtggtgcag ctggttaacg tgtttgctga gcaggacgac gccacggtga 300
gtcagctgtc ggtcatcctc ggctatgcca acagctgcgc caaccccatc ctctatggct 360
ttctctcaga caacttcaag cgctctttcc aacgcatcct atgcctcagc tggatggaca 420
acgccgcgga ggagccggtt gactattacg ccaccgcgct caagagccgt gcctacagtg 480
tgga 484

<210> SEQ ID NO 34
<211> LENGTH: 393
<212> TYPE: DNA
<213> ORGANISM: Homo sapiens

<400> SEQUENCE: 34
tctgacttcc agaacctacg ataatagact ccatgaaatc tgtaatcagt ggccacagga 60
aactcatgca acagcccttc caaggggctc cccagcaaag cctccgtggt gtctgccccc 120
aacccctgtg cctcctggga cacaagacag gcccagcaag ggtgggggtg ccacggaaag 180
cttggtggct gggcaggtcc ccagagggcc gccatcagtc ctcaaagaca tgctcagatg 240
cagtggctca ggcctggcac cagctggtcc caaggtgggg tggtgagggt acatctgctg 300
tgcacacgtg gctggacgcg ctgggggcag gtccaggtca gcttcaagga ctctgcccag 360
gctaacccta gaggcctcta gtgccagcag tta 393

<210> SEQ ID NO 35
<211> LENGTH: 493
<212> TYPE: DNA
<213> ORGANISM: Homo sapiens

<400> SEQUENCE: 35
aggcccatgt gctgtttttg acttcagtac ttcagattgc tgtgggaaca caggaggcag 60
cagccagatg agaaattgag tctgactctg gagtattata aagtccttat agttactggc 120
attaggtata gggtctgtat tattaaagag aaattattca ccaaacactt gttaaaaatg 180
gcaagacagt ttatttaaga gcattgcaat aggtaagtgc tatggtctca atgtttgtgt 240
ctccctcaaa ttcataagtt gaaacttcac ttccaagatg aaggaattag gaggtgggca 300
ctttaaggga tgattatgtc ataggccaga gccctcatga acgagatcag tgcccttcta 360
aaagaggcat tgggagagac ccctcacctt ttccatcata tgaggacaca gccaggaagc 420
atcatccacg aaccagaaaa ttggccctta ccagacactg aatctgctga tgtcctgacc 480
atggacttct gag 493

<210> SEQ ID NO 36
<211> LENGTH: 336
<212> TYPE: DNA
<213> ORGANISM: Homo sapiens

<400> SEQUENCE: 36
acgctgcagc gtcacattaa tctttgtgcc gccagtgcct atgccatgct tagtatgcat 60
caaatatttg agcagtacac aagtgagtac tctgagagct ccccccacca aaaatatgat 120
gattaaatac agttatgatc agatccccag agtgtggctc taaactgtat gggggccaag 180
tttgaatact gttgtgtctt acactgttat tacctatcca gtatctattt ccccatattc 240
cttataaata aaacctagat tttgattggg acagtaaggt gtcccactga aaactcattt 300
ctctaaccaa tgtgatgcca gtgcttgccc aaaaag 336

<210> SEQ ID NO 37
<211> LENGTH: 507
<212> TYPE: DNA
<213> ORGANISM: Homo sapiens

<400> SEQUENCE: 37
gtgagtgaac gtgaaggcct gcagcattac tgtacactac catagatttt tatcaacact 60
gtacacttag ggacactaaa cttatttaaa cattttttct tcaaaaataa attaacctca 120
gctcactgta actttataag ctttatattt aaaaaaactt tttgactctt ttgtagtaac 180
acttagctta aaacacaaac acattgtaca gttacacaaa atattttctt aaaaaatatt 240
ttattatatc ctattctata agcttttcct tgtttttcac ttttttttaa cttttaaact 300
ttttataaaa actaagacac aaacacacac attagtgcag gcctgcatag catcaggatc 360
atcagtatca ctgtctccca cctccgcatc ttgtcccact gaaaggtctt cagcgggaat 420
atcatgcatg gagctgtcat ctcctgtgat aacaatgcct tcttctggat acctcctgaa 480
ggacctggtt gagcctgttt tacagtt 507

<210> SEQ ID NO 38
<211> LENGTH: 423
<212> TYPE: DNA
<213> ORGANISM: Homo sapiens

<400> SEQUENCE: 38
gaatccctta agcagaacaa ccgtgatgcc atggaactca agcccaacgg cggtgctgac 60
caaaaatgtc tcaaagtcaa cagcccaata agaatgaaga atggaaatgg aaaagggtgg 120
ctgcgactca agaataatat gggagcccat gaggagaaaa aggaagactg gaataatgtc 180
actaaagctg agtcaatggg gctattgtct gaggacccca agagcagtga ttcagagaac 240
agtgtgacca aaaacccact aaggaaaaca gattcttgtg acagtggaat tacaaaaagt 300
gaccttcgtt tggataaggc tggggaggcc cgaagtccgc tagagcacag tcccatccag 360
gctgatgcca agcacccctt ttatcccatc cccgagcagg ccttacagac cacactgcag 420
gaa 423

<210> SEQ ID NO 39
<211> LENGTH: 365
<212> TYPE: DNA
<213> ORGANISM: Homo sapiens
<220> FEATURE:
<221> NAME/KEY: misc_feature
<222> LOCATION: (244)..(244)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u

<400> SEQUENCE: 39
ttactctgtg attaacttcc ttctccctca ccccaaaata cagaagagtg aaatctctga 60
ccagaaagtt cctggcacct accttgggtt ctgtgaaaaa ataatggccc tggttttcaa 120
tgctgccaaa gttaagaaaa gttttcaccc cttcatttta aagcagccat aaagtgccat 180
gtgtttaacc gcaggaaaaa aagggtcttt ttaactattg agaagtagct tttcatatcc 240
ccancagggg aangaaagag cgggaaccag gagactcgtg aggactgcaa agatggtcct 300
ccctgggtac ttctgctgct ctcttctctc cagagctact ttgtgattgg cctgatggtc 360
agacc 365

<210> SEQ ID NO 40
<211> LENGTH: 389
<212> TYPE: DNA
<213> ORGANISM: Homo sapiens

<400> SEQUENCE: 40
gatggagcat catgggttgg attattactg agttcaataa tctggtgggt tttgccagct 60
agaaacataa taaaatacat gataaaggaa tagaaaggaa atatatttat ttgaaattaa 120
attactgctt ataaattcat gtctctgatt ttacaaagtg taatgggtaa aattaccata 180
ttctttttct tatttcaatc catacaatga gagtcatgtt cagtttttca ctgacttcat 240
gctgggtaat gttcactctg cattagcggt tgccatgttc accgttttct tacaatgtct 300
atccagtgct tgttactgtc tcactgacag acagaagtct agctgttttc atccacataa 360
tggcaggcag ggctagtgtt gctgctgct 389

<210> SEQ ID NO 41
<211> LENGTH: 537
<212> TYPE: DNA
<213> ORGANISM: Homo sapiens

<400> SEQUENCE: 41
ttatgtccct gctggtattt ttgctttttc ataaaaatta tcatttattt ttctcaactg 60
catattgcca tcttcatttt ttaattttct cacatattca tagaattgtt ctctgtaata 120
gatactgtac agtaattatt tgttgatcga ttaacctttt caatgctact tccgacacct 180
acttcccatc ctccgtgtaa cagatactgt cagttaccta tccttaacag cctttccact 240
cccaacttct gtgaatggac aagagatgca attgtgatca ctgaacatga ggcaacatct 300
tctaggaaga catttccata gtcttcagac aaaagggaga gatatctttt cagacaatct 360
ttgaacaatc ctatatgaag cttacctgaa gttgctgtag ccgtttggca agtctgggga 420
gactaacaga cacactgagg atagcagaaa ataaagatag aaacagccca ggtttttggt 480
gaaattcatg agcttctgaa taacgaaccc cataccaccc tacctctata aaagaat 537

<210> SEQ ID NO 42

<211> LENGTH: 351
<212> TYPE: DNA
<213> ORGANISM: Homo sapiens

<400> SEQUENCE: 42

```
tggatcccag catcgttggc aatagggttt taggtggagt ctatctggca ttcagagaag     60

agtcaggaaa acaattgtat tcccagcctg tgtccctagg gcacaagcaa atcccaaatt    120

ctcctcctga accctccaaa tttgtctaag aacttcgaaa actttaacaa acaggctgat    180

atcttcataa tattcccagc ctagaccaag caggaagaac attgatttca ttgaaataat    240

tgataataat gaagataatg tttttatgat ttttatttga aaatttgcta attctttaaa    300

tggtttgttt tctacattga tggaattttt ctcttttaat ctatctacag c             351
```

<210> SEQ ID NO 43
<211> LENGTH: 528
<212> TYPE: DNA
<213> ORGANISM: Homo sapiens

<400> SEQUENCE: 43

```
tctgtttatc ccccaaatta ctacaaagca tagcgggctc tatgtttgct ctgttcgtaa     60

ctcagccact gggcaggaaa gctccacatc gttgacagtc aaagtctctg cttctacaag    120

aataggactt cttcctctcc ttaatccaac atagcagctg tgatgtcatt tctgtatttc    180

aggaagactg gcaggagatt tatggaaagg tctcttacaa ggactcttga atacaagctc    240

ctgataactt caagatcata ccactggact aagaactttc aaaattttaa tgaacaggct    300

gataccttca tgaaattcaa gacaaagaag aaaaatactc aatgttattg gactaaataa    360

tcaaaaggat aatgatttca taattttcta tttgaaaatg tgctgattct tggaatgttt    420

cattctccag atttatgaac atttttttctt gagcaattgg taaagtatac ttttgtaaac    480

aaaaattgaa acatttcctt ttgctctcta tctgagtgcc ccagaatt                528
```

<210> SEQ ID NO 44
<211> LENGTH: 545
<212> TYPE: DNA
<213> ORGANISM: Homo sapiens

<400> SEQUENCE: 44

```
gggacacacc agcacagtct ggtaggctac agcagcaagt ctctaaagaa aggctgagaa     60

cacccagaac aggagagttc aggtccagga tggccagcct gttccggtcc tatctgccag    120

caatctggct gctgctgagc caactcctta gagaaagcct agcagcagag ctgaggggat    180

gtggtccccg atttggaaaa cacttgctgt catattgccc catgcctgag aagacattca    240

ccaccacccc aggagggtgg ctgctggaat ctggacgtcc caaagaaatg gtgtcaacct    300

ccaacaacaa agatggacaa gccttaggta cgacatcaga attcattcct aatttgtcac    360

cagagctgaa gaaaccactg tctgaagggc agccatcatt gaagaaaata atactttccc    420

gcaaaaagag aagtggacgt cacagatttg atccattctg ttgtgaagta atttgtgacg    480

atggaacttc agttaaatta tgtacatagt agagtaatca tggactggac atctcatcca    540

ttctc                                                                545
```

<210> SEQ ID NO 45
<211> LENGTH: 166
<212> TYPE: DNA
<213> ORGANISM: Homo sapiens
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (38)..(41)
<223> OTHER INFORMATION: n is a, c, g, t or u
<220> FEATURE:
<221> NAME/KEY: misc_feature
<222> LOCATION: (43)..(45)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u

<400> SEQUENCE: 45
tgctgtttgt gtgaaacctc cactgtgcca agcannannn nannngactg tgaatanttt 60
aacatttatt cacagatagc atgaaaagcc acagtccatt tgccatttag cttatttgat 120
tgagagaaaa ctgaggcaca ggaaggcaca gtgactgagc aagagt 166

<210> SEQ ID NO 46
<211> LENGTH: 205
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, t or u

<400> SEQUENCE: 46
ggatcagtct taagaggagc ttttttngg agcgagaaat catataaaat aaaatgaaat 60
aaaacaagga ggaaggcaac cagctgttag gggaaaaata aggcagataa aggagcgggg 120
agagaaatta attgccaacc aggaggagtt gggctgtatt tttcaaaggt ggggagagtg 180
gagcacacac cttgaggagg aaagc 205

<210> SEQ ID NO 47
<211> LENGTH: 294
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, t or u
<220> FEATURE:
<221> NAME/KEY: misc_feature
<222> LOCATION: (132)..(132)
<223> OTHER INFORMATION: n is a, c, g, t or u
<220> FEATURE:
<221> NAME/KEY: misc_feature
<222> LOCATION: (193)..(193)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (219)..(220)
<223> OTHER INFORMATION: n is a, c, g, t or u
<220> FEATURE:
<221> NAME/KEY: misc_feature
<222> LOCATION: (242)..(242)
<223> OTHER INFORMATION: n is a, c, g, t or u
<220> FEATURE:
<221> NAME/KEY: misc_feature
<222> LOCATION: (260)..(260)

<223> OTHER INFORMATION: n is a, c, g, t or u
<220> FEATURE:
<221> NAME/KEY: misc_feature
<222> LOCATION: (267)..(267)
<223> OTHER INFORMATION: n is a, c, g, t or u

<400> SEQUENCE: 47
gaaccatttg agattcaatg cctgtgtcca gctcccagga gtccaaccgt gaaatccaca 60
agtgcagncc ccaccctgtc ctgcagttct ctttccctta tgataatgtg gttgagtcct 120
ttgtcactcc cntcctcctg ctggctgcag aaatgacctc agcccaggcc agagacccca 180
gctctggcaa ggncctcttg tggtcgncca ggncccagnn tgaaagccaa gcagaatcag 240
gncaggatct ctagcgggan gggaaancct gataggacct ttgtcagact tttg 294

<210> SEQ ID NO 48
<211> LENGTH: 432
<212> TYPE: DNA
<213> ORGANISM: Homo sapiens

<400> SEQUENCE: 48
acatttaccg tattacctag cactttcatt ccttgttgtc tactccaaag gaaaaaaacc 60
tatgtccaca caacacatga atgtgaatat tagtagcagc tttatccata atagtccata 120
aagtagaaac acatcaaata tctatcagct gatgaaagaa taaacaaatg ggagtgatcc 180
atacaattta atagaatcta gcacctaaaa aaataaaata ttgatacgtg ctacaacaca 240
ggtgaaccac aaaagcacat taatctaagt gaaagaagac agatacaaaa aaccacatgt 300
tgtatgactc tatttttatg atatccagaa aagacaaatc tgtagtgtca gtaagtcaat 360
taggggttgt ctggagctgg ggagtgggaa taaggggtgg tattgatgag catgagggat 420
ttcttaggaa tt 432

<210> SEQ ID NO 49
<211> LENGTH: 541
<212> TYPE: DNA
<213> ORGANISM: Homo sapiens
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (67)..(67)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u
<220> FEATURE:
<221> NAME/KEY: misc_feature
<222> LOCATION: (127)..(127)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (498)..(499)
<223> OTHER INFORMATION: n is a, c, g, t or u

<400> SEQUENCE: 49
gtgaatccta gagtagtttg ctatcaactt ctgatctttg cacattctgg attnggcata 60
taatgtnaca gcagtgccna ttgtaatgtt gcacaaagta gtntagcaat ttcttggttc 120
accaggntta gagataacat tgtagaaatg atccagcatc tttaacantc tgtggtttaa 180
ggtggggcac ttaggggtag aatcaataac aatgttagaa atcaaattag acaagataac 240
tgaaacagca tgatccatgt gtgactccaa gttataaagg aggacatgga ttaatggtat 300
acttctaggc tataggggta gtacaagtgg aaggacacca tcttagcatc agatcacttt 360
ctgagcaact ttggcaaatc ttttaaattc tctaatgtgt agttttttaa tatatgacac 420
aggtgtaaag aaaataaagc aagtgaatgt atgtgaaagc caatgctgac tgggcacggg 480
ggctcacgcc tgaaattnnt agcactttgg gaggcagagc cggggatatc acttgagccc 540
a 541

<210> SEQ ID NO 50
<211> LENGTH: 393
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (67)..(69)
<223> OTHER INFORMATION: n is a, c, g, t or u
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (88)..(88)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (285)..(285)
<223> OTHER INFORMATION: n is a, c, g, t or u

<400> SEQUENCE: 50
tcatctacac gctggccagc aaggagatgc ggcgggcctt cttccgtctg gtctgcaact 60
gcntngnnng gggacggggg gcccgngncc tcacccatcc agcctgcgct cgacccaagc 120
agaagtaaat caagcagcag caacaatagc agccactctc cgaaggtcaa ggaagacctg 180
ccccacacag ncccctcatc ctgcatcatg gacaagaacg cagcacttca gaatgggatc 240
ttctgcaact gatcgtctcc atgcgccctg ctctgcggct gtgtncttat ttattgcatg 300
cgtcgcttcc acaggggccc ctcaagagct gtgactcggg agagctacct tactttgacc 360
aacagcctgc ccagtgtgga tgtctcttac aga 393

<210> SEQ ID NO 51
<211> LENGTH: 543
<212> TYPE: DNA
<213> ORGANISM: Homo sapiens

<400> SEQUENCE: 51
cctccttagc cttagaagcc agtggtgccc tgaccagagg ggaccctgtg ttcacaggca 60

-continued

```
tcctcaagga ttatcttcga gagttgccca ccccactcat cacccagccc ctgtataagg    120

tggtactgga ggccatggcc cgggaccccc caaacagagt tccccccacc actgagggca    180

cccgagggct cctcagctgc ctgccagatg tggaaagggc cacgctgacg cttctcctgg    240

accacctgcg cctcgtctcc tccttccatg cctacaaccg catgacccca cagaacttgg    300

ccgtgtgctt cgggcctgtg ctgctgccgg cacgccaggc gcccacaagg cctcgtgccc    360

gcagctccgg cccaggcctt gccagtgcag tggacttcaa gcaccacatc gaggtgctgc    420

actacctgct gcagtcttgg ccaggtgagt tcatgcccag ggcctgcacc accaatctga    480

gccaggctgc tacaatcccc gcctgccccg acaatctcca gatgtcgcgc cttacttgcg    540

acc                                                                   543

<210> SEQ ID NO 52
<211> LENGTH: 367
<212> TYPE: DNA
<213> ORGANISM: Homo sapiens

<400> SEQUENCE: 52

tcgcctgtac cagctggcat atgacaccta tcaggagttt aacccccaga cctccctctg     60

cttctcagag tctattccaa caccttccaa cagggtgaaa acgcagcaga aatctaacct    120

agagctgctc cgcatctccc tgctgctcat ccagtcatgg ctggagcccg tgcagctcct    180

caggagcgtc ttcgccaaca gcctggtgta tggcgcctcg gacagcaacg tctatcgcca    240

cctgaaggac ctagaggaag gcatccaaac gctgatgtgg aggctggaag atggcagccc    300

ccggactggg cagatcttca atcagtccta cagcaagttt gacacaaaat cgcacaacga    360

tgacgca                                                               367

<210> SEQ ID NO 53
<211> LENGTH: 470
<212> TYPE: DNA
<213> ORGANISM: Homo sapiens

<400> SEQUENCE: 53

cccccgagga caacctggag atcgttctgc acagatggga gaacaacagc tgtgttgaga     60

agaaggtcct tggagagaag actgggaatc caaagaagtt caagatcaac tatacggtgg    120

cgaacgaggc cacgctgctc gatactgact acgacaattt cctgtttctc tgcctacagg    180

acaccaccac ccccatccag agcatgatgt gccagtacct ggccagagtc ctggtggagg    240

acgatgagat catgcaggga ttcatcaggg ctttcaggcc cctgcccagg cacctatggt    300

acttgctgga cttgaaacag atggaagagc cgtgccgttt ctagctcacc tccgcctcca    360

ggaagaccag actcccaccc ttccacacct ccagagcagt gggacttcct cctgcccttt    420

caaagaataa ccacagctca gaagacgatg acgtggtcat ctgtgtcgcc               470

<210> SEQ ID NO 54
<211> LENGTH: 504
<212> TYPE: DNA
<213> ORGANISM: Homo sapiens

<400> SEQUENCE: 54

gtgtgtggat tcaacagtcg accccagctg tcgcagagcg cgaggaagct gcgcagtaaa     60

ccccttacat atcaacctct gaggaccggt ttttctgcac ctggtggtcc ttctagacgt    120

ctaggaggat cgtgttctca ggagagggtt cttcagcatc tgtgctgaag aacactgccc    180

cagcgggtca catgcaagat tccaccttcg agcaacatag ctgacactct gcagcccagt    240
```

```
tgtcacttgt aacaaacccc agtgggtcac atagtgaggg gaggcaaggc agcgtaaggc    300

agtggctgaa ctatcccaga aaacaaggat cacaggcccc cagtgacacc aatgttgcag    360

aaacacctgc agtggcaagt cagatgtcct ccaggaccag gcagataaca aggagtaggg    420

gtctgcagag gcctcgggag ggtctgcacc atccaaagaa atcaattgtt ctgcacagtg    480

gtaaggatcc agtgttccca gcac                                            504


<210> SEQ ID NO 55
<211> LENGTH: 382
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (65)..(66)
<223> OTHER INFORMATION: n is a, c, g, t or u
<220> FEATURE:
<221> NAME/KEY: misc_feature
<222> LOCATION: (70)..(70)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (345)..(345)
<223> OTHER INFORMATION: n is a, c, g, t or u

<400> SEQUENCE: 55

gaacaccatt gtcttcaata acctgtnggg catatccagg aggcacatag ataggaggca     60

caganncatn tngggacatc attggaacct gagcaggacc tgtaatgcac tgaaactgtc    120

catcttctct tcttattgta aatgcttctc ctgggttaac ttgtaccaga ataacctgtt    180

gtgttccatc tgcacttaca ataggggcag acaaaagaga aatatcacta cttaagatct    240

gagttgtatc cagtagtggt ggatgttctg ccattatcaa taagacatta atatactgaa    300

taacgctcca attctccgag tcacgccgtt ctgaggcaga aggcngctcc tctggcgcct    360

cttcttaggg ttcctgatcg tt                                              382


<210> SEQ ID NO 56
<211> LENGTH: 440
<212> TYPE: DNA
<213> ORGANISM: Homo sapiens
<220> FEATURE:
<221> NAME/KEY: misc_feature
<222> LOCATION: (83)..(83)
<223> OTHER INFORMATION: n is a, c, g, t or u
<220> FEATURE:
<221> NAME/KEY: misc_feature
<222> LOCATION: (141)..(141)
<223> OTHER INFORMATION: n is a, c, g, t or u
<220> FEATURE:
<221> NAME/KEY: misc_feature
<222> LOCATION: (262)..(262)
<223> OTHER INFORMATION: n is a, c, g, t or u
<220> FEATURE:
<221> NAME/KEY: misc_feature
<222> LOCATION: (373)..(373)
<223> OTHER INFORMATION: n is a, c, g, t or u

<400> SEQUENCE: 56

gaagtgggag cggctcagca taggatgggc acgccatcag ccgtcaccag gcgcccggtg     60
```

-continued

```
gtggggtcgt aggtgcccgc cangtagtag aggtcctgcc ggtcctggca cttgcggctc    120

cgggccatct gctcatactg ntcgcgcgcc acgacctggc acttgtggga gatggtctgc    180

acgtcgttct catcctcgtg gcaggactgg tacagcgcat tcttgccgtc gcactgcctc    240

ttgcccagct tggtctcctc angggtggta gaaccacttg accttgacca ccatgttgct    300

gccccacgac tcccacatgc tctcgatgcg gccgatgtag gggaggttgg gccgcccagc    360

tgacaggaag acngcacagt ccccgacacg cagggtctcc tcgccccgca cgatggcctt    420

gtagaacagc ttccgggcct                                                440
```

<210> SEQ ID NO 57
<211> LENGTH: 265
<212> TYPE: DNA
<213> ORGANISM: Homo sapiens

<400> SEQUENCE: 57

```
catcgcccac caaggcctgg gtgggtgaga acagtgccca caaggagacc ctgagtaaca     60

gagactcaca gcccatccag gtctctgggc aggaaattga aggaatcatc acattttaca    120

gaggaggaga ctgcagctca gagtggggga agtgtgtgca ccaggccaca ggcaagtctg    180

tccagagcac tggtaggaat gagggaaact aggaatgacc actttaaaaa gttagatgag    240

aagaatttca aggccgggcg cggtg                                          265
```

<210> SEQ ID NO 58
<211> LENGTH: 355
<212> TYPE: DNA
<213> ORGANISM: Homo sapiens
<220> FEATURE:
<221> NAME/KEY: misc_feature
<222> LOCATION: (229)..(229)
<223> OTHER INFORMATION: n is a, c, g, t or u

<400> SEQUENCE: 58

```
gctttatgca gtttgtcctt tcagttttca ggaatgagac ctcttgaccc ctcccctcca     60

atgcagcccc tactaagggg gagtttaagg agccatacat agttctataa ttcaaatcaa    120

gtaaacatgc ttcttgtccc aggttaactt gtgctgcctc agtcgctgtt taaacatttt    180

tatacgcact gttaacctgc ctgcccatta ccctattact tttaatggnt aaactactgt    240

tccctgggca gttgtctctt ttaacgtccc accctaaact tgccaaccct catatgaagg    300

cctcaggctt gttattggca aaggtcagaa gtcttaagct agtgaccttg caggc         355
```

<210> SEQ ID NO 59
<211> LENGTH: 443
<212> TYPE: DNA
<213> ORGANISM: Homo sapiens

<400> SEQUENCE: 59

```
ccctgacggc agaagagccc agcttcctgc agcccctgag gcgacaggct ttcctgagga     60

gtgtgagtat gccagccgag acagcccaca tctcttcacc ccaccatgag ctccggcggc    120

cggtgctgca acgccagacg tccatcacac agaccatccg caggggggacc gccgactggt    180

ttggagtgag caaggacagt gacagcaccc agaaatggca gcgcaagagc atccgtcact    240

gcagccagcg ctacgggaag ctgaagcccc aggtcctccg ggagctggac ctgcccagcc    300

aggacaacgt gtcgctgacc agcaccgaga cgccaccccc actctacgtg gggccatgcc    360

agctgggcat gcagaagatc atagaccccc tggcccgtgg ccgtgccttc cgtgtggcag    420

atgacactgc ggaaggcctg agt                                            443
```

<210> SEQ ID NO 60
<211> LENGTH: 552
<212> TYPE: DNA
<213> ORGANISM: Homo sapiens

<400> SEQUENCE: 60
gtctcgaggc agggctgaca catggtgcca tagccagcgg agggcgctca gtgagtgccc 60
cgggccttct agacaacagg caggaaggat gaacctcagg gcacccccag gtggtgcgga 120
aagccaggca gttgggacag aggtgcccac gagggcagag gccggtgcta aggggatggg 180
gaagaaggga caagattccc agagaggaga ggaggctgtt ggtaggaaag tggcagggct 240
gggggagacc cagccccaag ggtccggggc ggaggatgct ttgttctttt ctggttttgg 300
ttcctctttc gcggggggtg ggggaggtca acagggactg agtggggcag aggcccagaa 360
gtgccagcct ggggagccgt ttgggggcag ccccttctgc ccaccccatc cttcttcctc 420
tccagagatg ccagggggc gtgtatgctc tgccccttcc ctcagacagg ggctgggtgg 480
ggaggctctt taggctcagg agaagcattt taaagaaacc cccaccctgc cgcccgcatt 540
ataaacacag ga 552

<210> SEQ ID NO 61
<211> LENGTH: 361
<212> TYPE: DNA
<213> ORGANISM: Homo sapiens

<400> SEQUENCE: 61
ctctttatcc ctcagattac tccaaagcat aatgggctct atgcttgctc tgctcgtaac 60
tcagccactg gcgaggaaag ctccacatcc ttgacaatca gagtcattgc tcctccagga 120
ttaggaactt tttgctttca ataatccaag tagcagccct gatgtcattt ttgtatttca 180
ggaagactgg caggagattt atggaaaaga ctatgaaaag gactcttgaa tacaagttcc 240
tgataacttc aagatcatac cactggacta agaactttca aaattttgat gaacaggctg 300
ataccttcat gaaattcaag acaaagaaga aaagaactcc atttcattgg actaaataac 360
a 361

<210> SEQ ID NO 62
<211> LENGTH: 238
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (77)..(77)
<223> OTHER INFORMATION: n is a, c, g, t or u
<220> FEATURE:
<221> NAME/KEY: misc_feature
<222> LOCATION: (91)..(91)

<223> OTHER INFORMATION: n is a, c, g, t or u

<400> SEQUENCE: 62
caaagtggga ggattacaag tgttatccna ccnatgcntg gacaggaata tttttaaata 60
atgaaaccna agttccnttt cgctttgtaa ngttaatgca tgtattgatg gtgagtagag 120
aacaatgaca caatctctag agagacatag gtgttcggcc tggctcaatc actagcctta 180
tagtctcaca ggaaaatatg aacttcatca aaatagctaa ttattaccac atcatgga 238

<210> SEQ ID NO 63
<211> LENGTH: 355
<212> TYPE: DNA
<213> ORGANISM: Homo sapiens

<400> SEQUENCE: 63
atgcagatga cgttgtggcc accgcactgg ccgtggagcc catgaagttt gtctacagag 60
gcaggatcgc tgtgttctct gtgaccgtgc tgcacgacga ccggattgtc ctggtggctg 120
agcagcggcc ggatgcctcg gaggaggaca gcttccagtg gatgagccgt gtgctgcagg 180
tgggcgcccc ggcacggcct atggttcggt gaatctccca agctggcacc cccactccac 240
tccaagtgcc aagtggttgg cttgtcccgc ccggtcctcc ctggctccag ctttgtttat 300
ctgtattttt cattgcaaat tgacaaatta cagctgtatg tatttacggg ataca 355

<210> SEQ ID NO 64
<211> LENGTH: 230
<212> TYPE: DNA
<213> ORGANISM: Homo sapiens

<400> SEQUENCE: 64
cctccctcaa agctactaaa catgaaaaca ttgtgcctat atgataaaaa tgtcaatatt 60
gctggtgata ctgatgctga tggaaatgac gatattagct gccattaacg tagtatctaa 120
tgtgtgccaa acaatattaa aaattgctgt atatacatgt ttgccattta ttatttataa 180
ccttaacaag atgtctcact cataagacta ctttccgcac tatgatacag 230

<210> SEQ ID NO 65
<211> LENGTH: 552
<212> TYPE: DNA
<213> ORGANISM: Homo sapiens

<400> SEQUENCE: 65
agtggcctta gacataactg ctgcccaagg agccacctgt gcccttttag gaacacaatg 60
ttgtacctta tccctgacaa tcagcagaac ataacagcag ccctgcaaag gggtcttcca 120
ggagattaag gtgactgaga gcctcactgt caaccccctg cagagatggt gagcatccct 180
aggttctggc gtacattggg ccctaatagt cataagtatc atagctgaga tcctagtagt 240
gagctgttgc tctctgtatt gttgttgtgg gttatggact cagggctccg ccatataggc 300
atgtgtccct gcctggagga cgccctcagc ctagggggtg tagtgtaagg gaaatggctg 360
tgctttagtc aggagtaggc tgaggcagcc ttctggtgca gcatgactca gtgggtttgg 420
agtgcaagca cacaaccttg ctcgttatgt aaccacacca catgaggccc attaggtaac 480
aactcacatg agctcgtgtt tggctcagag ccactattgt ctgtaaaagg tataccttgc 540
tgatgctgca ca 552

<210> SEQ ID NO 66
<211> LENGTH: 508

<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (127)..(129)
<223> OTHER INFORMATION: n is a, c, g, t or u
<220> FEATURE:
<221> NAME/KEY: misc_feature
<222> LOCATION: (132)..(137)
<223> OTHER INFORMATION: n is a, c, g, t or u
<220> FEATURE:
<221> NAME/KEY: misc_feature
<222> LOCATION: (139)..(139)
<223> OTHER INFORMATION: n is a, c, g, t or u
<220> FEATURE:
<221> NAME/KEY: misc_feature
<222> LOCATION: (378)..(378)
<223> OTHER INFORMATION: n is a, c, g, t or u
<220> FEATURE:
<221> NAME/KEY: misc_feature
<222> LOCATION: (421)..(421)
<223> OTHER INFORMATION: n is a, c, g, t or u
<220> FEATURE:
<221> NAME/KEY: misc_feature
<222> LOCATION: (474)..(474)
<223> OTHER INFORMATION: n is a, c, g, t or u

<400> SEQUENCE: 66
gggtgactgg tctaagtgct caattacctg tggcaaagga atgcagtncc gtgtnatcca 60
atgcatgcat aagatcacag gaagacatgg aaatgaatgt ttttcctcag aaaaacctgc 120
agcanannng cnnnnnnanc ttcaaccctg caatgagaaa attaatgtaa ataccataac 180
atcacccaga ctggctgctc tgactttcaa gtgcctggga gatcagtggc cagtgtactg 240
ccgagtgata cgtgaaaaga acctatgtca ggacatgcgg tggtatcagc gctgctgtga 300
aacatgcagg gacttctatg cccaaaagct gcagcagaag agttgacctc tagcaggctg 360
gctggatcac agctcttngc aattacatta tttataaaca cacacactag catgtttttc 420
nagaccaaat attatcagat tacatataat ttaatcaaat taatttattt tttntgcctg 480
ccaaacatcc aatgtggtgc ttgttttg 508

<210> SEQ ID NO 67
<211> LENGTH: 410
<212> TYPE: DNA
<213> ORGANISM: Homo sapiens

<400> SEQUENCE: 67
gcatgtgtaa aaagtccttc agccacaaaa ccaacctgcg gtctcatgag agaatccaca 60
caggagaaaa gccttataca tgtccctttt gtaagacaag ctaccgccag tcatccacat 120
accaccgcca tatgaggact catgagaaaa ttaccctgcc aagtgttccc tccacaccag 180
aagcttccta agctgctggt ctgataatgt gtataaatat gtatgcaagt atgtatattc 240
ctatagtatt tatctactta ggatataaga tataatctcc tgattatgct ttcaatttat 300
tgtcttgctt cattaaaatg taaggctaag gagagcatgg aatttgtcag ttttgttcac 360
taaagtattc caagtggttg ggaaagtgga acatttccaa gaaccaataa 410

<210> SEQ ID NO 68
<211> LENGTH: 291
<212> TYPE: DNA
<213> ORGANISM: Homo sapiens

<400> SEQUENCE: 68
cacaggatgt ggtctctacc gtgattcctg agcatgcatg cacccccttct cctgccaata 60 gaggggagga agtcggaggg gtgtctttat gcctataaac ttgccttgga atccagcctc 120
actccctttc ctcctggagt tgagaagccc ccacagagac tggctatggg ggagtgactg 180
tctataggtt ccttggatgt cctgcctatc tgcaaaatga gaatgagatc gataccttca 240
tgaggctgta agatggcaga tataaaagtg ctgtgttatc tcaaaagggt g 291

<210> SEQ ID NO 69
<211> LENGTH: 326
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (58)..(58)
<223> OTHER INFORMATION: n is a, c, g, t or u
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (218)..(219)
<223> OTHER INFORMATION: n is a, c, g, t or u

<400> SEQUENCE: 69
actgtgtgca gcatattgca ggctttcact catttaatat ctacaangtc ctcaatangn 60
atatnaatta cttatgattt ccctgttttt tcttcctata aggaagctga ggcacaagtt 120
aatcaaagtc tcttggccta gggtgacaca gctaagattt gtacctagag atttctgagt 180
gttgacttct ctcctgcccc cacctatctc cccccccnna aaaaaaaaca caacaacaac 240
aacaacagaa cataccaggg attcatggct tgcccaatgt tggaggggga gaagagagga 300
gagggatgag ataagctcct cccacc 326

<210> SEQ ID NO 70
<211> LENGTH: 352
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u

<400> SEQUENCE: 70
ttctgttttc ttcttaaagt catttatatt atgtattact cttaaagaat gttttagtct 60
ncattttagt agtctgtgca taaggtagta atacatgtac acaaagaaaa attcacaagn 120
cccattcagg tgtcttttag aacattattt anccactaaa tatttataca gttgacataa 180
tgcttattat gcccttgaat aatagaattt gttttgtttt tacttcttat ccataagcat 240
tggccttaca ttgcctcaag aggaacagaa tttattatta aacaggattc ttaaatccat 300
aactcatatt gtgacttcat acattttgta accctagtag tgaatatacc ct 352

<210> SEQ ID NO 71
<211> LENGTH: 414
<212> TYPE: DNA
<213> ORGANISM: Homo sapiens

<400> SEQUENCE: 71
gcccaaatcg cgcaggtctg ggacctgatt gcgggccacg aggcgcaatt cggggcggag 60
ctgctgctca ggctcttcac ggtgtacccc agcaccaagg tctacttccc gcacctgagc 120
gcctgccagg acgcgacgca gctgctgagc cacgggcagc gcatgctggc ggctgtgggc 180
gcggcggtgc agcacgtgga caacctgcgc gccgcgctga gcccgctggc ggacctgcac 240
gcgctcgtgc tgcgcgtgga cccagccaac tttccgctgc taatccagtg tttccacgtc 300
gtgctggcct cccacctgca ggacgagttc accgtgcaaa tgcaagcggc gtgggacaag 360
ttcctgactg gtgtggccgt ggtgctgacc gaaaaatacc gctgagccct gtgc 414

<210> SEQ ID NO 72
<211> LENGTH: 533
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n is a, c, g, t or u
<220> FEATURE:
<221> NAME/KEY: misc_feature
<222> LOCATION: (68)..(68)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (138)..(138)
<223> OTHER INFORMATION: n is a, c, g, t or u
<220> FEATURE:
<221> NAME/KEY: misc_feature
<222> LOCATION: (208)..(208)
<223> OTHER INFORMATION: n is a, c, g, t or u
<220> FEATURE:
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (242)..(242)
<223> OTHER INFORMATION: n is a, c, g, t or u
<220> FEATURE:
<221> NAME/KEY: misc_feature
<222> LOCATION: (251)..(251)
<223> OTHER INFORMATION: n is a, c, g, t or u
<220> FEATURE:
<221> NAME/KEY: misc_feature
<222> LOCATION: (258)..(258)

<223> OTHER INFORMATION: n is a, c, g, t or u
<220> FEATURE:
<221> NAME/KEY: misc_feature
<222> LOCATION: (281)..(281)
<223> OTHER INFORMATION: n is a, c, g, t or u
<220> FEATURE:
<221> NAME/KEY: misc_feature
<222> LOCATION: (286)..(286)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u

<400> SEQUENCE: 72
tgccagctac aggtgctcac ctgaaaagca agccagacca tattaaccct nggcattgct 60
ggtacctngg aagactttct gattcaatgc tttccacctc ctcctacccc tcaccacccc 120
cgtnggcatg aaatcctngg gggctgcttt agaaattgtt ttctttggct gctggtgggg 180
gtgctgctgg tgggggtttg cacagctngg canactgcan ccagtctggt gggggtttgc 240
anagctggca nactgcancc agtctcctgc ctgctgccaa naaggnccat ttcccaagca 300
ctggctttgg agaagttggg gctctgaagt gggaacacaa ggctgccttt tgcaggncca 360
ggtgtaaatt ctccccctgc cactttcagc ctagcgtgaa acagatggag tgtgcattcc 420
cacttccctt tatggtaccc tggaatgatg gagctgccca gggcatcgcc acgttactct 480
ctagacagtc tctttgtctt cctgcaatgg cagcgccgag gttgtatatt tct 533

<210> SEQ ID NO 73
<211> LENGTH: 492
<212> TYPE: DNA
<213> ORGANISM: Homo sapiens
<220> FEATURE:
<221> NAME/KEY: misc_feature
<222> LOCATION: (226)..(226)
<223> OTHER INFORMATION: n is a, c, g, t or u
<220> FEATURE:
<221> NAME/KEY: misc_feature
<222> LOCATION: (234)..(235)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u
<220> FEATURE:
<221> NAME/KEY: misc_feature
<222> LOCATION: (272)..(272)
<223> OTHER INFORMATION: n is a, c, g, t or u

<400> SEQUENCE: 73
gaagggctgc cttattttag agcacagatt ttctgaatat ctattttgac aggttcgatc 60
ctctcccctt cctgccttcc ttctgtcgat tttcaatgtc ttgatggtgt cccacctgag 120
tggcctttag agatgtgagt tgtgaggcac tggggaggca ggcacacgtc ctccagccca 180
agactgccta atttaacagg gatttctgca ttctggaaca agcctnccat tttnncccca 240
agcaggatta ctnccagagg gcaaaacaca gncccaatag tatcacattt cctttctgct 300
ttagcaaaaa taaccactgt ctcattcatg ggaaaaggcc gccaaacaaa tttgttactg 360
gaaccatttg taacaacttc tagtttgcac tgccttggag caagcacact ttgtagagga 420
gggatttgca gttacttggg caacaaggta accactgatc attacaggaa gcttcagaaa 480
ccgtgggacc ag 492

<210> SEQ ID NO 74
<211> LENGTH: 354

<212> TYPE: DNA
<213> ORGANISM: Homo sapiens
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (261)..(261)
<223> OTHER INFORMATION: n is a, c, g, t or u

<400> SEQUENCE: 74
ctgttgctgc tgctgagcat gggcggggca tgggcatcca gggagccgct tcggccatgg 60
tgccacccca tcaatgccat cctggctgtn gagaaggagg gctgcccngt gtgcatcacc 120
gtcaacacca ccatctgtgc cggctactgc cccaccatga tgcgcgtgct gcaggcggtc 180
ctgccgcccc tgcctcaggt ggtgtgcacc taccgtgatg tgcgcttcga gtccatccgg 240
ctccctggct gcccgcgtgg ngtggacccc gtggtctcct tccctgtggc tctcagctgt 300
cgctgtggac cctgccgccg cagcacctct gactgtgggg gtcccaaaga ccac 354

<210> SEQ ID NO 75
<211> LENGTH: 275
<212> TYPE: DNA
<213> ORGANISM: Homo sapiens

<400> SEQUENCE: 75
agttccagaa atccagtgac gaatgtggta tacaaaaaaa tatataaatt ctttcaactt 60
agaataatta agtcataaaa tacatagggt acaaatacca cattccgttc taaaatgata 120
tcttaggatc atcaaaagaa aaagaggatt tggattatgc aaaaaatgat tcctatatat 180
ataatcaatt atctaactga catttttgca aatctaccac aacttcgcct tttattgcat 240
atgctaaaca agcagatgct aagtctgtaa actgt 275

<210> SEQ ID NO 76
<211> LENGTH: 62
<212> TYPE: DNA
<213> ORGANISM: Homo sapiens

<400> SEQUENCE: 76
ttgcttaatc atgcgctttg ttttttatgc attcacttcc tgtctttatc tctattttct 60
tt 62

<210> SEQ ID NO 77
<211> LENGTH: 471
<212> TYPE: DNA
<213> ORGANISM: Homo sapiens

<400> SEQUENCE: 77
ttaacctaag tatcagccct ggcatgctta tactggtcca agcaagcatt acgtcacagc 60
ctgttcctct tctttatcta aaagtgcttt ttcctttctc agcattccac aagttacttc 120
ctccttcctt tgttctcctc tgcctttgcc tcttttaaat agttccaagg tgctggccaa 180
tcgggacaaa tacagaatgt gaggtcccat tccagccctg gaaactggac acagcagtag 240
ggcggacgca tcaagtgata aatgaccctg tccccttttgt tcgctgtact ctcctggcaa 300
aactgctgga gagtgtaccc tttctgcaga aagtaaaaaa aaatggcctt gctgaggaaa 360

```
ttaatgttca agtgctattt ctttatggca ctggggaaca agcatttcaa acagacctga    420

ggtttacccg atttctgctg gaaaagaaac ctcaggtctg ctgccttaga a             471


<210> SEQ ID NO 78
<211> LENGTH: 373
<212> TYPE: DNA
<213> ORGANISM: Homo sapiens

<400> SEQUENCE: 78

tctgtaggag atcttccaaa ttactgctta tatacatgta tattctatta caaaaattac     60

accactcaat gtagtctaaa ttattgagag taaattgtag ccattctttt acatgttttc    120

tgaacttagt tgccaataat cataatcatt agcttttcaa ggtttgctct gaaacttaca    180

aaccatgcaa aagtgaaaac ttaggcttaa catatttggc aatttaaatc aactaaattg    240

aatcaatcta aatactgctt tgcaaagtaa aaaaggaatc aaaatgacac ataagacaat    300

cactaatccc tatattttta gggtctattt caagaaattt actactactt cttaccagcc    360

taaggactgt gta                                                       373


<210> SEQ ID NO 79
<211> LENGTH: 505
<212> TYPE: DNA
<213> ORGANISM: Homo sapiens
<220> FEATURE:
<221> NAME/KEY: misc_feature
<222> LOCATION: (334)..(334)
<223> OTHER INFORMATION: n is a, c, g, t or u
<220> FEATURE:
<221> NAME/KEY: misc_feature
<222> LOCATION: (471)..(471)
<223> OTHER INFORMATION: n is a, c, g, t or u

<400> SEQUENCE: 79

aggccaggtg ctatgctcag agttcacacc tgcctgatac tgtgaggatt gggctacaga     60

ttctaaacca cactctccat agaggacatg gcaggtgagc ggctggcttc tgtgggtctg    120

ggcctggtgg gttagtgtgg gctgcatggc cccaaggctg ggagctgtgt tgggatctgg    180

tggcaggggg tttatctgac aacctcacta ttccatgtct cctctctgtg tggaggaatg    240

ggatgcagcg aggaggccag gctggagttc tgtagagtgt aaaatcctgg atgtcctctc    300

agcctgtctc cttgagagga cctgctgcct gccnttctgg agcacgtcat tctcttcttg    360

gatgaccaaa taaatcattc aagaatgaaa tgaaaactcc ttatctcctt ataggatctg    420

agctcagtga tgagaagtgg aaggacaata attgaccaat cacacattta natgaataaa    480

ttaggccgtt ggtgttcagc agcaa                                          505


<210> SEQ ID NO 80
<211> LENGTH: 366
<212> TYPE: DNA
<213> ORGANISM: Homo sapiens

<400> SEQUENCE: 80

tgtttccttt ccacttgcta gaagttattt tgccaatcac atatgattat tttatcattt     60

tttaattacc atcagtgcat gaaattatct ttattattca cttgttttta ttataatctt    120

ataatttcaa ataaaatgta aatctactgt cccttgcttt acctccgtgt cttcagtgcc    180

tagaacagga ctgtcataca cagtgactca atacacattt acttatgggt gattccctgc    240

ctgactgtta caggaagaag gaccaggaat atcagaatct gaagtgtcct ctaaagtcat    300

aaagactaga aggcattgaa taatgtttct taactatgca aggacttcag aattagatct    360
```

cacata 366

<210> SEQ ID NO 81
<211> LENGTH: 455
<212> TYPE: DNA
<213> ORGANISM: Homo sapiens

<400> SEQUENCE: 81
agatctcatt ttctggaggt gcatgtctcc cgtgaccccc tctttggatt gcccgcagag 60
cccgtgaaga tggtgttatc actcctgtga ttactttact gatcaggtga ctttgagtca 120
atcaaaaggt agattatcca ggtgtgcctg atttgatcag gtggtccctt aaggaggctt 180
aaaatgaccc tttctgaagt agagtaattg gaaaagtaag agggtctatg ggtggggtca 240
cctggcaagg aactgaactc agcctccatg agctctggcc accagctgac ctttagcaag 300
aaagcaaatc tttctttggt cagtctccac aacaggacga agctggctga gcccttgcct 360
ttggccctgt gagatgctga cccgagtatc cagcgaacac gtgccagagt cctgacccat 420
ggaaactgag atgatgagtc tgtgttgctt taagc 455

<210> SEQ ID NO 82
<211> LENGTH: 119
<212> TYPE: DNA
<213> ORGANISM: Homo sapiens

<400> SEQUENCE: 82
ccgattttct gtttgaagca gttcccttct atgttgcagt ctccttgaag gcaaaggttg 60
tgcactgtca tgttttgaag cccagtatcg ctgagaacaa tgacagacac atgcagtgg 119

<210> SEQ ID NO 83
<211> LENGTH: 137
<212> TYPE: DNA
<213> ORGANISM: Homo sapiens

<400> SEQUENCE: 83
tggctctcag agaaaccgta tttgatcaga gagctaaagg aagtgaggtt gtgagccaca 60
gggttatctt gaagaagagc attccaagga caggggaaac ttcctcaaag accagtaagc 120
cagagtgttc ttggtgc 137

<210> SEQ ID NO 84
<211> LENGTH: 345
<212> TYPE: DNA
<213> ORGANISM: Homo sapiens

<400> SEQUENCE: 84
agcttacaca gcattcttag agaggacaca gaatttggag tttgagtctt gccaagttat 60
agggccttga gaaacattta gggctttcca tggatccacc ctaacgaagc ataaaattaa 120
gcctaggatt ttagggtcat cagccaaaaa tggaactgcc ttctagaaca aaaaatgaca 180
tccttttgag gaagacagtc atccagagtc tttacaatct tttacccaca ttgcctagta 240
cataattaaa catttctaga tatgaatagg aacaggaaaa tgtgacccat aatcaagaca 300
acaagcaata aatggaaacc tacccttaag tagctaaact gttgc 345

<210> SEQ ID NO 85
<211> LENGTH: 459
<212> TYPE: DNA
<213> ORGANISM: Homo sapiens

<400> SEQUENCE: 85
tatgtttatt cagggctctg gaacataaaa aggctttgcc acactcttca catctataag 60
gtttctctcc agtatgaatt ttcttatgtt tactcaggta tgcagaccat ccaaaggctt 120
tgccacactc ttcacatttg taaggtttct ctccagtatg aattatctta tgtttattca 180
ggtctgtgga ccatccaaag gctttgccac actcttcaca tttgtggggc ctctctccag 240
tatgaattct cttatgttca ttaagggttg tgaaccgact aaaggctttt ccacattctt 300
cacatgtgta gggtttctct ccagtatgaa tactcttatg tttattaagg gttgcggatt 360
gtctaaaggc tttgccacat tgttcacatt tgtagggctt ctctccagta tgaattctct 420
tatgttcatt cagaactgag gacctactaa aggctttgc 459

<210> SEQ ID NO 86
<211> LENGTH: 229
<212> TYPE: DNA
<213> ORGANISM: Homo sapiens
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u

<400> SEQUENCE: 86
gggagtggac ctgcattagc aagcagagaa tgtccagagc ctagagacag ccagcccatg 60
cagagggtag ggcataancc naggcagtgg agagggtgag gagtggtgta tagaagagag 120
catggagttt aaggggttat tatggctgag atccagacca tgagcagaga aaagttcagt 180
ttatctcacg gaaaacttta atgttaggct taatcctctg ttccttcct 229

<210> SEQ ID NO 87
<211> LENGTH: 351
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n is a, c, g, t or u

<400> SEQUENCE: 87
ggttgatggt aatttatgta ccctgacagg ggtttggttt acatagctgt attcatttgt 60
caaaacttat attaaatggn tgcaattaat attgatgcat ttcattgtat gtaaatttta 120
ccctaaaata attttagaca aattgtaaaa cctagttaaa gacatatatg ctgatatttt 180
cagggttacc tctcttgatg tctgcaactt actttgaaat gcttcaaaag gaaaatagga 240
taatggatgg aaatagggag agagaaatgg atcgatgtgt aaataaaaca aatctatcta 300
aatgttaaag cttaattgta gatgatgaat gtaggagtgt tgaatgttaa a 351

<210> SEQ ID NO 88
<211> LENGTH: 482
<212> TYPE: DNA
<213> ORGANISM: Homo sapiens

<400> SEQUENCE: 88
aagagtctat gaagaaccca acggaagttt gtggcacatc cctaccctca aattcacagt 60
gagggtggaa tgacagtaac caaatctgtg aaaatattca catgagacag gaaagaagtc 120
agaatatcca gtgtacaatg agagtgaaag aggatgtcta aaaggggaca gcccattcac 180
aacccacaca caacccacgc acaaatattt ttgggggggc ctcccatggg catttataat 240
cttctaagtg ctccgaagaa catgtgtcac aaaagatgaa gagaatattt tccagaacat 300
agcccaacaa agaacttctt tgacattttt tagtgtaaag gtaactgacg gtatctacca 360
aattagcaat ttgtaaaact ggaatttcta aaagcaaata cttggagctg agattacctc 420
ccacttccca aattcgagtt atatgatctc aagtataata ccctttggta tagacctagc 480
ca 482

<210> SEQ ID NO 89
<211> LENGTH: 37
<212> TYPE: DNA
<213> ORGANISM: Homo sapiens

<400> SEQUENCE: 89
tctgagtggg cctgctctct gtagactgaa ttcagca 37

<210> SEQ ID NO 90
<211> LENGTH: 394
<212> TYPE: DNA
<213> ORGANISM: Homo sapiens
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
<222> LOCATION: (135)..(135)
<223> OTHER INFORMATION: n is a, c, g, t or u

<400> SEQUENCE: 90
tgcactcaat ggcttctgtt cgaagtccct attaaatgtt tctttcttaa atactgtatt 60
tgtcagcttc ttccttcagc atcccaactt cctcagactt tggggtactt ttgcacagac 120
ctagccaccn caaancactg tcatagatgc agcaatccac tttcacaaaa ccccatggac 180
aatgcagagg gggagaacag ggactgatta aagaaaggga cagaaatggc atcactatcc 240
aagactgaaa aacaggctga atggattatc actctgaccc aactgcacat ttctaatgtc 300
ttcatgtttt caattactcc atgaattccc ttatctgatg ctgattatgc acaggactgt 360
gtaagagtta aacaacacct gacactggtg actc 394

<210> SEQ ID NO 91
<211> LENGTH: 300
<212> TYPE: DNA
<213> ORGANISM: Homo sapiens
<220> FEATURE:
<221> NAME/KEY: misc_feature
<222> LOCATION: (175)..(175)
<223> OTHER INFORMATION: n is a, c, g, t or u

<400> SEQUENCE: 91
cctcatcact atgtcaccaa agtgttttgg aacttggtat tccagagact tctggaacgc 60
cgtgcaaggc ctgcccccag caagccacaa ccaggaaggt gcaggcacgc ccccactagc 120
tcctccccta tttattgcct cctggaaaac ccaggaccct cttccccatc tccanccccct 180 acccctgggg gcagcccagg gagagccagg cacaatgagg gctcccaaca gctgcaagga 240
tttatctgaa cctttgagaa agaggaggag ccatctaagt ttctggaaac ctgagcccca 300

<210> SEQ ID NO 92
<211> LENGTH: 490
<212> TYPE: DNA

<213> ORGANISM: Homo sapiens
<220> FEATURE:
<221> NAME/KEY: misc_feature
<222> LOCATION: (49)..(49)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u

<400> SEQUENCE: 92
cccattgcga tctggctctg ggggaccctg ggatgatatc cctaccccna gggacaggac 60
ccaaccccng gggacctgga gagactctgt gccctgcagg accgatgggg gactcctccc 120
tgtatgtacg tgtgcgtggc cctgccttgt tcttgccccg gacctggcct ggtgaaggag 180
gcacgaggaa gattgcagtc agggacgctc agcctgggag ctgaccctca ggtgaggccc 240
taaggaagtt cccagacctc cctgaacctc agtatgctca tctgtccagc agcaaccctg 300
ggccttaagt gagaacatct atgcggaaga ggcaggtgcc aatcaagccc tctgtaaagt 360
tacctcccct tttcccttct tctcctctca cagagctgaa gaatattttg caaagttcat 420
tgtaaacatt aaaataatct tgggtgttta tcattcgtta aacctgttgg gctgacttta 480
ggtctaccgc 490

<210> SEQ ID NO 93
<211> LENGTH: 317
<212> TYPE: DNA
<213> ORGANISM: Homo sapiens

<400> SEQUENCE: 93
gagaaaagta gactccccaa tgcctcgcag taaatgagga cgcctggcgc ctgcggcgag 60
gtcaactgag gtcagacgag cttatctctc ctgtcccggg aattaagggc atcctgggga 120
cagctgcaga gcaggaggct ccccgtgccc tcctcttcct aagcaagtca ggatcccaag 180
aggcgcgtgc ggggaggccc ctccgaaggg ctgctggctt gtgtcttcca ccagcgcaaa 240
gggaagctat cggttgcttc tgcagtgagg caagctcagc cggacgccca gaagagagac 300
gaggtgtcgc tgtcggg 317

<210> SEQ ID NO 94
<211> LENGTH: 208
<212> TYPE: DNA
<213> ORGANISM: Homo sapiens
<220> FEATURE:
<221> NAME/KEY: misc_feature
<222> LOCATION: (37)..(37)
<223> OTHER INFORMATION: n is a, c, g, t or u

<400> SEQUENCE: 94
atagatattt tttagtccac ttggctggat aataaantct taataacagg gggaaaaaaa 60
gaaagaaaaa ggaggaaaag atttaggaaa gaaaacaaca actttagtat ggaatgtgaa 120
gaactggcag gatattcacg ttgagctgtg cagtaagtag cttactggac atgtgaggct 180
gaagatacag ttgttcatat ggaagcaa 208

<210> SEQ ID NO 95
<211> LENGTH: 361
<212> TYPE: DNA
<213> ORGANISM: Homo sapiens

<400> SEQUENCE: 95
tccctcgtgt atcttatctt tattattgaa ttttccctca caatccactg ttaaaagaag 60
aaagtatcac acacgtgggt tcttttggct atggaagtgt ccttgagatc actttttgca 120
cgtgactcag ctgaagtgtt caaagcacat ggaaatcact tgccagtgac aggtggacgt 180
tgtatgtgtt ttctctctcc taaggatgcc taaactttct tttcttcaca ggtaaagtca 240
gtgataaatc ttttgtttgc tgcatatact ggagatgtgt ctgcacttcg aaggtatgtt 300
tacaggatgg attagcatgc actttacaga tatttatgaa gttgcttctg ggcgagcagc 360
c 361

<210> SEQ ID NO 96
<211> LENGTH: 377
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (49)..(49)
<223> OTHER INFORMATION: n is a, c, g, t or u
<220> FEATURE:
<221> NAME/KEY: misc_feature
<222> LOCATION: (170)..(170)
<223> OTHER INFORMATION: n is a, c, g, t or u
<220> FEATURE:
<221> NAME/KEY: misc_feature
<222> LOCATION: (270)..(270)
<223> OTHER INFORMATION: n is a, c, g, t or u

<400> SEQUENCE: 96
gaaacgccat ggaatgtatt gtatttctct antctatccc ttaaaatgnc cattgataat 60
tattggcaat ggttattgat agtctcaacg taatttcagt agaatttgtt ttgagatttt 120
ttttatgcac ataaaagatt tctttaggga ttattgtaca gagttctagn aaaatatata 180
attttttttt ctgggcttat aactttcttt tctaaaaatt tatttggcag cctgattaga 240
aatgtggtaa aatctgaaca ataaaatagn aaatagacta gttgcataga atgtttcaaa 300
aacaggcatt agattggcgg ctactcggga ggctgaggcg ggagaatcgc ttgagcctga 360
gaggtggagg ttgcggt 377

<210> SEQ ID NO 97
<211> LENGTH: 525
<212> TYPE: DNA
<213> ORGANISM: Homo sapiens
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u

<400> SEQUENCE: 97
cacctttctg ttctgtgacg ggctgtccct gcttgtcctg ctttaggagg taggtaccca 60
gtggctcccc gncccctcag cggctcattc ctctcgctct ccccacgttg gtctgtgtga 120
gctccgctgt gtggctgcca ttcatccgat ccatctgtgg acttgctggg gctgcgccgt 180
gcacggtgtg gtgaatgcta canccanccc caggggcggg gctgagagtg gctgggacct 240

```
ggagcacatg gggatgctgt gtgggaacca acttgccccc caccctgtgt ctctaggggt    300

ccgcagcagt agagaagcag acagccagcc ctgtccctgc ggcgtcaccc tccaccccat    360

actaacccag cagcgcatgg agagatttcg ggagtgctct aaaggccttt ggagcaattt    420

agggcaatta cgggcagttt tagaaatgct gaggggttgt tttgcctgcg gggcggggat    480

ggttgcctta tgcccacagt gaagcgggcg agatgcggta gctgg                    525


<210> SEQ ID NO 98
<211> LENGTH: 434
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, t or u

<400> SEQUENCE: 98

gaagttcaac tcaggaaggt gcaatataan caaatgtgct atattataat gaggaatggt     60

actaccgttc cagattttct gtaattgctt ctgcaaagta ataggcttct tgtccctttt    120

ttttctggca tgttatggaa tgatcattgt aaatcaggac catttatcaa gcagtacacc    180

aactcataag atcaaatttc attgaatggt ttgaggttgt agctctataa atagtagttt    240

ttaacatgcc tgtagtattg ctaactgcaa aaacatactc tttgtacaag aagtgcttct    300

aagaatttca ttgacattaa tgacactgta tacaataaat gtgtagtttc ttaatcgcac    360

tacctatgca acactgtgta ttaggtttat catcctcatg tatttttatg tgacctgtat    420

gtatattcta atct                                                      434


<210> SEQ ID NO 99
<211> LENGTH: 412
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (202)..(202)
<223> OTHER INFORMATION: n is a, c, g, t or u
<220> FEATURE:
<221> NAME/KEY: misc_feature
<222> LOCATION: (386)..(386)
<223> OTHER INFORMATION: n is a, c, g, t or u

<400> SEQUENCE: 99

gggagacaga tcacaatcag atccataagg aaaagtgtgt ctgtgtntat cttcctctct     60

agggaaaaat acagcagggt gaggggattg agtgggagtg caatcaggga agacttcctg    120

aaggcagtga ctggtgactg gaatgaagca tgagaatgag ccatgcaggt tgcccagaga    180

gagcatccag gcagagggag cngaaagttc catcctcacc cagctctgcc ggcccaggta    240

ctttctcctc tgccttctac tcccagtctc actccagtgc aacacacttc agttttctgg    300

gaactcctga tggaaagtgg ctgtatttgt tcatccctat agccttgggg cacagccagc    360

agcccctgga ggaagccccg caggtnggta aagagacaca gggctcccag cc            412


<210> SEQ ID NO 100
<211> LENGTH: 493
<212> TYPE: DNA
<213> ORGANISM: Homo sapiens

<400> SEQUENCE: 100
```

actgttttca gacctaacct tggcaaggtc agtcctactt tgatgttctt gtttcatcac 60
acttcttggc atttgtagat ttggaagaat tgggcctttg gtacctctga tctcttcgtt 120
tagcaactta ctgtgcaccc atatgcttag cttttgctgt tttagctttt tttttttttt 180
tttttaacct gccacctagt ggccgaaatg ttgctatact attgataagg tactcctaat 240
tttggcaaaa tagtaagagg caaagcacca aagattatgt tctctccctt ctccaaatct 300
ctcttggtga gaatgatctt taaaacatac cactcagatt attagcaatc ttggtatgga 360
acgtttttaa aaataataat aatgtacttt atgtggtgat ttatgttatt atttaggccc 420
aaagttttga tttaattgtt tccttttagc ttatttttga gatatgcagt ctgttaggaa 480
gctgtctctg tct 493

<210> SEQ ID NO 101
<211> LENGTH: 415
<212> TYPE: DNA
<213> ORGANISM: Homo sapiens

<400> SEQUENCE: 101
gccctcttgt gtagttttca ttgtgtctag tgcaatgccg taaaccttaa caccatgaga 60
cccatatgaa gtgccaacag tgatgatgga agcgctttca aagaaagaag tcatagacat 120
tataagaata aagcgacttg cttgatatgt acagtagata ggtacagctg tagctgctgg 180
ccatttcaga cagatgcttc atcttgtaaa cagcaacata aatgtatggt accaataaat 240
acagtacagt actgtaaatg tgttttctct tccttatgat tttcttggta catgttcttt 300
tctctagttt actttattgt taagaatata ctatataata cacatacaaa atatgtgtta 360
ttgcctgttt atgttgtggg tagggcttct ggtcaacagt gggctacatt atcga 415

<210> SEQ ID NO 102
<211> LENGTH: 530
<212> TYPE: DNA
<213> ORGANISM: Homo sapiens

<400> SEQUENCE: 102
ggactagcag tcttcttctt cagacgccat gggaccccca ggcgactgct ctactgccag 60
cgttccctgc tggacaaggt ctgacgccca ccgccggccc gcccactcct accacaagga 120
ctttgcctct gaagaccagt gtcagcaagg tggtggtggg tgggctgctc ccatccgtcc 180 ggagcccccct ccccgcagcc tccttgcttc tctcagtccc ctggctggcc tccttcaccc 240
tcaccgcctg tagcttgtgt ctgtccagcc ccatctgaat gtgttggggg ctctgcactt 300
gaaggcagga ccctcagacc tcgctggtaa aggtcaaatg ggtcatctg ctccttttcc 360 atcccctgac ataccttaac ctctgaactc tgacctcagg aggctctggg cactccagcc 420
ctgaaagccc caagtgtacc cagttggcag cctcccgtca ctctgactaa aaagaatctt 480
cagagtgcat atttggaggt ggaaagattg ttcagttacc ctaaagactt 530

<210> SEQ ID NO 103
<211> LENGTH: 509
<212> TYPE: DNA
<213> ORGANISM: Homo sapiens
<220> FEATURE:
<221> NAME/KEY: misc_feature
<222> LOCATION: (47)..(48)
<223> OTHER INFORMATION: n is a, c, g, t or u
<220> FEATURE:
<221> NAME/KEY: misc_feature
<222> LOCATION: (50)..(53)

<223> OTHER INFORMATION: n is a, c, g, t or u
<220> FEATURE:
<221> NAME/KEY: misc_feature
<222> LOCATION: (56)..(59)
<223> OTHER INFORMATION: n is a, c, g, t or u
<220> FEATURE:
<221> NAME/KEY: misc_feature
<222> LOCATION: (85)..(85)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (121)..(122)
<223> OTHER INFORMATION: n is a, c, g, t or u
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (179)..(179)
<223> OTHER INFORMATION: n is a, c, g, t or u
<220> FEATURE:
<221> NAME/KEY: misc_feature
<222> LOCATION: (266)..(266)
<223> OTHER INFORMATION: n is a, c, g, t or u
<220> FEATURE:
<221> NAME/KEY: misc_feature
<222> LOCATION: (272)..(272)
<223> OTHER INFORMATION: n is a, c, g, t or u
<220> FEATURE:
<221> NAME/KEY: misc_feature
<222> LOCATION: (277)..(277)
<223> OTHER INFORMATION: n is a, c, g, t or u
<220> FEATURE:
<221> NAME/KEY: misc_feature
<222> LOCATION: (285)..(285)
<223> OTHER INFORMATION: n is a, c, g, t or u
<220> FEATURE:
<221> NAME/KEY: misc_feature
<222> LOCATION: (359)..(359)
<223> OTHER INFORMATION: n is a, c, g, t or u
<220> FEATURE:
<221> NAME/KEY: misc_feature
<222> LOCATION: (467)..(467)
<223> OTHER INFORMATION: n is a, c, g, t or u

<400> SEQUENCE: 103
taattttagc tccaatccat ctttctcttc tccaaaaccc tacctcnntn nnntcnnnnc 60
caccccttaa gtacttagtc atgcntagcc ttatattctt gtttgaattc tnatgtnctg 120
nnccncccaa acagattata catttcttgg gtcccatact ttgcatttac catagcagnt 180
ttcatagccc atacaaacat taggccttca aaatatttgt caagtatttc ttcaataaaa 240
atgaaaacat cccaaatctt gatccnccta anatgtnaaa tgggnactta gttaagcaaa 300
ctaacatcat gatatactgg aaacaggtat ctctttcctt tacccttgtg cctgctgang 360
atcttattct cagccttgct gttttaaact caggggtgtg tgtacaacat atttaagcaa 420
attctggaat accaaagcca agcagtcttc caggggcttc atcctgncac acagcagctt 480
acctggtggg tgttgggtag cacacagta 509

<210> SEQ ID NO 104
<211> LENGTH: 338
<212> TYPE: DNA
<213> ORGANISM: Homo sapiens

<400> SEQUENCE: 104

```
catgatcagt gtattttagg gggactaata tggcaactaa agctactttg gaagagaaag     60
agtggagata catagattgc tattatagtt caggccaata gagaggaatt gggtttaaga    120
gatacattat ggaggcagaa gtgttcattc aacaagcgtt tgttaaatat ctactatgta    180
atcatgatta tacaactaga gagaatatga aaaaaatgaa ttacgtatgt tagcttatag    240
atggatgctc tcagtaccca tccctattaa tcgtcatttc cctttgttta gtgaaccttc    300
tgatatattg gatatcaaat atcctttcca agtattgt                            338
```

<210> SEQ ID NO 105
<211> LENGTH: 279
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (34)..(35)
<223> OTHER INFORMATION: n is a, c, g, t or u
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (238)..(238)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 105

```
gttccaggtc ccggatagcg agggcngccg cgcnngctcc nagggccatg aagcccccag     60
gaggagaatc gagcaatctt tttggaagtc cagaagaagc tactccttcc agcaggccta    120
ataggatggc atctaatatt tttggaccaa cagaagaacc tcagaacata cccaagagga    180
caaatccccc aggatcatgt tttcttatgt gaaggagaag aaccaaaatc ggatcttnaa    240
ngcttgcaag gagcatcccg gctgggagca gagccaggg                           279
```

<210> SEQ ID NO 106
<211> LENGTH: 395
<212> TYPE: DNA
<213> ORGANISM: Homo sapiens

<400> SEQUENCE: 106

```
ccaggctact gctaagactc gtacttccca gtttggtgtg ggcagctttc agactccatc     60
ctccttcagc tccatgtccc tccctggtgc cccaactgca tcgcctggtg ctgctgccta    120
ccctagtctc accaatcgtg gatctaactt tgctcctgag actggacaga ctgcaggaca    180
attccagaca cggacagcag agggtgtggg tgtctggcca cagtggcagg gccagcagcc    240
tcatcatcgt tcaagttcta gtgagcaaca tgttcaacaa ccgccagcac agcaacctgg    300
ccagcctgag gtcttccagg agatgctgtc catgctggga gatcagagca acagctacaa    360
caatgaagaa ttccctgatc taactatgtt tcccc                               395
```

<210> SEQ ID NO 107
<211> LENGTH: 412
<212> TYPE: DNA

<213> ORGANISM: Homo sapiens

<400> SEQUENCE: 107
acatagagag gtgactcatt ctttttaaag gttacattaa gtttgtagta tgtcagaatg 60
gcaatactat aattgtttta accagtgacg tttaagttgt ttccagattt tttgatctaa 120
caaataatgt gtcatgagta tagaattttt atgttcatgt actagtatag ttataggatg 180
actcatattt gaagcaaagt acaaaacgca tgctttctgt agctactcat aaattctggt 240
atgagcaaaa tgtcaagatg cttgcttatc accgaccaag tgatgattaa gctcttgcta 300
aactgtatca aaggagaaaa agggaaatac aggcttatcc taacaatttc acagtgaaca 360
gtaatctctg gcattcagtt aaagctagac ttgttctaat tactttgatt tt 412

<210> SEQ ID NO 108
<211> LENGTH: 531
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (248)..(248)
<223> OTHER INFORMATION: n is a, c, g, t or u

<400> SEQUENCE: 108
gtaagtggta ccagccacaa ctgaatatcc atctgggata aaataaaatt gcactcgtct 60
tagagatcca aatcaacttc agatggatta aaactttgaa tgtaaaaaac ataaatgact 120
nacagtcctg caaaatatct tggagacaac ctgtgccatc tggagagtgg gaagagcaca 180
tgcaaaggcc aaggggtgga gcagcccagc atgttctgga aaaggtaggg ctccccaagg 240
ctgggatnat ggtggagacc tgggtgtgtg ggagcacagg ggtgggggcc cgtgggccag 300
gaatgcacag agaggggctg gtgctctgcc gcaggcccaa gcccccaaag cccggtcatt 360
cccagcacca tcttcacggg tttctgccca ggtctttctg ctgcatctct tcctccccg 420 attccttaat catttttttt aaaatcagtt catgtctttg taaaccaaat tatttctaaa 480
aggcaaattt atattactgc cgaaatcaag ggtcagtgag ctagttgtgt a 531

<210> SEQ ID NO 109
<211> LENGTH: 541
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (98)..(98)
<223> OTHER INFORMATION: n is a, c, g, t or u

<400> SEQUENCE: 109
gacttgggat tccggagcag tcgcccctat cgctgctcct gcagttgcgg acnccaccga 60
ccccgccgcc ggaggactgg gcactgaaag gcctctangc ctaggcgcgg cccgcggagc 120
cagacgtgtt gctgccgtga gtaaaacgag cgccctctcc gcactcgttt acaaattaaa 180
atggaggaaa tttcgttggc caacctggat actaacaagc tagaggccat cgctcaggag 240
atttacgtag acctgataga ggattcttgt ttgggattct gctttgaggt gcaccgggca 300
gtcaagtgtg gctacttcta cctggagttc gcagagactg gtagcgtgaa ggattttggc 360
attcagccag tggaagacaa aggagcgtgc cgcctcccgc tttgctccct tcccggagaa 420
cctgggaatg ggcctgatca gcagctccag cgctcacctc cggaattcca gtagctgcaa 480
aatgagagtc tgaaagtggc caggacaata acatagactg gtcctgtggc ttcgaggagt 540
a 541

<210> SEQ ID NO 110
<211> LENGTH: 359
<212> TYPE: DNA
<213> ORGANISM: Homo sapiens

<400> SEQUENCE: 110
ctccctgcaa atgcacatgt caatcaatga ttaatgcacc caggttatgt acaaggcact 60
gggcttagca ccacagggaa cttccttcca gaggctcgct ttctagttgt gtagacaaga 120
atacatgcat gagaagatac aagacaattc acccatgcca aatgattcat acaggctgtt 180
taagtactgc agaaaataaa agaaggaaag gctaccagac ttttcaataa ggtctacagc 240
ttcccaagag catgtctttg ttaaatcagg aaatataaaa attatgtgtg tatgtgtatg 300
tatatatata taccacccta ttaactattt taaaatcgta ttctattttg ggggttgtg 359

<210> SEQ ID NO 111
<211> LENGTH: 491
<212> TYPE: DNA
<213> ORGANISM: Homo sapiens
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (151)..(151)
<223> OTHER INFORMATION: n is a, c, g, t or u

<400> SEQUENCE: 111
cagagtggac tgttccctga ggtgggagat gtggaaaagc caagaggctg cagccnaggc 60
cactggcccc tgagatctct gcaggaaatg gctgtggagt gtggcagttt ggcaaactct 120
ccaccacacg taatgaaact tggatttgct ncagtgtctg gctgcagagc agtgggcctg 180
gccagcaggt ccccagcttt ggctatgagg gccttgagtc ccccaaaaca ccgggttcca 240
gcaccacact cagccctcat tggctcttga actgagcttg gaagcttctg gtgaccttcc 300
aagagcctga gagtgaggtg gaattatttt aaaagataaa tattatatta tatatatata 360
tatttccctg aaggaaccaa agcgaatttt aaaagatgca atgtagaggg gaaaagagat 420
gatgaaaata tttaaaggcc ctatctgttt acagtgttcc gtggttaaac tcgctcactg 480
ctaagaatat t 491

<210> SEQ ID NO 112
<211> LENGTH: 287
<212> TYPE: DNA
<213> ORGANISM: Homo sapiens

<400> SEQUENCE: 112
gtgatcatga gaatgctgcc tttaaagatg tggccctggt cctgactgtt ctgctagagg 60
aggaaacatt agaagcaagt gtaggcccaa gggaaacgga agaaaaagtg agagacttac 120
tctgggccaa gtttaccaac tctgacactc ccacctcctt caaccacatg gactcagaca 180
aattgagtgg gctgtggagc cgaatttcac acctggtact gccagtccag ccaatcttag 240

-continued atgctagcgt tacatccaca aaaccagtgt tgccttgtat aactatt 287

<210> SEQ ID NO 113
<211> LENGTH: 389
<212> TYPE: DNA
<213> ORGANISM: Homo sapiens

<400> SEQUENCE: 113
tagccgatcg ttacctcaag ggagtgggaa ttgggcccag ctccggcccc tcctggtcac 60
ctttggccat gatggccggg gccatgcctt gacccgacgc cggagggcca agcgtagccc 120
taagcatcac tcacagcggg ccaggaagaa gaataagaac tgccggcgcc actcgctcta 180
tgtggacttc agcgatgtgg gctggaatga ctggattgtg gccccaccag gctaccaggc 240
cttctactgc catggggact gcccctttcc actggctgac cacctcaact caaccaacca 300
tgccattgtg cagaccctgg tcaattctgt caattccagt atccccaaag cctgttgtgt 360
gcccactgaa ctgagtgcca tctccatgc 389

<210> SEQ ID NO 114
<211> LENGTH: 499
<212> TYPE: DNA
<213> ORGANISM: Homo sapiens

<400> SEQUENCE: 114
gtacctcgct ggacctggag ttagacctgc aggcgacaag aacctggcac agccaactga 60
cccaggagat ctcggtgctg aaggagctca aggagcagct ggaacaagcc aagagccacg 120
gggagaagga gctgccacag tggttgcgtg aggacgagcg tttccgcctg ctgctgagga 180
tgctggagaa gcggatggac cgagcggagc acaagggtga gcttcagaca gacaagatga 240
tgagggcagc tgccaaggat gtgcacaggc tccgaggcca gagctgtaag gaaccccccag 300 aagttcagtc tttcagggag aagatggcat ttttcacccg gcctcggatg aatatcccag 360
ctctctctgc agatgacgtc taatcgccag aaaagtattt cctttgttcc actgaccagg 420
ctgtgaacat tgactgtggc taaagttatt tatgtggtgt tatatgaagg tactgagtca 480
caagtcctct agtgctctt 499

<210> SEQ ID NO 115
<211> LENGTH: 504
<212> TYPE: DNA
<213> ORGANISM: Homo sapiens

<400> SEQUENCE: 115
gagtttcagg accaggcagc ttgattacag catcaagggc ccctgtgttc tctgttttct 60
gcagccatag tattggcttc ttcccaagac ttatttttcc catcagtgtc acctgtgcta 120
caagctcctt cagtcacatc tatttttgat atttgtgggt acctaggagg tgcatatatt 180
tgtgggatac atgagatact ctgacacaga tgtgcagtgt gcacggatca cagggaaatg 240
gggcagccat ccatcccttc aagcattcat gatttctttg tgttgtgaac attcccgttg 300
tgctctctta gttattctga atgtacaaga aattattgct gactatagtc accctgtcgt 360
gctatcaaat actagacctc attcgtggta tctaactata ttttgtaccc attaaccatc 420
cccatctccc accccctacc tttcccacta tccatcccag cctctggtaa ccatccttcg 480
tctatctcca cgagttcaat tgaa 504

<210> SEQ ID NO 116
<211> LENGTH: 476

<212> TYPE: DNA
<213> ORGANISM: Homo sapiens
<220> FEATURE:
<221> NAME/KEY: misc_feature
<222> LOCATION: (423)..(423)
<223> OTHER INFORMATION: n is a, c, g, t or u

<400> SEQUENCE: 116
agcacagtct ggctggatga gacagggtcg tgcccagatg atggagaaat cgacccagaa 60
gcctgaggag gtgtcctggg tttggctggc tggctcctgc tccagcggcc cggcttcagg 120
tgtccggggg cgtggctgcc tggagcaggt gtgctgaata ccctggatgg gaactgagcg 180
aacccgggcc tccgctcaga gagacgtggc aggaccagcg aggaatccag cctgtccact 240
tccagaacag tgtttcccag gccccgctga gtggaccgga cctctgacac ctccaggttc 300
ttgctgactc cggcctggtg aaagggagcg ccatggtcct ggctgttggg gtcccaggga 360
gaggctctct tctggacaaa cacaccctcc cagcccccag ggctgtgcaa acacatgccc 420
ctnccataag caccaacaag aacttcttgc aggtggagtg gctgtttttt ataagt 476

<210> SEQ ID NO 117
<211> LENGTH: 494
<212> TYPE: DNA
<213> ORGANISM: Homo sapiens

<400> SEQUENCE: 117
atccttgtac ctgatgtctg agccactcag aactcaccaa aatgttcaac accataacaa 60
cagctgctca aactgtaaac aaggaaaaca agttgatgac ttcacactgt ggacagtttt 120
tcccaagatg tcagaataag actccccatc atgatgaggc tctcacccct cttagctgtc 180
cttgcttgtg cctgcctctt tcacttggca ggataatgca gtcattagaa tttcacatgt 240
agtataggag cttctgaggg taacaacaga gtgtcagata tgtcatctca acctcaaact 300
tttacataac atctcaggag gaaatgtggc tctctccatc ttgcatacag ggctcccaat 360
agaaatgaac acagagatat tgcctgtgtg tttgcagaga agatggtttc tataaagagt 420
aggaaagctg aaattatagt agagtcccct ttaaatgcac attgtgtgga tggctctcac 480
catttcctaa gaga 494

<210> SEQ ID NO 118
<211> LENGTH: 553
<212> TYPE: DNA
<213> ORGANISM: Homo sapiens
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (235)..(235)
<223> OTHER INFORMATION: n is a, c, g, t or u

<400> SEQUENCE: 118
gataacccca atctacgaag actagctatg gaacttccta cactgagaca actccagtgg 60
aactctgata attatcctaa aataaggagg cttcttcagt agccctcgaa atatgttcaa 120
atacatgatt acatttatgt ccttaatatt gctattagtt tctgatgtta atgtaaaagt 180
tggggaaaaa ngtggaaaag ttaaagcagt gcaggttaat tcaatgccag agtancttct 240
cagagggtgt atattcagtg tgaacaattt tcaacagaga aatgtcaact tctggccaca 300
acggcaacca gtaaaatgac tatttttact gtcttatcta ttaatgaaga ggagattgca 360

-continued

```
taatatagat gaaggagcat agtatttgca ggtggaacgc ctagcagggc ttgagtctca    420

actctgctgc ttttactcta attgaccgag acaagtcatt taaactaata gagcttcaat    480

tttctcatat ctaatgtaac ataacaattc acagcctttt actttgtagt tatcgtgaag    540

atctaatcgc agt                                                       553


<210> SEQ ID NO 119
<211> LENGTH: 462
<212> TYPE: DNA
<213> ORGANISM: Homo sapiens

<400> SEQUENCE: 119

ctcctgttca tcctgttcac agagtggctc ggctgatggt agctcgacca atggctgcaa     60

ccatgagagg gctcccctga aacttctctg tgacaatatg aagtaccaga tcctctccag    120

agccttctat ggatggctgg cctactgcag acacctgtcc accgtgagaa cccacctatc    180

agccctggtc aatcacatga tcgtgtctcc agacttgccc tgcgatgctg gacagggact    240

gacagccagg atctgggagc agtaccttca cgacagcaca agttacgagg agcaggagct    300

gctgcgcctc atctactacg ggggcatcca gcctgagatc cgcaaggccg tgtggccctt    360

cctcctgggc cactaccagt tcgggatgac ggaaacagaa aggaaagagg tggacgagca    420

gattcatgcc tgctatgcac agaccatggc tgagtggctg gg                      462


<210> SEQ ID NO 120
<211> LENGTH: 524
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 120

tctgctgctg aaggcctgtg attttgtngg ggaagggcct gttctangca actggnaaag     60

gcactgccac ctgccgttgg atgccaggac tcaagagctg gccccagtca ctgtgcgcag    120

agctgtctga gaatgtgtga gtggactggg tccttcggca ctgcctgcat tggctcaggg    180

cagtcaaccg tcgcagagga tgaggggcac actcaggcag cctccccggc cctggaggca    240

gaaaggccca ggcagaacca ctgactggga ggaaacagaa aaagcagagg agagccaggc    300

tgcaggcgtg tggatgggac cagctcaggc agacgctgtc tcatacccac tctcccctct    360

cttgccaggg cctggcctgg tgtctctcag gagcctgggc atgagacaaa agcagagatt    420

gttctcttgt ggtaccacag gctgtaacca gtccacccag tgttgtttta gaaatttaaa    480

tcggttgccc atctttttaa attggcaaca tcgtttacca catt                     524


<210> SEQ ID NO 121
<211> LENGTH: 326
<212> TYPE: DNA
<213> ORGANISM: Homo sapiens

<400> SEQUENCE: 121

ccccaagttg gcgggcctga ttgggcggca cgggccccag aacaagcagc ccttcatggt     60
```

ggctttcttc aaggccacgg aggtccactt ccgcagcatc cggtccacgg ggagcaaaca 120
gcgcagccag aaccgctcca agacgcccaa gaaccaggaa gccctgcgga tggccaacgt 180
ggcagagaac agcagcagcg accagaggca ggcctgtaag aagcacgagc tgtatgtcag 240
cttccgagac ctgggctggc aggactggat catcgcgcct gaaggctacg ccgcctacta 300
ctgtgagggg gagtgtgcct tccctc 326

<210> SEQ ID NO 122
<211> LENGTH: 372
<212> TYPE: DNA
<213> ORGANISM: Homo sapiens

<400> SEQUENCE: 122
atgcggagtg agaaaagcct gttgcagaag actacataca acaggatttg acacttgtaa 60
ggctccaaaa caaagaaaat taaatgatat tgtttaggtt ttcatacata ggtgataaaa 120
gtgtgtttct ttgtttttaa tgagaaaatt agtcacagaa tttaagatct tagttacttc 180
tatagggaag gcaggggaat gggacaagga ggaagcccac agcattggtc atgctctcat 240
gttgaagttg ggttcaaagg tgttcattat taaaatgctt cataatgatg accatacatt 300
tggtatttct aggacaatct tggtttacat ctattgtctc aacataatta ttcagtgcaa 360
gcctttcctt tc 372

<210> SEQ ID NO 123
<211> LENGTH: 197
<212> TYPE: DNA
<213> ORGANISM: Homo sapiens

<400> SEQUENCE: 123
ctaccttgcc tgctgagaca tagggctcca cgggtctctc tcctggggcc gggctgactg 60
tggcctgcga ggggcagtca tcgtgttggg ttttcctgcc agaggcagaa accacaaaat 120
tacctggaac atacacgccc caagtgacag attcaattca attccacaaa tattgacctc 180
gcgtctaatc cactcgt 197

<210> SEQ ID NO 124
<211> LENGTH: 379
<212> TYPE: DNA
<213> ORGANISM: Homo sapiens

<400> SEQUENCE: 124
ctctgagcct tgcttggttg tcagaggcca tgagaggtgc cagttatagg tggatgtgcc 60
aagatgctgg tgaacttggt cttcagctat acccaggctc agaaagggca agagccatgc 120
tgcagcgtag gtgactttgg aggtgcactt ggggcccagg gctttgagtg ttgcgggtgt 180
gcctgtccct ccagatagtg ctctgtttct ctctgttgtc cccctgcctg gtcctctggg 240
gccactgtgc tttctgctgt gtgcatttat aaatgatgtg tattttatat agacctgctt 300
gcattggctg atgctcctct aattccctga gtttgattca accacccttg ggttgttttg 360
ctatggcctt agcctttga 379

<210> SEQ ID NO 125
<211> LENGTH: 495
<212> TYPE: DNA
<213> ORGANISM: Homo sapiens

<400> SEQUENCE: 125
gaaccagaat ccttggaagc tctaggtcct acctcagaaa atctcatcgt catggttctg 60
cttcaagaac agaatttggg aattaggtat aagttcaatg ttcccatcac tcgaactggc 120
agtggagata atgaagttgg ctttacatgg aatcatcagc cttggtcaga atgctcagct 180
acttgtgctg gaggtaagat gcccactagg cagcccaccc agagggcaag atggagaaca 240
aaacacattc tgagctatgc tttgtgtttg ttaaaaaagc taattggaaa catttcttgc 300
aggtttgctt caagctgtaa tttagcaaaa gaaactttgc tttaattata ttatattcca 360
tttgttttca acctcatgta atttgtgcag atttgttggt aaaatacatc ttggcacaat 420
gagtgtctct gctggtgctt ctcccaagac tatcttgaag gtgggctgtt tgcctttcgt 480
gaacacattc ttggt 495

<210> SEQ ID NO 126
<211> LENGTH: 491
<212> TYPE: DNA
<213> ORGANISM: Homo sapiens

<400> SEQUENCE: 126
atacctcatg cagccttcag gttcagttct gacaccaggg atggaccatc ccatttctct 60
ccagcctgcc tccatgatgg gaccccttac ccagcaactg ggccatctct ccctcagcag 120
cacaggcacg tatatgccga cggctgcagc tatgcaagga gcttacatct cccagtacac 180
ccctgtgcct tcttccagtg tttcagtcga ggagagcagc ggccaacaga accaagtggc 240
agtggacgca ccctcagagc atggggtcta ttctttccag ttcaacaagt aacagtggga 300
ttcccctccc catctttact gaatagaaat gaattcttgg agatactcat gctcccagat 360
tccagagggt taaccaggaa tggagaccat ccgtcggccc tgctaaggac taacacttag 420
ccatcgtttt tcacaggcct gggcctggaa aaagaaatct ctacgttcct gccctttact 480
attgctgatg g 491

<210> SEQ ID NO 127
<211> LENGTH: 391
<212> TYPE: DNA
<213> ORGANISM: Homo sapiens

<400> SEQUENCE: 127
ggtgctgccc tgtgtacata taaatgaatc tggtgttggg gaaaccttca tctgaaaccc 60
acagatgtct ctggggcaga tccccactgt cctaccagtt gccctagccc agactctgag 120
ctgctcaccg gagtcattgg gaaggaaaag tggagaaatg gcaagtctag agtctcagaa 180
actcccctgg gggtttcacc tgggccctgg aggaattcag ctcagcttct tcctaggtcc 240
aagcccccca cacctttcc ccaaccacag agaacaagag tttgttctgt tctgggggac 300
agagaaggcg cttcccaact tcatactggc aggagggtga ggaggttcac tgagctcccc 360
agatctccca ctgcggggag acagaagcct g 391

<210> SEQ ID NO 128
<211> LENGTH: 458
<212> TYPE: DNA
<213> ORGANISM: Homo sapiens

<400> SEQUENCE: 128
tgtatggtcg ctggccagtg attctccttc tgagccgtgt ttcccctctc cctccctctc 60
cacgtgggca gggcaggccc catcgctttc ctctgataac cacatggaca catcctgaag 120
tcagcccagg cgccctgagc atcttggggc acctggaccc catcacaata ctccttcttc 180

```
cttcaggtcc ctgggtgaag gctttgctga aaccgacccc ccttttcacg tcccttctgc    240

ctctgccccg ttggatgccc tgactggggg caggggaaga gacagggcac agctggccac    300

agggctcagc cactgagcag gctgttccgg gcctttggct ttgcatcctg gacggggagt    360

gtcctgtcag ggaccagatg tgtcctgcct catccctagc tccaatccct tccccacgtg    420

accggggatt ctggttgcaa taaaacatgc tgctgctg                            458


<210> SEQ ID NO 129
<211> LENGTH: 496
<212> TYPE: DNA
<213> ORGANISM: Homo sapiens

<400> SEQUENCE: 129

gcagtctcgt ccaatttcta tagcaccgtg ggcaggaacg gcgtcctgcc acaggctttc     60

gaccagtttt tcgagacagc ctacggcacc ccggaaaacc tcgcctcctc cgactacccc    120

ggggacaaga gcgccgagaa ggggccccccg gcggccacgg cgacctccgc ggcggcggcg   180

gcggctgcaa cgggcgcgcc ggcaacttca agttcggaca gcggcggcgg cggcggctgc    240

cgggagacgg cggcggcagc agaggagaaa gagcggcggc ggcgccccga gagcagcagc    300

agccccgagt cgtcttccgg ccacactgag gacaaggccg gcggctccag tggccaacgc    360

acccgcaaaa agcgctgccc ctataccaag taccagatcc gagagctgga acgggagttc    420

ttcttcagcg tctacattaa caaagagaag cgcctgcaac tgtcccgcat gctcaacctc    480

actgatcgtc aagtca                                                    496


<210> SEQ ID NO 130
<211> LENGTH: 538
<212> TYPE: DNA
<213> ORGANISM: Homo sapiens
<220> FEATURE:
<221> NAME/KEY: misc_feature
<222> LOCATION: (475)..(475)
<223> OTHER INFORMATION: n is a, c, g, t or u

<400> SEQUENCE: 130

aggtcaccca gctgtgaatg aacgtggtca gaacacagaa tctgagttgg tcacacttcc     60

cactgatcca tggggccttt aagccctctg gaagcttcca ttaaagatga ttatttgagg    120

ataattgtat tgggatgcct atgatcttat ctagggtttt cctacccatc cccaacattc    180

agctcagctg cctctttctt gaggacaccc tcactgatca ccccagccca gccagagtgg    240

ttgctcctgc tcctgcccct gaacctatga catacccaag tcccaatact ttcgagccat    300

ctgccactgc cttttgacat ctctgccttg gctagattca aatggtgttt cataataaaa    360

gtctgagttt aagcagcttt accgaaaacg caagggaagt ttcattccat ttatacttct    420

ccagaccccc tgccatcctc tgctgctacc cacacaggca gaataaaagg cttanatgtg    480

taagtcccat gaaggcaaag attggtctct tgtgttcact gctgtctgta gtacttag      538


<210> SEQ ID NO 131
<211> LENGTH: 414
<212> TYPE: DNA
<213> ORGANISM: Homo sapiens

<400> SEQUENCE: 131

gtggcaaaag gggattcggc agctgtgatt aagaaccttg tgatggggag ggattcctgg     60

attacccagg tgagtttaat gtaaccacaa agatcctttc aagagggagg caggaaggtc    120
```

tgaggcagac gaaagagctg tgccaaggga agcaggcggc agtgggatgc aggtggcctc 180
tagaagctgg aaaaggcaag tccatgggtt ctttcctgga gccttcagaa ggagcacggc 240
cttgctgacc catcttagaa cggcaggata atcaatgtgt gttgtttgag gccactaagt 300
ttgtggcaat ttgttacagc agcaatagga aactactaca ctgtgtctga ttagatcagg 360
ccaatgaatg gagaaagtat tggatttcag ttgagtgcta aaacctggtc tgtt 414

<210> SEQ ID NO 132
<211> LENGTH: 408
<212> TYPE: DNA
<213> ORGANISM: Homo sapiens

<400> SEQUENCE: 132
ccagcttcac atggtctctc aagtgcttat gcttttcttc tctctgccac ccacattccc 60
acatcccgcc caccccccaa ctttcctccc ttcaccttcc catggagact ttttgcctgg 120
gctaaatctg atcctcagcc cactctcaga atcgataaat gcccctaggt gattgtaagc 180
tcacctaaga tatacttttt ctcctctaga attttagttt attagatttt tctagttgtc 240
tttgcaaaag cgttaacagg ctctgacttc tgacattcaa ctagatgtgg aatatccaac 300
ccctagcatt tcatggaatg tactgaccaa gataaaatgt gttcttatta aacaatgcca 360
tttcttgacc acttctgttt ttaggaattg tggtatctga gtcatggt 408

<210> SEQ ID NO 133
<211> LENGTH: 483
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (425)..(425)
<223> OTHER INFORMATION: n is a, c, g, t or u

<400> SEQUENCE: 133
gcgacaaggt tgtgatccac gtggcaggtg ttcagaaggc tgggggcggg cagcgctggg 60
gagagccctg ggtacttcga ggagaccccg aagngnggct gctcccacac ctgcgccagt 120
ttccaccctc tctgtgagca gggctgcggt cacctcccac atctgaagag aaccaacctg 180
aggatttcac gctggctgcg tgccagacca gtccctgaca ggttgtgcga ggcccttcgc 240
tggacagccc attgctggcc actggacgga gaggcagagg gggctgaaat tcgggcccat 300
gcctctgtga gcgatgacgg agcaacagct ctccagcacg tgaagctctc cagacagctg 360
ttcgtgagaa gccagacaga ggcctggggt ctcagtccag atttctgggg agtggggtgt 420
ccaancgtgg gccacgctgc tgggagccac ctagggaagc aggtcgcctg tttctatagt 480
gac 483

<210> SEQ ID NO 134
<211> LENGTH: 496
<212> TYPE: DNA
<213> ORGANISM: Homo sapiens

<400> SEQUENCE: 134
gggaaaaccc ttgtacctga agcatgagcc actcagaact caccaaaata ttcgacacca 60
taacaacaga tgctcaaact gtaaaccagg acaacaagtg gatgacttca cactgtggac 120
agtttttccc aagatgtcag aacaagactc cccatcatga tgaggctctc ccccctctta 180
actgtccttg ctcatgcctg cctctttcac ttggcaggat aatgcagtca ttagaatttc 240
acatgtagta gcttctgaga gtaacaacag agtgtcagat atgtcatctc aacctcaaac 300
ttttacataa catctcaggg ggaaatgtgg ctctctccac cttgcataca gggctcccaa 360
tagaaatgaa cacagagata ttgcctgtgt gtttgcagag aagatggttt gtatgaagac 420
gtaggaaagc tgaaattata atagagtccc ctttaaatcc acattgtgtg gatggctctt 480
gccgtttcct aagaga 496

<210> SEQ ID NO 135
<211> LENGTH: 479
<212> TYPE: DNA
<213> ORGANISM: Homo sapiens
<220> FEATURE:
<221> NAME/KEY: misc_feature
<222> LOCATION: (305)..(305)
<223> OTHER INFORMATION: n is a, c, g, t or u

<400> SEQUENCE: 135
gagtccgagg atttcagggg cagctgggcg caggagctgg tgggctgttg ggagtgcccc 60
tttactgggc aggcttcctt cctcctggtg atggggggtt cctcagcaca aaagtgaagg 120
ggtggagggg ctggaggagc aggaatctct cttgttgata ggtatgaggc cttgaagtcc 180
ttttctttgt cccaggattc atggacgctt cggggctgat ctttgagttt tcaagcatgg 240
ggtgcagaga cgtttaggta aactcttacc gtcctctctc ttcgtcaggg cttcccagga 300
atcancaatg cccaagaagg aagggattgt agaaatagct taaccctttc atttaccaac 360
gtggaaattg aagcccaggg aagggaaggg accggtcgtg gaagggagag ccatcagcag 420
aaagagaccc tgagatcttc gcctgggatt cccaggaagt ccagcccgag ctgattcac 479

<210> SEQ ID NO 136
<211> LENGTH: 393
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, t or u

<400> SEQUENCE: 136
tcccaagccc ttagggaccg cagaggactt ggggaccagc aagcaacccc cagggcacga 60
gaagagctct tgctgtctgc cctgcctcac cctgccccac nccaggcccg gtggccccca 120
gctgcatcaa gtggaggcgg aggaggaggc ggaggagggt ggcaccatgg gcccgggcgg 180
tgccctccat gcccggggga tgaagacact gctgccatgg acagcccgtg ccagccgcag 240
cccctaagtc aggctctccc tcagttacca gggtcttcgt cagagccctt ggagcctgag 300
cctggccggg ccaggatggg agtggagagt tacctgccct gtcccctgct cccctcctac 360
cactgtccag gagtgcctag tgaggcctcg gca 393

<210> SEQ ID NO 137
<211> LENGTH: 377
<212> TYPE: DNA
<213> ORGANISM: Homo sapiens

<400> SEQUENCE: 137

-continued

```
aacctatcgc tgacttagca accaaagcct ccatcgttag gcaaggaata aaataaaacc     60

agcacgcttt ttccactgtg atttttaaaa gtcattaaaa aatatctttt cccttatgta    120

cagaaaaatt ggaacagaaa aatatctaac ttgctgagca tttgatggga aaaagtaaaa    180

gataacttcc atttggtaca caacttattg tacatagagc tatgatttga ggaggcatct    240

aatttctgaa caaattcacc aagaaatacc atcacttaaa gtcattatcg caatcatgct    300

gcagtgaaca ctctatacaa aatggccagg tcattaaaca tcaaagatgg aaaacaagcc    360

agcaatctct tctgttc                                                   377
```

<210> SEQ ID NO 138
<211> LENGTH: 483
<212> TYPE: DNA
<213> ORGANISM: Homo sapiens

<400> SEQUENCE: 138

```
tgggcctcac ctatgatggg atgctgagtg atgtccagag catgcccaag actggcattc     60

tcatacttat cctaagcata atcttcatag agggctactg cacccctgag gaggtcatct    120

gggaagcact gaatatgatg gggctgtatg atgggatgga gcacctcatt tatggggagc    180

ccaggaagct gctcacccaa gattgggtgc aggaaaacta cctggagtac cggcaggtgc    240

ctggcagtga tcctgcacgg tatgagtttc tgtggggtcc aagggctcat gctgaaatta    300

ggaagatgag tctcctgaaa tttttggcca aggtaaatgg gagtgatcca agatccttcc    360

cactgtggta tgaggaggct ttgaaagatg aggaagagag agcccaggac agaattgcca    420

ccacagatga tactactgcc atggccagtg caagttctag cgctacaggt agcttctcct    480

acc                                                                  483
```

<210> SEQ ID NO 139
<211> LENGTH: 200
<212> TYPE: DNA
<213> ORGANISM: Homo sapiens

<400> SEQUENCE: 139

```
ttttgcttgt cttattggcc cagcaaccag cttgacactg gggactatca ggctccaaat     60

aataaccaat gtctcactcc aaacagacag gatactacgg agccagggtc agcaaacatt    120

ttctgtaaag ggccagatag taaatatttt gggctttgtg ggccctatgg tctctgtcac    180

aacgattcaa ctctgctgtt                                                200
```

<210> SEQ ID NO 140
<211> LENGTH: 243
<212> TYPE: DNA
<213> ORGANISM: Homo sapiens

<400> SEQUENCE: 140

```
gagcgcctcc agtctagaag gcataagcca ataggataat atattcaggg tgcagggtgg     60

gtaggttgct ctggggatgg gtttatttaa gggagattgc aaggaagcta tttaacatgg    120

tgctgagcta gccaggactg atggagcccc tgggggtgtg ggatggagga gggtctgcag    180

ccagttcatt cccagggccc catcttgatg ggccaagggc taaacatgca tgtgtcagtg    240

gct                                                                  243
```

<210> SEQ ID NO 141
<211> LENGTH: 554
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (187)..(187)
<223> OTHER INFORMATION: n is a, c, g, t or u
<220> FEATURE:
<221> NAME/KEY: misc_feature
<222> LOCATION: (189)..(189)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (199)..(199)
<223> OTHER INFORMATION: n is a, c, g, t or u
<220> FEATURE:
<221> NAME/KEY: misc_feature
<222> LOCATION: (204)..(204)
<223> OTHER INFORMATION: n is a, c, g, t or u
<220> FEATURE:
<221> NAME/KEY: misc_feature
<222> LOCATION: (206)..(206)
<223> OTHER INFORMATION: n is a, c, g, t or u
<220> FEATURE:
<221> NAME/KEY: misc_feature
<222> LOCATION: (211)..(211)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u
<220> FEATURE:
<221> NAME/KEY: misc_feature
<222> LOCATION: (223)..(223)
<223> OTHER INFORMATION: n is a, c, g, t or u
<220> FEATURE:
<221> NAME/KEY: misc_feature
<222> LOCATION: (237)..(237)
<223> OTHER INFORMATION: n is a, c, g, t or u
<220> FEATURE:
<221> NAME/KEY: misc_feature
<222> LOCATION: (246)..(246)
<223> OTHER INFORMATION: n is a, c, g, t or u
<220> FEATURE:
<221> NAME/KEY: misc_feature
<222> LOCATION: (265)..(265)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u
<220> FEATURE:
<221> NAME/KEY: misc_feature
<222> LOCATION: (275)..(275)
<223> OTHER INFORMATION: n is a, c, g, t or u
<220> FEATURE:
<221> NAME/KEY: misc_feature
<222> LOCATION: (278)..(279)
<223> OTHER INFORMATION: n is a, c, g, t or u
<220> FEATURE:
<221> NAME/KEY: misc_feature
<222> LOCATION: (407)..(407)
<223> OTHER INFORMATION: n is a, c, g, t or u

<400> SEQUENCE: 141
tgagtgggct ttgagagagg gggaagagtg agtctgagca cgagttgcag ccagggccag 60
tgnggagggg gtttgggcca gtgcaccttc cggggcccca tcccttagtt tccactgcct 120

```
cctgtgacgt gaggcccatt cttcactctt tgaagcgagc agtcagcatt cttagtagtg    180

ggttncngnt ctgtnggang actntngaga ntattcttng ttncctgttg gagttgntca    240

aatgtncctt ttaacggatg gttgnatgng cgtcngcnnc caggtttatg aatgacagta    300

gtcacacata gtgctgttta tatagtttag gagtaagagt cttgtttttt attcagattg    360

ggaaatccat tccattttgt gaattgtgac ataataatag cagtggnaaa agtatttgct    420

taaaattgtg agcgaattag caataacata catgagataa ctcaagaaat caaaagatag    480

ttgattcttg ccttgtacct caatctattc tgtaaaatta aacaaatatg caaaccagga    540

tttccttgac ttct                                                      554
```

<210> SEQ ID NO 142
<211> LENGTH: 479
<212> TYPE: DNA
<213> ORGANISM: Homo sapiens

<400> SEQUENCE: 142

```
ggacatggtt atctacagca ctgagataca ctactcttct aagggcacgc catctaagtt     60

tgtgatccca gtgtcatgtg ctgcccccca aaagtcccca tggctcacca agccctgctc    120

catgagagta gccagcaaga gcagggccac agcccagaag gatgagaaat gctacgaggt    180

gttcagcttg tcacagtcca gtcaaaggcc caactgcgat tgtccacctt gtgtcttcag    240

tgaagaagag catacccagg tcccttgtca ccaagcaggg gctcaggagg ctcaacctct    300

gcagccatct cactttcttg atatttctga ggattggtct cttcacacag atgatatgat    360

tgggtccatg tgatcctcag gtttggggtc tcctgaagat gctatttcta gaattagtat    420

atagtgtaca aatgtctgac aaataagtgc tcttgtgacc ctcatgtgag cacttttga     479
```

<210> SEQ ID NO 143
<211> LENGTH: 514
<212> TYPE: DNA
<213> ORGANISM: Homo sapiens

<400> SEQUENCE: 143

```
cagttgctgc cctacatgga gaacaggagg ggtgctgtca tcctggtctc ttccattgca     60

gcttataatc cagtagtggc gctgggtgtc tacaatgtca gcaagacagc gctgctgggt    120

ctcactagaa cactggcatt ggagctggcc cccaaggaca tccgggtaaa ctgcgtggtt    180

ccaggaatta taaaaactga cttcagcaaa gtgtttcatg ggaatgagtc tctctggaag    240

aacttcaagg aacatcatca gctgcagagg attggggagt cagaggactg tgcaggaatc    300

gtgtccttcc tgtgctctcc agatgccagc tacgtcaacg gggagaacat tgcggtggca    360

ggctactcca ctcggctctg agaggagtgg gggcggctgc gtagctgtgg tcccagccca    420

ggagcctgag gggtgtctca ggtgatcatt tggatctgga gcagagtctg ccattctgcc    480

agactagcaa tttgggggct tactcatgct aggc                                514
```

<210> SEQ ID NO 144
<211> LENGTH: 265
<212> TYPE: DNA
<213> ORGANISM: Homo sapiens
<220> FEATURE:
<221> NAME/KEY: misc_feature
<222> LOCATION: (74)..(75)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (126)..(126)
<223> OTHER INFORMATION: n is a, c, g, t or u

<400> SEQUENCE: 144

```
gtgtggtgtt tgtgtcttaa ctatgcactg ggcccttgtc tgcgtcggct tgcatacaga      60

gggcccctgg ggtnngccnt ccggcctggc ctcagccagt gggatggaca gggccaggca     120

ggcctntgaa cttccacctc ctggggcctc ccagacctcc tgtgccccca cctgtgtggg     180

caggtgggcc agtcttcggg tgatgggacc aaaccccttc agttcagtag agaaaggcta     240

ggtcctctac aaagagctgc aagac                                           265
```

<210> SEQ ID NO 145
<211> LENGTH: 419
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (61)..(61)
<223> OTHER INFORMATION: n is a, c, g, t or u
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (114)..(115)
<223> OTHER INFORMATION: n is a, c, g, t or u
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
<222> LOCATION: (144)..(144)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (177)..(177)
<223> OTHER INFORMATION: n is a, c, g, t or u
<220> FEATURE:
<221> NAME/KEY: misc_feature
<222> LOCATION: (189)..(190)
<223> OTHER INFORMATION: n is a, c, g, t or u
<220> FEATURE:
<221> NAME/KEY: misc_feature
<222> LOCATION: (192)..(192)
<223> OTHER INFORMATION: n is a, c, g, t or u
<220> FEATURE:
<221> NAME/KEY: misc_feature
<222> LOCATION: (218)..(218)
<223> OTHER INFORMATION: n is a, c, g, t or u
<220> FEATURE:

<221> NAME/KEY: misc_feature
<222> LOCATION: (225)..(225)
<223> OTHER INFORMATION: n is a, c, g, t or u

<400> SEQUENCE: 145
ggaggcgcag aagattgatc gcatgatgga ggctttcgct tctcgctact gcntgtncaa 60
ncccggggtc ttncagtnca cnaggtcagt gcagagccca cagcctggcc cctnnccagg 120
cacagcctcn agctctggag gggncggccc ctgtgggcac agccnagcgt gtgttcntgg 180
ggacctgcnn tnccctgagc gaggacgacc tgtgggcngg gcacntcttg caggcgggcc 240
cccagcacgc ggggtcccac tgtccactgg aggttctggc tgagcccagc accccggact 300
cgttgcagac acgtgctacg tgctgtcatt cgccatcatc atgctcaaca ccagcctcca 360
caaccacaac gtgcgtgaca agcccacggc agaacggttc atcgccatga accgcggca 419

<210> SEQ ID NO 146
<211> LENGTH: 492
<212> TYPE: DNA
<213> ORGANISM: Homo sapiens
<220> FEATURE:
<221> NAME/KEY: misc_feature
<222> LOCATION: (411)..(411)
<223> OTHER INFORMATION: n is a, c, g, t or u

<400> SEQUENCE: 146
tatgagaaac ctctgcgacc attcccagat gatgtctgcg ttgtccctga gaaatttgaa 60
ggagacatca agcaggaagg ggtcggtgca tttcgagagg ggccgcccta ccagcgccgg 120
ggtgccctgc agctgtggca atttctggtg gccttgctgg atgacccaac aaatgcccat 180
ttcattgcct ggacgggccg gggaatggag ttcaagctca ttgagcctga ggaggtcgcc 240
aggctctggg gcatccagaa gaaccggcca gccatgaatt acgacaagct gagccgctcg 300
ctccgatact attatgagaa aggcatcatg cagaaggtgg ctggtgagcg ttacgtgtac 360
aagtttgtgt gtgagcccga ggccctcttc tctttggcct tcccggacaa ntcagcgtcc 420
agctctcaag gctgagtttg accggcctgt cagtgaggag gacacagtcc ctttgtccca 480
cttggatgag ag 492

<210> SEQ ID NO 147
<211> LENGTH: 527
<212> TYPE: DNA
<213> ORGANISM: Homo sapiens

<400> SEQUENCE: 147
aatattgtct cataagcatc tttctatatt tgttcacatc gtacataatc atgtttttgc 60
acagatacat taatattatc atagtttgtt taactacttg gctttttcta acagtttttt 120
tttttgagat ggtcttgctc tgttgcccag gctggagtgc agtgacgtga tctcggctca 180
ctgcagcctt gacttcctgg gctcaagtga tcatcccacc tcagcctcct gagtagctgg 240
gactacaggt atgcaccacg accagctaat tttttgtatt ttttttttgt agagagggta 300
ttttgccatg ttgcccaggc tagtcttgaa ctcctgggct caagcgatct gcctgcttca 360
gcctcccaga gtgctaggat tacaggcatg agccactgca cccagcctct taacaaattt 420
tgaatataac tcctgtctta aaatctgcag aatattgaat ttttccagct attttttact 480
tttgcttagc ttatagatgc taaaggatac tgtcatttgc attttta 527

<210> SEQ ID NO 148
<211> LENGTH: 476

<212> TYPE: DNA
<213> ORGANISM: Homo sapiens
<220> FEATURE:
<221> NAME/KEY: misc_feature
<222> LOCATION: (50)..(50)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (105)..(105)
<223> OTHER INFORMATION: n is a, c, g, t or u

<400> SEQUENCE: 148
ctctctcact ttctatagct ttgttggacc agatggtgag gaaaggaatn ggcctcttcc 60
cttctagagg gggctggctg gagtgagacc tnggggcttg gcctnggaac ccaccacaca 120
gccccaaagt caggaagcct ggggaaacca gagctgagac ctcttcaaca gggtttcttt 180
gagatcctac acctccattg ggcccttttt cagtcttcaa tgggggccca gttggctcta 240
gaaggagaag aggtgaagca ggatcctttg ccctggggga gtctgagggc gcggtccttg 300
gactcattca ggccgtcttt gtagttgggg gagttccact gggcgatccc agcccctccc 360
cacccaccct ctaatggacc tcctcataga agccccattt cacttttgtt ttatctacct 420
cttagcaaaa caatagataa attaggtagt ggcagctcca cttgcttagg ttaggg 476

<210> SEQ ID NO 149
<211> LENGTH: 177
<212> TYPE: DNA
<213> ORGANISM: Homo sapiens

<400> SEQUENCE: 149
gggagtttga ccagagatgc aaggggtgaa ggagcgcttc ctaccgttag ggaactctgg 60
ggacagagcg ccccggccgc ctgatggccg aggcagggtg cgacccagga cccaggacgg 120
cgtcgggaac cataccatgg cccggatccc caagacccta aagttcgtcg tcgtcat 177

<210> SEQ ID NO 150
<211> LENGTH: 497
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (113)..(113)
<223> OTHER INFORMATION: n is a, c, g, t or u
<220> FEATURE:
<221> NAME/KEY: misc_feature
<222> LOCATION: (146)..(147)
<223> OTHER INFORMATION: n is a, c, g, t or u

<400> SEQUENCE: 150
ctaaccactg aggctctcta atcttcctct ggagttttag tgaaaggatt tattgagcag 60
cttctggaat ataatgtgca tgtccaaaat gaactcagcg cttcaaaang acnaagtctg 120
tagcctggag gggcttgagt ggatgnnagc tgatgctgtg attttgagct gtggttacat 180
gcagtcagta aacctgtgag actgctggag gaaatgtagc agacagcatg gaggctggga 240
cccagcagct actttgggtc atgtctttac tgtcctgcct ccaacccttt agtctcgtag 300
acttttgttc ttgtggaaat ttcttctgta ttccagttgt gtaaatatgt atggaaaact 360
gatattacta ggttttacgt tgcatctcca gtattgatct ttggaaactg atgttacatt 420
aggttccaat tcgcaatagt agcagagact gacatgcttt tattgagctg ctaagccccg 480
tggatgatgg agcgaga 497

<210> SEQ ID NO 151
<211> LENGTH: 529
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (393)..(393)
<223> OTHER INFORMATION: n is a, c, g, t or u
<220> FEATURE:
<221> NAME/KEY: misc_feature
<222> LOCATION: (403)..(403)
<223> OTHER INFORMATION: n is a, c, g, t or u
<220> FEATURE:
<221> NAME/KEY: misc_feature
<222> LOCATION: (417)..(417)
<223> OTHER INFORMATION: n is a, c, g, t or u
<220> FEATURE:
<221> NAME/KEY: misc_feature
<222> LOCATION: (431)..(433)
<223> OTHER INFORMATION: n is a, c, g, t or u
<220> FEATURE:
<221> NAME/KEY: misc_feature
<222> LOCATION: (435)..(435)
<223> OTHER INFORMATION: n is a, c, g, t or u
<220> FEATURE:
<221> NAME/KEY: misc_feature
<222> LOCATION: (440)..(440)
<223> OTHER INFORMATION: n is a, c, g, t or u
<220> FEATURE:
<221> NAME/KEY: misc_feature
<222> LOCATION: (442)..(443)
<223> OTHER INFORMATION: n is a, c, g, t or u

<400> SEQUENCE: 151
gccgacagct cctttaattt catggcgttt ttcttcatct tcggagccca gtttgtcctg 60
accgtcatcc aggcgattgg cttctccggc tggggcgcgt gcggctggct gtcggcaatt 120
ggattcttcc agtacagccc gggcgctgcc gtggtcatgc tgcttccagc catcatgttc 180
tccgtgtcgg ctgcnatgat ggccatcgcg atcatgaagg tgcacaggat ctaccgaggg 240
gctggcggaa gcttccagaa ggcacagacg gagtggaaca cgggcacttg gcggaaccca 300
ccgtcgaggg aggcccagta caacaacttc tcaggcaaca gcctgcccga gtaccccact 360
gtgcccagct acccgggcag tggccagtgg ccnttagagg gangcctgcc ctgcccncac 420
cgcccaccac nnncncccn tnnttcctgc tgctacccct gtgtcccgag ggctgggagt 480
acctggggcc ccatcccccc agctgtgatg gtggaagccg gtggtggcc 529

<210> SEQ ID NO 152
<211> LENGTH: 437
<212> TYPE: DNA
<213> ORGANISM: Homo sapiens
<220> FEATURE:
<221> NAME/KEY: misc_feature
<222> LOCATION: (145)..(146)
<223> OTHER INFORMATION: n is a, c, g, t or u

<400> SEQUENCE: 152
agatgaagcc cttcaagcgc tacgtgaaga agaaagccaa gcccaagaaa tgtgcccggc 60
gtttcaccga ctactgtgac ctgaacaaag acaaggtcat ttcactgcct gagctgaagg 120
gctgcctggg tgttagcaaa gaagnngacg cctcgtctaa ggagcagaaa acccaagggc 180
aggtggagag tccagggagg caggatggat caccagacac ctaaccttca gcgttgccca 240
tggccctgcc acatcccgtg taacataagt ggtgcccacc atgtttgcac ttttaataac 300
tcttacttgc gtgttttgtt tttggtttca ttttaaaaca ccaatatcta ataccacagt 360
gggaaaagga aagggaagaa agactttatt ctctctctta ttgtaagttt ttggatctgc 420
tactgacaac ttttaga 437

<210> SEQ ID NO 153
<211> LENGTH: 87
<212> TYPE: DNA
<213> ORGANISM: Homo sapiens

<400> SEQUENCE: 153
ttctttcaca ccctgtcggg agaatgtgtg ccctgcgact gtaatggcaa ttccaacgag 60
tgtttggacg gctcaggata ctgtgtg 87

<210> SEQ ID NO 154
<211> LENGTH: 417
<212> TYPE: DNA
<213> ORGANISM: Homo sapiens

<400> SEQUENCE: 154
cccgctggtg cagtggaaga gcccggcggc cgccgccgca gccttctcgg cccgcgcccc 60
cgccgcctgc acccccatct gctcttcccc gcgggggccg cgcggcgcgg gctgggggcc 120
cgggcagccg cgctcgggca gcgggggcgc ggggctgccg cctgcgctcg cagctggtgc 180
cggtgcgcgc gctcggcctg ggccaccgct ccgacgagct ggtgcgtttc cgcttctgca 240
gcggctcctg ccgccgcgcg cgctctccac acgacctcag cctggccagc ctactgggcg 300
ccggggccct gcgaccgccc ccgggctccc ggcccgtcag ccagccctgc tgccgaccca 360
cgcgctacga agcggtctcc ttcatggacg tcaacagcac ctggagaacc gtggacc 417

<210> SEQ ID NO 155
<211> LENGTH: 407
<212> TYPE: DNA
<213> ORGANISM: Homo sapiens

<400> SEQUENCE: 155
taagagactg agccgctagc agcgcctggg gaccagacag acgcatgtgg caaagctcac 60
catcttcact acaaacacgc ctgagagtgg cactggggaa acataactcc atctacacct 120
tggatttgga ctgattctcc attttatcac ctgaaggctt gggccagagc tcaacagcta 180
ctcaactgga ggggtgaggg ggataaggtc tgtagtatac agacaggaag atggtaggtt 240
tatgccttct gtggccagag tcttggactc atggaaatag aatgaataga ggggcattca 300
caaggcacac cagtgcaagc agatgacaaa aaggtgcaga aggcaatctt aaaacagaaa 360
ggtgcaggag gtaccttaac tcacccctca gcaaatacct atgtcaa 407

<210> SEQ ID NO 156
<211> LENGTH: 399
<212> TYPE: DNA
<213> ORGANISM: Homo sapiens

<400> SEQUENCE: 156
gagaccagtt cacggggcaa gagatgaacg tggcccagtt cctcatgcac atgggcttcg 60
acatgcagac ggtggcccag ccgcagggac tggagcccag tgagctgctg gggatgctga 120
gcaacggaag ctaggcagac tgtctggagg aggagccggc actgaggggc ccagacaccc 180
gctgccccag tgccacctca ccccccacca gcaggccctc ccgtctcttc gggacagggc 240
cccagccgtc ccccctgtct gggtctgccc actgccctcc tgccccggct ttccctgccc 300
ctctcccaca gcccagccag agacaaggga cctgctgtca tccccatctg tggcctgggg 360
gtccttcctg acaacgaggg ggtagccaga agagaagca 399

<210> SEQ ID NO 157
<211> LENGTH: 422
<212> TYPE: DNA
<213> ORGANISM: Homo sapiens

<400> SEQUENCE: 157
gtgaccagta ccgcaagggg atcatctcgg gctccgtctg ccaggacctg tgtgagctgc 60
atatggtgga gtggaggacc tgcctctcgg tggccccggg ccagcaggtg tacagcgggc 120
tctggcggga caaggatgta accatcaagt gtggcattga ggagaccctc gactccaagg 180
cccggtcgga tgcggccccc cggcgggagc tggtactgtt tgacaagccc acccggggca 240
cctccatcaa ggaattccgg gagatgaccc tcggcttcct caaggcgaac ctgggagacc 300
tgccttccct gccggcgctg gttggccagg tcctgctcat ggctgacttc aacaaggaca 360
accgggtgtc cctggcggaa gccaagtccg tgtgggccct gctgcagcgt aacgagttcc 420
tg 422

<210> SEQ ID NO 158
<211> LENGTH: 414
<212> TYPE: DNA
<213> ORGANISM: Homo sapiens
<220> FEATURE:
<221> NAME/KEY: misc_feature
<222> LOCATION: (364)..(364)
<223> OTHER INFORMATION: n is a, c, g, t or u
<220> FEATURE:
<221> NAME/KEY: misc_feature
<222> LOCATION: (373)..(373)
<223> OTHER INFORMATION: n is a, c, g, t or u
<220> FEATURE:
<221> NAME/KEY: misc_feature
<222> LOCATION: (375)..(376)
<223> OTHER INFORMATION: n is a, c, g, t or u
<220> FEATURE:
<221> NAME/KEY: misc_feature
<222> LOCATION: (378)..(380)
<223> OTHER INFORMATION: n is a, c, g, t or u
<220> FEATURE:
<221> NAME/KEY: misc_feature
<222> LOCATION: (383)..(384)
<223> OTHER INFORMATION: n is a, c, g, t or u

<400> SEQUENCE: 158
acgcagcccg cgacaacaaa aagacccgca tcatcccgcg ccacttgcag ctggccatcc 60
gcaacgacga ggagctcaac aagctgcttg gtaaagttac catcgctcag ggcggtgttc 120
tgcctaacat ccaggccgta ctgctcccca agaagactga gagccaccac aaagctaagg 180
gcaagtaagg gctgaacttt aaaaatgtaa acttacaaga caaaaggctc ttttcagagc 240
cacccaccat ttctacggaa gaactgagca ctctgttctc caaacctatc agaaatttgt 300
ggccgagttc aagcactgag gccattactt tcctattggg taaaataaaa gtattgaatc 360
aggnctagta aanannannn aanngctacc ttataacatg aaggaacctc ctta 414

<210> SEQ ID NO 159
<211> LENGTH: 470
<212> TYPE: DNA
<213> ORGANISM: Homo sapiens

<400> SEQUENCE: 159
tatcaagatt gcccctgcgg aaggcccaga cgtcagcgaa aggatggtca tcatcaccgg 60
gccaccggaa gcccagttca aggcccaggg acggatcttt gggaaactga aagaggaaaa 120
cttctttaac cccaaagaag aagtgaagct ggaagcgcat atcagagtgc cctcttccac 180
agctggccgg gtgattggca aaggtggcaa gaccgtgaac gaactgcaga acttaaccag 240
tgcagaagtc atcgtgcctc gtgaccaaac gccagatgaa aatgaggaag tgatcgtcag 300
aattatcggg cacttctttg ctagccagac tgcacagcgc aagatcaggg aaattgtaca 360
acaggtgaag cagcaggagc agaaataccc tcagggagtc gcctcacagc gcagcaagtg 420
aggctcccac aggcaccagc aaaacaacgg atgaatgtag cccttccaac 470

<210> SEQ ID NO 160
<211> LENGTH: 383
<212> TYPE: DNA
<213> ORGANISM: Homo sapiens

<400> SEQUENCE: 160
agagagactc agagacccgg gagggccttc ctctgaaagg ccaagccaag ccatgcttgg 60
cagggtgagg ggccagttga gttctgggag ctgggcacta ctctgccagt ccagagttgt 120
acagcagaag cctctctcct agactgaaaa tgaatgtgaa actaggaaat aaaatgtgcc 180
cctcccagtc tgggaggagg atgttgcaga gccctctccc atagtttatt atgttgcatc 240
gtttattatt attattgata atattattat tactattttt ttgtgtcatg tgagtcctct 300
ctccttttct ctttctgaca ttccaaaacc aggccccttc ctacctctgg ggctgcttga 360
gtctagaacc cttcgtatgt gtg 383

<210> SEQ ID NO 161
<211> LENGTH: 474
<212> TYPE: DNA
<213> ORGANISM: Homo sapiens

<400> SEQUENCE: 161
aggatgcccc tttgagaaat gctgttccac agaaccctgc ctttcaggcc ttggagacgt 60
gggcagggga gaagcagcgt ccctcagagc caggcctggc agtggtgcta gcaggggcca 120
aggccaggga gcagggtctc ctgtcggagg gacctgggca agcccctcca cgcgccagcg 180
ggtttctcag caggggaggt ccacaccaca ccgcttggga acctgggtgc ctaaacgcaa 240
caggagccaa ggcacaaatt taaccaaaca ccaaggttgc gtgaggcccc atttcatgag 300
ccgggctcca aggacgtgtc cttaggcggc tctggaaggc ccagcgccag cccccgtcct 360
ctgttaaagg gagccagccc cggcgtccgc ccaggcatgg tagcctgagc gcgcccccag 420
ggtagtaggg ggcacctgag gagcagggtc tgccctggca tgagcagagc ccag 474

<210> SEQ ID NO 162
<211> LENGTH: 371
<212> TYPE: DNA
<213> ORGANISM: Homo sapiens
<220> FEATURE:
<221> NAME/KEY: misc_feature
<222> LOCATION: (134)..(134)
<223> OTHER INFORMATION: n is a, c, g, t or u

<400> SEQUENCE: 162
gatacttgga tgcttttcct ctgactgatg aagatcctga ataccaaaga gggccgctga 60
caggtctagg agtacacttc tagcacctag cagagagagg cttcactaca tcatgcttcc 120
tgacatctct cccnttgaag agcagtcaga ctcctgcttt gctcttcaga cttaatttgg 180
gggtttaaca ggtgaggttg ctgggggaac tcttttacaa catctctctg aaagaatccg 240
ggctgccagt ttcatttggt ttgggtgtca gtagcatgat ggaaagacaa aaaaacacaa 300
cttgacatct gcagaaatgg gttcaaattt tacctgcaac tcaccaattc tgtggccttg 360
gttcagcaat t 371

<210> SEQ ID NO 163
<211> LENGTH: 445
<212> TYPE: DNA
<213> ORGANISM: Homo sapiens

<400> SEQUENCE: 163
caacaagacg gacctggctg ataagaggca gataaccatc gaggaggggg agcagcgcgc 60
caaagaactg agcgtcatgt tcattgagac cagtgcgaag actggctaca acgtgaagca 120
gctttttcga cgtgtggcgt cggctctacc cggaatggag aatgtccagg agaaaagcaa 180
agaagggatg attgacatca agctggacaa accccaggag cccccggcca gcgagggcgg 240
ctgctcctgc taatgcagag ccgacctgtg gcttcccatg acactccttg cttgttgtgt 300
tgcttcctat tggctagctt cctaaggggg gagggaaccg agttatcaag atgggaggat 360
ttttcttttc tctctgtctt taggagtagg gtgggatggg gagggaggct gggcatcagg 420
gatcacatca ctcttaacgg ctgtt 445

<210> SEQ ID NO 164
<211> LENGTH: 313
<212> TYPE: DNA
<213> ORGANISM: Homo sapiens

<400> SEQUENCE: 164
ggtggcctct ggatcctccg tggaccgaac cgtcccccca ggaacacacc ttcaggtaga 60
ccccgaagcc tcaaggccgg ggctggagcg gagaccccag ggcctctcag gagacagtga 120
ggctgcccct cctaccacct acctcattct gcctactcac cccaggggcc acagccacag 180
cctgctggac tcaggactgt cctgtcaact ccagacaact gaataaacag gccgggtaca 240
gtggctcgca cctgtaatcc tagcactttg ggaggccgaa gcgggtggac cacttgacgt 300
ccgtagttcg aga 313

<210> SEQ ID NO 165
<211> LENGTH: 344
<212> TYPE: DNA
<213> ORGANISM: Homo sapiens

<400> SEQUENCE: 165
aatgtcatgt ttattcaggc tgggaactgt attcacagta gaagtttcag tggtcaacat 60
atctatgact ctttaggctg ctgtagtttt acagtcaatt atttaaaagt gagtagttac 120
atttataaga gcctgagaat acttagactc agtcatttgt tagtattttt accaaaatct 180
cttagtttca gacatgtcag aagcagctat atagcatatc ttattctatg atatacatca 240
ggctatctca agttcctgtc tcacagttaa ttcaaagaag gattaggatt tctgtatttt 300
ttctcatttg aatctttatg tgcatttggt ttgtgtacat gctt 344

<210> SEQ ID NO 166
<211> LENGTH: 448
<212> TYPE: DNA
<213> ORGANISM: Homo sapiens

<400> SEQUENCE: 166
tcttacccca ctgaaaccaa cagggatcgg gccaggctcc cagattcttg aggacaggga 60
cttcggcatt tactaatggg ggactactgt ggggtaaggg ggcgcctgct tgcctgatac 120
aggatggggt caagggacag tgggcaggtc ctcactcagg agtggggggt gtaggctggc 180
cagcccccag ggcttgtcca ccagtcttct ccccgcaagg ccctcagagc agcgcctgtg 240
ggtgtcagta ttacctgagc ctaggccaaa gctagcccaa ggctggggaa ggggaggaga 300
ctccaggtca gaatgtgagg tctcagtctg tgatttaagg tgttgcatgt ggactcttaa 360
ctgtacgtgt agtttctagt ggagaaatca aggctctgat cattttgttt ttagtatgaa 420
aatgtgattt cctttctgtt tgtaactc 448

<210> SEQ ID NO 167
<211> LENGTH: 334
<212> TYPE: DNA
<213> ORGANISM: Homo sapiens

<400> SEQUENCE: 167
agatgccagt aatcaatatt gaggacctga cagaaaagga caaattgaag atggaagttg 60
accagctcaa gaaagaagtg acactggaaa gaatgctagt ttccaaatgt tgtgaagaag 120
taagagatta cgttgaagaa cgatctggcg aggatccact ggtaaagggc atcccagagg 180
acaaaaatcc cttcaaggag ctcaaaggag gctgtgtgat ttcataatac aaacaaaaag 240
aaaaaaaatt aaacaaattc ttggaaatat ctcaaatgtt aataacaata tgaatttttc 300
tcatgcatac tattactact aagcatgtac gtga 334

<210> SEQ ID NO 168
<211> LENGTH: 561
<212> TYPE: DNA
<213> ORGANISM: Homo sapiens

<400> SEQUENCE: 168
gcccccgact gaggcggaga cgaaggtgct gcaggcgcga cgggagcggc aagatcgcat 60
ctcccggctc atgggcgact atctgctgcg cggttaccgc atgctgggcg agacgtgtgc 120
ggactgcggg acgatcctcc tccaagacaa acagcggaaa atctactgcg tggcttgtca 180
ggaactcgac tcagacgtgg ataaagataa tcccgctctg aatgcccagg ctgccctctc 240
ccaagctcgg gagcaccagc tggcctcagc ctcagagctc cccctgggct ctcgacctgc 300
gccccagccc ccagtacctc gtccggagca ctgtgaggga gctgcagcag gactcaaggc 360
agcccagggg ccacctgctc ctgctgtgcc tccaaataca gatgtcatgg cctgcacaca 420
gacagccctc ttgcagaagc tgacctgggc ctctgctgaa ctgggctcca gcacctccct 480
ggagactagc atccagctgt gtggccttat ccgcgcatgt gcggaggccc tgcgcagcct 540
gcagcagcta cagcactaag a 561

<210> SEQ ID NO 169
<211> LENGTH: 244
<212> TYPE: DNA
<213> ORGANISM: Homo sapiens
<220> FEATURE:

<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (128)..(128)
<223> OTHER INFORMATION: n is a, c, g, t or u

<400> SEQUENCE: 169

```
aatgtgtatg tctgggtaag tgtatagatt ttacaactat tttgaaggcg acctttttaa     60

ctttaaacag accactctgg aggagacgcc tganccagag cgctttacct aaagttcggt    120

gcctaaantg caccccttcct ctggctggtg tctcccttct gccaagctat gcctcctgca    180

gaggtaggct ccgtggtgtc tcccactccg ccccaactgg agaacggtgt aaagaactgt    240

cagc                                                                 244
```

<210> SEQ ID NO 170
<211> LENGTH: 408
<212> TYPE: DNA
<213> ORGANISM: Homo sapiens
<220> FEATURE:
<221> NAME/KEY: misc_feature
<222> LOCATION: (262)..(262)
<223> OTHER INFORMATION: n is a, c, g, t or u
<220> FEATURE:
<221> NAME/KEY: misc_feature
<222> LOCATION: (268)..(268)
<223> OTHER INFORMATION: n is a, c, g, t or u

<400> SEQUENCE: 170

```
caggatggca ttagctctgt gtctgcaggt gctgtgcagc ctgtgtggct ggctctcgct     60

ctatatttct ttctgccacc tgaataagca ccgaagctat gagtggagct gccgcctggt    120

caccttcacc catggagtcc tctctatagg cctctccgct tatattggct tcattgatgg    180

cccatggcct tttacccacc caggctcacc caatacacct ctccaagttc atgtcctgtg    240

tctcaccttg ggctacttca tnttcganct tgggctgcat ctggcgcttt gcatggagga    300

agagcatcaa gaagtaccat gcttggagaa gcaggcggag tgaggaacgg cagctgaaac    360

acaacggaca tctcaaaata cactagccaa ggcttgctcc agattatg                408
```

<210> SEQ ID NO 171
<211> LENGTH: 359
<212> TYPE: DNA
<213> ORGANISM: Homo sapiens

<400> SEQUENCE: 171

```
aggacatcga ggctgcggtg aaccatgatt gtaccactgt attccagcct ggacgactga     60

gtgagaccct gtctcaaaca aaacaaaaca aaacaaaaaa aagtacaaga ggaaaaaaat    120

tgatttctga ttgcctcact caagataagg tcaacattga aggtggaggt ggaagatgca    180

gtttatgtag gggtctgaag attttaccat tctggggact gtctttaaga aagagaatcc    240

aaaattaggt agaaaagtga acgtctgacc gggcgcggtg gctcatccct gtaatcccag    300

cacttaagga gtacgagacg ggaggatcac gaggtcaaga gatcgacagc atgctggcc     359
```

<210> SEQ ID NO 172
<211> LENGTH: 386
<212> TYPE: DNA
<213> ORGANISM: Homo sapiens
<220> FEATURE:
<221> NAME/KEY: misc_feature
<222> LOCATION: (182)..(182)
<223> OTHER INFORMATION: n is a, c, g, t or u

<400> SEQUENCE: 172
gtttctgcct ttgaacgtgg ctgtgggaag acatgatgct tagtgttgct gcagctatct 60
catgaccttg ggcaaaacat cccaacacac aggagggcca aacaagcagt cagaagaagc 120
ctgagtcttg tgggtgttgt tgagcagctg aacaaaccct aggatggctt ccttccagac 180
tncttaggat tgcgaacaat gaagctctat tgtttaagca aggtatcgat ggctattttc 240
acttgccact gaaagcacca ggacagagaa tcgtctttct aggaatacag ccacaaaagc 300
cttcattatg gtatatgcac ataaagaata taaaagtttc ctttatgttt ctctttaaaa 360
tatagctgaa gtctgcctca ggcaaa 386

<210> SEQ ID NO 173
<211> LENGTH: 408
<212> TYPE: DNA
<213> ORGANISM: Homo sapiens

<400> SEQUENCE: 173
ggttccaggc tttgcatctg gagcctttac cggttgactg ttgccttcca cacaaacagc 60
ctctgaaaag cactttctcc atacataatt ctggagaaga tgagggatct tgccctccag 120
gagccttcct tcctccccca atgaggaaat cagtcactgc actggtgcaa aggcaagcag 180
attggaattt ctgctcttca ccgattttct cagggaaaga ccccttcccc ttgccagcag 240
aggaacctgt agttttttcc atttctttct tcagaaccaa agtatgtatc actcctcatg 300
ctcacaggga ttgacaggag agaattcacc aggatcttag ctcaaaagac acagcctcag 360
aatggccaga tggattgcac gaaacctgac ttggattcac catcttcc 408

<210> SEQ ID NO 174
<211> LENGTH: 331
<212> TYPE: DNA
<213> ORGANISM: Homo sapiens
<220> FEATURE:
<221> NAME/KEY: misc_feature
<222> LOCATION: (227)..(227)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u

<400> SEQUENCE: 174
gtggacgagt gactgtccct ggtttgggct ggtgccattt agagggcaac cagagtgcag 60
ggaagggagg agcttgggca agagggacat tgctgtcgct ggttgatggt gagatggcac 120
ttaatgagaa cctggtcatt gggaaagccc caagcctgcg tcttgctgtg atgccttccc 180
cattatgaag ggtccattgg catgggagtg gggagacctg gactcanana agctacaagg 240
gcaagggtgg aaaggcatag cttntgcaag ttgatgctga aaaagatcca agactcatat 300
tcagcagaca gcccataacc aagagccaag g 331

<210> SEQ ID NO 175
<211> LENGTH: 260
<212> TYPE: DNA
<213> ORGANISM: Homo sapiens

<400> SEQUENCE: 175

```
aggtcttcaa agaattggcc agtcttacag ctcaccttgg ggtgtagatg actctccact     60

gtggtgctag gcaattttat tgaacaggtg gccactggtg gtgatggctg aaccactcat    120

taaacaaatt gctctaaatg gcctcagtat caaggtgtgc tttctgtacc cttaatctga    180

ctttaatcct gcagaacctc agtcttacca tgtttaacag cattgccatg tacgatatgc    240

ctttatccta cactgtatat                                                260
```

<210> SEQ ID NO 176
<211> LENGTH: 528
<212> TYPE: DNA
<213> ORGANISM: Homo sapiens

<400> SEQUENCE: 176

```
gctggctatg tacatggtcc cattccctac ctgcacttct ttatgcctgt cttcaccctg     60

ctgaccatcc acagcagcca gcactaccag gccctcatag tgcctgagct cacccagcag    120

atggttgatg ccaagaacat gatggttccc tgagacccct gccatggcca ctacctaaag    180

gtggccacag tgttcacgga ctacatgtcc atgaaggagt tggatgagca aatgcttaat    240

gtccaaaaca agaacagcag ctactttgtt gagtgaatcc ccaactatgt gaaaacagct    300

gtctgtgaca tcccactctt ggggctataa atgtctgcca ccttcaacat caacagcgtg    360

gccatccagg agctgttcaa gcacatctct gagtggtcat gtttcggtgc aaagcctttc    420

tgcactggca catgggcaag agcatggact agatggagtt caccaaggct gagagcaaca    480

tgaacaacct ggtgtcccgg taccagtaat accaggacac ctcagcca                 528
```

<210> SEQ ID NO 177
<211> LENGTH: 540
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (48)..(49)
<223> OTHER INFORMATION: n is a, c, g, t or u
<220> FEATURE:
<221> NAME/KEY: misc_feature
<222> LOCATION: (52)..(52)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (76)..(76)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u

<400> SEQUENCE: 177
acttatctgt gctgtaacta ttgaaatgaa nccncttcaa atatgtannc cncntttctt 60
tttnanattt ctaganangg tttcaatata gactttctga cttttatggt atacatatag 120
gncaatattc tattcttctt tccttttaaa tacttactgt ttcaatttca aataaaaaat 180
cagcattcta gtttgtacat tttagcacag aaatgtttac aaccttcagc acaattgctt 240
ttgtaattta ctgacttggc attttgaggc gtttttaaca aattatgaga aataacacct 300
tcagaaagca tgtgactact ttgatgcaac tatttacaat gtattcataa gaagtcatta 360
acctgtagag ttcttagaca tgtggaacct ttaacaatta tactaaagag tacatacaaa 420
atacagagct atgtaataat aactaatttt aaatcctgac aaattagaag ttaagcctac 480
tatctgtaaa aatatgtcct gattcatttt tttaagtata tacctgagcc tttaaaaagt 540

<210> SEQ ID NO 178
<211> LENGTH: 560
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, t or u
<220> FEATURE:
<221> NAME/KEY: misc_feature
<222> LOCATION: (462)..(466)
<223> OTHER INFORMATION: n is a, c, g, t or u
<220> FEATURE:
<221> NAME/KEY: misc_feature
<222> LOCATION: (468)..(469)
<223> OTHER INFORMATION: n is a, c, g, t or u
<220> FEATURE:
<221> NAME/KEY: misc_feature
<222> LOCATION: (471)..(472)
<223> OTHER INFORMATION: n is a, c, g, t or u
<220> FEATURE:
<221> NAME/KEY: misc_feature
<222> LOCATION: (475)..(481)
<223> OTHER INFORMATION: n is a, c, g, t or u
<220> FEATURE:
<221> NAME/KEY: misc_feature
<222> LOCATION: (483)..(487)
<223> OTHER INFORMATION: n is a, c, g, t or u
<220> FEATURE:
<221> NAME/KEY: misc_feature
<222> LOCATION: (489)..(493)
<223> OTHER INFORMATION: n is a, c, g, t or u
<220> FEATURE:
<221> NAME/KEY: misc_feature
<222> LOCATION: (496)..(503)
<223> OTHER INFORMATION: n is a, c, g, t or u
<220> FEATURE:
<221> NAME/KEY: misc_feature
<222> LOCATION: (505)..(510)
<223> OTHER INFORMATION: n is a, c, g, t or u
<220> FEATURE:
<221> NAME/KEY: misc_feature
<222> LOCATION: (512)..(535)
<223> OTHER INFORMATION: n is a, c, g, t or u

<400> SEQUENCE: 178
gccattttga gtgccagatc tagttatttt gctgcaatgc tgagtggctg ttgggctgaa 60
agctcccaag agtacgttac tcttcaaggt ataagccatg tagaactgaa tgttatgatg 120
cattttatat atggaggaac tctggacatt ccagacaaaa ctaatgttgg tcagatactc 180
aatatggctg atatgtatgg actagaagga ttaaaagaag tagcaatcta tattttaaga 240
agagattact gtaatttctt tcagaagcct gttcccagaa cattgacgtc tatactagaa 300
tgcctgatta ttgctcattc agttggagtg gaaagtcttt ttgctgactg catgaagtgg 360
attgtaaagc attttgcaag gttttggtct gagagaagct ttgcaaatat acctcctgag 420
attcagaaaa gttgtcttaa tatgttgatt cagtccttan tnnnnntnnc nnganannnn 480
ntnnnnntnn nnnccnnnnn nnngnnnnnn cnnnnnnnnn nnnnnnnnnn nnnnncaggg 540
tgcactcaca gcacagaaca 560

<210> SEQ ID NO 179
<211> LENGTH: 385
<212> TYPE: DNA
<213> ORGANISM: Homo sapiens

<400> SEQUENCE: 179
gggttcacgt cattttcctg tctcagcctc cccagtagct gggactccag gcacccacca 60
ccactcccgg ctaatttttt gtatttttag tacagacagg gtttcactgt gttggccagg 120
atggtcttga tctcctgacc ttgtgatcca cccacctcgg cctcccaaag tgctgggatt 180
gcaggcatga atgaccgcgc ccagccgcag gcgcaacttt tttgagtttt cctggccagg 240
cgcggtggct caggcctgta gtcccagcat tttgggaggc cgaggtgggc ggatcacttg 300
aggtcaggag ttagaaacca gcctggccaa cgtggtgaaa ccccgtctcc agtaaacata 360
caaagccatt acagggcatg gtggg 385

<210> SEQ ID NO 180
<211> LENGTH: 173
<212> TYPE: DNA
<213> ORGANISM: Homo sapiens

<400> SEQUENCE: 180
gacaacctta gttcacttgg gtattcccat aatccttgtc tttcagggtt gacctgttac 60
agctgcttaa acacatcact gtatgctagg tattgcctac cttcacttac ttttctaacc 120
ttgccgatgt gctgccttca taaactgggt atatctccgc cacacttcta cgt 173

<210> SEQ ID NO 181
<211> LENGTH: 340
<212> TYPE: DNA
<213> ORGANISM: Homo sapiens
<220> FEATURE:
<221> NAME/KEY: misc_feature
<222> LOCATION: (167)..(167)
<223> OTHER INFORMATION: n is a, c, g, t or u

<400> SEQUENCE: 181
ggtaactttg gccaagactt ttcagtagga aatgcttcaa aatacaaagc aagagctatt 60
ttcaagaaag accttctaaa tttatattag gacatagtga gaagaaagcc atctgaaaac 120
caggaagaga gccctcacca gaatctgacc atgctggtgc cctgatnctt ggactttcag 180
cctccagaac tgcaaaattc tggtgtggtg tgaatgctgt ggctcagtcc gaacatgttt 240
ttttctgtaa ttttatcatt attacacgat tgcaatatca gttttgtttt ttaattggaa 300
agcaacattt tctactgttg aaagacgttt tttgacaaat 340

<210> SEQ ID NO 182
<211> LENGTH: 416
<212> TYPE: DNA
<213> ORGANISM: Homo sapiens

<400> SEQUENCE: 182

```
acagcttgtc tgtcacagtg cctgttctga ttgcaggctt tggtgttctc ctggtgttaa     60

tcctgacttt tttcctagtg atccaccctc tgggaaactt ctggctaatt cttagcgtca    120

cctcaattga gctgggcgtt ctgggcttaa tgacattatg gaacgtcgac atggattgca    180

tttctatctt gtgccttatc tacaccttga atttcgccat tgaccactgt gcaccactgc    240

ttttcacatt tgtattagca actgagcaca cccgaacaca atgtataaaa agctccttgc    300

aagaccatgg gacagccatt ttgcaaaatg ttacttcttt tcttattggg ttagtccccc    360

ttctatttgt gccttcgaac ctgaccttca cactgttcaa atgcttgctg ctcact        416
```

<210> SEQ ID NO 183
<211> LENGTH: 503
<212> TYPE: DNA
<213> ORGANISM: Homo sapiens
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (247)..(247)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u

<400> SEQUENCE: 183

```
aggccgggct cagaggcgga gaagcctgcc tggtgcccac agccgtctgg ctcagggact     60

ccaccctggc cccgagtngc cgtntgctgg gcctttcctt cctggctctg caccccatgc    120

tggctgcccg gtctggcttc ccttcttgtc tctgtcttgg gcgaggcagc tgtgagcatt    180

gcacagaggc aaagaccctc ctgcagcctn tgcgctgggc cgtagaaaca agagcctttg    240

taatacngaa cctcattcaa ggattaggag tggtggttag gtcagggcca cccccagtgc    300

tgcaggaacg gcctccaccc agctctgttg gtcagagcct gggtcatgca cctggagttg    360

ggagatcaag ntgggtctca gggcagtgag gtggccatat ccaccacatc gcatttcgtg    420

ggggaagagg tgacctcttt gttttaaact taaggtgtct gcttatccag ccagaaataa    480

aaatctgcca gtggtgttcc caa                                            503
```

<210> SEQ ID NO 184
<211> LENGTH: 377
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (294)..(294)
<223> OTHER INFORMATION: n is a, c, g, t or u

<400> SEQUENCE: 184

```
gagtcccgtc tcagtgtgga ggaacnggct gcacatggga cctgaaggtg ccctctgtgt     60
```

ttatgttggg ggtggggggg cagtgctggc tgcctctgtc ctgtgtgtga ccctaccctc 120
gaagggtcct gtcctgtcag tcccgaggga gccacaacca aagctgcgga gagaaggtgg 180
ggaagggtgc ggaatggccg tggggcacag cgtggcagac tgttcagtct ctgctgggtc 240
tttcctaggg acctggaagg ccagtgttgc ttccccctca ctccctttca ctgnaggcag 300
cctctctgct tccccaatgc cttatgcctg ggcacactgc cacagaatat gcaatatgtg 360
tgggtgacca tgccctc 377

<210> SEQ ID NO 185
<211> LENGTH: 390
<212> TYPE: DNA
<213> ORGANISM: Homo sapiens

<400> SEQUENCE: 185
gtcatcctgt gctcagttag cagctcatcc agctgggtca ggaaagcctt ttggaagcgt 60
aggaccttgc cagccagcgc tggatatgc aggaggacgg ggacagcatt cagcacctcg 120
cgcagaaagc ccgactcctc cttcagtccc tcctgagcta ggtccagcag cctgaggaag 180
cgagggtcgt cgtactcgaa gcggcgcccg caggtgaggg aggcgatcac gttgctcacg 240
gctttgtcca agagaccgtt ggggcgaaag gggcgtcgga gtggttggcg aaggcggcac 300
aaaggcaggc ggcctcctcg gtcacccact gctccagcga cttcttgccc aggcccaagt 360
tgcgcaaggt ggagacggag aagcgcctct 390

<210> SEQ ID NO 186
<211> LENGTH: 188
<212> TYPE: DNA
<213> ORGANISM: Homo sapiens

<400> SEQUENCE: 186
ggctggcaac ccagaaagat tggatttcag tgccatggtg ctggctgcgg agagcttcac 60
ctcagggagg cactactggg aggtggacgt ggaaaaggca accaggtggc aagtgggcat 120
ataccacggc tctgcagacg cgaagggcag cacggccaga gcttccggag agaaagtctt 180
gctcacgg 188

<210> SEQ ID NO 187
<211> LENGTH: 549
<212> TYPE: DNA
<213> ORGANISM: Homo sapiens
<220> FEATURE:
<221> NAME/KEY: misc_feature
<222> LOCATION: (213)..(213)
<223> OTHER INFORMATION: n is a, c, g, t or u

<400> SEQUENCE: 187
taggaatgga gcccgagcag tctcgctctc agggccctgt gtggagtcac tgtgctgtcc 60
cagctctgga gacgcagaat tccacatgag gaatgtggaa ttcagcatgg ggatgacgct 120
gcttcaccca gacttggagg agcgtggtga attgcccgtg cccatgctct gatgtgcctc 180
tctggccgct gcgttcctcc tttctccctg ccntgggtca gtgcctgtaa acactgccct 240
aaatcagcag ggccccccgtc acttctgctt tatgcacctt tttcctcaga cacattaata 300
caggggagtt ttgtttccaa gggaccacat ccagatggag gggctgtttt tggtgatctg 360
cactgccaaa tgcccgagtg tccctgacag tcggagctga tgaggccaag gctgtgtgtg 420
gttcctctgg atggccagaa gaggaaccaa aacactgaat tctgggcctt cttaagagtg 480
gtgatcagca cattgtgata gaagcatatc tgggaatgaa cttggcctca agcttttggc 540
cttttaatt 549

<210> SEQ ID NO 188
<211> LENGTH: 459
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, t or u

<400> SEQUENCE: 188
ctactctctg tctccataaa ctggtctatt ttggacattt cacataagcc tccctggatc 60
ccagtttaag catcctgggg tttgtctgcc tgccagagcc atggtgccac tggggctacn 120
tgtcctgtgg gatgacaagg caggtccaaa cctttgcctg ctctcccatc cattcctttt 180
gtgttagtcc atgtgtctcc cgactgttct ctccaacaac aacacagact gacaaaacct 240
actgacttgg agtcaggaac agactttgct attttctggc tgtgtgatcc tgatgagtcc 300
cttgaacctc ctggacttgt tcctcagcct aaaaaccaag actaataaat caagtctatc 360
tcacagcctt acgtggggat caaaaaacat ggagcatgtg aacacacatt gtacatcacg 420
aagctgtgtg caaataaata tcgtgtaact ccagcccctt 459

<210> SEQ ID NO 189
<211> LENGTH: 430
<212> TYPE: DNA
<213> ORGANISM: Homo sapiens
<220> FEATURE:
<221> NAME/KEY: misc_feature
<222> LOCATION: (112)..(112)
<223> OTHER INFORMATION: n is a, c, g, t or u

<400> SEQUENCE: 189
gcccgaggcc tgctgagaag catgggggcc ttgggatagt tccagaatga ggatgtgcgt 60
ttctagctgc tttgcgccct cctcccccaa aaatctgcta ccacaattcc ancccggcgg 120
cacgccccca agactccttt gtcgccccag gggcgggacc tgagctgtcg gtttcaggag 180
cccttcgtga cttcaaaagt cctgggcact gttgctcatg agtgctgcac aactgtcgcc 240
ctctaaagcc acctccatcc ctcactgggc tggcctcctg agccttcggt gaggaaacgg 300
ggttccgagt tgcccgcctg agagcttaac agtctgacta gaaaagggct aattcgcttt 360
ctgtgcaaat ctcttgagct aattatttaa tctgaaacat ggacaggtaa aggaccattg 420
gcgggcgtgg 430

<210> SEQ ID NO 190
<211> LENGTH: 406
<212> TYPE: DNA
<213> ORGANISM: Homo sapiens

<400> SEQUENCE: 190
acatcaagca gctttctcgc tttgctggag cttcaagtaa gattgctcca gtggaagcac 60
cagatgctaa ggtgaggatg gtgatgatcg ctggatcacc agaggctcgg ttcaaggctc 120
agggaagaat tatggaaaaa tgaaagaaga aaacttcgtt agtcctaaag aagaggtgaa 180
acttgaagct catatcagag tgccatcctt tgctgctggc agttactgga aaaggaggca 240
aaacggtgaa tgaacttcag aatttgtcaa gtgcagaagt tgttgtccct tgtgaccaga 300
cacctgatga gaatgaccaa gtggttgtca aaataactgg tcacttctat gcttgccagg 360
ttgcccagag aaaaattcag gaaattctga ctcaggtaaa gcagca 406

<210> SEQ ID NO 191
<211> LENGTH: 555
<212> TYPE: DNA
<213> ORGANISM: Homo sapiens

<400> SEQUENCE: 191
aatgctgtca gcccttaggc aagactaaat tggaaagaaa ggtgtctgcc aaagaaaaca 60
ggcaggcccc tgtcctcctt caaacataca gggaatcctg gaatggagaa aacatagaat 120
cagtgaaaca aagccgtagt ccagtttctg tgttttcctg ggacaatgaa aagaatgaca 180
aggactcctg gagtcaactt ttcactgaag attctcaagg ccagcgggtc attgcccaca 240
acactagagc tccttttcaa gatgtaacca ataactggaa ttgggactta gggccgtttc 300
ctaacagtcc ttgggctcag tgccaggagg atgggccaac tcaaaatctg aagcctgatt 360
tgctctttac ccaggactct gaaggtaatc aagttatcag acaccaattc taaatgtttg 420
aagctttgtt tctaaaagta ccttgaaatg atagagatgt aggaaaatat agttgtgggt 480
ggagagagga gtgagtttgt ttaggtggga aggtggcatg ggatgaagtt gtcattactg 540
agcatcttct ctgtg 555

<210> SEQ ID NO 192
<211> LENGTH: 554
<212> TYPE: DNA
<213> ORGANISM: Homo sapiens

<400> SEQUENCE: 192
gccctgctca gaggtcagag ggtctgggca gaggagggac cacattcccc tgccttgccc 60
ctgagcactt ctggagactg cgtcctgtcc tatctgctca ccatcaccct tcctgcccga 120
cggagctgct tctgctccct ggggcatatg gactgaccca cctcctgctg agaaccttcc 180
cctaggccct gtgcagaagg gctactgccc cttaggcctc agctggggga aaggcagttc 240
tggtgctgta gaggccctgg tgcagaaagt gggacgtctt ttttcctaag gtgtttaagc 300
acaggcttga taagtttggt ttttaaaaaa taatctagga aatgaataat tctaaatcta 360
gtaatgagga aactgagcat ttcttttgcc ctccagggtg ccaagaccct acatatgaca 420
gaacccttgg cccttctcca tgcctgtggg atctgtttct ttaaagcact ttgtactgtt 480
attcaggagg ttgataatct ccttgaccca tgtctttcta ccctaatccc cacttccctg 540
cagaatcaat ctga 554

<210> SEQ ID NO 193
<211> LENGTH: 319
<212> TYPE: DNA
<213> ORGANISM: Homo sapiens

<400> SEQUENCE: 193
acgcgtccaa catctcaaac ttgatctcca tctttggctc cggcttctcg gggctggtga 60
gccgacagcc ggactcctcg gagcagccgc cgccgctcaa cgggcagctg tgcgccaagc 120
aggcgctcgc cagcctcggc gcctggactc gagccattgt cgccttctag ggaccccega 180 gggcacaggg acccggggcc ccgcggggct ggggccagac aaagactcgg caaaggggcg 240
agaggaggga acgagcgggc gccgggccac tcggggctga gctgggggcg agcgggggca 300
ggcggctgat gttttataa 319

<210> SEQ ID NO 194
<211> LENGTH: 218
<212> TYPE: DNA
<213> ORGANISM: Homo sapiens

<400> SEQUENCE: 194
gaagactttc taaataatga taatcagagc tgtactctct ctggaggcaa acatcatggt 60
cctgttgaag ccctgaaaca aatgttattt aaccttcaag cagtacaaga acgttttaat 120
caaaataaga ccacagatcc aaaagaagag attaaacaag tttcagaaga tgatttctct 180
aaattacagt tgaaggaaag tatgattcct attactag 218

<210> SEQ ID NO 195
<211> LENGTH: 246
<212> TYPE: DNA
<213> ORGANISM: Homo sapiens

<400> SEQUENCE: 195
ccccacccaa atacaagtcc cagtggaaag gaaaggtagt acctattctt ctccatgggg 60
ttcctaacac cctccattac tctttcagtc tccaagcact ttgaatccat ttttaaacat 120
tcaggttgcc agacctgtca cacagtgggc tctgataggg ttacggaggg ggcctggctc 180
tcagtctcta ctctcctatg tcccatcagt tggttggagg ccaccttcca gggggtatgg 240
gagaca 246

<210> SEQ ID NO 196
<211> LENGTH: 283
<212> TYPE: DNA
<213> ORGANISM: Homo sapiens

<400> SEQUENCE: 196
caccttgacg gttccagtgt ctgtatttat gttgaaagtc caggtgaatg acatcatcag 60
tcgtcagtac ctgagccaag cagttgtaga agtgtttgta aactacacga agacaaattc 120
cacagtaact aaaagcaatg gagcagtgct gataaaagta ccctacaaat taggacttag 180
tttaactatt attgcttaca aagatggcta cgtgttgacc cctctgcctt ggaaaaccag 240
aagaatgcca atatattcat cagttacact ttcactgttc ccg 283

<210> SEQ ID NO 197
<211> LENGTH: 391
<212> TYPE: DNA
<213> ORGANISM: Homo sapiens

<400> SEQUENCE: 197
cgtccgagtg tgagtcagtc agcgacaagg ctcccagccc tgccaccctg ccagccacct 60
cctcctccct gcccagccca gccaccccat cccatggctc tcccagttcc catgggcctc 120
cagccaccca ccctacctcc cccactcccc cttcgacagc cagtggggcc accacagctg 180
ccaacggggg tagcttgaac tgcctgcaga caccatcctc caccagcagg gggcgcaaga 240
tgactgtcaa cggcgctccc gtgcccccct taacttgagg ccagggaccc tctcccttct 300
tccagccaag cctctccact ccttccactt tttctgggcc cttttttcca cctcttctac 360
tttccccagc tcttcccacc ttgggggtgg g 391

<210> SEQ ID NO 198
<211> LENGTH: 563
<212> TYPE: DNA
<213> ORGANISM: Homo sapiens
<220> FEATURE:

<221> NAME/KEY: misc_feature
<222> LOCATION: (116)..(116)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (175)..(175)
<223> OTHER INFORMATION: n is a, c, g, t or u
<220> FEATURE:
<221> NAME/KEY: misc_feature
<222> LOCATION: (225)..(225)
<223> OTHER INFORMATION: n is a, c, g, t or u

<400> SEQUENCE: 198
agaggcaggc atagaggctt ctccgccagc ctcctctgga cggcaggctc actgccaggc 60
cagcctccga gagggagaga gagagagaga ggacagcttg agccgggccc ctgggnttgg 120
cctgctgtga ttccactaca cctggctgag gttcctctgc ctgcnccngc ccccnagtcc 180
ccacccctgc ccccagcccc ggggtgagtc cattctccca ggtanccagc tgcgcttgct 240
tttctgtatt ttatttagac aagagatggg aatgaggtgg gaggtggaag aagggagaag 300
aaaggtgagt ttgagctgcc ttccctagct ttagaccctg ggtgggctct gtgcagtcac 360
tggaggttga agccaagtgg ggtgctggga ggagggagag ggaggtcact ggaaagggga 420
gagcctgctg gcacccaccg tggaggagga aggcaagagg gggtggaggg gtgtggcagt 480
ggttttggca aacgctaaag agcccttgcc tccccatttc ccatctgcac cccttctctc 540
ctccccaaat caatacacta gtt 563

<210> SEQ ID NO 199
<211> LENGTH: 591
<212> TYPE: DNA
<213> ORGANISM: Homo sapiens
<220> FEATURE:
<221> NAME/KEY: misc_feature
<222> LOCATION: (60)..(84)
<223> OTHER INFORMATION: n is a, c, g, t or u
<220> FEATURE:
<221> NAME/KEY: misc_feature
<222> LOCATION: (122)..(146)
<223> OTHER INFORMATION: n is a, c, g, t or u
<220> FEATURE:
<221> NAME/KEY: misc_feature
<222> LOCATION: (182)..(200)
<223> OTHER INFORMATION: n is a, c, g, t or u
<220> FEATURE:
<221> NAME/KEY: misc_feature
<222> LOCATION: (453)..(478)
<223> OTHER INFORMATION: n is a, c, g, t or u
<220> FEATURE:
<221> NAME/KEY: misc_feature
<222> LOCATION: (495)..(536)
<223> OTHER INFORMATION: n is a, c, g, t or u
<220> FEATURE:
<221> NAME/KEY: misc_feature
<222> LOCATION: (540)..(554)
<223> OTHER INFORMATION: n is a, c, g, t or u

<400> SEQUENCE: 199
ctggagagcc agtgcccatg gcccgctgcg tctccacagg gggtcgcccg ccagcccaan 60
nnnnnnnnnn nnnnnnnnnn nnnnggatgc ccaatacgag ccaggtgcca gggttcctgt 120
cnnnnnnnnn nnnnnnnnnn nnnnnntgga tattggtgcc ctcaagccag gtggacggca 180

```
annnnnnnnn nnnnnnnnnn gagcacgaga gctttgagaa gcctcagctg ctgactgtga    240

acctcaccgt gtactacccc ccagaggtat ccatctctgg ctatgataac aactggtacc    300

ttggccagaa tgaggccacc ctgacctgcg atgctcgcag caacccagag cccacaggct    360

ataattggag cacgaccatg ggtcccctgc cacccctttgc tgtggcccag ggcgcccagc   420

tcctgatccg tcctgtggac aaaccaatca acnnnnnnnn nnnnnnnnnn nnnnnnnntg    480

ccctaggagc tcgcnnnnnn nnnnnnnnnn nnnnnnnnnn nnnnnnnnnn nnnnnnagcn    540

nnnnnnnnnn nnnncatgtc tcctattcag ctgtgagcag agagaacagc t             591
```

<210> SEQ ID NO 200
<211> LENGTH: 485
<212> TYPE: DNA
<213> ORGANISM: Homo sapiens

<400> SEQUENCE: 200

```
catcagattt ctgcagatct gctttaaagc tgtacatttt tgttacagtc taagatgtgt     60

tcttaaatca ccattccttc ctggtcctca ccctccaggg tggtctcaca ctgtaattag    120

agctattgag gagtctttac agcaaattaa gattcagatg ccttgctaag tctagagttc    180

tagagttatg tttcagaaag tctaagaaac ccacctcttg agaggtcagt aaagaggact    240

taatatttca tatctacaaa atgaccacag gattggatac agaacgagag ttatcctgga    300

taactcagag ctgagtactg ctccagggtg gtgtgcaatc ttatattgat gcttgtgaat    360

ctgccatttg atttgtagga taaataaata tgtttaatat taacaacttc catcaaaact    420

ataataataa tattatatct actgttgacc tctaacaaca atcaggtgct gtattcagag    480

tcata                                                                485
```

<210> SEQ ID NO 201
<211> LENGTH: 432
<212> TYPE: DNA
<213> ORGANISM: Homo sapiens

<400> SEQUENCE: 201

```
gccctgactg actgtattct ctggccacat tcaagtcccc cattggtggg ggcagagaag     60

taggaccagg ccatccttgg ctccagagct cgaagacccc aagacagccc tctgctctca    120

gcggcgccac agagagcctg ggctcagcct tctgcatcag gacatggcct cgtccactga    180

gggcacgatt taaacatttg acatcagaag ctttatttgt aaacctcaca cagataagga    240

ccaagggctg gcggtgtggc cagaggacag gggaagctga aggccccgtg cttgagctcg    300

gcagtcctgc tccttgcagt gaagccacca tgggtgaccg tccagcctca cccggtggcc    360

tgcacagtga gggaagggct tcagggccat ctgctcccag ggcaggggac aggccaccaa    420

ggacctttgg ca                                                        432
```

<210> SEQ ID NO 202
<211> LENGTH: 499
<212> TYPE: DNA
<213> ORGANISM: Homo sapiens
<220> FEATURE:
<221> NAME/KEY: misc_feature
<222> LOCATION: (425)..(425)
<223> OTHER INFORMATION: n is a, c, g, t or u

<400> SEQUENCE: 202

```
ggtggagaag ctggcgcgtg agaacagcag catgcggctg gagctggacg ccctgcgctc     60
```

```
caagtacgag gcgctgcaga ccttcgcgcg caccgtggcc cggggacctg tggcgccctc    120

caaggtggcc accaccagcg tcatcaccat cgtcaagtcc accgagctct cctccacctc    180

cgtgcccttc tcggctgcat cctagtgccg gccgggggcg gggggtggcg ggcggcgggc    240

ggcgggcagg cgggtggggg cacacccctc gtacctgtca ctgggatgca gactctcgac    300

atccgagtcc aagcgcaggc ccctcgggcg caggcagctc acaccaggaa gagactgtat    360

tgcagggtga agagtgggct cccgtgggcc cagagctgca cgccggtcca cagacacact    420

cacgnccgcc acctgctccc cgcagatgtg tctgtgtgtg ggaattggta tcttgcaccc    480

gtgggagtcg ggacatata                                                  499


<210> SEQ ID NO 203
<211> LENGTH: 569
<212> TYPE: DNA
<213> ORGANISM: Homo sapiens
<220> FEATURE:
<221> NAME/KEY: misc_feature
<222> LOCATION: (107)..(107)
<223> OTHER INFORMATION: n is a, c, g, t or u

<400> SEQUENCE: 203

ttccagcacc attcttttcc tattaaatta cactggcaaa tttgattaaa aaaaacaact     60

gactatatat gcttgtaaac atttccagat tatgttattc ttttaancta aatatgtgtc    120

cttatgccaa taccccactc catctattac tgcagtgtat gataagtctt gaaatctagt    180

agtgtaagtt cttcaacgtt gcccttaatt tttaaaatca ctcttgctat ttaaaattgt    240

ttgtattaca tggaaatttt ataatcagct tgccaatttc tacaaaagtc ctgctgagat    300

tttaattggt attttgcttg ttctgcagct taatgcaaga aaattatctt aacaatattg    360

aatttttcaa tctattaaca tgttatatat tactgtttac ttaggatttt ttcacttttc    420

ctgccttgtt ttgaactgat attgtggttt taagtaattt tttttatttc tactattggc    480

ttagtaacta tgccccactt tttgattttg tagcacagtt gaccattgaa caacacaagt    540

ttgaattgtg catgtccaat tgtctatgg                                       569


<210> SEQ ID NO 204
<211> LENGTH: 266
<212> TYPE: DNA
<213> ORGANISM: Homo sapiens

<400> SEQUENCE: 204

ggagcagaga cagagcgacc catacctggc ccaggccccg gccccgcagg cagctgaatt     60

cctgagccca gtgacaaccc cttccccctg cactctgtcg tccgcccaag cctcaggccc    120

tgaggctgca gatgagactt gtccccagct ggctgtccat cctcctggtg tcagcaagct    180

gggtttgcag tgtcttccaa gcgacggtgt tcagaatgtg aaccagtgac tctcgggcgc    240

ccctgtggta actttgcagg cggccc                                          266


<210> SEQ ID NO 205
<211> LENGTH: 506
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (99)..(99)
<223> OTHER INFORMATION: n is a, c, g, t or u
```

<220> FEATURE:
<221> NAME/KEY: misc_feature
<222> LOCATION: (103)..(103)
<223> OTHER INFORMATION: n is a, c, g, t or u

<400> SEQUENCE: 205
gcaagagctt tatccagagc tcccacctga tccgccaccg nccgcatcca cacgggcaac 60
aagccgcaca agtgtgcggg ctgcggcaaa ggcttccgnt atnaaaacgc acctcgcgca 120
gcaccagaag ctgcacctgt gttaggggct gggtccgcgg gaggctgccg tctggggagc 180
ctgtgggggg tagatatcct gggactgacc caggggaagg aagtggggaa ggggcgggag 240
ggacaatctg agagtgactg gggagccttt ggtgtttggg gtttcctgaa gtgggaggag 300
tgttgagtaa gttggtcttt cccggtgcta tacttgcctc ctctccacgg aagaattgtt 360
caggagatgc gcttggggtg atgacttcct taaatacacg ctgtaggggg tgaagagctt 420
ggaggaccag gcactttgag gaagggcagt tcgtgggctg gggtgggaac aggatggcgg 480
gcaatagact agggtaggcc gcgatg 506

<210> SEQ ID NO 206
<211> LENGTH: 439
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (56)..(57)
<223> OTHER INFORMATION: n is a, c, g, t or u
<220> FEATURE:
<221> NAME/KEY: misc_feature
<222> LOCATION: (60)..(62)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 206
tcatttagcc ggtgtccact aactcagtgt tgtgggccat ttgtaaaccc ttntgnngtn 60
nncnccaggc agacgtaggg aaagaaagag aggatctgta tagacaagaa agctggccat 120
gtgggaagtc cagagctcaa accatgtgcc ccagaggact ggtgctggca ttaagcctgt 180
aaatcaaagg cttctttggc aggaccctgg gctgttagaa tcaccctagg gagcagagcc 240
aggggacatt ttggcccctg actagcaagg cacaacccta taatggcaga agcccttctt 300
tcccctcccc gtttcccacc agacccactt ccttgatggg cctctagcac ccttccaagc 360
tgatggggtc gggaatgtga gctggtaaaa tgggcagtgg aaggggctgt actgtttctt 420
tacatctcac ggggactag 439

<210> SEQ ID NO 207
<211> LENGTH: 375
<212> TYPE: DNA
<213> ORGANISM: Homo sapiens

<400> SEQUENCE: 207
aagaaatgct acctcggtgc catgttctgg actccgcaga acaaggactt tttggagaac 60
tccagcctat accctctatt gccatgacca gtacttcagc cactctggtg tcatctcagg 120
ctgatctccc tgaattccac ccttcagatt caatgcaaat caggcactgt tgcagaggtt 180
ataaacatga gataccagcc acgaccttgc cagtaccttc cttaggcaac caccatactt 240
attgtaacct gcctctgacg ctactcaacg gacagctacc ccttaataac accctgaaag 300
atacccagga atttcacagg aacagttctt tgctgccttt atcctccaaa gagcttagct 360
ttaccagtga tattt 375

<210> SEQ ID NO 208
<211> LENGTH: 502
<212> TYPE: DNA
<213> ORGANISM: Homo sapiens

<400> SEQUENCE: 208
gttcttgagt acatagccaa tgccaatggg agggatccca cttcttaccc atccctgtat 60
gaagatgctt tgagagagga gggagaggga gtctgagcat gagatgcaac cagggccagc 120
gggcagggaa atgggccaat gcatgcttca gggccacacc cagcagtttc cctgtcctgt 180
gtgaaatcag gcccattctt ccctctgtgt ttgatgagag aagtcagtgt tctcagtagt 240
agaaggcaca gtgaatggaa gggaacacat tgtatactgc ctttaggttt ctcttccatc 300
gggtgacttg gagatttctt tttgtttccc tttggtaatt ttcaaatatt gttcctgtaa 360
taaaagtttt agttagcttc aacatctaag tgtatggatg atactgacca cacatgttgt 420
tttgcttatc catttcaagt gcaagtgttt gccattttgt aaaacatttt gggaaatctt 480
ccatcttgct gtgatttgca at 502

<210> SEQ ID NO 209
<211> LENGTH: 250
<212> TYPE: DNA
<213> ORGANISM: Homo sapiens
<220> FEATURE:
<221> NAME/KEY: misc_feature
<222> LOCATION: (110)..(110)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (114)..(116)
<223> OTHER INFORMATION: n is a, c, g, t or u
<220> FEATURE:
<221> NAME/KEY: misc_feature
<222> LOCATION: (118)..(119)
<223> OTHER INFORMATION: n is a, c, g, t or u
<220> FEATURE:
<221> NAME/KEY: misc_feature
<222> LOCATION: (121)..(122)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (127)..(127)
<223> OTHER INFORMATION: n is a, c, g, t or u
<220> FEATURE:
<221> NAME/KEY: misc_feature
<222> LOCATION: (129)..(129)
<223> OTHER INFORMATION: n is a, c, g, t or u
<220> FEATURE:
<221> NAME/KEY: misc_feature
<222> LOCATION: (131)..(132)
<223> OTHER INFORMATION: n is a, c, g, t or u
<220> FEATURE:
<221> NAME/KEY: misc_feature
<222> LOCATION: (135)..(135)
<223> OTHER INFORMATION: n is a, c, g, t or u
<220> FEATURE:
<221> NAME/KEY: misc_feature
<222> LOCATION: (145)..(145)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u
<220> FEATURE:
<221> NAME/KEY: misc_feature
<222> LOCATION: (154)..(154)
<223> OTHER INFORMATION: n is a, c, g, t or u

<400> SEQUENCE: 209
tcccctagct tggggtccag acagcccagt ggacccaggc gcctgagcag gagggtaacc 60
caggccaccc ggccccttcg gccctctcgg ccccaccccc tgcagccggn gncnnncnnc 120
nncnacnana nngcngcgag aagangacag angngactga gcaaaggggg gtgggctcca 180
ggcgacccct agcccaattc tgcccctcca tcccaagggg cagagaaatt gtctttcttt 240
gctgactcct 250

<210> SEQ ID NO 210
<211> LENGTH: 440
<212> TYPE: DNA
<213> ORGANISM: Homo sapiens
<220> FEATURE:
<221> NAME/KEY: misc_feature
<222> LOCATION: (142)..(144)
<223> OTHER INFORMATION: n is a, c, g, t or u

<400> SEQUENCE: 210
tttggacatg tccattttgg aagaaacttt tgtgttaaaa taaactaata tattatgggc 60
tagaacataa aattcaccaa gaatttcaag ataaaaatac taatgttttg cttgtttggg 120
ttatttcaaa caataacttt gnnntctata attttttcac caccgaccct ctacctcctt 180
gcatgctcat tctcctgtgt ggctagatgc atttcgggtg ttttgaatat tatttcagag 240
caagtatcat tccagaaaat aagtttaaag tttgaaatgt ttattttttg taacccatga 300
atcttcagct taagtatctt ctgacataaa agcattttca taattataaa agtgctgata 360
ttactctcca cagtattata tctgatcctg caaagtagtt cagataccag agaatactct 420
taaacatttt gactcacgca 440

<210> SEQ ID NO 211
<211> LENGTH: 573
<212> TYPE: DNA
<213> ORGANISM: Homo sapiens

<400> SEQUENCE: 211
ggactcaggg agtacacact taccagtgcc cttaaagata gccgttttcc cccaatgaca 60
agggatgagc tgccacggct tttctgctca gtgtctctgc tcactaactt tgaagatgtc 120
tgtgattatt tggactggga ggtgggtgta catggcatta gaatagaatt catcaatgaa 180
aaaggatcaa aacgcaccgc cacctaccta ccggaggttg caaaggagca aggatgggac 240
catatacaga ccatagactc cttattgagg aaaggaggat acaaagctcc gattactaat 300
gaattcagga aaaccataaa actgaccagg tatcgtagtg aaaagatgac cctgagctat 360
gctgaatacc ttgctcatcg ccagcatcat catttccaaa atggcattgg gcatcccctt 420
ccgccataca accattattc ctgacactga gccgcacaac cagtcactgg gcctctctgc 480
agacctcttc ccaggagacc ctacaccttc ttggtctagc tatctctttt actgtaccat 540

-continued tttatgatga tagtttccgt tgccatggtg aag 573

<210> SEQ ID NO 212
<211> LENGTH: 514
<212> TYPE: DNA
<213> ORGANISM: Homo sapiens

<400> SEQUENCE: 212
cgtccttgtc atatcctttt aactaggcat ctcagagaag cagagacagg gcagccttcg 60
tcctggggga aaagggaccc tcaggatggc atgagaggtc ctcaatccca agtgtggaac 120
tgtccccctc aacttgttaa aatgcagatt tctgggtctt gccaatgggg cctgggactc 180
catgtgacaa ctggcccagg agcttctgat gtcacacaga attctgcagt cccaagctcc 240
agccccgacc tgctctgctg ttcctaggtg actgccctca cactgctgac cacagtggat 300
ttctccccct gctgctcggg ctcagctggg gtcagccctg cttataaggt caactgtgca 360
aaaccttata ctggccaaga acaaactagt gctgggggag gagggctggg tgccccggcc 420
actggtggag tccccaggaa atcctcagag ctgttgcgag gatgagacac atttgtggac 480
acgtccacct gtcctcctga ccgtctggag agaa 514

<210> SEQ ID NO 213
<211> LENGTH: 504
<212> TYPE: DNA
<213> ORGANISM: Homo sapiens

<400> SEQUENCE: 213
ccggctatgg gctcgagccg agttccttca acatgcactg cgcgcccttt gagcagaacc 60
tctccggggt gtgtcccggc gactccgcca aggcggcggg cgccaaggag cagagggact 120
cggacttggc ggccgagagt aacttccgga tctacccctg gatgcgaagc tcaggaactg 180
accgcaaacg aggccgccag acctacaccc gctaccagac cctggagctg gagaaagaat 240
ttcactacaa tcgctacctg acgcggcggc ggcgcatcga gatcgcgcac acgctctgcc 300
tcacggaaag acagatcaag atttggtttc agaaccggcg catgaagtgg aaaaaggaga 360
acaagaccgc gggcccgggg accaccggcc aagacagggc tgaagcagag gaggaagagg 420
aagagtgagg gatggagaaa gggcagagga agagacatga gaaagggaga ggaagagaag 480
cccagctctg ggaactgaat cagg 504

<210> SEQ ID NO 214
<211> LENGTH: 529
<212> TYPE: DNA
<213> ORGANISM: Homo sapiens

<400> SEQUENCE: 214
gaaattattc actccgtata ctgaaacaga aataaacgag gaagaactta caaagccaag 60
actcttgtgg gctctttatt ttaatatgag agattcctcg ggaatcagca gaagctcgta 120
taatggcttg ccttccaatg tttatgtctg ctctgggcct gactgtggcc tgggaaatga 180
gcatgctgtc aagcaagctg aaacactttt ccaggagatc tttccaactg aagaattctg 240
ccctccacct ccaaatccag aagacattat ctttgatggt gatgataagc agccagaggc 300
tcctggaacc aataatgtag taatggccaa actagaatcc tctgaggaaa gcaaaaacct 360
agaaagccca gagaagcacc ttcaaaatta gaaaagagca atctcgaaat gctgttttgg 420
acctccttca tggcatcaga attttctcat ttaaaggaca gtttcccata tgagtaatta 480
gaagtggtta tatatgatga atgctatgca gatgttgtct ttaactctc 529

<210> SEQ ID NO 215
<211> LENGTH: 480
<212> TYPE: DNA
<213> ORGANISM: Homo sapiens

<400> SEQUENCE: 215
tctttgctct agtattccac ggtgcctctg acatgagaac aggatggaga ctggcttctg 60
atttgacatg cattttgtag gtatgatcca aaatagcttg gaaactatcc cagtcttcaa 120
ccatcccatt ttttagaggt gaaatggcct ccatattctc cctcggaaca cgcagagcat 180
tagtatctat gtagtaggtg ggaccgcctt gtttgccttt atcgccatct atttccatta 240
atgtgcttcc gtcatctctt tctaccacca taccaatagc tgtaggaaaa tccaccttgg 300
ggcagtcctc accagcataa ccagctctca cagtatagga tccaatgtca aaaacaaggg 360
ctccaacttc atctccccg taccacgccg ccgctcatgg ctgctgccgg cgcgactcct 420
accctaaggg ctaactggcg aagtgactgc agtggccgcg actgcgagtc tcgaggagcg 480

<210> SEQ ID NO 216
<211> LENGTH: 282
<212> TYPE: DNA
<213> ORGANISM: Homo sapiens

<400> SEQUENCE: 216
tggaagcatt tgttgcctcg atcttccact ttagaaaaat gaagtttctc cttttctttg 60
ggagaggata tatctgaata cttgccttct tggcatttat acattcaaag ctcagtgcta 120
gattagagct attatttgca tagtcttttg gtattgccca cttttggcat taccatatta 180
tttgacaatt agaaggaata gggaaggaat attacatgac tgtaaaagag ttggttatat 240
tttatgttga cttcaagggt tccatttgaa ctattatggg ca 282

<210> SEQ ID NO 217
<211> LENGTH: 563
<212> TYPE: DNA
<213> ORGANISM: Homo sapiens

<400> SEQUENCE: 217
gcaggaccac cttgaattct gccctgacac actggattgg agagcagcag aacccagggc 60
ctggcccacc aagctggagt gggaaaggca caagattcgg gccaggcaga acagggccta 120
cctggagagg gactgccctg cacagctgca gcagttgctg gagctgggga gaggtgtttt 180
ggaccaacaa gtgaccactc tacggtgtcg ggccttgaac tactaccccc agaacatcac 240
catgaagtgg ctgaaggata agcagccaat ggatgccaag gagttcgaac ctaaagacgt 300
attgcccaat ggggatggga cctaccaggg ctggataacc ttggctgtac cccctgggga 360
agagcagaga tatacgtgcc aggtggagca cccaggcctg gatcagcccc tcattgtgat 420
ctgggagccc tcaccgtctg gcaccctagt cattggagtc atcagtggaa ttgctgtttt 480
tgtcgtcatc ttgttcattg gaattttgtt cataatatta aggaagaggc agggttcaag 540
aggagccatg ggcactacg tct 563

<210> SEQ ID NO 218
<211> LENGTH: 391
<212> TYPE: DNA
<213> ORGANISM: Homo sapiens
<220> FEATURE:
<221> NAME/KEY: misc_feature
<222> LOCATION: (100)..(100)

<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u

<400> SEQUENCE: 218
gccagacaac ctgagtgtga atccagcttc accacttcat tcattcactc acccattcat 60
tcaacaacat atttgaagca catactttgt accagggacn tttccaggca cnggactaca 120
gctatgaaca agacaaacag tccctagcct cccaagagcc gtcacttcag aagggcagac 180
atgacacgca aacaaaatga tgccaggtgg taccaagtgc cttggggaaa cagtgccacc 240
tttctgagac cgtttctcca tccgtccatg gagctgataa caccagtccc tcagggtgga 300
ggtgaagact aagaggttgc tttgagaggg ggaacttggt ggcttttttt caccacctag 360
aacctggcac atactaagct ctcaataaaa g 391

<210> SEQ ID NO 219
<211> LENGTH: 474
<212> TYPE: DNA
<213> ORGANISM: Homo sapiens
<220> FEATURE:
<221> NAME/KEY: misc_feature
<222> LOCATION: (417)..(417)
<223> OTHER INFORMATION: n is a, c, g, t or u

<400> SEQUENCE: 219
aactacgcct ggtacaagct ggcagaggag gtttctgggc gcacagaagt cactgtgaaa 60
cagccagaca gccgcctgag gctcagccaa gcccagggga acctgtcggt tctggagacc 120
cggcaggtac agctggagtg tgtggttctc aaccgcacca gcataacctc ccagctcatg 180
gtggaatggt ttgtatggaa gcccaaccac cctgagcggg agactgtggc ccgcttgagc 240
cgtgacgcca ccttccacta tggagagcag gcagccaaga acaatctgaa ggggcggctg 300
catttggaga gtccttcccc cggcgtgtac cgtctcttca tccagaacgt ggctgtgcag 360
gacagcggga cctacagctg ccatgtggag gagtggctgc ccagccccag tggcatntgg 420
tataagcggg cagaggacac cgctgggcag acagctctga cagtcatgcg acca 474

<210> SEQ ID NO 220
<211> LENGTH: 471
<212> TYPE: DNA
<213> ORGANISM: Homo sapiens
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (133)..(133)
<223> OTHER INFORMATION: n is a, c, g, t or u

<400> SEQUENCE: 220
gggaccttgt aacttccttg caagttaagt gagctatcct gtcacggttt tatgttgagt 60
gagtgggaag ctgggactct gttttacagc catctgtact ggagcctgga caaaccactg 120
gtctntatgg gangccccag cctcacattt ccctggcaag gagagagagg tttagccatg 180
tcctgggtct aggattacag cccagagatg ggcacttaag aagacctggt cattggtcca 240
gacttgggcc aaggctctcc tctgtgaggg atgggtttta ctggtgaatt acctgtgtgg 300
agaagctatc agggccatgt ttagcacact gaagggacca gtctccacca agcactttaa 360
catccctcca gccagcatag attgatctcg tgttacagag agggcaaggt tttggcccc 420 tgtttgcaga ctccatgtct taatcagaga ccacagtttt ctctttgttc c 471

<210> SEQ ID NO 221
<211> LENGTH: 527
<212> TYPE: DNA
<213> ORGANISM: Homo sapiens
<220> FEATURE:
<221> NAME/KEY: misc_feature
<222> LOCATION: (408)..(408)
<223> OTHER INFORMATION: n is a, c, g, t or u
<220> FEATURE:
<221> NAME/KEY: misc_feature
<222> LOCATION: (439)..(439)
<223> OTHER INFORMATION: n is a, c, g, t or u

<400> SEQUENCE: 221
taaataatgt cctctacgtg ccggtgtgga agtagcccgg atgcaattga atgaacaaca 60
gacggtgctt tccaggacgg cgctgtgctt tccaggatgg tgctgtgctt tcattcattt 120
gggtagctcc tctgtgagcc tcccagcgcc gactgcagag cccccactct ccagcctgca 180
agaccccgaa attcaagcca cacaaagaaa ggaggagggg gccgttggca tttactgaac 240
cttataaaac tgtcagcaaa acagccctta ggcttggact ccctgctagc cgggttttac 300
ggtgctgaag tcagcatctt gattcagctg cataaataat ctcctgcagt cctgcaaggc 360
ctggggtagg agagggtatg ggaccagggg cactctgtaa gggctggnat aggaacccca 420
gggaataaga cagaccaant gcgggacttc agactccact gcagccggga tcgggttgtt 480
gttaatttct taagcaattt ctaaattctg tattgactct ctcatgc 527

<210> SEQ ID NO 222
<211> LENGTH: 310
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, t or u
<220> FEATURE:
<221> NAME/KEY: misc_feature
<222> LOCATION: (110)..(110)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (189)..(189)
<223> OTHER INFORMATION: n is a, c, g, t or u
<220> FEATURE:
<221> NAME/KEY: misc_feature
<222> LOCATION: (236)..(236)
<223> OTHER INFORMATION: n is a, c, g, t or u
<220> FEATURE:
<221> NAME/KEY: misc_feature
<222> LOCATION: (252)..(252)
<223> OTHER INFORMATION: n is a, c, g, t or u

<400> SEQUENCE: 222
atacatgtgg ttatcttttg ccctgttgtg atggataatt tgnaaagaag tgggtttatg 60
tcaccttctc accttcttat aagaaagctc tgagaatggg catttttgtn ttttnttgtt 120
gttgttgaga tggagtctgc cacccaggct ggagtccagt ggcgtgatca tacctcactg 180
cagcttcanc ttcctgggct caagtaatcc tcccacccca gcctcccagg tagctngtac 240
tataggtgtg cnccaccacg cccagcaaat ttttaaattt attatagagt gggaggcagg 300
gtgcggtggc 310

<210> SEQ ID NO 223
<211> LENGTH: 283
<212> TYPE: DNA
<213> ORGANISM: Homo sapiens
<220> FEATURE:
<221> NAME/KEY: misc_feature
<222> LOCATION: (169)..(169)
<223> OTHER INFORMATION: n is a, c, g, t or u

<400> SEQUENCE: 223
cactgtctgt gtgagtccat tcacttcaat accagagcca cctctttgtt tcctatttac 60
taagaagcca taccagcatg agatctcctt gatagtgtta aatcccactg tggaaagatt 120
gaaaaatatc tcccagcctt accagaggtt acgatctagt gtggaggcna aagacattga 180
gaagaaaaaa gcaggtgcct cctcctggct ctcctgttag gttaacataa tcataattcc 240
cctttgaaat gtctcccaca tttgcccttt aacttcctat tgc 283

<210> SEQ ID NO 224
<211> LENGTH: 499
<212> TYPE: DNA
<213> ORGANISM: Homo sapiens

<400> SEQUENCE: 224
gacgactacg gtctggacaa ctttgacaca cagttcacca gcgagcccgt gcagctgacc 60
ccagacgatg aggatgccat aaagaggatc gaccagtcag agttcgaagg ctttgagtat 120
atcaacccat tattgctgtc caccgaggag tcggtgtgag gccgcgtgcg tctctgtcgt 180
ggacacgcgt gattgaccct ttaactgtat ccttaaccac cgcatatgca tgccaggctg 240
ggcacggctc cgagggcggc cagggacaga cgcttgcgcc gagaccgcag agggaagcgt 300
cagcgggcgc tgctgggagc agaacagtcc ctcacacctg gcccggcagg cagcttcgtg 360
ctggaggaac ttgctgctgt gcctgcgtcg cggcggatcc gcggggaccc tgccgagggg 420
gctgtcatgc ggtttccaag gtgcacattt tccacggaaa cagaactcga tgcactgacc 480
tgctccgcca ggaaagtga 499

<210> SEQ ID NO 225
<211> LENGTH: 562
<212> TYPE: DNA
<213> ORGANISM: Homo sapiens

<400> SEQUENCE: 225
tcttctgtgg aggaatggca tcccaggcct tcacccctcc aggtcagccg tggctgccgg 60
ccaagatggc cgcgtgggca gcctcacatt ccttctcggc ttttggcccc atgtcctcgg 120
cactcaggtc tgcagttcag cccaagtgtt gagactcagg tatgcagctc agggcggcct 180
taattaaccc tcccatgggc ctgggcaccg cctgcgcctc atcaactctg ggctgctggt 240
tttgttcctg acgctgcagc ctgacactgt gggcgggggt gcagtttgcg atggaaggct 300
gcctccgaat cgaggaagcc ttgaccttgg gaggggcctg ccttttcgct gggcttgcct 360
ttctctgggc agcgttcgct cagcacttca gtgcggccga ttcccctggg actgaattca 420
caccagccac gacgacttcc cggctacttc acgttctcta tgtttgcagc tgttctttgg 480
tggcagaaaa agatgatttt tcttcccccc actcccattc ccttttgtta gtttctctcc 540
ctgaaccaca ttttgagctg ag 562

<210> SEQ ID NO 226
<211> LENGTH: 47
<212> TYPE: DNA
<213> ORGANISM: Homo sapiens

<400> SEQUENCE: 226
ttccagaatt tcttccgagg tagtatggtt ttcttcatag gataaag 47

<210> SEQ ID NO 227
<211> LENGTH: 523
<212> TYPE: DNA
<213> ORGANISM: Homo sapiens
<220> FEATURE:
<221> NAME/KEY: misc_feature
<222> LOCATION: (476)..(476)
<223> OTHER INFORMATION: n is a, c, g, t or u

<400> SEQUENCE: 227
aggcagcgct gcggagagga gcggcagagt gggttgtctg ccgcaggcaa ccaggcaagt 60
gtgtcggggc tggggtgtga atgccagcct gtgagtcccg gaactatgtg ggtaccccta 120
cccctcacag aagccaaggg catggaggag gtccctccac agtgacaacg gtgtggggta 180
ggggaggtgc attcaggaca ccacccaggg acagtgccta tgtgatcacc tcttaaaggc 240
taagcttagg ggcatttccc aaagtgggga cagagggcag gacgcccagg ctgggggctc 300
tcctcgcccg ccctggtgtc tgacagcctc aaggaaggag cagtgcctgt gtcagccatg 360
gggcccttgg agctgccgct ggtgcctagg gggcctgggt ttctgcccag gcagccagtg 420
gctgttggga gcctctgttt cccctgtgct gggggccttg agtgctatgc tagcangggc 480
ctggccccaa gtgtgagtga tgagcaataa acgtaccgtc ccc 523

<210> SEQ ID NO 228
<211> LENGTH: 138
<212> TYPE: DNA
<213> ORGANISM: Homo sapiens

<400> SEQUENCE: 228
aagtgcgaag tcagggatgg tctaagaggg ctgagaggag aattccggaa cctcaggacc 60
ttgctcactg gctgctggct ggggctgtga agctgtccag tctagaactc aaagagtgat 120
ggtacaggct ttagagcc 138

<210> SEQ ID NO 229
<211> LENGTH: 396
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n is a, c, g, t or u

<400> SEQUENCE: 229
gggctgggta cctcttctgg ttgctgagtg gagtgcacca gcagccccac cccagagaag 60
ccctgttgga agcgctgtgg gaatccccca aggtagggga gtggacacca taaggaaggg 120
gaggagtgcc agctccatat gcggtctccc ccatcagtca ggccagcagc gggttcagct 180
gcctctgggc agccctancc catacagaca gggagacctc cctcccgatc ttctgtgaat 240
agtcccttat acccctgctt atgcctcagg ggctcctcca cccttttgtc ttcatactgc 300
atatgaaaac tgcccttgta tatgtggata tctgaatgtg tcagtgaagg cctatatgaa 360
tgtgcacatg tgggtatgtt ctcagccatg tgtata 396

<210> SEQ ID NO 230
<211> LENGTH: 432
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, t or u

<400> SEQUENCE: 230
gaactaaagg agccatctct ctcccctctc ctccgttcnc gagaggaggg gtgggtctca 60
gacgtttttc ctatggactt atttcttcca tgtccaggac tttgcacaac tttggtttta 120
aaagctgttg aaaaatagga aaacaaaggg cattgttcac agatagggcc aagtctcccc 180
ttgcaagggt gcctctgttc tgtccctgcc cccacctcac cttctctact cctccagtaa 240
gttggcagtt ttggtgccaa accccaaatc tccaaagaga catgccaggc aagacaaacc 300
cccaaacacc tcctttccgg tggccttgga aacagattgc tccgagctgg agaatgtcgg 360
gtgaggtgta tgggagagga ggggagagtt agaacttgtg cctttgggag taaggggtaa 420
ctgcctggag gg 432

<210> SEQ ID NO 231
<211> LENGTH: 549
<212> TYPE: DNA
<213> ORGANISM: Homo sapiens

<400> SEQUENCE: 231
atcagtgcca gaaattcctt acctaaagtg gcatatgcga cggccatgga ctggttcata 60
gccgtctgtt atgcctttgt attttctgca ctgattgaat ttgccactgt caactatttc 120
accaagcgga gttgggcttg ggaaggcaag aaggtgccag aggccctgga gatgaagaag 180
aaaacaccag cagccccagc aaagaaaacc agcactacct tcaacatcgt ggggaccacc 240
tatcccatca acctggccaa ggacactgaa ttttccacca tctccaaggg cgctgctccc 300
agtgcctcct caaccccaac aatcattgct tcacccaagg ccacctacgt gcaggacagc 360
ccgactgaga ccaagaccta caacagtgtc agcaaggttg acaaaatttc ccgcatcatc 420
tttcctgtgc tctttgccat attcaatctg gtctattggg ccacatatgt caaccgggag 480
tcagctatca agggcatgat ccgcaaacag tagatagtgg cagtgcagca accagagcac 540
tgtataccc 549

<210> SEQ ID NO 232
<211> LENGTH: 554
<212> TYPE: DNA
<213> ORGANISM: Homo sapiens

<400> SEQUENCE: 232
gatgagtcca tctcacttgc tcagaacttt gcctggtgag agcggttaca agcgaacaag 60
gtggaaatga aagaaaccct gactttccca ctaggaagga agagactgtt ccttcttgtg 120
atgtactctg aagaaaaatt ctaggatttg gacagatttc ttgggttata aaacatgatt 180
ttcttctctg tttcttgggc ttttataatg ggtactgttg ttttcttgca aagctttaat 240
gattccataa ggacttgtat aaagtttatg ggagaatttt caatgtagat gtgaatggca 300
gaaacccaag aatctgtgtg aggttgaata agatcctgtg tctccagaga ggtctgatgg 360
ggagacacag atctaaattt taaaggtggt ttgggccttc tcaatcatat attaaggtcc 420
ttttatgtta tagataagta aattaaggcc cagaaagatt aatagcccaa ggtcccaaga 480
cctgcttgag acctgtgccc catttctgac taatattctt catgatattg tatcactctg 540
tatcaaaacc aacc 554

<210> SEQ ID NO 233
<211> LENGTH: 539
<212> TYPE: DNA
<213> ORGANISM: Homo sapiens

<400> SEQUENCE: 233
gatggtgcag tacctgctag cactttgctg cagaatgcct ctgcactcag ttctgcaaat 60
gtactgtttt agtttcattt aaaacccctt tttttgtgag aagatttcaa acatcaggca 120
agtttgtaat gaattcaagc tgagttctct cgagggacaa acatgtataa ctacagttcc 180
agtgtcagtg ccagctgtca ggttttcact gtgcagctag ggctgcctgc atacccagtc 240
atgtaaacca aattcactct agaatcggcc aggtcttacc aaaatgcaaa tagaatacaa 300
agcaactgga aatatatttc gtaatttcat tttatgtgtg attttaaaag ttaagctact 360
tcaaaactca tctgtctaac ttattttcac taataagtgt aacttgcctg gaatttggca 420
gatctaagct gggcttgggc tagatggttt caagcctgag tcattaagat gtgaaattta 480
cagaaacaac agaggattga ggaacaagtt aaaggacact ctaatggtgc agtctgcat 539

<210> SEQ ID NO 234
<211> LENGTH: 431
<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is a, c, g, t or u

<400> SEQUENCE: 234
gtgagcatgg aagtagatct tccccggtca agcccccaga aggacccagc cctgcggaca 60
ccttgaccga aacctgtgag agctccggaa atagaggaac cnagcattcc ctctggaata 120
catcagcact gttgcctttg aggctggcct gcttgaatgc acacctgagc tccggattca 180
cagtggagga agccagatgc catgtcatga gggtgctcaa gcaacttttt ggagatgtat 240
gtatggagag aaactgaggc ctcctgccaa cagccagcac taacttggca agcatgtttg 300
agagccacct gggaagtgga gccttcagcc ccagttaagc cttcagatga gactgcagtc 360
ctggccacca tctggactgc aacttcacaa gagctcctaa gccagagcca tgcagatgga 420
ttcttggccc c 431

<210> SEQ ID NO 235
<211> LENGTH: 403
<212> TYPE: DNA
<213> ORGANISM: Homo sapiens
<220> FEATURE:
<221> NAME/KEY: misc_feature
<222> LOCATION: (139)..(139)
<223> OTHER INFORMATION: n is a, c, g, t or u

<400> SEQUENCE: 235
gatctcattg cctttttatg ccgattaaca tgcttttagc ccctactgag cttatagtta 60
acagaagttt ccaggtcttt cttcacctga actgtgtcta aagcaagttc cctccacctt 120
ctgtatttat acgcttgant ttttaaaacc taaatgttgg gcttcacatt tgttccttgt 180
aaatttcatc ttggtgattg cagtctaccc tctggccttt aaaaattgtc tgagccttga 240
ttcgatcatg aaaccagctt acccttcccc tgtgtgctgg ccccagtttt ctaaccaggt 300
gttgaatgaa ctggatggac tctgccagat ccctccgtgc aaggctggaa tcagtccatt 360
gttcaactgt gccctttggg gctgtggttc atttggctct gat 403

<210> SEQ ID NO 236
<211> LENGTH: 257
<212> TYPE: DNA
<213> ORGANISM: Homo sapiens

<400> SEQUENCE: 236
ctgctggaaa ggcatccttg ctgcagctgt gagtgtgatg ggacagcaga gtcactcctg 60
catgggattc tagggctggg ggtcccagag gggtggcctc cgcccctcct gggggccgag 120
gactgtcacc atgtcactac ggcactctcc agctgctgac caaagccctc gctaaccgca 180
gccctgccat actctgggtc tttcctctgg agcaaggtga agagactgca gcgaggcgtg 240
gaattgggaa gctcttc 257

<210> SEQ ID NO 237
<211> LENGTH: 446
<212> TYPE: DNA
<213> ORGANISM: Homo sapiens

<400> SEQUENCE: 237
actgtgactg cgcgcaggac gagaactgca agtccaccaa gcgcgccatt gagccgtgcc 60
tgccccggac gagcggcggc ggcgcgggcg gccccggcgc gggcggggtc atgggctgca 120
ccgaggcccg gcggcgctgc gaccgcgaca gccgctgcaa cctggcgctg agccgctacc 180
tgacctactg cggcaaagtc ttcaacgggc tgcgctgcac ggacgaatgc cgcaccgtca 240
ttgaggacat gctggctatg cccaaggcgg cgctgctcaa cgactgcgtg tgcgacggcc 300
tcgagcggcc catctgcgag tcggtcaagg agaacatggc ccgcctgtgc ttcggcgccg 360
agctgggcaa cggccccggc agcagcggct cggacggggg cctggacgac tactacgatg 420
aggactacga tgacgagcag cgcacc 446

<210> SEQ ID NO 238
<211> LENGTH: 340
<212> TYPE: DNA
<213> ORGANISM: Homo sapiens

<400> SEQUENCE: 238
ggaacagagg agagatgccg gctggaggac acagcaaatt tgaaccaaga ggagcttgga 60
ggaagcccga gcgacctgga ggggactggc tgaccttcct cattcttttc aagtgtgaat 120
aataaccaag cccagtttgg caactccttg agggtgagga cgaagcccca ttctcctttt 180
tggaacttgg tggggctcag gaagcaggtt ctctccagtc ggtggctttc ctttctgttg 240
cgggtctctt gagggcctgc cttcatgaag gcacatgagt gactcatcat ttgtgaatta 300
attgctatat gtgaagggca tctgagaaca aattatcttc 340

<210> SEQ ID NO 239
<211> LENGTH: 560
<212> TYPE: DNA
<213> ORGANISM: Homo sapiens

<400> SEQUENCE: 239
tgaccgccat gtggctgtgt ctgaccgcct gcgatactcg gccatcatgc atggagggct 60
gtgtgctagg ttggccatca catcctgggt cagtggctcc atcaactctc ttgtgcagac 120
tgctatcacc tttcagctgc ccatgtgcac taacaagttt attgatcaca tatcctgtga 180
actcctagct gtggtcaggc tggcttgtgt ggacacctcc tccaatgagg ctgccatcat 240
ggtgtctagc attgttcttc tgatgacacc tttctgcctg gttctgttgt cctacatccg 300
gatcatctcc accatcctaa agatccagtc cagagaagga agaaagaaag ccttccacac 360
gtgtgcctct cacctcacgg tggttgccct gtgctacggc acaacgattt tcacttacat 420
ccagccccac tctggtccct cagtccttca agagaagctg atctctgtct tctatgccat 480
tgttatgcct ctgctgaacc ctgtgattta tagtctaagg aataaagagg tgaagggggc 540
ctggcataaa ctattagaga 560

<210> SEQ ID NO 240
<211> LENGTH: 524
<212> TYPE: DNA
<213> ORGANISM: Homo sapiens

<400> SEQUENCE: 240
ggaaatagtt tgttcatatg gccaaattat aaagggactt agtaaaagaa agctatgttt 60
tctgattacg aaggaaatct atgctcacag tgggaaaaca agaaaatgtg gcaaagcaca 120
ggtaagaaaa taaaaatcaa taatatcaac attatgaata ttttaggtac ttaggaattt 180
ggggtagaat gatggaaagc aaactgttaa ttatagctgt atatttcagt gtagaggcta 240
caggtgcctt gcatttgttt tcttataaaa tctgttccca tacattttac ttactttatt 300
tgaatttagg aaactttcat taggtagcca tttttatttt ctgtttcttt aatcatttta 360
ctttgaaata attttaaatt tacagaaaat ttgcaaaaat agtgtagaaa tttcccattt 420
gcctttatcc agcttcctgt agtgttgcca ttttatgtaa ccatagtaca attattgaaa 480
ccaagacatt aactttgaga ggctgctact actctaagaa ccat 524

<210> SEQ ID NO 241
<211> LENGTH: 504
<212> TYPE: DNA
<213> ORGANISM: Homo sapiens
<220> FEATURE:
<221> NAME/KEY: misc_feature
<222> LOCATION: (71)..(72)
<223> OTHER INFORMATION: n is a, c, g, t or u
<220> FEATURE:
<221> NAME/KEY: misc_feature
<222> LOCATION: (197)..(197)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u
<220> FEATURE:
<221> NAME/KEY: misc_feature
<222> LOCATION: (233)..(233)
<223> OTHER INFORMATION: n is a, c, g, t or u
<220> FEATURE:
<221> NAME/KEY: misc_feature
<222> LOCATION: (289)..(289)
<223> OTHER INFORMATION: n is a, c, g, t or u
<220> FEATURE:
<221> NAME/KEY: misc_feature
<222> LOCATION: (309)..(309)
<223> OTHER INFORMATION: n is a, c, g, t or u
<220> FEATURE:
<221> NAME/KEY: misc_feature
<222> LOCATION: (346)..(346)
<223> OTHER INFORMATION: n is a, c, g, t or u
<220> FEATURE:
<221> NAME/KEY: misc_feature
<222> LOCATION: (390)..(390)

<223> OTHER INFORMATION: n is a, c, g, t or u
<220> FEATURE:
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (474)..(474)
<223> OTHER INFORMATION: n is a, c, g, t or u

<400> SEQUENCE: 241
tcctgtgtct tgacccagaa aattgtgaca tgtaaaaaga ataaattcct ggtttaagcc 60
agtaaggtta nnggtacatt gttacatctc agataattaa aaccttgaaa aactcatgag 120
agatcacaag tagaaccttg atctgaaaca tggcatgtgg cgatttatat tgagtattag 180
gttaaaaatg caagaangga gcatagttaa tattttacnt taaagctaaa acnataattg 240
cctacttaaa attttcagtt aattaggttg tcactttttg ttcttaacna agaaatcaac 300
tagttttant ccataaacag ttagaactga tgcacacatc cgtttntcct tactcatttt 360
aaacagctat ctgaaatagg aagtgtaatn taatntttaa agaatctgaa aacatgacag 420
aaatgtttaa actataaaca tatattgtat atgttagcat attgtataca ttgnatatta 480
acataagcta gaatcattga cata 504

<210> SEQ ID NO 242
<211> LENGTH: 317
<212> TYPE: DNA
<213> ORGANISM: Homo sapiens

<400> SEQUENCE: 242
cgaaccactc agggtcctgt ggacgctcac ctagctgcaa tggctacaga ggctggaaga 60
tggcagcccc cggactgggc agatcttcaa gcagacctac agcaagttcg acacaaactc 120
acacaacgat gacgcactac tcaagaacta cgggctgctc tactgcttca ggaaggacat 180
ggacaaggtc gagacattcc tgcgcatcgt gcagtgccgc tctgtggagg gcagctgtgg 240
cttctagctg cccgggtggc atccctgtga cccctcccca gtgcctctcc tggccttgga 300
agttgccact ccagtgc 317

<210> SEQ ID NO 243
<211> LENGTH: 437
<212> TYPE: DNA
<213> ORGANISM: Homo sapiens

<400> SEQUENCE: 243
aatgccggct ggctcagtga tggctctgtg caatatccca tcacaaagcc cagagagccc 60
tgtgggggcc agaacacagt gcccggagtc aggaactacg gattttggga taaagataaa 120
agcagatatg atgttttctg ttttacatcc aatttcaatg gccgttttta ctatctgatc 180
caccccacca aactgaccta tgatgaagcg gtgcaagctt gtctcaatga tggtgctcag 240
attgcaaaag tgggccagat atttgctgcc tggaaaattc tcggatatga ccgctgtgat 300
gcgggctggt tggcggatgg cagcgtccgc taccccatct ctaggccaag aaggcgctgc 360
agtcctactg aggctgcagt gcgcttcgtg ggttttccag ataaaaagca taagctgtat 420
ggtgtctact gcttcag 437

<210> SEQ ID NO 244
<211> LENGTH: 389
<212> TYPE: DNA
<213> ORGANISM: Homo sapiens
<220> FEATURE:
<221> NAME/KEY: misc_feature
<222> LOCATION: (299)..(299)
<223> OTHER INFORMATION: n is a, c, g, t or u

<400> SEQUENCE: 244
tagatcatgc cctcattggg cttacatgct gttgaaaaga taggatataa atccatgaaa 60
atttttacaa tgctatttat taacaataca tgacaagagt actagaaatg ttacttgtga 120
ctattttgtc tattctagcc aagctggatg cctggctgtt tctcagttat actaaatgag 180
ttctgctctc agggtcttca tacttgccct tccctctgcc tgcaacactc ttcctccagt 240 ttttttttt tttttttggc tctctccatc actttaggtc tccattaaaa ctgtcagcnt 300
tcagggaagt tgccttccct gaccacaacc acactaattc aaataccaat ccttccccgc 360
ctccgtttgg taactctcta gtctcttat 389

<210> SEQ ID NO 245
<211> LENGTH: 136
<212> TYPE: DNA
<213> ORGANISM: Homo sapiens
<220> FEATURE:
<221> NAME/KEY: misc_feature
<222> LOCATION: (68)..(69)
<223> OTHER INFORMATION: n is a, c, g, t or u
<220> FEATURE:
<221> NAME/KEY: misc_feature
<222> LOCATION: (91)..(91)
<223> OTHER INFORMATION: n is a, c, g, t or u

<400> SEQUENCE: 245
gccccaaggt ctttaagtat ctctgtcact tattagctca ccagagaaga cacaggaatg 60
agaggccnnt tgtttgtccc gagtgtcaaa naaggcttct tccagatatc agacctacgg 120
gtgcatcaga taattc 136

<210> SEQ ID NO 246
<211> LENGTH: 369
<212> TYPE: DNA
<213> ORGANISM: Homo sapiens

<400> SEQUENCE: 246
ggccctgggc taagtcgggg atgaaggcgg gagctgctgt gctggactgc agctcagcac 60
agagacagtg agcctagatt gcagagctgc ccagggaggg atgtcacctt gggggatgga 120
ggctgcaggt gctcctcaga ccttagggaa acatttggga gggagcttgt tgaggagata 180
caggcacctc agggtggctg ggctggatgg actttgatga cccttccttt tttgagacct 240
gatggttctc taatttggga atcatttcca aagatgggtc taaaaatcct tgtttcattg 300
gaaataatga gtttgctatg atgcttaaga ccaagcatgt caccatttgt tattactgca 360
cttttccct 369

<210> SEQ ID NO 247
<211> LENGTH: 444
<212> TYPE: DNA
<213> ORGANISM: Homo sapiens

<400> SEQUENCE: 247
gaggcttttg acacagttat tagttaaatc aaatgttcaa aaatacggag cagtgcctag 60
tatctggaga gcagcactac catttattct ttcatttata gttgggaaag tttttgacgg 120
tactaacaaa gtggtcgcag gagattttgg aacggctggt ttaaatggct tcaggagact 180

```
tcagtttttt gtttagctac atgattgaat gcataataaa tgctttgtgc ttctgactat    240

caatacctaa agaaagtgca tcagtgaaga gatgcaagac tttcaactga ctggcaaaaa    300

gcaagcttta gcttgtctta taggatgctt agtttgccac tacacttcag accaatggga    360

cagtcataga tggtgtgaca gtgtttaaac gcaacaaaag gctacatttc catggggcca    420

gcactgtcat gagcctcact aagc                                           444


<210> SEQ ID NO 248
<211> LENGTH: 394
<212> TYPE: DNA
<213> ORGANISM: Homo sapiens

<400> SEQUENCE: 248

ggggcggcgg aagcgagtag agtttgtgac atttgtgcca gcccctccag cccagtcacc     60

tgaggagcct gtaggggccc ctgctgtgca gtccatcctt gtggcaggcg aggaggacat    120

ccgctgggtg tgtgaggaca tggggctgaa ggaccctgag gagcttcgca actacatgga    180

gaggatccgg ggcagctcct gaccctccac agccacctgg tcagccacca gctggggcaa    240

cgagggtgga ggtcccactg agcctctcgc ctgccccccgc cactcgtctg gtgcttgttg    300

atccaagtcc cctgcctggt cccccacaag gactcccatc caggccccct ctgccctgcc    360

ccttgtcatg gaccatggtc gtgaggaagg gctc                                394


<210> SEQ ID NO 249
<211> LENGTH: 414
<212> TYPE: DNA
<213> ORGANISM: Homo sapiens

<400> SEQUENCE: 249

tttgctttgg gtactgtgat aactactttt tatactttat cccatttaat tataaaaacc     60

actcttgaga agtaattttt attttcagaa ccattttaca gatttaaaat aaacaggttt    120

gaggaattag tttaacttat ccaaagtttc gtggctatta agttctagta tttggagtca    180

aatgcaagtc tgtctaaatc tagagcccat gttctttaac tgcaacacta taatgtctca    240

ccccgtccta gtcccaccaa ttagtcaact cttttagggc agaagtctgt ctaattcatc    300

tttgcttcct gttactttat atttaattaa aaattttagt gactttttaa cttgtaaatt    360

gtagctgatt ttacatttat cttcctgaag gaaactctgt atcattttgt cttt          414


<210> SEQ ID NO 250
<211> LENGTH: 268
<212> TYPE: DNA
<213> ORGANISM: Homo sapiens

<400> SEQUENCE: 250

cttttattag aatgccatgc ctgcttatgt tatgcatgta ttttataata atttaatcta     60

ttttacaatt ttaaactcaa atatgattta gtattatgca cataatacaa acagtagtgg    120

tgagcaaacg tgtgtttccc ccacatgtgc agaatatgat ggattttatg aaaataaata    180

ttcttaactc caggaaatat gatctatatg gttccttaaa agattttcca atacactgaa    240

aatttagttc cttatgttca ttgtataa                                       268


<210> SEQ ID NO 251
<211> LENGTH: 443
<212> TYPE: DNA
<213> ORGANISM: Homo sapiens
<220> FEATURE:
<221> NAME/KEY: misc_feature
```

<222> LOCATION: (131)..(132)
<223> OTHER INFORMATION: n is a, c, g, t or u
<220> FEATURE:
<221> NAME/KEY: misc_feature
<222> LOCATION: (156)..(156)
<223> OTHER INFORMATION: n is a, c, g, t or u
<220> FEATURE:
<221> NAME/KEY: misc_feature
<222> LOCATION: (187)..(188)
<223> OTHER INFORMATION: n is a, c, g, t or u
<220> FEATURE:
<221> NAME/KEY: misc_feature
<222> LOCATION: (230)..(230)
<223> OTHER INFORMATION: n is a, c, g, t or u

<400> SEQUENCE: 251
cgtgcagcag atcccaggag ttggaaaagt taaagctccc cttctcctcc agaagtttcc 60
aagcatccag caactgagta atgcttccat tggggaactg gagcaggtgg tcggacaagc 120
agtggcacag nnagatccat gccttcttca cgcagnccca ggtgagggct ggcctcaggg 180
ccacggnnat cttctcccga gaccacaaac accaggatct tgttttcagn tttaaaaacc 240
aagagaatgg gccgggtgca ctggctcacg cctctaatct cagcactttg ggaggccgaa 300
gacagcggat catctgaggt caggagttca agaccagcct ggccaacatg gagaaacccc 360
taaaaatagg aacaattagc caggcatggt gacaggtgcc tgtaatccca gctacttggg 420
aggccgaggc atgagaatca ctt 443

<210> SEQ ID NO 252
<211> LENGTH: 281
<212> TYPE: DNA
<213> ORGANISM: Homo sapiens

<400> SEQUENCE: 252
gagaaattcc cacactaaaa acactacaag tttttggaat cgtgccagat ggtacccttc 60
aactgttaaa ggaagccctt cctcatctac agattaattg ctcccatttc accaccattg 120
ccaggccaac tattggcaac aaaaagaacc aggagatatg gggcatcaaa tgccgactga 180
cactgcaaaa gcccagttgt ctatgaagta tttattgcag gatggtgtct cttctttaga 240
acagggaaaa taggcaggaa gcccaattgc tggagtactt a 281

<210> SEQ ID NO 253
<211> LENGTH: 249
<212> TYPE: DNA
<213> ORGANISM: Homo sapiens

<400> SEQUENCE: 253
ccaaatatct agattctgat cccttttgag gtcctagacc ctttgagaaa ctgatgaagc 60
caggcacctc cttcctcagg aaaatgctgg tgtacaaata cacacaaagc tcttcaggca 120
gctgatagat ttcccccaga gagctattca aggacttcct aaggtgggtg gactgcaggg 180
ttaggacacc tgctatagag gtgacatttt tccaaggaca agcagggact ttggtcttga 240
ctgttctct 249

<210> SEQ ID NO 254
<211> LENGTH: 259
<212> TYPE: DNA
<213> ORGANISM: Homo sapiens

<400> SEQUENCE: 254
agaagagcct gaacctcaac atcttcctga agcaatttaa gtgctccaac gaggaggtcg 60

```
ctgctatgat ccgggctgga gataccacca agtttgatgt ggaggttctc aaacaactcc    120

ttaagctcct tcccgagaag cacgagattg aaaacctgcg ggcattcaca gaggagcgag    180

ccaagctggc cagcgccgac cacttctacc tcctcctgct ggccattccc tgctaccagc    240

tgcgaatcga gtgcatgct                                                 259


<210> SEQ ID NO 255
<211> LENGTH: 535
<212> TYPE: DNA
<213> ORGANISM: Homo sapiens

<400> SEQUENCE: 255

aaattctgca atgaacccta caccgaccgg acagaagaaa gggaagaatc caaagaggaa     60

gaagactggt ccctccgacc tgtcctttcg ggagctgaga aagatgacga agctgagcgt    120

ctcagagaaa caacagaaga cggagaagac ccgccaggct acaccaccga catgagaaca    180

gataaagaag ctgactcaaa tggcagaggg cagcctaaag gagaaacaac tggcaattat    240

cccgggtaat atgatcttgg ctgccttgat ggtaattacc gcggcggtaa gtctccctgc    300

tgtctggact gaagaaaatt ttacatactg gcttctgttc catttcctcc tttaattagg    360

ccagttactt ggatggattc ccctattgaa gtttatacaa atgatagtat tttggatgcc    420

tgggccgatt gatgatggct gtcctgcaca gcctgagaag gagggtatgt tgatgaatgt    480

aactggtatg aataccctcc aatttgttta ggaattgctc cttgatgttt accat         535


<210> SEQ ID NO 256
<211> LENGTH: 230
<212> TYPE: DNA
<213> ORGANISM: Homo sapiens

<400> SEQUENCE: 256

ggaagtaatg actttttttgc ccatttactc actgagtccc ataatgtggt aaatgtataa     60

tgctgacatt tgttccgtcc ttatagattg aggatagtac ggccctgaat tttgccttta    120

ctttagaaac ctgattcaac ttaaccgaac tctcaggaat ctgattccta agctgagtat    180

cacattttag attacttact aatttgtgca tctatccacc tagcaaatat               230


<210> SEQ ID NO 257
<211> LENGTH: 532
<212> TYPE: DNA
<213> ORGANISM: Homo sapiens
<220> FEATURE:
<221> NAME/KEY: misc_feature
<222> LOCATION: (97)..(97)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u

<400> SEQUENCE: 257

taaaaccaac cagctgaacc tttcaggcta caagagaacc cgggtcggta atgtcttttt     60

aagaataatt tttaattgct tataacaagc atatttngtg gcatttgaac tatatttact    120

gctccaatat ccgttatttt ccaaaggatt tngtatcttt ttgaaaatgt ttacatcatc    180

agatgatcca cagaattcac tttatgtgag atctcccgag agtttccatc ccaacataat    240

ggactttggt ttgaacacaa ttcgtttttt catttgaatt ggcatttccc aatatttgct    300

aaacatttgc tggagaaatc atttttcttt tttctttttt agaaaactca gaatgaaaat    360

tcattcccct gaaatattta ggtgtctata ttctatattt tgatctatta agggattagt    420
```

atttttccat gtttattgtg ttatcagagt gcattagaaa gattagtgat tcatcttcac 480
agcacatttt taatcaagca gttatttcaa ccagcacatt cgttttgttc at 532

<210> SEQ ID NO 258
<211> LENGTH: 489
<212> TYPE: DNA
<213> ORGANISM: Homo sapiens
<220> FEATURE:
<221> NAME/KEY: misc_feature
<222> LOCATION: (363)..(363)
<223> OTHER INFORMATION: n is a, c, g, t or u
<220> FEATURE:
<221> NAME/KEY: misc_feature
<222> LOCATION: (441)..(441)
<223> OTHER INFORMATION: n is a, c, g, t or u

<400> SEQUENCE: 258 atcacccct gttcattatg tcaggcctca tgggagcctg gccttctcca gaagctggcc 60
ccggcgtcct cccaagctgg accacgtagg ccccagatca cacctggggg tccagatgta 120
ggggtcccgt gtgcacgccc aatcagaccg agcacttgtg acactacccc aacacctctc 180
ccagggctga atgaggaacg cgccactgga cacatgagga agaggctgcc ctgggagcta 240
ctgatgctgt gacctcacct ctctggcttt gggcggcagg tccctgcacc taggatgcct 300
gcctggaaat gtccttgcat tcgtggcctc cttcacagcc tcctcctcag agaagcctct 360
gcnagtgcac agggagtgtg tgcagccttg tgaagggctg ggaccacttg cccagactgg 420
ggcccctcag gcacaggcgt ngggtcctac tgacctgtct ccccagctcc cacacagaaa 480
gcatctaaa 489

<210> SEQ ID NO 259
<211> LENGTH: 468
<212> TYPE: DNA
<213> ORGANISM: Homo sapiens

<400> SEQUENCE: 259
cagaaggaaa cggtgtctct cggctgtggc tctgagtgca aattgcatgg gcggaaaggc 60
gggggtggct gctcttcctg gcaggcctgg gccatcagcg aactgggccc cgtgaggagg 120
gcgggagtgt ggaggagggt gggcctctca cccaggcttt ctcggcccct ctcctcagct 180
tgcagagctg gccagccccc tccttagggg gtgggcgagg agcctctggg cagacccaag 240
aaccatgggg actggggtgg gttggtggca ccaatggcag ccctccccgc ccctctcctt 300
caaggagggt tcccgcagct ggggggtgtg cggaggcgca tggcctcccg ccacggggcc 360
gtgctgtgtt tatggctggc agaggcagcc agcgggtggg ggattctgct gctcgctcac 420
ctgcctggct cgctggtctc tcgaattttc ttccctctga aatcctat 468

<210> SEQ ID NO 260
<211> LENGTH: 531
<212> TYPE: DNA
<213> ORGANISM: Homo sapiens

<400> SEQUENCE: 260
ctgcaccaac tcatgctgga ctgttggcag aaggaccgca accaccggcc caagttcggc 60
caaattgtca acacgctaga caagatgatc cgcaatccca acagcctcaa agccatggcg 120
cccctctcct ctggcatcaa cctgccgctg ctggaccgca cgatccccga ctacaccagc 180
tttaacacgg tggacgagtg gctgaaggcc atcaagatgg ggcagtacaa ggagagcttc 240

```
gccaatgccg gcttcacctc ctttgacgtc gtgtctcaga tgatgatgga ggacattctc    300

cgggttgggg tcactttggc tggccaccag aaaaaaatcc tgaacagtat ccaggtgatg    360

cgggcgcaga tgaaccagat tcagtctgtg gaggtttgac attcacctgc ctcggctcac    420

ctcttcctcc aagccccgcc ccctctgccc cacgtgccgg ccctcctggt gctctatcca    480

ctgcagggcc agccactcgc caggaggcca cgggcacggg aagaaccaag c             531
```

<210> SEQ ID NO 261
<211> LENGTH: 379
<212> TYPE: DNA
<213> ORGANISM: Homo sapiens
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (331)..(331)
<223> OTHER INFORMATION: n is a, c, g, t or u

<400> SEQUENCE: 261

```
cctcggacac cagagacaat aactgagcgc ggaggacacg cctgccctgc ctgccatctg     60

tggcccgaag ccattgccat ccactgcaga cgcctggaga gggacaggcc gcttccgagt    120

gcagtcctgg cgcagcaccg actcccacgc acccggggaa ggacaccctc actcccacac    180

cccgggaaga acactagaac atcagcagan gggccctgcc cctccgcctg cagccgtgaa    240

aggaagctgg gtcatcagcc cagccccgcc caccccagcc cctatgtgtg tttccctcaa    300

taaggagatg ccttgttctt ttcaccatgc naataacatg cccagcaaaa acttgcttta    360

tgggtctgcc tggagaaaa                                                 379
```

<210> SEQ ID NO 262
<211> LENGTH: 486
<212> TYPE: DNA
<213> ORGANISM: Homo sapiens

<400> SEQUENCE: 262

```
aaccacacca gaagacatcc tcaggaacaa aggctgctcc agctctacca gtgtcctcct     60

caccccttgac aacaacgtgg tgaatggttc cagccctgcc atccgcacta actacattgg    120

ccacaagaca aaggacttgc aagccatctg cggcatctcc tgtgatgagc tgtccagcat    180

ggtcctggaa ctcaggggcc tgcgcaccat tgtgaccacg ctgcaggaca gcatccgcaa    240

agtgactgaa gagaacaaag agttggccaa tgagctgagg cggcctcccc tatgctatca    300

caacggagtt cagtacagaa ataacgagga atggactgtt gatagctgca ctgagtgtca    360

ctgtcagaac tcagttacca tctgcaaaaa ggtgtcctgc cccatcatgc cctgctccaa    420

tgccacagtt cctgatggag aatgctgtcc tcgctgttgg cccagcgact ctgcggacga    480

tggctg                                                               486
```

<210> SEQ ID NO 263
<211> LENGTH: 350
<212> TYPE: DNA
<213> ORGANISM: Homo sapiens

<400> SEQUENCE: 263

```
tctccgtgga ggctatggct tcagacaggc cccgaaggtc tgtcaccaat gtgctcggtt     60

gtgggtcaca taacgctctc tggagggctt gcctttcagc ttgggatcat gaaaagatga    120

tttgacgctg tttctcatgg tctccgacct aataaagcaa gataagagaa aacaaatgtt    180
```

attttaaaaa aatcaccctt tggcaaaaga aacatgtaaa attagaatct ggcacaaaca 240
aaacctgaat ctgggttgtg aactttcacc acccgccgca actctttgat aaaacctcaa 300
gtgatatcta ttaccattgt aaaaataaag cctgccccta tgcttagaat 350

<210> SEQ ID NO 264
<211> LENGTH: 507
<212> TYPE: DNA
<213> ORGANISM: Homo sapiens

<400> SEQUENCE: 264
ggcaaccggg gaagtattgt ggccttggag tttgctaaat ccaaatatga aaatcaaaag 60
ctttagtatt cctcatcttc tcttctggaa gatttgcgtt agagtttttg ttgggccttc 120
aaaaagctgt gttcagagtt aggagaatat atccaataaa agatggtttc gtctaccaat 180
tggggaagtt tcaccctctc cctatctgaa gaaaaaaatc aaaaacaaat gtccccggat 240
ctttcgatgc aagtcctgga ggcagggaga tcactgcctg cctggcccac gctgctggga 300
cggctcgtcc tccctgcttt ttgtttttca aacctcctgc ttctcccacc ttgggaagga 360
gaaatgtgaa acccggcagc ggccgaccta ggcggtcttg tggcccggag ccggcccggc 420
ccgaaaacca tagacctggt tgtactgtag cttgttgttt gggggaccaa atttctaga 480 gagaactaga gcacttttgt tgtgttt 507

<210> SEQ ID NO 265
<211> LENGTH: 192
<212> TYPE: DNA
<213> ORGANISM: Homo sapiens

<400> SEQUENCE: 265
cacaggcctt cagaggcgat ggctgggcga cagtgacgaa agcaaagcaa agcagggctg 60
tggagacact cctcgcattt gtctcttccc tccaaggatt atctgagcaa gtcgacttgt 120
tcattcaaag gcggggtctg ccaagccctg ctctatccaa tggggatagc ttctacgtaa 180
cggattccaa tt 192

<210> SEQ ID NO 266
<211> LENGTH: 202
<212> TYPE: DNA
<213> ORGANISM: Homo sapiens

<400> SEQUENCE: 266
agagcaacag ctctatatct ggatcactgc agtgcctaga agatacaaca gcacaattta 60
caaatccaaa tttccaggaa gtctctgcac atacctctag tacaaaagat gtttcagaga 120
ctagagggtc agaaggcaaa gagaggcaat attcaactcc cagttcaggt caaaagggaa 180
gaaagcctgg tgttgaaaga aa 202

<210> SEQ ID NO 267
<211> LENGTH: 278
<212> TYPE: DNA
<213> ORGANISM: Homo sapiens

<400> SEQUENCE: 267
gaaccacgtt ctttgtatgg gcccaatgag ctgtcaagct gccctgtgtt catttcattt 60
ggaattgccc cctctggttc ctctgtatac tactgcttca tctctaaaga cagctcatcc 120
tcctccttca cccctgaatt tccagagcac ttcatctgct ccttcatcac aagtccagtt 180
ttctgccact agtctgaatt tcatgagaag atgccgattt ggttcctgtg ggtcctcagc 240
actattcagt acagtgcttg atgcacagca ggcactca 278

<210> SEQ ID NO 268
<211> LENGTH: 392
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, t or u

<400> SEQUENCE: 268
ctcctggcct gatactctag ggatgcaggt gggagaagca ggggtcctgg gggctgcctg 60
gagctctggg aggcattctg aacggggtct actactgatc tcaggtgagc tctgccctcc 120
tctgaaagtc acttttctca tcagttaaat gggggcaagg gtccgtggtc cgaccaaggt 180
cttggcttca cagacatcac caggagcctg catgcccctg atcactcctt ctccttcctc 240
caggaaactc cagcctggcc tctgacccca gttcaatccg accatgccca agcccaagcg 300
gncctttcct ccagaactgc tccggggcct ggctgtgtga ctggagcaag gtgctaaacc 360
tctctgtgcc tcgctggtct aatctgtaaa at 392

<210> SEQ ID NO 269
<211> LENGTH: 417
<212> TYPE: DNA
<213> ORGANISM: Homo sapiens
<220> FEATURE:
<221> NAME/KEY: misc_feature
<222> LOCATION: (240)..(240)
<223> OTHER INFORMATION: n is a, c, g, t or u

<400> SEQUENCE: 269
taatctcatc caaaaccatg ctcacagaca cacccagcat aatgtttgac caagtatctg 60
ggcaccttgt ggttcagtca aattaacaca tattaactac cttagcaaga tgaaaagcag 120
tgaatgcagg atggtggttg aaattttaaa tacgttggtt atatagtctc attgaaaaag 180
gaacatttga gtgaagactt gaaggggtgg tggaataaac catttatttg cttattgccn 240
gtctccctct atcagaatga aagcttcatg aagcgagaga cttaattttt atctgttata 300
tccctagtgc ctggtgcagg gtaagtactc aaaaatattt gttgagtgaa taagtaatga 360
ttgaggatgg ggactggttt gtatctggtt atatctcttg tccttagcac agtacct 417

<210> SEQ ID NO 270
<211> LENGTH: 412
<212> TYPE: DNA
<213> ORGANISM: Homo sapiens

<400> SEQUENCE: 270
ggggccctag ggattatagc caggactcta atctgcctac catgccattt aacaagagat 60
cccactctcc agctgccttg tgtccctagg gtcctggcca tgtgtttagt gtgctaaact 120
ttctcctttg ttctcaggcc ttccaggtag tccccttcct ggacttaaga gtgcaaactc 180
ttctctgtgg ttctagcctt gggcagaatt atatcccaga gaccacagag caactgtcaa 240
gctgcttacc ccctcaccca gggctacagc ctgtgcccag ccctctaatt tgtgcctctc 300
ttgtgttggg ggtggtgggg gttattcctt tccctttcct gctctggcct ccttgaaagt 360
tcagagtacc cagtacaagt cagccaccat gctgacgggt atttttcctc at 412

<210> SEQ ID NO 271
<211> LENGTH: 372
<212> TYPE: DNA
<213> ORGANISM: Homo sapiens
<220> FEATURE:
<221> NAME/KEY: misc_feature
<222> LOCATION: (76)..(76)
<223> OTHER INFORMATION: n is a, c, g, t or u
<220> FEATURE:
<221> NAME/KEY: misc_feature
<222> LOCATION: (270)..(270)
<223> OTHER INFORMATION: n is a, c, g, t or u
<220> FEATURE:
<221> NAME/KEY: misc_feature
<222> LOCATION: (347)..(347)
<223> OTHER INFORMATION: n is a, c, g, t or u

<400> SEQUENCE: 271
tagccaggta tagtggcagg aacctgtaat cccagctaca ggggaggctg aggcaggaga 60
atcgcttgaa cccggnaggt gtaggttgca gtgagccgag attgcaccac tgcactccag 120
cctgggcgac agagcgagac tctgtctcga aaaaaaaaaa ggtccgtgcc aagctgctcc 180
ctgcccttgc cctttccctt tccctggggt ccaaaccaca tgtgtcctgc ctctcctggc 240
cctaccacat tctggtgctg tcctcactcn cccctggccc agaggctcct gaagatgctg 300
ggcggtcctg gcacagggag gagcagctct gtaaatctgt gcacatngcc actcttggcc 360
taataaagga gg 372

<210> SEQ ID NO 272
<211> LENGTH: 427
<212> TYPE: DNA
<213> ORGANISM: Homo sapiens

<400> SEQUENCE: 272
cctaccaccg tcttcgagag gatgtcatgc ggctctctcg cctagcactg ggctcagagg 60
cctggcgccg agtctggagc cgcagtctgc agctggcgag ttggccaaac cggggagggg 120
cacctggagc tccccagggt gaccctatga gggtattctc agttaggacc cggagacagg 180
acactcttcc tgaagcgggg cgcagatcag aggcagaaga ggaggaggcc aggaccatca 240
gagtgacacc tgtcaggggc cgagagaggc tcaatgagga ggagcctcca ggtgggcaag 300
acccttggaa attgctgaag gagcaagagg agcggaagaa gtgtgtcatc tgccaggacc 360
agagcaagac agtgttgctc ctgccctgcc ggcatctgtg cctgtgccag gcctgcactg 420
aaatcct 427

<210> SEQ ID NO 273
<211> LENGTH: 526
<212> TYPE: DNA
<213> ORGANISM: Homo sapiens

<400> SEQUENCE: 273
gtccacattc ctgcaagcat tgattgagac atttgcacaa tctaaaatgt aagcaaagta 60
gtcattaaaa atacaccctc tacttgggct ttatactgca tacaaattta ctcatgagcc 120
ttcctttgag gaaggatgtg gatctccaaa taaagattta gtgtttattt tgagctctgc 180
atcttaacaa gatgatctga acacctctcc tttgtatcaa taaatagccc tgttattctg 240
aagtgagagg accaagtata gtaaaatgct gacatctaaa actaaataaa tagaaaacac 300
caggccagaa ctatagtcat actcacacaa agggagaaat ttaaactcga accaagcaaa 360
aggcttcacg gaaatagcat ggaaaaacaa tgcttccagt ggccacttcc taaggaggaa 420
caaccccgtc tgatctcaga attggcacca cgtgagcttg ctaagtgata atatctgttt 480
ctactacgga tttaggcaac aggacctgta cattgtcaca ttgcat 526

<210> SEQ ID NO 274
<211> LENGTH: 429
<212> TYPE: DNA
<213> ORGANISM: Homo sapiens

<400> SEQUENCE: 274
tgtgtccact ggtttcagtc tgagttctct gcactttgag gatgcagaca gtgaagttct 60
cccatggtta tagggggaga gatcatagga atgctatgga aagaggcctg aagtcagagc 120
cagctagtgg ttattattta ttaattgcct gtgaggtgcc aggcgcacat attagaccat 180
atgtgattgc agtgagccac ccggatcccc ttcaagctgc tgctgcagct gatggaagtc 240
ctattggcag acagccttct ctcatcagcc ccttcaggac ttgcctcagt tgcagagagc 300
tgccttcccc aagatcacac ccttccctgg ggactcacaa ccaatggctg atccagaaga 360
atccataaag cccgtatcat ttcagcccaa tttaggacag ctttgttgag ccattagacc 420
tacatgcag 429

<210> SEQ ID NO 275
<211> LENGTH: 434
<212> TYPE: DNA
<213> ORGANISM: Homo sapiens
<220> FEATURE:
<221> NAME/KEY: misc_feature
<222> LOCATION: (376)..(390)
<223> OTHER INFORMATION: n is a, c, g, t or u

<400> SEQUENCE: 275
gaagctctac ttgcctggtg gtaattccag gatgacccag gagaggctgg aaagagcgtt 60
caaacggcag ggcagccagc ccgcacctgt caggaaaaat cagttgctgc cgtctgacaa 120
ggtggatggt gagctgggtg ccctgcggct cgaggatgtg gaggatgagt tgataaggga 180
agaggtcatc ctgtcgccag tcccatcagt gctcaagttg cagacagcat caaaaccaat 240
tgacctctca gtagcaaagg aaataaagac ccttctgttt ggttccagct tttgctgttt 300
caatgaagaa tggaaacttc agagtttttc ctttagtaac acagcctcat taaaatacgg 360
catagtgcag aacaannnnn nnnnnnnnnn agtcctggca gctgtccaag gctgtgtcct 420
acagaaactc ctgt 434

<210> SEQ ID NO 276
<211> LENGTH: 189
<212> TYPE: DNA
<213> ORGANISM: Homo sapiens

<400> SEQUENCE: 276
aaaatcactg ccactgactt ttaccctctt caggaagagg ccaaggagga ggaacgcctc 60
atagctttga agaaaatcct cagctcgggg gtgttctatt tctcatggcc aaacgatggg 120
tctcgctttg acctgactgt ccgcacgcag aagcaggggg atgacagctc tgaatggggg 180
aactccttc 189

<210> SEQ ID NO 277
<211> LENGTH: 542
<212> TYPE: DNA
<213> ORGANISM: Homo sapiens

<400> SEQUENCE: 277
gaggagcagg caaggctacg tgggcagctg aaggagcaaa gcgtgcgctg ccggcgcctc 60
gctcacctgc tggcctcggc ccagaaggag cctgaggcag cagccccagc cccagggacc 120
gggggtgatt ctgtgtgtgg ggagacccac cgggccctgc agggggccat ggagaagctg 180
cagagccgct ttatggagct catgcaggag aaggcagacc tgaaggagag gccagggagg 240
gttctccccg tgacaacccc actgcacagc agatcatgca gctgcttcgt gagatgcaga 300
acccccggga gcgcccaggc ttgggcagca acccctgcat tccttttttt taccgggctg 360
acgagaatga tgaggtgaag atcactgtca tctaaaagcc ggctactgtc agcaaagcct 420
gaagaagtgg ggctggatac cctgccccca ccatatccct accatccctt ctcagtcaac 480
cctttaccct tacagtagca agcatagacc cctgtctaac gggggtagac aggtgcagat 540
ga 542

<210> SEQ ID NO 278
<211> LENGTH: 475
<212> TYPE: DNA
<213> ORGANISM: Homo sapiens

<400> SEQUENCE: 278
gacagtctac cgtcacgaga agcgggtgaa actgcagatc tgggacacag ctgggcagga 60
gcggtaccgg accatcacaa cagcctatta ccgtggggcc atgggcttca ttctgatgta 120
tgacatcacc aatgaagagt ccttcaatgc tgtccaagac tgggctactc agatcaagac 180
ctactcctgg gacaatgcac aagttattct ggtggggaac aagtgtgaca tggaggaaga 240
gagggttgtt cccactgaga agggccagct ccttgcagag cagcttgggt ttgatttctt 300
tgaagccagt gcaaaggaga acatcagtgt aaggcaggcc tttgagcgcc tggtggatgc 360
catttgtgac aagatgtctg attcgctgga cacagacccg tcgatgctgg gctcctccaa 420
gaacacgcgt ctctcggaca ccccaccgct gctgcagcag aactgctcat gctag 475

<210> SEQ ID NO 279
<211> LENGTH: 294
<212> TYPE: DNA
<213> ORGANISM: Homo sapiens
<220> FEATURE:
<221> NAME/KEY: misc_feature
<222> LOCATION: (225)..(228)
<223> OTHER INFORMATION: n is a, c, g, t or u
<220> FEATURE:
<221> NAME/KEY: misc_feature
<222> LOCATION: (231)..(231)
<223> OTHER INFORMATION: n is a, c, g, t or u

<400> SEQUENCE: 279 tttttagat ctaccctctt gttgcccagg gggagtccag tggcgtgatc ttggctcact 60
gcaaccgccg cctcccgggt tcaagcaatt ctcctgcctc agtctcccga gtgtcttctg 120
tcttttgtaa aagtttttca tgcccaagtg agattaattg tttaaaaaaa aaaaaacaag 180
aagaaaacaa catagattta ccgcaagacc tattgatata ttatnnnnca nggtggtata 240
cccagggtgg gtgtgacaca gaccaaaaga ggctgtgtgt tctgttgttg ataa 294

<210> SEQ ID NO 280
<211> LENGTH: 421
<212> TYPE: DNA
<213> ORGANISM: Homo sapiens
<220> FEATURE:
<221> NAME/KEY: misc_feature
<222> LOCATION: (129)..(129)

<223> OTHER INFORMATION: n is a, c, g, t or u
<220> FEATURE:
<221> NAME/KEY: misc_feature
<222> LOCATION: (136)..(137)
<223> OTHER INFORMATION: n is a, c, g, t or u
<220> FEATURE:
<221> NAME/KEY: misc_feature
<222> LOCATION: (146)..(146)
<223> OTHER INFORMATION: n is a, c, g, t or u
<220> FEATURE:
<221> NAME/KEY: misc_feature
<222> LOCATION: (323)..(323)
<223> OTHER INFORMATION: n is a, c, g, t or u

<400> SEQUENCE: 280

```
ggaagcgtgt ctgctgggag tttgcgaccg atgactatga cattggcttt ggagtttatt     60

ttgactggac ccctgtaact agcactgaca taactgtgca ggtcagtgat tccagtgacg    120

atgaggatna agaagnnagg aagagnagga agagattgaa gaacccgttc cagctggaga    180

tgtggagaga ggctccagga gctccttgcg gggtcgctat ggggaggtca tgcctgtgta    240

ccggcgggac agccaccgag acgtgcaggc tggcagccat gactaccctg gtgagggcat    300

ctacctgctc aagttcgaca acncctactc cctgctgcgc aacaagactc tctacttcca    360

catctactac accagctgaa ggactgctgt gacaggggca ggctgtattt gctggctgaa    420

g                                                                    421
```

<210> SEQ ID NO 281
<211> LENGTH: 544
<212> TYPE: DNA
<213> ORGANISM: Homo sapiens

<400> SEQUENCE: 281

```
atgagaacgg cgtcttcatg tgcgccgagg gcaccggcaa gttctgtccc ctgaggtcct     60

tcccagacac tgtctacaag aagctggtcc agagagagaa gactttaaag gttagaggag    120

tggaccgcac tccctacctg ggggatgtcg ctgttgtcgt gcaccctggg aaaaaagaga    180

tgggaacccc actcgcagac actcctaccc ggcccgtcac ccggcatggg ggcatgaggg    240

accttcacga atccagcttc agcctctctg gctctcagat cgatgaccat gttccaaagc    300

gagcttcagc tcggatcctc gctcctcccg gaggcaggtc gagtggcatt tggtaaaggc    360

attgccaagc cccccgagtg aggacgcacc gccgccacca gcccgcaact ctccagccga    420

agctgcaggg gcaggagagg ctgggctggg tggcacacca cccgaggggg gccccgggac    480

ccacggagcc ctccctatgt ctgcaaagtg attcactgtg cttcgagcca actctaacag    540

gcac                                                                 544
```

<210> SEQ ID NO 282
<211> LENGTH: 430
<212> TYPE: DNA
<213> ORGANISM: Homo sapiens

<400> SEQUENCE: 282

```
ctgattctac ttctgcaggg ttccacagaa gtctccagtc ttcaaatctt cagtgtatga     60

aagcacagat tcctgaaaga atggcctcaa atgaccagga gtaggagctc tctatatccc    120

tgctcctgaa aaacaagcta actggagtct ccatcacctg ccaccagcta tacacactac    180

caactaccca actgaactcc atgactgatt tgccagctaa tcatgcccct gacccagccc    240

acatggacat gggaaggaca tcagtgaact gtgaaaagag gcagagactc actcccgttt    300

gtattatgaa aacacacgcc aataggacat aaaaagaagc aagagtactg ggctttacca    360
```

tgagttcaaa tctcatttct ggcaattcct atgtctaaaa aaagcttcgt aatctctttt 420
gagccctcac 430

<210> SEQ ID NO 283
<211> LENGTH: 219
<212> TYPE: DNA
<213> ORGANISM: Homo sapiens

<400> SEQUENCE: 283
ccagaggatg atagcacctg tcagtgccag gcgtgcgggc ctcaccaagc cgcgggtcca 60
gatcttggtt cctctaatga tggctgccct cagctgttcc aggagcggtc agtcatagtg 120
gagaactcct caggctctac cagcgcttct gagctcctca aacccatgaa gaagaggaag 180
cgcagggaat accagagccc atcagaggag gagtcggag 219

<210> SEQ ID NO 284
<211> LENGTH: 232
<212> TYPE: DNA
<213> ORGANISM: Homo sapiens

<400> SEQUENCE: 284
tttgcctgag gttgactata catacaaata ttgagcattt cctcctggtc tccgtgataa 60
acaaaggttt tgatattgtt cggcgagatg gaaagaaaat atcaaggagt gagctgaagc 120
cactgccctt gagaaccctc tcgaggagtc tggcctcatg aagatgccag aataaacggc 180
agatatatcc tgaatgaatg tgagattttt accctgtgaa tttcctgtga gg 232

<210> SEQ ID NO 285
<211> LENGTH: 249
<212> TYPE: DNA
<213> ORGANISM: Homo sapiens
<220> FEATURE:
<221> NAME/KEY: misc_feature
<222> LOCATION: (208)..(208)
<223> OTHER INFORMATION: n is a, c, g, t or u

<400> SEQUENCE: 285
agtgcttcca gtggcccaaa aatgcttttt gaagtgtgtt ttgaaacagc ccccaccaac 60
atacacccca ccaggagtac tgatcctgcc tcccttcatg tctaggggaa gcattcgcct 120
ttgagcactt gtttgcaaat ctggggagtt tgagacctcc tagcatctct tcccttcttt 180
ccctgcagtc tattcactcc cgcagccnaa aaatctctgg cgttcaggtt agcagtttct 240
gggttggtt 249

<210> SEQ ID NO 286
<211> LENGTH: 510
<212> TYPE: DNA
<213> ORGANISM: Homo sapiens
<220> FEATURE:
<221> NAME/KEY: misc_feature
<222> LOCATION: (138)..(140)
<223> OTHER INFORMATION: n is a, c, g, t or u
<220> FEATURE:
<221> NAME/KEY: misc_feature
<222> LOCATION: (142)..(143)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u

<400> SEQUENCE: 286

```
gggaattacc ttttgtattg cttgaattta ctgctgtctg tatgaactct ttttcagata     60

aatttttaag aaatcagata agtgaagtga aagagagaga tcaaagtgtt gtggcagcac    120

aaaggagaga ctgactannn tnntgctggg gaatctgaaa gagtgctttg gtggaggtaa    180

catgagatca gggccttgaa gggtgagtca agtctgtcaa ggagacaaga gggagagaag    240

agcttgccag aggcccagag accagcgagg aggctgtggt gtcctggaat gagggcgaga    300

tacttggtgg gactggtcaa cacggcaatg aagagggata tggccgagga aaatggagag    360

gggcactgga nctgtgccag caaggactgg gatgcgtgga cttgatcctg tagataacgg    420

gaggaagaaa ggcctggatg cagcgccatg tcatgagcac atctgatcat gacagctcac    480

ctatgggagg attctccctc aacatttttc                                     510
```

<210> SEQ ID NO 287
<211> LENGTH: 555
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (89)..(89)
<223> OTHER INFORMATION: n is a, c, g, t or u
<220> FEATURE:
<221> NAME/KEY: misc_feature
<222> LOCATION: (106)..(107)
<223> OTHER INFORMATION: n is a, c, g, t or u
<220> FEATURE:
<221> NAME/KEY: misc_feature
<222> LOCATION: (272)..(274)
<223> OTHER INFORMATION: n is a, c, g, t or u

<400> SEQUENCE: 287

```
aggatgtgac agtgactcgg ggcgaccagg ctatgtttnc ttgcatcgta aacttccagc     60

tgccaaagga ggagatcacc tattcctgna agttcgcagg aggagnnctc cggactcagg    120

acttgtccta tttccgagat atgccgcggg ccgaaggata cctggcgcgg atccggccgg    180

ctcagctcac gcaccgcggg acgttctcct gcgtgatcaa gcaagaccag cgccccctgg    240

cccggctcta cttctttctt aacgtgacgg gnnngccccc gcgggcggag acagagttgc    300

aggcctcgtt ccgggaagtg ctgcgctggg cgccgcggga tgccgagctg atcgagccct    360

ggaggcccag cctgggcgag ctgctggcca ggcccgaggc tctgacgccc agcaatctgt    420

tcctgcttgc agtcctcggg gccctcgcat cagcgagtgc gacagtgttg gcgtggatgt    480

tctttcgatg gtactgcagt ggcaactaac aaaggtatct ttcctccttc cctatcctat    540

ttccatcctg aaaat                                                     555
```

<210> SEQ ID NO 288
<211> LENGTH: 381
<212> TYPE: DNA
<213> ORGANISM: Homo sapiens

<400> SEQUENCE: 288

```
atgtatccgc tgtcaactac gaatttgagg atgaatactt cagtaatacc agtgccctag     60

ccaaagattt cataagaaga cttctggtca aggatccaaa gaagagaatg acaattcaag    120

atagtttgca gcatccctgg atcaagccta aagatacaca acaggcactt agtagaaaag    180

catcagcagt aaacatggag aaattcaaga agtttgcagc ccggaaaaaa tggaaacaat    240

ccgttcgctt gatatcactg tgccaaagat tatccaggtc attcctgtcc agaagtaaca    300
```

tgagtgttgc cagaagcgat gatactctgg atgaggaaga ctcctttgtg atgaaagcca 360
tcatccatgc catcaacgat g 381

<210> SEQ ID NO 289
<211> LENGTH: 488
<212> TYPE: DNA
<213> ORGANISM: Homo sapiens

<400> SEQUENCE: 289
cacgctcctg gaacgtcaga tcattattga ggcaaatgat cgccatctag aatcagcagg 60
acagactgag atcttccgaa agcacccccg caaagcctcc atcctcaaca tgccactagt 120
gacaacactt ttctactcct gcttctatca ctacacagag gctgagggga cattcagcag 180
tcccgtcaac ctgaagaaga catttaagat cccagataaa cagtatgtgc tgacagccct 240
ggctgctcgt gccaagcttc gagcctggaa tgatgtagat gccctattca ccacaaagaa 300
ctggctgggc tataccaaga agagagcacc cattggcttc catcgggttg tcgaaatttt 360
gcacaagaac aatgcccctg tgcagatatt acaggagtat gtcaatctgg tggaagatgt 420
ggacacgaag ttgaacttag ccactaagtt caagtgccat gatgtcgtca ttgataccta 480
ccgggacc 488

<210> SEQ ID NO 290
<211> LENGTH: 306
<212> TYPE: DNA
<213> ORGANISM: Homo sapiens

<400> SEQUENCE: 290
tttcatgact tctccttcac ctaagcacct caaaacagat gatagcactt caggattgac 60
gcgaagcatc ttcaaatatt tggagagcta acaccatcaa aggtgccaaa atctacattg 120
agactgcttt gagaagtttc tagcactgaa agttggaatt gacactccag ccaatgatcc 180
ttccttcttt cataatcaat gcaataagat tgcagacaga aattccagtg atttctactg 240
cacagctctg gacatctctt ttcctagtat tattccctga attggccact gatttcaatt 300
ctgcag 306

<210> SEQ ID NO 291
<211> LENGTH: 348
<212> TYPE: DNA
<213> ORGANISM: Homo sapiens

<400> SEQUENCE: 291
ctcctgggtc cgcagtgtac tgcgagggag cacagatgtc catcccccgc tggggtggag 60
agcggcagca ggcctgatgg atgagggatc gtggcttccc ggcccagaga catgaggtgt 120
ccagggccag gccccccacc ctcagttggg gctgttccgg gggtgactgt gagcgatccc 180
accccaaacc tgagatgggg tagcccgtcc tgtgtcctcc acagggacaa gcagtgggag 240
gagtctgaat ggtcaccagg aagcccgggc tccatcttga cctccttttt cagggacagg 300
agcaacaggc ccctcttccc tgactctaag cccttccctg taaggtga 348

<210> SEQ ID NO 292
<211> LENGTH: 395
<212> TYPE: DNA
<213> ORGANISM: Homo sapiens
<220> FEATURE:
<221> NAME/KEY: misc_feature
<222> LOCATION: (343)..(343)

<223> OTHER INFORMATION: n is a, c, g, t or u
<220> FEATURE:
<221> NAME/KEY: misc_feature
<222> LOCATION: (361)..(361)
<223> OTHER INFORMATION: n is a, c, g, t or u

<400> SEQUENCE: 292
tctctgcttt ccctcttatg aaaatggcag atgccttttt gtgaaggtct caaagcccac 60
ttcatcctgg ctgcagcacc aaaaggacaa aggcccgctt ttgaagtgcc tgataaggca 120
ttcctttcac ccctccatga ggaaggtggc aaatcttgag actccctatt agagagcttc 180
gattttcctg aaattgtgtt aggaaaatag ggtgacttgg tttgatcttg gtttctatac 240
ctattatggc tgcctgactc tggtcatttg gcccctgcag gcctaagcca cttggttttg 300
cttcacatat tggggtttat tagaacagta cgtagggaag canatgccag aggcacccgt 360 ncctttccc tgccttctag gtgctcctgg gaaat 395

<210> SEQ ID NO 293
<211> LENGTH: 557
<212> TYPE: DNA
<213> ORGANISM: Homo sapiens

<400> SEQUENCE: 293
accaagatct ctgcctggca caataacgtg gagaaaaccc tgccctccac caaggccacg 60
cgggtgggcg tgcttctcaa ctgtgaccac ggctttgtca tcttcttcgc tgttgccgac 120
aaggtccacc tgatgtataa gttcagggtg gactttactg aggctttgta cccggctttc 180
tgggtatttt ctgctggtgc cacactctcc atctgctccc ccaagtaggc aggctgtagg 240
cacttgggct gactgcctgc agaagtccca agaccctagt gaaaatacag caggcagaac 300
tctccttgga taattccccc aagaggtccc caaggattgg gagcatggga ggggagctgg 360
cgggagggtg ggaggtggga tttagccagg aaaggggtga gagtgattgt gttgtgggcg 420
aggaggcgtt tccacccccct ggtgcctatc agggcagggt gacctactcc ccattgttct 480
ggaaatctcc aggctgctgg gcagctgggc agctgggcag agctctggga agtgaagtca 540
tgagtgcccg attcctc 557

<210> SEQ ID NO 294
<211> LENGTH: 547
<212> TYPE: DNA
<213> ORGANISM: Homo sapiens

<400> SEQUENCE: 294
ggttcgggtg agggcactct atgactacgc tggccaggaa gctgatgagc tgagcttccg 60
agcaggggag gagctgctga agatgagtga ggaggacgag cagggctggt gccaaggcca 120
gttgcagagt ggccgcattg gcctgtaccc tgccaactac gtggagtgtg tgggcgcctg 180
agtgtcctga cagcccttct gcaacgttta cccaccctgg ttcagagccc agcttctcct 240
ggagagccgg accctcaggg ccctgaaccg tcgctctctg gctgctcctc tgtcccttga 300
gggaggaagt cctgggaccc agggagggga ggggcctttg tctagggaag ggactggtag 360
ggaagggacg agtctaggct gagggcaaga tgggaggtca gaggtgacag aagcgttcag 420
gggtgcctgg gcctccccag gagctgtgga ctcagttcct gacctctgct ttggggttcc 480
tggggtgggc ttggggtgag tgtagttctg gcctagcagc accctcttgt ggcttgttct 540
agcgtgt 547

<210> SEQ ID NO 295
<211> LENGTH: 147
<212> TYPE: DNA
<213> ORGANISM: Homo sapiens

<400> SEQUENCE: 295
tgtatgtgac caaaggtagg tcctgggatg acagcaatgc tgacactggc ctaaggagtt 60
actcatccat ttaataagta ttccagcaga tacagatgtg aacagtcaag tctctgccat 120
ccacaatgct tgtgttctaa tgcaaga 147

<210> SEQ ID NO 296
<211> LENGTH: 83
<212> TYPE: DNA
<213> ORGANISM: Homo sapiens

<400> SEQUENCE: 296
atgtgttcaa ccaagcggga aactctccgg gtagagtgaa atccgaagtt gctatgctac 60
aagataacct gggccgtgcg ccg 83

<210> SEQ ID NO 297
<211> LENGTH: 545
<212> TYPE: DNA
<213> ORGANISM: Homo sapiens

<400> SEQUENCE: 297
gtctttctga gagtttcatt gccattatca acaagagaag ttgaaattta caagtcagga 60
ggttattttt ccagattgat aaccatagaa agtgaataaa cacttttaag gtcgcaaaca 120
tttgctaggt tgtccttctc aatgcatgtg caggctgcat cctgtccttg tttttaagcc 180
agggtttata aataagtaga tttataccaa tcttaataga attgtatatt ttatgcaaga 240
attaaatgct ttacaacatg aagtataact caacccattg taaactttgg tggcaatatg 300
gatttgaaac tcgacagttc tcttgtattt gcttcctagg tttctgcatg caagttatga 360
caggtaggac tgaaaaaaca ctgccttttg acttctagca tttagcaacc gagagtcgta 420
gagtcaataa agctgtaagt gtcttcactt aatctgtggt tctcctaaaa ctattatctg 480
aaacctacag catcccacca tgaaatattt ggtaaattta tgttgtgacg tgttgcagca 540
tgtaa 545

<210> SEQ ID NO 298
<211> LENGTH: 485
<212> TYPE: DNA
<213> ORGANISM: Homo sapiens

<400> SEQUENCE: 298
aatttgtctg tgacccagat gccctcttct ccatggcttt cccggataac cagcgtccgt 60
tcctgaaggc agagtccgag tgccacctca gcgaggagga caccctgccg ctgacccact 120
ttgaagacag ccccgcttac ctcctggaca tggaccgctg cagcagcctc ccctatgccg 180
aaggctttgc ttactaagtt tctgagtggc ggagtggcca aaccctagag ctagcagttc 240
ccattcaggc aaacaagggc agtggttttg tttgtgtttt tggttgttcc taaagcttgc 300
cctttgagta ttatctggag aacccaagct gtctctggat tggcaccctt aaagacagat 360
acattggctg gggagtggga acagggaggg gcagaaaacc accaaaaggc cagtgcctca 420
actcttgatt ctgatgaggt ttctgggaag agatcaaaat ggagtctcct taccatggac 480
aatac 485

<210> SEQ ID NO 299
<211> LENGTH: 409
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (312)..(312)
<223> OTHER INFORMATION: n is a, c, g, t or u

<400> SEQUENCE: 299
acagcttagc gatggagaaa atggcatccc tgttgntntn tcaccagata aattgcctgg 60
atctctggga cacccccgtc cccaggagaa ggatgtttgg gaagagatgg atgccaacaa 120
aaacaagata aagcttggaa tttgtaaggc tgctactgaa gaggagaaca gccatggcca 180
ggcaaatggt cttctcaatg ctccaagcct tgggtcacca attcgtgtcc gctcagagat 240
tactcagcca gacagagata ttccactggt gcgaaagtta cgttccattc acagctttga 300
gctggaaaaa cntctgaccc tggagccaaa gccagacact gacaagttcc ttgagacctg 360
gtataaaata gtgtattttt ctttttaaag cttctaaggt accattatt 409

<210> SEQ ID NO 300
<211> LENGTH: 430
<212> TYPE: DNA
<213> ORGANISM: Homo sapiens
<220> FEATURE:
<221> NAME/KEY: misc_feature
<222> LOCATION: (150)..(150)
<223> OTHER INFORMATION: n is a, c, g, t or u
<220> FEATURE:
<221> NAME/KEY: misc_feature
<222> LOCATION: (164)..(164)
<223> OTHER INFORMATION: n is a, c, g, t or u
<220> FEATURE:
<221> NAME/KEY: misc_feature
<222> LOCATION: (170)..(170)
<223> OTHER INFORMATION: n is a, c, g, t or u
<220> FEATURE:
<221> NAME/KEY: misc_feature
<222> LOCATION: (173)..(174)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (187)..(187)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (393)..(393)
<223> OTHER INFORMATION: n is a, c, g, t or u
<220> FEATURE:
<221> NAME/KEY: misc_feature
<222> LOCATION: (395)..(398)
<223> OTHER INFORMATION: n is a, c, g, t or u
<220> FEATURE:
<221> NAME/KEY: misc_feature
<222> LOCATION: (400)..(400)
<223> OTHER INFORMATION: n is a, c, g, t or u
<220> FEATURE:
<221> NAME/KEY: misc_feature
<222> LOCATION: (403)..(403)
<223> OTHER INFORMATION: n is a, c, g, t or u

<400> SEQUENCE: 300
gagggccaag agctagggac agggggaaga gactggccca ggtggtaggg aggaaagaac 60
tcccagagtt tcctttagcc aggaaacctg ctctactgac cccgtgactt ggacagtcag 120
acatcaccct gagagtgaca agtgtaaaan tgactccctt cctnccccgn ccnncggaag 180
tatantnaga tacttgaaag cagtccnttn ctaaaatggn cttacctatg tggcctgaac 240
gattaaaaga aagaactcag agttacaagg gaaaaagaaa aagagttaca agggaattgt 300
agtctttttc tgaatagaat attagtactg tggtattgca tttcatggga atggaaatgt 360
attggtaaag ctacctgatg gaagctttcn ctngnnnncn aanatggagg gtgtattatg 420
tgcagttatt 430

<210> SEQ ID NO 301
<211> LENGTH: 536
<212> TYPE: DNA
<213> ORGANISM: Homo sapiens
<220> FEATURE:
<221> NAME/KEY: misc_feature
<222> LOCATION: (68)..(69)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (74)..(76)
<223> OTHER INFORMATION: n is a, c, g, t or u
<220> FEATURE:
<221> NAME/KEY: misc_feature
<222> LOCATION: (78)..(82)
<223> OTHER INFORMATION: n is a, c, g, t or u
<220> FEATURE:
<221> NAME/KEY: misc_feature
<222> LOCATION: (100)..(100)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (129)..(129)
<223> OTHER INFORMATION: n is a, c, g, t or u
<220> FEATURE:
<221> NAME/KEY: misc_feature
<222> LOCATION: (134)..(134)
<223> OTHER INFORMATION: n is a, c, g, t or u
<220> FEATURE:
<221> NAME/KEY: misc_feature
<222> LOCATION: (168)..(168)

<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u
<220> FEATURE:
<221> NAME/KEY: misc_feature
<222> LOCATION: (254)..(254)
<223> OTHER INFORMATION: n is a, c, g, t or u
<220> FEATURE:
<221> NAME/KEY: misc_feature
<222> LOCATION: (276)..(276)
<223> OTHER INFORMATION: n is a, c, g, t or u

<400> SEQUENCE: 301
atcgaagaac aaagagtgct ccaaaaaata ggtcattctt ttattttcat aaagtatcta 60
aactgtanna anannnannn nngtgtttca ttctaaattn gcagctgaaa taaatttatt 120
ngcgatagna gaantatctt attattcatc ctcagaaata aaggattnga agggatagag 180
attatatgat aaatttatag aagactttca gaattntgaa tgcatttngt ttagtgttat 240
gaaatgacaa tagnaaaaaa gtctcgactt caattnaaaa gttacacaaa caaacaaatc 300
tacaggcatg tctttatata ccatcaggtc taagttttca aagaaaatgg tagatataac 360
tgcagataac tcattacagt cataatctct gcccatgtgt attgagaggg ggcagttgtg 420
cacgaaaaaa gaatttatgt ggccatttta ataaattcag tttaaaatag acttgtgtat 480
atgcatgaat catcagagat gaaactggtt tgagagactc atgtgaacct tacgaa 536

<210> SEQ ID NO 302
<211> LENGTH: 371
<212> TYPE: DNA
<213> ORGANISM: Homo sapiens

<400> SEQUENCE: 302
ctggtacgct gctgctgcag ttaccagaaa aactcataag caaatacaac tggatcaagc 60
aatggaaact tggactgaaa tttgatggga agaatgagga cctggttgat aaaattaaag 120
agtcccttac tctgctgagg aagaaggttt ggaacctgta gtgtcctgtc tgataagggt 180
gaagctctcg ttcttgcttg ccccagaaga ccagttttta gtcttcactc agtggatttt 240
caaatgctct tggctgattt ttaggcaaaa tggttttaaa tgaattcaaa ctcttcccac 300
gagggcttta gtaaaatggg aagtaccaac attatatatt cttagagcag atgccatgta 360
ctagggtatc a 371

<210> SEQ ID NO 303
<211> LENGTH: 355
<212> TYPE: DNA
<213> ORGANISM: Homo sapiens
<220> FEATURE:
<221> NAME/KEY: misc_feature
<222> LOCATION: (223)..(223)
<223> OTHER INFORMATION: n is a, c, g, t or u
<220> FEATURE:
<221> NAME/KEY: misc_feature
<222> LOCATION: (227)..(227)
<223> OTHER INFORMATION: n is a, c, g, t or u

<400> SEQUENCE: 303
gaagctgtgt ggagtggaag atggacattg aggaagaagg gcaggtgtgg tctcacccag 60
aatggttcct gctgcttccg cggtgcccag gcttttctca cggcctctgc tgggttctcc 120
cctgggtgct gtggatgcat cctgcctgct ggaaattctg tgctctctgt ttccatccct 180
ttgtcgtggt aatgaccgta tacctctccc ctgtaccctc ctntgcntgc tctccgtgca 240
ggcccctctc cctctggttg tcccatcagc atttccccac agctcgttgt tcctccttcc 300
tcttttctgg tgacctttct actgattgca ttgtacctct ttccctgata ttaaa 355

<210> SEQ ID NO 304
<211> LENGTH: 362
<212> TYPE: DNA
<213> ORGANISM: Homo sapiens

<400> SEQUENCE: 304
gcctgtgtct tcgggctgaa tttgatctgg ccatcccagg gggtctcctc cctgagtgcc 60
cttgtgcccc tgaacatgtt cactgaactg ctgatcgagt actatgaaaa gatcttcagc 120
accccggagg cacctgggga gcacggcctg gcaccatggg aacaggggag cagggcagcc 180
cctttgcagg aggctgtgcc acggacacaa gccacgggcc tcaccaagcc taccctacct 240
ccgagtcccc tgatggcagc cagaagacgt ctctagtgtt gcgaacactc tgtatgtttc 300
gagctacctc ccacacctgt ctgtgcactt gtatgttttg taaacttggc atctgtaaaa 360
at 362

<210> SEQ ID NO 305
<211> LENGTH: 533
<212> TYPE: DNA
<213> ORGANISM: Homo sapiens

<400> SEQUENCE: 305
cgaagagcaa gacccactct gttccagaag ccctataagc tggaggtgga caactcgatg 60
taaatttcat gggaaaaccc ttgtacctga catgtgagcc actcagaact caccaaaatg 120
ttcgacacca taacaacagc tactcaaact gtaaaccagg ataagaagtt gatgacttca 180
cactgtggac agtttttcca aagatgtcag aacaagactc cccatcatga taaggctccc 240
acccctctta actgtccttg ctcatgcctg cctctttcac ttggcaggat aatgcagtca 300
ttagaatttc acatgtagta gcttctgagg gtaacaacag agtgtcagat atgtcatctc 360
aacctcaaac ttttacgtaa catctcaggg gaaatgtggc tctctccatc ttgcatacag 420
ggctcccaat agaaatgaac acagagatat tgcctgtgtg tttgcagaga agatggtttc 480
tataaagagt aggaaagctg aaattatagt agagtctcct ttaaatgcac att 533

<210> SEQ ID NO 306
<211> LENGTH: 434
<212> TYPE: DNA
<213> ORGANISM: Homo sapiens
<220> FEATURE:
<221> NAME/KEY: misc_feature
<222> LOCATION: (131)..(131)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (205)..(205)
<223> OTHER INFORMATION: n is a, c, g, t or u

<400> SEQUENCE: 306
ggaaccctcc tcttggcaag ggctttccga agttaacctg aaaaactggt tcaggccatg 60

-continued

```
acagcaaagg gttggatagc ctcattatcc ctcctccctt cagaactctg gaacagccag    120

cgttaacatc nacacaggcc ttcagtctga tgagaaacat ttaccatcta ttgtctcgga    180

agcctgctac ntggaggctt catcntgatg ataaagcctt ggtctccaca accccgtata    240

acccagacat tcctttctat tgataactct tgcaagcgat tgccaaccag aagatgttta    300

aatccaccta taacctggaa gcccccagtt ccagctgccc acctttctgg actaaaccaa    360

tgtatatctt caatatattt gattgatgtc tcatgtctcc ctaaaatggg taccatcaag    420

ctgtgcactg acca                                                      434
```

<210> SEQ ID NO 307
<211> LENGTH: 157
<212> TYPE: DNA
<213> ORGANISM: Homo sapiens

<400> SEQUENCE: 307

```
cctccgcaca ctggatgaga atccatcttc cattcgagct gggaatagac tttgtgaaag     60

atattatgta atggagtctc gggaaccctg agacctctcc agcgaagctg aagtgaatta    120

attaagtgct ttaaacggtc ttggtgctgt gttacgg                             157
```

<210> SEQ ID NO 308
<211> LENGTH: 367
<212> TYPE: DNA
<213> ORGANISM: Homo sapiens
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (38)..(40)
<223> OTHER INFORMATION: n is a, c, g, t or u
<220> FEATURE:
<221> NAME/KEY: misc_feature
<222> LOCATION: (43)..(47)
<223> OTHER INFORMATION: n is a, c, g, t or u
<220> FEATURE:
<221> NAME/KEY: misc_feature
<222> LOCATION: (52)..(53)
<223> OTHER INFORMATION: n is a, c, g, t or u
<220> FEATURE:
<221> NAME/KEY: misc_feature
<222> LOCATION: (58)..(58)
<223> OTHER INFORMATION: n is a, c, g, t or u
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (62)..(64)
<223> OTHER INFORMATION: n is a, c, g, t or u
<220> FEATURE:
<221> NAME/KEY: misc_feature
<222> LOCATION: (67)..(68)
<223> OTHER INFORMATION: n is a, c, g, t or u
<220> FEATURE:
<221> NAME/KEY: misc_feature
<222> LOCATION: (71)..(71)
<223> OTHER INFORMATION: n is a, c, g, t or u
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (84)..(86)
<223> OTHER INFORMATION: n is a, c, g, t or u
<220> FEATURE:
<221> NAME/KEY: misc_feature
<222> LOCATION: (89)..(91)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (289)..(289)
<223> OTHER INFORMATION: n is a, c, g, t or u

<400> SEQUENCE: 308
aggtgatgca ctatgcccag tacgtcctcc tggcnctnnn ctnnnnngcg tnncctgntn 60
cnnntcnntg ncntntgcna antnnngann nanaaccgtg taaaaccatt tttatgtggc 120
ttcaacgtca actataaatt agcttggtta tcttctagga gaaatgctat ttattttgga 180
gtagtagtaa aaagggctca aaggataagg aggccattca ggcctattct gaatccctga 240
tgacatcagc tcccaagggc tctgtgctgc aggaagcaaa actgtaggng ggtaccaggt 300
aatgccgtgc gcctccccgc cccctcccat atcaagtaga atgctggcgg cttacagact 360
gaagatg 367

<210> SEQ ID NO 309
<211> LENGTH: 484
<212> TYPE: DNA
<213> ORGANISM: Homo sapiens

<400> SEQUENCE: 309
accccaccac gtaccagatg gatgtgaacc ccgagggcaa atacagcttt ggtgccacct 60
gcgtgaagaa gtgtccccgt aattatgtgg tgacagatca cggctcgtgc gtccgagcct 120
gtggggccga cagctatgag atggaggaag acggcgtccg caagtgtaag aagtgcgaag 180
ggccttgccg caaagtgtgt aacggaatag gtattggtga atttaaagac tcactctcca 240
taaatgctac gaatattaaa cacttcaaaa actgcacctc catcagtggc gatctccaca 300
tcctgccggt ggcatttagg ggtgactcct tcacacatac tccccctctg gatccacagg 360
aactggatat tctgaaaacc gtaaaggaaa tcacaggttt gagctgaatt atcacatgaa 420
tataaatggg aaatcagtgt tttagagaga gaacttttcg acatatttcc tgttcccttg 480
gaat 484

<210> SEQ ID NO 310
<211> LENGTH: 526
<212> TYPE: DNA
<213> ORGANISM: Homo sapiens

<400> SEQUENCE: 310
ccatggggcc atctgggcca ttcagagact ggagtgagat ttgggtgtgg agggggaggc 60
gccaaggtgg aggagcttcc cactccagga ctgttgatga aagggacaga ttgaggagga 120
agtgggctct gaggctgcag ggctggaagt ccttgcccac ttcccactct cctgccccaa 180

-continued

```
tctatctagt acttcccagg caaataggcc cctttgaggc tcctgagtgc cctcagatgg    240

tcaaaaccca gttttccctc tgggagccta aaccaggctg catcggaggc caggacccgg    300

atcattcact gtgataccct gccctccaga gggtgcgctc agagacacgg gcaagcatgc    360

ctcttccctt ccctggagag aaagtgtgtg atttctctcc cacctccttc cccccaccag    420

acctttgctg ggcctaaagg tcttggccat ggggacgccc tcagtctagg gatctggcca    480

cagactccct cctgtgaacc aacacagaca cccaagcaga gcaatc                   526


<210> SEQ ID NO 311
<211> LENGTH: 319
<212> TYPE: DNA
<213> ORGANISM: Homo sapiens
<220> FEATURE:
<221> NAME/KEY: misc_feature
<222> LOCATION: (264)..(264)
<223> OTHER INFORMATION: n is a, c, g, t or u

<400> SEQUENCE: 311

taaattgcct ggatctctgg gacacccccg tccccaggag aaggatgttt gggaagagat     60

ggatgccaac aaaaacaaga taaagcttgg aatttgtaag gctgctactg aagaggagaa    120

cagccatggc caggcaaatg gtcttctcaa tgctccaagc cttgggtcac caattcgtgt    180

ccgctcagag attactcagc cagacagaga tattccactg gtgcgaaagt tacgttccat    240

tcacagcttt gagctggaaa aacntctgac cctggagcca aagccagaca ctgacaagtt    300

ccttgagacc tggtataaa                                                 319


<210> SEQ ID NO 312
<211> LENGTH: 234
<212> TYPE: DNA
<213> ORGANISM: Homo sapiens
<220> FEATURE:
<221> NAME/KEY: misc_feature
<222> LOCATION: (85)..(87)
<223> OTHER INFORMATION: n is a, c, g, t or u
<220> FEATURE:
<221> NAME/KEY: misc_feature
<222> LOCATION: (89)..(90)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (94)..(95)
<223> OTHER INFORMATION: n is a, c, g, t or u
<220> FEATURE:
<221> NAME/KEY: misc_feature
<222> LOCATION: (97)..(97)
<223> OTHER INFORMATION: n is a, c, g, t or u
<220> FEATURE:
<221> NAME/KEY: misc_feature
<222> LOCATION: (186)..(186)
<223> OTHER INFORMATION: n is a, c, g, t or u

<400> SEQUENCE: 312

gcgcttgcgc agtagctgaa cgcgggcgtt tctttcctcc ctttttttcg aattggtttt     60

gggggtagat tcgagttaca aaatnnncnn cngnngngtg ttcggcgcgg ttcccccagc    120

tgtctctggc tgaaccggcg ctctcgcctc cctgccgaac acagcgtgag gagccccccc    180

aggganatgg tgtttgagtc tctgggcttg ccgagcacta agtcctctga gttc          234


<210> SEQ ID NO 313
<211> LENGTH: 125
```

<212> TYPE: DNA
<213> ORGANISM: Homo sapiens

<400> SEQUENCE: 313
gtactgcaaa aatcaccctc ggcaagacga atgtctgacg tgccggaagg agtcatacgg 60
gtccatgctc cacttctctc caaggtgtcc atggccattc aactcaacaa tcaaaccaaa 120
gccaa 125

<210> SEQ ID NO 314
<211> LENGTH: 446
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
<222> LOCATION: (205)..(205)
<223> OTHER INFORMATION: n is a, c, g, t or u
<220> FEATURE:
<221> NAME/KEY: misc_feature
<222> LOCATION: (211)..(211)
<223> OTHER INFORMATION: n is a, c, g, t or u

<400> SEQUENCE: 314
aagtcattcg tttaagcgtg gattattttg ccgaatgaat aatgatgatg gcngctttca 60
tctcttatga agttttcctg gccaagagcc agnagttgga agtttggatc attctttttt 120
cttttttaan catttcttct cttctttctc ttttttatca ctaaatgaat gacatgtgga 180
gaaactattc agcttttaaa gtatnctcca nttacttgtc tcaactacca ctatttattg 240
tgtttatcaa aatcataaaa agctcatttt tggcatttac cttcgtggtt gagactgctg 300
tctgtatgtc tgggaatgga agtcctcttc agggattcag caagggctgt actttgctt 360 aatactagtg gttccttatt ctaagtgatg acatcatcca cctttcctag aaatgggtct 420
ttgtgcctag tatgatatct ttccaa 446

<210> SEQ ID NO 315
<211> LENGTH: 473
<212> TYPE: DNA
<213> ORGANISM: Homo sapiens
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u
<220> FEATURE:
<221> NAME/KEY: misc_feature
<222> LOCATION: (375)..(375)
<223> OTHER INFORMATION: n is a, c, g, t or u
<220> FEATURE:
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (405)..(405)

<223> OTHER INFORMATION: n is a, c, g, t or u

<400> SEQUENCE: 315
tgtttcaggc ccatccacag ttgaagcagt gtgtgcgtca ggcaattgaa cgggctgtcc 60
aggagctggt ccatcctgtg gtggatcgat caattaagat tgccatgact acttgtgagc 120
aaatagtcag gaaggatttt gccctggatt cggaggaatc tcgaatgcga atagcagctc 180
atcacatgat gcgtaacttg acagctngga atggctatga ttacatgcag ggaacctttg 240
ctcatgagca tatctaccaa cttnaaaaaa cagttttgcc tcagcccttc gtgtaagttg 300
gctatttcct tggtataggt acaaaacgta ttactgcttg tctgtaataa tttttttctt 360
tgtctatata tggcnctggg cgttaccact tattnttaat aatcnccata tttgtttgat 420
gtcttccatc attttagatt gtaattctgt gaggcaaagc atcatgtctg tgt 473

<210> SEQ ID NO 316
<211> LENGTH: 576
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (351)..(352)
<223> OTHER INFORMATION: n is a, c, g, t or u
<220> FEATURE:
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (496)..(496)
<223> OTHER INFORMATION: n is a, c, g, t or u

<400> SEQUENCE: 316
aggacaccag gctggtggcc acagtgctgc tgtccgtggt cgtgctgctc cacgccctcc 60
tgnccatggg ctgtaagttg tacttcttcc agtcgctgcc tccggagaac gtggctcctc 120
caccccaaat cacatctctg ccctcaaaca tcgcgctgtc ccctaccttg ccgcagtccc 180
tggccccctc ctaggaaggc ccgggtccca caggcaacac ctaagtggac caacccctct 240
gcctgtcctg ccccccagac gatgactgaa ggctcctttg acaccttgag atgattctgc 300
tactttccag acttttctta caaagcaaac acttttattt tctatgcaaa nntgattcag 360
agaatttata taaaggcggg cgaggggcag ccgancaggg agctttggga cagggctggg 420
gcccccatat cccccccggg ccacctgctt tccctcctat ggctcccctg gaacaggagg 480
gagagccaag ggggcngccc agcctggaca gcgcccgctc ctgcctgggt gcacacacgg 540
cgggcctgag ctccagcatc tgagtttggg ggtatg 576

<210> SEQ ID NO 317
<211> LENGTH: 265
<212> TYPE: DNA
<213> ORGANISM: Homo sapiens

<400> SEQUENCE: 317
ccaggagcag ctgcgtgacg tcatgttcta cctggagaca cagcagaaga tcaaccatct 60
gcctgccgag acccggcaga aatccaggag ggacagatca acatcgccat ggcctcggcc 120
tcgagccctg cctcttcggg gggcagtggg aagttgccct ccaggaaggg ccgcagcaag 180
aggggcaagt gaccttcaga gcaacagaca tccctgagac tgttctccct gacactgtga 240
gagtgtgctg ggaccttcag ctaaa 265

<210> SEQ ID NO 318
<211> LENGTH: 515
<212> TYPE: DNA
<213> ORGANISM: Homo sapiens
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 318
atacgtgggt agtgttgcat ttcaaatgag gctcttctgg ttgaaatgat atatttataa 60
gaccagaata tcacaaatgg gtgatgtata atgtctcttt agtttttngg tattnggcct 120
cttttaaagc ctgtcggatg tatgggagaa aacaatgaac gtgctttgat ttcctatcag 180
tcactcttaa gaacatacat atngtttaag taactcggtc ttttttatct gattcttgag 240
ncactatggg tagcaagtaa ccacttacaa atttaaatgt aatatacact ccttttctgt 300
gtgtcaagtc cttattttta ggtgcatatt gacatttaaa tgttaattat tgtttggcat 360
ataatatcaa aaatctatta tttattttat gctgttacag ttaaaagatg tgatttatga 420
catactgaat caacttgcct tccaatttag tgtgtaatat ggtaagcatt tatactttta 480
gatatgtctt atttttattt ggatgcctgt ctacc 515

<210> SEQ ID NO 319
<211> LENGTH: 541
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, t or u
<220> FEATURE:
<221> NAME/KEY: misc_feature
<222> LOCATION: (141)..(141)
<223> OTHER INFORMATION: n is a, c, g, t or u
<220> FEATURE:
<221> NAME/KEY: misc_feature
<222> LOCATION: (147)..(147)
<223> OTHER INFORMATION: n is a, c, g, t or u
<220> FEATURE:
<221> NAME/KEY: misc_feature
<222> LOCATION: (159)..(159)
<223> OTHER INFORMATION: n is a, c, g, t or u
<220> FEATURE:
<221> NAME/KEY: misc_feature
<222> LOCATION: (161)..(161)
<223> OTHER INFORMATION: n is a, c, g, t or u
<220> FEATURE:
<221> NAME/KEY: misc_feature
<222> LOCATION: (167)..(167)
<223> OTHER INFORMATION: n is a, c, g, t or u
<220> FEATURE:
<221> NAME/KEY: misc_feature
<222> LOCATION: (172)..(172)
<223> OTHER INFORMATION: n is a, c, g, t or u
<220> FEATURE:

<221> NAME/KEY: misc_feature
<222> LOCATION: (181)..(181)
<223> OTHER INFORMATION: n is a, c, g, t or u
<220> FEATURE:
<221> NAME/KEY: misc_feature
<222> LOCATION: (188)..(188)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (260)..(260)
<223> OTHER INFORMATION: n is a, c, g, t or u
<220> FEATURE:
<221> NAME/KEY: misc_feature
<222> LOCATION: (509)..(509)
<223> OTHER INFORMATION: n is a, c, g, t or u

<400> SEQUENCE: 319
gagttaatgc agcactcgtc attcagaaat attggcgaag agtcttagca cagagaaaat 60
tattaatgtt aaaaaaggaa aagctggaaa aagttcaaaa taaagcagca tcacttattc 120
agggatattg gagaanatat nccactngac aaagatttnc ngaaatngaa anattattca 180
ntcatccngc naatntagga taagaatgat aattgctgtn acatcttata aacgatatct 240
ttgggctaca gttacaattn cagaggcatt ggcgtgctta tttaagaaga aaacaagatc 300
aacaaagata tgaaatgcta aaatcatcaa ctcttataat ccaatctatg ttcagaaaat 360
ggaagcaacg taaaatgcaa tcacaagtaa aagctacagt aatattgcaa agagctttta 420
gagaatggca tttaagaaaa caagctaaag aagaaaattc tgctattatc atacaatcat 480
ggtatagaat gcataaagaa ttacggaant atatttatat tagatcttgt gttgttatca 540
t 541

<210> SEQ ID NO 320
<211> LENGTH: 495
<212> TYPE: DNA
<213> ORGANISM: Homo sapiens
<220> FEATURE:
<221> NAME/KEY: misc_feature
<222> LOCATION: (144)..(145)
<223> OTHER INFORMATION: n is a, c, g, t or u

<400> SEQUENCE: 320
cttcggattt ttattgactc aaaatagtgc cattcccctt aatgaaatag attttgagtc 60 ttttttttcat tgtaaccccc aaatgagaat catctacctg attcttgtac caaaaaaaaa 120
tttttttcag tctttttttt tttnnagaga gggtctcttg tcaacgcaag actgggagtg 180
gcagtggcac gatcttagct cactacaact tctggcctcc caggctcaag caattctcct 240
gcctcagcct cctgagtagc tggggattac aggcatgcac caccacgccc agctaatttt 300
ggtattttta gtagagacag ggtttcacca ttgtttggcc aggctggtcc cgaactcctg 360
acctcaggtg atccacccac ctcggcctcc caaagtgctg ggattatagg tgcgagccat 420
tgcgcccagc ctcagttatt ttatttaaca gtgtaagtac ttagaaagta agaaaatggc 480
gtgattagtt ttttg 495

<210> SEQ ID NO 321
<211> LENGTH: 429
<212> TYPE: DNA
<213> ORGANISM: Homo sapiens

<400> SEQUENCE: 321
ggctgaggag gctggtctga acatcactca catttgcctc cctccagata gcagtgaagc 60
cgagattata gatgaaatct taaagatcaa tgaagatacc agagtacatg gccttgccct 120
tcagatctct gagaacttgt ttagcaacaa agtcctcaat gccttgaaac cagaaaaaga 180
tgtggatgga gtaacagaca taaacctggg gaagctggtg cgaggggatg cccatgaatg 240
ttttgtttca cctgttgcca aagctgtaat tgaacttctt gaaaaatcag taggtgtcaa 300
cctagatgga aagaagattt tggtagtggg ggcccatggg tctttggaag ctgctctaca 360
atgcctgttc cagagaaaag ggtccatgac aatgagcatc cagtggaaaa cacgccagct 420
tcaaagcaa 429

<210> SEQ ID NO 322
<211> LENGTH: 467
<212> TYPE: DNA
<213> ORGANISM: Homo sapiens

<400> SEQUENCE: 322
tctgagggtg ccttgatgct ggctcatcac acattgagta tcttgggcat tatcatggcc 60
cttgtgcttg gggagtctgg cacagaggtc aatgcagtcc tctttggaag tgagcttacc 120
aaccccttgc tacagatgcg ctggtttctc cgggaaacag ggcactatca cagtttcact 180
ggagatgtag tggacttcct ctttgtggct ctgttcacag gagtgaggat tggtgtggga 240
gcttgcctcc ttttctgtga aatggtctcc cccacgccta agtggtttgt gaaggctggg 300
ggagtagcga tgtatgctgt gtcttggtgt ttcatgttta gcatctggcg ctttgcatgg 360
aggaagagca tcaagaagta ccatgcttgg agaagcaggc ggagtgagga acggcagctg 420
aaacacaacg gacatctcaa aatacactag ccaaggcttg ctccaga 467

<210> SEQ ID NO 323
<211> LENGTH: 504
<212> TYPE: DNA
<213> ORGANISM: Homo sapiens

<400> SEQUENCE: 323
ttggcacttc agaagtctcc ccaatcttga caaagccctg gagaaagggc cgggcctccc 60
gttgataaga atatcactgc agataaatgg aggtttcaaa ttgaaagaaa ggaggagggc 120
ctcctgttga taagattatt gtcactgcag gtaaatggag gcttcaaata gaaatacatt 180
tcagttacag aaaaaaaaat tatctttgtt acacatttga gtttgcaggc ctaaggttac 240
tcccgctaca ctatcatctg taaccataac gcactcaaca ttttaagcta actataagga 300
ttgttgcttc actcaaagat cctgaggttt tattcactaa catttttatt tggtgactat 360
agttgacaag aacaaagctg tggggaacca acaaacactg caatgcctgg cattgtcacc 420
tcactagatt gtgagttcct ctgggacagg gtccgtacat tttcttagaa tccctcactt 480
agccattagc ctgcacagtg cttg 504

<210> SEQ ID NO 324
<211> LENGTH: 163
<212> TYPE: DNA

<213> ORGANISM: Homo sapiens

<400> SEQUENCE: 324
catggaggag tgcatttcct tggctattcc agaagtccta cctcccttct gagattttat 60
aatggtattt cttatggtta tcccaaatat acttggcaag tcgtcttata aaccaccaat 120
aatagcctct taaaaattca aaaattactc ctcttggcta aca 163

<210> SEQ ID NO 325
<211> LENGTH: 441
<212> TYPE: DNA
<213> ORGANISM: Homo sapiens

<400> SEQUENCE: 325
cctccgcgga aggcgtggca gggaggcagt cgccctgcgg tgcaagctgc tgctccagag 60
cataccgtgg cccaggtggt atccccaagg cctcgtgccg tggctggggt cctgggaggt 120
ggtcgccctg cagtgcaagc tgctgctcca gagcgtaccg tggcccagac tgatcctcga 180
ggcctcctgc cgtggctggg gtcatggtcg gctgcgcatg tccagaagca tttccttcct 240
gcgaccatcc cggcgcccct agggggagaa gccaggacag cagcttccgc tgtctccaca 300
gcagacacgg gacggattcc acagacggga gcctcattcg taccatgcca aacgcattca 360
ctcggggcag tattaaccgt tctagaaagc cactgtttta tagcaaaaca ggaaaggaaa 420
agctaccagt tttttattca g 441

<210> SEQ ID NO 326
<211> LENGTH: 457
<212> TYPE: DNA
<213> ORGANISM: Homo sapiens

<400> SEQUENCE: 326
tttcccctag ttgacctgtc tataagagaa ttatatattt ctaactatat aaccctagga 60
atttagacaa cctgaaattt attcacatat atcaaagtga gaaaatgcct caattcacat 120
agatttcttc tctttagtat aattgaccta ctttggtagt ggaatagtga atacttacta 180
taatttgact tgaatatgta gctcatcctt tacaccaact cctaatttta aataatttct 240
actctgtctt aaatgagaag tacttggttt tttttttctt aaatatgtat atgacattta 300
aatgtaactt attatttttt ttgagaccga gtcttgctct gttacccagg ctggagtgca 360
gtgggtgatc ttggctcact gcaagctctg ccctccccgg gttcgcacca ttctcctgcc 420
tcagcctccc aattagcttg gcctacagtc atctgcc 457

<210> SEQ ID NO 327
<211> LENGTH: 438
<212> TYPE: DNA
<213> ORGANISM: Homo sapiens
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (218)..(218)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u

<400> SEQUENCE: 327
ttgtccttta tgtatcttct ttccatagtg cttactggag ccttccaaaa taatgtctcc 60
tcaangtgac agcccctcag gaatttgaag gcaatngtca caccctcacc cnctttcctg 120
agttttttct ggtttattaa cgtcagtctt tacagtcagt gctcattgac ggtggttttc 180
tctggttgtt tcctgaacac gtagtgctct taaagcantg ccctgaggng aatacaattc 240
tccaggggca ttctgattgg caggtgaagc acagtgccat gttcccagca ctgatttggg 300
aagtggcttg tcacatccca cagtgaactc agtcaactgg aatgcctaac tctctttcat 360
aagacctcct gctacattat gtttctccca gactgtactc aggtccaaga acagaattta 420
ctagtctatc cttctcaa 438

<210> SEQ ID NO 328
<211> LENGTH: 535
<212> TYPE: DNA
<213> ORGANISM: Homo sapiens
<220> FEATURE:
<221> NAME/KEY: misc_feature
<222> LOCATION: (40)..(40)
<223> OTHER INFORMATION: n is a, c, g, t or u

<400> SEQUENCE: 328
cccttcttgc tgccacagga tgaataaagt gttgagattn gtctatggag aaagctgtgt 60
gtctgttttt atctcccctc tcaggaccag tcagccactg gtcaatcagg ctgatcatgg 120
aacattagga attctccaat taagggagaa aaagtccagg gacttagtta tatcttcaga 180
ccagtgcagc tgggacacac aaagttctcc tgtctcacca tctgatatgg tttggatgct 240
cgtcccctcc aaatctcatg ttgaaatgta attcccagtg ttggaagtgg agcctggtgg 300
gaagtatttg gatcatgaga gaggatcctt catgaatggc tcagcaccat ctccttggtg 360
atgagtgagt tctcactcaa ttcacataga tatggttgtt taaaagagtc tgagacctct 420
cccctctttc tcgccatgtg atatgcctgc tccccccttca ccttccgcct ttactgtaag 480
cttcctgagg ccctcaccag aagctgagca aatgttggtg ccatgccagt acagc 535

<210> SEQ ID NO 329
<211> LENGTH: 432
<212> TYPE: DNA
<213> ORGANISM: Homo sapiens

<400> SEQUENCE: 329
gccacagact gaactcgcag ggagtgcagc aggaaggaac aaagacaggc aaacggcaac 60
gtagcctggg ctcactgtgc tggggcatgg cgggatcctc cacagagagg aggggaccaa 120
ttctggacag acagatgttg ggaggataca gaggagatgc cacttctcac tcaccactac 180
cagccagcct ccagaaggcc ccagagagac cctgcaagac cacggaggga gccgacactt 240
gaatgtagta ataggcaggg ggccctgcca ccccatccag ccagacccca gctgaaccat 300
gcgtcagggg cctagaggtg gagttcttag ctatccttgg ctttctgtgc cagcctggct 360
ctgcccctcc cccatgggct gtgtcctaag gcccatttga gaagctgagg ctagttccaa 420
aaacctctcc tg 432

<210> SEQ ID NO 330

<211> LENGTH: 234
<212> TYPE: DNA
<213> ORGANISM: Homo sapiens

<400> SEQUENCE: 330
agcaaatcta gctttcagta ttcctaattt ttacctaagc tcattgctcc aggctttgat 60
tacctaaaat aagcttggat aaaattgaac caacttcaag aatgcagcac ttcttaatct 120
ttagctcttt cttgggagaa gctagacttt attcattata ttgctatgac aacttcactc 180
tttcataata tataggataa attgtttaca tgattggacc ctcagattct gtta 234

<210> SEQ ID NO 331
<211> LENGTH: 317
<212> TYPE: DNA
<213> ORGANISM: Homo sapiens

<400> SEQUENCE: 331
acttaggagt ggtgcttttt ctcagaaaac aggccacggt gtttcataca gaatgtcttc 60
atatcatctg aaatggtatg gctgaagttc atttgtttac agggtcggga atgtcttcag 120
ttcttgagag tcaacagtaa tgattggttg taagccaagg gacattttaa gctagtgaag 180
agttttttct ggaattgatt tttcccaaaa gaatatatta attgaggtta agaagtcagt 240
gggaaacaca cagaaatttg ttttaaaatc tttcaggagc tttactgaaa gacttggtta 300
tcaagtcttt tggggag 317

<210> SEQ ID NO 332
<211> LENGTH: 415
<212> TYPE: DNA
<213> ORGANISM: Homo sapiens

<400> SEQUENCE: 332
gacttacttt aacaaccagc caatccctac ctaagcctag tagccatggt ttggctaaga 60
ccgcagcgac tgtatttagt aaatcctttg aacaagtcag tggtgtcaca gtcccacata 120
acccgtcatc tgctgttggt tgtggggctg ggacagatgc caataggttt tccgcttgta 180
gtctccaaga agaaaagctt atttacgttt cagaaagaac tgaacttcca atgaagcatc 240
aatcaggtca gcagagacct cctagtatta gcattactct gtccacagat taattagtaa 300
catatttttc tcccataacc tagtgaacct ggaaatacaa ctttgcttct ttatgaaagt 360
accctgggtc tttcatccgt attcctgaca ggagccctga tgtcttaaat tctga 415

<210> SEQ ID NO 333
<211> LENGTH: 489
<212> TYPE: DNA
<213> ORGANISM: Homo sapiens

<400> SEQUENCE: 333
gacgggtcca ttaacaaagc gggctttgcc gtcaactttt tcaaagaggt ggacgagtgc 60
tctcggccca accgcggggg ctgtgagcag cggtgcctca acaccctggg cagctacaag 120
tgcagctgtg accccgggta cgagctggcc ccagacaagc gccgctgtga ggctgcttgt 180
ggcggattcc tcaccaagct caacggctcc atcaccagcc cgggctggcc caaggagtac 240
ccccccaaca agaactgcat ctggcagctg gtggccccca cccagtaccg catctccctg 300
cagtttgact tctttgagac agagggcaat gatgtgtgca agtacgactt cgtggaggtg 360
cgcagtggac tcacagctga ctccaagctg catggcaagt tctgtggttc tgagaagccc 420
gaggtcatca cctcccagta caacaacatg cgcgtggagt tcaagtccga caacaccgtg 480
tccaaaaag 489

<210> SEQ ID NO 334
<211> LENGTH: 239
<212> TYPE: DNA
<213> ORGANISM: Homo sapiens

<400> SEQUENCE: 334
cacagataga acctgcacat tgcccattaa tgcacacttg tgtatgccta ttacagtctg 60
tgaagtttgg tttagggtca gatgctgggc agagagctgt gaagccatta catattcctt 120
cccttgcaca gtctgaatca tcccgacact tctcagactt tgacttgaat gcacactgtg 180
ctgtacaaca aggaccttga cttggactgc actgtttccc aggtttcagt ttgcatttt 239

<210> SEQ ID NO 335
<211> LENGTH: 432
<212> TYPE: DNA
<213> ORGANISM: Homo sapiens

<400> SEQUENCE: 335
gccctgactg actgtattct ctggccacat tcaagtcccc cattggtggg ggcagagaag 60
taggaccagg ccatccttgg ctacagagct cgaagacccc aagacagccc tctgctctca 120
gcggcgccac agagagcctg ggctcagcct tctgcatcag gacatggcct cgtccactga 180
gggcacgatt taaacatttg acatcagaag ctttatttgt aaacctcaca cagataagga 240
ccaagggctg gcggtgtggc cagaggacag gggaagctga aggccccgtg cttgagctcg 300
gcagtcctgc tccttgcagt gaagccacca tgggtgaccg tccagcctca cccggtggcc 360
tgcacagtga gggaagggct tcagggccat ctgctcccag ggcaggggac aggccaccaa 420
ggacctttgg ca 432

<210> SEQ ID NO 336
<211> LENGTH: 380
<212> TYPE: DNA
<213> ORGANISM: Homo sapiens

<400> SEQUENCE: 336
aatgttgaca tatttcctct atctcataga tggtaaaagt gttgctttta aactggcaaa 60
tgcactcttc agaaatcctt ttctatctga tccacatgga gaggttaaag gttcaatttc 120
atgacctcta tgcaggcagc gctctcattg gatgtaagaa tattacctgc aaggatagaa 180
tgcagttgtg caacagagac acattcttat ttcttttttt tcacaatttt gttttgtttt 240
taatgaccct tttattgaat attggactga aatataaatt ttaaaaaaca cgttggaaag 300
gatgtacaac agaaggctat gtatgtatat acagtatgtc aaaagccttt tatttttata 360
cttcaaatgc tctaaattaa 380

<210> SEQ ID NO 337
<211> LENGTH: 544
<212> TYPE: DNA
<213> ORGANISM: Homo sapiens

<400> SEQUENCE: 337
gagtctctgc ttgataagtg cctctatacc aaccgctctc ctcatcctga catcttgata 60
cggacttctg gagaagtgcg gctgagtgac ttcttgctat ggcagacctc tcactcctgc 120
ctggtgttcc aacccgttct gtggccagag tatacatttt ggaacctctt cgaggccatc 180

-continued

```
ctgcagttcc agatgaacca tagcgtgctt cagaaggccc gagacatgta tgcagaggag    240

cggaagaggc agcagctgga gagggaccag gctacagtga cagagcagct gctgcgagag    300

gggctccaag ccagtgggga cgcccagctc cgaaggacac gcttgcacaa actctcggcc    360

agacgggaag agcgagtcca aggcttcctg caggccttgg aactcaagcg agctgactgg    420

ctggcccgtc tgggcactgc atcagcctga atgaggctgg ccacctgcca ctttgccctg    480

ccctctgcct ccagggctcc actccccttc cttttcttgg tgaaaggcac ctcctttcct    540

gata                                                                 544
```

<210> SEQ ID NO 338
<211> LENGTH: 530
<212> TYPE: DNA
<213> ORGANISM: Homo sapiens

<400> SEQUENCE: 338

```
tcaaagaacg cgtactgcag accccaaatg accttctggc tgctggcttt gaggagcaca     60

agttcagaaa cttcttcaat gctttttaca gtgtggtgga actggtagag aaggacggct    120

cagtgtccag cctgctgaag gtgttcaacg accagagtgc ctcggaccac atcgtgcagt    180

tcctgcgcct gctcacgtcg gccttcatca ggaaccgagc agacttcttc cggcacttca    240

ttgatgagga gatggacatc aaagacttct gcactcacga agtagagccc atggccacgg    300

agtgtgacca catccagatc acggcgttgt cgcaggccct gagcattgcc ctgcaagtgg    360

agtacgtgga cgagatggat accgccctga accaccacgt gttccctgag gccgccaccc    420

cttccgttta cctgctctat aaaacatccc actacaacat cctttatgca gccgataaac    480

attgattaat tttaggccat gcagtggaac ctgtcaccta atgggactgc               530
```

<210> SEQ ID NO 339
<211> LENGTH: 75
<212> TYPE: DNA
<213> ORGANISM: Homo sapiens

<400> SEQUENCE: 339

```
agtcatgcga ccaggtgagg gtccacgtcc ccaagcttcc actccctctg gtgtttccca     60

tttaagtata ctgtt                                                      75
```

<210> SEQ ID NO 340
<211> LENGTH: 376
<212> TYPE: DNA
<213> ORGANISM: Homo sapiens

<400> SEQUENCE: 340

```
gatgctcacg tcacttggtg taggtttcag gatcgcctct ttgaggaagg acttcaggac     60

caactggggc ctgcataaga aaacttatct cattattaga gtactcacag cttgtatctc    120

ccagctacat cctagaaccc cattgtcctt tattccacca aaccagctcc aggtgaccag    180

actctactca gaaagcaaat tcgtcatcaa agaacagaga ctggccacca caaggacatg    240

caggagaact gtcgggacca ggaagactca ttccaaaaag cccaggccgg gcacagtcgt    300

caagcctgta atcccaacac tttgggagac cgaggtgggg gtatcgattg agcctcggag    360

gtcgagatca gcctgg                                                    376
```

<210> SEQ ID NO 341
<211> LENGTH: 499
<212> TYPE: DNA
<213> ORGANISM: Homo sapiens

<400> SEQUENCE: 341
ccccgcctgt ggcattttct atgggctcag gttacacctt cccagctggt gtttctgtcc 60
caggaacctt tcttcagcct acagctcact ctccagcagg aaaccaggtg caagctggga 120
aacagtccca cattccttac agccagcaac ggccctctgg accagggcca atgaaccagg 180
gacctcaaca atcacagcca ccttcccagc aaccccttac atctttacca gctcagccaa 240
cagcacagtc tacaagccag ctgcaggttc aagctctaac tcagcaacaa caatccccta 300
caaaagctgt gccggctttg gggaaaagcc cgcctcacca ctctggattc cagcagtatc 360
aacaggcaga tgcctccaaa cagctgtgga atccccctca ggttcaaggc ccattaggga 420
aaattatgcc tgtgaaacag ccctactacc ttcagaccca agaccccata aaactgtttg 480
agccgtcatt gcaacctcc 499

<210> SEQ ID NO 342
<211> LENGTH: 183
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, t or u

<400> SEQUENCE: 342
cacccgagac tgacacactg aactccactt cctcctctta aatttatttc tacttaatag 60
ccactcgtct ctttntttcc ccatctcatt gctccaagaa ttttttttctt cttactcgcc 120 aaagtcaggg ttccctctgc ccgtcccgta ttaatatttc cacttttgga actactggcc 180
ttt 183

<210> SEQ ID NO 343
<211> LENGTH: 558
<212> TYPE: DNA
<213> ORGANISM: Homo sapiens
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (239)..(242)
<223> OTHER INFORMATION: n is a, c, g, t or u
<220> FEATURE:
<221> NAME/KEY: misc_feature
<222> LOCATION: (400)..(400)
<223> OTHER INFORMATION: n is a, c, g, t or u
<220> FEATURE:
<221> NAME/KEY: misc_feature
<222> LOCATION: (405)..(409)
<223> OTHER INFORMATION: n is a, c, g, t or u
<220> FEATURE:
<221> NAME/KEY: misc_feature
<222> LOCATION: (411)..(416)
<223> OTHER INFORMATION: n is a, c, g, t or u

<400> SEQUENCE: 343
tgggccttcc cttaaacatc agaacaatga gatttgtccc tattttacag gggttagaat 60
agactattaa gngacaactg agaaaggaca gagaagtgac agccagaggt tgagaggggc 120
cataaaaaca tacaatcaga catatatctg ctaccacttt gtagcaagat ggttcctatc 180
ataactctgg gtcaaaaaga tagtaatttg gtttataatg ttgaaagaaa gcagaaagnn 240
nnagatgggg tctcactgtc gttctggagt gtagtggttc aatcatctct cactgcagcc 300
ttgaacccct aggctcaaag gatcctccca cctcagcctc ctgaatagct gggactagag 360
gcatgagcca ctatgtcttg ctgattaaaa attgtttttn caaannnnna nnnnnnactt 420
tactgcctaa gctggtcttg aaatcctggc ttcaagcaat cctttcactt tggcctccca 480
aaatgctggg attacaggca tgagtcaata tgcccagtct cttttctttc ttagttactc 540
tagaaaatgg cttgttga 558

<210> SEQ ID NO 344
<211> LENGTH: 526
<212> TYPE: DNA
<213> ORGANISM: Homo sapiens

<400> SEQUENCE: 344
aataatgttc tgtcacgtga aatatttaag tatatagtat atttatactc tagaacatgc 60
acatttatat atatatgtat atgtatatat atatagtaac tactttttat actccataca 120
taacttgata tagaaagctg tttatttatt cactgtaagt ttattttttc tacacagtaa 180
aaacttgtac tatgttaata acttgtccta tgtcaatttg tatatcatga aacacttctc 240
atcatattgt atgtaagtaa ttgcatttct gctcttccaa agctcctgcg tctgttttta 300
aagagcatgg aaaaatactg cctagaaaat gcaaaatgaa ataagagaga gtagtttttc 360
agctagtttg aaggaggacg gttaacttgt atattccacc attcacattt gatgtacatg 420
tgtagggaaa gttaaaagtg ttgattacat aatcaaagct acctgtggtg atgttgccac 480
ctgttaaaat gtacactgga tatgttgtta aacacgtgtc gataat 526

<210> SEQ ID NO 345
<211> LENGTH: 435
<212> TYPE: DNA
<213> ORGANISM: Homo sapiens
<220> FEATURE:
<221> NAME/KEY: misc_feature
<222> LOCATION: (334)..(334)
<223> OTHER INFORMATION: n is a, c, g, t or u

<400> SEQUENCE: 345
ttgtgtacac ataatctcat tttgagatat ataactattt ttgtctttca gaagtgaatc 60
aaaatatttc aaaatgctgt cttatgaaac tacaatattc tcacagatta gaaaagtttt 120
tctgtaaaag tcagatagta aatattttag gttttgcagt gtcttttgca actactcaac 180
tttcctactg tagcacaaga gtagctgtgg tactgtgcaa ataaattgct tgtgttccaa 240
taaagcttca tttacaaaaa catgccatgg gccatatttg gcctgtacac tgttgtttgc 300
caagtcctaa tatagttgct tagcaagtat tgtnagctat ttgaggaaga catgaaagtt 360
cattgggttg ctaaaaagta tgtagaaatt caaaggaaaa ttaaaattta ggctaagtta 420
taatacactg tttta 435

<210> SEQ ID NO 346
<211> LENGTH: 343
<212> TYPE: DNA
<213> ORGANISM: Homo sapiens
<220> FEATURE:
<221> NAME/KEY: misc_feature
<222> LOCATION: (95)..(95)
<223> OTHER INFORMATION: n is a, c, g, t or u
<220> FEATURE:
<221> NAME/KEY: misc_feature
<222> LOCATION: (227)..(227)
<223> OTHER INFORMATION: n is a, c, g, t or u

<400> SEQUENCE: 346
tctcatttac cttctctctt gagcaacgtc agtaattgat cttgcatctc agagagagag 60
aaagagcatg tgtgagagag aaactggttt ctatngccag cactcctgaa accccttact 120
gtaaggatat tttctcttac cccttgggat ccaggctctg agtctcttct ctttgggagt 180
atccatcaaa atgacttttt ttaaaaacag attttccccc aaccagnaga atctgcacaa 240
acttggcagc gtttttactt gtttaatgag tttaagacat tacatggtga aagagaagca 300
ttttggactc ctgcattttt atttaccatt cccagactga cga 343

<210> SEQ ID NO 347
<211> LENGTH: 534
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (74)..(74)
<223> OTHER INFORMATION: n is a, c, g, t or u

<400> SEQUENCE: 347
gcctaacaat caaatctctt tcttttaaag cacnaccttc taggcaggga caggagctca 60
ttttccacac catnctttgt caactctcat agaaagtttt ccttgtatcg agctcaaatc 120
tgcctcctgg aaattcttct tcttcttccc tccctgttgg taccagctct gctgtcagag 180
acttcacagt ctgtgctccc tctgccctgt gacgtcttca gactatttga gaacaggaat 240
catgactcct gggacttgcc ttttctctag gtcaaatacc tctataattc catctgctgt 300
tcttcatagg gtcttctccc tatcctgccc ttttcctcca atccatcttt taactgctct 360
tgagcagtct aactgagaag tatgattcaa agcaaaataa atcttaaggt ggcatgactc 420
tgaaaaaatt gagaaaattg aactcagaga tcccgatccc aaccccttc tcctgggagt 480 gaaaccttag tttctaccag agagtgtggg aaaccacttc tggtggaagc ccct 534

<210> SEQ ID NO 348
<211> LENGTH: 580
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 348
aacattccct tgtcaaccaa gaatactcaa agctacttgt attggaaatg gcagaaggcc 60
taaatccaaa tttcttattt tttataattt accatagaag ttttgtgant aaattcttac 120
ttctgccagt ggaggtttat gcctgaaagg tcatggggtc ctgtctgtaa atagacctaa 180
agagaagtgc agtatttatt ctttgtaggc ataatgtgtt tgtcactgac aagcattcat 240
nttcatccca ctagtctttt attgcagtct tttattgtca ttttcagcct tatgttggag 300
agctttgctt tctcatcatg ttcacattgt cttaagtttt gtgagcttct gagaaagagc 360
ttggtaaagg tttaaagggg actttgttcc accagggagc attttatttg ggcgtctcac 420
ccttttctaa tgaaagctgt tgtaagccac ctctgacttg gaaattctga aagtatgaat 480 atttttttata tcttaattgt aaaatgccag ttctccatta tttagatgaa tagtagaaca 540
ctgcaccctt tgtgcagtgt ttttgtttct ctactgcatt 580

<210> SEQ ID NO 349
<211> LENGTH: 541
<212> TYPE: DNA
<213> ORGANISM: Homo sapiens

<400> SEQUENCE: 349
ccagtcttcc tggcaagggt aaacagatcc cctctcctca tccttcctct ttcctgtcaa 60
gtgcctcctt tggtgaaggt gacacatcat gtgacctctt cagtgaccac tctacggtgt 120
cgggccttga actactaccc ccagaacatc accatgaagt ggctgaagga taagcagcca 180
atggatgccg aggagttcga acctaaagac gtattgccca atggggatgg gacctaccag 240
ggctggataa ccttggctgt accccctggg gaagagcaga gatatacgtg ccaggtggag 300
cacccaggcc tggatcagcc cctcattgtg atctggggta tgtgactgat gagagccagg 360
agctgagaaa atctattggg ggttgagagg agtgcctgag gagagccctc accgtctggc 420
accctagtca ttggagtcat cagtggaatt gctgtttttg tcgtcatctt gttcattgga 480
attttgttca taatattaag gaagaggcag ggttcaagag gagccatggg gcactacgtc 540
t 541

<210> SEQ ID NO 350
<211> LENGTH: 415
<212> TYPE: DNA
<213> ORGANISM: Homo sapiens

<400> SEQUENCE: 350
gaataaatct ctgggaccgg gtctcaccat attgctctgg ctggtttcaa actcctgggc 60
tcaagcgatc ctcctgcctc agccttccaa aaccaggtgt ttaacttggg actaacatga 120
agcacttaga agactacgtg gaacatagca atgactatat atgtactaca acgtaaacag 180
cacctcctgg attgaataga acataactga catgaccagc agagacaggc taaagacact 240
gagctgaaaa ccctggactc tattgctaaa ttgaggctcc tgaatccgtt cgctctgagc 300
aactgttgct gtggtgctgc cttcacaagc actctgctga gcactcagat agaggggctg 360
tgctatccgt caacagacaa gctgcagcca gaactgctca gctgacaaac tggta 415

<210> SEQ ID NO 351
<211> LENGTH: 438
<212> TYPE: DNA
<213> ORGANISM: Homo sapiens

<400> SEQUENCE: 351
gtggggaagc ctgaacacag tcctataaac taaaggccac tgcagacttt tagcacaagg 60
agatccttac agggaacatg tgccatcagc tctttggagt gaacaaggaa ttagaccccc 120
atcatgccaa aaaactagga tttttaggtg gtctttccat cccttcagat ttaagtattc 180
aaagaaagag agacagacct acattccaag ggtcttctga gtgcaaggcc ttgtgttgtt 240
tgtttattta ggggagggcc tggtgctctt ctctgtttta tgctttacct tcttttattt 300
ctcagatctc atgttagcac tatgttctga attccctaat aatggctctt gagaactgat 360
ttacattttg ttggtttgtt tacttcttga gcacataaaa ggaccccaaa ttagagatac 420
tatcccttgg gcttctga 438

<210> SEQ ID NO 352
<211> LENGTH: 224
<212> TYPE: DNA
<213> ORGANISM: Homo sapiens

<400> SEQUENCE: 352
gtccactgct ggaaatagaa gttttttcgc tgcagggcaa ttctgtaaat gtgcttccca 60
gctttaggag gtctgaggct actcttctcc aataaccttc cttcccactg gaccttctca 120
ctcacagcac tgctgccctc tggacaagcc acagtggaca aatatgtcaa gctgaagatg 180
cacaaataat ttcaagttca gttctcaggg attcaaagga catg 224

<210> SEQ ID NO 353
<211> LENGTH: 415
<212> TYPE: DNA
<213> ORGANISM: Homo sapiens
<220> FEATURE:
<221> NAME/KEY: misc_feature
<222> LOCATION: (177)..(177)
<223> OTHER INFORMATION: n is a, c, g, t or u

<400> SEQUENCE: 353
tgtcctgggg atcttggagc ctgaattcat tggcacaaaa ggcagcagca tcctcactgt 60
atctgcagtc catttggact caataaaaac tttgaaagtc acatgtgtta tggaattcct 120
tctcagtgac acattcatct gtgctcagtt gtcccagcaa gggtcagccc ctcatanccc 180
tgcagcatcc gctgctatga agcagagctg taaacgccct ccctgtgtat aggaaaagct 240
acatggagca aatcctcctg cctgaagaag tgcatctcag catcacttca gctgtcgggg 300
catttgtggg gagaaccaga ccacctctgc ggaaggcagc agaccctctt ccagccatgg 360
atggagttga attctctata aacggttcac cagcaaacca ccaatacatt ccatt 415

<210> SEQ ID NO 354
<211> LENGTH: 186
<212> TYPE: DNA
<213> ORGANISM: Homo sapiens

<400> SEQUENCE: 354
gccaggttaa tggtatcgat cctaatgggg attcggcaga gtttgatttg ttgtttgaaa 60
atgcttttga ccagtgggta gccagcacag cgtcagaaaa atgcaccttc ttccagatcc 120
tccaccatac ctgccagagg tacctcacgg acaggaagcc agagtttatt aactgccaat 180
ccaaaa 186

<210> SEQ ID NO 355
<211> LENGTH: 457
<212> TYPE: DNA
<213> ORGANISM: Homo sapiens

<400> SEQUENCE: 355
ctttacccta ggtcaggggt cagcaaacta ctgcctgtgg gccaaatttg cccaccacct 60
gtatctgtaa ataaggtttc attggaacac agctgtggcc atatgtttgt atattgtgtg 120
tggctgcttt tgcattagga tgacagaggt gaatagttgc aacagagact ggctggtctg 180
caaagcctaa aatatgtcct gtgtggccct ttacagaaaa agttttctaa cccctgctct 240
aggttacgga gaaaaaaaaa tggaataatg ttctctgcta cttttaacct gattttcttt 300
gtacctaaat aggcagctag aatgctgcct atattttaat aaggatttgg atctcacaag 360
acaccttagg cctacacaag ttgttcagat tctttgcccc agttctaatc tagtgacaaa 420
ggcatagaat tctcctccca caggaatgta tttctat 457

<210> SEQ ID NO 356
<211> LENGTH: 373
<212> TYPE: DNA
<213> ORGANISM: Homo sapiens

<400> SEQUENCE: 356
cagtctcctg ctcgtttaga agtaagggat aataatgtat ccatagctaa atgcccagtc 60
gttatatttt ctagatcaag atgcttgttg tgtacagttt cacagagcct tcggattttt 120
tctttaattt tgttcatgtc tttttcattc agtagcttgg ctgatgaagc atcttgttcc 180
agttccaaaa gtcgaatcat tagatccaag ctagctctat caagatccat gttcaaacga 240
tctctactca gtatatacat gagggcagct gtacagaggg acagattctg atggtgctgg 300
gaatcatcca aggttttaaa gaccattgct accatcccat gtgctctcag gtgcattcgc 360
cagtaggcca aca 373

<210> SEQ ID NO 357
<211> LENGTH: 116
<212> TYPE: DNA
<213> ORGANISM: Homo sapiens

<400> SEQUENCE: 357
tttgctccta acttgctctt ggacaggaac cagggaaaat gtgtagaggg catggtggag 60
aggctagaga tcctgatgat tggtctcgtc tggcgctcca tggatgcagg gagagg 116

<210> SEQ ID NO 358
<211> LENGTH: 522
<212> TYPE: DNA
<213> ORGANISM: Homo sapiens
<220> FEATURE:
<221> NAME/KEY: misc_feature
<222> LOCATION: (297)..(297)
<223> OTHER INFORMATION: n is a, c, g, t or u
<220> FEATURE:
<221> NAME/KEY: misc_feature
<222> LOCATION: (418)..(418)
<223> OTHER INFORMATION: n is a, c, g, t or u
<220> FEATURE:
<221> NAME/KEY: misc_feature
<222> LOCATION: (483)..(483)
<223> OTHER INFORMATION: n is a, c, g, t or u
<220> FEATURE:
<221> NAME/KEY: misc_feature
<222> LOCATION: (486)..(486)
<223> OTHER INFORMATION: n is a, c, g, t or u
<220> FEATURE:
<221> NAME/KEY: misc_feature
<222> LOCATION: (490)..(490)
<223> OTHER INFORMATION: n is a, c, g, t or u

<400> SEQUENCE: 358
gggcatctgg aattgacaca ccattacatt ctgtttgcag gatttttttt gtaaccatga 60
aattgaacat ttccaaatta taaactatgt taatacctat aaaatatata gccaggaacc 120
atttatcatc aagaaaagtg taagaaatta tttttgagat gtaatttaag attgttttat 180
gtaaaaggaa aatcttgtat ggcatcgaat agccttaatg aatttaattc tttcacaaaa 240
atgatttcaa attatcctag agtataacat ttttatcaaa gatattattt ccggagntct 300
tctttctttc tttttttttt ttttttagta atttagcaaa aacattactg ttctaatgct 360
gaagtgactt ttgccagtgc catgtccagg gggggaggta taagttactt gctcttanca 420
tttgggctgg attttttggt ttgggggaca cctttgggag tattcccaaa gcatgtctca 480
agnggnggcn cccgagagca tggtttaaaa gcttggaccc ct 522

<210> SEQ ID NO 359
<211> LENGTH: 369
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is a, c, g, t or u

<400> SEQUENCE: 359
gctgggccag tgcatctaac agccctgtgc agcagcttcc cttgcctcgt gtaacatgag 60
gcccattctt cactctgttt gaagaaaata gtcagtgttc ttagtagtgg gtttctattt 120
ngttggatga cttggagatt tatctctgtt tccttttaca attgttgaaa tgttcctttt 180
aatggatggt tgaattaact tcagcatcca agtttatgaa tcgtagttaa cgtatattgc 240
tgttaatata gtttaggagt aagagtcttg ttttttattc agattgggaa atccgttcta 300
ttttgtgaat ttgggacata ataacagcag tggagtaagt atttagaagt gtgaattcac 360
cgtgaaata 369

<210> SEQ ID NO 360
<211> LENGTH: 378
<212> TYPE: DNA
<213> ORGANISM: Homo sapiens

<400> SEQUENCE: 360
agatactcag cactagacta acataacagg tcactacacg ggtgcagaat cactttacaa 60
aagaagactc tgttttacga aggggattca ctacagggac ttagagaaca gtctcttttc 120
tgcctttaaa atgagagttc ctccatttac caaaatttga cacgcacaca ttcttcaggg 180
gcatgccaat tgcgtaaagt gaggctcgcc tgcatagcta atcctgttaa agacaacttc 240
tcaaagcaca acgtgcttgt ttcctatcgg gctccctgcg gggctttctc tcactacaag 300
tcaagcttgg gctctcaaag ccctgcgcct gttaccacgg atgcccacag ggcctgggca 360
gttgctgtgg cgacagga 378

<210> SEQ ID NO 361
<211> LENGTH: 291
<212> TYPE: DNA
<213> ORGANISM: Homo sapiens

<400> SEQUENCE: 361
acagtggatc aaatttaggc ttcttgatgc aggcatggtg tagattacta cttctgtatt 60
gtcccaggag ctcagcacat tccttgccag agatgataag gagctcaatc ttgaatactt 120
gttcaagctt ttgaataaaa aaccacagtt cctcaaagaa gaagaagaat tgcgaaatca 180
ccggaaataa ccgaaaactt ccccctgttt gactttcaac attcttgaat gcaccaagat 240
agcctctttc tgtgagatta ataaatgaat aaatgcctcc atatttttca a 291

<210> SEQ ID NO 362
<211> LENGTH: 313
<212> TYPE: DNA
<213> ORGANISM: Homo sapiens
<220> FEATURE:
<221> NAME/KEY: misc_feature
<222> LOCATION: (200)..(200)
<223> OTHER INFORMATION: n is a, c, g, t or u

<400> SEQUENCE: 362
aagccggatg gcaaaagagc ccagaaccta ttggaactga caaaatcaag tcacggcgcc 60
tacaaagatg aggggcagat tctggctgcc ttttaatttc gtccttcacc tgatatctgt 120
gccagagaat gtcttccagg agttctgcta cagagaagag agtaaccccc atccatcatg 180
gccaaagcac ccagtcaggn tccgctctgg atccagcccg acaaatgcaa cccttgaata 240
gggtttgtgc aagcaaactg gatgacgacc gaagaaaccc tgtcgcttct gagaagacac 300
ccaatccaag aat 313

<210> SEQ ID NO 363
<211> LENGTH: 318
<212> TYPE: DNA
<213> ORGANISM: Homo sapiens

<400> SEQUENCE: 363
cctggaccca actttgttac tgtgagaaag ggtcttcatt cattcaagat ggcatttgtt 60
aagcacctac tgctggagtg cagtggttca atcacggatc actgcagcct ccacctccca 120
gttcaagaaa ttctcatgtc tcagcctcct gagcagctag gattacagac aaaccttgga 180
aatcaagaaa gttctggaat gatgaagctg ttcatgccaa gaccgaaagt gctggcccag 240
tatgagtcca ttcagttcat gccgtgacaa ttttcttgga actccttttt attgttagtt 300
ctcacttgtt tccatatt 318

<210> SEQ ID NO 364
<211> LENGTH: 531
<212> TYPE: DNA
<213> ORGANISM: Homo sapiens
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (119)..(119)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (153)..(153)
<223> OTHER INFORMATION: n is a, c, g, t or u
<220> FEATURE:
<221> NAME/KEY: misc_feature
<222> LOCATION: (155)..(155)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 364
ttagcatctt ggttactgga gaactataac ttttatgtag tcatgcttgg aaaacactaa 60
aagggaaatc gagtctgttt gacaatattc tgtcttcact gttgttcact tcataangng 120
tnggaatata aagttctata cagttaatat gangntctct ttagcattta aaacatgatt 180
tgcattttca tgaggcattt tggctaattt tattgatttc cttatatttc atagtcctta 240
nccttatgag aatcttatgt ttctgtgtgt tttctatcat gtagcacaat ttctgacaca 300
caaaacatac aataaacttg tgttaatttt tctatcaaag tcagaattta ttcataagga 360
atctgaagta aggtgtacta agcttgttta tgggttaagt gatatagcca aattcaaaac 420
tttacttttt atgtcagtct agaaatatct cagattaaaa catatcactt cttagttcca 480
attagataag ggaaatcttt tataataatg ccaggattgc tataatctga t 531

<210> SEQ ID NO 365
<211> LENGTH: 525
<212> TYPE: DNA
<213> ORGANISM: Homo sapiens
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (234)..(234)
<223> OTHER INFORMATION: n is a, c, g, t or u

<400> SEQUENCE: 365
aggccatagt aatcatcctg ctgatattgc aagtnngtng ctagaatgag gttatataat 60
atatacaaaa acattttntc aactgntaaa gntgccttag taatataggg taataccagc 120
aacattatgg atatataatt atagtctatt gggccacact taagtttgga gtctaataaa 180
gtcacaatca aattctgcaa tttcaattga agataacctt gtctttatat tatnaattag 240
aagctaaagt tgatttttct aagagttctt tatttaaatg aagtactctg ggactgacct 300
tttcggaaat ggaatcttca ttggtcaggt gattcaacat ttttatacaa tttatccatc 360
ctcatctctt caggatttgc ataccttgcc agtttctact ggccattgtt gaaaatacat 420
ttatttggag aagtccaaag ccaaggggct catggggctg tgaggtcctt cttgctgcat 480
cgtcctgtgg tagaaggtgg aggagtcaag agagtgcccc agagt 525

<210> SEQ ID NO 366
<211> LENGTH: 267
<212> TYPE: DNA
<213> ORGANISM: Homo sapiens

<400> SEQUENCE: 366
gggccaatga aagcagggtc aaggacagga ccagcgcagg ccaaggaagg gaatatctga 60
cagcgcccac ccagccaaac cctcagccca aggacaggaa tgaggagatg ctggtgaact 120
agccatccat cagtacctgc cttcccccga ggctgcagcc ccactcccag gcgcctggcc 180
aggggagttt tctaggttct gagagccacg ttgtcatccc tgggctttga agttaaacat 240
cacacagctg tctataaaca agatttt 267

<210> SEQ ID NO 367
<211> LENGTH: 199
<212> TYPE: DNA
<213> ORGANISM: Homo sapiens
<220> FEATURE:

<221> NAME/KEY: misc_feature
<222> LOCATION: (67)..(67)
<223> OTHER INFORMATION: n is a, c, g, t or u
<220> FEATURE:
<221> NAME/KEY: misc_feature
<222> LOCATION: (107)..(107)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u

<400> SEQUENCE: 367
gattcaggga ttggatgagt ctctatggtt tgttttgccc tgaagagcag aaggcttctg 60
tcccaantgg tgttgccaaa gcaacatatt aattccatgc catgatnctg ggtcaagatn 120
tgcacaatct gattgggcat gtcacctcgg atggcaaggg agtggaagtg gtcaaaatca 180
tggagtccca gctttcgga 199

<210> SEQ ID NO 368
<211> LENGTH: 372
<212> TYPE: DNA
<213> ORGANISM: Homo sapiens

<400> SEQUENCE: 368
gccccatgtt gcataggtgg cctataacca gtcagacaca ggagacaaca tgaagcccca 60
tctgtgcttc cctttctgac attaccacat ttgcctgatg gagtggccag ctccctttca 120
ctgctggaat gaatacaatc cagaaaacct accttctatt gctttaccta atggggtaag 180
gaaatttaag tagaaattgc taaccgaaga ctttgctaag caaacccagg tctgcttgat 240
gtcagagccc ttgctgttaa ccccatttac tgcttagcct ccaaagagaa gcaatagcat 300
cacatgggga aatgtcaaca gcataagagg actttcataa tcagaattta aactggctat 360
tatccctctg ga 372

<210> SEQ ID NO 369
<211> LENGTH: 296
<212> TYPE: DNA
<213> ORGANISM: Homo sapiens

<400> SEQUENCE: 369
gaccgtgact cctgaagctt ttcagcgcag gtgtagccgg cttggcgtcg ccgcagtgag 60
gtttggagcc gctttggatt gctgagtcac tttcttcagc cacttaggga aaccgaaagt 120
ggaaactcgt ggggcttgaa atagtgtgtt ctcttgagaa ccaccgaggc agtgagattt 180
gggattccgg ggtctggaga tcgtgctttt tgtggactgc gtttgcagtt cctagggtgc 240
tgctgattca caggccttct ctgtctttaa gtgtgcagat cattgaccgc tcagtt 296

<210> SEQ ID NO 370
<211> LENGTH: 228
<212> TYPE: DNA
<213> ORGANISM: Homo sapiens

<400> SEQUENCE: 370
aaacccagag ccttctggat gtgtgaggta gtaggcttca accctcattc atgcataggt 60
cacacttctc caaagttggt atggcctgtc tccttggcat gttcccttgc ttctgcttgt 120
ccagttaatc ctttctgaca taccatgcat ctcagggtga agcggttgac atcagtaaac 180
tgtctccttc ttctagcttc atctgctaat tccagtgctt gtacaaga 228

<210> SEQ ID NO 371
<211> LENGTH: 206
<212> TYPE: DNA
<213> ORGANISM: Homo sapiens

<400> SEQUENCE: 371
cctcctgatc accatagctt tatgcaacaa caagaaacaa atttattagc taacctaacc 60
actaatgacg caagagacaa ttctaaggac tttcaaaaca gcaaagtagg agcagctgct 120
acctctaggg atgagggatg caattgtcca attattggtg aaattgtcat ttcatgctat 180
tggctatttg aaattcctcc tctaat 206

<210> SEQ ID NO 372
<211> LENGTH: 463
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (382)..(382)
<223> OTHER INFORMATION: n is a, c, g, t or u

<400> SEQUENCE: 372
ccctgcctgt actaatgatc caaaaattag ccaggtgtgg tggtgcgtgt ctgtagtgcc 60
agctactcgg gaggctgagg caggagaatc tcangaaccc gggaggcgga ggttgcagtg 120
ngccgaggtt gcactactgc agtccagcct ggctctgtct tggtgttcag ccatgttccc 180
atgctcactc ccaaggtgac tctgggaagg tctcagcctt tttgtcttcc cagttaggat 240
ggtcccatgc ccctgttacc atcagacttg gtaagtttcc cgaggagact ctgcaagagg 300
cactgttctg gatggtggag gagagactag ttgttctgct ctcctggcca cagtgggtgc 360
agtggacccc atcatggaga anttcaacac atccagccta cgaccagcac ctgtgggagg 420
tggatattca aggcagcaga gcctacagcc ggggcatgga gaa 463

<210> SEQ ID NO 373
<211> LENGTH: 451
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (87)..(88)
<223> OTHER INFORMATION: n is a, c, g, t or u
<220> FEATURE:
<221> NAME/KEY: misc_feature
<222> LOCATION: (231)..(231)
<223> OTHER INFORMATION: n is a, c, g, t or u
<220> FEATURE:
<221> NAME/KEY: misc_feature
<222> LOCATION: (406)..(408)
<223> OTHER INFORMATION: n is a, c, g, t or u
<220> FEATURE:
<221> NAME/KEY: misc_feature
<222> LOCATION: (421)..(421)
<223> OTHER INFORMATION: n is a, c, g, t or u

<400> SEQUENCE: 373
agggtctcaa atgaactctg agttaccatc tttggacnga cttttaatat aaagctgtaa 60
tccttaaatc tgtgtcagta gtcccannta ctatgtcact ttaattggat gaatgcgtta 120
atgaaaagtt tgttttcaaa cctcactaaa ctgctactta agatcacagt taatgtgagt 180
cctgcttaat ttggaaagca tttaaaaaat ggaaaagttt cttagggaag naaaaatttt 240
gcaactctgc ctacaaggta cagtaattgg ctaggttctt ttgaagagca gtgttgacta 300
gagttaagga aaagtcagtt gtgaaaaatg gacattttta atagcaaaat gatgtgcttt 360
actgtagaaa caggaggaag ggtgcattat cctggggaaa atgaannntt cttcagttat 420
nttttatgct gctctacttt attgcaaaac g 451

<210> SEQ ID NO 374
<211> LENGTH: 46
<212> TYPE: DNA
<213> ORGANISM: Homo sapiens

<400> SEQUENCE: 374
cagtcaccga ccttccctga gattgctacc tggaagctct ttctat 46

<210> SEQ ID NO 375
<211> LENGTH: 519
<212> TYPE: DNA
<213> ORGANISM: Homo sapiens

<400> SEQUENCE: 375
gaataagtac acagagtccc caaagactag tgaggccaag atgtgtgagt cattttccat 60
cacacacaaa aaacccaatt gttctaagta tgtattttac caagcagctt tatagaaaga 120
aaaacaaaca aacaaaccaa acaacaacaa caacaaaaaa ccttggccag gcacagtggc 180
ttacacctgt aatcccagca ttttgggaga ttcaggcggg tggatccttt gagcttggga 240
gtttgagatc agcctgggta atgtggcgaa acctcatctc taccaaaaat ataaaaacta 300
gccaggtgtg gtggtgcacg cctgtagtcc cagctgctta ggaaactgag gtgggaagat 360
tgcctgagcc caagaggtag aggtttcagt gagccgtggg aagattgcct gagcccaaga 420
ggtagaggtt tcagtgagcc gtgggaagat tgcctgagcc caagaggtag aggtttcagt 480
gagccaagat tgtatcactg cacaactgtt gcctgggca 519

<210> SEQ ID NO 376
<211> LENGTH: 222
<212> TYPE: DNA
<213> ORGANISM: Homo sapiens

<400> SEQUENCE: 376
cctgctggac agccgcgcag gatgagccgg agaccccgag ggccgtggcc ttccaggact 60
gccccgtgga cctgttcttt gtgctggaca cctctgagag cgtggccctg aggctgaagc 120
cctacggggc cctcgtggac aaagtcaagt ccttcaccaa gcgcttcatc gacaacctga 180
gggacaggta ctaccgctgt gaccgaaacc tggtgtggaa cg 222

<210> SEQ ID NO 377
<211> LENGTH: 460
<212> TYPE: DNA
<213> ORGANISM: Homo sapiens

<400> SEQUENCE: 377
atagtagggg caattttgtc tgtagatggc agtatgacaa ttcttgctag agaatatatt 60
gaaaaaaact tcaacacaaa gggttgtagc actgtcctca gtaccattgt gtgcatgagg 120
atcagaatag tctgggctag atacatcaca ttaaagcttt tcagaatctg ataaatagct 180
ctaaatacta atgatattga gaagcctagc ttcacttggg aaaatctgtg gctgttcaca 240
gaaattcagc accaagttat tccccccata ctctaccagg ccttcaggtc ctcataaaga 300
aaagtgtcgt tttcagatta ggaactcaaa attattttgg tgcatcaaat ctacagtcac 360
acaatataac aagaatggga ttagaaaaat gaaagcctac tcattctcat ctttaagcca 420
gagaatgaaa tatatatgag gtctctggat agctatttaa 460

<210> SEQ ID NO 378
<211> LENGTH: 544
<212> TYPE: DNA
<213> ORGANISM: Homo sapiens

<400> SEQUENCE: 378
cgccgcatca agccgtggcg gagatcgacg cgctctacga cgtgtacctg gacgtgatcg 60
acaagtgggg caccgacgac atgctgttcc tgggcgactt caacgccgac tgcagctatg 120
tgcgggcgca ggactgggcc gccatccgtc tgaggagcag tgaggtcttc aagtggctca 180
tccctgacag cgccgacacc acggtgggca actcagactg cgcctacgac cgcattgtgg 240
cctgtggcgc ccgcctgcgc cggagcctga agccccagtc ggccaccgtg cacgacttcc 300
aggaggaatt cggcctggac cagactcagg ctcttgccat cagcgaccac tttccagtgg 360
aggtgaccct caagttccac cgatgactcg aggcctgact ggggcatgcc acctgcagac 420
cctggctctg aggaatggcc caacagtggc cccttcaggg tggcagccac ccttcagtga 480
ggccccaagg cagagtcggc tgggcgtgga ccaggggcat ggacacgtga tgtgctgctc 540
tgta 544

<210> SEQ ID NO 379
<211> LENGTH: 254
<212> TYPE: DNA
<213> ORGANISM: Homo sapiens

<400> SEQUENCE: 379
gaagtttgtc ttcctacaac cacgtgatcc tctctctggg atttccccac tcaaccaggg 60
acaagaggtc aaagttgacc tgattatgtg tccatcaagg aagtgcccct ggaaggcaaa 120
taaagaaggc accatttaca ttacagtctc ctaagtgcag gcaatgatac cccaaggtgg 180
ggctctgcag accctccagc aaagagcttt tgaaaataaa tgtgaagctg ggcttaggag 240
ctcatgcctg caat 254

<210> SEQ ID NO 380
<211> LENGTH: 398
<212> TYPE: DNA
<213> ORGANISM: Homo sapiens
<220> FEATURE:
<221> NAME/KEY: misc_feature
<222> LOCATION: (140)..(140)
<223> OTHER INFORMATION: n is a, c, g, t or u
<220> FEATURE:
<221> NAME/KEY: misc_feature
<222> LOCATION: (295)..(295)
<223> OTHER INFORMATION: n is a, c, g, t or u

<400> SEQUENCE: 380
aacctgctaa ccaagaatgc tttacctggc aaagctgtcc ttcagaaatg agggagaaat 60
gaaagctttc tcagacaaac aaaaacaaag gaaacatgta aaagtgaaaa aataaatggt 120
ataagtaata tatagtcccn actcagaatt ctctaatact gttaaggtgg tgtgtgaagc 180
aatcttatta ctactaggag ggttaagaga caaaactatt aaaaacaact gcagctacag 240
tatattgtta aaggacacaa attttaagtt tacatcaaaa tcagaaaaca tgggnaagga 300
aggaatgaaa gtgcagagtt tttgtatgtg attaaaggca aattgttatc agtttaaagc 360
ctgttttaag gataaaatat tttatgtaag cctcatgg 398

<210> SEQ ID NO 381
<211> LENGTH: 276
<212> TYPE: DNA
<213> ORGANISM: Homo sapiens

<400> SEQUENCE: 381
cccgccgcgc gagattaaag gacagaccaa gagggcgcgg gagctaccag cttggagggg 60
aggacagatg gggacccagg gctggccagg gctggtctct ggagctgttc tgccagagtg 120
atgggggcgc ttggcgaggc caaggatttg gttgggtcct atctctgaga cattttgaag 180
tctcacaccc cttccatttg ttgcctattc cacttaactt tgtatttgtt tgaaatctac 240
tgttcggatg ctggactaga agagggacac ttggcc 276

<210> SEQ ID NO 382
<211> LENGTH: 119
<212> TYPE: DNA
<213> ORGANISM: Homo sapiens

<400> SEQUENCE: 382
aaacataaca gaggagttgc gaattttatg aaatttctga gtcttacaaa cttctcttta 60
agactatgag gaaatgctga cttgtattat ttatatcatt aaatttgctt gtgtatggt 119

<210> SEQ ID NO 383
<211> LENGTH: 490
<212> TYPE: DNA
<213> ORGANISM: Homo sapiens

<400> SEQUENCE: 383
gtccctgctg tttagtatgc tggagtggag gttctgtgac ttcctgttta gtggtgctga 60
ttctagttgg tgtgaaacgt cagatttcat cccagtcgcg tggctgattt ttttatgtgt 120
ggttctctgt gtttccagcc tggtcctgct ggtcaggatc ctctgtggat cccggaagat 180
gccgctgacc aggctgtacg tgaccatcct gctcacagtg ctggtcttcc tcctctgcgg 240
cctgcccttc ggcattctgg gggccctaat ttacaggatg cacctgaatt tggaagtctt 300
atattgtcat gtttatctgg tttgcatgtc cctgtcctct ctaaacagta gtgccaaccc 360
catcatttac ttcttcgtgg gctcctttag gcagcgtcaa aataggcaga acctgaagct 420
ggttctccag agggctctgc aggacaagcc tgaggtggat aaaggtgaag ggcagcttcc 480
tgaggaaagc 490

<210> SEQ ID NO 384
<211> LENGTH: 458
<212> TYPE: DNA
<213> ORGANISM: Homo sapiens
<220> FEATURE:
<221> NAME/KEY: misc_feature
<222> LOCATION: (72)..(73)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u

<400> SEQUENCE: 384
gatacctcat tatacatctt acagagagca tcattggtgt ttccaaggtc acagggctag 60
gcaagggtgg anncctgagt ctgcttgtct gtttgcccca tgacagccca ggggtggtgg 120
cctcactcca cctccaggca cccacaagaa tataaaatct tgtacaagga tgtcgatatt 180
actattgcca ttcccaagtg cacctgcacc tgtagtatca ggtggtttnc agccttggct 240
gcatagctgc atatgagaat cacctgggaa gcttttaaag atcccagtat ccccacctct 300
tccccagtta cagtggagtc ttgcgggtgg tgggggacat cattattttt gaagcttcca 360
agtaattctg gtgtgcagtg gggtgaccag ctgtcccagg gacctccttt aaaaaataat 420
atcccgggca catgacaggc caattgccct aatgcaac 458

<210> SEQ ID NO 385
<211> LENGTH: 510
<212> TYPE: DNA
<213> ORGANISM: Homo sapiens
<220> FEATURE:
<221> NAME/KEY: misc_feature
<222> LOCATION: (343)..(343)
<223> OTHER INFORMATION: n is a, c, g, t or u
<220> FEATURE:
<221> NAME/KEY: misc_feature
<222> LOCATION: (467)..(467)
<223> OTHER INFORMATION: n is a, c, g, t or u
<220> FEATURE:
<221> NAME/KEY: misc_feature
<222> LOCATION: (471)..(476)
<223> OTHER INFORMATION: n is a, c, g, t or u

<400> SEQUENCE: 385
cacctctgca cttttgtagg ctcaacaagt actggggagc ctgccaccac tgtatgcctt 60
tgaggcccct gccctgcctc cctggctggc cacggagctc gccctccctg gtagggggtg 120
agtttggaag tgagaggctg gtgtgggtct gtcccatgag ctgactcaca cttgcctcac 180
cacacatacc atcagaagac ccacgtggtg gagctaccgc tgctgctccc cacagtgcac 240
ctaggcaccc tcctgtcctt cccatggcac tcggttgacc tgggggttcc tgtccaacag 300
gtgaggcctg gtgtgcacag acactctgcc attgctagaa ggnggctgtg ccccctgcta 360
agatatcagt aggtccttca cagcctcacc ttgttcctcc catttgtttt taaaaattgt 420
ttcttatata tacagtttat ttagcttacg taaacatttg gtgcacntaa nnnnnntcaa 480
agatcatgat gtctcttttg tggttttata 510

<210> SEQ ID NO 386
<211> LENGTH: 92
<212> TYPE: DNA
<213> ORGANISM: Homo sapiens

<400> SEQUENCE: 386
cctctgccat tgcccaaaga aagtacgcag gagggaaggc gccgggggcg caggagtcgg 60
ggggaagtga aatctcggca ttagaacccc cg 92

<210> SEQ ID NO 387
<211> LENGTH: 394
<212> TYPE: DNA
<213> ORGANISM: Homo sapiens

<400> SEQUENCE: 387
aaggcgccgt caagtcaaat aaataaatgc cctacaacac caacccagga ctgagatctg 60

-continued catgctggaa tgacggtggt ggtggtggct ttcagtattc cccaggtttt gtccggagca 120
ccggcacgcc ctctcttgaa gtccgctctc cgcacagtgg ttagacggga agatccggag 180
ctgtccagtg tcttgggtaa tgcacggcat cgcctgatgt ctgacgctag aacaccacgt 240
aaagtcaagc agagggaagt gaatgcgccc taggcccctg caggccacca agaagagcta 300
gagggagttg gtgcaatcct agagatgccg gcaggtgcac caatctgtgg cacacgtacg 360
ctctccaatg gaagacaact caagaccaca ccaa 394

<210> SEQ ID NO 388
<211> LENGTH: 289
<212> TYPE: DNA
<213> ORGANISM: Homo sapiens

<400> SEQUENCE: 388
actataatgc acttcgcaaa atgtaagggg ccggcttcac gccagcgggg ccttctggga 60
ctttgaattc aaccaggtga gcgctccagg tgccccgaca ggcgcactgt agccactggg 120
tgttaggggc gggagtctgg aaggtgacgg tagacggcca cttgggccct tctgggggcg 180
agcctactgg tggggtcagg gctctccgtg ctcagagcaa ggtagaggag caaggcccta 240
cttttggggg gcagggtcca gaccaaggac cctatgcgcg gagggtggc 289

<210> SEQ ID NO 389
<211> LENGTH: 139
<212> TYPE: DNA
<213> ORGANISM: Homo sapiens

<400> SEQUENCE: 389
aggcctgacc gaagagaact ttaaggaact aaagcaagac atttctagtt tccgctttga 60
agtcctggga ttactaagag gaagcaaact ttccacaata caatctgcga atgcctcgaa 120
ggagtcttca aattcggca 139

<210> SEQ ID NO 390
<211> LENGTH: 528
<212> TYPE: DNA
<213> ORGANISM: Homo sapiens

<400> SEQUENCE: 390
caggttcttg aagttctcca ccatgacatc tcggtacagc ttcctctggg taagatcgag 60
cagtcgcagt tcctccctgg agaagaccac agccacatcc ttgaatgtca cagcctccta 120
caatatcaaa cacatgtaac ctcaatctta caaccaacct tcactagaag aagggtggca 180
tcaagaagga aaagagcacc acaaaaaagt tgttatagat tccaagagat ctcagtcaat 240
tttcagctgt tacagttttc cctgtctcac tatctcctac gctcatcccc ataaagcctg 300
tagtttatca ctgtttttttg tttttttctt ttttgagatg gagtctcact ctgtcaccca 360
ctgcactcca gcctgggtga caggggtgag acactgtctt aaaataaata aatttttaga 420
attaaaataa atagatcata aagtgtttga aaggatcaga tgaatgaata tatgtcaagc 480
acttagaagt gcctagcaca ccatacatgc tcaataaact cgaacaac 528

<210> SEQ ID NO 391
<211> LENGTH: 443
<212> TYPE: DNA
<213> ORGANISM: Homo sapiens

<400> SEQUENCE: 391
gccaggggtc gccaatcctg gaaccccact ggcttagagg gctgggggag agaaacatgc 60
tgccctcttt gtagcagtca ggcgctgacc caagagaact caccttattc ttcatttcgc 120
ctggtaatcc tccaggccct tctctacacc ctgaagggga gggaggaaaa tggatgaatg 180
agagagggag ggaacagtgc ccaagcgctt ggcctctcct tctcttcctt cactttgcag 240
aggctggaag acggcagccg ccggactggg cagatcctca agcagaccta cagcaagttt 300
gacacaaact cacacaacca tgacgcactg ctcaagaact acgggctgct ctactgcttc 360
aggaaggaca tggacaaggt cgagacattc ctgcgcatgg tgcagtgccg ctctgtagag 420
ggtagctgtg gcttctaggt gcc 443

<210> SEQ ID NO 392
<211> LENGTH: 463
<212> TYPE: DNA
<213> ORGANISM: Homo sapiens

<400> SEQUENCE: 392
tattggcacg tagcagtaca aggatggtga ggggtgggta gggggcagac agctaggcac 60
ttgaaaggaa agctcatctg gaaagattgg atcgtctcaa atgcacatac tcgtacactc 120
gattgaagcg tactctgtgc ctactagatc ttttcacagc caaaaacacc tggcaaccct 180
tggagaagta actattcctt tttttcacaa gtaagaaaat agagcctcag aaaatttaac 240
agttgtctaa gctagaaagt agcaggactg gactttgaag tagtctttag gttgtgctgt 300
acattttgtg gatatgctta aatcacagtt tagcttgtac acattttcct ttattagaat 360
tggaagtaag tattaatgtt tgaaaaaata ttttagcctg acaatattta ttctatcttc 420
atatgttttt gaaattagat attttaaact aggcacggtg gct 463

<210> SEQ ID NO 393
<211> LENGTH: 376
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (99)..(99)
<223> OTHER INFORMATION: n is a, c, g, t or u
<220> FEATURE:
<221> NAME/KEY: misc_feature
<222> LOCATION: (123)..(123)
<223> OTHER INFORMATION: n is a, c, g, t or u

<400> SEQUENCE: 393
agctcatttt agtctcattt ctctcnctcc cttcttccct gatgaataaa gtttattggg 60
atggntttca gatgctcagc ttttccatat gattaggtna gtgatccaga acccttccaa 120
agnaccctgt ggactcaacc ctctgtttga acaacataca agataatatg agacatttat 180
ttatcgagga ccctctgagc acctggcact gtgccagatt ctttcagata tataaaattt 240
cacttgctcc tgttgattct ggaaaggagc aacggcatct tatgaagctg tagcagatac 300
tgtcctggcc tcgctcatgt gtgtcagatg tgttggagtg ccctggctgc tgctctgcat 360
gtgtagctga ggtcct 376

<210> SEQ ID NO 394

<211> LENGTH: 220
<212> TYPE: DNA
<213> ORGANISM: Homo sapiens

<400> SEQUENCE: 394
tggattcatg ccaaaggaaa ctgaaagcct gcctttcttt ttttcccagt gcacatctca 60
gattatttgg cctttgtccg aggactgaaa acagttctgt gtccaagtat gtttttaata 120
cctgatattt atttcacaaa aaaactgaaa ttgctttgtg tgtccaggct tgaatgttta 180
aggcatactt gattaataca tgtgtgctga gtgcttcctg 220

<210> SEQ ID NO 395
<211> LENGTH: 553
<212> TYPE: DNA
<213> ORGANISM: Homo sapiens

<400> SEQUENCE: 395
caaccgccac atagtcacat tgtcaaatag cgtattcacc ttctcttata agaaggctca 60
gcgagatctg gcgtataagc cactctacag ctgggaggaa gccaagcaga aaacggtgga 120
gtgggttggt tcccttgtgg accggcacaa ggagaccctg aagtccaaga ctcagtgatt 180
taaggatgac agagatgtgc atgtgggtat tgttaggaga tgtcatcaag ctccaccctc 240
ctggcctcat acagaaagtg acaagggcac aagctcaggt cctgctgcct ccctttcata 300
caatggccaa cttattgtat tcctcatgtc atcaaaacct gcgcagtcat tggcccaaca 360
agaaggtttc tgtcctaatc atataccaga ggaaagacca tgtggtttgc tgttaccaaa 420
tctcagtagc tgattctgaa caatttaggg actcttttaa cttgagggtc gttttgacta 480
ctagagctcc atttctactc ttaaatgaga aaggatttcc tttcttttta atcttccatt 540
ccttcacata gtt 553

<210> SEQ ID NO 396
<211> LENGTH: 357
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u
<220> FEATURE:
<221> NAME/KEY: misc_feature
<222> LOCATION: (111)..(111)
<223> OTHER INFORMATION: n is a, c, g, t or u
<220> FEATURE:
<221> NAME/KEY: misc_feature
<222> LOCATION: (114)..(114)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (132)..(132)
<223> OTHER INFORMATION: n is a, c, g, t or u

<400> SEQUENCE: 396
ctagaaactc actcagtcct gtggttgcca acctttctcc atctcccgca gacgttttac 60
tgcatgccag ataccatgtg cagtaacttn tgaatcctct cancccccta nctnccagaa 120
cacnggacta tnagttactt gaaagctgag gcttggtaga gggctggagc caattgcgtt 180
aaactaacta acattattgc aaaatatatt ctagggcttt tactctaata aaaatgactc 240
ctggaactgc agtactatat tcttggaacc ccaagaaacc aggtgacaac ccataaattt 300
accatcactt ttcagatgag gaaggcaaat ctggaaggcc aaattacttg tccaaag 357

<210> SEQ ID NO 397
<211> LENGTH: 423
<212> TYPE: DNA
<213> ORGANISM: Homo sapiens
<220> FEATURE:
<221> NAME/KEY: misc_feature
<222> LOCATION: (184)..(184)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (350)..(350)
<223> OTHER INFORMATION: n is a, c, g, t or u

<400> SEQUENCE: 397
gttagcacat accattgaat tcactgagac acatgagaaa atatgggaaa gtcggagagt 60
ggaagtaaat gtaaagaccc ccctcctccc caaagagtac gttgtgtagt ggggtagagt 120
ggaaaatcaa tccaagaaaa gtagcaaacg gacccaaaga tgaagaggaa gaaaagaaac 180
agcnacacga aacgnaaaaa aaaagccacc agatttgttg caacgttgat gtaaacctgg 240
ccgtcttcct gaaccagtga cccagggttt ccgcttccct ttgctgtcat cttgctcaag 300
tctagaagct gaaatatcat catcaactcg acatgagggg ataacctctn gatccactca 360
tcagatgctc atcagacgtt ccaattacaa aactgaacct cttcttagtg ctggggcggt 420
tag 423

<210> SEQ ID NO 398
<211> LENGTH: 515
<212> TYPE: DNA
<213> ORGANISM: Homo sapiens
<220> FEATURE:
<221> NAME/KEY: misc_feature
<222> LOCATION: (132)..(132)
<223> OTHER INFORMATION: n is a, c, g, t or u
<220> FEATURE:
<221> NAME/KEY: misc_feature
<222> LOCATION: (150)..(150)
<223> OTHER INFORMATION: n is a, c, g, t or u

<400> SEQUENCE: 398
ggacaaaaac tttcccaagt cagcttttta ctatgattac gtcctagcct cagatgtggt 60
ctaccatcac tacttcctgg acaagctgct caccaccatg gtgtaccttt cccagccagg 120
gacggtgctg cnttgggcaa acaaattcan ggttcagcac cgactatgaa tttttagata 180
aattcaagca agtttttgac acaacactgt tggctgaata tccagagtca tcagtcaaac 240
tttttaaggg gatactaaaa tgggactaaa tccaacaaaa tgcctttcac aacgttactg 300
tgtcttttga gcaatgtgtt agaaattgct ttggtaatag acttctttca caggattgag 360
aaggtagtgc atagaaacaa cttgtatact tggaacaaat gtaacaatac tgcagaaact 420
ttctaatttc taagataatt taagattatc tggttaatct aaatatctaa aaagaacaac 480
ataaaaacat gaaagtagct ttgttggttc caacg 515

<210> SEQ ID NO 399

<211> LENGTH: 483
<212> TYPE: DNA
<213> ORGANISM: Homo sapiens
<220> FEATURE:
<221> NAME/KEY: misc_feature
<222> LOCATION: (55)..(60)
<223> OTHER INFORMATION: n is a, c, g, t or u
<220> FEATURE:
<221> NAME/KEY: misc_feature
<222> LOCATION: (62)..(63)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (85)..(85)
<223> OTHER INFORMATION: n is a, c, g, t or u
<220> FEATURE:
<221> NAME/KEY: misc_feature
<222> LOCATION: (88)..(88)
<223> OTHER INFORMATION: n is a, c, g, t or u
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (134)..(134)
<223> OTHER INFORMATION: n is a, c, g, t or u
<220> FEATURE:
<221> NAME/KEY: misc_feature
<222> LOCATION: (278)..(278)
<223> OTHER INFORMATION: n is a, c, g, t or u
<220> FEATURE:
<221> NAME/KEY: misc_feature
<222> LOCATION: (304)..(304)
<223> OTHER INFORMATION: n is a, c, g, t or u

<400> SEQUENCE: 399
gactgccatc tgatcaacag ctacccttca gccaatttca cctttctgtt acttnnnnnn 60
anngngccct tgtgtggata atgtncancn cantaaggaa tgcatgttag gtactttaag 120
tcccagtaga atancagttc ataatatcac acatgtggtg aaatctaaaa aggcaatagg 180
gctaattttg gcaggagttg gaatagcccc ttgggatggc tttgcatact gtcagacagc 240
tttgagaaac tttcaaaccc ttgaaacact ggcaactnag tacaggcaga gccataaaag 300
gacntcaagc ctccctgcac tccctagcca atgctgtctt ggataacaga tttgccctgg 360
aatatcttct ggctgaacaa gggcgggtat gcacagtaat aaaccacatc tgttgttctt 420
acattaacag ttcaggattg gctaaactgc aagttcaaaa gatttaccaa gaccaggcac 480
aat 483

<210> SEQ ID NO 400
<211> LENGTH: 555
<212> TYPE: DNA
<213> ORGANISM: Homo sapiens
<220> FEATURE:
<221> NAME/KEY: misc_feature
<222> LOCATION: (483)..(483)
<223> OTHER INFORMATION: n is a, c, g, t or u

<400> SEQUENCE: 400
ggagcaaaac acttggaacc cacaagactc ccagaaggtg aagttaagag ctcccagact 60
cataaggtta ttagaacagc aaactggcac cccaaagaac tttacggaga cttgcaacct 120
atcaacaagt tggatgaggg attaaaagcc ttcaacaacc aacaacccca agcatcaaac 180
tgaaggaaac attctaacct tcacagacag actggaggct ggatggggac ctggctgaag 240
acatctggag aatgaaagtt aagtaccagc ttgcattttt gtgcccctag attatttttg 300
cattttaaaa taagaagcat caaattgcgt gtctctgtgt aaaagttcta gcaatttgtt 360
ttaaggtgaa cttattttgg cttagggact acaaaaagag aaggtaattc ctagggaagg 420
aagaagagaa agaaatgaaa attagagaat aagattattt tgaatgactt caggtagcga 480
ggngtgtgtg tttgtgagtg tgtatttgag agacttggct catgcctgtg ggtcttctct 540
tctagtatca gtgag 555

<210> SEQ ID NO 401
<211> LENGTH: 327
<212> TYPE: DNA
<213> ORGANISM: Homo sapiens

<400> SEQUENCE: 401
ggctgagaaa ctactggagc accagggaca gtctgtaaag ttggatggac caccaatggg 60
aaaatgagag ctgcccaccc tggccttaca ctccttcaat taatacataa acagaaagga 120
ggatatacag agagccaaag gcccatggga cgtgaccaac attccactga gtctatacga 180
tcaaacagca aactgtttat catgaataca gaatgtgggc aaactcatga ctgtgcctgc 240
cccagaaggt ttgctgaggg caattgcttc ctgacgccaa gctccttgag gttatctatt 300
gggacatcca gagaatgcag tcttgca 327

<210> SEQ ID NO 402
<211> LENGTH: 497
<212> TYPE: DNA
<213> ORGANISM: Homo sapiens

<400> SEQUENCE: 402
gggtggcctg gggatagtgg cttcatcttt tggggcttca agattctttg tctttaaaat 60
caggggttat atcaagatca tcaaagttcc cattccatta aagaaaaccc tgcatgtatc 120
cataatgatg cttcttcctg ttaaatttac aatgaaggga aacccatcac ttaactgtag 180
gaatttccca aaatgaactg atgaccagtg atctctctat cagaaaatgg cagatttcta 240
gccttccaga actttgattt tcttggacat tcaatggttc ctttttccca aatatttttc 300
aactgatgcc aaaccttgga tttggtttaa tccacctttg gtttaggttt ggggaccctt 360
ttcctggacc gtcccagttt tgggttaaac cgatttggat gaccctgtga gtcgccactg 420
gataccgaca gtctgctgtg gtgcttagaa gccactgaaa cattggtgaa tgtgaagtca 480
cttttggggt gcctgcc 497

<210> SEQ ID NO 403
<211> LENGTH: 512
<212> TYPE: DNA
<213> ORGANISM: Homo sapiens

<400> SEQUENCE: 403
gaaagctcca aatccatgac agtcgaagtc tctgctcctt caggaacagg acatcttcct 60
ggccttaatc cattatagca gccgtgatgt catttctgta tttcaggaag actggcagac 120
agttgctttc attcttcctc aaagtattta ccatcagcta cagtccaaaa ttgctttttg 180
ttcaaggaga tttatgaaaa gactctgaca aggactcttg aatacaagtt cctgataact 240

-continued

```
tcaagatcat accactggac taagaacttt caaaatttta atgaacaggc tgatacttca    300

tgaaattcaa gacaaagaaa aaaacccaat tttattggac taaatagtca aaacaatgtt    360

ttcataattt tctatttgaa aatgtgctga ttctttgaat gttttattct ccagatttat    420

gcactttttt tcttcagcaa ttggtaaagt atacttttgt aaacaaaaat tgaaacattt    480

gcttttgctc cctaagtgcc ccagaattgg ga                                  512
```

<210> SEQ ID NO 404
<211> LENGTH: 229
<212> TYPE: DNA
<213> ORGANISM: Homo sapiens

<400> SEQUENCE: 404

```
caccccattc aaactcaagc acagtatgcc tccccagtct ttatgcagcc tgtatataat     60

cctcaccaac agtactcggt ctatagtatt gtgcctcagt cttggtctcc aaatcctaca    120

ccttactttg aaacaccact ggctcccttt cccaatggta gttttgtgaa tggctttaat    180

tcgccaggat cttataaaac aaatgctgct gctatgaata tgggtcgac                229
```

<210> SEQ ID NO 405
<211> LENGTH: 495
<212> TYPE: DNA
<213> ORGANISM: Homo sapiens

<400> SEQUENCE: 405

```
acagctcagg ttttatcacc gactgggaat agacaacctc aatgctgaac cgcactggag     60

aaaaggggca aggtacccct gctgaggtgt atgggctgcc atctcaggct gtcttgagga    120

cctgggctcc ctctgctact cccaggaaat gggctcctga cacagcagtc tgccaccaca    180

gccccaggag ggtgtcaaca ccagcaaatg ctgtatttgc agcatgtcca agatgaccct    240

tctcccctac ctctacctag ccactggcag ggaggggaga cagtggtgat agcagcagca    300

ctctaggcat ggtgaacgcc tgggaccaag ccatgtggcg tttttttattt tgcctttctg    360

gaagactcaa gatatgtctc ttcattctct ctcagtattt gtttactttg gttttttttgt    420

ttttaatctc agagagaggt gtgtttagtg ggcacaagct gtaatattca gcaaaacttt    480

gtcgactggc actgt                                                     495
```

<210> SEQ ID NO 406
<211> LENGTH: 472
<212> TYPE: DNA
<213> ORGANISM: Homo sapiens
<220> FEATURE:
<221> NAME/KEY: misc_feature
<222> LOCATION: (77)..(77)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u

<400> SEQUENCE: 406

```
ttcctcttgc tgagaaaacc caccctgctc acctaaaccc tggccttgcc tggtaattcc     60

atccatgcgc ctggaangnc ccagacatca aggctctgag gggccaggca cggggagaac    120

ccagcagtgc cctgccctgc agtctgagct accagattcc ttgtgaagat aatttgagga    180

ccatgactca cccaaccaca tttcctgggg cctcaaattg aaaattcagg atgggctttt    240

ctatatgact ggctgatatc caactatgcc atggtcttta catgccatga acattctttc    300

ctgccagagt tctaagaatc tgtgttctct gccttagacc ttctgcagat gagcccacag    360
```

gaagctccac gtgtagctga gctacatgca ccaggcctca gtttgcccca agtcccctgt 420
gtactctctc atggcctgtg gccaagaaat gtattctctc actttggact ta 472

<210> SEQ ID NO 407
<211> LENGTH: 395
<212> TYPE: DNA
<213> ORGANISM: Homo sapiens

<400> SEQUENCE: 407
agcagatgga ccctactgga agtcagttgg attcagattt ctctcagcaa gatactcctt 60
gcctgataat tgaagattct cagcctgaaa gccaggttct agaggatgat tctggttctc 120
acttcagtat gctatctcga caccttccta atctccagac gcacaaagaa aatcctgtgt 180
tggatgttgt gtccaatcct gaacaaacag ctggagaaga acgaggagac ggtaatagtg 240
ggttcaatga acatttgaaa gaaaacaagg ttgcagaccc tgtggattct tctaacttgg 300
acacatgtgg ttccatcagt caggtcattg agcagttacc tcagccaaac aggacaagca 360
gtgttctggg aatgtcagtg gaatctgctc ctgct 395

<210> SEQ ID NO 408
<211> LENGTH: 397
<212> TYPE: DNA
<213> ORGANISM: Homo sapiens

<400> SEQUENCE: 408
attttcctca taaagcattg ctccagctaa tcttatctat ttttctccag aatctccatc 60
cccttcccgt cagatacatc taaaactttt tttgtatctt tgtttttcct cgtgttgtat 120
catcttccta aaacatgttc tacttgtgaa aaccctaaga aattctctct gtcttattga 180
aattctatct ccactgtgaa gcattatcat ggtgtggcca tatatgatct atccctatct 240
gaagtcactg catttattcc ctgatcctca tttgcaggtc cagtaccttg tacaagtttc 300
tttttgtgcc atattagact gtaagctcca agagggcagg gcccaagtct tatgaatttg 360
tgtctgcata gtgtctagta cttgtctgag gcccaca 397

<210> SEQ ID NO 409
<211> LENGTH: 48
<212> TYPE: DNA
<213> ORGANISM: Homo sapiens

<400> SEQUENCE: 409
aggacgtacc ttgtgagatg cgagccggcc aacagcttgc aagcatgc 48

<210> SEQ ID NO 410
<211> LENGTH: 459
<212> TYPE: DNA
<213> ORGANISM: Homo sapiens

<400> SEQUENCE: 410
gcaagtcgcg tgatttctac cacacctgct actgcctgag cggcctgtcc atagcccagc 60
acttcggcag cggagccatg ttgcatgatg tggtcctggg tgtgcccgaa aacgctctgc 120
agcccactca cccagtgtac aacattggac cagacaaggt gatccaggcc actacatact 180
ttctacagaa gccagtccca ggttttgagg agcttaagga tgagacatcg gcagagcctg 240
caaccgacta gaggacctgg gtcccggcag ctctttgctc acccatctcc ccagtcagac 300
aaggtttata cgtttcaata catactgcat tctgtgctac acaagcctta gcctcagtgg 360
agctgtggtt ctcttggtac tttcttgtca aacaaaacca atggctctgg gtttggagaa 420
cacagtggct ggttttaaaa ttctttccac acctgtcaa 459

<210> SEQ ID NO 411
<211> LENGTH: 275
<212> TYPE: DNA
<213> ORGANISM: Homo sapiens

<400> SEQUENCE: 411
agagggcaag gggctggatg caggcagaga atgactttaa gaaaagattc tatgatccct 60
tcctttagta tggagctcga ttttccagct ggcgcttggt gagaaagtac ttgaagaact 120
catagacaga ccaagaaatg gcggtggagg gcatctggta gatgacacgc gcctggatgc 180
ctttgaagta gccggccagg ccgttgagct ggtacaccgt ccggaaggca ttggccatac 240
ccgacagccg gccgctgatg ttggccagcg agagg 275

<210> SEQ ID NO 412
<211> LENGTH: 536
<212> TYPE: DNA
<213> ORGANISM: Homo sapiens

<400> SEQUENCE: 412
gcagataagc tccgtctgca gttccaggcc agccagaaac tcctgtgtcc acatagagct 60
gacgtgagaa atatctttca gcccaggaga gaggggtcct gatcttaacc ctttcctggg 120
tctcagacaa ctcagaaggt tggggggata ccagagaggt ggtggaatag gaccgccccc 180
tccttacttg tgggatcaaa tgctgtaatg gtggaggtgt gggcagagga gggaggcaag 240
tgtcctttga aagttgtgag agctcagagt ttctggggtc ctcattagga gcccccatcc 300
ctgtgttccc caagaattca gagaacagca ctggggctgg aatgatcttt aatgggccca 360
aggccaacag gcatatgcct cactactgcc tggagaaggg agagattcag gtcctccagc 420
agcctccctc acccagtatg ttttacagat tacgggggga ccgggtgagc cagtgacccc 480
ctgcagcccc cagcttcagg cctcagtgtc tgccagtcaa gcttcacagg cattgt 536

<210> SEQ ID NO 413
<211> LENGTH: 286
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u

<400> SEQUENCE: 413
ttaatttctg tgaagagtgc ccctggtgtt tcatcttggc ctgttttgat gagaatgtta 60
tcntttgtgt ctggataacg cgtcagcttc ttaaagtaca tataaagata ttctgtcacc 120
nccccacatg cacacacttt taaaatctat ttttattctc ttgctaaagt tgtaattatg 180
tcaagaattt tccagctcta actgccttct tagtacatgt ctttctgcct ttgaagcata 240
tgagtttgcc aaagtcattc tcccctaatg acatattgtg gactta 286

<210> SEQ ID NO 414
<211> LENGTH: 166
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (74)..(74)
<223> OTHER INFORMATION: n is a, c, g, t or u

<400> SEQUENCE: 414
gaaagacgga ggaaacaatc aaaatcncca ttctattgct ttgacacctt tactaggtga 60
attggtggca ttcncaaagc taatagggac gtttatatca agaaacattt ctgtatatat 120
tgttgaattt tagttgtaca tatactttgt atgtttttgt cttctt 166

<210> SEQ ID NO 415
<211> LENGTH: 552
<212> TYPE: DNA
<213> ORGANISM: Homo sapiens

<400> SEQUENCE: 415
tgcaggctag gggaggagcc accccccgctt ccctattgtg accaggccta tggggaggag 60
ctgtccatac gccaccgtga gacctgggcc tggctctcaa ggacagacac cgcctggcct 120
ggtgctccag gggtgaagca ggccagaatc ctgggggagc tgctcctggt ttgagctgca 180
ttcaggaagt gcgggacatg gtaggggagg caaaaagcct tgggcactac cctccctgtg 240
gagctgttcg gtgtccgtcg agctagccac accctgacac catgttcaag ggtaccggaa 300
gagaagggtg tctgccccca acctcccctg tgggtgtcac tggccagatg tcatgaggga 360
agcaggcctt gtgagtggac actgaccatg agtccctggg gggagtgatc ccccaggcat 420
cgtgtgccat gttgcacttc tgcccaggca gcagggtggg tgggtaccat gggtgcccac 480
ccctccacca catggggccc caaagcactg caggccaagc agggcaaccc cacacccttg 540
acataaaagc at 552

<210> SEQ ID NO 416
<211> LENGTH: 524
<212> TYPE: DNA
<213> ORGANISM: Homo sapiens

<400> SEQUENCE: 416
acgccgcgcg aaggtgatga gctcgcccgg ctgccctacc tacggacctg gttccgcacc 60
cgcagcgcca tcatcctgca cctcagcaac ggcagcgtgc agatcaactt cttccaggat 120
cacaccaagc tcatcttgtg cccactgatg gcagccgtga cctacatcga cgagaagcgg 180
gacttccgca cataccgcct gagtctcctg gaggagtacg gctgctgcaa ggagctggcc 240
agccggctcc gctacgcccg cactatggtg gacaagctgc tgagctcacg ctcggccagc 300
aaccgtctca aggcctccta atagctgccc tcccctccgg actggtgccc tcctcactcc 360
cacctgcatc tggggcccat actggttggc tcccgcggtg ccatgtctgc agtgtgcccc 420
ccagccccgg tggctgggca gagctgcatc atccttgcag gtgggggttg ctgtataagt 480
tatttttgta catgttcggg tgtgggttct acagacttgt cccc 524

<210> SEQ ID NO 417
<211> LENGTH: 378
<212> TYPE: DNA
<213> ORGANISM: Homo sapiens

<400> SEQUENCE: 417
aaatgactgc attcgtctct tttttaaagg tagagattaa actgtataga cagcataggg 60
atgaaaggaa ccaagcgttt ctgtgggatt gagactggta cgtgtacgat gaacctgctg 120
ctttgttttc tgagaagagg tttgaagaca ttttattaac agcttaattt ttctctttta 180
ctccatagga acttatttta atagtaacat taacaacaag aatactaaga ctgtttggga 240
attttaaaaa gctactagtg agaaaccaaa tgataggttg tagagcctga tgactccaaa 300
caaagccatc acccgcattc ttcctccttc ttctggtgct acagctccaa gggcccttca 360
ccttcatgtc tgaaatgg 378

<210> SEQ ID NO 418
<211> LENGTH: 116
<212> TYPE: DNA
<213> ORGANISM: Homo sapiens

<400> SEQUENCE: 418
agtatggaag ctgagaagag ttattggaat cacccccacc gttgacagag gaaggcaggg 60
ggtgagaatt aactgcttga gggtaggaga gtctgagatg tgggggccct attccg 116

<210> SEQ ID NO 419
<211> LENGTH: 147
<212> TYPE: DNA
<213> ORGANISM: Homo sapiens

<400> SEQUENCE: 419
cctgagccac cacgcagaag aggcactttc caagttgttt accaagaatt tacattaaaa 60
taacaagcta ttgtttggct atacattgtt ctttgtatca catattccag gaactacagg 120
aaaataatgg gtgaggcagc tagttag 147

<210> SEQ ID NO 420
<211> LENGTH: 310
<212> TYPE: DNA
<213> ORGANISM: Homo sapiens

<400> SEQUENCE: 420
gaaattccat caatacatct agacagatgt ttgcttgtag tttttggtat ccaaaacctt 60
ttttccacac atcgcacaga tgccttttt gtaggcacag ccctggcagt aatgagaacc 120
tggttggtgc acagaacttt tacaaattct acaagtggag aacttattct ttccatatgg 180
atcaaatctt gctttttttg aagtcaaagc tttattttca ttcagctttc ttccaccact 240
ttctgtggta ttcctagcac cacctttcca tgtatctgga gtgataacag taccaagttt 300
cttttcacat 310

<210> SEQ ID NO 421
<211> LENGTH: 154
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, t or u

<400> SEQUENCE: 421
agatataact ggtagagcac gtcaaagata tacagaaata accagagaaa agtttgaggc 60
attaaaanaa gaaaatatgg acctaaacaa tatgaatcaa agccttaccc ttgaactaaa 120
cacaatgaaa caagcaatga aagaactaca gtta 154

<210> SEQ ID NO 422
<211> LENGTH: 444
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u

<400> SEQUENCE: 422
tttttgtgca tgattacact ccactgacat cttccaagta ctgcatgtga ttgaataaga 60
aacaagaaag tgaccacacc aaagcctccc tnggctggtg tacagggatc aggtccacag 120
tggtgcagat tcaaccacca cccagggagt gcttgcagac tctgcataga tgttgctgca 180
tgcgtcccat gtgcctgtca gaatggcagt gtttaattct cttgaaagaa agttatttgc 240
tcactatccc cagcctcaag gagnccaagg aagagtcatt cacatggaag gtccgggact 300
ggtcagccac tctgactttt ctaccacatt aaattctcca ttacatctca ctattggtaa 360
tggcttaagt gtaaagagcc atgatgtgta tattaagcta tgtgccacat atttattttt 420
agactctcca cagcattcat gtca 444

<210> SEQ ID NO 423
<211> LENGTH: 510
<212> TYPE: DNA
<213> ORGANISM: Homo sapiens
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
<222> LOCATION: (454)..(454)
<223> OTHER INFORMATION: n is a, c, g, t or u
<220> FEATURE:
<221> NAME/KEY: misc_feature
<222> LOCATION: (462)..(462)
<223> OTHER INFORMATION: n is a, c, g, t or u

<400> SEQUENCE: 423
gctttggact ggctcgcatg gaaaaccagg catttgatcc cgagaaaggg aacttcaaca 60
ctttgttttg caggctctgc gtgctgctgc tggtgtgtgc cgcccaggcc tggctcatgt 120
ggcgcttcat ccactcccag ctgcggcact ggcgggaata ctggaatgag cagagtgcaa 180
agcggagagt cccagccaca cccagactac cagccaggct catcaagagg gaatctggtt 240
accatgaaaa tggagtggtg aaggcagaga acggaacctc cccacggact aagaaactca 300
agtctcccta aggccaaagt gctaagaaca ggaatcctct tggtgggggc cgagcanggg 360
gcaaggagcc caggccccct ccctgcctcc tccttcctgc ctgtgatgct ccgtctcaaa 420
cagccgaaac ctgtcttgca atggggggag gggngcgttt cnctttcctt cttcttggct 480
tcctcttatt cttccacaaa ccattctcaa 510

<210> SEQ ID NO 424
<211> LENGTH: 191
<212> TYPE: DNA
<213> ORGANISM: Homo sapiens

<400> SEQUENCE: 424
acattgtgcc tcaggatttt gataataatt ctggatattg gaacagaata gaaatgtact 60
gtcgagagct gacagaaagg tttgaagatg tttgggtggt atctgggcct ttgaccttac 120
ctcagactag aggcgatgga aagaaaatag ttagttacca ggtgattggc gaggacaacg 180
tggcagtccc c 191

<210> SEQ ID NO 425
<211> LENGTH: 186
<212> TYPE: DNA
<213> ORGANISM: Homo sapiens

<400> SEQUENCE: 425
gcggtgtgga ccgaggaaca acttggaaga tctacctgca acacaacatt tgtgtcactg 60
tacagttttg tggactgagc gaggaaaaac aacaaataat ttaagttggc tagagcttct 120
gtattttcaa agactgccac gtgccttagg aatactgttt tatctccata ctttggatga 180
cttgtt 186

<210> SEQ ID NO 426
<211> LENGTH: 465
<212> TYPE: DNA
<213> ORGANISM: Homo sapiens

<400> SEQUENCE: 426
gttttggacc aacaagtgcc tcctttggtg aaggtgacac atcatgtgac ctcttcagtg 60
accactctac ggtgtcgggc cttgaactac tacccccaga acatcaccat gaagtggctg 120
aaggataagc agccaatgga tgccaaggag ttcgaaccta aagacgtatt gcccaatggg 180
gatgggacct accagggctg gataaccttg gctgtacccc ctggggaaga gcagagatat 240
acgtgccagg tggagcaccc aggcctggat cagcccctca ttgtgatctg ggagccctca 300
ccgtctggca ccctagtcat tggagtcatc agtggaattg ctgtttttgt cgtcatcttg 360
ttcattggaa ttttgttcat aatattaagg aagaggcagg gttcaagagg agccatgggg 420
cactacgtct tagctgaacg tgagtgacac gcagcctgca gactc 465

<210> SEQ ID NO 427
<211> LENGTH: 480
<212> TYPE: DNA
<213> ORGANISM: Homo sapiens

<400> SEQUENCE: 427
tcctttgtgt agcattatca gcctcggtct ggcctctggc acctcaccct tgccatggct 60
gaccccaccc attccaaggc ggggtcacgg taccagcagc acttggggtg aggcctccaa 120
agcttcctca gaattgtggc tgtgccacgc tggaccacag ggtccccctc aagcatctcg 180
gggccctatt ctctctgagc acctggaggg ctggactcag gcttgtgcca gggcctgact 240
tgggcctggg ggccctagaa cactcctcct cctgagccta ctgccaaacg tcctcagtgt 300
tgtctgcacc tgctccgact ccttcagccg ccccattcag cgcccgctcc gtccagtgcc 360
cgccctgtgg ggccaaggcg gccgtgcctt actactctgt gtcttctgcc tcctctgagg 420
aatctggccc tgtctgacag tcccagaccc cccgttctct cctctttagt tgcatgagtt 480

<210> SEQ ID NO 428
<211> LENGTH: 533
<212> TYPE: DNA
<213> ORGANISM: Homo sapiens

<400> SEQUENCE: 428
ttcattcaca aacttccgct gtacctgcgt ctaaaaaggc ccaaacccga gagagacctg 60
atgccggagc cccctcactg ttcttctcca ggaagtggct ggggtcgggg aacagatgaa 120
tatttcatcc ggaagccgcc aagtgatttt ctcttcccca aacccaatag gttccagcct 180
gaactgtctg cccctgatct gcggcgattt atcgatggtc caaaccgggc tgtggccctg 240
cttccggagc tacgggaggt cgtctcctct atcagctaca tcgctcgaca gctgcaggaa 300
caggaggacc acgatgcgct gaaggaggac tggcagtttg tggccatggt agtggaccgc 360
ctcttcctgt ggactttcat catcttcacc agcgttggga ccctagtcat cttcctggac 420
gccacgtacc acttgccccc tccagacccc tttccttgaa gactggaggg ttgagaccag 480
gccccctgcc agttgaagtg agagagtttg gtgatactgt caagccctat cct 533

<210> SEQ ID NO 429
<211> LENGTH: 486
<212> TYPE: DNA
<213> ORGANISM: Homo sapiens

<400> SEQUENCE: 429
gtgacctttc acgaacatgg gcatggctgc ggctccctcg tcatcaggtg catagcaagt 60
gaaagcaagt gttcacaacg gtgaaacttg agcgtcattt ttcttagtgt gccaagagtt 120
cgatgttagt gtttccattg tattttctta cagtgtgcca ttctgttaga tactatcctt 180
ataattgatg agcaagacat actgaatgca tatttcggtt tgtgtatcca tgcacctacg 240
tcagaaaaca agtattgtca ggtattctct ccatagaaca gcactatcct catctctccc 300
cagatgtgac tactgagggc agttctgagt gtttaatttc agactttttc ctctgcattt 360
acacacacac acacacacac acgcacacac acacaccaag taccagtata agcatctccc 420
atctgctttt cccattgcca tgcgtcctgg tcaagccccc ctcactctgt ttcctggtca 480
gcatgt 486

<210> SEQ ID NO 430
<211> LENGTH: 97
<212> TYPE: DNA
<213> ORGANISM: Homo sapiens

<400> SEQUENCE: 430
tattagttaa ttagtgattt cacagtatcc tttcgcaggc cgatccccac tccaaccgtt 60
ccctcagcaa ccccaggggt gtcagacggg gcaccct 97

<210> SEQ ID NO 431
<211> LENGTH: 241
<212> TYPE: DNA
<213> ORGANISM: Homo sapiens
<220> FEATURE:
<221> NAME/KEY: misc_feature
<222> LOCATION: (88)..(88)
<223> OTHER INFORMATION: n is a, c, g, t or u

<400> SEQUENCE: 431
gctgcctttg cactggcgaa gggaggggca ctggttatgt tgtttccatt cgacagtcct 60
tccaaaggct tccctccagc gccactancc aaatccagaa aagcgtcctc ctccagaagg 120
taccaccaaa cctttaaaac ctttaaaggc tcctccagtg tcagattcaa atccaacatt 180
tctgcgcttt gctttcttta tggctctatt cttcaagact tcctcactgg ccatggagaa 240
t 241

<210> SEQ ID NO 432

<211> LENGTH: 537
<212> TYPE: DNA
<213> ORGANISM: Homo sapiens

<400> SEQUENCE: 432
tgagcctgtg cgttttgcat actgggttgg tttgctgggg ctgcggtgac agcatatgcc 60
gcgagctggg ctttaacaga gatgtgtgct ctcacagctt tgcaggcggg ggtctgagat 120
cagggtgtcg cgggtggggg gtcactgctg aggccgtgag gggaatctgc tcaggcctgt 180
ccctggcttc tgggggctgc tggtggtatt ttcagttcct tggtgtgtgg atacttcgcc 240
ccatctctgc cttcacctgt gtcctccctg tgtgggtgct ggtgtccaaa atttcccctt 300
ttcgtagtga caccagctgt gttggattgg ggcccaccct gctccagcat ggcctaatct 360
taactaatta catttgcaag gatcttatgt ccacaaaagt cacagtctga ggtgctgggg 420
gttaggactt caatatataa attttgcggt tacacaattc aatccatgac agaatccaaa 480
ggtttactct ggttataaaa acagtacaat aaaatattgt ttatagcctt ccctgta 537

<210> SEQ ID NO 433
<211> LENGTH: 355
<212> TYPE: DNA
<213> ORGANISM: Homo sapiens
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (186)..(186)
<223> OTHER INFORMATION: n is a, c, g, t or u

<400> SEQUENCE: 433
gaaaacccgt tatgagacac aacttgaatt aaatgatgaa ctagaaaagc aaattnttta 60
tctcaaggag aaagtggaaa aaatccatgg aaactcttca gatagactnt cttctattcg 120
tgtctatgaa cgaatgccag tggaatcctt aaacacatta cttaaacagc tagaagaaga 180
aaagangact cttgaaagtc aagtgaaata ctatgcactt aaactggaac aagaatcaaa 240
ggcttaccag aagatcaaca atgaacgccg tacataccta gctgaaatgt ctcagggttc 300
tggtttacat caagtttcta aaaggcaaca ggtggatcaa ctgcctagga tgcaa 355

<210> SEQ ID NO 434
<211> LENGTH: 319
<212> TYPE: DNA
<213> ORGANISM: Homo sapiens

<400> SEQUENCE: 434
ggcaagaagc caggtaaggc atgcagtctt tctgttcccc gttgggggag tggtattaag 60
gaactgtgtc ttcaggatac agtgagctgt aaaaatagac aacaagaaca cggaaactat 120
ggtagacgaa tgggctgagg acacagttca tgaaagagaa atatactcaa gatagaagaa 180
cctgcttcat cttagtggtg atttttgtaa aatgtaattt aaaatattcc ccgatgctgg 240
gagctaagta aaaaataaat aagtaaataa aatacaaaat tacatgtaca tttaaatgtt 300
ttttctctat caagtttat 319

<210> SEQ ID NO 435
<211> LENGTH: 511

<212> TYPE: DNA
<213> ORGANISM: Homo sapiens

<400> SEQUENCE: 435
cacgatgacc ccagacatga gatccatcac taataatagc tcagatcctt tcctcaatgg 60
agggccatat cattcgaggg agcagagcac tgacagtggc ctggggttag ggtgctacag 120
tgtccccaca actccggagg acttcctcag caatgtggat gagatggata caggagaaaa 180
cgcaggacaa acacccatga acatcaatcc ccaacagacc cgtttccctg atttccttga 240
ctgtcttcca ggaacaaacg ttgacttagg aactttggaa tctgaagacc tgatccccct 300
cttcaatgat gtagagtctg ctctgaacaa aagtgagccc tttctaacct ggctgtaatc 360
actaccattg taacttggat gtagccatga ccttacattt cctgggcctc ttggaaaaag 420
tgatggagca gagcaagtct gcaggtgcac cacttcccgc ctccatgact cgtgctccct 480
cctttttatg ttgccagttt aatcattgcc t 511

<210> SEQ ID NO 436
<211> LENGTH: 515
<212> TYPE: DNA
<213> ORGANISM: Homo sapiens
<220> FEATURE:
<221> NAME/KEY: misc_feature
<222> LOCATION: (89)..(89)
<223> OTHER INFORMATION: n is a, c, g, t or u
<220> FEATURE:
<221> NAME/KEY: misc_feature
<222> LOCATION: (91)..(92)
<223> OTHER INFORMATION: n is a, c, g, t or u
<220> FEATURE:
<221> NAME/KEY: misc_feature
<222> LOCATION: (96)..(98)
<223> OTHER INFORMATION: n is a, c, g, t or u
<220> FEATURE:
<221> NAME/KEY: misc_feature
<222> LOCATION: (100)..(100)
<223> OTHER INFORMATION: n is a, c, g, t or u

<400> SEQUENCE: 436
taagatccag ggttccagga ctgccaccaa ctcctgtcca gctgctctat ccagtgtccc 60
gattcagcaa tgtcaaatcc ctccagcanc nntgcnnntn ccggatacga cagctcgtca 120
ggatagatca catcccagat ctcccactgc ctaaacctct gatctcttat atccgaaagt 180
tctactacta tgatcctcag gaagaggtat acctgtctct aaaggaagcg cagctcattt 240
ccaaacagaa gcaagaggtg gaaccctcca cgtagcgagg ggctccctgc tggtcaccac 300
caagggcatt tggttgccaa gctccagctt tgaagaacca aattaagcta ccatgaaaag 360
aagaggaaaa gtgagggaac aggaaggttg ggattctctg tgcagagact ttggttcccc 420
acgcagccct ggggcttgga agaagcacat gaccgtactc tgcgtggggc tccacctcac 480
acccacccct gggcatctta ggactggagg ggctc 515

<210> SEQ ID NO 437
<211> LENGTH: 489
<212> TYPE: DNA
<213> ORGANISM: Homo sapiens

<400> SEQUENCE: 437
gctttgagga aaccactgtg caacttgaga tgtctgtggt tgtggggatg ttccatccct 60
ccgttcagtt gtgaagacct ctgctctgcc ctcagcaacc agagcctcgt cactctggac 120
ctgggtcaga atcccttggg gtctagtgga gtgaagatgc tgtttgaaac cttgacatgt 180

```
tccagtggca ccctccggac actcaggttg aaaatcgatg actttaatga tgaactcaat    240

aagctgctgg aagaaataga agaaaaaaac ccacaactga ttattgatac tgagaaacat    300

catccctggg cagaaaggcc ttcttctcat gacttcatga tctgaatccc cccgagtcat    360

tcattctcca tgaagtcatc gattttccag gtgttggtga actgcctgtg actcctctcc    420

tccccggccc ctacccctca gggataatga gttcattgct gggctagatg ttttagccat    480

gattctgcc                                                            489
```

<210> SEQ ID NO 438
<211> LENGTH: 580
<212> TYPE: DNA
<213> ORGANISM: Homo sapiens
<220> FEATURE:
<221> NAME/KEY: misc_feature
<222> LOCATION: (275)..(275)
<223> OTHER INFORMATION: n is a, c, g, t or u
<220> FEATURE:
<221> NAME/KEY: misc_feature
<222> LOCATION: (284)..(285)
<223> OTHER INFORMATION: n is a, c, g, t or u
<220> FEATURE:
<221> NAME/KEY: misc_feature
<222> LOCATION: (293)..(294)
<223> OTHER INFORMATION: n is a, c, g, t or u
<220> FEATURE:
<221> NAME/KEY: misc_feature
<222> LOCATION: (303)..(304)
<223> OTHER INFORMATION: n is a, c, g, t or u
<220> FEATURE:
<221> NAME/KEY: misc_feature
<222> LOCATION: (313)..(314)
<223> OTHER INFORMATION: n is a, c, g, t or u
<220> FEATURE:
<221> NAME/KEY: misc_feature
<222> LOCATION: (322)..(323)
<223> OTHER INFORMATION: n is a, c, g, t or u
<220> FEATURE:
<221> NAME/KEY: misc_feature
<222> LOCATION: (327)..(327)
<223> OTHER INFORMATION: n is a, c, g, t or u
<220> FEATURE:
<221> NAME/KEY: misc_feature
<222> LOCATION: (332)..(333)
<223> OTHER INFORMATION: n is a, c, g, t or u
<220> FEATURE:
<221> NAME/KEY: misc_feature
<222> LOCATION: (350)..(351)
<223> OTHER INFORMATION: n is a, c, g, t or u
<220> FEATURE:
<221> NAME/KEY: misc_feature
<222> LOCATION: (369)..(370)
<223> OTHER INFORMATION: n is a, c, g, t or u
<220> FEATURE:
<221> NAME/KEY: misc_feature
<222> LOCATION: (386)..(386)
<223> OTHER INFORMATION: n is a, c, g, t or u
<220> FEATURE:
<221> NAME/KEY: misc_feature
<222> LOCATION: (389)..(389)
<223> OTHER INFORMATION: n is a, c, g, t or u
<220> FEATURE:
<221> NAME/KEY: misc_feature
<222> LOCATION: (408)..(408)
<223> OTHER INFORMATION: n is a, c, g, t or u
<220> FEATURE:
<221> NAME/KEY: misc_feature
<222> LOCATION: (427)..(427)
<223> OTHER INFORMATION: n is a, c, g, t or u
<220> FEATURE:
<221> NAME/KEY: misc_feature
<222> LOCATION: (446)..(446)
<223> OTHER INFORMATION: n is a, c, g, t or u
<220> FEATURE:
<221> NAME/KEY: misc_feature
<222> LOCATION: (523)..(523)
<223> OTHER INFORMATION: n is a, c, g, t or u

<400> SEQUENCE: 438
agcgagaccc agactcgtac aacaaacacc tcttcgtgca cattgggcat gccaaccatt 60
cttacagtga cccattgctt gaatcagtgg acattcgtca gatttatgac aaatttcctg 120
aaaagaaagg tggcttaaag gaactgtttg gaaagggccc tcaaaatgcc ttcttcctcg 180
taaaattctg ggctgattta aactgcaata ttcaagatga tgctggggct ttttatggtg 240
taaccagtca gtacgagagt tctgaaaata tgacngtcac ctgnnccacc aanntttgct 300
ccnntgggaa gcnngtagta gnnaaantag anncggagta tgcaaggttn nagaatggcc 360
gatttgtann ccgaataaac cgctcnccna tgtgtgaata tatgatcnac ttcatccaca 420
agctcanaca cttaccagag aaatanatga tgaacagtgt tttggaaaac ttcacaattt 480
tattggtggt aacaaacagg gatacacaag aaactctact ctngcatggc ctgtgtgttt 540
gaagtttcaa atagtgaaca cggagcacaa catcatattt 580

<210> SEQ ID NO 439
<211> LENGTH: 581
<212> TYPE: DNA
<213> ORGANISM: Homo sapiens

<400> SEQUENCE: 439
gcacggacac ctatgaagac cagcagtgga gaccccccaa gcccactggt gaaacagctg 60
agtgaagtat ttgaaactga agactctaaa tcaaatcttc ccccagagcc tgttctgccc 120
ccagaggcac ctttatcttc tgaattggac ttgcctctgg gtacccagtt atctgttgag 180
gaacagatgc caccttggaa ccagactgag ttcccctcca aacaggtgtt ttccaaggag 240
gaagcaagac agcccacaga aacccctgtg gccagccaga gctccgacaa gccctcaagg 300
gaccctgaga ctcccagatc ttcaggttct atgcgcaata gatggaaacc aaacagcagc 360
aaggtactag ggagatcccc cctcaccatc ctgcaggatg acaactcccc tggcaccctg 420
acactacgac agggtaagcg gccttcaccc ctaagtgaaa atgttagtga actaaaggaa 480
ggagccattc ttggaactgg acgacttctg aaaactggag gacgagcatg ggagcaaggc 540
caggaccatg acaaggaaaa tcagcacttt cccttggtgg a 581

<210> SEQ ID NO 440
<211> LENGTH: 449
<212> TYPE: DNA
<213> ORGANISM: Homo sapiens

<400> SEQUENCE: 440
ggcgtataat tcagccctgt ttaaatatac ttgcctttca aattcttcaa gtaacatggg 60
aagtattctt gaaatgtcac attttctgcc ttccctctaa gtatgctttc tgaagaagtc 120
agggaaagtt agagtctgtg gcctgaggtg tctgctctgg gtggcgatag tgggcacctc 180
aggcaggtcg gtgacgttta gcacaggtgc cagggctcct gcctgctcct cctgtgttag 240
ctctgtgaag ttcatttagg aatttttttt tcctatgcag tttaagaaat aatcctaatt 300
gtttttcttt attacctaag caatatattt ttattatagc aacctcagaa aagaaaaata 360
aaaggataat ttaaaaaact cattcatagt ctcagttacc cagataacct cggttgtcac 420
cttggagtat cttgttgtag tccctttac 449

<210> SEQ ID NO 441

<211> LENGTH: 457
<212> TYPE: DNA
<213> ORGANISM: Homo sapiens

<400> SEQUENCE: 441
agcagaggct catccgggag cagatacgcc aggagcgtga ccagaggttg agaggaaagg 60
cagaaaatac tgaaggccaa ggaacccccca aactaaagct aaaatggaag tgcaagaagg 120
aggatgagtc aaaaggtggc tactccaaag acgtcctcct acggcttttg cagaagtatg 180
gtgaggttct caacctggtg ctttccagta agaagccagg cactgctgtg gtggagtttg 240
caaccgtcaa ggcagcggag ctggctgtcc agaatgaagt tggcctggtg gataaccctc 300
tgaagatttc ctggttggag ggacagcccc aggatgccgt gggccgcagc cactcaggac 360
tgtcaaaggg ctcagtgctg tcagagaggg actacgagag cctcgtcatg atgcgcatgc 420
gccaggcggc cgagcggcaa cagctgatcg cacggat 457

<210> SEQ ID NO 442
<211> LENGTH: 498
<212> TYPE: DNA
<213> ORGANISM: Homo sapiens

<400> SEQUENCE: 442
aaggctatta acgacgcgat ttcacaaagt cggcagagtt ctgcgggaaa tcccctggaa 60
agactcaatt aaagagcagt gaagagagtg cagatcccgt cactggaagt tcggaaaatg 120
cagtgtcatc ttcagaactg atgtcccaga ctcccagtga agttctgggt accaacgaga 180
atgagaaact gagccctaca agtaatacct catatagttt agaaaaaatc tccagtctgg 240
cccctcctag catggagtac tgcgttttac tcttctgctg ttgtatttgt ggttttgaat 300
caaccagcaa agaaaacctc ttggatcata tgaaagagca cgagggtgaa attgtaaaca 360
tcatcctgaa taaggaccac aatacagctc taaacacaaa ttaggtggaa taatgactcg 420
agcaggaaag cagtagaaga ggattccttc accacagttt cacctttacg ctgtcagaca 480
acttcctgcc acagaaga 498

<210> SEQ ID NO 443
<211> LENGTH: 476
<212> TYPE: DNA
<213> ORGANISM: Homo sapiens
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (243)..(243)
<223> OTHER INFORMATION: n is a, c, g, t or u
<220> FEATURE:
<221> NAME/KEY: misc_feature
<222> LOCATION: (245)..(245)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u
<220> FEATURE:
<221> NAME/KEY: misc_feature
<222> LOCATION: (320)..(320)
<223> OTHER INFORMATION: n is a, c, g, t or u
<220> FEATURE:
<221> NAME/KEY: misc_feature
<222> LOCATION: (362)..(362)
<223> OTHER INFORMATION: n is a, c, g, t or u
<220> FEATURE:
<221> NAME/KEY: misc_feature
<222> LOCATION: (370)..(370)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (398)..(398)
<223> OTHER INFORMATION: n is a, c, g, t or u
<220> FEATURE:
<221> NAME/KEY: misc_feature
<222> LOCATION: (419)..(420)
<223> OTHER INFORMATION: n is a, c, g, t or u
<220> FEATURE:
<221> NAME/KEY: misc_feature
<222> LOCATION: (429)..(429)
<223> OTHER INFORMATION: n is a, c, g, t or u
<220> FEATURE:
<221> NAME/KEY: misc_feature
<222> LOCATION: (438)..(438)
<223> OTHER INFORMATION: n is a, c, g, t or u

<400> SEQUENCE: 443
caaccgagag ggccggcagg agcttgaaat cattattgga gatgaacaca tttcttttac 60
aacatcaaaa atnggttccc ttattgatgt cagtcaatcc aaggatccag aaggcttatg 120
agtattttat tatcctgtcc aggaccctga agtgtttggt cttcagtctt actggattac 180
acttcaagat taaaccaatc taaactgaat attgatgtgg acatgggggg gtgggagtag 240
ttntnaatta ccattatcaa gaacatttng tgtcagggca gtatattttt ataaactata 300
tatgattatc tttaataaan tatgtgataa aatttaaaaa aagcaaaaca aaacttctag 360
angaataccn tcaaaacctt ggtgagggan attcttanac agcacaaaaa tcattaggnn 420
aagatcaant ttaacatngt caaattaatc aatgacttct cttcctcaaa agacat 476

<210> SEQ ID NO 444
<211> LENGTH: 133
<212> TYPE: DNA
<213> ORGANISM: Homo sapiens

<400> SEQUENCE: 444
ttccagagct acccagacca tatggtgcac ccacagatcc agctgcagct ggtcctttag 60
gtccatgggg atccatgtct tctggacctt gggcgccagg aatgggaggg cagtatccta 120
cccctaatat gcc 133

<210> SEQ ID NO 445
<211> LENGTH: 353
<212> TYPE: DNA
<213> ORGANISM: Homo sapiens

<400> SEQUENCE: 445
cgccgctgcg aattctcgga caaaactgtc aacagcccgg gcgcgccttt tggctctgcg 60
ggtccctcta tttatgcaaa gccgacctat gctacagccc cccaaccccc gacctggggt 120
agggaggaag agggtgccgg ggaagggagt ccgccctgtc caggcactag aggctccctt 180
gacgtttggc agatgaaaaa caactaagcc tttttgaggt gtagagattc tcaggtccag 240
gcgttaaaaa ataatggtca aaagaataat acaaaaatag taaaggtctt gaagaatgcc 300
agcgaagcaa ttcttttta tttgaggaca cttgtctggt gtactttttc atg 353

<210> SEQ ID NO 446
<211> LENGTH: 416
<212> TYPE: DNA

<213> ORGANISM: Homo sapiens
<220> FEATURE:
<221> NAME/KEY: misc_feature
<222> LOCATION: (275)..(278)
<223> OTHER INFORMATION: n is a, c, g, t or u

<400> SEQUENCE: 446
gaggaagata tcctggctgg cactctttca gttgacagag agtgacctca ggctggggcg 60
gctcctcctc cgtgtggccc cggatcagca caccaggctg ctgcctttcg ctttttacag 120
tcttctctcc tacttccatg aagacgcggc catcagggaa gaggccttcc tgcatgttgc 180
tgtggacatg tacttgaagc tggtccagct cttcgtggct ggggatacaa gcacagtttc 240
acctccagct ggcaggagcc tggagctcaa gggtnnnnca gggcaacccc gtggaactga 300
taacaaaagc tcgtcttttt ctgctgcagt taatacctcg gtgcccgaaa aagagcttct 360
cacacgtggc agagctgctg gctgatcgtg gggactgcga cccagaggtg agcgcc 416

<210> SEQ ID NO 447
<211> LENGTH: 409
<212> TYPE: DNA
<213> ORGANISM: Homo sapiens

<400> SEQUENCE: 447
gctccccaca tgctggtggt gtactctgct aatggagaga tgtttaaact gagagctgct 60
gatgcaaaag agaaacaatt ctgggtgact cagcttcgag cttgtgccaa ataccacatg 120
gaaatgaatt ctaagagtgc tccaagctcc cgaagccgaa gtctcacttt gctcccacat 180
ggaacaccca attctgcgtc tccctgtagc cagagacacc tcagtgtggg ggcccccggt 240
gttgtcacaa tcacgcatca caagtcgcct gcagccgccc gaagagccaa gagtcagtat 300
tccggccagc ttcacgaagt cagagaggta cacactctcc tgacagagga aagctgtttg 360
ctgcactggt ttactggata gattaactgg gttgaggctg tgtaattta 409

<210> SEQ ID NO 448
<211> LENGTH: 316
<212> TYPE: DNA
<213> ORGANISM: Homo sapiens

<400> SEQUENCE: 448
gaggggcaca tgcaagtcac caaagtggga agccttcacc aaggccacac ccaaagtcta 60
ctgattgtct gtccaaagtt cgttgattcc tggccatgaa caagcacaat agaaaaagac 120
acagggtcct agtggctaca agtcaatgtg aattggcaca tggtctagca gttttaaaat 180
ctgacagtag agtatggcaa tgggcaaggg ccaagaagtc ctgagatggg aggtcagcgc 240
tctaactggg ctcagtggag gtctgtgacc agtgtctgga cactagctac aggggaccgg 300
gcagaggatt ctgggc 316

<210> SEQ ID NO 449
<211> LENGTH: 473
<212> TYPE: DNA
<213> ORGANISM: Homo sapiens
<220> FEATURE:
<221> NAME/KEY: misc_feature
<222> LOCATION: (241)..(241)
<223> OTHER INFORMATION: n is a, c, g, t or u
<220> FEATURE:
<221> NAME/KEY: misc_feature
<222> LOCATION: (341)..(341)
<223> OTHER INFORMATION: n is a, c, g, t or u
<220> FEATURE:
<221> NAME/KEY: misc_feature
<222> LOCATION: (384)..(385)
<223> OTHER INFORMATION: n is a, c, g, t or u
<220> FEATURE:
<221> NAME/KEY: misc_feature
<222> LOCATION: (417)..(417)
<223> OTHER INFORMATION: n is a, c, g, t or u
<220> FEATURE:
<221> NAME/KEY: misc_feature
<222> LOCATION: (420)..(420)
<223> OTHER INFORMATION: n is a, c, g, t or u
<220> FEATURE:
<221> NAME/KEY: misc_feature
<222> LOCATION: (427)..(427)
<223> OTHER INFORMATION: n is a, c, g, t or u
<220> FEATURE:
<221> NAME/KEY: misc_feature
<222> LOCATION: (430)..(430)
<223> OTHER INFORMATION: n is a, c, g, t or u

<400> SEQUENCE: 449
gcactttagt gattgctttt attacattag ttaagatgtc ttgagagacc atctcctatc 60
ttttatttca ttcatatcct ccgccctttt tgtcctagag tgagagtttg gaaggtgtcc 120
aaatttaatg tagacattat cttttggctc tgaagaagca aacatgacta gagacgcacc 180
ttgctgcagt gtccagaagc ggcctgtgcg ttcccttcag tactgcagcg ccacccagtg 240
naaggacact cttggctcgt ttgggctcaa ggcaccgcag cctgtcagcc aacattgcct 300
tgcatttgta ccttattgat ctttgcccat ggaagtctca nagatctttc gttggttgtt 360
tctctgagct ttgttactga aatnngcctc gtggggagca tcagagaagg ccaggangan 420
tggtgtnttn ccctagactc tgtaaccacc tctctgtctt tgtccttcct gag 473

<210> SEQ ID NO 450
<211> LENGTH: 512
<212> TYPE: DNA
<213> ORGANISM: Homo sapiens
<220> FEATURE:
<221> NAME/KEY: misc_feature
<222> LOCATION: (363)..(363)
<223> OTHER INFORMATION: n is a, c, g, t or u

<400> SEQUENCE: 450
gggaagtagg tgatgccagc cctcaagtct gtcttcagcc agggacttga gaagttatat 60
tgggcagtgg ctccaatctg tggaccagta tttcagcttt ccctgaagat caggcagggt 120
gccattcatt gtctttctct cctagccccc tcaggaaaga aggactatat ttgtactgta 180
ccctaggggt tctggaaggg aaaacatgga atcaggattc tatagactga taggccctat 240
ccacaagggc catgactggg aaaaggtatg ggagcagaag gagaattggg attttagggt 300
gcagctacgc tcaccctaaa cttttggtgg cctggggcat gtcttgaggc ccagactgtt 360
aancaggctc tgctggcctg tttactcgtc accacctctg cacctgctgt cttgagactc 420
catccagccc caggcacgcc acctgctcct gagcctccac tatctccctg tgacgggtga 480
acttcgtgta ctgtgtctcg ggtccatata tg 512

<210> SEQ ID NO 451
<211> LENGTH: 397
<212> TYPE: DNA
<213> ORGANISM: Homo sapiens

<400> SEQUENCE: 451
gtgaacattt caaccagcct tatagctgtt ctcatcatca ccttctgcat tgtgaccgtg 60
cttggaaggg aggctctcac caaaggggcg ctgtgggcag tctttctgct cgcagggtct 120
gccctcctct gtgccgtggt cacgggcgtc atctggaggc agcccgagag caagaccaag 180
ctctcattta aggttccctt cctgccagtg ctccccatcc tgagcatctt cgtgaacgtc 240
tatctcatga tgcagctgga ccagggcacc tgggtccggt ttgctgtgtg gatgctgata 300
ggcttcatca tctactttgg ctatggcctg tggcacagcg aggaggcgtc cctggatgcc 360
gaccaagcaa ggactcctga cggcaacttg gaccagt 397

<210> SEQ ID NO 452
<211> LENGTH: 426
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, t or u

<400> SEQUENCE: 452
gactgtaggt gcgtgggaga aactttgcag gntggggacc cggcggctgc tggccggtag 60
tgactggtgg gcgcgctcga ggactccaag gggcgcagcc cgggggcaga cccttgggtc 120
gggcggggat cttacgcttc ccttacccgc cccctttttgt ctttcacctc agccccgccg 180
gctgctgtgg gagcggcggc cgtccctctc ctggaggtcg tctcctggca tcctcggggc 240
cgcaggaagg aagaggaggc agcggccgga gccctggtgg gcggcctgag gtgagagccc 300
gaccggcccc tttgggaata tggcgaccgg tggctaccgg accagcagcg gcctcggcgg 360
cagcaccaca gacttcctgg aggagtggaa ggcgaaacgc gagaagatgc gcgccaagca 420
gaaccc 426

<210> SEQ ID NO 453
<211> LENGTH: 384
<212> TYPE: DNA
<213> ORGANISM: Homo sapiens

<400> SEQUENCE: 453
ctaaagaaag tacacacact ctctcgctct ctctcggtct tataaaactc gttggtgtct 60
tataaaacaa acagtgataa tctcaagtta gaaaacagta ggtcctgaga accataagaa 120
aaatgactgg tgtgatgttg agtaacaagt tggtacagtt actttagcta tttattaact 180
tgctcatctc atagaacatt ttaatagatt tttcacacac ctcattatta aaaaaaaaca 240
aacatgctgg tgtcttggtt acccattatt cctctgtacc tgaattcagg ttggtttttc 300
tatttggaaa agactttata aatgttggct taaaaagagg ttgagcacca gaatctcaga 360
atttaccacc aaagaactca tcca 384

<210> SEQ ID NO 454
<211> LENGTH: 407
<212> TYPE: DNA
<213> ORGANISM: Homo sapiens

<400> SEQUENCE: 454
agcataatga agcctgcatg tgcccagctt caataattac caatatcttg ccagttttgt 60
ttcgtttctc ctttgattct ctgtattgag caagtcttag acatcatacg tttcccgcgt 120
aagtacctta ttctacatca ttaaccagta aggacttttt aattaaccac aataccacta 180
tcacacctaa taatagtaat tccttatgga tcttttcttt agacctattt ttgaaggcat 240
aaaagcagtt gagtttctgg agaatttttg gatggtgatt aatgacttga ctggctgctc 300
ttcccagagc tgtggcagct ctccccccgt agaagatggg gtttgtattg gcgcaccaag 360
atctccaaca gccagtgtgt gtttcccatt tcctgtaggt tccatca 407

<210> SEQ ID NO 455
<211> LENGTH: 223
<212> TYPE: DNA
<213> ORGANISM: Homo sapiens

<400> SEQUENCE: 455
tagtcagagt gacccatgta tctgggaaga ctctagtctg gactgtggcc cagcttgggg 60
accttgtgtg ctcagatcat cttcaggaag gaaaaggcat cctggagaca ggagtccatt 120
cactcctctg ctctctaccc actcatttgc ttgccaaact tagctttgcc agtgatagtc 180
aatattaaag tgtacttttt tcccctttaa tccaatatag ttg 223

<210> SEQ ID NO 456
<211> LENGTH: 160
<212> TYPE: DNA
<213> ORGANISM: Homo sapiens

<400> SEQUENCE: 456
tataattata accttaccgc atggacagtt ttgaatccta tgctaattgg ggtaattaag 60
tcaattattt catatgttat gttctcttca tgtgcatttt tcaatgatat attatgttcc 120
attgtgttgg aatgtgaatg ttcaattact tttccctata 160

<210> SEQ ID NO 457
<211> LENGTH: 465
<212> TYPE: DNA
<213> ORGANISM: Homo sapiens

<400> SEQUENCE: 457
ccacatccat ggcctaggag ctactgggca ggttcccggc cacacatctg gtgggctgtt 60
ttgttttttt ttttcctctt cccccagatg tcttgacggg atcactgggg ctctttgtga 120
gtgagggtgg ccaaactacc gccggaggag atggggtctc agagcgagag ctgcggaggg 180
ggaggggaag aagaaggcct cacttttgct gctgcggggc ccacacagcc gctgctactt 240
tggggggtgg ggaaggggcc aagctgcaga cacacacagt cattcatttc tgtccacacc 300
cctgtgggtg gcgggtgtgc gtgtgtgtgc ttgtgtgtgc gcacgtgtcg gcgctcacac 360
acacatgcta gcccactgat gcacccagcc cagggctggc agtctttgca gcgtggggcc 420
gtctcaccct ggagcctgga gaggatctat gcttgtttgt ttttg 465

<210> SEQ ID NO 458
<211> LENGTH: 212
<212> TYPE: DNA
<213> ORGANISM: Homo sapiens
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (158)..(158)
<223> OTHER INFORMATION: n is a, c, g, t or u

<400> SEQUENCE: 458
gtgccgctgg cacccgggaa gacgctgggg gccggcgctg tagagccggg catgggctgg 60
gatgtgtttg gattccaatc cgggcctgac accagttcag tgacctcggg aagttcccca 120
ancctccggg cctgtttcct ccctctgaag tggcgacnag tagtagaacc gacctcgtag 180
gctcatcggg aggtcctgat gggagaaccc at 212

<210> SEQ ID NO 459
<211> LENGTH: 342
<212> TYPE: DNA
<213> ORGANISM: Homo sapiens
<220> FEATURE:
<221> NAME/KEY: misc_feature
<222> LOCATION: (161)..(162)
<223> OTHER INFORMATION: n is a, c, g, t or u

<400> SEQUENCE: 459
ggttgtactc aagatgtttt cctggaaaaa ttcattctgc tttctgacca ggatttccag 60
aaactctgac ccttctaaga ggtctgggtg gaattgtgat ggtgattctg ctagtagaca 120
gtgtaacttc tgcgtctaca aaaagaggat aggccgtcac nnctcacatg gctttgcgtg 180
aaagcccaat ggtactgtct ctatggcaga gatgaggaag gaacaccagc gtcctccaac 240
tttcctgttc ttcctttggg ttaatggcca ctgtaaggaa acagttttct gccacgtgtg 300
gggtgatttg aatgtaaaat gcccaactct catagcaggc tg 342

<210> SEQ ID NO 460
<211> LENGTH: 519
<212> TYPE: DNA
<213> ORGANISM: Homo sapiens

<400> SEQUENCE: 460
aaggggaaga tttgctgctg ctgccgggcc aagttcccgc tgttctcgtg gccgcccagc 60
tgtctcttct gcaagagagc cgtctgcact tcctgtagca taaagatgaa gatgccttct 120
aagaaatttg gacacatccc tgtctacaca ctgggctttg agagtcctca gagggtatca 180
gctgccaaaa ccgcgccaat ccagagaaga gacatctttc agtctctgca agggccacag 240
tggcagagcg tggaggaggc gttcccccac atctactccc acggctgtgt cctgaaggat 300
gtctgcagtg agtgcaccag ctttgtggca gacgtggtgc gttccagccg caagagcgtg 360
gacgtcctca acactacgcc acgacgcagt cgccagaccc aatccctcta catccctaac 420
accaggactc ttgacttcaa gtgacagccc caggtggcca ggcctccagg aggcaccagg 480
caggccctgt atcaggctag gacgctctga gctgtgcat 519

<210> SEQ ID NO 461
<211> LENGTH: 208
<212> TYPE: DNA
<213> ORGANISM: Homo sapiens

<400> SEQUENCE: 461 tccccctct gaattttact gatgaagaaa ctgaggccac agagctaaag tgacttttcc 60
caaggtcgcc cagcgaggac gtgggacttc tcagacgtca ggagagtgat gtgagggagc 120
tgtgtgacca tagaaagtga cgtgttaaaa accagcgctg ccctctttga aagccaggga 180
gcatcattca tttagcctgc tgagaaga 208

<210> SEQ ID NO 462
<211> LENGTH: 532
<212> TYPE: DNA
<213> ORGANISM: Homo sapiens

<400> SEQUENCE: 462
ctcagcattt agtgaaggta attccaaaat actggtatca gtactcttat ttataagtgt 60
acggaatgca taacatgaac attagtcaaa gaacttttaa tataattcac tttttaagtg 120

```
ttaaaattta aaggtcaagt aaaattgtaa atttgtaata tggaaacatt aagcgtcatt    180

atcatacaaa ttattagcag ataaccttaa taaaaataaa cgtttgcggg tttttttga     240

gacagggtct cgctttgtca cctaagctgg agtgcagtgc gcgatctcgg ctcactgcaa    300

cttccgcctc ctgggatcaa gtgattctcc tgccttagcc tcctgagtat ctgggtttac    360

aggtgtgtac cgccacaccc gtctctacta aaaatacaaa aaacaaaaaa agattagctg    420

ggcgtggtgg caggtgcctg tggtcccagc tgctcgggag gctgaggcag gagaatagca    480

tggacctggg aggcggagct tgcagtgagc tgaaatggtg ccactgcact cc            532


<210> SEQ ID NO 463
<211> LENGTH: 542
<212> TYPE: DNA
<213> ORGANISM: Homo sapiens

<400> SEQUENCE: 463

attatcgatc atgtctattg ctccccgtcc cttcgctgcg ttcagactgc acacaatatc     60

ttgaaaggtt tacaacaaga aaatcacttg aagatccgtg tagagcccgg cttatttgag    120

tggacaaaat gggttgctgg gagcacatta cctgcatgga tacctccatc agagttagct    180

gcagccaacc tgagtgttga tacaacctac agacctcaca ttccaatcag caaattagtt    240

gtttcagaat cctatgatac ttatatcagt agaagtttcc aagtaacaaa agaaataata    300

agtgaatgta aaagtaaagg aaataacatc ctgattgtgg cccacgcatc ttcccttgaa    360

gcgtgtacct gccaacttca gggcctgtca cctcagaact ccaaggactt cgtacaaatg    420

gtccgaaaga tcccatatct gggattttgt tcctgtgaag aattaggaga aactggaata    480

tggcagctga cagatccacc aatccttcct cttacccatg gaccaactgg gggcttcaac    540

tg                                                                   542


<210> SEQ ID NO 464
<211> LENGTH: 451
<212> TYPE: DNA
<213> ORGANISM: Homo sapiens
<220> FEATURE:
<221> NAME/KEY: misc_feature
<222> LOCATION: (368)..(368)
<223> OTHER INFORMATION: n is a, c, g, t or u

<400> SEQUENCE: 464

cagccccatg acagcgaagg gacctttctg tccccgcccc tgtccctgtg ctgggcccac     60

gtactcaccc acgtactggt gcccggctcc cctgggcacc cagagccccc cagataggcc    120

ggtggaggag gtggaggagc tgtcccccca aaactactgg cctgtggtct ggactccagg    180

gccccatttc tgatgtcgcc aggtgtgcct gagcccatcg gggccaggcc tgaggaagtg    240

tttcttggga ggatgggatg accccctgtt cccaagagat ggcagcacag tggaggccat    300

ggtggaaaag gccctgccat ggggtccttg agggccagga cagcctgagg gagggatggt    360

ggccactncc cacaaggggc ctggtgggaa cgggtcccag gacagactca tagctagacc    420

ccgttggcgg cctctgtgtt gaaccagaac t                                   451


<210> SEQ ID NO 465
<211> LENGTH: 467
<212> TYPE: DNA
<213> ORGANISM: Homo sapiens

<400> SEQUENCE: 465
```

ggccccaggc agttttatga tgacacctgt gttgtcccag aaaaattcga tggagacatc 60
aaacaagagc caggaatgta tcgggaagga cccacatacc aacggcgagg atcacttcag 120
ctctggcagt tttggtagc tcttctggat gacccggcaa attctcattt tattgcctgg 180
actggtcgag gcatggaatt taaactgatt gagcctgaag aggtggcccg acgttggggc 240
attcagaaaa acaggccagc tatgaactat gataaactta gccgttcact ccgctattac 300
tatgagaaag gaattatgca aaaggtggct ggagagagat atgtctacaa gtttgtgtgt 360
gatccagaag cccttttctc catggccttt ccagataatc agcgtccact gctgaagaca 420
gacatggaac gtcacatcaa cgaggaggac acagtgcctc tttctca 467

<210> SEQ ID NO 466
<211> LENGTH: 405
<212> TYPE: DNA
<213> ORGANISM: Homo sapiens
<220> FEATURE:
<221> NAME/KEY: misc_feature
<222> LOCATION: (162)..(162)
<223> OTHER INFORMATION: n is a, c, g, t or u
<220> FEATURE:
<221> NAME/KEY: misc_feature
<222> LOCATION: (301)..(301)
<223> OTHER INFORMATION: n is a, c, g, t or u

<400> SEQUENCE: 466
catacaccta ttaccataca ggggaagtcc ccaagctctc cggcctcaca gactctcacc 60
cacgggcaga gcattcttgg ctgattgagg ggaagttcca gcaatcagca caagtgttct 120 ttataccccca aatcactaaa acatatagag gggtctatgt cngtttcatc cataactcag 180
ccactggtgg aacaaatctc ataatcaaga ggatcatagt ccctggtaag tggatccctg 240
gagcattggc accatgtttt ccagtaaagt ctatctagct gtcagggaag agccacctgc 300
nctctgcaaa gggagaggga aaatcaaaac ccaggaaagg gaatatgttt ctgctccaaa 360
accaccagct tctgcctgtc cccttcactc tttctagatc attct 405

<210> SEQ ID NO 467
<211> LENGTH: 110
<212> TYPE: DNA
<213> ORGANISM: Homo sapiens

<400> SEQUENCE: 467
gaaagagcga gagaagggga aagacaagtc gggagaggcc ggtaggcgtg aggcgggcct 60
gaagcggcag cgggcggcct tcgtccggcg agagctaggc cgaggacccg 110

<210> SEQ ID NO 468
<211> LENGTH: 204
<212> TYPE: DNA
<213> ORGANISM: Homo sapiens

<400> SEQUENCE: 468
ctgcccccca gggctagtga agtggcctct tggataccag ctcaggggac actggcccca 60
caggagttgt gagccctcta gggcagggtg ggagccggga ccctcaggtg tagctgagct 120
gtgacattgc tggtcatcct tggtgctctt gcttttttga aagatgcttt tttttttttt 180
aactgacgta gaatgaagaa ctgc 204

<210> SEQ ID NO 469
<211> LENGTH: 139
<212> TYPE: DNA
<213> ORGANISM: Homo sapiens

<400> SEQUENCE: 469
tcagatagga aggatggata tgtctttatc tacagcagaa gttagttacc ctttcatgag 60
gtgattagtt tacttctagg tggaaaaaga gaggactttg aacttggtgt tgtcacagga 120
gctgctctca tggacaaga 139

<210> SEQ ID NO 470
<211> LENGTH: 115
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, t or u

<400> SEQUENCE: 470
ctcagagatt actcagccag acagagatat tccactggtg cgaaagttac gttccattca 60
cagctttgag ctggaaaaac ntctgaccct ggagccaaag ccagacactg acaag 115

<210> SEQ ID NO 471
<211> LENGTH: 475
<212> TYPE: DNA
<213> ORGANISM: Homo sapiens

<400> SEQUENCE: 471
cagcgcctcc ggttataagt tgaagaaata agaccagttt ccaaataaat gacaaagagc 60
ttggtattcc tgcaggcatc agaatcacct ggaggaggag atgctgctgc tggtggtggc 120
ccagagacca cacattgaga accactgctc tagaaaacca tttgtctttg ctgatggaga 180
aacctggctc taatagaagg gcttgtatgt gtccaggaag tctagtgaat tcgaccatga 240
atccagacat ggccagtggc taaatcctgt gggaagacac tgtgcttctc tctgacccat 300
gaacactctg ctagtcaagc tctctgtcac aaagacaact tgaagagaca gagtggacct 360
cacagaagat accatcgtca ctcttaccaa tgcaactgtg gtgaacagga ccactattat 420
tccttagatc aaaaggacag cacattcaac agcatcctca tggcatgcca gcaat 475

<210> SEQ ID NO 472
<211> LENGTH: 446
<212> TYPE: DNA
<213> ORGANISM: Homo sapiens

<400> SEQUENCE: 472
cggcttgttg ggaccaccaa ccaaggggac cagcgcatcc tgcgcagcag cgcccctccc 60
tccctggctg gccctgctgt tagtcacaga ggccgcaagg ccaagacgtg agtgggctgc 120
ccctccacct aggctttcca ccgtggccac tccctccatg accaggcctg actctgttaa 180
ccactacttg aagtcttgag ggggaaagcc tccagggaga catagggggcc ttctcccttc 240 ttcccaccaa agtagggggt aggcaactgg ttgtcatgga aatggggatc atcacagtcc 300
ccttcccctt caccccacgt ggctgggcag tgttaagggt ggcaagatag tctctgtccc 360 caccccccttg tacttgattc cccagctgtc tttcacacag ccccccaccc ttaggggaag 420
ggggaggggc ttctctacaa tgaggt 446

<210> SEQ ID NO 473
<211> LENGTH: 443
<212> TYPE: DNA
<213> ORGANISM: Homo sapiens

<400> SEQUENCE: 473
gagacttggt ggtctgagct gtcccaagtc ctccggttct tcctcgggat tggcgggtcc 60
acttgccagg gctctggggg cagatttgtg gggacctcag cctgcaccct cttctcctct 120
ggcttccctc tctgaaatag ccgaactcca ggctgggctg agccaaagcc agagtggcca 180
cggcccaggg agggtgagct ggtgcctgct ttgacgggcc aggccctgga gggcagagac 240
aatcacgggc ggtcctgcac agattcccag gccagggctg ggtcacagga aggaaacaac 300
attttcttga aaggggaaac gtctcccaga tcgctccctt ggctttgagg ccgaagctgc 360
tgtgactgtg tcccccttact gagcgcaagc cacagcctgt cttgtcaggt ggaccctgta 420
aatacatcct ttttctgcta acc 443

<210> SEQ ID NO 474
<211> LENGTH: 465
<212> TYPE: DNA
<213> ORGANISM: Homo sapiens

<400> SEQUENCE: 474
cctaattcac acaaagactc cttgtggact ggctgtgccc ctgatgcagc ctgtggctgg 60
agtggccaaa taggagggag actgtggtag gggcagggag gcaacactgc tgtccacatg 120
acctccattt cccaaagtcc tctgctccag caactgccct tccaggtggg tgtgggacac 180
ctgggagaag gtctccaagg gagggtgcag ccctcttgcc cgcacccctc cctgcttgca 240
cacttcccca tctttgatcc ttctgagctc cacctctggt ggctcctcct aggaaaccag 300
ctcgtgggct gggaatgggg gagagaaggg aaaagatccc caagaccccc tggggtggga 360
tctgagctcc cacctccctt cccacctact gcactttccc ccttcccgcc ttccaaaacc 420
tgcttccttc agtttgtaaa gtcggtgatt atatttttgg gggct 465

<210> SEQ ID NO 475
<211> LENGTH: 443
<212> TYPE: DNA
<213> ORGANISM: Homo sapiens

<400> SEQUENCE: 475
agaatgcaaa gaggccgctt ccctaagagg cttggaggag ctgggctcta tcccacaccc 60
acccccaccc cacccccacc cagcctccag aagctggaac catttctccc gcaggcctga 120
gttcctaagg aaaccaccct accggggtgg aagggagggt cagggaagaa acccactctt 180
gctctacgag gagcaagtgc ctgccccctc ccagcagcca gccctgccaa agttgcatta 240
tctttggcca aggctgggcc tgacggttat gatttcagcc ctgggcctgc aggagaggct 300
gagaccagcc cacccagcca gtggtcgagc actgccccgc cgccaaagtc tgcagaatgt 360
gagatgaggt tctcaaggtc acaggcccca gtcccagcct gggggctggc agaggccccc 420
atatactctg ctacagctcc tat 443

<210> SEQ ID NO 476
<211> LENGTH: 458
<212> TYPE: DNA
<213> ORGANISM: Homo sapiens

<400> SEQUENCE: 476
gactcagtgg gcactagaac gcctgaggct gcagctgggc tccccggggt ccttgcagag 60
gaaactcagt ctgctggagc aggaatccca gcagcaggag ctgcagatcc agggcttcga 120
gagtgacctc gccgagatcc gcgccgacaa acagaacctg gaggccattc tgcacagcct 180
gcccgagaac tgtgccagct ggcagtgagg gctgcccaga tccccggcac acactccccc 240
acctgctgtt tacatgaccc aggggggtgca cactacccca caggtgtgcc catacagaca 300
ttccccggag ccggctgctg tgaactcgac cccgtgtgga tagtcacact ccctgccgat 360
tctgtctgtg gcttcttccc tgccagcagg actgagtgtg cgtacccagt tcacctggac 420
atgagtgcac actctcaccc ctgcacatgc ataaacgg 458

<210> SEQ ID NO 477
<211> LENGTH: 475
<212> TYPE: DNA
<213> ORGANISM: Homo sapiens
<220> FEATURE:
<221> NAME/KEY: misc_feature
<222> LOCATION: (342)..(342)
<223> OTHER INFORMATION: n is a, c, g, t or u

<400> SEQUENCE: 477
agcatcctga accagctgtg ttttattatg cacagatatc gtaaaaattt gactgccgca 60
aagaaaaatg agttggtaca aaagacaaaa tcagagttca atttcagcag caagacttat 120
caagaattta attactattt gacatcaatg gttggttgcc tgtggacgtc caaacccttt 180
gcgaaaggaa tatatattga ccctgaaatc ctagaaaaaa ctggagtggc tgaatataaa 240
aacagtttaa atgtagtcca tcatccttct ttcttgagtt acgctgtttc ctttttgcta 300
caggaaagcc cagaagaaag gacagtaaac gtgagctcta tncggggaaa gaaatggagc 360
tggtatttgg actatttatt ttcacagggg ttacaaggct tgaaactttt tataagaagt 420
agtgttcatc attcttccat tcccagagca gagggcataa actgcaacaa tcaat 475

<210> SEQ ID NO 478
<211> LENGTH: 490
<212> TYPE: DNA
<213> ORGANISM: Homo sapiens

<400> SEQUENCE: 478
ctcgcagagt tccgtcgatc aggactggag gaagccacgt ttcaacagat atatagtcaa 60
catgtggcac tgtgcagaat ggagggactg ccgtacccca ccatgtcaga gaccatggcc 120
gtgtgttctc acctgggctc ctgtcgcctc ctgcttgtgg agcccagcag gaacgatctg 180
ctccttcggg tgcggctcaa cgtcagccag gatgatgtgc tgtatgcgct gaaagacgag 240
taaaggggct tcacaagtta aaagactggg gtcttgctgg gttttgtttt ttgagacagg 300
gtcttgctct gtcgcccagg ctggagtgca gtggcacgat catggctcac tgcagccttg 360
acttctcagg cttaggtgac cccccaacct catcctccca ggtggctgaa actacaggca 420
catgccacca tgcccagctg attttttgta gagacagggc ttcaccatgt tgccaagcta 480
gtctacaaag 490

<210> SEQ ID NO 479
<211> LENGTH: 460
<212> TYPE: DNA
<213> ORGANISM: Homo sapiens
<220> FEATURE:
<221> NAME/KEY: misc_feature
<222> LOCATION: (72)..(77)
<223> OTHER INFORMATION: n is a, c, g, t or u
<220> FEATURE:
<221> NAME/KEY: misc_feature
<222> LOCATION: (364)..(364)
<223> OTHER INFORMATION: n is a, c, g, t or u

<400> SEQUENCE: 479 tttttaggg actctcaacc tcctggcagg gttaaaggga gagtacttta aacccatata 60
ccagctgtgc tnnnnnntct ctcactttgc cctgggtaag ctgctgtagg gtcagaagta 120
accctttctg tgccagttga gaatgagcct gtgtggtagc tgatgtcaga ggacaaagct 180
ctctgcaagg gctggacaca gagctgcaga gtcctgaaca tccctccttt caggctgcag 240
aagggagagg caatgaagac aggtgctccg gaagcagcat cagggctctt ggaggggact 300
ggtggggact caggctgggt gcagcctcca aacagagaac ggaacttagg tgtgtctcta 360
cagnctaggc ccagcctagc ccagcccaga acaaacaccc ttcagagcct aaccaaagaa 420
cataagctgc aaaatgtgca cccatatttt aagctgcttt 460

<210> SEQ ID NO 480
<211> LENGTH: 492
<212> TYPE: DNA
<213> ORGANISM: Homo sapiens
<220> FEATURE:
<221> NAME/KEY: misc_feature
<222> LOCATION: (77)..(77)
<223> OTHER INFORMATION: n is a, c, g, t or u

<400> SEQUENCE: 480
cctgtctcct acatttagcc aatgaaaaga atctaaaact ggaaggaaca gaggacctct 60
ctgatgttct tgtgagncaa ggagattgag ttcactatgg agaagtcagc agcaggaggc 120
ccatccctta ctcagttgcc gggacatccc cagtctcggg ggaagaagat gccatgggct 180
tatacccagg ctgtagccaa ctaccaacgt gcctgtttgt ttgttgctct ttccttctct 240
ccatcatagt ctgggtgcca gcgccctgaa gctccgtgct caactgatta aactttactg 300
ccctatggtg accatctagg agaggggagg gcagaggggg tgagggtact attctggatt 360
gagaaaacct atatccattc tttatatcaa tgtatagttt tagtctccta aattgatctg 420
ttattttcca aactattctc ttgtagaaaa ttttccagtg ggcacttaat ggtgcccttg 480
aagaacttcc ta 492

<210> SEQ ID NO 481
<211> LENGTH: 501
<212> TYPE: DNA
<213> ORGANISM: Homo sapiens
<220> FEATURE:
<221> NAME/KEY: misc_feature
<222> LOCATION: (197)..(197)
<223> OTHER INFORMATION: n is a, c, g, t or u
<220> FEATURE:
<221> NAME/KEY: misc_feature
<222> LOCATION: (247)..(247)
<223> OTHER INFORMATION: n is a, c, g, t or u

<400> SEQUENCE: 481
ggagggagag gtccctgcaa ggtcccttcc cgggcagggg agggatggaa atgccgtcac 60
agtagtaggg actggagcgt ctacaaggat ggaggggagc tactcaggcc taacgttagc 120
tacaaggaaa aaggacgcct tccgtgacag atccttgagg tgtctgtgtc tgccccaagt 180
ggccggcagt ggccttncct ccgggcccaa ggcctgcagc cacctgctct aactcttgag 240
tgggggngcg ggggggggacc tgcaggggct cggggacagg acagcagcaa gaggcagggg 300
ccgaggacgg aggccttccc gacagtgggg tgggttgtac attcaagtgt gaggtgaacc 360
ctttggtggg gagggggccc ctgaagcctc ggcggggcca cccctccccg cggcgcctct 420
gagtctaggg agaggggctg ctggctcggc ccggccggcc tggcttcaca gagggtctgc 480
ggattgacac tggttctttt c 501

<210> SEQ ID NO 482
<211> LENGTH: 490
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (271)..(271)
<223> OTHER INFORMATION: n is a, c, g, t or u
<220> FEATURE:
<221> NAME/KEY: misc_feature
<222> LOCATION: (306)..(306)
<223> OTHER INFORMATION: n is a, c, g, t or u
<220> FEATURE:
<221> NAME/KEY: misc_feature
<222> LOCATION: (313)..(313)
<223> OTHER INFORMATION: n is a, c, g, t or u
<220> FEATURE:
<221> NAME/KEY: misc_feature
<222> LOCATION: (352)..(354)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
<222> LOCATION: (359)..(359)
<223> OTHER INFORMATION: n is a, c, g, t or u
<220> FEATURE:
<221> NAME/KEY: misc_feature
<222> LOCATION: (361)..(362)
<223> OTHER INFORMATION: n is a, c, g, t or u
<220> FEATURE:
<221> NAME/KEY: misc_feature
<222> LOCATION: (365)..(365)
<223> OTHER INFORMATION: n is a, c, g, t or u
<220> FEATURE:
<221> NAME/KEY: misc_feature
<222> LOCATION: (367)..(367)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u
<220> FEATURE:
<221> NAME/KEY: misc_feature
<222> LOCATION: (373)..(374)
<223> OTHER INFORMATION: n is a, c, g, t or u
<220> FEATURE:
<221> NAME/KEY: misc_feature
<222> LOCATION: (376)..(377)
<223> OTHER INFORMATION: n is a, c, g, t or u

<400> SEQUENCE: 482
gtgaggagct gttttcatct gtgtctgttg gagatcaaga tgattgctat tccctgttag 60
atgatcagga cttcacttct tttgatttat ttcctgaggg gagtgtctgc agtgatgtcn 120
cntcttctat tagcacttac tgggattggt cagatagcga gtttgaatgg cagttaccag 180
gcagntgaca ttgccagtgg gagtgatgta ctttctgatg tcatacccag tattccaagt 240
tcaccttgcc tgcttcctaa aaagaaaaac nagcaccgga atttagatga actcccttgg 300
agtgcnatga canatgatga gcaggtggaa tatattgagt atctgagtcg gnnngtnant 360
nntgngntgg ncnncnntac tgtcctgtgg tctagtgggc agggacctgg gggccatcag 420
tggctgtagg acttttttac ccctctgttc ctggcctaaa tatgtgatgg gtatgcttca 480
ccttaagtgg 490

<210> SEQ ID NO 483
<211> LENGTH: 231
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u

<400> SEQUENCE: 483
ctttcacact gtggcagccc agtgaagcag actgggccat gaactctcct agccctgggg 60
ccnagcctgt tccacaggca cccctgcagg aggcgctgcc aggagagcct tccatctcgg 120
ggctctttga ggttccctcc ttctgggtgt tcttcaggct gagcagagag gctcctgtac 180
cctctctctc ggaatctgaa gagccagatt taggccgggc aaaggggctc a 231

<210> SEQ ID NO 484
<211> LENGTH: 414
<212> TYPE: DNA
<213> ORGANISM: Homo sapiens

<400> SEQUENCE: 484
ggtgctggaa aaactactat cttgtttaag ttaaaacagg atgaattcat gcagcccatt 60
ccaacaattg gttttaacgt ggaaactgta gaatataaaa atctaaaatt cactatttgg 120
gatgtaggtg gaaaacacaa attaagacca ttgtggaaac attattacct caatactcaa 180
gctgttgtgt ttgttgtaga tagcagtcat agagacagaa ttagtgaagc acacagcgaa 240
cttgcaaagt tgttaacgga aaaagaactc cgagatgctc tgctcctgat tttgctaac 300 aaacaggatg ttgctggagc actgtcagta gaagaaatca ctgaactact cagtctccat 360
aaattatgct gtggccgtag ctggtatatt cagggctgtg atgctcgaag tgtt 414

<210> SEQ ID NO 485
<211> LENGTH: 508
<212> TYPE: DNA
<213> ORGANISM: Homo sapiens

<400> SEQUENCE: 485
tcctctgtcc tctatattca gcatgttcct tgtcagctgc tgggccggcc ctgccttgcg 60
ctagcagagc ctctcctggc agcttctcag gtctccctaa tggagacacc aggctactag 120
gacactggct ggggccaccc cctcctgcct aatgcctcac cttacagctg gggaaactga 180
ggcctggaat ggcccagagt caccaaggca aagttggggc tggtcccagc ctgaggctcc 240
agctgatgcc ctcagctccc agagaggggg tgccccatct agctgggtgc aggggtcact 300
gcttgtcagc tcagggccct gtgcccgctt gcctgttccc ctacatctgt gcctgcacat 360
ccagaactgc ctccttgccg ctgcctccag gaagcccacc ttgagccaga gtcaagggct 420
gcagcactgc ccgatagaac acgcccgccc tcactgctgt tcttgcctta cagccaccat 480
gggaaagctg caacctttct gttttatt 508

<210> SEQ ID NO 486
<211> LENGTH: 555
<212> TYPE: DNA
<213> ORGANISM: Homo sapiens
<220> FEATURE:
<221> NAME/KEY: misc_feature
<222> LOCATION: (400)..(401)
<223> OTHER INFORMATION: n is a, c, g, t or u
<220> FEATURE:
<221> NAME/KEY: misc_feature
<222> LOCATION: (410)..(410)
<223> OTHER INFORMATION: n is a, c, g, t or u

<400> SEQUENCE: 486
tgtcaacttg tcatatacac ctccagggac caaaaacaaa agcagctcgg agtctgtgtt 60
gcctgattgg aaagtagaag ctctggtgta tgctacagca cataacacat ttttactaaa 120
ggaaaaaagc taattatgtc catgcctctc gtaaaactgg ggggaacctt aaagagaaag 180
aactaaggct taagttatct gtagtataat caattagaag taatgaatgg atgcatgtaa 240
aatggatgtg attttttttc aagcttattt tgaaatctta aaaatcaggt tacaccatag 300
ctactcaaaa gttttacaca cttaaaactc agatcagtaa gtgttggtac cttttagact 360
cataaaattg aataaaccat tgcaatgctt taaaaaaaan naaaaaaaan ggttttattg 420
ctatgatttt atggcagaca catccaagca aaaccatttt ccaaatgcag accttcctga 480
tgttatctga aatctgataa aatgacccta ctctctgctg tggttcattc ttgctccatg 540
ctgtccatat ttatg 555

<210> SEQ ID NO 487
<211> LENGTH: 541
<212> TYPE: DNA
<213> ORGANISM: Homo sapiens

<400> SEQUENCE: 487
gtggcactta ggcactatat tattgatatc tacaatggcc tcctggatgc acaaaagacc 60
ctgaagggct tttttgatca gcaaaacaaa aacagaaaag caaaaaacag ttaatttttg 120
tttggtcaag tttactcaac cagaccacct tgataccaac aatgctggag agcatttggc 180
aagagcaggg ccacaatgcc aaattccttg gaaaggtaga cttcctatga tactttcatg 240
gattggcaaa tttgtggggt ttttttggta gtagcttttg agaatgttag tttctggctg 300
gggtagtgac ttacatctgt aatcccagca cttcgggagg cgaaggcagg tggattgctt 360
gtgcccagga gtttgagacc agcctgggta acatggtgag accccatctc tatttttata 420
aaattaaaaa aaaaaaaaaa gatagagaat gttactttcc tataaagcca tgatacccta 480
agtactaaga catgtctgtt gttgtccttt ccttcataac atttctcata acccgtaatt 540
t 541

<210> SEQ ID NO 488
<211> LENGTH: 523
<212> TYPE: DNA
<213> ORGANISM: Homo sapiens
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (106)..(106)
<223> OTHER INFORMATION: n is a, c, g, t or u
<220> FEATURE:
<221> NAME/KEY: misc_feature
<222> LOCATION: (140)..(140)

<223> OTHER INFORMATION: n is a, c, g, t or u

<400> SEQUENCE: 488
cagccctgac gtgaactcat tttattttgg ccaggaccca gaaaggagtc tactgctaag 60
atttcagcat gtcctgtggc tgagtnaatc agagttatga cagganggta ccgggcacac 120
catcgcaatg ctccatcaan gctagtatgt tgtgttcttt ccttcatatc aagtcaactc 180
aagcttgctc tacttacctg gtgtacacag tctaagaact gtaagaagac tggagcaaaa 240
ccactcccct gacagttgag ggtcaagctg ctcctctgac tgaatttgtg accaaaagag 300
agccactctt tttcaaccaa catctggaag ccttcaagtg tcctataaaa gggatcactg 360
agtaactgaa ccagggatgt cacctagggc ataagcagga tggattgtca ttaattttag 420
ttctgaaaaa ggcctattac taagataaaa gcacttcctt ctgatgatag ctaattcaca 480
aatttacctg gacagcaaat ttgttcacta accattccag gat 523

<210> SEQ ID NO 489
<211> LENGTH: 306
<212> TYPE: DNA
<213> ORGANISM: Homo sapiens

<400> SEQUENCE: 489
cggctgtacg actccataat gggcatgggg actcaagata aggtcctgat cagaatcatg 60
gtctcccaca atgaagtgga catgttgaaa attaggtctg aattcaagag aaagtatagc 120
aagtccctgt actactatat ccagcaagac actaagggtg ctgtacctgt gtggtggaga 180
tggctgaagt ccgacacagc acgagcgtcc agaaatggtg ctccccatgc ttccagctaa 240
caggtctaga aaacccgctt gtgactagca gtccctgtgg ctgttcctgt gaggatgacg 300
ttagca 306

<210> SEQ ID NO 490
<211> LENGTH: 170
<212> TYPE: DNA
<213> ORGANISM: Homo sapiens

<400> SEQUENCE: 490
agaagattcc cttgaagcct tctccttcca aaaagtttcg gtctggctca tctttctctc 60
ggcgagcagg ctccagtggc aactcctgca ttacttacca gccatcggtc tctggggaac 120
acaaggcaca agtgacaaca aaggcagaag tggagccagg cgttcacctt 170

<210> SEQ ID NO 491
<211> LENGTH: 532
<212> TYPE: DNA
<213> ORGANISM: Homo sapiens

<400> SEQUENCE: 491
tgggggtgac tgctgcttat taagatgatt catttcattt ccactcgtgg ttgtgatttt 60
caccttctca aaactgagtc agcaagagaa aatcttgtct tagaagggcc agataacact 120
tcgctgtgag aacaggaggg ataatggatt ggagatggct atgtgtaaag cagccctgcc 180
tgctgattta acacactttc aaaatagatg tgtcagtatt catttaaagc aagactctga 240
tgacagaagg aaccttgaaa actacctgat attgaaatgg ttgtgccctt tatagccctt 300
ttgcatctcc ttgactttcc agtcatgcct cctaaatcag aagaaaagct gcaaagaaaa 360
tgttttgtgt ggttctgggc ttatttgaat aatgttcatg accacaggct gccatagcac 420
aagtgagaat ttcagaccac aagggtttaa ggagcagtgc tctcttctct caaagctcag 480
aacggtctct ggatccatgg tatcgtacac ccagtgtgga tattaacatt ct 532

<210> SEQ ID NO 492
<211> LENGTH: 559
<212> TYPE: DNA
<213> ORGANISM: Homo sapiens
<220> FEATURE:
<221> NAME/KEY: misc_feature
<222> LOCATION: (232)..(232)
<223> OTHER INFORMATION: n is a, c, g, t or u
<220> FEATURE:
<221> NAME/KEY: misc_feature
<222> LOCATION: (259)..(259)
<223> OTHER INFORMATION: n is a, c, g, t or u

<400> SEQUENCE: 492
aagggaagtt agcaccttcc tcttggaggt gctgaggatt aaatgagata atacgtggaa 60
agcattaggc atgtagcaca gttagcagat ggtggttggc tccctctgct tttccatcag 120
tctgtggcct agtttaaatg gtgggaggaa gggtgtgaga tttaaggctg gttgtaaggg 180
atcagtcagt gtagttggaa aaattgtaag atgaagttat aggatataga cncaaacctt 240
cctggaaggc cagaaagtnt gcatagcttc aataaaggat ttggctgaaa gcagcgtaat 300
cccctttacc ttgagttgat agcaatagag caaataacat gggaacgtgg gggagtttat 360
tgaatagctt gtttactcat gtggtcctaa gaccaacctt tgattatcca cgggtgcatg 420
attgctctct actcggtggt cggcaaattt aattacccac aggtgtgttg actcaaagcc 480
tctgtcatta aatctatgct gaataaatgc cgtcaggcca gctagtcaag gtgcacaact 540
ctttttgtgc gtggtgtgg 559

<210> SEQ ID NO 493
<211> LENGTH: 287
<212> TYPE: DNA
<213> ORGANISM: Homo sapiens

<400> SEQUENCE: 493
gtaagtctca gtcctttaaa actcagaaaa aggtgtgttt tccaaattta atatttcctt 60
tctgtaagtc tcagtgtctg cactatttgt cttggagact taaaattatc ccttgaaagc 120
ataagaagta caccccaaac cagctttgtc cttcctgtcc tcttctagtt tacattttat 180
gtggttagta attttgtacc taaaagtatt tgaaattcta taaatttgga cttgacgtga 240
gcaaaagaaa atttctacgt aagcgaaact aataaaacta cagtcac 287

<210> SEQ ID NO 494
<211> LENGTH: 476
<212> TYPE: DNA
<213> ORGANISM: Homo sapiens

<400> SEQUENCE: 494
ctgtggcatc tataacctga gttcagtcac ttaataccga ggtcctgcgc tctgctgtgt 60
gcctggccct gggctgggca ctggggacat agcagtgacc gagacagaca ggctcacaag 120
gagacatacg acaaccaggt aaacatggca gacaagagca tgtcagatgc gctgtgaaga 180
acactgcggg gcccctccta ggaggtggca tgagttacat gcagacagag acgatccggg 240
ggcagacgga gttccatgtg ggcagtggt gagggcagac gctctggggc tgggatccct 300
gggagtgttc gagaagcacc gagaaggctt ctgtggctgg agccggccag ctgggggaga 360
tggggccagg gagatggcag gggcctctcc ctgtcccagg acccagagcc aagggaggct 420
ttaagcccag gaccaggggt ctgaaaacga aaagcactca cagtccttga acattg 476

<210> SEQ ID NO 495
<211> LENGTH: 542
<212> TYPE: DNA
<213> ORGANISM: Homo sapiens

<400> SEQUENCE: 495
ggcaacctcc tggacaagga cgacctggcc atcccacccc ccgattacgg cgccgcctcc 60
cgggccttcc ccgcccagac ggccagcggc ttcaagcaga ggccctacag tgtggccgtg 120
cccgccttct cccagggcct ggatgactat ggagcgcggt ccatgagcag tggcagcggc 180
acgctggtgt ccacagtgtg aggacgctga ccccgggcag ccgctgctct gaagagcttc 240
cgcgccttcc ccctggtctc gtccgttttc ctcctcagct ctcgctggtt tgttcttggg 300
ttgtttttct tttccacctg ccccatgcct tttggttggt gaccccagac tctgtgatcc 360
cccagggtcc atggtgctgc tccatccgcc ccccctcccc tgtgtttacg cgccccatcc 420
tgtgtgtccc agccttttga gcagaaactg ccaggcagga cctgctgggc cgtgcggggc 480
accctcggcc tcaccctgca gtgtctgtgg cactcactgc ttttctaagg ctcgccgtga 540
gc 542

<210> SEQ ID NO 496
<211> LENGTH: 438
<212> TYPE: DNA
<213> ORGANISM: Homo sapiens

<400> SEQUENCE: 496
gagaggtatt atcgagacat tgcaaagatg gcatccatca gcgaccagga catggatgcc 60
tacctggtgg agcagtcccg cctccacgcc agcgacttca gcgtcctgag tgcgctcaac 120
gagctgtatt tctatgtcac caagtaccgc caggagattc tcacggctct ggaccgagat 180
gcctcttgtc ggaagcataa gttgcggcag aaactggaac agatcatcag cctcgtgtcc 240
agcgacagct aaggtggtgg aatcggtgag gagggggctt ctcagtcctg tgccgtcctc 300
ccatccaggg gagtggctgg ctcaagcctg ggtccccggg ctgagccctg gattgggtat 360
cgtggggcag gtcaccctgg ccacgatgcc cccggcacac ccaggccccc ttcattagtg 420
ccttgctttg ggccctgc 438

<210> SEQ ID NO 497
<211> LENGTH: 419
<212> TYPE: DNA
<213> ORGANISM: Homo sapiens
<220> FEATURE:
<221> NAME/KEY: misc_feature
<222> LOCATION: (248)..(251)
<223> OTHER INFORMATION: n is a, c, g, t or u

<400> SEQUENCE: 497
taagttctca tccaacattt ctcctggcca tccattctcc atctttaaag gcaatcacca 60
ttgccagttt cttctgtatc cttctggaaa tacaatatat tacataaatg acagcattct 120
atattctctc ttctatatct tacctatttc tgtgaataat ttattttgga cagcatttta 180
tgtatgaata ttcacaaatg tgcttcctta tttcagaggc tgaactaata aaaattttgt 240
ttattttnnn nttgaggcaa tatttttata tggtacccta atctttaata cttaacctgc 300
cagactttaa ccgtaacaca ataatgtatt gccaaatagc accattcttc ttctctcact 360
ctcttgccat gggggctctt aaaaaaaaaa gtatacatct aaggtgtaca acatgctgt 419

<210> SEQ ID NO 498
<211> LENGTH: 477
<212> TYPE: DNA
<213> ORGANISM: Homo sapiens

<400> SEQUENCE: 498
accagtttac ctaggccttg gactgccaaa tagctacaca actgcttaag ctggcctata 60
aggacagacc agagacaaag caagaagatc attggtccag actgagaaga aagttgccag 120
agggatgtct ccactaaggc ctttgagcag ggattaatgc tgtcaccacc ttggtggaga 180
acaagaaagc tcagctggtg gtgactgcac gtgacaatgg atctcataga gctagctgtc 240
ttcctgcctg ccctgcatca taaaatacaa agggaagaga agactgggat gtctagtcca 300
caggaagact tgcaccactg tcgccttcac acagattaac ttggcagaca aaggagcttt 360
ggctaagctg gtggaagcca tcagaaccaa tgacaatgac agacaggatg agatccactg 420
tcactaggga ggcaatatcc tgggtccaaa atctctggct ctcattgcca agctgga 477

<210> SEQ ID NO 499
<211> LENGTH: 366
<212> TYPE: DNA
<213> ORGANISM: Homo sapiens

<400> SEQUENCE: 499
tgagggaggg atgtgcctct ggccacgtgg ttaccttgca gtgcacagcc tgtggtcata 60
gaaggggcta cagctcacgc atcgtgggtg gaaacatgtc cttgctctcg cagtggccct 120
ggcaggccag ccttcagttc cagggctacc acctgtgcgg gggctctgtc atcacgcccc 180
tgtggatcat cactgctgca cactgtgttt atgacttgta cctccccaag tcatggacca 240
tccaggtggg tctagtttcc ctgttggaca atccagcccc atcccacttg gtggagaaga 300
ttgtctacca cagcaagtac aagccaaaga ggctgggcaa tgacatcgcc cttatgaagc 360
tggccg 366

<210> SEQ ID NO 500
<211> LENGTH: 537
<212> TYPE: DNA
<213> ORGANISM: Homo sapiens
<220> FEATURE:
<221> NAME/KEY: misc_feature
<222> LOCATION: (193)..(193)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (379)..(379)
<223> OTHER INFORMATION: n is a, c, g, t or u
<220> FEATURE:
<221> NAME/KEY: misc_feature
<222> LOCATION: (443)..(444)
<223> OTHER INFORMATION: n is a, c, g, t or u
<220> FEATURE:
<221> NAME/KEY: misc_feature
<222> LOCATION: (446)..(446)
<223> OTHER INFORMATION: n is a, c, g, t or u
<220> FEATURE:
<221> NAME/KEY: misc_feature
<222> LOCATION: (448)..(451)
<223> OTHER INFORMATION: n is a, c, g, t or u

<400> SEQUENCE: 500
gaacaatcgt cttttgaact tccagtaggc ccacagttgt tggttgttcc tcaaaacagg 60
ttgtggctcc tgttgaataa gatgatccat taaaaactga acaaggttga ggagaaatag 120
tgcttacgtt gaaaaatctt taagtctttg tccccgttct ctaacttcct tacgttttcg 180
tttatttagc tcnatcccca ctatctactn gaatttctca tatttaaacc aagatgggag 240
actaggtcat taggaaaata ttaccgtcta caattttctt atactttgat ctgtctttta 300
tttgattgta agttgctgat ggacagtgat cattagaaac tgaattttgt ataatactag 360
ttttatatga aactagatnt ttattgcgct caggttatgt tccttttacc tccttcctta 420
ataaagagac cacttgaaat aannananna nttccaagta ctgtctgcac cttatcccac 480
ctctttccca tttatgagat agtgcaaaac cctagcacag tcttttccat ttagtaa 537

<210> SEQ ID NO 501
<211> LENGTH: 332
<212> TYPE: DNA
<213> ORGANISM: Homo sapiens

<400> SEQUENCE: 501
aagtatctcc atacaaaata cggttgaatt acaaaaagaa aattgtaaca ttagcatgga 60
caaacctggc aggtactcct taactctcct aagtaataaa aactgtaaaa tgcaaataag 120
ccttcgatga catttactaa cctttactaa agtatcaatg atgacttggt tgtttaaaca 180
gctgacattt gggcaatttg agtatgtcaa actcaataat actggttttc atttgcaaga 240
tccacttaaa acttaaggag gccaaaaaac atcatttaaa ataccctata aattataatc 300
atacatatga tacgaaaaat atcctacttc ag 332

<210> SEQ ID NO 502
<211> LENGTH: 375
<212> TYPE: DNA
<213> ORGANISM: Homo sapiens

<400> SEQUENCE: 502
agggtaactt ccagtgtcac aatgagcagt tctgtaagtg ggtgcctctc agcacatttc 60
tatgaatata ttatgtagat aggctgtatt gattttggta gcattgacac cttcttaggc 120
aattagttga agaaaactgc aaaatatttt cttatgtaat agctgtatag agcaatagca 180
atcaaagcat gagaaggcac taacgctggg atgaaagatg agattcagag gtgactgaga 240
atcatgtgag tgatggctgt atattttgtg taaaatatat gtgtgaaaat gaactaagag 300
tgagttactc agcactctca agaattatgc agattctgca tttttcttat gccgtgtgcc 360
taaaaaccta cttga 375

<210> SEQ ID NO 503
<211> LENGTH: 468
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, t or u

<400> SEQUENCE: 503
gggacaggat gaccttcccg aggaactcan tggcctgggg tagtttaaga agtaatgttc 60
tttctttctt tctcttttcc ctacctcctg ctaacccaac cagagatccc cttccttgct 120
gagagggttg ggggcaggag gagatttggc agtgcctgca ggttgcctgg ccaggtggag 180
agggggaaag aggaagggca ccgtgggtgt aagatgcctt tctcctccac ccatcgaaac 240
cagccacccc ttccctgtgc caccaagaca gccttttcca gtggccatcc taaggggaac 300
tcccaaatgg gtgttgctgg tggacacaga tgctcccccc aatggaagcc ccaagctctg 360
aggtatgcgg gtagaggctt tggataggtt ttcttctgct cccctctttt atagatctag 420
gctgcttggc tgcctgtctt tctaggcagt ccccctagag gaaaaatg 468

<210> SEQ ID NO 504
<211> LENGTH: 484
<212> TYPE: DNA
<213> ORGANISM: Homo sapiens

<400> SEQUENCE: 504
accccaccac gtaccagatg gatgtgaacc ccgagggcaa atacagcttt ggtgccacct 60
gcgtgaagaa gtgtccccgt aattatgtgg tgacagatca cggctcgtgc gtccgagcct 120
gtggggccga cagctatgag atggaggaag acggcgtccg caagtgtaag aagtgcgaag 180
ggccttgccg caaagtgtgt aacggaatag gtattggtga atttaaagac tcactctcca 240
taaatgctac gaatattaaa cacttcaaaa actgcacctc catcagtggc gatctccaca 300
tcctgccggt ggcatttagg ggtgactcct tcacacatac tcctcctctg gatccacagg 360
aactggatat tctgaaaacc gtaaaggaaa tcacaggttt gagctgaatt atcacatgaa 420
tataaatggg aaatcagtgt tttagagaga gaacttttcg acatatttcc tgttcccttg 480
gaat 484

<210> SEQ ID NO 505
<211> LENGTH: 277
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, t or u

<400> SEQUENCE: 505
ctgcacagtc tccagtgtgg aaagctgtgg gaaaggaagg agcaggttct aggtcttcag 60
gattttctgc atcttaaagc agctcatctc ctttgccctc ctagggagca ggggggccta 120
gctttgggat cgtccnccta gcctcagaaa taattgttca agaaataaca tttctcacac 180
aaaggataaa tgtttgaggg gatggatacc ccatcttcca tgatttgatt attacacatt 240
gcatgcctgt atcaaaaatc tcatatatac acctact 277

<210> SEQ ID NO 506
<211> LENGTH: 515
<212> TYPE: DNA
<213> ORGANISM: Homo sapiens
<220> FEATURE:
<221> NAME/KEY: misc_feature
<222> LOCATION: (380)..(380)
<223> OTHER INFORMATION: n is a, c, g, t or u

<400> SEQUENCE: 506
gggggtgatt agtatgttgg gacaaacacg ctgttgctaa atggaaacac tgacctcaca 60
gtgcatcctc ctgccaacac acacacacac acacctctca cacatgcacg cttacacaca 120
cacacacaca cacacacaca cacacacata cacacacaca cacacacgct ctctctctct 180
ctctctctct ctctctgtca gtgtgttatc ggtgtggagc ggaggccgcg gaggctcctc 240
ggtccttcag cacccctcgg cccgacgcac ccacgcccct caccccccga gagccgaacg 300
ctccccgcac cgcccccggt cccttccctc ggccgggagc gacttctgca gctcgttctt 360
ccgaatcgca ccagcaatgn cggccagccg tagagggagg aagagcccgg ggagcccgag 420
catagcgtaa acggctctct gaccttaatt tcatcctgca tggcgaatct ctgccgtctc 480
tctgaacgca gaagggtctg agactggccg tctcc 515

<210> SEQ ID NO 507
<211> LENGTH: 259
<212> TYPE: DNA
<213> ORGANISM: Homo sapiens

<400> SEQUENCE: 507
ttcagtttat actcaaagcc ctgcagtttc ctgacagcac agagcacacc tgtcacgcga 60
gcaggatgaa gcccagaggc tgcctggtga agtgggcggc gcgctggaaa atccacgtag 120
ctttgttccc tccacgggga gcgtgcaagg ccctctcgag cactacggga gcctcgcctt 180
ctgcacagac ttcggagcca ggtgctggag cggcagcaac tgaggggcgt ggatgtcttt 240
gcatggttcc catacgttt 259

<210> SEQ ID NO 508
<211> LENGTH: 285
<212> TYPE: DNA
<213> ORGANISM: Homo sapiens
<220> FEATURE:
<221> NAME/KEY: misc_feature
<222> LOCATION: (189)..(189)
<223> OTHER INFORMATION: n is a, c, g, t or u

<400> SEQUENCE: 508
atagcagtgg actgtcactc atcagtatct gcagttctgt ttaccaaagc ctgcttgcta 60
gagacgtttc agggcctcct tccctcaaag cgtccactgt acctccatct ggatacaatt 120
agctggctcc ccacttcctg gactgacggt aaccaccttt tccaatgacc ctgaagaaaa 180
catgcaatnt aagctgcttt aagagtaacc tacaactgag gacaaatttt ctatcaactc 240
ccagtacccc tctctgccgt ggctgatttg ttactggttt tcctt 285

<210> SEQ ID NO 509
<211> LENGTH: 274
<212> TYPE: DNA
<213> ORGANISM: Homo sapiens

<400> SEQUENCE: 509
gaggtgcatg ggatcaatgg gacccaatgg ggccagactc tgaggatggg atggtagtag 60
tgaaggacat aggatggggg tagagtgtgg agactttttg aaatagtata gatgaatgcc 120
ctgaggggac tgtgaacaag ctctgcccct cttaggaaat caatggggaa tcaactaaat 180
taaataaaaa atggggtcaa gattaagagg cagggtcacc cagggaatgg tttaggtcct 240
ggcaactctg aaggggttgg aagggctggc agga 274

<210> SEQ ID NO 510
<211> LENGTH: 470
<212> TYPE: DNA
<213> ORGANISM: Homo sapiens

<400> SEQUENCE: 510
gcgtgggttt ttgtatccag agctgtttgg atacagctgc tttgagctac aggacaaagg 60
ctgacagact cactgggaag ctcccacccc actcagggga ccccactccc ctcacacacc 120 ccccccaca aggaaccctc aggccaccct ccacgaggtg tgactaacta tgcaataatc 180
caccccaggt gcagccccag ggcctgcgga ggcggtggca gactagagtt tagatgcccc 240
gagcccaggc agctatttca gcctcctgtt tggtggggtg gcacctgttt cccgggcaat 300
ttaacaatgt ctgaaaaggg actgtgagta atggctgtca cttgtcgggg gcccaagtgg 360
ggtgctctgg tctgaccgat gtgtctccca gaactattct gggggcccga caggtgggcc 420
tgggaggaaa atgtttacat ttttaaaggc acactggtat ttatatttca 470

<210> SEQ ID NO 511
<211> LENGTH: 193
<212> TYPE: DNA
<213> ORGANISM: Homo sapiens

<400> SEQUENCE: 511
gaaaatgaat tccatgttct tgaaggaaag actgtaacta tgtacattca tgatgttcct 60
ttggtgtgtg gtttctgtga gtaacaggta gatgtcattt ctggaaatgg tatgtttatg 120
tctatacatt gttttataaa actccatgga gaaagaaggg gtttacttgc tttgtatcac 180
atagcaataa cat 193

<210> SEQ ID NO 512
<211> LENGTH: 452
<212> TYPE: DNA
<213> ORGANISM: Homo sapiens

<400> SEQUENCE: 512
ctggcccacc caggaacagt gagggcgacg agaactacat ggagttcctc gaggtgctga 60
ccgagggcct tgagcgggtg ctgttggtgc gcggtggtgg ccgtgaagtc atcaccatct 120
actcctgagc ccagtgtcat cttgtggcct ggagtcgagg tcttggccag gacataacaa 180
gctgtggtct ggggtaacag cctcttccca gcacccacct gccagccctg cttgcctggc 240
cctgtcctgg acccagcttt gctaggtctc cttggaaacc aggcctgggc ctcaaaatgg 300
agatggatcc caggtcttgt gggaccctgg gatgtttggg gactttacta tctagcaccc 360
cagtaggcct gtcctggcca gagaagactg gtaggggccg agtggggttt gaaggcagcc 420
ggcccggccc agcccaggag cgctatttat tg 452

<210> SEQ ID NO 513
<211> LENGTH: 411
<212> TYPE: DNA
<213> ORGANISM: Homo sapiens

<400> SEQUENCE: 513
ttggaggcct ttgcagcggc ctacaaaggc acgcggccgt ttgccagtgc caacagcgtg 60
ctggacccca tcctcttcta cttcacccag aagaagttcc gccggcgacc acatgagctc 120
ctacagaaac tcacagccaa atggcagagg cagggtcgct gagtcctcca ggtcctgggc 180
agccttcata tttgccattg tgtccggggc accaggagcc ccaccaaccc caaaccatgc 240
ggagaattag agttcagctc agctgggcat ggagttaaga tccctcacag gacccagaag 300
ctcaccaaaa actatttctt cagccccttc tctggcccag accctgtggg catggagatg 360
gacagacctg ggcctggctc ttgagaggtc ccagtcagcc atggagagct g 411

<210> SEQ ID NO 514
<211> LENGTH: 423
<212> TYPE: DNA
<213> ORGANISM: Homo sapiens
<220> FEATURE:

<221> NAME/KEY: misc_feature
<222> LOCATION: (110)..(111)
<223> OTHER INFORMATION: n is a, c, g, t or u

<400> SEQUENCE: 514
tcgtttctct gaacacacaa cacccatcgt cctcttttat gttacttgaa atatcaaaag 60
aattattaca gctgaaaaca aatctatgta aatcggatct tgaaagagan naagctttct 120
ccagttttga aaggcgccat ttttaacttt gatcttgtaa tgacaaataa gaatgttgaa 180
tcggctggct tttttctatc ctaggtaatg tggactgtgg agctctgtgc tggtcacttt 240
caaccctgaa cctgatgcta cttattttgc agttctaagt gcaaagtcgg cctggtggat 300
gcttcccatt ataatattaa atttgcttct tcgtgaggtc acacctcaca tccccagtgt 360
cactttaata actagtgttt tttacatggt gggccatgac ccattagtgg actctgcatt 420
taa 423

<210> SEQ ID NO 515
<211> LENGTH: 230
<212> TYPE: DNA
<213> ORGANISM: Homo sapiens

<400> SEQUENCE: 515
ccctggcaag gcccgggaca ggaaggccta cacggtcctc ctatacggaa acggtccagg 60
ctatgtgctc aaggacggcg cccggccgga tgttaccgag agcgagagcg ggagccccga 120
gtatcggcag cagtcagcag tgcccctgga cgaagagacc cacgcaggcg aggacgtggc 180
ggtgttcgcg cgcggcccgc aggcgcacct ggttcacggc gtgcaggagc 230

<210> SEQ ID NO 516
<211> LENGTH: 426
<212> TYPE: DNA
<213> ORGANISM: Homo sapiens

<400> SEQUENCE: 516
atgaccttcg aatgcatagg cctttaatgg tgcagacaga ggaccagtat gttttcctca 60
atcagtgtgt tttggatatt gtcagatccc agaaagactc aaaagtagat cttatctacc 120
agaacacaac tgcaatgaca atctatgaaa accttgcgcc cgtgaccaca tttggaaaga 180
ccaatggtta catcgcctaa ttccaaagga ataacctttc tggagtgaac cagaccgtcg 240
cacccacagc gaaggcacat gcccgatgtc gacatgtttt atatgctaat atcttaattc 300
tttgttctgt tttgtgagaa ctaattttga gggcatgaag ctgcatatca tagatgacaa 360
attggggctg tcgggggctg tggatgggtg gggagcaaat catctgcatt cctgatgacc 420
aatggg 426

<210> SEQ ID NO 517
<211> LENGTH: 448
<212> TYPE: DNA
<213> ORGANISM: Homo sapiens

<400> SEQUENCE: 517
gagcaagttg taaattgtct cttatcggac ttaaaagggt gcctggctct tacttagttg 60
attatctcct ggatctggaa agaaaggaag gaaaacaaag gcggaagggg aatctctata 120
gaatgtggat tttcccaca agagactttg cagggcaatt tcaaggtatg gcacggaaat 180
atattttggg gttaaatatt tttttccttg tctcataatg ttatgccaga gtcagattga 240
aaagtaaatc acaacatata gggtcaaata aaacccatct gatgagaatg tgtggtttgt 300
agggcatgac ttcctagacc tcttaggtag gaatctgggt aagacagaat atcagactta 360
gtcctcaatt cctaatgcaa agttctgaga tccaaaatgc tccaaaatct aaaacatttt 420
ttagcaccga cataatgcca caagtgga 448

<210> SEQ ID NO 518
<211> LENGTH: 148
<212> TYPE: DNA
<213> ORGANISM: Homo sapiens

<400> SEQUENCE: 518
aattaacacc aggaacagca ccttgaatat tcctttttca agttcctctt cctcaggaga 60
tattcaaggt cgaaacacaa gccccaatgt ttctgtacag aaatccaatc ccatgaggat 120
tactgagagt catgccacca agggccac 148

<210> SEQ ID NO 519
<211> LENGTH: 173
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, t or u

<400> SEQUENCE: 519
gaaaatcaca actctaacca taatcatctg cactatatgc ctcgcatcag gtaatgtgtc 60
taaaataata agtaacattt agcatttctg accttatccc aaagtatttt aatagtatct 120
gttaatgttt taattaatgg nttttgtatt gcatctcctg gataacaaag tag 173

<210> SEQ ID NO 520
<211> LENGTH: 441
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

<400> SEQUENCE: 520
catgagtgtg agctgatttg cacccnanca ccctctgtaa gtgcctgctg tggntttggt 60
tttgattatt ccgttaatgc tgagtctgtt tcacaaacga gattagcaga attaattatt 120
gaagatgcag tatgctttat ggttttaata acactgttaa aaactaaaca aggaagttaa 180
atatgttgat gattatcggt gactgctcac cacacagcat ccctcaggcc gagtcagttg 240
gcccagtgac tcccacatca caaactgccc tttcttggtc agaagaagca gagtggagcc 300
ttctcatccc cacgcgcgca gctgtggggc cccgtggtca cctggccaca tgggagtttg 360
catactgagt ggttcatctt ttccaatgtg ttgtgtcctt taatttacat ttatatttca 420
ttgccctttc taatgatcag a 441

<210> SEQ ID NO 521
<211> LENGTH: 488
<212> TYPE: DNA

<213> ORGANISM: Homo sapiens
<220> FEATURE:
<221> NAME/KEY: misc_feature
<222> LOCATION: (456)..(456)
<223> OTHER INFORMATION: n is a, c, g, t or u

<400> SEQUENCE: 521
tttgagttct gctctggcca atccccaagc tccacgctgt cagccacccc gctctcctac 60
ctcccagagg agcaggctac actcctgttc cttttagaga gagaaatatt gcggccgggc 120
gcggtggctc acgtctgtaa tcccagcatt ttggcaggcc aagggttttg ccatgttcgt 180
ggggctggtc tcaaactaat tacctcagat gatccgccca cctcggcctc ccaaagtgct 240
gggattacag ccgtcctggg ccgccggaca cccccgctgg ggccgatgcc caacagtgac 300
atcgacttga gcaacctgga gcggctggag aagtaccgga gcttcgaccg ctaccggcgc 360
cgggcagagc aggaggcgca ggccccgcac tggtggcgga cctaccgaga gtatttcggg 420
gagaagacag agttccagct tctaaaatat ttgctnctaa aatcttgacc acctgacttt 480
ccggattg 488

<210> SEQ ID NO 522
<211> LENGTH: 339
<212> TYPE: DNA
<213> ORGANISM: Homo sapiens
<220> FEATURE:
<221> NAME/KEY: misc_feature
<222> LOCATION: (117)..(119)
<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u

<400> SEQUENCE: 522
aaaatggatc ctgtctttct tagccaagga ctggtctctt ttctccaatg tgtccctaac 60
agagtggtga ggctggctct tcccaccagt acaggaagat cattccttaa aagaaannnc 120
catatggctt ataagtgttc tttcctgtat gaagcccaag ctgtccactt ggagagacat 180
ctggccagcc ccccgttgtt ccagccatcc ccagttcagg catcaganat gtggtgaaga 240
agccatccta gatgcccagc cccagctacc atctgatgca accacactgc tcaccccgag 300
caagaactgc ctgcaggagc ctagtattat cctctctca 339

<210> SEQ ID NO 523
<211> LENGTH: 396
<212> TYPE: DNA
<213> ORGANISM: Homo sapiens

<400> SEQUENCE: 523
gcggcagcaa ccggaaccgg aactcgtcgc ggccaccacc actgagcgct gcggggaggg 60
ggagcaagga ccggacgaga cgctacgcct gaaaacaggc ggcgggcgag ggacgaggct 120
taccacggca ccacgcgagt ggaaagggtc gtctccgcta gcggcggccc acaccagctc 180
accgaggggc ggcagcgcgc ggcccggctg ccggaccgta ccatcccggg cggtggagcc 240
gccgcggagg ggcgcgcgcg agccgaaggc gcacccggga ggcccaggta gcccgggggc 300
cggtgctggg gcgccgggca ggcccggctc ccgcctcgac ccacccggag ccagcccccct 360 ctgcggacac gacatcccca tggggacggt ggcgcg 396

<210> SEQ ID NO 524
<211> LENGTH: 194

<212> TYPE: DNA
<213> ORGANISM: Homo sapiens

<400> SEQUENCE: 524
ccccacaggt gttcctctgt gagctggtcg ggcggccggg gccggggccg ggcttcgctg 60
ctccgtgcct tccacctccc tggcggtgcg gggcctcagg gtgggcctgg gaagctggaa 120
acacctttgg aaacagccgc ctgaggcagc tgtggacaga agaccctgcc cagcagccaa 180
gggagctggc ctct 194

<210> SEQ ID NO 525
<211> LENGTH: 526
<212> TYPE: DNA
<213> ORGANISM: Homo sapiens
<220> FEATURE:
<221> NAME/KEY: misc_feature
<222> LOCATION: (424)..(430)
<223> OTHER INFORMATION: n is a, c, g, t or u
<220> FEATURE:
<221> NAME/KEY: misc_feature
<222> LOCATION: (443)..(443)
<223> OTHER INFORMATION: n is a, c, g, t or u
<220> FEATURE:
<221> NAME/KEY: misc_feature
<222> LOCATION: (445)..(445)
<223> OTHER INFORMATION: n is a, c, g, t or u

<400> SEQUENCE: 525
caagggcacg aggcagtacc tttgctccat gcctttgctt ggactagtcc taccaccagc 60
aattcctgca tttctgtgtt tggcaagttt ctgctcagcc tccaaagcct taaccaagtg 120
tcaccttttc tctgcagcat tttctgccac cctccccatt tcttccaata gaaccaggga 180
tcttttactt gggatccaga agcactgtgg acatattgcc atcacaacac ctttcatgtc 240
acaatggcaa ggtttgcact gtcttggagg agaggaagga agccatattc atccctgaac 300
cctcatctcc cagcactggt tgtaaaactg aaacaaaaat ggaaaacctt gatgaaattc 360
attgttggtg tggctatggg gaaacagatt ttccatttct gatagtaaat gaaataggca 420
ccannnnnnn aaaaaaaaaa aananattat taacactgaa aatgcacaca tctttcaacc 480
cagcaatttt atttcttgct ttctagagga atgtttgccc atgtgc 526

<210> SEQ ID NO 526
<211> LENGTH: 197
<212> TYPE: DNA
<213> ORGANISM: Homo sapiens

<400> SEQUENCE: 526
cattattaat tataccaatc ctttcatata tgtagaaaaa atgtttgagt tggtcatctg 60
tcttttattg aagatgcatt tcaaatatca aatatatttg aaagataaaa tagcatctgt 120
gaaattgaat attattttat gtgcgcttgg ctatgcccta aaatgtcagt ttattgtccc 180
taaagacgta tttattg 197

<210> SEQ ID NO 527
<211> LENGTH: 275
<212> TYPE: DNA
<213> ORGANISM: Homo sapiens

<400> SEQUENCE: 527
ggatgaacgg gtgggctgaa gaacagctga atccaatagc ttggcagaac atgaagacag 60
gtttgttttc cagattctta aaactccaaa cttgatatta ttacagacac aaagtaaatg 120
gcacataaca agaggaagga gatcacagtt tgcaaaactt ttatgtggac cttggtactg 180
ggatcttgag atcctttgcc atggaggtgc atcttcttga gatgtttaca cagagaacag 240
actaacagca gaaaagatat cagggttaca gtaaa 275

<210> SEQ ID NO 528
<211> LENGTH: 496
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, t or u
<220> FEATURE:
<221> NAME/KEY: misc_feature
<222> LOCATION: (46)..(46)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 528
aataaatcct gcgagttcac gcccgcgtag ttcgccccct ganttntnga ngcgactcct 60
ttcgcatggg atctacaaaa ccgaactgcc ttaaagacct ctttcacacg gacgtgaagt 120
cacagaactg acaaaatccc atcctgtcaa agtgcacggg tctttgaaat ctaacacaaa 180
aagccataga aagattctct aaacaccctg tactaagagg aacacggaca gggcactgcg 240
ttctgaagta gaggccaggg cactggccct tagacacgtc tcgctgtcac cgggctaaca 300
acattggcaa gggcggcggc agcagcactg atatttgcag cccccaaggg ctctggcgaa 360
accccctcta ttactctgta tcctgcctgc ttccaagatg aacctgttgc tgggaaagaa 420
caggctaaat tagaaaaggg agtattttgt caaagttgaa ggtgagtgat agcctgcccg 480
cctcaaatag gatggg 496

<210> SEQ ID NO 529
<211> LENGTH: 524
<212> TYPE: DNA
<213> ORGANISM: Homo sapiens

<400> SEQUENCE: 529
agcgcagtgg cgaggcgagt gtggaaggac tcctgaacca gctcgtcctg gagcacctgc 60
agctggcgcc tctgcagtgg gatgtgctgg tggacggaca gccatgtgac cgcgaggctg 120
tggcggcctg ccaggtgggc gaccccgtgc gcctggaggt gcggctgacc aaccggagcc 180
cgcgcagcgt agggcccttc gccctcactg tggtcccctt ccaggaccac cagaacggcg 240
tgcacaacta cgacctgcac gacaccgtct ccttcgtggg ctccagcacc ttctacctcg 300
acgcggtgca gccgtccggc cagtcggcct gcctcggggc cctcctcttc ctctacacgg 360
gagacttctt cctccacatc cggttccacg aggacagcac cagcaaggag ctgccaccct 420
cttggttctg cctgcccagt gtgcacgtgt gtgccctgga ggcgcaggcc tgagcccgcc 480
tacttccgtc cctctttctg cagggccaga ggtgaccctg cctg 524

<210> SEQ ID NO 530
<211> LENGTH: 497
<212> TYPE: DNA
<213> ORGANISM: Homo sapiens

<400> SEQUENCE: 530
aggtcaatct cgtattctct atgtgatatt gctgacaaag tcaaagtaag gaaagacata 60
tcaagggaag gcaatggaag caccttttct ttatagtaca ttcacctacc ttaacagacc 120
aagataacat aggagagaaa ctggggctta agtccttgat agagcttctg gggcacagt 180 agttataggg ccaggtcaga aaatgtcctc acacactaag aaggcatttt aaaatcagaa 240
aagacagtca cactcacttt ggtcaccaag tcatttagcc atcctgtctg gaaagcatgt 300
tttcctctgg ggtcttcctc tggggtatct tgggaaaggg tagagttttg aggagctaga 360
gaagagaaag aggtcatgag ggagattagt cctttctgaa tagcctagga aacccctcac 420
caaatagatg cctacacttt cttaaatcga gaagtaagaa ggaaatcaaa aacagcactc 480
ctacttcaaa gcatcag 497

<210> SEQ ID NO 531
<211> LENGTH: 253
<212> TYPE: DNA
<213> ORGANISM: Homo sapiens

<400> SEQUENCE: 531
gtgaaaagca accaaaggca acagagtcta gctcatggcc accagaccaa aagcatccag 60
cttctgtgca cctcctgcaa agctggcaga ggccctggaa ttccagatca cctgagggga 120
aagggttgtc tctctccttt ctgttggggg agggggatgg gggacttttg ttggtggctc 180
ccacccatat atccctcctt taccatagta ctcccaccca cttccatcac ccatccaata 240
aaatgcagcc agg 253

<210> SEQ ID NO 532
<211> LENGTH: 567
<212> TYPE: DNA
<213> ORGANISM: Homo sapiens

<400> SEQUENCE: 532
cacctcggtc accagtgtga accaagccag cacatcccgc ctggagggcc tacagtcaga 60
aaaccatcgc ctgcgaatga agatcacaga gctggataaa gacttggaag aggtcaccat 120
gcagctgcag gacacaccag aaaagaccac ctacattaaa cagaaccact accaagagct 180
caatgacatc ctcaacctgg gaaacttcac tgagagcaca gatggaggaa aggccatttt 240
aaaaaatcac ctcgatcaaa atccccagct acagtggaac acaacagagc cctctcgaac 300
atgcaaagat cctatagaag atataaactc tccagaacac atccagcgtc ggctgtccct 360
ccagctcccc atcctccacc acgcctacct cccatccatc ggaggcgtgg acgccagctg 420
tgtcagcccc tgcgtcagcc ccaccgccag cccccgccac agacatgtgc caccctcctt 480
ccgagtcatg gtctcgggcc tgtaagggtg gggggcctgg gcccggggcc tcccccgtga 540
cagaaccaca ctgggcagag gggtctg 567

<210> SEQ ID NO 533
<211> LENGTH: 402
<212> TYPE: DNA
<213> ORGANISM: Homo sapiens

<400> SEQUENCE: 533
cagtattctg taccatagcg ctgctcttat gccatttgtt tatttttata tagcttgaaa 60
catagaggga gagagggaga gagcctatac cccttactta gcatgcacaa agtgtattca 120
cgtgcagcag caacacaatg ttattcgttt tgtctacgtt tagtttccgt ttccaggtgt 180
ttatagtggt gttttaaaga gaatgtagac ctgtgagaaa acgttttgtt tgaaaaagca 240
gacagaagtc actcaattgt ttttgttgtg gtctgagcca aagagaatgc cattctcttg 300
ggtgggtaag actaaatctg taagctcttt gaaacaactt tctcttgtaa acgtttcagt 360
aataaaacat ctttccagtc cttggtcagt ttggttgtgt aa 402

<210> SEQ ID NO 534
<211> LENGTH: 279
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, t or u

<400> SEQUENCE: 534
tgcattgtac ctgtagccat tccattgtga ataacacaaa aagtggagga aatatttttc 60
tcgcatttgg aaattattct gtgattcagc aaagaagttg ttcatgtcat taacaagttc 120
agaaatacat gctgccaaag ccaaaaagag tcttcagttt aataaaaata attaacanga 180
aggtgagaaa tggtttacca gctgttcact tactggattt aaggttactt gttggggaaa 240
gagcagagta agatgcaact ctgtcaaatc atggctgaa 279

<210> SEQ ID NO 535
<211> LENGTH: 354
<212> TYPE: DNA
<213> ORGANISM: Homo sapiens

<400> SEQUENCE: 535
tagcaaagga catggaagcc tggaaagatg taaccagtgg aaatgctaaa atttaccagc 60
ttccaggggg tcacttttat cttctggatc ctgcgaacga gaaattaatc aagaactaca 120
taatcaagtg tctagaagta tcatcgatat ccaattttta gatattttcc ctttcacttt 180
taaaataatc aaagtaatat catactcttc tcagttattc agatatagct cagttttatt 240
cagattggaa attacacatt ttctactgtc agggagattc gttacataaa tatatttacg 300
tatctgggga caaaggtcaa gccagtaaag aatacttctg gcagcacttt ggga 354

<210> SEQ ID NO 536
<211> LENGTH: 497
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, t or u
<220> FEATURE:
<221> NAME/KEY: misc_feature
<222> LOCATION: (304)..(306)
<223> OTHER INFORMATION: n is a, c, g, t or u
<220> FEATURE:
<221> NAME/KEY: misc_feature
<222> LOCATION: (308)..(309)
<223> OTHER INFORMATION: n is a, c, g, t or u
<220> FEATURE:
<221> NAME/KEY: misc_feature
<222> LOCATION: (311)..(313)
<223> OTHER INFORMATION: n is a, c, g, t or u
<220> FEATURE:
<221> NAME/KEY: misc_feature
<222> LOCATION: (315)..(317)
<223> OTHER INFORMATION: n is a, c, g, t or u
<220> FEATURE:
<221> NAME/KEY: misc_feature
<222> LOCATION: (354)..(354)
<223> OTHER INFORMATION: n is a, c, g, t or u
<220> FEATURE:
<221> NAME/KEY: misc_feature
<222> LOCATION: (361)..(361)
<223> OTHER INFORMATION: n is a, c, g, t or u

<400> SEQUENCE: 536
ttccctgatg actcacttac aagttagtga actccttgtt taagtattac aaactgcaca 60
ccttctccct tctcaatcta gcttcacatc aggccttcct gccaaagcgg caaacttgcc 120
acatggggca aggtactccc caagcagaca aggcccatct gtgtcatgag tgatacccaa 180
tgctaatgcc atgctctgaa atgtagtgcc caccttggct tcccaaagtg ctgggattgc 240
agacgtgagt cactgcgccc agccattcca tgtctcttaa gtctcagaat ctcccctagc 300
tncnnncnng nnncnnnagt ggttgtcccc tcaaagctgt cccacaccct cctncgagga 360
ncctttgtgt atctcctcca gctaccgcag agcccacaaa cccaggcatc tatcaaagtc 420
cctcattcat gagggtggtg aggacacaga ctgcgaccag aacagaaata tgaaaatgtg 480
aatgacagcg tcccccg 497

<210> SEQ ID NO 537
<211> LENGTH: 340
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (118)..(118)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u

<400> SEQUENCE: 537
tggagttagc aaacctttc atgcctgtga cctcactgga gttctttgat gttgggactt 60
cataagtntg ccaaatcctg ncacttactg ctttatgacc ttgaccattt accgnttntn 120
tntggacctc agtgttctca ggatgcaaaa ggagggtcag gggtaaaata gcgactttcg 180
aactgtcagg ggtaaaatag cgactttcaa acttttcaaa cttctgggac aagggtgaag 240
ggcaggactc tgcctctctc cttcccttca ccttattcca cttaaattgt gtgattctac 300
aagcttatgt ttaaaggaat atgttcctcc attacaaaga 340

<210> SEQ ID NO 538
<211> LENGTH: 527
<212> TYPE: DNA
<213> ORGANISM: Homo sapiens
<220> FEATURE:
<221> NAME/KEY: misc_feature
<222> LOCATION: (133)..(133)

-continued

<223> OTHER INFORMATION: n is a, c, g, t or u
<220> FEATURE:
<221> NAME/KEY: misc_feature
<222> LOCATION: (148)..(148)
<223> OTHER INFORMATION: n is a, c, g, t or u

<400> SEQUENCE: 538
tgggaccacg ggcatttttg gcatgtacaa gggtataggt gcctcctact tccgcctcgg 60
cccccacacc atcctctccc tcttcttctg ggaccagctg cgctccctct actacacaga 120
cactaaataa canccgcttt cccagtcntc caccaaatga gcactccttg gccacttgtg 180
cctccaccac tatgtcctgg tgactactga ttaggtgacc tttcatccat ccatggggga 240
cagccaaccc cactccccat ctgttctcag ggttgaatca ctacaagaga tgagtttccc 300
ttctttcctt gggtgttgct ttaaaccttc cctacccatt ccctgggtaa ctcacacccc 360
tctctcaggg ctgaacgagt catcccaaag tgtatttcct cccactcacc actgccaccc 420
ttgagtccct cctgctccca tgcacagttt taaactcctc cctccaaaac caaagggaat 480
tgagagaccc aattcccagg cgtctgggac ccaggtgtcc tgttaga 527

<210> SEQ ID NO 539
<211> LENGTH: 532
<212> TYPE: DNA
<213> ORGANISM: Homo sapiens

<400> SEQUENCE: 539
gacatgtttt ctagccttag ttccccatct acaaaatggg cctcatggaa tggaatgtct 60
ccacttcact ccagcatcaa caagtgggga attctgatgg attcaattcg acttctttcc 120
atgggcgtgt tctaagcagc ctctttgttc cagaagctgc cctcagccag agttggataa 180
gccaatcctc actccccagc ctcctctgga tagggatgaa gaccccactg gggttggaag 240
tgcagaggca gacaggtgta tggagtcacc tgtaaattga ttcaagtgag ccaggaaagc 300
agcaaaggaa agagaaacct gagtgacgac gtggtggagg aacagggctg gaaagaggct 360
gctggctgtc tggcttcgca gctctggcct cctaatcagc ctcgctcttg tctctggtgt 420
tctctggctc ttgtccatct gtctgtgttt ctttttgcca gctattgact aatctttgct 480
gaagctgagc tagaattctg gtgtttataa gcaggtaact agctgagcac ta 532

<210> SEQ ID NO 540
<211> LENGTH: 811
<212> TYPE: DNA
<213> ORGANISM: Homo sapiens

<400> SEQUENCE: 540
ctttgggagg ctgaggcagg cagatcacct aaggccagga attcgacacc agcctggcca 60
acgtggcaaa acccgtctct actaaaaata caaaaattag ccgggcgtgg tggtgtgcgc 120
ctggaatccc agctacccag gaggctgagg caggagaaat gctggaaccc gggaggcaga 180
ggctgcagtg agctgagatc atgccactac tgcactccag cctgggtgac acagcaagac 240
tccctctaaa aaaagaaaaa aagaaaagaa aagaaaagaa aatgatatat ccatgatgaa 300
ttaaaatgga gtggaaccca ctgatgggaa agccacagaa ggtaccagtt atccactcac 360
tgacttaggt gcctccacta gaattctcag cacgtttttg cagaacctgg gcaacaagag 420
cgaaacccca tctcaaaacc acaacaacaa caacaggaca acagagatgg acgacggatc 480
gggaaagcca accagacagc gtgaggccag gacggaaaga ggcacaggga gctctgctca 540
gtgtcgctac aggggatctc tcaggctcac aacgggccac tcctctaggg aagttctggt 600
ctcatcatga tccttgtttg gtctcactcc ccatgtcctt ctctgtccct cctccaactg 660
ccatttattt atttaactga aaaagtacca atcacccaca taggcatgac atactcatcc 720
atgtacccat ttcttaaaat tgatcattgt taacatttgg tgtaatttgc tttatttatt 780
tttaatgaaa taaataaaac tttacagaaa a 811

<210> SEQ ID NO 541
<211> LENGTH: 3874
<212> TYPE: DNA
<213> ORGANISM: Homo sapiens

<400> SEQUENCE: 541
aaaaaggtac aactaccttg ctgatgctgt acatatggct cacttgtgcc cagagagaga 60
ataaagccat gtcgaaacta tctacgattc cttgagtgtt tttccagcta cctgccactt 120
gcccacccac tcccctcaga tctcagttag aacatgacaa ttgggctcat gaacaggatc 180
ctgagtggtt gcaggtgaac aagcagttgg cacaagggca aagtgatcac atcctgattg 240
agtggctatg gacagccata cagactgtgt ggaacaacgc tggtgaaata cccaaaccat 300
ttagaagcag taatgcctca cttgcctggg actgggatgg tgtggctgag actgccttac 360
tggcagccag gtgcgctatt cagcagccac aagccctaca agtaattaac caggggcacc 420
tgtttgagct ggaggtgcat gtggccacag acggttttgg ttgaggcttg tggcaatgca 480
cagagcgcct aagaatgcca gtaggctttt ggtcccaact atggaaagga gctgaactcc 540
ggtattcatt gatagagaaa cagctagcag ctgtatatgc tggccttcgg gctcatgaga 600
gcatgacagg acaggctgca gtcatcatat ggacaactta cccaataaca ggatggatgc 660
gtctatgtgt aatgaccacc tggagtggga tagcacagat gtccactttg gcaaaatggg 720
gcgactcctt gcagcagtgg agtaagctga gtacaagtcc catagcagca gagttgcaag 780
aggtcttggg acgtgtagtc ctaatgcaag ataaggccat gcggcctgag gcacccctag 840
atcctgagtc ttcaccattt aaggaagggc atcccaggat tcctgagggg gcatggtaca 900
cagtagatga ggtgctactg ctgcctggac cactgttgca gtccaaccta gtactgacac 960
catatggttt gaaactgggt gcggacaaag tagccaatgg gctgaactca gagcagtgtg 1020
gatggtaatc accaaggagg tgacacctgt ggtaatctgt actgatagct gggcagtcta 1080
ctgaggctta accttgtggt taactacttg gaaaatacag aattggctag tgagccacag 1140
acccatttga ggccaagcca tatggcaaga cctttgggga ataggtcatc aaaaagaggt 1200
aactatttat catgtgtcag gccatatgcc tttggccacc cctagtaatg atgaggcaga 1260
tgccttggct aaggtcagat ggtcagagtc agcaccaaca caagatgtga ccttgtggct 1320
acaccggaaa ctgggacatg caggggggtaa actgatgtaa caattcaata agtgttgggg 1380
tctgtccctt cccaagcaag acatttgtga ggcttgtcag aaatgcctgg catgtgttca 1440
gacatatcct aaaaagaggc agctgcccgg tgttatacaa caagtaacaa tagggtgagt 1500
gcccttgacc aggtgggaag tagactacat cgggccgccg ccaaagtcgc gagggtatac 1560
gcatgcacta acggctgtag acatggccac aggcctgttg ttcacctacc cttgcagggt 1620
ggccaaccaa cagaacacca tccaggccct gcaacactta tgttccctgt atggttgtcc 1680
tctggccatt gagagtgata ggggaacaca tttcactgga caacaggtac aatgatgggc 1740
acagcaaatg gacataaagt ggggattcca tgtgccatac agcccacaag ctgaggtatt 1800
attgaatgat ataatgggat cttgaagaat ggattacgct tgcatgtcaa acccctgtct 1860

```
ttgcggagct ggagttccag gctggacctg gtgctccaaa ccttaaatga atggccacag   1920
aaaggtggcc cggccccagt ggaggctttg tttcactagg ccaccacccc cattcaattg   1980
gagatacata ccaaggatga cctcctccga tcaggtatgg ggacaaatgg taacctgttg   2040
ttgcctgccc caacaaccct gaaggcaggg gaacagaaaa cctggctgtg gccatggacc   2100
ctccaagctc tccactgctg gtggttggcc atcatagctc cctgtgggga gggcctacag   2160
tatgacttgc atgtcacttt ttgagtgttc aatacatggc ttccaaggtt gactgtttgt   2220
agaggaacag ccagggaagg aaccctcctc tgagggacat atgtactatc tgatgggcct   2280
attatgagct acgctgtgac tttggcatgg atacaggatt ctaaggaacc atggagattt   2340
gagaaggtgt ggtaccatca cccagggcaa aagcccttgg tggctgcatt gttatccagg   2400
gatggaaagt tagcctatat tttgcctgag ggatgtgatt tacctctgtt agtacctgtg   2460
cctgctctgt catttcaacc gtaggttaac atgctccaat tgcattgtgg actgacccca   2520
cacctatgct gaggtgacca atgtttccaa ctgttggacc tgcactgcct ttccagcagc   2580
agctgcagac agcttgcccc gacacataca tcccgtgtct gcagagaact ggacatgcct   2640
ggagacttga gatcccatgg ctgatgcctg gaacacaatg tggcaagctt tggacaaagg   2700
acacagcaag acccatggct ggaccgtagc attcgtgatg agtggggctg gctagtaggg   2760
gaacatgtag tagcccaagc ccaggcattg cagtgcacag agcaacattg gggtaacagg   2820
atgggtacct gtcacggcct gtgcaaacat aacatgtgtc accacactga aggtatggta   2880
gaacaagtgg cctcaccaag gtcggacccc aatggacttt ttgcctcttg ggagcttatg   2940
ggtctatgag gacacagtag cctttcctat cagcaaactg gagtggatgt tgtatctggg   3000
ggtggcctta tgtacctgct actgttctcc ccacattgcc cagatgcctg tataactggg   3060
aggcactgtg ctctcagttt ttgcgaatgt gatgagcccc ctggtgtttc taccctttgg   3120
caatgactat ccctggagca ggtgtcaaaa ctgtagaagc acaatttact gctcttgcgg   3180
agcacaccgc tcaggctctg aattacacct gagtgtccct cctcctgtta atgaatgagg   3240
ttgatcagat caaaaagtgg tgttgcaaaa ccaagtggcc ttagacataa ctgctgccca   3300
aggagccacc tgtgcccttt taggaacaca atgttgtacc ttatccctga caatcagcag   3360
aacataacag cagccctgca aaggggtctt ccaggagatt aaggtgactg agagcctcac   3420
tgtcaacccc ctgcagagat ggtgagcatc cctaggttct ggcgtacatt gggccctaat   3480
agtcataagt atcatagctg agatcctagt agtgagctgt tgctctctgt attgttgttg   3540
tgggttatgg actcagggct ccgccatata ggcatgtgtc cctgcctgga ggacgccctc   3600
agcctagggg gtgtagtgta agggaaatgg ctgtgcttta gtcaggagta ggctgaggca   3660
gccttctggt gcagcatgac tcagtgggtt tggagtgcaa gcacacaacc ttgctcgtta   3720
tgtaaccaca ccacatgagg cccattaggt aacaactcac atgagctcgt gtttggctca   3780
gagccactat tgtctgtaaa aggtatacct tgctgatgct gcacatatgg ctcgcttgtg   3840
cccagagaga gagtaaagcc atgttgaaac tgtc                               3874
```

<210> SEQ ID NO 542
<211> LENGTH: 177
<212> TYPE: PRT
<213> ORGANISM: Homo sapiens

<400> SEQUENCE: 542

```
Met Pro Val Gly Phe Trp Ser Gln Leu Trp Lys Gly Ala Glu Leu Arg
1               5                   10                  15
```

```
Tyr Ser Leu Ile Glu Lys Gln Leu Ala Ala Val Tyr Ala Gly Leu Arg
            20                  25                  30

Ala His Glu Ser Met Thr Gly Gln Ala Ala Val Ile Ile Trp Thr Thr
        35                  40                  45

Tyr Pro Ile Thr Gly Trp Met Arg Leu Cys Val Met Thr Thr Trp Ser
    50                  55                  60

Gly Ile Ala Gln Met Ser Thr Leu Ala Lys Trp Gly Asp Ser Leu Gln
65                  70                  75                  80

Gln Trp Ser Lys Leu Ser Thr Ser Pro Ile Ala Ala Glu Leu Gln Glu
                85                  90                  95

Val Leu Gly Arg Val Val Leu Met Gln Asp Lys Ala Met Arg Pro Glu
            100                 105                 110

Ala Pro Leu Asp Pro Glu Ser Ser Pro Phe Lys Glu Gly His Pro Arg
        115                 120                 125

Ile Pro Glu Gly Ala Trp Tyr Thr Val Asp Glu Val Leu Leu Leu Pro
    130                 135                 140

Gly Pro Leu Leu Gln Ser Asn Leu Val Leu Thr Pro Tyr Gly Leu Lys
145                 150                 155                 160

Leu Gly Ala Asp Lys Val Ala Asn Gly Leu Asn Ser Glu Gln Cys Gly
                165                 170                 175

Trp
```

<210> SEQ ID NO 543
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 543
catgaacagg atcctgagtg g 21

<210> SEQ ID NO 544
<211> LENGTH: 24
<212> TYPE: DNA
<213> ORGANISM: artificial
<220> FEATURE:
<223> OTHER INFORMATION: Description of artificial sequence: Oligonucleotide

<400> SEQUENCE: 544
tgaggcatta ctgcttctaa atgg 24

<210> SEQ ID NO 545
<211> LENGTH: 2863
<212> TYPE: DNA
<213> ORGANISM: Homo sapiens

<400> SEQUENCE: 545
cacgccaaac acgcagcccc ctcccgctgg agtgacaact ggccagcata ctctaggctg 60
ttgtcccttt aaaacttgaa tccaaggggg taatgattta tcaaacttgt attatcaaga 120
aaatgtcaaa ccaagggcac cttgctttgc actgacgcaa acccggcctt tcccaaggag 180
atatagaaag cgcctctcct gcctgagcca aacccagtct tgtcaatagc gggtttcacc 240
ctccaccagt tcagtctgtt gcctgtgtca gacatggatt gcagtgctcc caaggaaatg 300
aataaactgc cagccaacag cccggaggcg gcggcggcgc agggccaccc ggatggccca 360
tgcgctccca ggacgagccc ggagcaggag cttcccgcgg ctgccgcccc gccgccgcca 420

-continued

```
cgtgtgccca ggtccgcttc caccggcgcc caaactttcc agtcagcgga cgcgcgagcc    480
tgcgaggctg agcggccagg agtggggtct tgcaaactca gtagcccgcg ggcgcaggcg    540
gcctctgcag ctctgcggga cttgagagag gcgcaaggcg cgcaggcctc gccccctccc    600
gggagctccg ggcccggcaa cgcgctgcac tgtaagatcc cttttctgcg aggcccggag    660
ggggatgcga acgtgagtgt gggcaagggc accctggagc ggaacaatac ccctgttgtg    720
ggctgggtga acatgagcca gagcaccgtg gtgctggcca cggatggaat cacgtccgtg    780
ctcccgggca gcgtggccac cgttgccacc caggaggacg agcaagggga tgagaataag    840
gcccgaggga actggtccag caaactggac ttcatcctgt ccatggtggg gtacgcagtg    900
gggctgggca atgtctggag gtttccctac ctggccttcc agaacggggg aggtgctttc    960
ctcatccctt acctgatgat gctggctctg gctggattac ccatcttctt cttggaggtg   1020
tcgctgggcc agtttgccag ccagggacca gtgtctgtgt ggaaggccat cccagctcta   1080
caaggctgtg gcatcgcgat gctgatcatc tctgtcctaa tagccatata ctacaatgtg   1140
attatttgct atacactttt ctacctgttt gcctcctttg tgtctgtact accctggggc   1200
tcctgcaaca acccttggaa tacgccagaa tgcaaagata aaaccaaact tttattagat   1260
tcctgtgtta tcagtgacca tcccaaaata cagatcaaga actcgacttt ctgcatgacc   1320
gcttatccca acgtgacaat ggttaatttc accagccagg ccaataagac atttgtcagt   1380
ggaagtgaag agtacttcaa gtactttgtg ctgaagattt ctgcagggat tgaatatcct   1440
ggcgagatca ggtggccact agctctctgc ctcttcctgg cttgggtcat tgtgtatgca   1500
tcattggcta aaggaatcaa gacttcagga aaagtggtgt acttcacggc cacgttcccg   1560
tatgtcgtac tcgtgatcct cctcatccga ggagtcaccc tgcctggagc tggagctggg   1620
atctggtact tcatcacacc caagtgggag aaactcacgg atgccacggt gtggaaagat   1680
gctgccactc agattttctt ctctttatct gctgcatggg gaggcctgat cactctctct   1740
tcttacaaca aattccacaa caactgctac agggacactc taattgtcac ctgcaccaac   1800
agtgccacaa gcatctttgc cggcttcgtc atcttctccg ttatcggctt catggccaat   1860
gaacgcaaag tcaacattga gaatgtggca gaccaagggc caggcattgc atttgtggtt   1920
tacccggaag ccttaaccag gctgcctctc tctccgttct gggccatcat ctttttcctg   1980
atgctcctca ctcttggact tgacactatg tttgccacca tcgagaccat agtgacctcc   2040
atctcagacg agtttcccaa gtacctacgc acacacaagc cagtgtttac tctgggctgc   2100
tgcatttgtt tcttcatcat gggttttcca atgatcactc agggtggaat ttacatgttt   2160
cagcttgtgg acacctatgc tgcctcctat gcccttgtca tcattgccat ttttgagctc   2220
gtggggatct cttatgtgta tggcttgcaa agattctgtg aagatataga gatgatgatt   2280
ggattccagc ctaacatctt ctggaaagtc tgctgggcat ttgtaacccc aaccatttta   2340
acctttatcc tttgcttcag cttttaccag tgggagccca tgacctatgg ctcttaccgc   2400
tatcctaact ggtccatggt gctcggatgg ctaatgctcg cctgttccgt catctggatc   2460
ccaattatgt ttgtgataaa aatgcatctg gcccctggaa gatttattga gaggctgaag   2520
ttggtgtgct cgccacagcc ggactggggc ccattcttag ctcaacaccg cggggagcgt   2580
tacaagaaca tgatcgaccc cttgggaacc tcttccttgg gactcaaact gccagtgaag   2640
gatttggaac tgggcactca gtgctagtcc agtggtgtgg gatggtccag acttgatcct   2700
gtttttcctc tctgcctcct cctaatgttt tccatagctc tcctcccatt tttcttcatc   2760
```

```
tttcttccta catcttggtt cacatccacg catgagagtg attatgtaga aaagtaggca   2820

tagtgtcgca tgctgcagta aagagctaca tagaccacct gaa                     2863


<210> SEQ ID NO 546
<211> LENGTH: 797
<212> TYPE: PRT
<213> ORGANISM: Homo sapiens

<400> SEQUENCE: 546

Met Asp Cys Ser Ala Pro Lys Glu Met Asn Lys Leu Pro Ala Asn Ser
1               5                   10                  15

Pro Glu Ala Ala Ala Ala Gln Gly His Pro Asp Gly Pro Cys Ala Pro
            20                  25                  30

Arg Thr Ser Pro Glu Gln Glu Leu Pro Ala Ala Ala Ala Pro Pro Pro
        35                  40                  45

Pro Arg Val Pro Arg Ser Ala Ser Thr Gly Ala Gln Thr Phe Gln Ser
    50                  55                  60

Ala Asp Ala Arg Ala Cys Glu Ala Glu Arg Pro Gly Val Gly Ser Cys
65                  70                  75                  80

Lys Leu Ser Ser Pro Arg Ala Gln Ala Ala Ser Ala Ala Leu Arg Asp
                85                  90                  95

Leu Arg Glu Ala Gln Gly Ala Gln Ala Ser Pro Pro Pro Gly Ser Ser
            100                 105                 110

Gly Pro Gly Asn Ala Leu His Cys Lys Ile Pro Phe Leu Arg Gly Pro
        115                 120                 125

Glu Gly Asp Ala Asn Val Ser Val Gly Lys Gly Thr Leu Glu Arg Asn
    130                 135                 140

Asn Thr Pro Val Val Gly Trp Val Asn Met Ser Gln Ser Thr Val Val
145                 150                 155                 160

Leu Ala Thr Asp Gly Ile Thr Ser Val Leu Pro Gly Ser Val Ala Thr
                165                 170                 175

Val Ala Thr Gln Glu Asp Glu Gln Gly Asp Glu Asn Lys Ala Arg Gly
            180                 185                 190

Asn Trp Ser Ser Lys Leu Asp Phe Ile Leu Ser Met Val Gly Tyr Ala
        195                 200                 205

Val Gly Leu Gly Asn Val Trp Arg Phe Pro Tyr Leu Ala Phe Gln Asn
    210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
                245                 250                 255

Gln Gly Pro Val Ser Val Trp Lys Ala Ile Pro Ala Leu Gln Gly Cys
            260                 265                 270

Gly Ile Ala Met Leu Ile Ile Ser Val Leu Ile Ala Ile Tyr Tyr Asn
        275                 280                 285

Val Ile Ile Cys Tyr Thr Leu Phe Tyr Leu Phe Ala Ser Phe Val Ser
    290                 295                 300

Val Leu Pro Trp Gly Ser Cys Asn Asn Pro Trp Asn Thr Pro Glu Cys
305                 310                 315                 320

Lys Asp Lys Thr Lys Leu Leu Leu Asp Ser Cys Val Ile Ser Asp His
                325                 330                 335

Pro Lys Ile Gln Ile Lys Asn Ser Thr Phe Cys Met Thr Ala Tyr Pro
            340                 345                 350

Asn Val Thr Met Val Asn Phe Thr Ser Gln Ala Asn Lys Thr Phe Val
```

-continued

```
        355                 360                 365

Ser Gly Ser Glu Glu Tyr Phe Lys Tyr Phe Val Leu Lys Ile Ser Ala
    370                 375                 380

Gly Ile Glu Tyr Pro Gly Glu Ile Arg Trp Pro Leu Ala Leu Cys Leu
385                 390                 395                 400

Phe Leu Ala Trp Val Ile Val Tyr Ala Ser Leu Ala Lys Gly Ile Lys
                405                 410                 415

Thr Ser Gly Lys Val Val Tyr Phe Thr Ala Thr Phe Pro Tyr Val Val
            420                 425                 430

Leu Val Ile Leu Leu Ile Arg Gly Val Thr Leu Pro Gly Ala Gly Ala
        435                 440                 445

Gly Ile Trp Tyr Phe Ile Thr Pro Lys Trp Glu Lys Leu Thr Asp Ala
    450                 455                 460

Thr Val Trp Lys Asp Ala Ala Thr Gln Ile Phe Phe Ser Leu Ser Ala
465                 470                 475                 480

Ala Trp Gly Gly Leu Ile Thr Leu Ser Ser Tyr Asn Lys Phe His Asn
                485                 490                 495

Asn Cys Tyr Arg Asp Thr Leu Ile Val Thr Cys Thr Asn Ser Ala Thr
            500                 505                 510

Ser Ile Phe Ala Gly Phe Val Ile Phe Ser Val Ile Gly Phe Met Ala
        515                 520                 525

Asn Glu Arg Lys Val Asn Ile Glu Asn Val Ala Asp Gln Gly Pro Gly
    530                 535                 540

Ile Ala Phe Val Val Tyr Pro Glu Ala Leu Thr Arg Leu Pro Leu Ser
545                 550                 555                 560

Pro Phe Trp Ala Ile Ile Phe Phe Leu Met Leu Leu Thr Leu Gly Leu
                565                 570                 575

Asp Thr Met Phe Ala Thr Ile Glu Thr Ile Val Thr Ser Ile Ser Asp
            580                 585                 590

Glu Phe Pro Lys Tyr Leu Arg Thr His Lys Pro Val Phe Thr Leu Gly
        595                 600                 605

Cys Cys Ile Cys Phe Phe Ile Met Gly Phe Pro Met Ile Thr Gln Gly
    610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
                645                 650                 655

Gly Leu Gln Arg Phe Cys Glu Asp Ile Glu Met Met Ile Gly Phe Gln
            660                 665                 670

Pro Asn Ile Phe Trp Lys Val Cys Trp Ala Phe Val Thr Pro Thr Ile
        675                 680                 685

Leu Thr Phe Ile Leu Cys Phe Ser Phe Tyr Gln Trp Glu Pro Met Thr
    690                 695                 700

Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
                725                 730                 735

Met His Leu Ala Pro Gly Arg Phe Ile Glu Arg Leu Lys Leu Val Cys
            740                 745                 750

Ser Pro Gln Pro Asp Trp Gly Pro Phe Leu Ala Gln His Arg Gly Glu
        755                 760                 765

Arg Tyr Lys Asn Met Ile Asp Pro Leu Gly Thr Ser Ser Leu Gly Leu
    770                 775                 780
```

Lys Leu Pro Val Lys Asp Leu Glu Leu Gly Thr Gln Cys
785 790 795

<210> SEQ ID NO 547
<211> LENGTH: 24
<212> TYPE: DNA
<213> ORGANISM: artificial
<220> FEATURE:
<223> OTHER INFORMATION: Description of artificial sequence: Oligonucleotide

<400> SEQUENCE: 547
ggatttgcaa gttgtgtagt gtgc 24

<210> SEQ ID NO 548
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 548
aagcagatgg tcatcttcca g 21

<210> SEQ ID NO 549
<211> LENGTH: 2426
<212> TYPE: DNA
<213> ORGANISM: Homo sapiens

<400> SEQUENCE: 549
ctctttcaac tcaagagctc agtcctgtgt ctctcatgga ggcgtctcta accaggaggc 60
tactctttaa agacaggcat tttacttgca gcaaaataat aggaaggaga ttcgcttgct 120
ttgcacagag gctgagccac aggagaaagc aaagccaatg tgatttattg aatgaaagca 180
ctggacaatt accaacaact tgttcctctg ctgcctcgaa cagcataaac tggaattgtc 240
gtgtgaaaat gacgcaacaa atgcaaaatt tacatctctg tcagtcaaaa aaacatagtg 300
ctccctcatc tcccaacgca gccaaacgcc tgtacaggaa cctctctgag aaactgaaag 360
ggagccactc ttccttcgat gaggcctatt ttaggacaag aactgatcgg ctgagtctca 420
ggaagacctc ggtgaatttc cagggcaatg aagccatgtt tgaggcagtc gaacagcagg 480
acatggatgc tgtgcagatc ctcctgtatc agtacacacc agaagaactt gacctcaaca 540
cacctaacag cgagggcttg acacccctgg atattgccat catgaccaac aatgtgccca 600
ttgcaaggat tcttctgagg acaggggccc gagaaagtcc acactttgtc agcctggaaa 660
gccgagcaat gcacctcaac acactggtcc aggaagccca ggagagggtg agtgaactgt 720
ctgcccaggt ggagaatgaa ggattcactc tggacaacac agagaaagag aagcagctga 780
aagcttggga gtggaggtat cggctctaca gacgcatgaa aacaggcttt gagcatgcca 840
gagcccctga gatgccaacc aatgtctgtc tcatggtaac cagcagcaca tcactcactg 900
tcagcttcca agagcctctt agcgtcaatg cagctgtagt aaccaggtat aaagtggaat 960
ggagtatgtc cgaagacttt tctcctttgg ctggagaaat catcatggat aatctgcaga 1020
ctctgagatg cacaatcaca ggacttacaa tgggccaaca gtattttgtt caagtctcgg 1080
cttacaatat gaaaggatgg ggacctgctc agaccacgac accggcatgt gcctctcctt 1140
ctaactggaa agactatgac gacagagagc ccagacacaa gggacagagt gaagttttgg 1200
aaggtctgct gcagcaggtc cgagcccttc atcagcatta cagttgccgg gaaagcacaa 1260

```
aattacaaac cacaggccgc aagcagtcag tctcaagaag cctgaaacac ctgttccatt   1320

cctcgaacaa gtttgtgaag accttaaaac ggggactcta catagccgtt atattttatt   1380

acaaagacaa tatcttagtc accaatgaag atcaagtacc aattgttgaa atagatgact   1440

ctcacaccag ttctattaca caagattttc tgtggttcac gaagctgtct tgtatgtggg   1500

aagatataag gtggctgagg caaagcatac caatatcctc atcctcatcc acagtgctgc   1560

aaactcggca gaagatgctc gcagcaacag cacagctaca gaatttactt gggacacaca   1620

acttgggaag agtttactat gagcccatta aagatcgaca tggaaacata ctcatagtca   1680

ccatcaggga ggtggagatg ctttattcat tttttaatgg caaatggatg cagatctcaa   1740

agctgcaaag ccagagaaag tctctatcaa cacctgagga gccaacagct ttagacattc   1800

tactgataac catccaggat attctatcct atcacaaaag gagtcatcag cgtctctttc   1860

ctggattata tctgggttac ctaaagctct gtagctctgt ggatcaaatc aaagttcttg   1920

ttacccaaaa gttgcccaac attctctgcc acgtgaagat ccgtgaaaac aataatattt   1980

ctagagagga atgggaatgg atccaaaagc tttctggctc tgaatctatg gaaagtgtgg   2040

atcatacttc tgactgcccc atgcaattgt tcttctacga gctccagatg gcagtgaaag   2100

ctctccttca gcagatcaat atacctctac accaggcaag gaacttccgc ctctacacac   2160

aggaggtgtt ggaaatgggt cacaatgtgt cctttcttct cctgctccct gcctcagacg   2220

acgtctgtac agccccagga cagaataatc cttacacccc acactcaggg tttcttaacc   2280

tccctcttca gatgtttgaa cttggtatag tagcttgttt cacctagaaa tattaaccca   2340

gcctccttat aataaaatca caaagttata tctgttcccc cttgtcccag tggagggtca   2400

ataaatcaca tgatggcttt ggcaac                                        2426
```

<210> SEQ ID NO 550
<211> LENGTH: 763
<212> TYPE: PRT
<213> ORGANISM: Homo sapiens

<400> SEQUENCE: 550

```
Met Glu Ala Ser Leu Thr Arg Arg Leu Leu Phe Lys Asp Arg His Phe
1               5                   10                  15

Thr Cys Ser Lys Ile Ile Gly Arg Arg Phe Ala Cys Phe Ala Gln Arg
            20                  25                  30

Leu Ser His Arg Arg Lys Gln Ser Gln Cys Asp Leu Leu Asn Glu Ser
        35                  40                  45

Thr Gly Gln Leu Pro Thr Thr Cys Ser Ser Ala Ala Ser Asn Ser Ile
    50                  55                  60

Asn Trp Asn Cys Arg Val Lys Met Thr Gln Gln Met Gln Asn Leu His
65                  70                  75                  80

Leu Cys Gln Ser Lys Lys His Ser Ala Pro Ser Ser Pro Asn Ala Ala
                85                  90                  95

Lys Arg Leu Tyr Arg Asn Leu Ser Glu Lys Leu Lys Gly Ser His Ser
            100                 105                 110

Ser Phe Asp Glu Ala Tyr Phe Arg Thr Arg Thr Asp Arg Leu Ser Leu
        115                 120                 125

Arg Lys Thr Ser Val Asn Phe Gln Gly Asn Glu Ala Met Phe Glu Ala
    130                 135                 140

Val Glu Gln Gln Asp Met Asp Ala Val Gln Ile Leu Leu Tyr Gln Tyr
145                 150                 155                 160
```

```
Thr Pro Glu Glu Leu Asp Leu Asn Thr Pro Asn Ser Glu Gly Leu Thr
                165                 170                 175

Pro Leu Asp Ile Ala Ile Met Thr Asn Asn Val Pro Ile Ala Arg Ile
            180                 185                 190

Leu Leu Arg Thr Gly Ala Arg Glu Ser Pro His Phe Val Ser Leu Glu
        195                 200                 205

Ser Arg Ala Met His Leu Asn Thr Leu Val Gln Glu Ala Gln Glu Arg
    210                 215                 220

Val Ser Glu Leu Ser Ala Gln Val Glu Asn Glu Gly Phe Thr Leu Asp
225                 230                 235                 240

Asn Thr Glu Lys Glu Lys Gln Leu Lys Ala Trp Glu Trp Arg Tyr Arg
                245                 250                 255

Leu Tyr Arg Arg Met Lys Thr Gly Phe Glu His Ala Arg Ala Pro Glu
            260                 265                 270

Met Pro Thr Asn Val Cys Leu Met Val Thr Ser Ser Thr Ser Leu Thr
        275                 280                 285

Val Ser Phe Gln Glu Pro Leu Ser Val Asn Ala Ala Val Val Thr Arg
    290                 295                 300

Tyr Lys Val Glu Trp Ser Met Ser Glu Asp Phe Ser Pro Leu Ala Gly
305                 310                 315                 320

Glu Ile Ile Met Asp Asn Leu Gln Thr Leu Arg Cys Thr Ile Thr Gly
                325                 330                 335

Leu Thr Met Gly Gln Gln Tyr Phe Val Gln Val Ser Ala Tyr Asn Met
            340                 345                 350

Lys Gly Trp Gly Pro Ala Gln Thr Thr Thr Pro Ala Cys Ala Ser Pro
        355                 360                 365

Ser Asn Trp Lys Asp Tyr Asp Asp Arg Glu Pro Arg His Lys Gly Gln
    370                 375                 380

Ser Glu Val Leu Glu Gly Leu Leu Gln Gln Val Arg Ala Leu His Gln
385                 390                 395                 400

His Tyr Ser Cys Arg Glu Ser Thr Lys Leu Gln Thr Thr Gly Arg Lys
                405                 410                 415

Gln Ser Val Ser Arg Ser Leu Lys His Leu Phe His Ser Ser Asn Lys
            420                 425                 430

Phe Val Lys Thr Leu Lys Arg Gly Leu Tyr Ile Ala Val Ile Phe Tyr
        435                 440                 445

Tyr Lys Asp Asn Ile Leu Val Thr Asn Glu Asp Gln Val Pro Ile Val
    450                 455                 460

Glu Ile Asp Asp Ser His Thr Ser Ser Ile Thr Gln Asp Phe Leu Trp
465                 470                 475                 480

Phe Thr Lys Leu Ser Cys Met Trp Glu Asp Ile Arg Trp Leu Arg Gln
                485                 490                 495

Ser Ile Pro Ile Ser Ser Ser Ser Ser Thr Val Leu Gln Thr Arg Gln
            500                 505                 510

Lys Met Leu Ala Ala Thr Ala Gln Leu Gln Asn Leu Leu Gly Thr His
        515                 520                 525

Asn Leu Gly Arg Val Tyr Tyr Glu Pro Ile Lys Asp Arg His Gly Asn
    530                 535                 540

Ile Leu Ile Val Thr Ile Arg Glu Val Glu Met Leu Tyr Ser Phe Phe
545                 550                 555                 560

Asn Gly Lys Trp Met Gln Ile Ser Lys Leu Gln Ser Gln Arg Lys Ser
                565                 570                 575

Leu Ser Thr Pro Glu Glu Pro Thr Ala Leu Asp Ile Leu Leu Ile Thr
```

```
            580                 585                 590

Ile Gln Asp Ile Leu Ser Tyr His Lys Arg Ser His Gln Arg Leu Phe
        595                 600                 605

Pro Gly Leu Tyr Leu Gly Tyr Leu Lys Leu Cys Ser Ser Val Asp Gln
    610                 615                 620

Ile Lys Val Leu Val Thr Gln Lys Leu Pro Asn Ile Leu Cys His Val
625                 630                 635                 640

Lys Ile Arg Glu Asn Asn Asn Ile Ser Arg Glu Glu Trp Glu Trp Ile
                645                 650                 655

Gln Lys Leu Ser Gly Ser Glu Ser Met Glu Ser Val Asp His Thr Ser
            660                 665                 670

Asp Cys Pro Met Gln Leu Phe Phe Tyr Glu Leu Gln Met Ala Val Lys
        675                 680                 685

Ala Leu Leu Gln Gln Ile Asn Ile Pro Leu His Gln Ala Arg Asn Phe
    690                 695                 700

Arg Leu Tyr Thr Gln Glu Val Leu Glu Met Gly His Asn Val Ser Phe
705                 710                 715                 720

Leu Leu Leu Leu Pro Ala Ser Asp Asp Val Cys Thr Ala Pro Gly Gln
                725                 730                 735

Asn Asn Pro Tyr Thr Pro His Ser Gly Phe Leu Asn Leu Pro Leu Gln
            740                 745                 750

Met Phe Glu Leu Gly Ile Val Ala Cys Phe Thr
        755                 760


<210> SEQ ID NO 551
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 551

agctctgtag ctctgtggat c                                               21


<210> SEQ ID NO 552
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 552

aggcggaagt tccttgcctg g                                               21


<210> SEQ ID NO 553
<211> LENGTH: 2281
<212> TYPE: DNA
<213> ORGANISM: Homo sapiens

<400> SEQUENCE: 553

gcgggccgca gccagcgcac ccagaccctg cgctgccctc ggacggccgg gcgcggagcc      60

ccagctgcgg aggccgacgg cacccggccc cgagcgcctc gacgccgagc cgcgcgcgcc     120

ttctccgcca ggcccggcgg gcgggagcgg gggcgaggga gcaggagcgg ccagtgcccc     180

cgacaccccc ggcccggcac ccccggcccg gcatccccccg ccgccgccgc cgccgcctca    240

aggccgcccg ctccccgcag gtggacgcgg ccatgggccg aggggtgcgc gtgctgctgc     300
```

```
tgctgagcct gctgcactgc gccgggggca gcgagggcag gaagacctgg cggcgccggg    360

gtcagcagcc gcctcctccc ccgcggaccg aggcggcgcc ggcggccgga cagcccgtgg    420

agagcttccc gctggacttc acggccgtgg agggtaacat ggacagcttc atggcgcaag    480

tcaagagcct ggcgcagtcc ctgtacccct gctccgcgca gcagctcaac gaggacctgc    540

gcctgcacct cctactcaac acctcggtga cctgcaacga cggcagcccc gccggctact    600

acctgaagga gtccaggggc agccggcggt ggctcctctt cctggaaggc ggctggtact    660

gcttcaaccg cgagaactgc gactccagat acgacaccat gcggcgcctc atgagctccc    720

gggactggcc gcgcactcgc acaggcacag ggatcctgtc ctcacagccg gaggagaacc    780

cctactggtg gaacgcaaac atggtcttca tcccctactg ctccagtgat gtttggagcg    840

gggcttcatc caagtctgag aagaacgagt acgccttcat gggcgccctc atcatccagg    900

aggtggtgcg ggagcttctg ggcagagggc tgagcggggc caaggtgctg ctgctggccg    960

ggagcagcgc gggggggcacc ggggtgctcc tgaatgtgga ccgtgtggct gagcagctgg   1020

agaagctggg ctacccagcc atccaggtgc gaggcctggc tgactccggc tggttcctgg   1080

acaacaagca gtatcgccac acagactgcg tcgacacgat cacgtgcgcg cccacggagg   1140

ccatccgccg tggcatcagg tactggaacg gggtggtccc ggagcgctgc cgacgccagt   1200

tccaggaggg cgaggagtgg aactgcttct ttggctacaa ggtctacccg accctgcgct   1260

gccctgtgtt cgtggtgcag tggctgtttg acgaggcaca gctgacggtg gacaacgtgc   1320

acctgacggg gcagccggtg caggagggcc tgcggctgta catccagaac ctcggccgcg   1380

agctgcgcca cacactcaag gacgtgccgg ccagctttgc cccgcctgc ctctcccatg   1440

agatcatcat ccggagccac tggacggatg tccaggtgaa ggggacgtcg ctgccccgag   1500

cactgcactg ctgggacagg agcctccatg acagccacaa ggccagcaag acccccctca   1560

agggctgccc cgtccacctg gtggacagct gcccctggcc ccactgcaac ccctcatgcc   1620

ccaccgtccg agaccagttc acggggcaag agatgaacgt ggcccagttc ctcatgcaca   1680

tgggcttcga catgcagacg gtggcccagc cgcagggact ggagcccagt gagctgctgg   1740

ggatgctgag caacggaagc taggcagact gtctggagga ggagccggca ctgaggggcc   1800

cagacacccg ctgccccagt gccacctcac cccccaccag caggccctcc cgtctcttcg   1860

ggacagggcc ccagccgtcc cccctgtctg ggtctgccca ctgccctcct gccccggctt   1920

tccctgcccc tctcccacag cccagccaga gacaagggac ctgctgtcat ccccatctgt   1980

ggcctggggg tccttcctga caacgagggg gtagccagaa gagaagcact ggattcctca   2040

gtccaccagc tcagacagca cccaccggcc ccacccatca agccctttta tattatttta   2100

taaagtgact tttttattac tttaattttt taaaaaaagg aaaataagaa tatatgatga   2160

atgatattgt tttgtaactt tttaaaaatg attttaaaga gacaaaaaag aacctcaaaa   2220

aaaaaaaaaa aaaaaaaaaa aaaaaaaaaa aaaaaaaaaa aaaaaaaaaa aaaaaaaaaa   2280

a                                                                   2281
```

```
<210> SEQ ID NO 554
<211> LENGTH: 496
<212> TYPE: PRT
<213> ORGANISM: Homo sapiens

<400> SEQUENCE: 554

Met Gly Arg Gly Val Arg Val Leu Leu Leu Leu Ser Leu Leu His Cys
1               5                   10                  15
```

```
Ala Gly Gly Ser Glu Gly Arg Lys Thr Trp Arg Arg Arg Gly Gln Gln
            20                  25                  30

Pro Pro Pro Pro Pro Arg Thr Glu Ala Ala Pro Ala Ala Gly Gln Pro
        35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
            100                 105                 110

Glu Ser Arg Gly Ser Arg Arg Trp Leu Leu Phe Leu Glu Gly Gly Trp
        115                 120                 125

Tyr Cys Phe Asn Arg Glu Asn Cys Asp Ser Arg Tyr Asp Thr Met Arg
    130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Ser Lys Ser Glu Lys Asn Glu Tyr Ala Phe Met Gly Ala Leu Ile Ile
        195                 200                 205

Gln Glu Val Val Arg Glu Leu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
        275                 280                 285

Glu Ala Ile Arg Arg Gly Ile Arg Tyr Trp Asn Gly Val Val Pro Glu
    290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
            340                 345                 350

Gly Gln Pro Val Gln Glu Gly Leu Arg Leu Tyr Ile Gln Asn Leu Gly
        355                 360                 365

Arg Glu Leu Arg His Thr Leu Lys Asp Val Pro Ala Ser Phe Ala Pro
    370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
```

```
        435                 440                 445

Cys Pro Thr Val Arg Asp Gln Phe Thr Gly Gln Glu Met Asn Val Ala
    450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495


<210> SEQ ID NO 555
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 555

gagatcatca tccggagcca c                                               21


<210> SEQ ID NO 556
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 556

tagcttccgt tgctcagcat c                                               21


<210> SEQ ID NO 557
<211> LENGTH: 522
<212> TYPE: DNA
<213> ORGANISM: Homo sapiens

<400> SEQUENCE: 557

atgtaagcaa agtagtcatt aaaaatacac cctctacttg ggctttatac tgcatacaaa     60

tttactcatg agccttcctt tgaggaagga tgtggatctc caaataaaga tttagtgttt    120

attttgagct ctgcatctta acaagatgat ctgaacacct ctcctttgta tcaataaata    180

gccctgttat tctgaagtga gaggaccaag tatagtaaaa tgctgacatc taaaactaaa    240

taaatagaaa acaccaggcc agaactatag tcatactcac acaaagggag aaatttaaac    300

tcgaaccaag caaaaggctt cacggaaata gcatggaaaa acaatgcttc cagtggccac    360

ttcctaagga ggaacaaccc cgtctgatct cagaattggc accacgtgag cttgctaagt    420

gataatatct gtttctacta cggatttagg caacaggacc tgtacattgt cacattgcat    480

tatttttctt caagcgttaa taaaagtttt aaataaatgg ca                       522


<210> SEQ ID NO 558
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 558

actacggatt taggcaacag g                                               21


<210> SEQ ID NO 559
<211> LENGTH: 24
```

<212> TYPE: DNA
<213> ORGANISM: artificial
<220> FEATURE:
<223> OTHER INFORMATION: Description of artificial sequence:
Oligonucleotide

<400> SEQUENCE: 559
gagatctcga gatctcgatc gtac 24

<210> SEQ ID NO 560
<211> LENGTH: 2383
<212> TYPE: DNA
<213> ORGANISM: Homo sapiens

<400> SEQUENCE: 560
cttttctctt gttgagtgca aatggagaac agctgctcac gctcgtcgtc tgacatcagc 60
tatttctcag gatgaccctg cgagacaggc cagggtcatt agacccaatt tggttctcag 120
caaatatgtg tttattcctg catgcgtggg ccacaggctg gtttcttggg tgcaatgaat 180
agctgcaggt ttattagggt gtctttttag atggatgtat gtttcccgat gtctatagaa 240
cactccggac cccggagagt gaagactctg cctgtcggac ttgctttgag aagatccttc 300
tccacctccc catggcagaa gttgcttcac agaggggaac agttttatgg atgtggctga 360
gaccttaaac ttgaggcaac ccatctgagg tggcatccag aggagactgg ctggcccctc 420
cttcaccttg gatgtagtgc tgtttctagg atctcttttc aatcagcaaa acaggggatg 480
ttccaagagg gtgtggattc cctgccatcc cacatggtca agtggagggg acgggaaaaa 540
gctatgaagg gtttgtgacc acacagactc tcctggcccc ctgtcctttt ggaaagaaga 600
cagggatgaa atataatcaa gcaattaacc acccccatca tcaccaagaa caacagtatc 660
aacaagaaga acagggacaa caaaacccac ggatgaaaca ttcctttctc agctcagatc 720
ttatctggtg cgttctctct ctgctctgtc ttggtgtgtg gtttagagaa acatggacaa 780
cgctgtttgg aagaacaggt gagcgagggt ggggaatttc agaggcctgg gcccaccgcc 840
tccacccctt ccccagttta acctttgaca ggatcttcac ctctctctga tcagcattgc 900
ttcttgttca aaggcctcag ccacccagct gtgtcccttt ccccagaaag caagggcaga 960
tggcagtggg tctgttgatg agagaacttt aagggcccaa tcagtccctg ggcacccccct 1020 cctgggctcg ttttctccag gaggctgcat tctgatccat aaaccttctc ctcggggttt 1080
agggtcgagc tgttcctgat gtttatcgga gactgggatc aaagctatcc aggtcataaa 1140
tctctctctg tggctgttgg gccccagggc agctgaagag ggttgacagc cctttggacc 1200
tcaaaggaaa aaatgtgctc tactccaccc actcccagct ctgccaagaa gctgtcctct 1260
gagaagccat ggctgggccg ttccattctg gggagctgct gaaaagagct gggaggccga 1320
gaagaacttg cgtgtgctgg gggagaggaa gcctggcctt gagggagggg tgcaggtgtg 1380
gctcctctgt gtgtgggggc tgggggacct tgtgtgcctt ttccttgtgg ctgtgaaatg 1440
ctttatgagt acttccatag gaggatggac agggagtcgg ggagataaac tcagccacaa 1500
ggccccaggg cctcaggaaa cttgcaccca accctctcat tttacagaag aaaactgtgc 1560
ctggaaggtt gaagggtttg ttcccagtca cacaaccagg gatccttagg acagccagac 1620
caggaaacca tttccaaact gccaagccat ggcagagtat caagacctca ggaaccatcg 1680
agacaccatg gaagcattgg gaaaagcctc cttagctttt gaagctcctc attgttcttg 1740
agtgtgcatg gagcccatga ctgcggggtt ttgtagacac ctcagggatt acatgactgg 1800 taccctgac aaagtcaagg ctgctggaca aaatgagtcc gaggatttca ggggcagctg 1860
ggcgcaggag ctggtgggct gttgggagtg cccctttact gggcaggctt ccttcctcct 1920
ggtgatgggg ggttcctcag cacaaaagtg aaggggtgga ggggctggag gagcaggaat 1980
ctctcttgtt gataggtatg aggccttgaa gtccttttct ttgtcccagg attcatggac 2040
gcttcggggc tgatctttga gttttcaagc atggggtgca gagacgttta ggtaaactct 2100
taccgtcctc tctcttcgtc agggcttccc aggaatcaac aatgcccaag aaggaaggga 2160
ttgtagaaat agcttaaccc tttcatttac caacgtggaa attgaagccc agggaaggga 2220
agggaccggt cgtggaaggg agagccatca gcagaaagag accctgagat cttcgcctgg 2280
gattcccagg aagtccagcc cgagctgatt cacagaacaa atgcatgcaa accttgctat 2340
caataaatta cacatgcact tacgtaaaaa aaaaaaaaaa aaa 2383

<210> SEQ ID NO 561
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 561
cagagacgtt taggtaaact c 21

<210> SEQ ID NO 562
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 562
taccaacgtg gaaattgaag c 21

<210> SEQ ID NO 563
<211> LENGTH: 2336
<212> TYPE: DNA
<213> ORGANISM: Homo sapiens

<400> SEQUENCE: 563
aaaaaaacct atctaaggag gagccaagat ggccgcatag gaacagctcc agtccacagc 60
tcccagcgtg agcgacgcag aagacgggtg atttctgcat ttccatctga ggtaccgggt 120
tcttctcact agggagttcc agacagtggg cgcagcaggc ttttcttctt ggagctgaaa 180
caggcgcact ggcgagggtt gtgaggaaag gtttgcagcc ccctgccttg gtctgctata 240
gccagtgaca cgatcaatac cagggtgagc agcagaggaa gctcagggaa gattatgaag 300
atgagaattc attacctatc aaagaaaatg cgtaaactct agaagtattg cttgctcctt 360
tgccacaaag tgtacattca agagtaaatt gtttaaagcc aaagggcctt gcgccacgtc 420
cttagcctca gctttctact tgctaaaatg gaaataacaa cagtacctac cttacagacc 480
tggcgtgagg attaaattat accagcaaag tgcctggcac ctagaatttg cctgagttct 540
gatcaatgct aaaaacacca tttaacagtg ccctttcctg cctgggaagc ccacaaagat 600
ttcgcttttc acttattact catcaaactg actctggttc acagtggaaa agagaagaaa 660
agctgatgga gaaatggcag tgaagaagga gaacaaaatg tcagagcaat acttttgagc 720
gacttatcct ctgttctgca atatttgcaa aagtcagtct atagacgtga agccaacagg 780

```
gaccctcagg cctgtgcatc aggatggtgg gctgcctaag tcctctgggg acagcagtgc    840
cagaaggagt attggacaca gtgacccgac tgtatgagat gagaaaaaac aaaaacagga    900
ggtccgcagt actgatgaac taatctgtca ctcacaagct caggtctgca aaaaaaagaa    960
acgaagcact aaacatggcc ataagagatg gaaatgcaag tcttcatttc taaatgataa   1020
tcaaaccaac gatcagaaac tgattaactg tgtaattgaa ttgaattgaa aatcatccca   1080
tgaataacaa tccatcctac cttcaagggg ttaggaagct aactacaggt aattgctatc   1140
agaaatctga tttgatttcc aaaaattgtg tgaatgaacc aagtttcttc atcttgatat   1200
actaggcagg gagtttgttc ttccaagtac tagactgctt aattgcttgc ttgggggagg   1260
agaaatccta ggggaaaggc atatatgagc aatttctact ctgtgaagcc agcgctgtgt   1320
cctgagctgg atcatggcca gaaacagaaa agtctactct tccctacagt ggaagcaact   1380
gtggatattt catcctagga gtgaatgaaa aaacctaaag ctcatacttc atgggaatct   1440
ttcaatattc tgactgaaaa ctggttattt gctcctccaa cccaaagcca tctaggaaca   1500
gcactcagaa caggaaaaaa aaaagacaaa aataataatt attccaaaac gtatttgagc   1560
agaaacaaac acaaacattt gcattattaa atgggcttgt tcacacctgc tgagtagata   1620
taagacgata tttaagacaa gagctaaaaa ataaaccatc cctttctggt tttgagtgac   1680
agcagagcaa taaaaattat tttcacattc ttttccctat tgttagaagt aatcatttga   1740
gtaaatacac ttatctgtgc tgtaactatt gaaatgaatc cacttcaaat atgtatacca   1800
cctttctttt ttatatttct agatatggtt tcaatataga ctttctgact tttatggtat   1860
acatatagga caatattcta ttcttctttc cttttaaata cttactgttt caatttcaaa   1920
taaaaaatca gcattctagt ttgtacattt tagcacagaa atgtttacaa ccttcagcac   1980
aattgctttt gtaatttact gacttggcat tttgaggcgt ttttaacaaa ttatgagaaa   2040
taacaccttc agaaagcatg tgactacttt gatgcaacta tttacaatgt attcataaga   2100
agtcattaac ctgtagagtt cttagacatg tggaaccttt aacaattata ctaaagagta   2160
catacaaaat acagagctat gtaataataa ctaattttaa atcctgacaa attagaagtt   2220
aagcctacta tctgtaaaaa tatgtcctga ttcatttttt taagtatata cctgagcctt   2280
taaaaagtat atgcctttac aattgatttc caataaacaa tactgaataa catact       2336
```

```
<210> SEQ ID NO 564
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 564

gcaatacttt tgagcgactt atcc                                            24


<210> SEQ ID NO 565
<211> LENGTH: 23
<212> TYPE: DNA
<213> ORGANISM: artificial
<220> FEATURE:
<223> OTHER INFORMATION: Description of artificial sequence:
      Oligonucleotide

<400> SEQUENCE: 565

gatagcaatt acctgtagtt agc                                             23
```

<210> SEQ ID NO 566
<211> LENGTH: 1187
<212> TYPE: DNA
<213> ORGANISM: Homo sapiens

<400> SEQUENCE: 566
gaacaacatg gcttccccca gcgtgagact cgcttgtcct cccaccgcct gctctctcct 60
gatgaccagg ttccaggagt tatcaaagaa cagcctctga gctgcgtgga gaaagccatg 120
gagacagcca gaagaaaacg gcaggattag attaacctgt gattcctggc tggccacgag 180
gtcacccatg gcatggagct gcccacaacg cccttctcag catgaagcat cctgaaagat 240
ccagggccag gttccccagg attggggagt tggaagctca ttggcactgt caaatttgaa 300
gaagaggcgt gctctgactg cctggacagg acccggaatc aaaccgcagg ccctgggtca 360
ccgctgccgg aaagagccag ttcctgtccg tccatgcacc caccaccaaa acccaggcct 420
tcctggaggt gctaggggag gccatgcccc ttttctgagt gcttggaagt gactgctgca 480
agtgacaagt gaccacgcct ttcccccgc gggtataaat tcagaggcgc tgcgctccga 540
ttctggcagt gcagctgtgg gaacctctcc acgcgcacga actcagccaa cgatttctga 600
tagatttttg ggagtttgac cagagatgca aggggtgaag gagcgcttcc taccgttagg 660
gaactctggg gacagagcgc cccggccgcc tgatggccga ggcagggtgc gacccaggac 720
ccaggacggc gtcgggaacc ataccatggc ccggatcccc aagaccctaa agttcgtcgt 780
cgtcatcgtc gcggtcctgc tgccagtgag tccccgccgc ggtccctggc tggggaagag 840
cgcacctggc gccgggaggg ggcagggaga cggggacacg gcagggatgc ctggccctgg 900
tcacctgcgg ccgggcatgt ccgggcagga cgaactcgcc gtcggagtca ggggaagaac 960
tgggtccccg ggctgggcag gagggacccg gccgcgaggg agcagagagg cggtccccct 1020
ggctgccccg agcccgcgaa gggagggaag ttccagaatc gagagaggga gggagtcaag 1080
gtggaaccca tagagtgagc ctcctgaaga cacagagcgg ttgcctctct cattaattaa 1140
ttaattagtt aataaaatta accccatgtt taaaaaaaaa aaaaaaa 1187

<210> SEQ ID NO 567
<211> LENGTH: 155
<212> TYPE: PRT
<213> ORGANISM: Homo sapiens

<400> SEQUENCE: 567

Met Gln Gly Val Lys Glu Arg Phe Leu Pro Leu Gly Asn Ser Gly Asp
1               5                   10                  15

Arg Ala Pro Arg Pro Pro Asp Gly Arg Gly Arg Val Arg Pro Arg Thr
            20                  25                  30

Gln Asp Gly Val Gly Asn His Thr Met Ala Arg Ile Pro Lys Thr Leu
        35                  40                  45

Lys Phe Val Val Val Ile Val Ala Val Leu Leu Pro Val Ser Pro Arg
    50                  55                  60

Arg Gly Pro Trp Leu Gly Lys Ser Ala Pro Gly Ala Gly Arg Gly Gln
65                  70                  75                  80

Gly Asp Gly Asp Thr Ala Gly Met Pro Gly Pro Gly His Leu Arg Pro
                85                  90                  95

Gly Met Ser Gly Gln Asp Glu Leu Ala Val Gly Val Arg Gly Arg Thr
            100                 105                 110

Gly Ser Pro Gly Trp Ala Gly Gly Thr Arg Pro Arg Gly Ser Arg Glu
        115                 120                 125

```
Ala Val Pro Leu Ala Ala Pro Ser Pro Arg Arg Glu Gly Ser Ser Arg
    130                 135                 140

Ile Glu Arg Gly Arg Glu Ser Arg Trp Asn Pro
145                 150                 155


<210> SEQ ID NO 568
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 568

ggattgggga gttggaagct c                                               21


<210> SEQ ID NO 569
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 569

agaaatcgtt ggctgagttc g                                               21


<210> SEQ ID NO 570
<211> LENGTH: 857
<212> TYPE: DNA
<213> ORGANISM: Homo sapiens

<400> SEQUENCE: 570

catccctctg gctccagagc tcagagccac ccacagccgc agccatgctg tgcctcctgc      60

tcaccctggg cgtggccctg gtctgtggtg tcccggccat ggacatcccc cagaccaagc     120

aggacctgga gctcccaaag ttggcaggga cctggcactc catggccatg gcgaccaaca     180

acatctccct catggcgaca ctgaaggccc ctctgagggt ccacatcacc tcactgttgc     240

ccacccccga ggacaacctg gagatcgttc tgcacagatg ggagaacaac agctgtgttg     300

agaagaaggt ccttggagag aagactgaga atccaaagaa gttcaagatc aactatacgg     360

tggcgaacga ggccacgctg ctcgatactg actacgacaa tttcctgttt ctctgcctac     420

aggacaccac cacccccatc cagagcatga tgtgccagta cctggccaga gtcctggtgg     480

aggacgatga gatcatgcag ggattcatca gggctttcag gcccctgccc aggcacctat     540

ggtacttgct ggacttgaaa cagatggaag agccgtgccg tttctaggtg agctcctgcc     600

tggtcctgcc tcctggctca cctccgcctc caggaagacc agactcccac ccttccacac     660

ctccagagca gtgggacttc ctcctgccct ttcaaagaat aaccacagct cagaagacga     720

tgacgtggtc atctgtgtcg ccatcccctt cctgctgcac acctgcacca cggccatggg     780

gaggctgctc cctgggggca gagtctctgg cagaggttat taataaaccc ttggagcatg     840

aaaaaaaaaa aaaaaaa                                                   857


<210> SEQ ID NO 571
<211> LENGTH: 180
<212> TYPE: PRT
<213> ORGANISM: Homo sapiens

<400> SEQUENCE: 571

Met Leu Cys Leu Leu Leu Thr Leu Gly Val Ala Leu Val Cys Gly Val
```

```
1               5                   10                  15

Pro Ala Met Asp Ile Pro Gln Thr Lys Gln Asp Leu Glu Leu Pro Lys
            20                  25                  30

Leu Ala Gly Thr Trp His Ser Met Ala Met Ala Thr Asn Asn Ile Ser
        35                  40                  45

Leu Met Ala Thr Leu Lys Ala Pro Leu Arg Val His Ile Thr Ser Leu
    50                  55                  60

Leu Pro Thr Pro Glu Asp Asn Leu Glu Ile Val Leu His Arg Trp Glu
65                  70                  75                  80

Asn Asn Ser Cys Val Glu Lys Lys Val Leu Gly Glu Lys Thr Glu Asn
                85                  90                  95

Pro Lys Lys Phe Lys Ile Asn Tyr Thr Val Ala Asn Glu Ala Thr Leu
            100                 105                 110

Leu Asp Thr Asp Tyr Asp Asn Phe Leu Phe Leu Cys Leu Gln Asp Thr
        115                 120                 125

Thr Thr Pro Ile Gln Ser Met Met Cys Gln Tyr Leu Ala Arg Val Leu
    130                 135                 140

Val Glu Asp Asp Glu Ile Met Gln Gly Phe Ile Arg Ala Phe Arg Pro
145                 150                 155                 160

Leu Pro Arg His Leu Trp Tyr Leu Leu Asp Leu Lys Gln Met Glu Glu
                165                 170                 175

Pro Cys Arg Phe
            180
```

<210> SEQ ID NO 572
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 572
agttcaagat caactatacg g 21

<210> SEQ ID NO 573
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 573
tagaaacggc acggctcttc c 21

<210> SEQ ID NO 574
<211> LENGTH: 4415
<212> TYPE: DNA
<213> ORGANISM: Homo sapiens

<400> SEQUENCE: 574
agagaagcaa catctttaag gtactgaggg caggagaagt taatgtagaa tactatgcca 60
gaaaaaataa attcccaaaa gtggaagtga aataaggaca tttagagatg tacaaaagct 120
gaccgaattc actaccagtc aacccacact acaagaaaca tcaaatgagt cctccaagca 180
gaaggaaccc aataccagat gaaaatccag atctccacga ggaaatgaag aacaccagaa 240
atggatcggc cctttcttca aataagagca gttggaataa caaagctgtt cagttgtacc 300

-continued

```
cttggaatcc actgaaatcc tgggtaggga agctccagta ccaccaactg gaaagactgg    360
gaatgcctaa tagctggtac tggccattgt cgtaggcttt gtccactctg acaaactgaa    420
gatggggact cgactcacct tcgccagcca caggaggacc tccagacgag gttaggtcga    480
cttcccgata actttagatc ctgaaacctc acgggatttt tcttctcttc cctttgatct    540
ctcttccgct tgctcaacag gacaggactc gctgcctttc tttcccgtca gaaagggatc    600
ccttgcggac aggacctaag tgagtagctg gtttccccta cttgtccttc cgggcctggg    660
tgtctcggga gctcaggctg acgggagacc taactaccgg cgagtgagac cagcaggagc    720
ctggaggggc gcgcaccagg gtggaggttt ggtgccgggg gttgagaaca acagtcaaac    780
cctcttcttc ccctggcacc acgcacctgc cccccgggac gccgaacgaa gtggtcccta    840
aagctcctct gcaggcccaa ccgaaacagg cctgaagctc caggatgggc gagaggatcc    900
tctttgagcg aaaccagcct tctgcctggc tggccctggt caacaccctg ggaagaggcc    960
gatttggcgg acagaacgga agaaaagacc taaaggtaga atctcatgat gtcgagatgt   1020
taaaacactc aaattttaag gttcgactgt gagggggaga tagggggtct cgagcaggat   1080
cgacccctga gccttcatct gcagagtcct gtgcaccagc tcagaggaca ggactatgtg   1140
caccaatggt tctcatcagg cggcaacttc accctcacat gcctccccca tccctgctgg   1200
tacacaagac cacgactagg ggaagcccgg agggagaatg ttaacccctg gcatctatct   1260
agtcagcaga ggtgagggat gctgctaaac accttacaat ccaccggagg acacccgccc   1320
ccaccgaccc cgaagtagcc attccctgga ggtggggaaa ctcgcctgta gatcaatgcc   1380
cacgcacttg gcggacagga aatcacgaat tggccactaa ctggatcttg gatctgagga   1440
aaaaattcca gcgtcagagg gaactctcgg agatttgccc agagcataag gaacgtactc   1500
cttccctcag tgatggatca tcacatctgg gggaaatcat agacaatttc ttttgtaggg   1560
cgaactctgc tatacagttt atgatgtcag agtgaatact ttctttgagt tgcagtcaga   1620
aactgtagat ttttaaaaat ttaaaattca ttattctctg tcagtatttc aaagtgtata   1680
cagaaagcta ttgcactgtt caggagatgg cgcctaacat tttggaaatt caaggtgatg   1740
aatgtccaga taagactatc tctcctggta caaagtttga caatgctgaa catttttaaa   1800
ggttcttttt gatatacaaa gtgcaccaat gagtgctttt taattcttac aataattctg   1860
ggtgaggtag gtatttttcc aattcccatt ttatgcttcg gtagcccttt gtatttatac   1920
ttcaaaacac ttggctctct tgtaattatt taagaaatta gttgtgatta tttgtttaat   1980
gtgcaggagt tacaaaaggc aagcgttaga acaagacaga cctggttatg attcctggct   2040
ctgaaagctg tacaccctgt gaccctagac aggtgtttta atgcctcgct gcctctgttt   2100
cttgctctgt aaaatgtgaa caataacagt attggcctca tgcttttttt gggttttaaa   2160
agtaataatg tggacaaaga tcagtggagt gcctggcatg ctgaacccat tccatgactg   2220
atagctatag ttgttatgat ttgtatcaat ccattttcac actgctataa ggaactacct   2280
gagactgggt aatctatgaa gaaaagaggt ttaattgact cacagttctg catggctggg   2340
agtcctcagg aacttacaat catggcagaa ggggaagcaa gacatttctt atatggcagc   2400
aggacagaaa gagagagagt gaagggggaa gtgccacaca cttccaaaca accatatctt   2460
gtggttaatt aaaaagtact cattggtgtg ccttgtatag aaaaaaatat acactcacta   2520
tcatgagaac agcaaggagg gagtctgccc ccaaggttca atcacctccc agtagacccc   2580
tcccctgaca tgtggggatt acaattcaag atgagatttg ggtggggaaa cagagtcaaa   2640
ccatatcgtg attgttctat aataaagaga tgcccacatg tgtttcatca gggacagtgc   2700
```

tcattaacca gttgtcctgc cgtaattatt aatagtatcc cctttgcttt caaaagtgtc 2760
ctagtttaca aaaagtatag aaatggagga cagaatagtg gttgcccaag attggaaaag 2820
ggtaagggta aagggtgcag aggtggatgt ggttataaaa ggcaacatgg gagatcctcg 2880
tagtgaagga accgtttagt atctccactg tggtggtaga tacccgaacc taaacatgtg 2940
aaaaattgca tgaaactaaa cacacacacc aacaagtaca agttaagtta ggaaaatcca 3000
aataagattt ctacattgta tcaataggta tatcttgatt atgatattgc aagatggtac 3060
tattcaagga aactgggtag aggctacatg agactcccct gtattatttc ctataactcc 3120
atgtgaatct acaaggatct caggattaag gaagatatcc tagtttggaa gataaaaaat 3180
atatcccagt agtaatatcc actgtcccac cagggcctga ctaccttcta taaaaagaag 3240
tgcctttgtt cccctcaagt tcctttattt ggttttattc ttcttcacag tacctacctc 3300
cacttggcag attacattta ttttttcatc tttcaacagc tatttactga atgcctacta 3360
gatgccaggc ttgagatcta gcaatgaaca agatctctgt gaaacttaca ttccaggagg 3420
agaaataaat aataaaccaa aaatataatc agtaaattat ttaatatgct gggaaacaat 3480
atgtgtaatg gaagaaatat gtaaagtgat ggattagggt tctccagaga aacagaacca 3540
acaattgact catgtgatta tggaggctga gaagtctcaa gatcacagtt ggcaagcttg 3600
agacacagga gagcccatgg tgtgtttctg atttgagtcc aaaggcctga gaaccaggag 3660
agatgatggt gtgattacag ttcaaaagct ggcaggcttg aggcccagga agagccagtg 3720
ttgcagttca attccaaagg caggaaaagg ctgatatctt agctgaagca atcaggcaga 3780
aggagctctc tcttactcat gggcaggtca gacttttggt tctattcagg cctttaagtg 3840
attggatgag gatcatctac tgtggaaaga aataagcttt attcagtgta ctgattcaaa 3900
tgttaatctc atccaaaacc atgctcacag acacacccag cataatgttt gaccaagtat 3960
ctgggcacct tgtggttcag tcaaattaac acatattaac taccttagca agatgaaaag 4020
cagtgaatgc aggatggtgg ttgaaatttt aaatacgttg gttatatagt ctcattgaaa 4080
aaggaacatt tgagtgaaga cttgaagggg tggtggaata aaccatttat ttgcttattg 4140
cctgtctccc tctatcagaa tgaaagcttc atgaagcgag agacttaatt tttatctgtt 4200
atatccctag tgcctggtgc agggtaagta ctcaaaaata tttgttgagt gaataagtaa 4260
tgattgagga tggggactgg tttgtatctg gttatatctc ttgtccttag cacagtacct 4320
ggcacatcct aagccatcca aaagagttgg ttatatgatt gtctttgaat tctatgactg 4380
tttataatat acagtaaact tcactgaaga cactg 4415

<210> SEQ ID NO 575
<211> LENGTH: 22
<212> TYPE: DNA
<213> ORGANISM: artificial
<220> FEATURE:
<223> OTHER INFORMATION: Description of artificial sequence: Oligonucleotide

<400> SEQUENCE: 575
gaagaacacc agaaatggat cg 22

<210> SEQ ID NO 576
<211> LENGTH: 21
<212> TYPE: DNA
<213> ORGANISM: artificial
<220> FEATURE:
<223> OTHER INFORMATION: Description of artificial sequence:

Oligonucleotide

<400> SEQUENCE: 576
cttcagtttg tcagagtgga c 21

<210> SEQ ID NO 577
<211> LENGTH: 484
<212> TYPE: DNA
<213> ORGANISM: Homo sapiens

<400> SEQUENCE: 577
tgtcagcttt gtctgtgcct cgcaaatcag aggcaaggga gaggttgtta ccaggggaca 60
ctgagaatgt acatttgatc tgccccagcc acggaagtca gagtaggatg cacagtacaa 120
aggagggggg agtggaggcc tgagagggaa gtttctggag ttcagatact ctctgttggg 180
aacaggacat ctcaacagtc tcaggttcga tcagtgggtc ttttggcact ttgaaccttg 240
accacaggga ccaagaagtg gcaatgagga cacctgcagg aggggctagc ctgactccca 300
gaactttaag actttctccc cactgccttc tgctgcagcc caagcaggga gtgtcccccct 360 cccagaagca tatcccagat gagtggtaca ttatataagg attttttta agttgaaaac 420 aactttcttt tctttttgta tgatggtttt ttaacccagt cattaaaaat gtttataaat 480
caaa 484

<210> SEQ ID NO 578
<211> LENGTH: 21
<212> TYPE: DNA
<213> ORGANISM: artificial
<220> FEATURE:
<223> OTHER INFORMATION: Description of artificial sequence:
Oligonucleotide

<400> SEQUENCE: 578
cagccacgga agtcagagta g 21

<210> SEQ ID NO 579
<211> LENGTH: 24
<212> TYPE: DNA
<213> ORGANISM: artificial
<220> FEATURE:
<223> OTHER INFORMATION: Description of artificial sequence:
Oligonucleotide

<400> SEQUENCE: 579
ccactcatct gggatatgct tctg 24

<210> SEQ ID NO 580
<211> LENGTH: 592
<212> TYPE: DNA
<213> ORGANISM: Homo sapiens
<220> FEATURE:
<221> NAME/KEY: misc_feature
<222> LOCATION: (62)..(62)
<223> OTHER INFORMATION: n is a, c, g, t or u

<400> SEQUENCE: 580
ggtgcatgtt cattgggcat cttccattcg accccctttgc ccacgtggtg accgctgggg 60
anctgtgaga gtgtgagggg cacgttccag ccgtctggac tctttctctc ctactgagac 120
gcagcctata ggtccgcagg ccagtcctcc caggaactga aatagtgaaa tatgagttgg 180
cgaggaagat caacatatag gcctaggcca agaagaagtt tacagcctcc tgagctgatt 240
ggggctatgc ttgaacccac tgatgaagag cctaaagaag agaaaccacc cactaaaagt 300

```
cggaatccta cacctgatca gaagagagaa gatgatcagg gtgcagctga gattcaagtg    360

cctgacctgg aagccgatct ccaggagcta tgtcagacaa agactgggga tggatgtgaa    420

ggtggtactg atgtcaaggg gaagattcta ccaaaagcag agcactttaa aatgccagaa    480

gcaggtgaag ggaaatcaca ggtttaaagg aagataagct gaaacaacac aaactgtttt    540

tatattagat attttacttt aaaatatctt aataaagttt taagcttttc tc            592
```

<210> SEQ ID NO 581
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 581

```
attggggcta tgcttgaacc c                                               21
```

<210> SEQ ID NO 582
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 582

```
tttcccttca cctgcttctg g                                               21
```

<210> SEQ ID NO 583
<211> LENGTH: 2514
<212> TYPE: DNA
<213> ORGANISM: Homo sapiens

<400> SEQUENCE: 583

```
actggggtct tctccatgcg gctcgggcta tgacagcctc cgtgctcctc cacccccgct     60

ggatcgagcc caccgtcatg tttctctacg acaacggcgg cggcctggtg gccgacgagc    120

tcaacaagaa catggaaggg gcggcggcgg ctgcagcagc ggctgcagcg gcggcggctg    180

ccggggccgg gggcgggggc ttcccccacc cggcggctgc ggcggcaggg ggcaacttct    240

cggtggcggc ggcggccgcg gctgcggcgg cggccgcggc caaccagtgc cgcaacctga    300

tggcgcaccc ggcgcccttg gcgccaggag ccgcgtccgc ctacagcagc gcccccgggg    360

aggcgccccc gtcggctgcc gccgctgctg ccgcggctgc cgctgcagcc gccgccgccg    420

ccgccgcgtc gtcctcggga ggtcccggcc cggcgggccc ggcgggcgca gaggccgcca    480

agcaatgcag cccctgctcg gcagcggcgc agagctcgtc ggggcccgcg gcgctgccct    540

atggctactt cggcagcggc tactacccgt gcgcccgcat gggcccgcac cccaacgcca    600

tcaagtcgtg cgcgcagccc gcctcggccg ccgccgccgc cgccttcgcg gacaagtaca    660

tggataccgc cggcccagct gccgaggagt tcagctcccg cgctaaggag ttcgccttct    720

accaccaggg ctacgcagcc gggccttacc accaccatca gcccatgcct ggctacctgg    780

atatgccagt ggtgccgggc ctcgggggcc ccggcgagtc gcgccacgaa cccttgggtc    840

ttcccatgga aagctaccag ccctgggcgc tgcccaacgg ctggaacggc caaatgtact    900

gccccaaaga gcaggcgcag cctccccacc tctggaagtc cactctgccc gacgtggtct    960

cccatccctc ggatgccagc tcctatagga gggggagaaa gaagcgcgtg ccttatacca   1020
```

-continued

```
aggtgcaatt aaaagaactt gaacgggaat acgccacgaa taaattcatt actaaggaca   1080

aacggaggcg gatatcagcc acgacgaatc tctctgagcg gcaggtcaca atctggttcc   1140

agaacaggag ggttaaagag aaaaaagtca tcaacaaact gaaaaccact agttaatgga   1200

ttaaaaatag agcaagaagg caacttgaag aaacgcttca gaactcgttg ctttgcccag   1260

ataatgataa taatgcttaa taataattga agaatgggaa agagaaagag acagagactg   1320

gcattttcct ctcccgaagg agatctcttt ctctttaatg gaatctacaa ctgttttaaa   1380

actttaagaa aggtaaagac tgccagttct tccgccaacc ccatcagccc agcccgttaa   1440

atgtcaaacg tcaaccccca aaatacgcaa tttcagataa gttacgcagt tactgaaatc   1500

ttgtaagtat ttaagtgatc gttacatttt aggacactgc gttagatggt aataatctgg   1560

aagttggtta caaacgcaag aggccattgt aaacatctgc ttgtccttct taggtcgcca   1620

ttccctttgc atgttaagcg tctgctcagg taaatcttag tgaaattcct accgttgttg   1680

tacgttctgc aaaacatttt atgtatagat ttagagggga aacgagaagg tactgaaata   1740

atgatcttgg aatatttgct gtgaagggag aaagggagag aaaactcttc tgaggatcat   1800

ttgtcttggt agtatagtaa aaccaaccag ctgaaccttt caggctacaa gagaacccgg   1860

gtcggtaatg tctttttaag aataattttt aattgcttat aacaagcata ttttgtggca   1920

tttgaactat atttactgct ccaatatccg ttattttcca aaggattttg tatctttttg   1980

aaaatgttta catcatcaga tgatccacag aattcacttt atgtgagatc tcccgagagt   2040

ttccatccca acataatgga ctttggtttg aacacaattc gtttttttcat ttgaattggc   2100

atttcccaat atttgctaaa catttgctgg agaaatcatt tttcttttttt ctttttttaga   2160

aaactcagaa tgaaaattca ttcccctgaa atatttaggt gtctatattc tatattttga   2220

tctattaagg gattagtatt tttccatgtt tattgtgtta tcagagtgca ttagaaagat   2280

tagtgattca tcttcacagc acatttttaa tcaagcagtt atttcaacca gcacattcgt   2340

tttgttcata ttcactatag aatgatatct tgtaaataaa gacattcagc acactgtgaa   2400

aatgtatttg tgcacctgct ttttaaatat ttctactaaa aatgaaaaaa aaaaaccctt   2460

agacctgtag atagtgatat cgtaatatta attgttaata aaatagtcac tgcc         2514
```

<210> SEQ ID NO 584
<211> LENGTH: 388
<212> TYPE: PRT
<213> ORGANISM: Homo sapiens

<400> SEQUENCE: 584

```
Met Thr Ala Ser Val Leu Leu His Pro Arg Trp Ile Glu Pro Thr Val
1               5                   10                  15

Met Phe Leu Tyr Asp Asn Gly Gly Gly Leu Val Ala Asp Glu Leu Asn
            20                  25                  30

Lys Asn Met Glu Gly Ala Ala Ala Ala Ala Ala Ala Ala Ala Ala Ala
        35                  40                  45

Ala Ala Ala Gly Ala Gly Gly Gly Gly Phe Pro His Pro Ala Ala Ala
    50                  55                  60

Ala Ala Gly Gly Asn Phe Ser Val Ala Ala Ala Ala Ala Ala Ala Ala
65                  70                  75                  80

Ala Ala Ala Ala Asn Gln Cys Arg Asn Leu Met Ala His Pro Ala Pro
                85                  90                  95

Leu Ala Pro Gly Ala Ala Ser Ala Tyr Ser Ser Ala Pro Gly Glu Ala
            100                 105                 110
```

```
Pro Pro Ser Ala Ala Ala Ala Ala Ala Ala Ala Ala Ala Ala Ala Ala
        115                 120                 125

Ala Ala Ala Ala Ala Ser Ser Ser Gly Gly Pro Gly Pro Ala Gly Pro
    130                 135                 140

Ala Gly Ala Glu Ala Ala Lys Gln Cys Ser Pro Cys Ser Ala Ala Ala
145                 150                 155                 160

Gln Ser Ser Ser Gly Pro Ala Ala Leu Pro Tyr Gly Tyr Phe Gly Ser
                165                 170                 175

Gly Tyr Tyr Pro Cys Ala Arg Met Gly Pro His Pro Asn Ala Ile Lys
            180                 185                 190

Ser Cys Ala Gln Pro Ala Ser Ala Ala Ala Ala Ala Ala Phe Ala Asp
        195                 200                 205

Lys Tyr Met Asp Thr Ala Gly Pro Ala Ala Glu Glu Phe Ser Ser Arg
    210                 215                 220

Ala Lys Glu Phe Ala Phe Tyr His Gln Gly Tyr Ala Ala Gly Pro Tyr
225                 230                 235                 240

His His His Gln Pro Met Pro Gly Tyr Leu Asp Met Pro Val Val Pro
                245                 250                 255

Gly Leu Gly Gly Pro Gly Glu Ser Arg His Glu Pro Leu Gly Leu Pro
            260                 265                 270

Met Glu Ser Tyr Gln Pro Trp Ala Leu Pro Asn Gly Trp Asn Gly Gln
        275                 280                 285

Met Tyr Cys Pro Lys Glu Gln Ala Gln Pro Pro His Leu Trp Lys Ser
    290                 295                 300

Thr Leu Pro Asp Val Val Ser His Pro Ser Asp Ala Ser Ser Tyr Arg
305                 310                 315                 320

Arg Gly Arg Lys Lys Arg Val Pro Tyr Thr Lys Val Gln Leu Lys Glu
                325                 330                 335

Leu Glu Arg Glu Tyr Ala Thr Asn Lys Phe Ile Thr Lys Asp Lys Arg
            340                 345                 350

Arg Arg Ile Ser Ala Thr Thr Asn Leu Ser Glu Arg Gln Val Thr Ile
        355                 360                 365

Trp Phe Gln Asn Arg Arg Val Lys Glu Lys Lys Val Ile Asn Lys Leu
    370                 375                 380

Lys Thr Thr Ser
385


<210> SEQ ID NO 585
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 585

tctggaagtc cactctgccc gacg                                          24


<210> SEQ ID NO 586
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 586

tgtgacctgc cgctcagaga g                                             21
```

<210> SEQ ID NO 587
<211> LENGTH: 8769
<212> TYPE: DNA
<213> ORGANISM: Homo sapiens

<400> SEQUENCE: 587
atttagaggc ggcgccaggg cggccgcgga gaaacgtgac acaccagccc tctcggaggg 60
gtttcggacc gaagggaaga agctgcgccg tgtcgtccgt ctccctgcgc gccgcgggca 120
cttctcctgg gctctccccg aactctcccg cgacctctgc gcgccctcag gccgccttcc 180
ccgccctggg ctcgggacaa cttctggggt ggggtgcaaa gaaagtttgc ggctcctgcc 240
gccggcctct ccgcctcttg gcctaggagg ctcgccgccc gcgcccgctc gttcggcctt 300
gcccgggacc gcgtcctgcc ccgagaccgc caccatgaac aagctttaca tcggcaacct 360
caacgagagc gtgacccccg cggacttgga gaaagtgttt gcggagcaca agatctccta 420
cagcggccag ttcttggtca aatccggcta cgccttcgtg gactgcccgg acgagcactg 480
ggcgatgaag gccatcgaaa ctttctccgg gaaagtagaa ttacaaggaa aacgcttaga 540
gattgaacat tcggtgccca aaaaacaaag gagccggaaa attcaaatcc gaaatattcc 600
accccagctc cgatgggaag tactggacag cctgctggct cagtatggta cagtagagaa 660
ctgtgagcaa gtgaacaccg agagtgagac ggcagtggtg aatgtcacct attccaaccg 720
ggagcagacc aggcaagcca tcatgaagct gaatggccac cagttggaga accatgccct 780
gaaggtctcc tacatccccg atgagcagat agcacaggga cctgagaatg ggcgccgagg 840
gggctttggc tctcggggtc agccccgcca gggctcacct gtggcagcgg gggccccagc 900
caagcagcag caagtggaca tccccccttcg gctcctggtg cccacccagt atgtgggtgc 960
cattattggc aaggaggggg ccaccatccg caacatcaca aaacagaccc agtccaagat 1020
agacgtgcat aggaaggaga acgcaggtgc agctgaaaaa gccatcagtg tgcactccac 1080
ccctgagggc tgctcctccg cttgtaagat gatcttggag attatgcata aagaggctaa 1140
ggacaccaaa acggctgacg aggttcccct gaagatcctg gcccataata actttgtagg 1200
gcgtctcatt ggcaaggaag gacggaacct gaagaaggta gagcaagata ccgagacaaa 1260
aatcaccatc tcctcgttgc aagaccttac cctttacaac cctgagagga ccatcactgt 1320
gaagggggcc atcgagaatt gttgcagggc cgagcaggaa ataatgaaga aagttcggga 1380
ggcctatgag aatgatgtgg ctgccatgag cctgcagtct cacctgatcc ctggcctgaa 1440
cctggctgct gtaggtcttt tcccagcttc atccagcgca gtcccgccgc ctcccagcag 1500
cgttactggg gctgctccct atagctcctt tatgcaggct cccgagcagg agatggtgca 1560
ggtgtttatc cccgcccagg cagtgggcgc catcatcggc aagaaggggc agcacatcaa 1620
acagctctcc cggtttgcca gcgcctccat caagattgca ccacccgaaa cacctgactc 1680
caaagttcgt atggttatca tcactggacc gccagaggcc caattcaagg ctcagggaag 1740
aatctatggc aaactcaagg aggagaactt ctttggtccc aaggaggaag tgaagctgga 1800
gacccacata cgtgtgccag catcagcagc tggccgggtc attggcaaag gtggaaaaac 1860
ggtgaacgag ttgcagaatt tgacggcagc tgaggtggta gtaccaagag accagacccc 1920
tgatgagaac gaccaggtca tcgtgaaaat catcggacat ttctatgcca gtcagatggc 1980
tcaacggaag atccgagaca tcctggccca ggttaagcag cagcatcaga agggacagag 2040
taaccaggcc caggcacgga ggaagtgacc agcccctccc tgtcccttcg agtccaggac 2100

-continued

```
aacaacgggc agaaatcgag agtgtgctct ccccggcagg cctgagaatg agtgggaatc   2160
cgggacacct gggccgggct gtagatcagg tttgcccact tgattgagaa agatgttcca   2220
gtgaggaacc ctgatctctc agccccaaac acccacccaa ttggcccaac actgtctgcc   2280
cctcggggtg tcagaaattc tagcgcaagg cacttttaaa cgtggattgt ttaaagaagc   2340
tctccaggcc ccaccaagag ggtggatcac acctcagtgg gaagaaaaat aaaatttcct   2400
tcaggtttta aaaacatgca gagaggtgtt ttaatcagcc ttaaaggatg gttcatttct   2460
tgaccttaat gtttttccaa tcttcttccc cctacttggg taattgatta aaatacctcc   2520
atttacggcc tctttctata tttacactaa tttttttatc tttattgcta ccagaaaaaa   2580
atgcgaacga atgcattgct ttgcttacag tattgactca agggaaaaga actgtcagta   2640
tctgtagatt aattccaatc actccctaac caataggtac aatacggaat gaagaagagg   2700
ggaaaatggg gagaaagatg gttaaaatac ataataatcc acgtttaaaa ggagcgcact   2760
tgtggctgat ctatgccaga tcaccatctt caaattggca caactgaaat ttccccactc   2820
tgttggggct tccccaccac attcatgtcc ctctcccgtg taggtttcac attatgtcca   2880
ggtgcacata ggtggtattg aatgctcagc agggtagggg ctgaccactg tccctgattc   2940
ccatcgttct caggcggatt ttatattttt ttaaagtcta ttttaatgat tggatatgag   3000
cactgggaag gggacgctaa ctccccttga taaagtctcg gttccatgga ggacttgagt   3060
ggccccaaag gctgccacgg tgccctcacc ccagcccatg tgctcccata agggctggtt   3120
cctagaggca ggggttgtgg ggcactccca gccacggcac tgttaccttg gtggtgggac   3180
ttggaaccca accctgagct cccgataaag ctaaagtcca tcatctggca aattcagtaa   3240
attggagagt acttgcttct gtttgtatct gagaggaatt tttaactgac ggcttctgtc   3300
tccatgaatc attatcagca tgatgaaagg tgtgtctaaa aaacaattca gaataccagc   3360
agcattgtac agcaaggggt aaataagctt aatttattaa tttaccaggc ttaattaaga   3420
tcccatggag tgtttagccc ttgtgggaga cagaagccat cagttaaatg aggttaggcc   3480
tctcctccta atatactgat tgacaatgca tattagccag gtaatgcact ttagctaccc   3540
tggacaatgc tatcaagtgt gctgggaagg gaggaaggcc tctctacata tggaaaagcc   3600
catgcgtgga gttcccctcc tttcaacatt gcaacaacag taacaacaag acaaccgcaa   3660
catgtgggcg tagtcaggca atgctgtgtg cgaagtaaac tacctcaagg tatgaagtta   3720
cctcagcaat tattttcctt tttgttcccc ccaaccccat taaaaaaatt tttttttgat   3780
ttttgttttt ttgcagcttg ctgatatttt atataaaaaa gaaaagcaaa gcaaaagaga   3840
agctgatagt cttgaatatt ttattttttt aatgaaaaga aaaaacaaga aagttatgtt   3900
tcataatttc ttacaacatg agccagtaac cctttaggaa ctctctatgg agaacaggcc   3960
tggtgggaaa ggctttgggg gctgcccct taggaggagg ctagtgctaa gagggaaggc   4020
ccaggtttga gagagcccag aggggcagag cccagagcct tgtttggccc tgatctctga   4080
cttctagagc cccagctgct ggcggctgct ggaatatcct acctgatagg attaaaaggc   4140
ctagtggagc tgggggctct cagtggttaa acaatgccca acaaccaacc agctggccct   4200
tggtctcctc tctttcctcc tttggttaaa gagcatctca gccagctttt cccaccagtg   4260
gtgctgttga gatattttaa aatattgcct ccgttttatc gaggagagaa ataataacta   4320
aaaaatatac cctttaaaaa aacctatatt tctctgtcta aaaatatggg agctgagatt   4380
ccgttcgtgg aaaaaagaca aggccaccct ctcgccctca gagaggtcca cctggtttgt   4440
cattgcaatg cttttcattt tttttttttg ttattgtttc atttcagttc cgtcttgcta   4500
```

-continued

```
ttcttcctaa tctatatcca tagatctaag gggcaaacag atactagtta actgccccca   4560
cctctgtctc cctgtcttct ttagatcggt ctgattgatt ttaaaagtgg acccaaactt   4620
agggaattct tgatttaggg tggctggtgg caaggagggg caggggatat ggggacgtga   4680
ctgggacagg ttcctgcctt atcattttct ccctaggaca ttcccttgta gcccccagaa   4740
ttgtctggcc caaattgaat agaagcagaa aaacatttag ggataacatc aggccagtag   4800
aattaagcct ctccacctgt cccaaccata aaaagggtct cccagctttc catctctggc   4860
tctatatgct ttatcccaaa acaaagcaga taacgttcag acgtcggcca tttagtaatt   4920
taaagcgaat ttccagcagc aagcatgctt tgatatctgg ttcagactat catcaggaag   4980
aaaaaaaaat cccacagtac ctgaaatgtg attgttgcag tgttcagttt ccttgggggc   5040
ctgctccctt cacaccttga gcccaagtcc ttttccgttg gctgattcag ctcccagaag   5100
agacgaggaa gtgtgtggca agggactgga aaacttcact tgcttggatt aggcaaggct   5160
ccactcattg ttgatatttg cccagcagga aaatcatgta agttatacca ccagaaagca   5220
aaaggagcat ggtttggtgg ttaaggttta gtgggatgaa ggacctgtct tggtgggccg   5280
ggccctcttg tgccccgtag gctaggtctt agggcaactc cttgccctcc tgctcagcac   5340
ctccatttcc ccatccttgg tgagataaca agctatcgcg aaaagcactt gggagatttg   5400
gatgatttga gaagagtgac ttaaaaaaaa tgcttctgtg ctctaagata tatatgtgtg   5460
tgtgtgtgct acatatatat ttttaagaaa ggaccatctc tttaggatat atttttaaat   5520
tctttgaaac acataaccaa aatggtttga ttcactgact gactttgaag ctgcatctgc   5580
cagttacacc ccaaatggct ttaatcccct ctcgggtctg gttgcctttt gcagtttggg   5640
ttgtggactc agctcctgtg aggggtctgg ttaggagaga gccattttta aggacaggga   5700
gttttatagc ccttttctac tttcctcccc tcctcccagt ccttatcaat ctttttttcct   5760
ttttcctgac cccctccttc tggaggcagt tgggagctat ccttgtttat gcctcactat   5820
tggcagaaaa gaccccattt aaaacccaga gaacactgga gggggatgct ctagttggtt   5880
ctgtgtccat tttcctctgt gccaaagaca gacagacaga ggctgagaga ggctgttcct   5940
gaatcaaagc aatagccagc tttcgacaca tacctggctg tctgaggagg aaggcctcct   6000
ggaaactggg agctaagggc gaggcccttc ccttcagagg ctcctggggg attagggtgt   6060
ggtgtttgcc aagccaaggg gtagggagcc gagaaattgg tctgtcggct cctggttgca   6120
ctttggggaa ggagaggaag tttggggctc caggtagctc cctgttgtgg gactgctctg   6180
tcccctgccc ctactgcaga gatagcactg ccgagttccc ttcaggcctg gcagacgggc   6240
agtgaggagg ggcctcagtt agctctcaag ggtgccttcc cctcctccca acccagacat   6300
accctctgcc aaactgggaa ccagcagtgc tagtaactac ctcacagagc cccagagggc   6360
ctgcttgagc cttcttgctc cacaggagaa gctggtgcct ctaggcaacc ccttcctccc   6420
acctctcatc aggggtgggg gttctccttt ctttcccctg aagtgtttat ggggagatcc   6480
tagtggcttt gccattcaaa ccactcgact gtttgcctgt ttcttgaaaa ccagtagaag   6540
ggaaacagca cagcctgtca cagtaattgc aggaagattg aagaaaaatc ctcatcaatg   6600
ccaggggaca taaaagccat ttcccttcca aatactcgac aatttagatg cagaacattt   6660
ctctgtattc agacttagag taacaccagc tgaaaactgc agtttctttc ctttggatac   6720
ataaggcttc tctatcgggg tacgggacag ggaggaggcc tcatgtctga agggggattt   6780
aggggcgaga gccccagccc tgaccctcgg tcctgtgcac cgctttgggg cacagtctga   6840
```

```
tggcgccttt gctggcgcct tagtatggtt gactccggat ggacaaaaga aaaaaaattt   6900
tttttcttga atgaaatagc aggaagctcc tcgggagcat gtgttttgat taaccgcagg   6960
tgatggatgc tacgagtata aatggattaa ctacctcaat ccttacagta agattggaac   7020
taagggcagg gactcatgca taagggtatg aatcccagcc aggacaagtg agttgaggct   7080
tgtgccacaa aaggtttgtc cttggggaac aggcaggcct gccaggatcc cccccatatc   7140
gattgggctg ggagggctgg ccatgaggtc cccactttct gctttccttg cccatgtgtc   7200
accccttgg cctccagctt gtccctctct cactttctat agctttgttg gaccagatgg    7260
tgaggaaagg aatggcctct tcccttctag agggggctgg ctggagtgag acctggggct   7320
tggcctggaa cccaccacac agccccaaag tcaggaagcc tggggaaacc agagctgaga   7380
cctcttcaac agggtttctt tgagatccta cacctccatt gggccctttt tcagtcttca   7440
atgggggccc agttggctct agaaggagaa gaggtgaagc aggatccttt gccctggggg   7500
agtctgaggg cgcggtcctt ggactcattc aggccgtctt tgtagttggg ggagttccac   7560
tgggcgatcc cagcccctcc ccacccaccc tctaatggac ctcctcatag aagccccatt   7620
tcacttttgt tttatctacc tcttagcaaa acaatagata aattaggtag tggcagctcc   7680
acttgcttag gttagggggg gaaaaagatt tctttttcca aaggaaaaaa atattacctt   7740
gagaatactt tccaaaaaat aaaattaaaa aaaaaaaaac caaaaaaaaa aattttttt    7800
taaaagggag acattttcca gtgaccactg gattgtttta atttcccaag cttttttttc   7860
ccccataaat aagtttcact ctttggcgat tttcttcact tgtttaagat aacgtgctag   7920
ctattccaac aggtaacagc tttcacagtc tgcccctggc ctgtctcacc ccatccccca   7980
ccctattcct gccagtgagt ccttcctgtg cttctctccc ttctccccctc ccagccagct  8040
gacttcagtc acccctgtcc cccctcccct gccaataagc tcccccagga ataaaggctt   8100
tgttttgggg atgcttaaat cttgactggc acttcccggc tgtgggggct ggggagccac   8160
ttgtaacatt tctgtgcaga ttttatgtta gccactgcta tgtaaaagca cgttcaaaat   8220
gaatttcagc agattatgtg ttaccataat gaataaacgt cctctatcac catttggagt   8280
ctccctttc tccaggatct tgatcctggt ccccaaaacc agagtgaatc aaaagagctt    8340
cctcccctga ggcaaagtgg atttgtaagc agttctgaaa catcacttac tcagaagagg   8400
gaacgatgta ttttgatgag tgcaaattgg gaagagctgg aggcctactg cttgggacag   8460
ttttttttt ttttttttt ttaaatatga gtgctagctt attctgtaat tgcggcaact     8520
ttgaaaattg tattttactg gaaatctgcc agccatcacc acccgatttt gattgtatcc   8580
ttcctcccat cctttaatct gttcattgct ttgggggagg tggggcagct ggctcacacg   8640
ttggagtttg ttctttgatg gatgaacgaa cactccagtt ttctttcccg tgaaggttgt   8700
ttcagccaca aaccacttca ttttgctgtt tcaatttcaa aataaaagga aacttatatt   8760
gaaagacaa                                                           8769
```

<210> SEQ ID NO 588
<211> LENGTH: 577
<212> TYPE: PRT
<213> ORGANISM: Homo sapiens

<400> SEQUENCE: 588

```
Met Asn Lys Leu Tyr Ile Gly Asn Leu Asn Glu Ser Val Thr Pro Ala
1               5                   10                  15

Asp Leu Glu Lys Val Phe Ala Glu His Lys Ile Ser Tyr Ser Gly Gln
            20                  25                  30
```

```
Phe Leu Val Lys Ser Gly Tyr Ala Phe Val Asp Cys Pro Asp Glu His
        35                  40                  45

Trp Ala Met Lys Ala Ile Glu Thr Phe Ser Gly Lys Val Glu Leu Gln
    50                  55                  60

Gly Lys Arg Leu Glu Ile Glu His Ser Val Pro Lys Lys Gln Arg Ser
65                  70                  75                  80

Arg Lys Ile Gln Ile Arg Asn Ile Pro Pro Gln Leu Arg Trp Glu Val
                85                  90                  95

Leu Asp Ser Leu Leu Ala Gln Tyr Gly Thr Val Glu Asn Cys Glu Gln
            100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
    130                 135                 140

Glu Asn His Ala Leu Lys Val Ser Tyr Ile Pro Asp Glu Gln Ile Ala
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
            180                 185                 190

Gln Val Asp Ile Pro Leu Arg Leu Leu Val Pro Thr Gln Tyr Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
            260                 265                 270

Thr Ala Asp Glu Val Pro Leu Lys Ile Leu Ala His Asn Asn Phe Val
        275                 280                 285

Gly Arg Leu Ile Gly Lys Glu Gly Arg Asn Leu Lys Lys Val Glu Gln
    290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
            340                 345                 350

Asn Asp Val Ala Ala Met Ser Leu Gln Ser His Leu Ile Pro Gly Leu
        355                 360                 365

Asn Leu Ala Ala Val Gly Leu Phe Pro Ala Ser Ser Ser Ala Val Pro
    370                 375                 380

Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
                405                 410                 415

Val Gly Ala Ile Ile Gly Lys Lys Gly Gln His Ile Lys Gln Leu Ser
            420                 425                 430

Arg Phe Ala Ser Ala Ser Ile Lys Ile Ala Pro Pro Glu Thr Pro Asp
        435                 440                 445
```

Ser Lys Val Arg Met Val Ile Ile Thr Gly Pro Pro Glu Ala Gln Phe
    450                 455                 460

Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
                485                 490                 495

Ser Ala Ala Gly Arg Val Ile Gly Lys Gly Gly Lys Thr Val Asn Glu
            500                 505                 510

Leu Gln Asn Leu Thr Ala Ala Glu Val Val Val Pro Arg Asp Gln Thr
        515                 520                 525

Pro Asp Glu Asn Asp Gln Val Ile Val Lys Ile Ile Gly His Phe Tyr
    530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Gln Ala Gln Ala Arg Arg
                565                 570                 575

Lys

<210> SEQ ID NO 589
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 589
atttctatgc cagtcagatg g 21

<210> SEQ ID NO 590
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 590
gtgggcaaac ctgatctaca g 21

<210> SEQ ID NO 591
<211> LENGTH: 5016
<212> TYPE: DNA
<213> ORGANISM: Homo sapiens

<400> SEQUENCE: 591
taacattctg ttcttccgcg tgatggattt tcttttggag attcgaactg aagcctgtac 60
ggaggaaatg ttgtttttaa gggaaatgaa tagaaacaat ccactttgaa gaagccatgg 120
cgaaatcaaa gacaaaacat agactttgtt ctcaggaatc ttcagtatct gccctgctgg 180
caagctgcac cctgagtggt agtaattcct ctaattctga tggctcgttt cactataaag 240
ataagctgta cagatctgct tctcaagctc tacaggctta tattgatgat tttgatctag 300
gccaaatata tcctggtgca agcactggaa aaattaacat tgatgaggat tttactaata 360
tgtcacagtt ctgcaactat atttacaaac caaacaatgc ttttgaaaac cttgatcacg 420
aaaagcactc aaacttcata tcctgtagaa gacacatcgt taatgacata gactccatga 480
gcctaacaac tgatgatcta ttaagactcc cagcagatgg atcattttct tatacttatg 540
ttggaccgag tcaccgaacg agcaagaaaa acaagaaatg ccgtggaagg ctgggttcat 600

```
tggacattga gaagaatcca cattttcaag gaccctacac ttccatgggc aaggataact    660
ttgttactcc tgttatacgc tcaaatataa atggaaagca atgtggtgac aaaattgaat    720
tgcttatctt gaaggccaag agaaatctag agcagtgtac tgaagaatta ccaaagtcca    780
tgaaaaagga tgacagtcct tgctcattag ataaacttga agcagacaga tcatgggaaa    840
atattcctgt tactttcaaa tctcctgttc ccgttaactc tgatgatagt cctcaacaaa    900
cttcaagggc aaagagtgct aaaggggttc ttgaagactt tctaaataat gataatcaga    960
gctgtactct ctctggaggc aaacatcatg gtcctgttga agccctgaaa caaatgttat   1020
ttaaccttca agcagtacaa gaacgtttta atcaaaataa gaccacagat ccaaaagaag   1080
agattaaaca agtttcagaa gatgatttct ctaaattaca gttgaaggaa agtatgattc   1140
ctattactag gtcacttcag aaggctttgc accatttatc tcgcctgaga gacctggttg   1200
atgatacgaa tggagaacgg tcaccgaaaa tgtgaagagg aaaatgaaac tgtcaccacg   1260
ataaatagtc accacagaac aaataggcat tttttctatt acttaaactg acaaagtaaa   1320
tataagccat acattatttt gtggttggtt caaggattat atatttctaa aacactaaac   1380
ttgaaaatac ccataggttt tggacctat ctttattttg tgccaacata ctagaatgtg    1440
aactgcaagg acccacaatg tatcctgaag tcttactttc gccttctggc cagcaaatgt   1500
ctaatattta aagatggatg acttctgttc ttgaagctta cctggattta accttcttca   1560
gcatcctcaa cattttatta cctggttcag gatcattaag aaacttactg gtttttatcc   1620
aaaatctttt acgttaaata gacttttta aagatatagt tagcatcact tttaaacagc    1680
ttaaaggaat atcaaaattg ttattgtgta tctcatctat aaggaagtct gttactttga   1740
aattttcata aatttaatat ttaagataca ttgtatttga aaattgcatt aatagtgggg   1800
tgatactgtg ttaaaaggaa cgttgtgttg tgacattcaa gagaacctcc tcatttaatt   1860
agtactttga ttctgtgtaa gataatcttg gtagtgcttg acagtttcca aaccttttt    1920
tggagagata tttaagaatt taatattttg atattagatt gtttcccaga ttttaatttt   1980
ggggttggct caaactagtg aaaactatga ctcaatggcc aattgcttta tcaaatttga   2040
taactaaaac ttaaaatgaa tatggaaaat cagaaagcaa ctctatttta gagctatttt   2100
gtaagagttg tgctttcttt aacaccatct gtagtcttaa gtttgtctct agctagaact   2160
gaacaaagct ctataatttt taccaagcac ttattattaa tacttcttat aagtagtaag   2220
catctttact aacacaactg agaattaagt cataaaacat aactaataca gcacattact   2280
gcctgacaaa attaaagagt actgtgtgta tgtataacta ctacaggtta acacttcacc   2340
caaatgatag cgtttttcct cagtagatta ttgtcaaata ggaatttcta agcacattga   2400
gtcaaagcat tttttccagg ttaataaagt gttatttact atctttgtta gaggtgacat   2460
gtcaaacact acagtgagct ctgtggggtt tttttttttt tttttgcccg tgagtttttt   2520
accatgctgc tctgaccagt ttgagtggca attaccaata gatttgtttt ctttattcta   2580
tggagatgtt tttaccactg acactgtttt ctgattatag tctgcttcat agaaaatagc   2640
ctgcataatc aaacaaggag ttactttgaa attaaagtat gcctggctat taaaaatgca   2700
gattttaggt gggtaaacat caggtaggtc tgggtgggtc atgttctagg cctagaaaaa   2760
tacactatta gacaagttct aaagaaggca aggagataaa ggcatcaggt ggtaacttct   2820
aattgaatat tatatgttga tcatacataa tatatactat gcctggaaat tatgactgaa   2880
aagcacctat tcggttagtg ctcctattca tgagaacata tctccaatac taaatgagat   2940
```

aagcctgttc taaaatctta tagccagtat tttaagaaac ttgattatac ttaccaaagg 3000
aacattgttt gttttctctt gttttaaata tggagaggtt taatccttta cataacaaag 3060
gaattaattt tagcaaaatg attcattcca accttcttat aagaaatatc taggagagtc 3120
aagtaagaaa aataacgaat ctaagtgata aacattcaag aaattctcta aataagagat 3180
ttatttataa ttttaatatc tcagggttct ttttaggttt ccaggggaaa agagcaggat 3240
aacagtgtgg agactgctaa gttgagaatt taaaacaaat gagaacataa gatttttaaa 3300
attgcattgt gaatgtaaaa tttttatcaa tcctttgctc ttttagacat attgagaaaa 3360
tgttaaatag aaaaaattaa gaaattttaa taagatgttt cagatctttg agtatgaaaa 3420
acataacaaa aaagcctaat ttcaaaaaac tatttgagat caagggacaa tggtgtgacc 3480
aatatgaagg gtcaagactg aaatgtattg tctttactat caagaactct actttcagtt 3540
gtttctcaga cagttaattt cagcttcata gagatttctg agcaaattaa gaaacactgt 3600
tttcctgggt ttgttttggg tatatgtcat tatagttatg ttatttcttg ttgaaattta 3660
taattgtagg ttttttgtat tgttttggta tttaatggtg tataatgtgt tattacatta 3720
tatgtagtta taccaaaata ttgcctgaag agaaatcatg acaaggtccc ctgtttattc 3780
ctgtgttaca gacgcatgga attgctcctg tagatttgaa tttttgtttc atttttttct 3840
gtcccaccct tcactctctc tgtttcagaa catttttggt agaagtgcta tccagaagtg 3900
aacttgtcaa aaggcaagta gcatgaaaga agacagaaga agcaaaaggc taatacagtg 3960
gataatttct gagcacttga agtttcttca aatgtgcaag actgtgtgtc ttcctattag 4020
atgtataaat tggatatttc atgcctaatt aaatgttgcg ttggattgca gtgcctatca 4080
tacagtgatt ggagtaaatt gaggcctaat cctgaacaca tatagagcat attgttagat 4140
atttttcctg tgacatttga agttattatt ctcccatttc ctttttcttt ttttgtttat 4200
aatcatatgt ccctaagatt gttttccttt tttggaccaa aaaaaagaaa aaaaaaatct 4260
tagcttttca tcctcccagt gtattctgca ttgtccttac cctagatcag ccccttctgt 4320
gtaacagttt ttctcacaat gtagcaactt ttatccaccc ttcaggacct tcactgggac 4380
tagttcattc attttcaaat agctatttca acctttaaca tctactgtct tagtctttta 4440
cacagaagcc agagtgactg gtcttggcaa gactctgttg tgtatcacca ctctaacctt 4500
actgatttgt ttcagcaaat ttgctttagt taaattgctt tactcagatt cccccaaact 4560
ttatatgtgt attgtcatct ttgtgcatat tatttctcat gcatgaaata ctcaattttt 4620
attcttttat ctaacgctta ctcttacatt tctttaaagc tctggccaag tattttattt 4680
cgtccctaaa cattctaact atccaccaaa ctggtaagtt ggcttttctt tttcctcccc 4740
ctgtcattca tttagctgtt atatttcatt ttaatgtttt gggtggtgcc tcttatacta 4800
tgttgtattc ctagacaagg aaatgtatat caaaatatgt tagatgattg attgttttat 4860
ctccttgatg atagcacctc ttatactgct ttacagaatc aggaaaaagt aaactgcatt 4920
ttacatagtg gttttaaata ttgattgatt gatattctaa acctggtttc ctatataaag 4980
ttgtaagttc aagataaaaa aaaaaaaaaa aaaaca 5016

<210> SEQ ID NO 592
<211> LENGTH: 372
<212> TYPE: PRT
<213> ORGANISM: Homo sapiens

<400> SEQUENCE: 592

Met Ala Lys Ser Lys Thr Lys His Arg Leu Cys Ser Gln Glu Ser Ser

```
1               5                   10                  15

Val Ser Ala Leu Leu Ala Ser Cys Thr Leu Ser Gly Ser Asn Ser Ser
            20                  25                  30

Asn Ser Asp Gly Ser Phe His Tyr Lys Asp Lys Leu Tyr Arg Ser Ala
        35                  40                  45

Ser Gln Ala Leu Gln Ala Tyr Ile Asp Asp Phe Asp Leu Gly Gln Ile
    50                  55                  60

Tyr Pro Gly Ala Ser Thr Gly Lys Ile Asn Ile Asp Glu Asp Phe Thr
65                  70                  75                  80

Asn Met Ser Gln Phe Cys Asn Tyr Ile Tyr Lys Pro Asn Asn Ala Phe
                85                  90                  95

Glu Asn Leu Asp His Glu Lys His Ser Asn Phe Ile Ser Cys Arg Arg
            100                 105                 110

His Ile Val Asn Asp Ile Asp Ser Met Ser Leu Thr Thr Asp Asp Leu
        115                 120                 125

Leu Arg Leu Pro Ala Asp Gly Ser Phe Ser Tyr Thr Tyr Val Gly Pro
    130                 135                 140

Ser His Arg Thr Ser Lys Lys Asn Lys Lys Cys Arg Gly Arg Leu Gly
145                 150                 155                 160

Ser Leu Asp Ile Glu Lys Asn Pro His Phe Gln Gly Pro Tyr Thr Ser
                165                 170                 175

Met Gly Lys Asp Asn Phe Val Thr Pro Val Ile Arg Ser Asn Ile Asn
            180                 185                 190

Gly Lys Gln Cys Gly Asp Lys Ile Glu Leu Leu Ile Leu Lys Ala Lys
        195                 200                 205

Arg Asn Leu Glu Gln Cys Thr Glu Glu Leu Pro Lys Ser Met Lys Lys
    210                 215                 220

Asp Asp Ser Pro Cys Ser Leu Asp Lys Leu Glu Ala Asp Arg Ser Trp
225                 230                 235                 240

Glu Asn Ile Pro Val Thr Phe Lys Ser Pro Val Pro Val Asn Ser Asp
                245                 250                 255

Asp Ser Pro Gln Gln Thr Ser Arg Ala Lys Ser Ala Lys Gly Val Leu
            260                 265                 270

Glu Asp Phe Leu Asn Asn Asp Asn Gln Ser Cys Thr Leu Ser Gly Gly
        275                 280                 285

Lys His His Gly Pro Val Glu Ala Leu Lys Gln Met Leu Phe Asn Leu
    290                 295                 300

Gln Ala Val Gln Glu Arg Phe Asn Gln Asn Lys Thr Thr Asp Pro Lys
305                 310                 315                 320

Glu Glu Ile Lys Gln Val Ser Glu Asp Asp Phe Ser Lys Leu Gln Leu
                325                 330                 335

Lys Glu Ser Met Ile Pro Ile Thr Arg Ser Leu Gln Lys Ala Leu His
            340                 345                 350

His Leu Ser Arg Leu Arg Asp Leu Val Asp Asp Thr Asn Gly Glu Arg
        355                 360                 365

Ser Pro Lys Met
    370
```

<210> SEQ ID NO 593
<211> LENGTH: 21
<212> TYPE: DNA
<213> ORGANISM: artificial
<220> FEATURE:
<223> OTHER INFORMATION: Description of artificial sequence:
Oligonucleotide

<400> SEQUENCE: 593
aatggaaagc aatgtggtga c 21

<210> SEQ ID NO 594
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 594
tccagagaga gtacagctct g 21

<210> SEQ ID NO 595
<211> LENGTH: 2061
<212> TYPE: DNA
<213> ORGANISM: Homo sapiens

<400> SEQUENCE: 595
atgaggcgga caggccccga ggaggaggcc tgcggcgtgt ggctggacgc ggcggcgctg 60
aagaggcgga aagtgcagac acatttaatc aaaccaggca ccaaaaatgct aacactcctt 120 cctggagaaa gaaaggctaa tatttatttt actcaaagaa gagctccatc tacaggcatt 180
caccagagaa gcattgcttc cttcttcacc ttgcagccag gaaagacaaa tggcagtgac 240
cagaagagtg tttcatctca tacagaaagt cagatcaaca aagagtccaa gaaaaatgcg 300
acccagctag accatttgat cccaggctta gcacacgatt gcatggcatc ccctttagcc 360
acttcaacca ctgcggacat ccaggaagct ggactctctc ctcagtccct ccagacttct 420
ggccaccaca gaatgaaaac cccattttca actgagctat ctttgctcca gcctgatact 480
ccagactgtg ctggagatag tcatacccca ctggcttttt ccttcaccga ggacttggaa 540
agttcttgtt tgctagaccg aaaggaagaa aaaggggatt ctgccaggaa atgggaatgg 600
cttcatgagt ctaagaagaa ctatcagagt atggagaaac acaccaaact acctggggac 660
aaatgctgtc agcccttagg caagactaaa ttggaaagaa aggtgtctgc caaagaaaac 720
aggcaggccc ctgtcctcct tcaaacatac agggaatcct ggaatggaga aaacatagaa 780
tcggtgaaac aaagccgtag tccagtttct gtgttttcct gggacaatga aaagaatgac 840
aaggactcct ggagtcaact tttcactgaa gattctcaag gccagcgggt cattgcccac 900
aacactagag ctcctttcca agatgtaacc aataactgga attgggactt agggccgttt 960
cctaacagtc cttgggctca gtgccaggag gatgggccaa ctcaaaatct gaagcctgat 1020
ttgctcttta cccaggactc tgaaggtaat caagttatca gacaccaatt ctaaatgttt 1080
gaagctttgt ttctaaaagt accttgaaat gatagagatg taggaaaata tagttgtggg 1140
tggagagagg agtgagtttg tttaggtggg aaggtggcat gggatgaagt tgtcattact 1200
gagcatcttc tctgtgtaaa taaagggcag taccattgtt aagacagtgg gattggcatc 1260
atggctttcc ctcaggaagg tggtggctgg taaattccct gaatgagtct atgatgaaca 1320
ctgaggcagc acagtgggta tttatctcta tgaaagtgcc ttttactcag cctgcacaga 1380
gccatctctt tgcccttcca gatgtctgac tgggaccttg cttatggatg tgtttttttt 1440 ttttttttt tgagatggag tctcgctctg tcgccaggct ggagtgcagt ggtgcgacct 1500
cagctcactg caccctctgt gtcccggatt caagcgattc tcctgcctca gcctcccgaa 1560
tagcagggac tacaggcatg cgccaccacg cccagctaat ttttttgga tttttagtag 1620

```
agacgaggtt tcaccatatt agccaggatg gtctccatct cctgacctcc tgatccgccc   1680

acctcagcct cccaaagtgc tgagattaca ggcataagcc accgcgccca gccagatgtg   1740

tgagctttta atctctggct gatcttaacc cacatcagcc taagcttggg atgattactc   1800

ttgacccttt tttttcagtg attagcaaat ctccccacaa cccaggtgtg gagagaagag   1860

aggtagaatg gtgctagttt cctattttat ttttgtggta actgtacagc actttaaagt   1920

tatatactct atgtttaaat atctccctta aaaagcctga gctgtacaac aatctggatg   1980

tgactctgtt accctttttcc cacaagatag gagggaatcc cctttgtaaa actatgaatc   2040

caaataaatg tttacaaagt g                                              2061
```

<210> SEQ ID NO 596
<211> LENGTH: 357
<212> TYPE: PRT
<213> ORGANISM: Homo sapiens

<400> SEQUENCE: 596

```
Met Arg Arg Thr Gly Pro Glu Glu Glu Ala Cys Gly Val Trp Leu Asp
1               5                   10                  15

Ala Ala Ala Leu Lys Arg Arg Lys Val Gln Thr His Leu Ile Lys Pro
            20                  25                  30

Gly Thr Lys Met Leu Thr Leu Leu Pro Gly Glu Arg Lys Ala Asn Ile
        35                  40                  45

Tyr Phe Thr Gln Arg Arg Ala Pro Ser Thr Gly Ile His Gln Arg Ser
    50                  55                  60

Ile Ala Ser Phe Phe Thr Leu Gln Pro Gly Lys Thr Asn Gly Ser Asp
65                  70                  75                  80

Gln Lys Ser Val Ser Ser His Thr Glu Ser Gln Ile Asn Lys Glu Ser
                85                  90                  95

Lys Lys Asn Ala Thr Gln Leu Asp His Leu Ile Pro Gly Leu Ala His
            100                 105                 110

Asp Cys Met Ala Ser Pro Leu Ala Thr Ser Thr Thr Ala Asp Ile Gln
        115                 120                 125

Glu Ala Gly Leu Ser Pro Gln Ser Leu Gln Thr Ser Gly His His Arg
    130                 135                 140

Met Lys Thr Pro Phe Ser Thr Glu Leu Ser Leu Leu Gln Pro Asp Thr
145                 150                 155                 160

Pro Asp Cys Ala Gly Asp Ser His Thr Pro Leu Ala Phe Ser Phe Thr
                165                 170                 175

Glu Asp Leu Glu Ser Ser Cys Leu Leu Asp Arg Lys Glu Glu Lys Gly
            180                 185                 190

Asp Ser Ala Arg Lys Trp Glu Trp Leu His Glu Ser Lys Lys Asn Tyr
        195                 200                 205

Gln Ser Met Glu Lys His Thr Lys Leu Pro Gly Asp Lys Cys Cys Gln
    210                 215                 220

Pro Leu Gly Lys Thr Lys Leu Glu Arg Lys Val Ser Ala Lys Glu Asn
225                 230                 235                 240

Arg Gln Ala Pro Val Leu Leu Gln Thr Tyr Arg Glu Ser Trp Asn Gly
                245                 250                 255

Glu Asn Ile Glu Ser Val Lys Gln Ser Arg Ser Pro Val Ser Val Phe
            260                 265                 270

Ser Trp Asp Asn Glu Lys Asn Asp Lys Asp Ser Trp Ser Gln Leu Phe
        275                 280                 285
```

```
Thr Glu Asp Ser Gln Gly Gln Arg Val Ile Ala His Asn Thr Arg Ala
    290                 295                 300

Pro Phe Gln Asp Val Thr Asn Asn Trp Asn Trp Asp Leu Gly Pro Phe
305                 310                 315                 320

Pro Asn Ser Pro Trp Ala Gln Cys Gln Glu Asp Gly Pro Thr Gln Asn
                325                 330                 335

Leu Lys Pro Asp Leu Leu Phe Thr Gln Asp Ser Glu Gly Asn Gln Val
            340                 345                 350

Ile Arg His Gln Phe
        355
```

<210> SEQ ID NO 597
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 597
caccttgcag ccaggaaaga c 21

<210> SEQ ID NO 598
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 598
cagcacagtc tggagtatca g 21

<210> SEQ ID NO 599
<211> LENGTH: 1907
<212> TYPE: DNA
<213> ORGANISM: Homo sapiens

<400> SEQUENCE: 599

```
aatgcacacg agcagacaga gaagcaacat ctttaaggta ctgagggcag gagaagttaa     60

tgtagaatac tatgccagaa aaaataaatt cccaaaagtg gaagtgaaat aaggacattt    120

agagatgtac aaaagctgac cgaattcact accagtcaac ccacactaca agaaacatca    180

aatgagtcct ccaagcagaa ggaatccaat accagatgaa aatccagatc tccacgagga    240

aatgaagaac accagaaatg ggtaactata ctagatcggc cctttcttca aataagagca    300

gttggaataa caaagctgtt cagttgtacc cttggaatcc actgaaatcc tgggtaggga    360

agctccagta ccaccaactg gaaagactgg gaatgcctaa tagctggtac tggccattgt    420

cgtaggcttt gtccactctg acaaactgaa gatggggact cgactcacct tcgccagcca    480

caggaggacc tccagacgag gacaggactc gctgcctttc tttcccgtca gaaagggatc    540

ccttgcggac aggacctaag caccacgcac ctgccccccg ggatgccgaa cgaagtggtc    600

cctaaagctc ctctgcaggc ccaaccgaaa caggcctgaa gctccaggat gggcgagagg    660

atcctctttg agcgaaacca gccttctgcc tggctggccc tggtcaacac cctgggaaga    720

ggccgatttg gcggacagaa cggaagaaaa gacctaaagg tagaatctca tgatgtcgag    780

atgttaaaac actcaaattt taaggttcga ctgtgagggg gagatagggg gtctcgagct    840

ggatcgaccc ctgagccttc atctgcagag tcctgtgcac cagctcagag gacaggacta    900
```

```
tgtgcaccaa tggttctcat caggcggcaa cttcaccctc acatgcctcc cccatccctg    960

ctggtacaca agaccacgac taggggaagc ccggagggag aatgttaacc cctggcatct   1020

atctagtcag cagaggtgag ggatgctgct aaacacctta caatccaccg gaggacaccc   1080

gcccccaccg accccgaagt ggccattccc tggaggtggg gaaactcgcc tgtagatcaa   1140

tgcccacgca cttggcggac aggaaatcac gaattggcca ctaactggat cttggatctg   1200

agaaaaaaat tccagcgtca gagggaactc tcggagattt gcccagagca taaggaacgt   1260

actccttccc tcagtgatgg atcctcacat ctgggggaaa tcatagacaa tttcttttgt   1320

agggcgaact ctgctataca gtttatgatg tcagagtgaa tactttcttt gagttgcagt   1380

cagaaactgt agatttttaa aaatttaaaa ttcattattc tctgtcagta ttccaaagtg   1440

tatacagaaa gctattgcac tgttcaggag atggcgctta acattttgga aattcaaggt   1500

gatgaatgtc cagataagac tatctctcct ggtacaaagt ttgacaatgc tgaacatttt   1560

taaaggttct ttttgatata caaagtgcac caatgagtgc tttttaattc ttacaataat   1620

tctgggtgag gtaggtattt ttccaattcc cattttatgc ttcggtagcc ctttgtattt   1680

atacttcaaa acacttggct ctcttgtaat tatttaagaa attagttgtg attatttgtt   1740

taatgtgcag gagttacaaa aggcaagctt tagaacaaga cagacctggt tatgattcct   1800

ggctctgaaa gctgtacacc ctgtgaccct agacaggtgt tttaatgcct cgctgcctct   1860

gtttcttgct ctgtaaaatg tgaacaataa cagtattggc ctcatgc                 1907
```

<210> SEQ ID NO 600
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 600

```
ttgcggacag gacctaagca c                                               21
```

<210> SEQ ID NO 601
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 601

```
tagtcctgtc ctctgagctg g                                               21
```

<210> SEQ ID NO 602
<211> LENGTH: 2553
<212> TYPE: DNA
<213> ORGANISM: Homo sapiens

<400> SEQUENCE: 602

```
tgcgtgtcgg ggtccgctcg tgcgcgcctc tccggggtct gtgcgcgtgg ccctccgctc     60

gcgccggagg gcgtgggcgt ggcctcggcg tgggtgtggc cgctcgggga ggggcctccc    120

gggggcgggg ccggcctggt ccgcgcggtg acgcgccctg cagccccgag cgagcgagcg    180

agcgagcgag ttgccgagcg cgccccgtcc ctcgcgcgcg atgctcccct ggacggcgct    240

cggcctggcc ctgagcttgc ggctggcgct ggcgcggagc ggcgcggagc gcggtccacc    300

agcatcagcc ccccgagggg acctgatgtt cctgctggac agctcagcca gcgtctctca    360
```

```
ctacgagttc tcccgggttc gggagtttgt ggggcagctg gtggctccac tgcccctggg    420
caccggggcc ctgcgtgcca gtctggtgca cgtgggcagt cggccataca ccgagttccc    480
cttcggccag cacagctcgg gtgaggctgc ccaggatgcg gtgcgtgctt ctgcccagcg    540
catgggtgac acccacactg gcctggcgct ggtctatgcc aaggaacagc tgtttgctga    600
agcatcaggt gcccggccag gggtgcccaa agtgctggtg tgggtgacag atggcggctc    660
cagcgaccct gtgggccccc ccatgcagga gctcaaggac ctgggcgtca ccgtgttcat    720
tgtcagcacc ggccgaggca acttcctgga gctgtcagcc gctgcctcag cccctgccga    780
gaagcacctg cactttgtgg acgtggatga cctgcacatc attgtccaag agctgagggg    840
ctccattctc gacgcgatgc ggccgcagca gctccatgcc acggagatca cgtccagcgg    900
cttccgcctg gcctggccac ccctgctgac cgcagactcg ggctactatg tgctggagct    960
ggtgcccagc gcccagccgg gggctgcaag acgccagcag ctgccaggga acgccacgga   1020
ctggatctgg gccggcctcg acccggacac ggactacgac gtggcgctag tgcctgagtc   1080
caacgtgcgc ctcctgaggc cccagatcct gcgggtgcgc acgcggcccg gtgaggcagg   1140
gccgggggct tcgggcccgg agtcgggggc tgggccggcc cccacgcagc tcgccgccct   1200
ccccgcccca gaggaggccg ggccagagcg catcgtcatc tcccacgccc ggccgcgcag   1260
cctccgcgtg agttgggccc cagcgctggg ctcagccgcg gcgctcggct accacgtgca   1320
gttcgggccg ctgcggggcg gggaggcgca gcgggtggag gtgcccgcgg gccgcaactg   1380
caccacgctg cagggcctgg cgccgggcac cgcctacctg gtgaccgtga ccgccgcctt   1440
ccgctcgggc cgcgagagcg cgctgtccgc caaggcctgc acgcccgacg gcccgcgccc   1500
gcgcccacgc cccgtgcccc gcgccccgac cccggggacc gccagccgtg agccgtaagc   1560
cggcgtcccc gcccagccga gagggccggc gcctacctga gggcccctgt gtcccgaacc   1620
cggagcggag gcgcccaacc cggcagacgg gtgcaggccc ggcctttccc cacgcggact   1680
ccgcgcgacc ccggccctct ccctgcggcc gcagggcttc cccgcctggc gcctgccctc   1740
cagggctggg gcctcgcctg gcgggacccc gcagcagccc cggccccatc cccgcccaga   1800
gccgggcgtc gtgtgggtcc gtgggtgata attgagagcg tcagacccag gactgttcag   1860
ggaggagccc cggtcagact cccacgtgtg aagaccgggc cccaagtggc aagggctggc   1920
ctggggcggg cagcttgggt cctggacgtt gataggaagc ggaaggggaa tcgcgggaag   1980
ctggcccagg tcaggtccgc aaaggcttct gaagaagagg aagggcgagt aggggcacct   2040
ggacgctgat ggtggccagg atgctcagct ggccaggagg gcagcacctg ctggggacgg   2100
tggccctgcc ttcatgccca ggacaccagc tgggtccagc tagcagccac tgggaatcag   2160
aggaatgggg cagagctggg cattcaggac cttgaggaca cgtgacccca cccgcccacc   2220
gccactatca ggccccggga ccgcactgac aggaaacctt ccgtcgtgag ggagcacttc   2280
ccaggggccg cagggacgac actctccagg gaggccccag caaccacacc atcttcttgc   2340
tgtgagaggt ctcaccccgg gctacctcct gtcactactc actgccctgg ggtccgtggg   2400
caagttgccc agggtggggg tgcctagcca ggtgcagtcc ccgccccgcc tagtcctcgg   2460
cgtcacgcaa tgctcacctc gcctcttccc cactaacatc ccagacttta aaattcagta   2520
aatcagatgt acaccgaaaa aaaaaaaaaa aaa                                2553
```

<210> SEQ ID NO 603
<211> LENGTH: 445
<212> TYPE: PRT

<213> ORGANISM: Homo sapiens

<400> SEQUENCE: 603

Met Leu Pro Trp Thr Ala Leu Gly Leu Ala Leu Ser Leu Arg Leu Ala
1 5 10 15

Leu Ala Arg Ser Gly Ala Glu Arg Gly Pro Pro Ala Ser Ala Pro Arg
20 25 30

Gly Asp Leu Met Phe Leu Leu Asp Ser Ser Ala Ser Val Ser His Tyr
35 40 45

Glu Phe Ser Arg Val Arg Glu Phe Val Gly Gln Leu Val Ala Pro Leu
50 55 60

Pro Leu Gly Thr Gly Ala Leu Arg Ala Ser Leu Val His Val Gly Ser
65 70 75 80

Arg Pro Tyr Thr Glu Phe Pro Phe Gly Gln His Ser Ser Gly Glu Ala
85 90 95

Ala Gln Asp Ala Val Arg Ala Ser Ala Gln Arg Met Gly Asp Thr His
100 105 110

Thr Gly Leu Ala Leu Val Tyr Ala Lys Glu Gln Leu Phe Ala Glu Ala
115 120 125

Ser Gly Ala Arg Pro Gly Val Pro Lys Val Leu Val Trp Val Thr Asp
130 135 140

Gly Gly Ser Ser Asp Pro Val Gly Pro Pro Met Gln Glu Leu Lys Asp
145 150 155 160

Leu Gly Val Thr Val Phe Ile Val Ser Thr Gly Arg Gly Asn Phe Leu
165 170 175

Glu Leu Ser Ala Ala Ala Ser Ala Pro Ala Glu Lys His Leu His Phe
180 185 190

Val Asp Val Asp Asp Leu His Ile Ile Val Gln Glu Leu Arg Gly Ser
195 200 205

Ile Leu Asp Ala Met Arg Pro Gln Gln Leu His Ala Thr Glu Ile Thr
210 215 220

Ser Ser Gly Phe Arg Leu Ala Trp Pro Pro Leu Leu Thr Ala Asp Ser
225 230 235 240

Gly Tyr Tyr Val Leu Glu Leu Val Pro Ser Ala Gln Pro Gly Ala Ala
245 250 255

Arg Arg Gln Gln Leu Pro Gly Asn Ala Thr Asp Trp Ile Trp Ala Gly
260 265 270

Leu Asp Pro Asp Thr Asp Tyr Asp Val Ala Leu Val Pro Glu Ser Asn
275 280 285

Val Arg Leu Leu Arg Pro Gln Ile Leu Arg Val Arg Thr Arg Pro Gly
290 295 300

Glu Ala Gly Pro Gly Ala Ser Gly Pro Glu Ser Gly Ala Gly Pro Ala
305 310 315 320

Pro Thr Gln Leu Ala Ala Leu Pro Ala Pro Glu Glu Ala Gly Pro Glu
325 330 335

Arg Ile Val Ile Ser His Ala Arg Pro Arg Ser Leu Arg Val Ser Trp
340 345 350

Ala Pro Ala Leu Gly Ser Ala Ala Ala Leu Gly Tyr His Val Gln Phe
355 360 365

Gly Pro Leu Arg Gly Gly Glu Ala Gln Arg Val Glu Val Pro Ala Gly
370 375 380

Arg Asn Cys Thr Thr Leu Gln Gly Leu Ala Pro Gly Thr Ala Tyr Leu
385 390 395 400

```
Val Thr Val Thr Ala Ala Phe Arg Ser Gly Arg Glu Ser Ala Leu Ser
                405                 410                 415

Ala Lys Ala Cys Thr Pro Asp Gly Pro Arg Pro Arg Pro Arg Pro Val
            420                 425                 430

Pro Arg Ala Pro Thr Pro Gly Thr Ala Ser Arg Glu Pro
        435                 440                 445
```

<210> SEQ ID NO 604
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 604
aaccaacctg aggatttcac g 21

<210> SEQ ID NO 605
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 605
agacagctgt tcgtgagaag c 21

<210> SEQ ID NO 606
<211> LENGTH: 1999
<212> TYPE: DNA
<213> ORGANISM: Homo sapiens

<400> SEQUENCE: 606

```
cactctgtaa gttcaccgcc ggtcgggtcc ggccgccgcg ctgtccagct cctgagacct     60

tgctgtccgc cggtctgccg tctgcgcgcc tcacgctcct cagccctgga ccggggacaa    120

gtaaccctcg gtgacaagac caaagtgcac tgctgcccac acagttccta cctttctggc    180

ttcaattctt cagaagagtt tgccgtcctt tggggagaac gtgatttttg ttatctcagc    240

ccactgactt cattgatctc taatcttttt taattccttg ggccaacttt gttcgtgccc    300

ccacactgta gccagaagcc cgttggcgag ctctggcacc tgcaaaccac cccgtggaac    360

gagtgtttcc tctggctgag ggttggagag gaggtgtggt ctcagcaggc ggcccgtagc    420

ctcacagcca ggcctggtgg tgaggtcacc atgtccacca aggtgcccat ctatctgaag    480

cgtggcagtc gcaagggcaa gaaggagaag cttcgggacc tgctgtcctc ggacatgatc    540

agcccaccgc tgggggactt ccgccacacc attcatattg gcagtggcgg cggcagtgac    600

atgtttggcg acatctcctt cctgcagggc aagttccacc tcctgccggg gaccatggtg    660

gaggggcctg aagaagatgg caccttcgac ctccccttcc agttcacccg caccgccacc    720

gtgtgtgggc gggagctccc ggacggccca tcccctctgc tcaagaacgc catctccctc    780

ccggttatcg gtggacccca ggctctcacc ctgcccacag cccaggctcc acccaagccc    840

cctcgcctgc acctggagac ccctcagcct tccccacagg agggagggag tgtggacatc    900

tggaggattc cagagactgg ctcccccaac agtggactga ccccggagtc aggggccgag    960

gagcccttcc tgtccaatgc cagctccctg ctgtccctgc acgtggacct ggggccttcc   1020

atcctggatg atgtcctgca gatcatggat caggacctgg acagcatgca gatccccaca   1080
```

```
taggacacga ggctgcctag gctggggtcc caggtggggc ccagccagga ggtggggtgt   1140

ggacccggcc ctggcggcgg agtcagggtc ccaagatccc acctgtatgg tcgctggcca   1200

gtgattctcc ttctgagccg tgtttcccct ctccctccct ctccacgtgg gcagggcagg   1260

ccccatcgct ttcctctgat aaccacatgg acacatcctg aagtcagccc aggcgccctg   1320

agcatcttgg ggcacctgga ccccatcaca atactccttc ttccttcagg tccctgggtg   1380

aaggctttgc tgaaaccgac ccccctttc acgtcccttc tgcctctgcc ccgttggatg   1440

ccctgactgg gggcagggga agagacaggg cacagctggc cacagggctc agccactgag   1500

caggctgttc cgggcctttg gctttgcatc ctggacgggg agtgtcctgt cagggaccag   1560

atgtgtcctg cctcatccct agctccaatc ccttccccac gtgaccgggg attctggttg   1620

caataaaaca tgctgctgct ggtggcggag ctccctgtcc ctttgcccca ggtttcctcc   1680

cggaggcaga cagtctccca gagctgaggg cttgcctctg gagaccccag ccccagaggg   1740

ctttgtggag gacaggcctt gccctcaaga acgtcgtacc tgacgctgag cctgtcatga   1800

gaatgcaaca ggagcaaacc aagtgttgct gtgacattga ttcagatgtt tggcaagagg   1860

tggctgagca ctggggtggg cttggcactg tgccaagcct ggggccaatc cctgcccagt   1920

cagctggggt ctggtggggg acacccaaga ataaaagaat aaccacaaag tgtgcaaggg   1980

aaaaaaaaaa aaaaaaaaa                                                1999


<210> SEQ ID NO 607
<211> LENGTH: 210
<212> TYPE: PRT
<213> ORGANISM: Homo sapiens

<400> SEQUENCE: 607

Met Ser Thr Lys Val Pro Ile Tyr Leu Lys Arg Gly Ser Arg Lys Gly
1               5                   10                  15

Lys Lys Glu Lys Leu Arg Asp Leu Leu Ser Ser Asp Met Ile Ser Pro
            20                  25                  30

Pro Leu Gly Asp Phe Arg His Thr Ile His Ile Gly Ser Gly Gly Gly
        35                  40                  45

Ser Asp Met Phe Gly Asp Ile Ser Phe Leu Gln Gly Lys Phe His Leu
    50                  55                  60

Leu Pro Gly Thr Met Val Glu Gly Pro Glu Glu Asp Gly Thr Phe Asp
65                  70                  75                  80

Leu Pro Phe Gln Phe Thr Arg Thr Ala Thr Val Cys Gly Arg Glu Leu
                85                  90                  95

Pro Asp Gly Pro Ser Pro Leu Leu Lys Asn Ala Ile Ser Leu Pro Val
            100                 105                 110

Ile Gly Gly Pro Gln Ala Leu Thr Leu Pro Thr Ala Gln Ala Pro Pro
        115                 120                 125

Lys Pro Pro Arg Leu His Leu Glu Thr Pro Gln Pro Ser Pro Gln Glu
    130                 135                 140

Gly Gly Ser Val Asp Ile Trp Arg Ile Pro Glu Thr Gly Ser Pro Asn
145                 150                 155                 160

Ser Gly Leu Thr Pro Glu Ser Gly Ala Glu Glu Pro Phe Leu Ser Asn
                165                 170                 175

Ala Ser Ser Leu Leu Ser Leu His Val Asp Leu Gly Pro Ser Ile Leu
            180                 185                 190

Asp Asp Val Leu Gln Ile Met Asp Gln Asp Leu Asp Ser Met Gln Ile
        195                 200                 205
```

Pro Thr
210

<210> SEQ ID NO 608
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 608
aacgtcgtac ctgacgctga g 21

<210> SEQ ID NO 609
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 609
ccaagtgttg ctgtgacatt g 21

<210> SEQ ID NO 610
<211> LENGTH: 986
<212> TYPE: DNA
<213> ORGANISM: Homo sapiens

<400> SEQUENCE: 610
attcaagatg atgttagaga gatgacagag tctaggttag ggagggcctg agtccttgta 60
gactctgagt acggtgctga gcagggaaga gacaggctct ggcttagggt ttagaaggaa 120
cacaggctac tgcgatgagg attgtctgaa ggggaacaaa ggccaagatg ttgtttgaag 180
ccgtgagact gagtgagatc atggaggaag tgaatgtaaa tagaaaaggg aagaagtctg 240
aagacggagc cctgagacac tccattgtaa actggaagat gaggaagagc cagcaaagga 300
gactgagaag gggcagccag tgaagatgga gccagggcta gagtaagagc cccttctggg 360
atgctgtgac ccccaagttt gaagactgct gataacccca atctacgaag actagctatg 420
gaacttccta cactgagaca actccagtgg aactctgata attatcctaa aataaggagg 480
cttcttcagt agccctcgaa atatgttcaa atacatgatt acatttatgt ccttaatatt 540
gctattagtt tctgatgtta atgtaaaagt tggggaaaaa gtggaaaagt taaagcagtg 600
caggttaatt caatgccaga gtaacttctc agagggtgta tattcagtgt gaacaatttt 660
caacagagaa atgtcaactt ctggccacaa cggcaaccag taaaatgact atttttactg 720
tcttatctat taatgaagag gagattgcat aatatagatg aaggagcata gtatttgcag 780
gtggaacgcc tagcagggct tgagtctcaa ctctgctgct tttactctaa ttgaccgaga 840
caagtcattt aaactaatag agcttcaatt ttctcatatc taatgtaaca taacaattca 900
cagcctttta ctttgtagtt atcgtgaaga tctaatcgca gtgaaatata tttatatatc 960
tgtctgccga taaaaaaaaa aaaaaa 986

<210> SEQ ID NO 611
<211> LENGTH: 21
<212> TYPE: DNA
<213> ORGANISM: artificial
<220> FEATURE:
<223> OTHER INFORMATION: Description of artificial sequence: Oligonucleotide

<400> SEQUENCE: 611
gactctgagt acggtgctga g        21

<210> SEQ ID NO 612
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 612
tcttactcta gccctggctc c        21

<210> SEQ ID NO 613
<211> LENGTH: 899
<212> TYPE: DNA
<213> ORGANISM: Homo sapiens

<400> SEQUENCE: 613
cccgagcgcc ggccgggcca tgaccccgc tgctctgtct tgcaggctcg tcgccgcggc        60
cccccgagcc cgaccgccgc cgccaccacc accagcgccc gggcgggcct cgcgcgcctc       120
gggcgcggct ccgcagtgag cccaccaaga aggaagcggc ctgcagaggt gccgacatgg       180
ggcttaagat gtcctgcctg aaaggctttc aaatgtgtgt cagcagcagc agcagcagcc       240
acgacgaggc ccccgtcctg aacgacaagc acctggacgt gcccgacatc atcatcacgc       300
cccccacccc cacgggcatg atgctgccga gggacttggg gagcacagtc tggctggatg       360
agacagggtc gtgcccagat gatggagaaa tcgacccaga agcctgagga ggtgtcctgg       420
gtttggctgg ctggctcctg ctccagcggc ccggcttcag gtgtccgggg gcgtggctgc       480
ctggagcagg tgtgctgaat accctggatg ggaactgagc gaacccgggc ctccgctcag       540
agagacgtgg caggaccagc gaggaatcca gcctgtccac ttccagaaca gtgtttccca       600
ggccccgctg agtggaccgg acctctgaca cctccaggtt cttgctgact ccggcctggt       660
gaaagggagc gccatggtcc tggctgttgg ggtcccaggg agaggctctc ttctggacaa       720
acacaccctc ccagccccca gggctgtgca aacacatgcc cctgccataa gcaccaacaa       780
gaacttcttg caggtggagt ggctgttttt tataagttgt tttacagata cggaaacagt       840
ccaaaatggg atttataatt tcttttttgc attataaata aagatcctct gtaacaaaa        899

<210> SEQ ID NO 614
<211> LENGTH: 76
<212> TYPE: PRT
<213> ORGANISM: Homo sapiens

<400> SEQUENCE: 614

Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
                20                  25                  30

Leu Asp Val Pro Asp Ile Ile Ile Thr Pro Pro Thr Pro Thr Gly Met
            35                  40                  45

Met Leu Pro Arg Asp Leu Gly Ser Thr Val Trp Leu Asp Glu Thr Gly
        50                  55                  60

Ser Cys Pro Asp Asp Gly Glu Ile Asp Pro Glu Ala
65                  70                  75

<210> SEQ ID NO 615
<211> LENGTH: 21
<212> TYPE: DNA
<213> ORGANISM: artificial
<220> FEATURE:
<223> OTHER INFORMATION: Description of artificial sequence:
Oligonucleotide

<400> SEQUENCE: 615
tgtcctgcct gaaaggcttt c 21

<210> SEQ ID NO 616
<211> LENGTH: 21
<212> TYPE: DNA
<213> ORGANISM: artificial
<220> FEATURE:
<223> OTHER INFORMATION: Description of artificial sequence:
Oligonucleotide

<400> SEQUENCE: 616
catccagggt attcagcaca c 21

<210> SEQ ID NO 617
<211> LENGTH: 432
<212> TYPE: DNA
<213> ORGANISM: Homo sapiens

<400> SEQUENCE: 617
ttatgtgcct gaagtcgcac agtgaataag ctaaaacacc tgcttttaac aatggtacca 60
tacaaccact actccattaa ctccacccac ctcctgcacc cctccccaca cacacaaaat 120
gaaccacgtt ctttgtatgg gcccaatgag ctgtcaagct gccctgtgtt catttcattt 180
ggaattgccc cctctggttc ctctgtatac tactgcttca tctctaaaga cagctcatcc 240
tcctccttca cccctgaatt tccagagcac ttcatctgct ccttcatcac aagtccagtt 300
ttctgccact agtctgaatt tcatgagaag atgccgattt ggttcctgtg ggtcctcagc 360
actattcagt acagtgcttg actcacagca ggcactcaga aaatactgga ggaaataaaa 420
caccaaagat at 432

<210> SEQ ID NO 618
<211> LENGTH: 21
<212> TYPE: DNA
<213> ORGANISM: artificial
<220> FEATURE:
<223> OTHER INFORMATION: Description of artificial sequence:
Oligonucleotide

<400> SEQUENCE: 618
ctgctccttc atcacaagtc c 21

<210> SEQ ID NO 619
<211> LENGTH: 24
<212> TYPE: DNA
<213> ORGANISM: artificial
<220> FEATURE:
<223> OTHER INFORMATION: Description of artificial sequence:
Oligonucleotide

<400> SEQUENCE: 619
gagatctcga gatctcgatc gtac 24

<210> SEQ ID NO 620
<211> LENGTH: 2575

<212> TYPE: DNA
<213> ORGANISM: Homo sapiens

<400> SEQUENCE: 620

```
gagaacgggg tagcccggcg cttacacatg tcacatgtgc tttttaagac ggccgggagc      60
gcctgcgagc tggatctggt ggaggatgct gcggcaggtg cttcgcagag ggctccagtc     120
gttctgccac aggctgggtt tgtgcgtgag ccggcacccg gtctttttcc tcaccgtgcc     180
cgcagtcctg acaatcacct tcggcctcag cgcgctcaac cgcttccagc ccgagggcga     240
cctggagcgc ctggtcgctc ccagccacag cctggccaag atcgagcgca gcctggccag     300
cagccttttc cccctggacc agtccaaaag ccagctctat tcggacttac acacccctgg     360
gaggtatggc agggtgatcc tcctctcccc aaccggggac aatattttgc tccaggctga     420
ggggatcctg cagacccacc gagccgtgct ggaaatgaag gatgggagga acagttttat     480
tggacaccaa ctgggcgggg tagtggaagt gccaaacagc aaagatcagc gggtcaagtc     540
agccagagcc attcaaatca cctactacct ccagacctat ggctctgcca cccaagacct     600
catagggggag aagtgggaga atgagttctg taagcttata aggaagctcc aggaggagca     660
tcaagaactc cagctctact ctttagcatc ctttagcctc tggagggact ttcataagac     720
cagcatcctg gccagaagca aggtcctggt gagcctcgtg ctgatcctga ccacagccac     780
cctctccagc tccatgaagg actgcttgcg cagtaagccc ttcctgggcc tcctgggggt     840
gctcacagta tgcatctcca tcatcacagc agcagggatc ttcttcatca ccgatggaaa     900
gtacaactcc accctgctgg gaatcccgtt cttcgccatg ggtcatggaa ctaaaggagt     960
gtttgagctt ctgtccggat ggcggagaac caaagagaac ttgcccttca aagacaggat    1020
agcagatgcc tattctgatg tgatggtcac ctataccatg accagctccc tgtacttcat    1080
cacttttggc atgggtgcca gcccattcac aaacatagag gctgtgaagg tcttctgtca    1140
aaacatgtgt gtctctattc tgttgaacta cttctacatt ttctccttct ttggctcctg    1200
tctggtcttt gctggccaac tagagcaaaa ccgctaccac agcatctttt gctgtaagat    1260
cccttctgca gaatacctgg atcgcaaacc tgtgtggttc cagacagtga tgagtgatgg    1320
gcatcaacag acgtcccatc atgagacgaa cccctaccag caccacttca ttcagcactt    1380
cctccgtgaa cattataatg aatggattac caatatatat gtgaagccat ttgttgtcat    1440
cctctatctc atttatgcct ccttctcctt catggggtgc ttacagatca gtgacggagc    1500
caacatcatc aatctactag ccagtgattc gccaagtgtt tcctatgcca tggttcagca    1560
gaaatatttc agcaactata gccctgtgat aggattctac gtctatgagc ccctagagta    1620
ctggaacagc agcgtccagg atgacctaag aagactctgt agtggattca ctgcagtgtc    1680
ctgggtggag cagtactacc agttcctgaa agtcagcaac gtcagtgcca ataacaaaag    1740
tgacttcatc agtgtcctgc aaagctcatt tttaaaaaag ccagaattcc agcattttcg    1800
aaatgatatc atcttctcca aggcagggga tgaaagcaat atcattgctt ctcgcttgta    1860
tctggtggcc aggactagca gagacaagca gaaagaaatc acagaagtgt tggaaaagct    1920
gaggccccta tccctctcaa agagcatccg attcatcgtg ttcaacccct cctttgtctt    1980
catggaccat tacagcttgt ctgtcacagt gcctgttctg attgcaggct ttggtgttct    2040
cctggtgtta atcctgactt ttttcctagt gatccaccct ctgggaaact tctggctaat    2100
tcttagcgtc acctcaattg agctgggcgt tctgggctta atgacattat ggaacgtcga    2160
catggattgc atttctatct tgtgccttat ctacaccttg aatttcgcca ttgaccactg    2220
```

```
tgcaccactg cttttcacat ttgtattagc aactgagcac acccgaacac aatgtataaa    2280

aagctccttg caagaccatg ggacagccat tttgcaaaat gttacttctt ttcttattgg    2340

gttagtcccc cttctatttg tgccttcgaa cctgaccttc acactgttca aatgcttgct    2400

gctcactggg ggttgcacac ttctgcactg ttttgttatt ttacctgtgt tcctaacgtt    2460

tttcccccct tccaaaaagc accacaagaa aaagaaacgt gccaagcgaa aggagagaga    2520

ggaaattgaa tgcatagaaa ttcaagagaa cccggatcac gtcaccacag tatga         2575

<210> SEQ ID NO 621
<211> LENGTH: 829
<212> TYPE: PRT
<213> ORGANISM: Homo sapiens

<400> SEQUENCE: 621
```

Met Leu Arg Gln Val Leu Arg Arg Gly Leu Gln Ser Phe Cys His Arg
1               5                   10                  15

Leu Gly Leu Cys Val Ser Arg His Pro Val Phe Phe Leu Thr Val Pro
            20                  25                  30

Ala Val Leu Thr Ile Thr Phe Gly Leu Ser Ala Leu Asn Arg Phe Gln
        35                  40                  45

Pro Glu Gly Asp Leu Glu Arg Leu Val Ala Pro Ser His Ser Leu Ala
    50                  55                  60

Lys Ile Glu Arg Ser Leu Ala Ser Ser Leu Phe Pro Leu Asp Gln Ser
65                  70                  75                  80

Lys Ser Gln Leu Tyr Ser Asp Leu His Thr Pro Gly Arg Tyr Gly Arg
                85                  90                  95

Val Ile Leu Leu Ser Pro Thr Gly Asp Asn Ile Leu Leu Gln Ala Glu
            100                 105                 110

Gly Ile Leu Gln Thr His Arg Ala Val Leu Glu Met Lys Asp Gly Arg
        115                 120                 125

Asn Ser Phe Ile Gly His Gln Leu Gly Gly Val Val Glu Val Pro Asn
    130                 135                 140

Ser Lys Asp Gln Arg Val Lys Ser Ala Arg Ala Ile Gln Ile Thr Tyr
145                 150                 155                 160

Tyr Leu Gln Thr Tyr Gly Ser Ala Thr Gln Asp Leu Ile Gly Glu Lys
                165                 170                 175

Trp Glu Asn Glu Phe Cys Lys Leu Ile Arg Lys Leu Gln Glu Glu His
            180                 185                 190

Gln Glu Leu Gln Leu Tyr Ser Leu Ala Ser Phe Ser Leu Trp Arg Asp
        195                 200                 205

Phe His Lys Thr Ser Ile Leu Ala Arg Ser Lys Val Leu Val Ser Leu
    210                 215                 220

Val Leu Ile Leu Thr Thr Ala Thr Leu Ser Ser Ser Met Lys Asp Cys
225                 230                 235                 240

Leu Arg Ser Lys Pro Phe Leu Gly Leu Leu Gly Val Leu Thr Val Cys
                245                 250                 255

Ile Ser Ile Ile Thr Ala Ala Gly Ile Phe Phe Ile Thr Asp Gly Lys
            260                 265                 270

Tyr Asn Ser Thr Leu Leu Gly Ile Pro Phe Phe Ala Met Gly His Gly
        275                 280                 285

Thr Lys Gly Val Phe Glu Leu Leu Ser Gly Trp Arg Arg Thr Lys Glu
    290                 295                 300

Asn Leu Pro Phe Lys Asp Arg Ile Ala Asp Ala Tyr Ser Asp Val Met
305                 310                 315                 320

-continued

```
Val Thr Tyr Thr Met Thr Ser Ser Leu Tyr Phe Ile Thr Phe Gly Met
                325                 330                 335

Gly Ala Ser Pro Phe Thr Asn Ile Glu Ala Val Lys Val Phe Cys Gln
            340                 345                 350

Asn Met Cys Val Ser Ile Leu Leu Asn Tyr Phe Tyr Ile Phe Ser Phe
        355                 360                 365

Phe Gly Ser Cys Leu Val Phe Ala Gly Gln Leu Glu Gln Asn Arg Tyr
    370                 375                 380

His Ser Ile Phe Cys Cys Lys Ile Pro Ser Ala Glu Tyr Leu Asp Arg
385                 390                 395                 400

Lys Pro Val Trp Phe Gln Thr Val Met Ser Asp Gly His Gln Gln Thr
                405                 410                 415

Ser His His Glu Thr Asn Pro Tyr Gln His His Phe Ile Gln His Phe
            420                 425                 430

Leu Arg Glu His Tyr Asn Glu Trp Ile Thr Asn Ile Tyr Val Lys Pro
        435                 440                 445

Phe Val Val Ile Leu Tyr Leu Ile Tyr Ala Ser Phe Ser Phe Met Gly
    450                 455                 460

Cys Leu Gln Ile Ser Asp Gly Ala Asn Ile Ile Asn Leu Leu Ala Ser
465                 470                 475                 480

Asp Ser Pro Ser Val Ser Tyr Ala Met Val Gln Gln Lys Tyr Phe Ser
                485                 490                 495

Asn Tyr Ser Pro Val Ile Gly Phe Tyr Val Tyr Glu Pro Leu Glu Tyr
            500                 505                 510

Trp Asn Ser Ser Val Gln Asp Asp Leu Arg Arg Leu Cys Ser Gly Phe
        515                 520                 525

Thr Ala Val Ser Trp Val Glu Gln Tyr Tyr Gln Phe Leu Lys Val Ser
    530                 535                 540

Asn Val Ser Ala Asn Asn Lys Ser Asp Phe Ile Ser Val Leu Gln Ser
545                 550                 555                 560

Ser Phe Leu Lys Lys Pro Glu Phe Gln His Phe Arg Asn Asp Ile Ile
                565                 570                 575

Phe Ser Lys Ala Gly Asp Glu Ser Asn Ile Ile Ala Ser Arg Leu Tyr
            580                 585                 590

Leu Val Ala Arg Thr Ser Arg Asp Lys Gln Lys Glu Ile Thr Glu Val
        595                 600                 605

Leu Glu Lys Leu Arg Pro Leu Ser Leu Ser Lys Ser Ile Arg Phe Ile
    610                 615                 620

Val Phe Asn Pro Ser Phe Val Phe Met Asp His Tyr Ser Leu Ser Val
625                 630                 635                 640

Thr Val Pro Val Leu Ile Ala Gly Phe Gly Val Leu Leu Val Leu Ile
                645                 650                 655

Leu Thr Phe Phe Leu Val Ile His Pro Leu Gly Asn Phe Trp Leu Ile
            660                 665                 670

Leu Ser Val Thr Ser Ile Glu Leu Gly Val Leu Gly Leu Met Thr Leu
        675                 680                 685

Trp Asn Val Asp Met Asp Cys Ile Ser Ile Leu Cys Leu Ile Tyr Thr
    690                 695                 700

Leu Asn Phe Ala Ile Asp His Cys Ala Pro Leu Leu Phe Thr Phe Val
705                 710                 715                 720

Leu Ala Thr Glu His Thr Arg Thr Gln Cys Ile Lys Ser Ser Leu Gln
                725                 730                 735
```

```
Asp His Gly Thr Ala Ile Leu Gln Asn Val Thr Ser Phe Leu Ile Gly
            740                 745                 750

Leu Val Pro Leu Leu Phe Val Pro Ser Asn Leu Thr Phe Thr Leu Phe
        755                 760                 765

Lys Cys Leu Leu Leu Thr Gly Gly Cys Thr Leu Leu His Cys Phe Val
    770                 775                 780

Ile Leu Pro Val Phe Leu Thr Phe Phe Pro Pro Ser Lys Lys His His
785                 790                 795                 800

Lys Lys Lys Lys Arg Ala Lys Arg Lys Glu Arg Glu Glu Ile Glu Cys
                805                 810                 815

Ile Glu Ile Gln Glu Asn Pro Asp His Val Thr Thr Val
            820                 825


<210> SEQ ID NO 622
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 622

cagctctact ctttagcatc c                                                21


<210> SEQ ID NO 623
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 623

cctttagttc catgacccat g                                                21


<210> SEQ ID NO 624
<211> LENGTH: 6035
<212> TYPE: DNA
<213> ORGANISM: Homo sapiens

<400> SEQUENCE: 624

ggcggcggcg gcggcggccc cgggcgctga gcgggtgccc ggcgcggaga gcggcgagcg      60

cagccatgcc ccaggccgcc tccggggcag cagcagcggc ggccggggcc gaggcgcggg     120

ccgggggcgc cggggggccg gcggcggccc gggcgggacg atgaagcggc agaacgtgcg     180

cacgctggcg ctcatcgtgt gcaccttcac ctacctgctg gtgggcgccg cggtcttcga     240

cgcgctggag tcggagcccg agctgatcga gcggcagcgg ctggagctgc ggcagcagga     300

gctgcgggcg cgctacaacc tcagccaggg cggctacgag gagctggagc gcgtcgtgct     360

gcgcctcaag ccgcacaagg ccggcgtgca gtggcgcttc gccggctcct tctacttcgc     420

catcaccgtc atcaccacca tcggctacgg gcacgcggcg cccagcacgg atggcggcaa     480

ggtgttctgc atgttctacg cgctgctggg catcccgctc acgctcgtca tgttccagag     540

cctgggcgag cgcatcaaca ccttggtgag gtacctgctg caccgcgcca agaaggggct     600

gggcatctcg tggccttcgc ttcgtctcat ccttacgggc ctcacggtca tcggcgcctt     660

cctcaacctc gtggtgctgc gcttcatgac catgaacgcc gaggacgaga agcgcgacgc     720

cgagcaccgc gcgctgctca cgcgcaacgg gcaggcgggc ggcggcggag ggagtggcag     780

cgcgcacact acggacaccg cctcatccac ggcggcagcg ggcggcggcg gcttccgcaa     840
```

```
cgtctacgcg gaggtgctgc acttccagtc catgtgctcg tgcctgtggt acaagagccg    900
cgagaagctg cagtactcca tccccatgat catcccgcgg gacctctcca cgtccgacac    960
gtgcgtggag cagagccact cgtcgccggg agggggcggc cgctacagcg acacgccctc   1020
gcgacgctgc ctgtgcagcg gggcgccacg ctccgccatc agctcggtgt ccacgggtct   1080
gcacagcctg tccaccttcc gcggactcat gaagcgcagg agctccgtgt gactgccccg   1140
aggggcctgg agcacctggg ggcgcgggcg ggggacccct gctgggaggc caggagactg   1200
cccctgctgc cttctgccca gtgggacccc gcacaacatc cctcaccact ctcccccagc   1260
acccccatct ccgactgtgc ctgcttgcac cagccggcag gaggccgggc tctgaggacc   1320
cctggggccc ccatcggagc cctgcaaatt ccgagaaatg tgaaacttgg tggggtcagg   1380
gaggaaaggc agaagctggg agcctccctt ccctttgaaa atctaagaag ctcccagtcc   1440
tcagagaccc tgctggtacc cagaccccca ccttcggagg ggacttcatg ttccgtgtac   1500
gtttgcatct ctatttatac ctctgtcctg ctaggtctcc caccttccct tggttccaaa   1560
agccagggtg tctttgtcca agtcacccct actcagcccc actccctttc ctcatcccca   1620
gctgtgtctc ccaacctccc ttcgtgttgt tttgcatggc tttgcagtta tggagaaagt   1680
ggaaacccag cagtccctaa agctggtccc cagaaagcag gacagaaaga aggagggaca   1740
ggcaggcagc aggaggggcg agctgggagg caggaggcag cggcctgtca gtctgcagaa   1800
tggtcgcact ggaggttcaa gctaactggc ctccagccac attctcatag caggtaggac   1860
ttcagccttc cagacactgc ccttagaatc tggaacagaa gacttcagac tcaccataat   1920
tgctgataat tacctactct taaatttgtc gagtgatttt tagcctctga aaactctatg   1980
ctggccactg attcctttga gtctcacaaa accctactta ggtcatcagg gcaggagttc   2040
tcactcccat tttacagatg agaatactga ggcctggaca ggtgaagtga ccagagagca   2100
aaaggcaaag gggtgggggc tgggtgcagt ggctcacacc tgtattccca acacttttgg   2160
aggctgaggt tagaggattg cttgagccca ggaattcgag accagcctag gcgacatagt   2220
gagaccccat ctctacaaaa aataaaaaat ttaccaggtg tggtggcacg tgcctgggag   2280
tcccagcgac ttgggaggct gaggtgggag gattgtttga gcctgggagg tcaaggctgt   2340
agtgagccct gattacacca ctgtactcca gcctgggtga cagggcaaga ccctgtctca   2400
aaaaaaaaaa aaaaatggca aagggagaca agagcccagc ctacttgttc ctagccaaag   2460
tgttctttcc ttccagcttg gcctgctctt aaaagcaaag ctcctgcagt gtacatcctg   2520
gcattgtgtg gctacctggg ttttaaacca gaatcagaag tcccgggtca gagggcactg   2580
ctgaggctca gcctcttctc ttcttggcca ggaggcagca gctctgaatg ggcccctgag   2640
gctgcacagg ggcctttgtc actggggtgc atgcttacaa acagtgcagt tcttggcacc   2700
gaggtaagca gggctgggtc tcatggcaga aaggccagga tctggggctc taggaatttg   2760
ggaattgggc agagtggcca agaaagctgg caggcatatc ctatgggaca tcacacctgg   2820
caccattgtc attgttggtg cctgtgtccc aagtagctag tgataagctg aggctgcagc   2880
aagaaacacc cttcccaggt gggggagttt ggaccagagg tgccctctgc ccaccacacc   2940
tgcaacccag aagcccagat ggaacgcagc tgatgaaggt gatgcttgag gctcactttt   3000
ggggccccac agctggagcc ggtatagtga ctgggacaac atcaaggggt ggatgagggg   3060
cctctcctcc cgcaacactg ccttcccatg ctgttcccct gccagctcct taacactgcc   3120
gaccaaggcc agacctggca ttcaggaaag ttggagggca gcacccatag ggtggccagc   3180
```

-continued ctcaggcccc accccagctg tgtcctctag tctctgggga cccctggggg gaagaagtct 3240
accctgcttg tgagtcccgt ctcagtgtgg aggaactggc tgcacgtggg acctgaaggt 3300
gccctctgtg tttatgttgg gggggggggg gcagtgctgg ctgcctctgt cctgtgtgtg 3360
accctgccct cgaagggtcc tgtcctgtca gtcccgaggg agccacaacc aaagctgcgg 3420
agagaaggtg gggaacggtg cggagtggcc gtggggcaca gcgtggcaga ctgttcagtc 3480
tctgctgggt ctttcctagg gacctggaag gccagtgttg cttccccctc actccctttc 3540
actgcaggca gcctctctcc ttccccaatg ccttatgcct gggcacactg ccacagaata 3600
tgcaatatgt gtgggtgacg atgccctcac gaccacaccc ccaccccggg cagccccccgg 3660 actccaaagg tcgtggctgc cacagcctcc ctcagctctt cctgcctatc tgtcttcaca 3720
ctgagaatgg cgcccaataa atgctatcca cggagaccag gctcaggctc cagctgcctc 3780
tgtcatcgta tgcccttgct gctgccaggg aggggccatc tcccaccccc tcccctgccg 3840
gggtctacaa acatacctag ctgctgggtg ccgtggctca cacctataat cacagcacta 3900
ggcgggcaga tcacctgagg tcagaagttc aagaccagcc tggccaacat ggtaaaaccc 3960
cgtctctact aaaaatacaa aaattagctg agcgtggtgg cgcctgtctg tagtcccagc 4020
tactcggcta ctcaggaggc tgacgcacga gaatcgcttg aacccgggag gcggaggttg 4080
cagtgagctg agatcgcgcc actgcactcc agcctgagcg atagagtgag accctgtcta 4140
aaaaaaacaa taataataaa ataaaataac atacctagct gactcgccat gggctcgctg 4200
gcctgtgggc gacactggct tcccttttgg gatttcccag aagatccaga ttttcttaag 4260
tccccttgga acagactaag aaagaaacac cttagaaatc acctggtcct attgtccccc 4320
cgtacatgag taactgaggc ccacagagag caaatcgcct gcctgagtca cacagcagtg 4380
agtggcagac ctaggctagg aactagaact ggggattgct attccagtgc tccccatcct 4440
cacacagcct gtggagtccg cctggacaca ccccagctga cagtggtacc tcccagtcag 4500
ccaggagaat ggattccttc tcctgcagta ggggccccct ggctgagtgg cctgattgac 4560
taaaacatat gtctttgaag gagagtgcat cacaagcacc tttctttggg gtagattttt 4620
ctctgggtct agagggacac ctcaggcttg ggactgggcc tcagaaccta ggacagaccc 4680
tgagagcaga cccaccttat ccatctggtg ccagctcccc aggtcagcta cagcaacccc 4740
cgaacttcat agagtacaat ccacagtaat agcacacagc tctgtaccta tctagctcca 4800
tgcctatcta tctgcctacc tttcacaaaa taattcttag caaccctgct acagccaatg 4860
attctaatac gttctgttct attacatgtt ataaaatgct ggtcacgatc cactaaattg 4920
atgtctctac ctgctaatgg tttaatacct gcagattgaa atatactgga gaaataaaga 4980
gagtaggagt agggacactt tctcccagtg cccacaccgc ccctcgttac ccgcataggt 5040
caactgaaag atacagagag ggaagctttg atggggggtt cagagttcaa aggaagaaat 5100
gatggcacct gcactccctg cccccagagg caggacacag ccagccctcc tgtgacagca 5160
ctcctggcag ctccttgttg gcctgcagcc cttagttgcc attgactcac ccactcctaa 5220
ggccaccaca tcaaaatctg aggcttactg ccctggccca cctgcctctg tctttcttaa 5280
aacagctaaa tgcaacgata gcagaaatta gcttgttttt gaggttggca atgaccagtt 5340
caactcttat tttcttaagc agtgcttgca ggacataaat gtgatgacac ttgccctcct 5400
ttctttatcg cctggggcag actttacaaa cagacctggg aggagtcccc taaggggctg 5460
catttatccc catctcccta ggggtgatca gcattgtgac agctgggcag agcagtggtg 5520
aactgcaccc atgtccctgc tcacatctcc taagatctca gaattgcctg aggttctagc 5580

```
gtgggctcct tctctccaga tgatgccatc cccaccccc tcatttccac acagcatctg   5640

aggcatcctg cactaaaaga tatatgtaca gcaaaacaaa aatagaaaac cagcacagca   5700

gagtggaggt ggggtataaa tatacccaga tccccgctga tttggttact cggggtgagc   5760

atcagatgga aatagaagtt tccgggggcc aagagagaaa gagggatgta acgacaattc   5820

ttttcaaaac gtgtcccatg gtatgcctcg tggaaaaaat ggttcgttgg tcaaatgaat   5880

ttgggaaaat gctgtcaata tcaccgactc atggagcttc gcaaggcatc ttagcttaat   5940

aaaggttatg aaaagtcttg cagcaaagat gctgtttacc ccacttaatc cagcactgcc   6000

caaactcatt ccaaatacca gagcctctgt ttgca                              6035
```

<210> SEQ ID NO 625
<211> LENGTH: 323
<212> TYPE: PRT
<213> ORGANISM: Homo sapiens

<400> SEQUENCE: 625

```
Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

Arg Ala Arg Tyr Asn Leu Ser Gln Gly Gly Tyr Glu Glu Leu Glu Arg
    50                  55                  60

Val Val Leu Arg Leu Lys Pro His Lys Ala Gly Val Gln Trp Arg Phe
65                  70                  75                  80

Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Ile Ser Trp Pro Ser Leu Arg Leu Ile Leu Thr Gly
145                 150                 155                 160

Leu Thr Val Ile Gly Ala Phe Leu Asn Leu Val Val Leu Arg Phe Met
                165                 170                 175

Thr Met Asn Ala Glu Asp Glu Lys Arg Asp Ala Glu His Arg Ala Leu
            180                 185                 190

Leu Thr Arg Asn Gly Gln Ala Gly Gly Gly Gly Gly Ser Gly Ser Ala
        195                 200                 205

His Thr Thr Asp Thr Ala Ser Ser Thr Ala Ala Ala Gly Gly Gly Gly
    210                 215                 220

Phe Arg Asn Val Tyr Ala Glu Val Leu His Phe Gln Ser Met Cys Ser
225                 230                 235                 240

Cys Leu Trp Tyr Lys Ser Arg Glu Lys Leu Gln Tyr Ser Ile Pro Met
                245                 250                 255

Ile Ile Pro Arg Asp Leu Ser Thr Ser Asp Thr Cys Val Glu Gln Ser
            260                 265                 270

His Ser Ser Pro Gly Gly Gly Gly Arg Tyr Ser Asp Thr Pro Ser Arg
        275                 280                 285
```

-continued

```
Arg Cys Leu Cys Ser Gly Ala Pro Arg Ser Ala Ile Ser Ser Val Ser
    290                 295                 300

Thr Gly Leu His Ser Leu Ser Thr Phe Arg Gly Leu Met Lys Arg Arg
305                 310                 315                 320

Ser Ser Val


<210> SEQ ID NO 626
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 626

agactttaca aacagacctg g                                              21


<210> SEQ ID NO 627
<211> LENGTH: 23
<212> TYPE: DNA
<213> ORGANISM: artificial
<220> FEATURE:
<223> OTHER INFORMATION: Description of artificial sequence:
      Oligonucleotide

<400> SEQUENCE: 627

gcttgcagga cataaatgtg atg                                            23


<210> SEQ ID NO 628
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 628

tgacactggc aaaacaatgc a                                              21


<210> SEQ ID NO 629
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 629

ggtccttttc accagcaagc t                                              21


<210> SEQ ID NO 630
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 630

ccacagaagg uaccaguuau u                                              21


<210> SEQ ID NO 631
<211> LENGTH: 21
<212> TYPE: DNA
<213> ORGANISM: artificial
<220> FEATURE:
<223> OTHER INFORMATION: Description of artificial sequence: siRNA
```

<400> SEQUENCE: 631
uaacugguac cuucuguggu u 21

<210> SEQ ID NO 632
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 632
cagcaagacu cccucuaaau u 21

<210> SEQ ID NO 633
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 633
uuuagaggga gucuugcugu u 21

<210> SEQ ID NO 634
<211> LENGTH: 21
<212> TYPE: RNA
<213> ORGANISM: artificial
<220> FEATURE:
<223> OTHER INFORMATION: Description of artificial sequence: target RNA
<220> FEATURE:
<221> NAME/KEY: misc_feature
<222> LOCATION: (1)..(2)
<223> OTHER INFORMATION: n is a, c, g, t or u

<400> SEQUENCE: 634
nnccacagaa gguaccaguu a 21

<210> SEQ ID NO 635
<211> LENGTH: 21
<212> TYPE: RNA
<213> ORGANISM: artificial
<220> FEATURE:
<223> OTHER INFORMATION: Description of artificial sequence: target RNA
<220> FEATURE:
<221> NAME/KEY: misc_feature
<222> LOCATION: (1)..(2)
<223> OTHER INFORMATION: n is a, c, g, t or u

<400> SEQUENCE: 635
nncagcaaga cucccucuaa a 21

<210> SEQ ID NO 636
<211> LENGTH: 6
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (3)..(4)
<223> OTHER INFORMATION: Xaa is any amino acid

<400> SEQUENCE: 636

Cys Cys Xaa Xaa Cys Cys
1 5